United States Patent
Wacker et al.

(10) Patent No.: US 12,227,496 B2
(45) Date of Patent: *Feb. 18, 2025

(54) SUBSTITUTED BICYCLIC COMPOUNDS AS FARNESOID X RECEPTOR MODULATORS

(71) Applicant: BRISTOL-MYERS SQUIBB COMPANY, Princeton, NJ (US)

(72) Inventors: Dean A. Wacker, Yardley, PA (US); Susheel Jethanand Nara, Mumbai (IN); Srinivas Cheruku, Bangalore (IN); Kandhasamy Sarkunam, Hosur (IN); Firoz Ali Jaipuri, Bangalore (IN); Rishikesh Narayan, Mumbai (IN); Subba Reddy Bandreddy, Bangalore (IN); Srinivas Jogi, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 751 days.

This patent is subject to a terminal disclaimer.

(21) Appl. No.: 17/431,006

(22) PCT Filed: Feb. 14, 2020

(86) PCT No.: PCT/US2020/018210
§ 371 (c)(1),
(2) Date: Aug. 13, 2021

(87) PCT Pub. No.: WO2020/168148
PCT Pub. Date: Aug. 20, 2020

(65) Prior Publication Data
US 2022/0162201 A1 May 26, 2022
US 2023/0109670 A9 Apr. 6, 2023

Related U.S. Application Data

(60) Provisional application No. 62/806,042, filed on Feb. 15, 2019.

(51) Int. Cl.
| | |
|---|---|
| C07D 413/12 | (2006.01) |
| C07D 217/06 | (2006.01) |
| C07D 271/06 | (2006.01) |
| C07D 403/12 | (2006.01) |
| C07D 413/14 | (2006.01) |
| C07D 417/12 | (2006.01) |
| C07D 417/14 | (2006.01) |

(52) U.S. Cl.
CPC ......... *C07D 413/12* (2013.01); *C07D 217/06* (2013.01); *C07D 271/06* (2013.01); *C07D 403/12* (2013.01); *C07D 413/14* (2013.01); *C07D 417/12* (2013.01); *C07D 417/14* (2013.01)

(58) Field of Classification Search
CPC .. C07D 413/12; C07D 217/06; C07D 403/12; C07D 413/14; C07D 417/12; C07D 417/14

See application file for complete search history.

(56) References Cited

U.S. PATENT DOCUMENTS

| | | | |
|---|---|---|---|
| 8,158,665 B2 | 4/2012 | Caldwell et al. | |
| 8,907,095 B2 | 12/2014 | Xia et al. | |
| 9,539,244 B2 | 1/2017 | Kinzel et al. | |
| 9,751,874 B2 | 9/2017 | Gege et al. | |
| 11,254,663 B2 * | 2/2022 | Wacker | A61P 11/00 |

(Continued)

FOREIGN PATENT DOCUMENTS

| | | |
|---|---|---|
| EP | 3034499 A1 | 6/2016 |
| EP | 3034501 A1 | 6/2016 |

(Continued)

OTHER PUBLICATIONS

Boothroyd, S.; et al. "Why Do Some Molecules Form Hydrates or Solvates?" 2018, Cryst. Growth Des., vol. 18, pp. 1903-1908. (Year: 2018).*

Agana, M.; et al. "Common metabolic disorder (inborn errors of metabolism) concerns in primary care practice" 2018, Annals of Translational Medicine, vol. 6, article 469. (Year: 2018).*

The Organic Chemistry of Drug Design and Drug Action, Richard B. Silverman, Chemical Industry Press, Jan. 2008, 1st Edition, pp. 19-22.

(Continued)

*Primary Examiner* — Eric Olson
*Assistant Examiner* — Benjamin M Brandsen
(74) *Attorney, Agent, or Firm* — Gary Greenblatt

(57) ABSTRACT

Disclosed are compounds of Formula (I): or a stereoisomer, a tautomer, or a salt or solvate thereof, wherein Q is $C_{2-6}$ alkenyl or $C_{2-6}$ alkynyl, each substituted with zero to 2 $R^1$; and the other variables are as defined herein. These compounds modulate the activity of farnesoid X receptor (FXR), for example, as agonists. Also disclosed are pharmaceutical compositions comprising these compounds and methods of treating a disease, disorder, or condition associated with FXR dysregulation, such as pathological fibrosis, transplant rejection, cancer, osteoporosis, and inflammatory disorders, by using the compounds and pharmaceutical compositions.

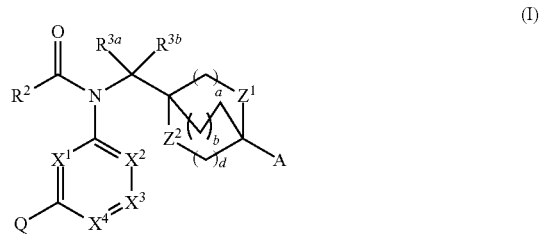

(I)

11 Claims, 4 Drawing Sheets

(56) References Cited

U.S. PATENT DOCUMENTS

| | | | |
|---|---|---|---|
| 11,713,312 B2* | 8/2023 | Wacker | A61P 11/00 |
| | | | 514/340 |
| 2010/0152166 A1 | 6/2010 | Genin et al. | |
| 2011/0034507 A1 | 2/2011 | Akwabi-ameyaw et al. | |
| 2015/0366856 A1 | 12/2015 | Tully et al. | |
| 2016/0176861 A1 | 6/2016 | Gege et al. | |
| 2017/0298068 A1 | 10/2017 | Gege et al. | |
| 2017/0304270 A1 | 10/2017 | Or et al. | |
| 2017/0304271 A1 | 10/2017 | Or et al. | |
| 2017/0304272 A1 | 10/2017 | Or et al. | |
| 2017/0333399 A1 | 11/2017 | Or et al. | |
| 2017/0355693 A1 | 12/2017 | Blomgren et al. | |
| 2017/0355694 A1 | 12/2017 | Gege | |
| 2017/0368038 A1 | 12/2017 | Badman et al. | |
| 2019/0002452 A1 | 1/2019 | Zhang et al. | |
| 2019/0127358 A1 | 5/2019 | Yoon et al. | |
| 2022/0213026 A1* | 7/2022 | Wacker | C07D 277/64 |

FOREIGN PATENT DOCUMENTS

| | | | |
|---|---|---|---|
| EP | 3401315 A1 | 11/2018 | |
| WO | 9313101 A1 | 7/1993 | |
| WO | 9817276 A1 | 4/1998 | |
| WO | 03099821 A1 | 12/2003 | |
| WO | 2004046162 A2 | 6/2004 | |
| WO | 2006006490 A1 | 1/2006 | |
| WO | 2007076260 A2 | 7/2007 | |
| WO | 2008051942 A2 | 5/2008 | |
| WO | 2008094556 A2 | 8/2008 | |
| WO | 2008109177 A2 | 9/2008 | |
| WO | 2008109179 A1 | 9/2008 | |
| WO | 2008109180 A2 | 9/2008 | |
| WO | 2009009059 A1 | 1/2009 | |
| WO | 2009149795 A2 | 12/2009 | |
| WO | 2010058318 A1 | 5/2010 | |
| WO | 2011006935 A2 | 1/2011 | |
| WO | 2011045292 A1 | 4/2011 | |
| WO | 2012087520 A1 | 6/2012 | |
| WO | 2013007387 A1 | 1/2013 | |
| WO | 2013186159 A1 | 12/2013 | |
| WO | 2014054053 A1 | 4/2014 | |
| WO | 2015138969 A1 | 9/2015 | |
| WO | 2015172747 A1 | 11/2015 | |
| WO | 2016096115 A1 | 6/2016 | |
| WO | 2017049173 A1 | 3/2017 | |
| WO | 2017049176 A1 | 3/2017 | |
| WO | 2017133521 A1 | 8/2017 | |
| WO | 2017145040 A1 | 8/2017 | |
| WO | 2017145041 A1 | 8/2017 | |
| WO | 2017161002 A1 | 9/2017 | |
| WO | 2018059314 A1 | 4/2018 | |
| WO | 2018170165 A1 | 9/2018 | |
| WO | 2018170166 A1 | 9/2018 | |
| WO | 2018170167 A1 | 9/2018 | |
| WO | 2018170173 A1 | 9/2018 | |
| WO | 2018170182 A1 | 9/2018 | |
| WO | 2020061114 A1 | 3/2020 | |
| WO | WO-2020061118 A1 * | 3/2020 | |

OTHER PUBLICATIONS

Claudel, Thierry et al., "The Farnesoid X Receptor: A Novel Drug Target?", Expert Opin. Investig. Drugs, vol. 13(9), pp. 1135-1148, (2004).

Crawley, Matthew Lantz, "Farnesoid X receptor modulators: a patent review," Expert Opinion on Therapeutic Patents, (2010) 20:8, pp. 1047-1057.

International Preliminary Report on Patentability Application No. PCT/US2020/018210, Issued Aug. 10, 2021.

International Search Report Application No. PCT/US2020/018210, mailed Jul. 24, 2020.

Sepe, Valentina et al., "Farnesoid X Receptor Modulators 2014-present: A Patent Review", Expert Opinion on Therapeutic Patents, vol. 28, No. 5, pp. 351-364 (2018).

Tully, David C. et al., "Discovery of Tropifexor (LJN452), a Highly Potent Non-bile Acid FXR Agonist for the Treatment of Cholestatic Liver Diseases and Nonalcoholic Steatohepatitis (NASH)", Journal of Medicinal Chemistry, vol. 60, pp. 9960-9973 (2017).

* cited by examiner

SUBSTITUTED BICYCLIC COMPOUNDS AS FARNESOID X RECEPTOR MODULATORS

CROSS REFERENCE TO RELATED APPLICATIONS

This application is a 371 application of International Application No. PCT/US2020/018210 filed on Feb. 14, 2020, which claims the benefit of U.S. Provisional Application Ser. 62/806,402, filed Feb. 15, 2019, the content of each is hereby fully incorporated by reference in its entirety for all purposes.

The present invention relates generally to compounds useful as farnesoid X receptor (FXR) modulators, pharmaceutical compositions comprising such compounds and to their use in therapy, especially in the treatment or prophylaxis of diseases, disorders, and conditions for which an FXR modulator is indicated.

FXR or NR1H4 (nuclear receptor subfamily 1, group H, member 4) is a nuclear receptor that can activate the expression of specific target genes in a ligand-dependent manner. FXR is expressed in the liver, throughout the gastrointestinal tract, colon, ovary, adrenal gland, kidney, and in the gall bladder and biliary tree in humans. FXR forms a heterodimer with Retinoid X Receptor (RXR) and binds to specific response elements in target genes to regulate gene transcription (B. M. Forman et al., *Cell* 1995; 81: 687; W. Seol et al., *Mol. Endocrinol.* 1995; 9: 72). The FXR/RXR heterodimer typically binds to an inverted repeat of a consensus hexanucleotide sequence (AGGTCA) separated by a single nucleotide, i.e. an IR-1 sequence. The relevant physiological ligands of FXR are bile acids including chenodeoxycholic acid and its taurine-conjugate (D. J. Parks et al., *Science* 1999; 284: 1365; M. Makishima et al., *Science* 1999; 284: 1362). FXR activation regulates the expression of multiple genes that encode enzymes and transporters involved in bile acid synthesis, influx, and efflux from the liver and intestine resulting in a net decrease in total endogenous bile acids in a negative feedback loop. FXR is involved in paracrine and endocrine signaling by upregulating the expression of the cytokine Fibroblast Growth Factor 15 (rodents) or 19 (primates), which can also contribute to the regulation of bile acid concentrations (Holt et al., *Genes Dev.* 2003; 17: 1581; Inagaki et al., *Cell Metab* 2005; 2: 217). Therefore, FXR is considered to be a master regulator of bile acid homeostasis.

One use of FXR agonists is for the treatment of diseases in which bile acids are dysregulated, including cholestatic diseases (e.g. primary biliary cirrhosis and primary sclerosing cholangitis) that can lead to fibrosis, cirrhosis, cholangiocarcinoma, hepatocellular carcinoma, liver failure, and death. While elevated bile acid concentrations in the liver have deleterious effects, bile acids also affect the microflora and integrity of the small intestine. Obstruction of bile flow in humans or rodents causes proliferation of intestinal bacteria and mucosal injury, which can lead to bacterial translocation across the mucosal barrier and systemic infection (Berg, *Trends Microbiol.* 1995; 3: 149-154). Mice lacking FXR have increased ileal levels of bacteria and a compromised epithelial barrier, while activation of intestinal FXR plays an important role in preventing bacterial overgrowth and maintaining the integrity of the intestinal epithelium (Inagaki et al., *Proc Natl Acad Sci* 2006; 103: 3920-3925). Over time, FXR null mice spontaneously develop hepatocellular carcinoma, and this can be abrogated by selective re-activation of FXR in the intestine (Degirolamo et al., *Hepatology* 61: 161-170). Pharmacological activation of FXR with a small molecule agonist or transgenic expression of FXR in the intestine can normalize bile acid concentrations, decrease cellular proliferation in hepatic bile ducts, and reduce inflammatory cell infiltration, necrotic area, and liver fibrosis in rodent models of cholestasis (Liu et al., *J. Clin. Invest.* 2003; 112:1678-1687; Modica et al., *Gastroenterology.* 2012; 142: 355-365). Some of these beneficial effects observed in preclinical models of cholestasis have translated to human patients, and the FXR agonist, obeticholic acid (OCA or OCALIVA™), has been approved for the treatment of primary biliary cirrhosis (https://www.fda.gov/newsevents/newsroom/pressannouncements/ucm503964.htm).

In addition to controlling bile acid homeostasis, FXR agonists regulate the hepatic expression of hundreds of genes encoding proteins involved in cholesterol and lipid metabolism and transport, glucose homeostasis, inflammation, chemotaxis, and apoptosis among other pathways (Zhan et al., *PLoS One* 2014; 9: e105930; Ijssennagger et al., *J Hepatol* 2016; 64: 1158-1166). Consistent with these broad effects on gene expression, FXR agonists have also been investigated in preclinical models of fibrosis, cancer, inflammatory diseases, and metabolic disorders, including dyslipidemia, obesity, type 2 diabetes, nonalcoholic fatty liver disease (NAFLD) and metabolic syndrome (Crawley, *Expert Opin. Ther. Patents* 2010; 20:1047-1057).

FXR agonists are also being investigated in human clinical trials for the treatment of NAFLD, a more advanced form of fatty liver disease, nonalcoholic steatohepatitis (NASH), and associated complications. NAFLD is one of the most common causes of chronic liver disease in the world today (Vernon et al., *Aliment Pharmacol Ther* 2011; 34:274-285). The risk factors for developing NAFLD include obesity, type 2 diabetes mellitus (T2DM), insulin resistance, hypertension, and dyslipidemia. In a 6-week clinical trial in T2DM patients with NAFLD, the FXR agonist OCA statistically significantly improved insulin sensitivity and reduced body weight, showing beneficial effects on some of these risk factors (Mudaliar et al., *Gastroenterology* 2013; 145: 574-582). NASH is the most severe and progressive form of NAFLD and includes the histological findings of hepatic steatosis, inflammation, and ballooning degeneration with varying amounts of pericellular fibrosis (Sanyal et al., *Hepatology* 2015; 61:1392-1405). In a 72-week clinical trial in patients with NASH, OCA statistically significantly improved hepatic steatosis, lobular inflammation, hepatocyte ballooning, and fibrosis as assessed by histological analyses of liver biopsies (Neuschwander-Tetri et al., *Lancet* 2015; 385: 956-965). These data also suggest the potential for FXR agonists to show benefit on clinical outcomes given that NASH is the second leading cause of hepatocellular carcinoma (HCC) and liver transplantation in the United States (Wong et al., *Hepatology* 2014; 59: 2188-2195).

The present invention provides novel compounds for treating a disease, disorder, or condition associated with farnesoid X receptor (FXR) activity in a patient in need thereof.

SUMMARY OF THE INVENTION

In one aspect, the present invention provides compounds of Formula (I) as well as the subgenera and species thereof, including stereoisomers, tautomers, pharmaceutically acceptable salts, and solvates thereof, which are useful as FXR modulators.

In another aspect, the present invention also provides processes and intermediates for making the compounds of the present invention.

In another aspect, the present invention also provides pharmaceutical compositions comprising a pharmaceutically acceptable carrier and at least one of the compounds of the present invention or stereoisomers, tautomers, pharmaceutically acceptable salts, or solvates thereof.

In another aspect, the compounds of the invention may be used in therapy, either alone or in combination with one or more additional therapeutic agents.

The compounds of the invention may be used in the treatment of a disease, disorder, or condition associated with activity of farnesoid X receptor (FXR) in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used, either as a single agent or in combination with other agents, in the treatment of a disease, disorder, or condition selected from nonalcoholic steatohepatitis (NASH), non-alcoholic fatty liver disease (NAFLD), chronic kidney disease, diabetic kidney disease, primary sclerosing cholangitis (PSC), and primary biliary cirrhosis (PBC). The compounds of the invention may be used, either as a single agent or in combination with other agents, in the treatment of idiopathic pulmonary fibrosis (IPF).

The compounds of the invention may be used for the manufacture of a medicament for the treatment of a disease, disorder, or condition in a patient in need of such treatment.

Other features and advantages of the invention will be apparent from the following detailed description and claims.

BRIEF DESCRIPTION OF THE DRAWINGS

The invention is illustrated by reference to the accompanying drawing described below.

DETAILED DESCRIPTION

Figure 1:
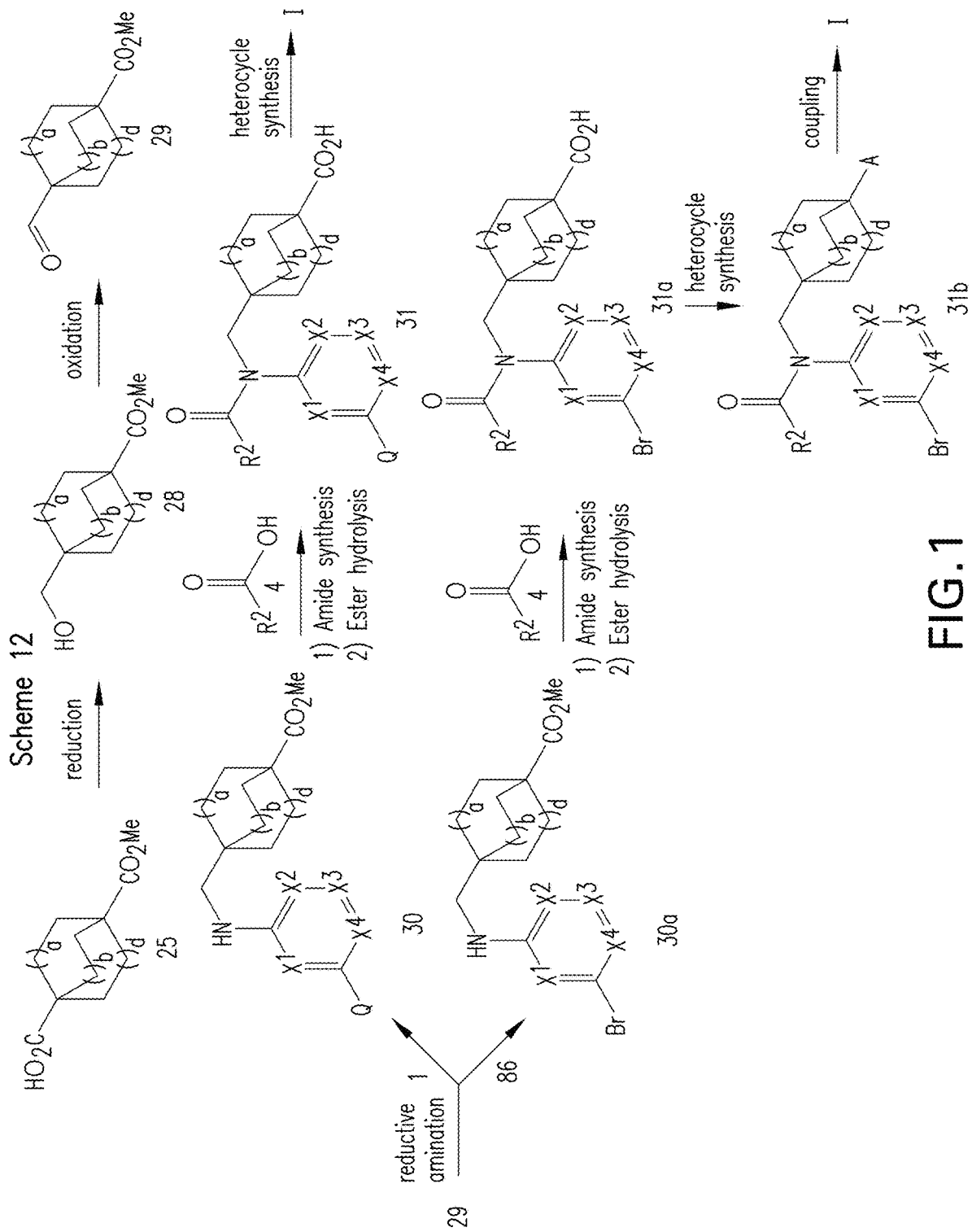
FIG. 1 shows the general reaction Scheme 12.

The present application provides compounds, including all stereoisomers, solvates, prodrugs and pharmaceutically acceptable salt and solvate forms thereof, according to Formula (I). The present application also provides pharmaceutical compositions containing at least one compound according to Formula (I), or a stereoisomer, a tautomer, or a pharmaceutically acceptable salt or a solvate thereof, and optionally at least one additional therapeutic agent. Additionally, the present application provides methods for treating a patient suffering from a FXR-modulated disease or disorder such as for example, biliary fibrosis, liver fibrosis, renal fibrosis, Non-Alcoholic Fatty Liver Disease (NAFLD), Non-Alcoholic Steato-Hepatitis (NASH), primary sclerosing cholangitis (PSC), primary biliary cirrhosis (PBC), and pancreatic fibrosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

The first aspect of the present invention provides a compound of Formula (I):

(I)

or a stereoisomer, a tautomer, or a salt or solvate thereof, wherein:

$X^1$ is $CR^{5a}$ or N;
$X^2$ is $CR^{5b}$ or N;
$X^3$ is $CR^{5c}$ or N;
$X^4$ is $CR^{5d}$ or N; provided that zero, 1, or 2 of $X^1$, $X^2$, $X^3$, and $X^4$ are N;
$Z^1$ and $Z^2$ are independently $CH_2$ or O; provided that at least one of $Z^1$ and $Z^2$ is $CH_2$;
a is zero or 1;
b is zero, 1, or 2;
d is zero, 1, or 2; provided that $Z^1$ and $Z^2$ are each $CH_2$ when a, b, and d are each zero;
Q is a cyclic group selected from 3- to 8-membered carbocyclyl, 6- to 10-membered aryl, 4- to 10-membered heterocyclyl, and 5- to 10-membered heteroaryl, wherein said cyclic group is substituted with zero to 4 $R^1$;
each $R^1$ is independently hydrogen, halo, cyano, hydroxyl, oxo, $C_{1-6}$ alkyl, $C_{2-6}$ alkenyl, $C_{2-6}$ alkynyl, $C_{1-6}$ alkoxy, —$NH_2$, —$NH(C_{1-6}$ alkyl), —$N(C_{1-6}$ alkyl$)_2$, —$C(O)(C_{1-6}$ alkyl), —$C(O)(C_{3-6}$ cycloalkyl), —$NR^xC(O)R^y$, —$C(O)OR^x$, —$C(O)NR^wR^w$, —$S(O)_2(C_{1-6}$ alkyl), —$S(O)_2(C_{3-6}$ cycloalkyl), —$NR^xS(O)_2(C_{1-6}$ alkyl), —$NR^xS(O)_2(C_{3-6}$ cycloalkyl), —$S(O)_2NR^zR^z$, —$P(O)R^yR^y$, —$(CH_2)_{0-3}(C_{3-6}$ carbocyclyl), —$O(C_{3-6}$ cycloalkyl), —$O(4-$ to 6-membered heterocyclyl), —$(CH_2)_{0-3}(4-$ to 6-membered heterocyclyl), or —$(CH_2)_{0-3}(5-$ or 6-membered heteroaryl), wherein each of said alkyl, alkoxy, alkenyl, and alkynyl is substituted with zero to 4 $R^{1a}$ and each of said cycloalkyl, heterocyclyl, and heteroaryl is substituted with zero to 4 $R^{1b}$;
each $R^{1a}$ is independently halo, hydroxyl, —$NR^wR^w$, oxo, cyano, $C_{1-3}$ alkoxy, $C_{1-3}$ haloalkoxy, —$C(O)OR^x$, —$C(O)NR^wR^w$, or —$NR^xC(O)R^y$;
each $R^{1b}$ is independently halo, oxo, cyano, hydroxyl, —$NH_2$, $C_{1-6}$ alkyl, $C_{1-6}$ alkoxy, —$NH(C_{1-6}$ alkyl), —$N(C_{1-6}$ alkyl$)_2$, or —$NR^xC(O)(C_{1-6}$ alkyl), wherein each of said alkyl and alkoxy is substituted with zero to 6 $R^{1a}$;
$R^2$ is $C_{6-8}$ carbocyclyl, 6- to 7-membered heterocyclyl, phenyl, or 6-membered heteroaryl, wherein each of said carbocyclyl, heterocyclyl, phenyl, and heteroaryl is substituted with zero to 3 $R^{2b}$;
each $R^{2a}$ is independently halo, cyano, hydroxyl, oxo, $C_{1-3}$ haloalkyl, $C_{1-3}$ alkoxy, $C_{1-3}$ haloalkoxy, —$NR^xR^x$, —$C(O)(C_{1-6}$ alkyl), —$C(O)(C_{3-6}$ cycloalkyl), —$NR^xC(O)R^y$, —$C(O)(C_{1-6}$ alkyl), —$C(O)OR^x$, —$C(O)$ NR$^w$R$^w$, —S(O)$_2$R$^y$, —S(O)$_2$(C$_{1-3}$ fluoroalkyl), —NR$^x$S(O)$_2$(C$_{1-3}$ alkyl), —NR$^x$S(O)$_2$(C$_{3-6}$ cycloalkyl), —S(O)$_2$NR$^z$R$^z$, or —P(O)R$^y$R$^y$;

each R$^{2b}$ is independently halo, cyano, hydroxyl, oxo, C$_{1-6}$ alkyl, C$_{1-6}$ alkoxy, —NR$^x$R$^x$, —NR$^x$C(O)O(C$_{1-3}$ alkyl), —C(O)(C$_{1-4}$ alkyl), —C(O)O(C$_{1-4}$ alkyl), —C(O)NR$^w$R$^w$, —NR$^x$C(O)R$^y$, —NR$^x$S(O)$_2$(C$_{1-3}$ alkyl), —NR$^x$S(O)$_2$(C$_{3-6}$ cycloalkyl), —S(O)$_2$NR$^z$R$^z$, or —S(O)$_2$(C$_{1-3}$ alkyl), wherein each of said alkyl and alkoxy is substituted with zero to 6 R$^{2a}$.

R$^{3a}$ and R$^{3b}$ are independently hydrogen, C$_{1-3}$ alkyl, C$_{1-3}$ haloalkyl, or C$_{3-6}$ cycloalkyl, or R$^{3a}$ and R$^{3b}$ taken together with the carbon atom to which they are attached, form a C$_{3-6}$ cycloalkyl;

A is:
(i) cyano;
(ii) a 5-membered heteroaryl containing 1 to 4 heteroatoms independently selected from N, O, and S, substituted with zero to 3 R$^{4a}$; or (iii)

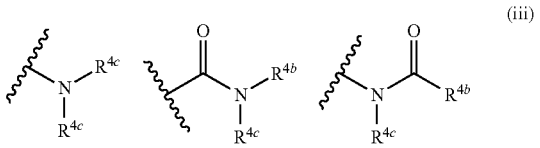

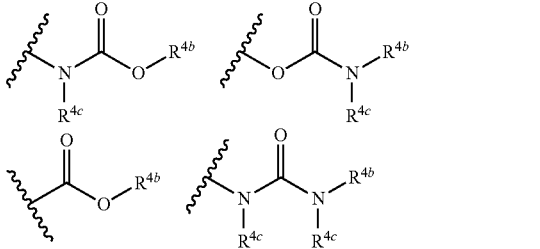

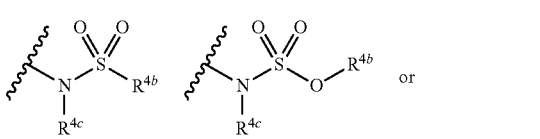

 or each R$^{4a}$ is independently halo, cyano, hydroxyl, —NH$_2$, C$_{1-6}$ alkyl, C$_{2-6}$ alkenyl, C$_{2-6}$ alkynyl, C$_{1-6}$ alkoxy, —(CH$_2$)$_{0-3}$NH(C$_{1-6}$ alkyl), —(CH$_2$)$_{0-2}$N(C$_{1-6}$ alkyl)$_2$, —(CH$_2$)$_{0-3}$(C$_{3-6}$ cycloalkyl), or —(CH$_2$)$_{0-3}$(4- to 6-membered heterocyclyl), wherein each of said alkyl, alkoxy, alkenyl, and alkynyl is substituted with zero to 6 R$^{4d}$ and each of said cycloalkyl and heterocyclyl is substituted with zero to 3 R$^{4e}$;

R$^{4b}$ is C$_{1-6}$ alkyl, —(CH$_2$)$_{0-3}$(C$_{3-6}$ cycloalkyl), or —(CH$_2$)$_{0-3}$(4- to 6-membered heterocyclyl), wherein each of said alkyl is substituted with zero to 6 R$^{4d}$ and each of said cycloalkyl and heterocyclyl is substituted with zero to 3 R$^{4e}$;

each R$^{4c}$ is independently hydrogen, C$_{1-6}$ alkyl, C$_{3-6}$ cycloalkyl, —S(O)$_2$(C$_{1-3}$ alkyl), 4- to 6-membered heterocyclyl, phenyl, or 5- to 6-membered heteroaryl;

each R$^{4d}$ is independently halo, hydroxyl, —NR$^x$R$^x$, oxo, cyano, C$_{1-3}$ alkoxy, or C$_{1-3}$ haloalkoxy;

each R$^{4e}$ is independently halo, oxo, cyano, hydroxyl, —NH$_2$, C$_{1-6}$ alkyl, C$_{1-6}$ alkoxy, —NH(C$_{1-6}$ alkyl), or —N(C$_{1-6}$ alkyl)$_2$, wherein each of said alkyl and alkoxy is substituted with zero to 6 R$^{4d}$;

each of R$^{5a}$, R$^{5b}$, R$^{5c}$, and R$^{5d}$ is independently hydrogen, halo, hydroxy, cyano, C$_{1-6}$ alkyl substituted with zero to 6 R$^{5e}$, C$_{1-6}$ alkoxy substituted with zero to 6 R$^{5e}$, —C(O)OR$^x$, —C(O)NR$^w$R$^w$, —S(O)$_2$R$^y$, —S(O)$_2$NR$^z$R$^z$, or phenyl substituted with zero to 3 R$^{5f}$;

each of R$^{5f}$ is independently halo, hydroxyl, —NR$^x$R$^x$, oxo, cyano, C$_{1-3}$ alkoxy, or C$_{1-3}$ haloalkoxy;

each R$^{5f}$ is independently halo, oxo, cyano, hydroxyl, —NH$_2$, C$_{1-6}$ alkyl, C$_{1-6}$ alkoxy, —NH(C$_{1-6}$ alkyl), or —N(C$_{1-6}$ alkyl)$_2$, wherein each of said alkyl and alkoxy is substituted with zero to 6 R$^{5e}$;

each R$^w$ is independently hydrogen, C$_{1-6}$ alkyl, or C$_{3-6}$ cycloalkyl; or alternatively, two R$^w$, taken together with the nitrogen atom to which they are attached, form a 4- to 7-membered ring moiety containing zero to 2 additional heteroatoms independently selected from N, O, and S;

each R$^x$ is independently hydrogen, C$_{1-6}$ alkyl, or C$_{3-6}$ cycloalkyl;

R$^y$ is C$_{1-6}$ alkyl or C$_{3-6}$ cycloalkyl; and each R$^z$ is independently hydrogen, C$_{1-6}$ alkyl, or C$_{3-6}$ cycloalkyl; or alternatively, two R$^z$, taken together with the nitrogen atom to which they are attached, form a 4- to 7-membered ring moiety containing zero to 2 additional heteroatoms independently selected from N, O, and S.

One embodiment provides a compound of Formula (I) or a stereoisomer, a tautomer, or a salt or solvate thereof, wherein X$^1$ is CR$^{5a}$; X$^2$ is CR$^{5b}$; X$^3$ is CR$^{5c}$; X$^4$ is CR$^{5d}$. Compounds of this embodiment have the structure:

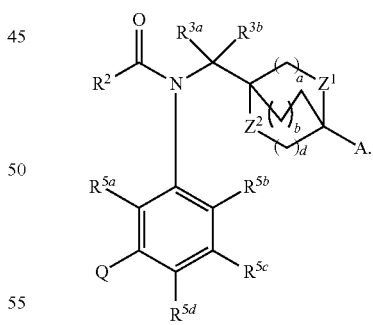

Included in this embodiment are compounds in which one of R$^{5a}$, R$^{5b}$, R$^{5c}$, and R$^{5d}$ is F, Cl, cyano, or —OCH$_3$; and three of R$^{5a}$, R$^{5b}$, R$^{5c}$, and R$^{5d}$ are hydrogen.

One embodiment provides a compound of Formula (I) or a stereoisomer, a tautomer, or a pharmaceutically acceptable salt or solvate thereof, wherein: X$^1$ is N; X$^2$ is CR$^{5b}$; X$^3$ is CR$^{5c}$; and X$^4$ is CR$^{5d}$. Compounds of this embodiment have the structure:

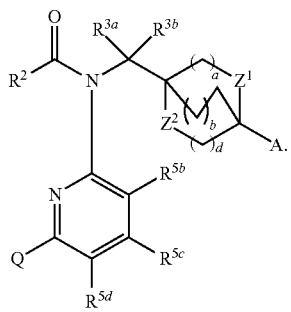

One embodiment provides a compound of Formula (I) or a stereoisomer, a tautomer, or a pharmaceutically acceptable salt or solvate thereof, wherein: $X^1$ is $CR^{5a}$; $X^2$ is N; $X^3$ is $CR^{5c}$; and $X^4$ is $CR^{5d}$. Compounds of this embodiment have the structure:

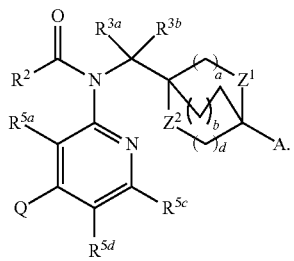

One embodiment provides a compound of Formula (I) or a stereoisomer, a tautomer, or a pharmaceutically acceptable salt or solvate thereof, wherein: $X^1$ is $CR^{5a}$; $X^2$ is $CR^{5b}$; $X^3$ is N; and $X^4$ is $CR^{5d}$. Compounds of this embodiment have the structure:

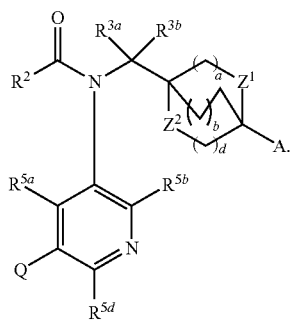

One embodiment provides a compound of Formula (I) or a stereoisomer, a tautomer, or a pharmaceutically acceptable salt or solvate thereof, wherein: $X^1$ is $CR^{5a}$; $X^2$ is $CR^{5b}$; $X^3$ is $CR^{5c}$; and $X^4$ is N. Compounds of this embodiment have the structure:

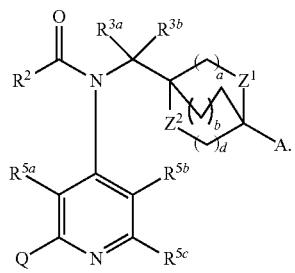

One embodiment provides a compound of Formula (I) or a stereoisomer, a tautomer, or a pharmaceutically acceptable salt or solvate thereof, wherein: $X^1$ is $CR^{5a}$; $X^2$ is $CR^{5b}$; $X^3$ is $CR^{5c}$; $X^4$ is $CR^{5d}$; and $Z^1$ and $Z^2$ are each $CH_2$. Compounds of this embodiment have the structure:

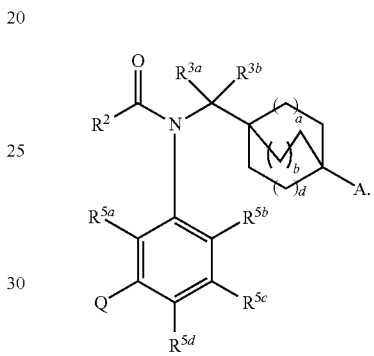

One embodiment provides a compound of Formula (I) or a stereoisomer, a tautomer, or a pharmaceutically acceptable salt or solvate thereof, wherein: $X^1$ is $CR^{5a}$; $X^2$ is $CR^{5b}$; $X^3$ is $CR^{5c}$; $X^4$ is $CR^{5d}$; $Z^1$ and $Z^2$ are each $CH_2$; and a, b, and d are each 1. Compounds of this embodiment have the structure:

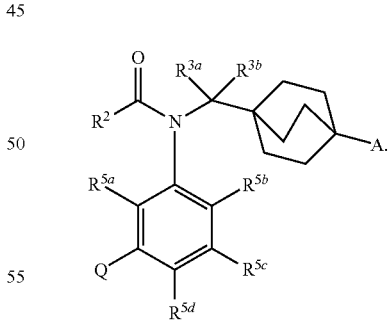

One embodiment provides a compound of Formula (I) or a stereoisomer, a tautomer, or a pharmaceutically acceptable salt or solvate thereof, wherein: a is 1; b is 1; and d is 1. Compounds of this embodiment have the structure:

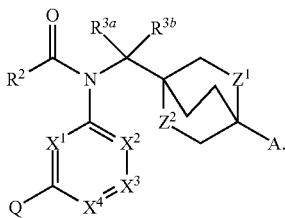

Included in this embodiment are compounds in which $X^1$ is $CR^{5a}$ or N; $X^2$ is $CR^{5b}$ or N; $X^3$ is $CR^{5c}$, or N; and $X^4$ is $CR^{5d}$ or N; provided that zero or 1 of $X^1$, $X^2$, $X^3$, and $X^4$ is N. Also included in this embodiment are compounds in which $X^1$ is $CR^{5a}$; $X^2$ is $CR^{5b}$; $X^3$ is $CR^{5e}$; and $X^4$ is $CR^{5d}$. Additionally, included in this embodiment are compounds in which $R^{5a}$, $R^{5b}$, $R^{5c}$, and $R^{5d}$ are selected from hydrogen and F, provided that zero or 1 of $R^{5a}$, $R^{5b}$, $R_{5c}$ and $R^{5d}$ is F.

One embodiment provides a compound of Formula (I) or a stereoisomer, a tautomer, or a pharmaceutically acceptable salt or solvate thereof, wherein: a is 1; b is 1; d is 1; $Z^1$ is $CH_2$; and $Z^2$ is $CH_2$. Compounds of this embodiment have the structure:

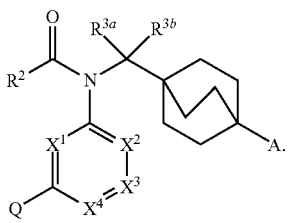

Included in this embodiment are compounds in which $X^1$ is $CR^{5a}$ or N; $X^2$ is $CR^{5b}$ or N; $X^3$ is $CR^{5c}$ or N; and $X^4$ is $CR^{5d}$ or N; provided that zero or 1 of $X^1$, $X^2$, $X^3$, and $X^4$ is N. Also included in this embodiment are compounds in which $R^{5a}$, $R^{5b}$, $R^{5c}$, and $R^{5d}$ are selected from hydrogen and F, provided that zero or 1 of $R^{5a}$, $R^{5b}$, $R^{5c}$, and $R^{5d}$ is F.

One embodiment provides a compound of Formula (I) or a stereoisomer, a tautomer, or a pharmaceutically acceptable salt or solvate thereof, wherein: a is 1; b is 1; d is 1; $Z^1$ is $CH_2$; and $Z^2$ is O. Compounds of this embodiment have the structure:

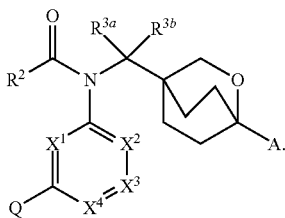

Included in this embodiment are compounds in which $X^1$ is $CR^{5a}$ or N; $X^2$ is $CR^{5b}$ or N; $X^3$ is $CR^{5c}$, or N; and $X^4$ is $CR^{5d}$ or N; provided that zero or 1 of $X^1$, $X^2$, $X^3$, and $X^4$ is N. Also included in this embodiment are compounds in which $X^1$ is $CR^{5a}$; $X^2$ is $CR^{5b}$; $X^3$ is $CR^{5e}$; and $X^4$ is $CR^{5d}$. Additionally, included in this embodiment are compounds in which $R^{5a}$, $R^{5b}$, $R^{5c}$, and $R^{5d}$ are selected from hydrogen and F, provided that zero or 1 of $R^{5a}$, $R^{5b}$, $R^{5c}$ and $R^{5d}$ is F.

One embodiment provides a compound of Formula (I) or a stereoisomer, a tautomer, or a pharmaceutically acceptable salt or solvate thereof, wherein: a is 1; b is 1; d is 1; $Z^1$ is O; and $Z^2$ is $CH_2$. Compounds of this embodiment have the structure:

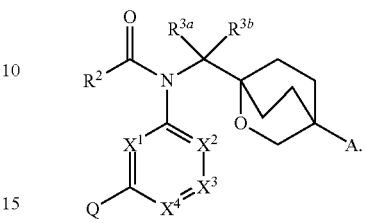

Included in this embodiment are compounds in which $X^1$ is $CR^{5a}$ or N; $X^2$ is $CR^{5b}$ or N; $X^3$ is $CR^{5c}$ or N; and $X^4$ is $CR^{5d}$ or N; provided that zero or 1 of $X^1$, $X^2$, $X^3$, and $X^4$ is N. Also included in this embodiment are compounds in which $X^1$ is $CR^{5a}$; $X^2$ is $CR^{5b}$; $X^3$ is $CR^{5e}$; and $X^4$ is $CR^{5d}$. Additionally, included in this embodiment are compounds in which $R^{5a}$, $R^{5b}$, $R^{5c}$, and $R^{5d}$ are selected from hydrogen and F, provided that zero or 1 of $R^{5a}$, $R^{5b}$, $R^{5c}$ and $R^{5d}$ is F.

One embodiment provides a compound of Formula (I) or a stereoisomer, a tautomer, or a pharmaceutically acceptable salt or solvate thereof, wherein Q is a cyclic group selected from 3- to 8-membered carbocyclyl, phenyl, 4- to 10-membered heterocyclyl, and 5- to 10-membered heteroaryl, wherein said cyclic group is substituted with zero to 3 $R^1$;

One embodiment provides a compound of Formula (I) or a stereoisomer, a tautomer, or a pharmaceutically acceptable salt or solvate thereof, Q is a 3- to 8-membered carbocyclyl substituted with zero to 4 $R^1$. Included in this embodiment are compounds in which Q is $C_{3-6}$ cycloalkyl substituted with zero to 4 $R^1$.

One embodiment provides a compound of Formula (I) or a stereoisomer, a tautomer, or a pharmaceutically acceptable salt or solvate thereof, wherein Q is a 6- to 10-membered aryl substituted with zero to 4 $R^1$. Included in this embodiment are compounds in which Q is phenyl or naphthalenyl, each substituted with zero to 4 $R^1$. Also included in this embodiment are compounds in which Q is phenyl substituted with zero to 3 $R^1$.

One embodiment provides a compound of Formula (I) or a stereoisomer, a tautomer, or a pharmaceutically acceptable salt or solvate thereof, wherein Q is a 4- to 10-membered heterocyclyl substituted with zero to 4 $R^1$. Included in this embodiment are compounds in which Q is a 4- to 6-membered heterocyclyl substituted with zero to 4 $R^1$. Also included in this embodiment are compounds in which Q is azetidinyl, pyrrolidinyl, piperazinyl, piperidinyl, or morpholinyl.

One embodiment provides a compound of Formula (I) or a stereoisomer, a tautomer, or a pharmaceutically acceptable salt or solvate thereof, wherein Q is a 5- to 10-membered heteroaryl substituted with zero to 4 $R^1$. Included in this embodiment are compounds in which Q is a 5- to 6-membered heteroaryl substituted with zero to 4 $R^1$. Also included in this embodiment are compounds in which Q is pyrazolyl, imidazolyl, isoxazolyl, oxazolyl, oxadiazolyl, thiazolyl, triazolyl, pyridinyl, pyrimidinyl, pyrazinyl, pyridazinyl, indolyl, indazolyl, indolinyl, quinolinyl, isoquinolinyl, [1,2,4]triazolo[1,5-a]pyridinyl, [1,2,4]triazolo[4,3-a]pyridinyl, 1H-pyrazolo[3,4-b]pyridinyl, 2,3-dihydrobenzo[d]oxazolyl, 7,8-dihydro-5H-pyrano[4,3-b]pyridinyl, benzo[d][1,3]dioxolyl, benzo[d]oxazolyl, benzo[d]thiazolyl, imidazo[1,2-a]pyridinyl, imidazo[1,2-b]pyridazinyl, pyrrolo[2,1-f][1,2,4]triazinyl, thiazolo[4,5-b]pyridinyl, thiazolo[5,4-b]pyridinyl, or thieno[3,2-b]pyridinyl. Additionally, included in this embodiment are compounds in which Q is imidazolyl, isoxazolyl, oxazolyl, oxadiazolyl, pyrazolyl, thiazolyl, pyridinyl, pyridazinyl, pyrimidinyl, benzo[d]oxazolyl, benzo[d]thiazolyl, or pyrazolo[1,5-a]pyrimidinyl, each substituted with zero to 2 $R^1$.

One embodiment provides a compound of Formula (I) or a stereoisomer, a tautomer, or a pharmaceutically acceptable salt or solvate thereof, wherein each $R^1$ is independently each $R^1$ is independently F, Cl, Br, cyano, hydroxyl, oxo, —$NR^xR^x$, $C_{1-5}$ alkyl, $C_{1-4}$ alkoxy, —$NR^x(C_{1-4}$ alkyl), —$NR^xC(O)R^y$, —$C(O)(C_{1-4}$ alkyl), —$C(O)OR^x$, —$C(O)NR^wR^w$, —$S(O)_2(C_{1-4}$ alkyl), —$S(O)_2(C_{3-6}$ cycloalkyl), —$NR^xS(O)_2(C_{1-4}$ alkyl), —$NR^xS(O)_2(C_{3-6}$ cycloalkyl), —$S(O)_2NR^zR^z$, —$P(O)R^yR^y$, —$(CH_2)_{0-3}(C_{3-6}$ carbocyclyl), —$O(C_{3-6}$ cycloalkyl), —$O$(4- to 6-membered heterocyclyl), —$(CH_2)_{0-3}$(4- to 6-membered heterocyclyl), or —$(CH_2)_{0-3}$(5- or 6-membered heteroaryl), wherein each of said alkyl and alkoxy is substituted with zero to 4 $R^{1a}$ and each of said cycloalkyl, heterocyclyl, and heteroaryl is substituted with zero to 3 $R^{1b}$. Included in this embodiment are compounds in which each $R^{1a}$ is independently F, Cl, hydroxyl, —$NR^wR^w$, oxo, cyano, $C_{1-3}$ alkoxy, $C_{1-3}$ haloalkoxy, or —$C(O)OH$; and each $R^{1b}$ is independently F, Cl, cyano, hydroxyl, oxo, —$NH_2$, $C_{1-4}$ alkyl, $C_{1-4}$ alkoxy, —$NH(C_{1-4}$ alkyl), —$N(C_{1-4}$ alkyl)$_2$, or —$NR^xC(O)(C_1$-6 alkyl), wherein each of said alkyl and alkoxy is substituted with zero to 6 Ria Additionally, included in this embodiment are compounds in which each $R^1$ is independently F, Cl, oxo, —$CH_3$, —$CH_2CH_3$, —$CH_2CH_2CH_3$, —$CHF_2$, —$C(CH_3)_2OH$, —$CH_2OCH_3$, —$OCH_3$, —$OCH_2CH_3$, —$OCHF_2$, —$C(O)OCH_3$, —$C(O)OCH_2CH_3$, —$S(O)_2CH_3$, —$P(O)(CH_3)_2$, cyclopropyl, —$CH_2$ (cyclopropyl), —$O$(cyclopropyl), or tetrahydropyranyl.

One embodiment provides a compound of Formula (I) or a stereoisomer, a tautomer, or a pharmaceutically acceptable salt or solvate thereof, wherein $R^2$ is $C_{6-8}$ carbocyclyl substituted with zero to 3 $R^{2b}$. Included in this embodiment are compounds in which $R^2$ is $C_{6-8}$ cycloalkyl and bicyclo[2.2.2]octanyl, each substituted with zero to 3 $R^{2b}$. Also included in this embodiment are compounds in which $R^2$ is cyclohexyl substituted with zero to 3 $R^{3b}$, wherein each $R^{3b}$ is independently F, Cl, hydroxyl, oxo, —$CH_3$, —$CF_3$, —$CH_2OH$, —$OCH_3$, —$OCHF_2$, —$C(O)OC(CH_3)_3$, or piperidinyl.

One embodiment provides a compound of Formula (I) or a stereoisomer, a tautomer, or a pharmaceutically acceptable salt or solvate thereof, wherein $R^2$ is phenyl substituted with zero to 3 $R^{2b}$. Included in this embodiment are compounds in which each $R^{2b}$ is independently F, Cl, hydroxyl, oxo, —$CH_3$, —$CF_3$, —$CH_2OH$, —$OCH_3$, —$OCHF_2$, —$C(O)OC(CH_3)_3$, or piperidinyl.

One embodiment provides a compound of Formula (I) or a stereoisomer, a tautomer, or a pharmaceutically acceptable salt or solvate thereof, wherein $R^2$ is a 6- to 7-membered heterocyclyl substituted with zero to 3 $R^{2b}$. Included in this embodiment are compounds in which $R^2$ is a 6-membered heterocyclyl substituted with zero to 3 $R^{2b}$. Also included in this embodiment are compounds in which $R^2$ is morpholinyl, piperazinyl, piperidinyl, tetrahydropyranyl, or tetrahydrothiopyranyl, each substituted with zero to 3 $R^{2b}$. Additionally, included in this embodiment are compounds in which each $R^{2b}$ is independently F, Cl, hydroxyl, oxo, —$CH_3$, —$CF_3$, —$CH_2OH$, —$OCH_3$, —$OCHF_2$, —$C(O)OC(CH_3)_3$, or piperidinyl.

One embodiment provides a compound of Formula (I) or a stereoisomer, a tautomer, or a pharmaceutically acceptable salt or solvate thereof, wherein $R^2$ is a 6-membered heteroaryl substituted with zero to 3 $R^{2b}$.

One embodiment provides a compound of Formula (I) or a stereoisomer, a tautomer, or a pharmaceutically acceptable salt or solvate thereof, wherein $R^{3a}$ and $R^{3b}$ are independently hydrogen, $C_{1-3}$ alkyl, $C_{1-3}$ fluoroalkyl, or $C_{3-6}$ cycloalkyl, or $R^{3a}$ and $R^{3b}$, taken together with the carbon atom to which they are attached, form a $C_{3-6}$ cycloalkyl. Included in this embodiment are compounds in which $R^{3a}$ and $R^{3b}$ are independently hydrogen, $C_{1-2}$ alkyl, $C_{1-2}$ fluoroalkyl, or $C_{3-6}$ cycloalkyl. Also included in this embodiment are compounds in which $R^{3a}$ and $R^{3b}$ are independently hydrogen, —$CH_3$, or —$CF_3$. Additionally, included in this embodiment are compounds in which one of $R^{3a}$ and $R^{3b}$ is hydrogen and the other of $R^{3a}$ and $R^{3b}$ is hydrogen or —$CH_3$.

One embodiment provides a compound of Formula (I) or a stereoisomer, a tautomer, or a pharmaceutically acceptable salt or solvate thereof, wherein A is cyano.

One embodiment provides a compound of Formula (I) or a stereoisomer, a tautomer, or a pharmaceutically acceptable salt or solvate thereof, wherein A is:

(i) a 5-membered heteroaryl containing 1 to 4 heteroatoms independently selected from N, O, and S, substituted with zero to 3 $R^{4a}$; or

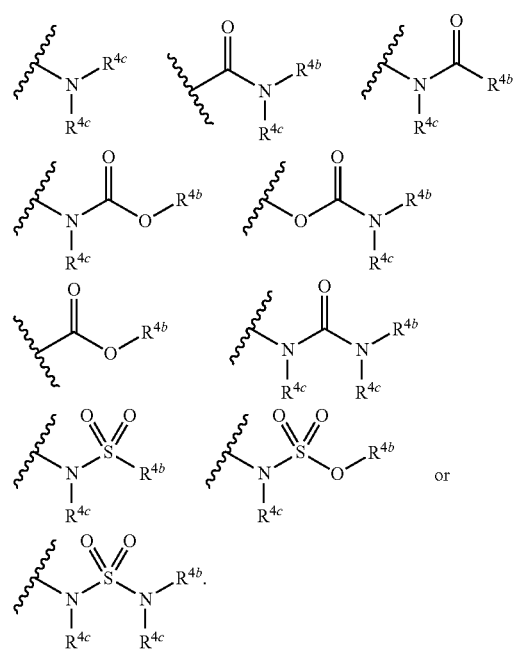

(ii)

Included in this embodiment are compounds in which A is:

(i) a 5-membered heteroaryl containing 1 to 4 heteroatoms independently selected from N, O, and S, substituted with zero to 3 $R^{4a}$; or

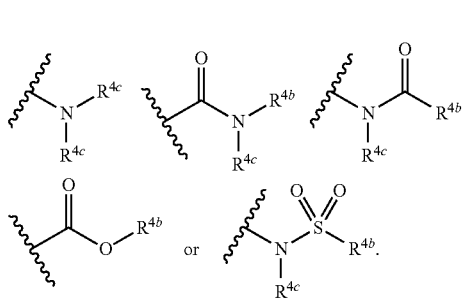

(ii)

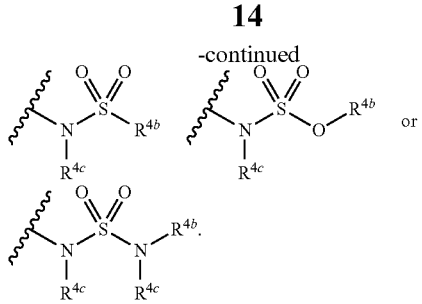

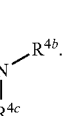 or

One embodiment provides a compound of Formula (I) or a stereoisomer, a tautomer, or a pharmaceutically acceptable salt or solvate thereof, wherein A is a 5-membered heteroaryl containing 1 to 4 heteroatoms independently selected from N, O, and S, substituted with zero to 3 $R^{4a}$. Included in this embodiment are compounds in which A is pyrazolyl, oxazolyl, thiazolyl, oxadiazolyl, thiadiazolyl, or tetrazolyl, each substituted with zero to 2 $R^{4a}$. Also included in this embodiment are compounds in which each $R^{4a}$ is independently —$CH_3$, —$C(CH_3)_3$, —$CF_3$, —$CF_2CH_3$, —$C(CH_3)_2F$, —$CH_2$(cyclopropyl), cyclopropyl, trifluoromethylcyclobutyl, trifluoromethyl-hydroxycyclobutyl, or tetrahydropyranyl.

One embodiment provides a compound of Formula (I) or a stereoisomer, a tautomer, or a pharmaceutically acceptable salt or solvate thereof, wherein A is a 5-membered heteroaryl containing 1 to 4 heteroatoms independently selected from N, O, and S, substituted with zero to 3 $R^{4a}$; each $R^{4a}$ is independently F, Cl, cyano, hydroxyl, —$NH_2$, $C_{1-4}$ alkyl, $C_{1-4}$ alkoxy, —$(CH_2)_{0-3}NH(C_{1-6}$ alkyl), —$(CH_2)_{0-3}N(C_{1-6}$ alkyl)$_2$, —$(CH_2)_{0-3}(C_{3-6}$ cycloalkyl), or —$(CH_2)_{0-3}$(4- to 6-membered heterocyclyl), wherein each of said alkyl and alkoxy is substituted with zero to 4 $R^{4d}$ and each of said cycloalkyl and heterocyclyl is substituted with zero to 3 $R^{4e}$; each $R^{4d}$ is independently F, Cl, hydroxyl, —$NR^xR^x$, oxo, cyano, $C_{1-3}$ alkoxy, or $C_{1-3}$ fluoroalkoxy; and each $R^{4e}$ is independently F, Cl, oxo, cyano, hydroxyl, —$NH_2$, $C_{1-4}$ alkyl, $C_{1-4}$ alkoxy, or —$NH(C_{1-6}$ alkyl), or —$N(C_{1-6}$ alkyl)$_2$, wherein each of said alkyl and alkoxy is substituted with zero to 4 $R^{4d}$. Included in this embodiment are compounds in which each $R^{4a}$ is independently $C_{1-4}$ alkyl, $C_{1-3}$ fluoroalkyl, —$CH_2(C_{3-6}$ cycloalkyl), cyclopropyl, trifluoromethylcyclobutyl, trifluoromethyl-hydroxycyclobutyl, or tetrahydropyranyl.

One embodiment provides a compound of Formula (I) or a stereoisomer, a tautomer, or a pharmaceutically acceptable salt or solvate thereof, wherein A is:

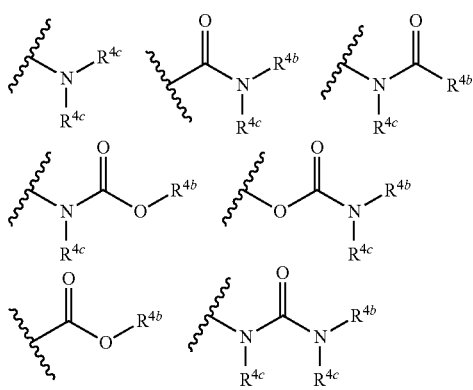

Included in this embodiment are compounds in which A is:

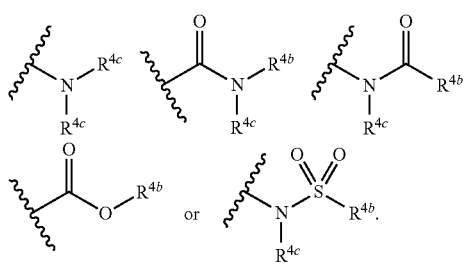

Also included in this embodiment are compounds in which $R^{4b}$ is $C_{1-4}$ alkyl, —$(CH_2)_{0-3}(C_{3-6}$ cycloalkyl), or —$(CH_2)_{0-3}$(4- to 6-membered heterocyclyl), wherein each of said alkyl is substituted with zero to 4 $R^{4d}$ and each of said cycloalkyl and heterocyclyl is substituted with zero to 3 $R^{4}$; and each $R^{4c}$ is independently hydrogen, $C_{1-3}$ alkyl, or $C_{3-6}$ cycloalkyl. Additionally included in this embodiment are compounds in which A is —C(O)NH(cyclopropyl).

One embodiment provides a compound of Formula (I) or a stereoisomer, a tautomer, or a pharmaceutically acceptable salt or solvate thereof, wherein each $R^w$ is independently hydrogen, $C_{1-4}$ alkyl, or $C_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S.

One embodiment provides a compound of Formula (I) or a stereoisomer, a tautomer, or a pharmaceutically acceptable salt or solvate thereof, wherein each $R^w$ is independently hydrogen, $C_{1-6}$ alkyl, or $C_{3-6}$ cycloalkyl. Included in this embodiment are compounds in which each $R^w$ is independently hydrogen, $C_{1-4}$ alkyl, or $C_{3-6}$ cycloalkyl. Also included in this embodiment are compounds in which each $R^w$ is independently hydrogen or $C_{1-3}$ alkyl.

One embodiment provides a compound of Formula (I) or a stereoisomer, a tautomer, or a pharmaceutically acceptable salt or solvate thereof, wherein each $R^x$ is independently hydrogen, $C_{1-4}$ alkyl, or $C_{3-6}$ cycloalkyl. Included in this embodiment are compounds in which each $R^x$ is independently hydrogen or $C_{1-4}$ alkyl.

One embodiment provides a compound of Formula (I) or a stereoisomer, a tautomer, or a pharmaceutically acceptable salt or solvate thereof, wherein each $R^y$ is independently $C_{1-4}$ alkyl or $C_{3-6}$ cycloalkyl. Included in this embodiment are compounds in which each $R^y$ is independently $C_{1-4}$ alkyl.

One embodiment provides a compound of Formula (I) or a stereoisomer, a tautomer, or a pharmaceutically acceptable salt or solvate thereof, wherein each $R^z$ is independently hydrogen, $C_{1-4}$ alkyl, or $C_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S.

One embodiment provides a compound of Formula (I) or a stereoisomer, a tautomer, or a pharmaceutically acceptable salt or solvate thereof, wherein each $R^z$ is independently hydrogen, $C_{1-6}$ alkyl, or $C_{3-6}$ cycloalkyl. Included in this embodiment are compounds in which each $R^w$ is independently hydrogen, $C_{1-4}$ alkyl, or $C_{3-6}$ cycloalkyl. Also included in this embodiment are compounds in which each $R^z$ is independently hydrogen or $C_{1-3}$ alkyl.

One embodiment provides a compound of Formula (I) or a stereoisomer, a tautomer, or a pharmaceutically acceptable salt or solvate thereof, wherein:
Q is a cyclic group selected from 3- to 8-membered carbocyclyl, phenyl, 4- to 10-membered heterocyclyl, and 5- to 10-membered heteroaryl, wherein said cyclic group is substituted with zero to 3 $R^1$;
each $R^1$ is independently F, Cl, Br, cyano, hydroxyl, oxo, —$NR^xR^x$, $C_{1-5}$ alkyl, $C_{1-4}$ alkoxy, —$NR^x(C_{1-4}$ alkyl), —$NR^xC(O)R^y$, —$C(O)(C_{1-4}$ alkyl), —$C(O)OR^x$, —$C(O)NR^wR^w$, —$S(O)_2(C_{1-4}$ alkyl), —$S(O)_2(C_{3-6}$ cycloalkyl), —$NR^xS(O)_2(C_{1-4}$ alkyl), —$NR^xS(O)_2(C_{3-6}$ cycloalkyl), —$S(O)_2NR^zR^z$, —$P(O)R^yR^y$, —$(CH_2)_{0-3}(C_{3-6}$ carbocyclyl), —$O(C_{3-6}$ cycloalkyl), —$O(4$- to 6-membered heterocyclyl), —$(CH_2)_{0-3}(4$- to 6-membered heterocyclyl), or —$(CH_2)_{0-3}(5$- or 6-membered heteroaryl), wherein each of said alkyl and alkoxy is substituted with zero to 4 $R^{1a}$ and each of said cycloalkyl, heterocyclyl, and heteroaryl is substituted with zero to 3 $R^{1b}$;
each $R^{1a}$ is independently F, Cl, hydroxyl, —$NR^wR^w$, oxo, cyano, $C_{1-3}$ alkoxy, $C_{1-3}$ haloalkoxy, or —$C(O)OH$;
each $R^{1b}$ is independently F, Cl, cyano, hydroxyl, oxo, —$NH_2$, $C_{1-4}$ alkyl, $C_{1-4}$ alkoxy, —$NH(C_{1-4}$ alkyl), —$N(C_{1-4}$ alkyl)$_2$, or —$NR^xC(O)(C_{1-6}$ alkyl), wherein each of said alkyl and alkoxy is substituted with zero to 6 $R^{1a}$;
$R^2$ is cyclohexyl, phenyl, or 6-membered heterocyclyl, wherein each of said cyclohexyl, phenyl, and heterocyclyl is substituted with zero to 3 $R^{2b}$;
each $R^{2a}$ is independently F, Cl, cyano, hydroxyl, oxo, $C_{1-3}$ haloalkyl, $C_{1-3}$ alkoxy, $C_{1-3}$ haloalkoxy, —$NR^xR^x$, —$C(O)(C_{1-4}$ alkyl), —$C(O)(C_{3-6}$ cycloalkyl), —$NR^xC(O)R^y$, —$C(O)(C_{1-4}$ alkyl), —$C(O)OR^x$, —$C(O)NR^wR^w$, —$S(O)_2R^y$, —$S(O)_2(C_{1-3}$ fluoroalkyl), —$NR^xS(O)_2(C_{1-3}$ alkyl), —$NR^xS(O)_2(C_{3-6}$ cycloalkyl), —$S(O)_2NR^zR^z$, or —$P(O)R^yR^y$;
each $R^{2b}$ is independently F, Cl, cyano, hydroxyl, oxo, $C_{1-4}$ alkyl, $C_{1-4}$ alkoxy, —$NR^xR^x$, —$NR^xC(O)O(C_{1-3}$ alkyl), —$C(O)(C_{1-4}$ alkyl), —$C(O)O(C_{1-4}$ alkyl), or —$S(O)_2(C_{1-3}$ alkyl), wherein each of said alkyl and alkoxy is substituted with zero to 6 $R^{2a}$.
A is:
  (i) cyano;
  (ii) a 5-membered heteroaryl containing 1 to 4 heteroatoms independently selected from N, O, and S, substituted with zero to 3 $R^{4a}$; or

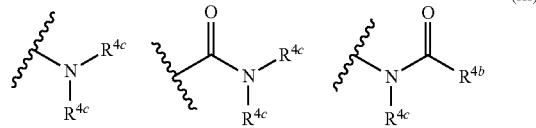

(iii)

-continued

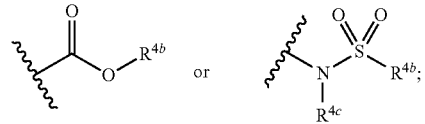

each $R^{4a}$ is independently F, Cl, cyano, hydroxyl, —$NH_2$, $C_{1-4}$ alkyl, $C_{1-4}$ alkoxy, —$(CH_2)_{0-3}NH(C_{1-6}$ alkyl), —$(CH_2)_{0-3}N(C_{1-6}$ alkyl)$_2$, —$(CH_2)_{0-3}(C_{3-6}$ cycloalkyl), or —$(CH_2)_{0-3}(4$- to 6-membered heterocyclyl), wherein each of said alkyl and alkoxy is substituted with zero to 4 $R^{4d}$ and each of said cycloalkyl and heterocyclyl is substituted with zero to 3 $R^{4e}$;
$R^{4b}$ is $C_{1-4}$ alkyl, —$(CH_2)_{0-3}(C_{3-6}$ cycloalkyl), or —$(CH_2)_{0-3}(4$- to 6-membered heterocyclyl), wherein each of said alkyl is substituted with zero to 4 $R^{4d}$ and each of said cycloalkyl and heterocyclyl is substituted with zero to 3 $R^{4e}$;
each $R^{4c}$ is independently hydrogen, $C_{1-3}$ alkyl, or $C_{3-6}$ cycloalkyl;
each $R^{4d}$ is independently F, Cl, hydroxyl, —$NR^xR^x$, oxo, cyano, $C_{1-3}$ alkoxy, or $C_{1-3}$ fluoroalkoxy;
each $R^{4e}$ is independently F, Cl, oxo, cyano, hydroxyl, —$NH_2$, $C_{1-4}$ alkyl, $C_{1-4}$ alkoxy, or —$NH(C_{1-6}$ alkyl), or —$N(C_{1-6}$ alkyl)$_2$, wherein each of said alkyl and alkoxy is substituted with zero to 4 $R^{4d}$;
each of $R^{5a}$, $R^{5b}$, $R^{5c}$, and $R^{5d}$ is independently hydrogen, F, Cl, hydroxy, cyano, $C_{1-3}$ alkyl substituted with zero to 4 $R^{5e}$, $C_{1-3}$ alkoxy substituted with zero to 4 $R^{5e}$, —$C(O)OR^x$, —$C(O)NR^wR^w$, —$S(O)_2R^y$, —$S(O)_2NR^zR^z$, or phenyl substituted with zero to 3 $R^{5f}$;
each $R^w$ is independently hydrogen, $C_{1-4}$ alkyl, or $C_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S;
each $R^x$ is independently H, $C_{1-4}$ alkyl, or $C_{3-6}$ cycloalkyl;
$R^y$ is $C_{1-4}$ alkyl or $C_{3-6}$ cycloalkyl; and
each $R^z$ is independently hydrogen, $C_{1-4}$ alkyl, or $C_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S.

One embodiment provides a compound of Formula (I) or a stereoisomer, a tautomer, or a pharmaceutically acceptable salt or solvate thereof, wherein: $X^1$ is CH; $X^2$ is CH; $X^3$ is $CR^{5c}$; $X^4$ is $CR^{5d}$; a is zero or 1; b is zero or 1; d is zero or 1; $Z^1$ and $Z^2$ are each $CH_2$; Q is a cyclic group selected from cyclopropyl, imidazolyl, isoxazolyl, oxazolyl, oxadiazolyl, pyrazolyl, thiazolyl, phenyl, pyridinyl, pyridazinyl, pyrimidinyl, benzo[d]oxazolyl, benzo[d]thiazolyl, and pyrazolo[1,5-a]pyrimidinyl, wherein said cyclic group is substituted with zero to 2 $R^1$; each $R^1$ is independently F, Cl, oxo, —$CH_3$, —$CH_2CH_3$, —$CH_2CH_2CH_3$, —$CHF_2$, —$C(CH_3)_2OH$, —$CH_2OCH_3$, —$OCH_3$, —$OCH_2CH_3$, —$OCHF_2$, —$C(O)OCH_3$, —$C(O)OCH_2CH_3$, —$S(O)_2CH_3$, —$P(O)(CH_3)_2$, cyclopropyl, —$CH_2$(cyclopropyl), —$O$(cyclopropyl), or tetrahydropyranyl; $R^2$ is cyclohexyl, morpholinyl, phenyl, piperazinyl, piperidinyl, tetrahydropyranyl, or tetrahydrothiopyranyl, each substituted with zero to 3 $R^{2b}$; each $R^{2b}$ is independently F, Cl, hydroxyl, oxo, —$CH_3$, —$CF_3$, —$CH_2OH$, —$OCH_3$, —$OCHF_2$, —$C(O)OC$ (CH$_3$)$_3$, or piperidinyl; R$^{3a}$ is hydrogen or —CH$_3$; R$^{3b}$ is hydrogen; A is: (i) cyano; (ii) pyrazolyl, oxazolyl, thiazolyl, oxadiazolyl, thiadiazolyl, or tetrazolyl, each substituted with zero to 2 R$^{4a}$; or (iii) —C(O)NH(cyclopropyl); each R$^{4a}$ is independently —CH$_3$, —C(CH$_3$)$_3$, —CF$_3$, —CF$_2$CH$_3$, —C(CH$_3$)$_2$F, —CH$_2$(cyclopropyl), cyclopropyl, trifluoromethylcyclobutyl, trifluoromethyl-hydroxycyclobutyl, or tetrahydropyranyl; and one R$^{5c}$ and R$^{5d}$ is hydrogen or F, and the other of R$^{5c}$ and R$^{5d}$ is hydrogen.

One embodiment provides a compound of Formula (I) or a stereoisomer, a tautomer, or a pharmaceutically acceptable salt or solvate thereof, wherein: X$^1$ is CH; X$^2$ is CH; X$^3$ is CH; X$^4$ is CH or CF; Z$^1$ and Z$^2$ are each CH$_2$; a, b, and d are each zero; or a, b, and d are each 1; Q is a cyclic group selected from cyclopropyl, imidazolyl, isoxazolyl, oxazolyl, oxadiazolyl, pyrazolyl, thiazolyl, phenyl, pyridinyl, pyridazinyl, pyrimidinyl, benzo[d]oxazolyl, benzo[d]thiazolyl, and pyrazolo[1,5-a]pyrimidinyl, wherein said cyclic group is substituted with zero to 2 R$^1$; each R$^1$ is independently F, Cl, oxo, —CH$_3$, —CH$_2$CH$_3$, —CH$_2$CH$_2$CH$_3$, —CHF$_2$, —C(CH$_3$)$_2$OH, —CH$_2$OCH$_3$, —OCH$_3$, —OCH$_2$CH$_3$, —OCHF$_2$, —C(O)OCH$_3$, —C(O)OCH$_2$CH$_3$, —S(O)$_2$CH$_3$, —P(O)(CH$_3$)$_2$, cyclopropyl, —CH$_2$(cyclopropyl), —O(cyclopropyl), or tetrahydropyranyl; R$^2$ is cyclohexyl, morpholinyl, phenyl, piperazinyl, piperidinyl, tetrahydropyranyl, or tetrahydrothiopyranyl, each substituted with zero to 3 R$^{2b}$; each R$^{2b}$ is independently F, Cl, hydroxyl, oxo, —CH$_3$, —CF$_3$, —CH$_2$OH, —OCH$_3$, —OCHF$_2$, —C(O)OC(CH$_3$)$_3$, or piperidinyl; R$^{3a}$ is hydrogen or —CH$_3$; R$^{3b}$ is hydrogen; A is: (i) cyano; (ii) pyrazolyl, oxazolyl, thiazolyl, oxadiazolyl, thiadiazolyl, or tetrazolyl, each substituted with zero to 2 R$^{4a}$; or (iii) —C(O)NH(cyclopropyl); and each R$^{4a}$ is independently —CH$_3$, —C(CH$_3$)$_3$, —CF$_3$, —CF$_2$CH$_3$, —C(CH$_3$)$_2$F, —CH$_2$(cyclopropyl), cyclopropyl, trifluoromethylcyclobutyl, trifluoromethyl-hydroxycyclobutyl, or tetrahydropyranyl.

One embodiment provides a compound of Formula (I) or a stereoisomer, a tautomer, or a pharmaceutically acceptable salt or solvate thereof, wherein said compound is: N-((4-(3-methyl-1,2,4-oxadiazol-5-yl)bicyclo[2.2.2]octan-1-yl)methyl)-N-(3-(3-methyl-1,2,4-oxadiazol-5-yl)phenyl)cyclohexanecarboxamide (1); methyl 5-(3-(N-((4-(3-cyclopropyl-1,2,4-oxadiazol-5-yl)bicyclo[2.2.2]octan-1-yl)methyl) cyclohexanecarboxamido)phenyl)-1,2,4-oxadiazole-3-carboxylate (2); N-(4'-methoxy-[1,1'-biphenyl]-3-yl)-N-((4-(3-methyl-1,2,4-oxadiazol-5-yl)bicyclo[2.2.2]octan-1-yl)methyl)cyclohexane carboxamide (3); N-((4-(3-cyclopropyl-1,2,4-oxadiazol-5-yl) bicyclo[2.2.2]octan-1-yl)methyl)-N-(3-(3-ethyl-1,2,4-oxadiazol-5-yl)phenyl)cyclohexanecarboxamide (4); N-((4-(3-cyclopropyl-1,2,4-oxadiazol-5-yl) bicyclo[2.2.2]octan-1-yl)methyl)-N-(3-(3-ethyl-1,2,4-oxadiazol-5-yl)phenyl)-4,4-difluorocyclohexane-1-carboxamide (5); N-(3-(2-methoxyoxazol-5-yl)phenyl)-N-((4-(3-methyl-1,2,4-oxadiazol-5-yl)bicyclo[2.2.2]octan-1-yl)methyl) cyclohexanecarboxamide (6); N-((4-(3-cyclopropyl-1,2,4-oxadiazol-5-yl)bicyclo[2.2.2]octan-1-yl)methyl)-N-(3-(2-methoxyoxazol-5-yl)phenyl)cyclohexanecarboxamide (7); N-((4-(3-cyclopropyl-1,2,4-oxadiazol-5-yl)bicyclo[2.2.2]octan-1-yl)methyl)-N-(3-(2-ethoxyoxazol-5-yl)phenyl)cyclohexanecarboxamide (8); N-((4-(3-cyclopropyl-1,2,4-oxadiazol-5-yl) bicyclo[2.2.2]octan-1-yl)methyl)-N-(3-(2-ethoxyoxazol-5-yl)phenyl)-4,4-difluorocyclohexane-1-carboxamide (9); N-(3-(2-ethoxyoxazol-5-yl)phenyl)-N-((4-(3-methyl-1,2,4-oxadiazol-5-yl)bicyclo[2.2.2]octan-1-yl)methyl)cyclohexanecarboxamide (10); N-(3-(5-methoxyisoxazol-3-yl)phenyl)-N-((4-(3-methyl-1,2,4-oxadiazol-5-yl) bicyclo[2.2.2]octan-1-yl)methyl)cyclohexanecarboxamide (11); N-((4-(3-cyclopropyl-1,2,4-oxadiazol-5-yl)bicyclo[2.2.2]octan-1-yl)methyl)-N-(3-(5-methoxyisoxazol-3-yl)phenyl)cyclohexanecarboxamide (12); N-((4-(3-cyclopropyl-1,2,4-oxadiazol-5-yl) bicyclo[2.2.2]octan-1-yl)methyl)-N-(3-(3-cyclopropyl-1,2,4-oxadiazol-5-yl)phenyl)cyclohexanecarboxamide (13); N-((4-(3-cyclopropyl-1,2,4-oxadiazol-5-yl) bicyclo[2.2.2]octan-1-yl)methyl)-N-(3-(3-cyclopropyl-1,2,4-oxadiazol-5-yl)phenyl)-4,4-difluorocyclohexane-1-carboxamide (14); N-((4-(3-cyclopropyl-1,2,4-oxadiazol-5-yl) bicyclo[2.2.2]octan-1-yl)methyl)-N-(3-(3-cyclopropyl-1,2,4-oxadiazol-5-yl)phenyl) tetrahydro-2H-pyran-4-carboxamide (15); N-((4-(3-cyclopropyl-1,2,4-oxadiazol-5-yl) bicyclo[2.2.2]octan-1-yl)methyl)-N-(3-(3-cyclopropyl-1,2,4-oxadiazol-5-yl)phenyl) tetrahydro-2H-pyran-3-carboxamide, racemate (16); N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-1-methylpiperidine-4-carboxamide (17); N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl) tetrahydro-2H-thiopyran-4-carboxamide 1,1-dioxide (18); ethyl 2-(3-(N-((4-(3-methyl-1,2,4-oxadiazol-5-yl)bicyclo[2.2.2]octan-1-yl)methyl)cyclohexanecarboxamido)phenyl) oxazole-4-carboxylate (19); ethyl 2-(3-(N-((4-(3-cyclopropyl-1,2,4-oxadiazol-5-yl)bicyclo[2.2.2]octan-1-yl)methyl) cyclohexanecarboxamido)phenyl)oxazole-4-carboxylate (20); N-((4-(3-cyclopropyl-1,2,4-oxadiazol-5-yl)bicyclo [2.2.2]octan-1-yl)methyl)-N-(3-(4-(2-hydroxypropan-2-yl) oxazol-2-yl)phenyl)cyclohexanecarboxamide (21); N-((4-(3-cyclopropyl-1,2,4-oxadiazol-5-yl)bicyclo[2.2.2]octan-1-yl)methyl)-N-(3-(2-cyclopropyloxazol-5-yl)phenyl) cyclohexanecarboxamide (22); N-((4-(3-cyclopropyl-1,2,4-oxadiazol-5-yl)bicyclo[2.2.2]octan-1-yl)methyl)-N-(3-(2-cyclopropyloxazol-5-yl)phenyl)tetrahydro-2H-pyran-4-carboxamide (23); N-((4-(3-cyclopropyl-1,2,4-oxadiazol-5-yl)bicyclo[2.2.2]octan-1-yl)methyl)-N-(3-(2-cyclopropyloxazol-5-yl)phenyl)-1-methylpiperidine-4-carboxamide (24); N-((4-(3-cyclopropyl-1,2,4-oxadiazol-5-yl) bicyclo[2.2.2]octan-1-yl)methyl)-N-(3-(2-cyclopropyloxazol-5-yl)phenyl)tetrahydro-2H-pyran-3-carboxamide, racemate (25); N-((4-(3-cyclopropyl-1,2,4-oxadiazol-5-yl) bicyclo[2.2.2]octan-1-yl)methyl)-N-(3-(2-cyclopropyloxazol-5-yl)phenyl)-4,4-difluorocyclohexane-1-carboxamide (26); N-((4-(3-cyclopropyl-1,2,4-oxadiazol-5-yl) bicyclo[2.2.2]octan-1-yl)methyl)-N-(3-(5-ethoxyisoxazol-3-yl)phenyl)cyclohexanecarboxamide (27); N-((4-(3-cyclopropyl-1,2,4-oxadiazol-5-yl) bicyclo[2.2.2]octan-1-yl)methyl)-N-(3-(2-propyloxazol-5-yl)phenyl)cyclohexanecarboxamide (28); N-((4-(3-cyclopropyl-1,2,4-oxadiazol-5-yl) bicyclo[2.2.2]octan-1-yl)methyl)-N-(3-(2-propyloxazol-5-yl)phenyl)tetrahydro-2H-pyran-4-carboxamide (29); N-((4-(3-cyclopropyl-1,2,4-oxadiazol-5-yl)bicyclo[2.2.2]octan-1-yl)methyl)-N-(3-(2-propyloxazol-5-yl)phenyl)tetrahydro-2H-pyran-3-carboxamide, racemate (30); ethyl 4-(3-(N-((4-(3-cyclopropyl-1,2,4-oxadiazol-5-yl) bicyclo[2.2.2]octan-1-yl)methyl)cyclohexanecarboxamido) phenyl)thiazole-2-carboxylate (31); N-((4-(3-cyclopropyl-1,2,4-oxadiazol-5-yl)bicyclo[2.2.2]octan-1-yl)methyl)-N-(3-(2-(2-hydroxypropan-2-yl)thiazol-4-yl)phenyl) cyclohexanecarboxamide (32); N-((4-(3-methyl-1,2,4-oxadiazol-5-yl)bicyclo[2.2.2]octan-1-yl)methyl)-N-(3-(2-(tetrahydro-2H-pyran-4-yl)oxazol-5-yl)phenyl) cyclohexanecarboxamide (33); N-((4-(3-cyclopropyl-1,2,4-oxadiazol-5-yl)bicyclo[2.2.2]octan-1-yl)methyl)-N-(3-(2-(tetrahydro-2H-pyran-4-yl)oxazol-5-yl)phenyl) cyclohexanecarboxamide (34); N-(3-(3-cyclopropyl-1,2,4- oxadiazol-5-yl)phenyl)-N-((4-(5-methyloxazol-2-yl)bicyclo[2.2.2]octan-1-yl)methyl)cyclohexanecarboxamide (35); N-((4-(3-cyclopropyl-1,2,4-oxadiazol-5-yl) bicyclo[2.2.2]octan-1-yl)methyl)-N-(3-(4-(difluoromethyl)oxazol-2-yl)phenyl)tetrahydro-2H-pyran-4-carboxamide (36); N-((4-(3-cyclopropyl-1,2,4-oxadiazol-5-yl) bicyclo[2.2.2]octan-1-yl)methyl)-N-(3-(4-(difluoromethyl)oxazol-2-yl)phenyl)cyclohexanecarboxamide (37); tert-butyl 4-(((4-(3-cyclopropyl-1,2,4-oxadiazol-5-yl) bicyclo[2.2.2]octan-1-yl)methyl)(3-(4-(difluoromethyl)oxazol-2-yl)phenyl)carbamoyl) piperidine-1-carboxylate (38); N-((4-(3-cyclopropyl-1,2,4-oxadiazol-5-yl) bicyclo[2.2.2]octan-1-yl)methyl)-N-(3-(5-ethoxy-1,3,4-oxadiazol-2-yl)phenyl)-4,4-difluorocyclohexane-1-carboxamide (39); N-((4-(3-cyclopropyl-1,2,4-oxadiazol-5-yl)bicyclo[2.2.2]octan-1-yl)methyl)-N-(3-(5-cyclopropylisoxazol-3-yl)phenyl)tetrahydro-2h-pyran-4-carboxamide (40); N-((4-(3-(cyclopropylmethyl)-1,2,4-oxadiazol-5-yl) bicyclo[2.2.2]octan-1-yl)methyl)-N-(3-(3-(cyclopropylmethyl)-1,2,4-oxadiazol-5-yl)phenyl)tetrahydro-2H-pyran-4-carboxamide (41); N-((4-(3-(cyclopropylmethyl)-1,2,4-oxadiazol-5-yl)bicyclo[2.2.2]octan-1-yl)methyl)-N-(3-(3-(cyclopropylmethyl)-1,2,4-oxadiazol-5-yl)phenyl)-4,4-difluorocyclohexane-1-carboxamide (42); N-((4-(3-cyclopropyl-1,2,4-oxadiazol-5-yl)bicyclo[2.2.2]octan-1-yl)methyl)-N-(3-(3-(cyclopropylmethyl)-1,2,4-oxadiazol-5-yl)phenyl)-4,4-difluorocyclohexane-1-carboxamide (43); N-((4-(3-cyclopropyl-1,2,4-oxadiazol-5-yl)bicyclo[2.2.2]octan-1-yl)methyl)-N-(3-(3-(cyclopropylmethyl)-1,2,4-oxadiazol-5-yl)phenyl)tetrahydro-2H-pyran-4-carboxamide (44); N-(3-(3-cyclopropyl-1,2,4-oxadiazol-5-yl)phenyl)-N-((4-(3-(cyclopropylmethyl)-1,2,4-oxadiazol-5-yl)bicyclo[2.2.2]octan-1-yl)methyl)tetrahydro-2H-pyran-4-carboxamide (45); N-(3-(3-cyclopropyl-1,2,4-oxadiazol-5-yl)phenyl)-N-((4-(3-(cyclopropylmethyl)-1,2,4-oxadiazol-5-yl)bicyclo[2.2.2]octan-1-yl)methyl)-4,4-difluorocyclohexane-1-carboxamide (46); N-((4-(3-cyclopropyl-1,2,4-oxadiazol-5-yl)bicyclo[2.2.2]octan-1-yl)methyl)-N-(3-(2-(methoxymethyl)thiazol-4-yl)phenyl)tetrahydro-2H-pyran-4-carboxamide (47); tert-butyl 4-(((4-(3-cyclopropyl-1,2,4-oxadiazol-5-yl)bicyclo[2.2.2]octan-1-yl)methyl)(3-(2-(methoxymethyl)thiazol-4-yl)phenyl)carbamoyl)piperidine-1-carboxylate (48); N-((4-(3-cyclopropyl-1,2,4-oxadiazol-5-yl)bicyclo[2.2.2]octan-1-yl)methyl)-N-(3-(2-(methoxymethyl)thiazol-4-yl)phenyl)cyclohexanecarboxamide (49); N-((4-(3-cyclopropyl-1,2,4-oxadiazol-5-yl) bicyclo[2.2.2]octan-1-yl)methyl)-N-(3-(5-cyclopropyl-1-methyl-1H-pyrazol-3-yl)phenyl)tetrahydro-2H-pyran-4-carboxamide (50); N-((4-(3-cyclopropyl-1,2,4-oxadiazol-5-yl) bicyclo[2.2.2]octan-1-yl)methyl)-N-(3-(3-ethyl-2-oxo-2,3-dihydrooxazol-5-yl)phenyl)tetrahydro-2H-pyran-4-carboxamide (51); N-((4-(3-cyclopropyl-1,2,4-oxadiazol-5-yl) bicyclo[2.2.2]octan-1-yl)methyl)-N-(3-(3-ethyl-2-oxo-2,3-dihydrooxazol-5-yl)phenyl)tetrahydro-2H-pyran-3-carboxamide, racemate (52); N-((4-(3-cyclopropyl-1,2,4-oxadiazol-5-yl)bicyclo[2.2.2]octan-1-yl)methyl)-N-(3-(4-(methoxymethyl)oxazol-2-yl)phenyl)tetrahydro-2H-pyran-4-carboxamide (53); N-((4-(3-cyclopropyl-1,2,4-oxadiazol-5-yl)bicyclo[2.2.2]octan-1-yl)methyl)-N-(3-(5-cyclopropyl-1,3,4-oxadiazol-2-yl)phenyl)tetrahydro-2H-pyran-4-carboxamide (54); N-((4-(3-cyclopropyl-1,2,4-oxadiazol-5-yl) bicyclo[2.2.2]octan-1-yl)methyl)-N-(3-(5-cyclopropyl-1,3,4-oxadiazol-2-yl)phenyl)tetrahydro-2H-pyran-3-carboxamide, racemate (55); N-((4-(3-cyclopropyl-1,2,4-oxadiazol-5-yl)bicyclo[2.2.2]octan-1-yl)methyl)-N-(3-cyclopropyl-1,2,4-oxadiazol-5-yl)phenyl)morpholine-4-carboxamide (56); N-((4-(3-cyclopropyl-1,2,4-oxadiazol-5-yl) bicyclo[2.2.2]octan-1-yl) methyl)-N-(3-(3-cyclopropyl-1,2,4-oxadiazol-5-yl)phenyl)piperidine-1-carboxamide (57); N-((4-(3-cyclopropyl-1,2,4-oxadiazol-5-yl) bicyclo[2.2.2]octan-1-yl)methyl)-N-(3-(3-cyclopropyl-1,2,4-oxadiazol-5-yl)phenyl)-4,4-difluoropiperidine-1-carboxamide (58); N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-4-methylpiperazine-1-carboxamide (59); N-((4-(3-cyclopropyl-1,2,4-oxadiazol-5-yl) bicyclo[2.2.2]octan-1-yl)methyl)-N-(3-(3-cyclopropyl-1,2,4-oxadiazol-5-yl)phenyl)-4-methylpiperidine-1-carboxamide (60); N-((4-(3-cyclopropyl-1,2,4-oxadiazol-5-yl) bicyclo[2.2.2]octan-1-yl)methyl)-N-(3-(3-cyclopropyl-1,2,4-oxadiazol-5-yl)phenyl)-4-hydroxypiperidine-1-carboxamide (61); N-((4-(3-cyclopropyl-1,2,4-oxadiazol-5-yl) bicyclo[2.2.2]octan-1-yl)methyl)-N-(3-(3-cyclopropyl-1,2,4-oxadiazol-5-yl)phenyl)-3,3-dimethylpiperidine-1-carboxamide, racemate (62); N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-2,6-dimethylmorpholine-4-carboxamide (63); N-((4-(3-cyclopropyl-1,2,4-oxadiazol-5-yl) bicyclo[2.2.2]octan-1-yl)methyl)-N-(3-(3-cyclopropyl-1,2,4-oxadiazol-5-yl)phenyl)-[1,4'-bipiperidine]-1'-carboxamide (64); N-((4-(3-cyclopropyl-1,2,4-oxadiazol-5-yl) bicyclo[2.2.2]octan-1-yl)methyl)-N-(3-(3-cyclopropyl-1,2,4-oxadiazol-5-yl)phenyl)-3-(hydroxymethyl)piperidine-1-carboxamide, racemate (65); N-(3-(3-cyclopropyl-1,2,4-oxadiazol-5-yl)phenyl)-N-((4-(4-cyclopropylthiazol-2-yl)bicyclo[2.2.2]octan-1-yl)methyl)tetrahydro-2H-pyran-3-carboxamide, racemate (66); N-(3-(3-cyclopropyl-1,2,4-oxadiazol-5-yl)phenyl)-N-((4-(5-cyclopropyl-1-methyl-1H-pyrazol-3-yl)bicyclo[2.2.2]octan-1-yl)methyl)tetrahydro-2H-pyran-3-carboxamide (67); N-((4-(3-cyclopropyl-1,2,4-oxadiazol-5-yl)bicyclo[2.2.2]octan-1-yl)methyl)-N-(3-(2-cyclopropyl-1-methyl-1H-imidazol-4-yl)phenyl)tetrahydro-2H-pyran-3-carboxamide, racemate (68); N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)phenyl)tetrahydro-2H-pyran-4-carboxamide (69); N-(3-(3-ethyl-1,2,4-oxadiazol-5-yl)phenyl)-N-(1-(4-(3-methyl-1,2,4-oxadiazol-5-yl)bicyclo[2.2.2]octan-1-yl)ethyl)cyclohexanecarboxamide (70-71); N-(3'-methoxy-[1,1'-biphenyl]-3-yl)-N-((4-(3-methyl-1,2,4-oxadiazol-5-yl)bicyclo[2.2.2]octan-1-yl)methyl)cyclohexanecarboxamide (72); N-(3-(2-methoxypyridin-4-yl)phenyl)-N-((4-(3-methyl-1,2,4-oxadiazol-5-yl)bicyclo[2.2.2]octan-1-yl)methyl)cyclohexane carboxamide (73); N-((4-(3-cyclopropyl-1,2,4-oxadiazol-5-yl)bicyclo[2.2.2]octan-1-yl)methyl)-N-(3'-methoxy-[1,1'-biphenyl]-3-yl)cyclohexanecarboxamide (74); N-((4-(3-cyclopropyl-1,2,4-oxadiazol-5-yl)bicyclo[2.2.2]octan-1-yl)methyl)-N-(3-(2-methoxypyridin-4-yl)phenyl)cyclohexane carboxamide (75); N-(4'-methoxy-[1,1'-biphenyl]-3-yl)-N-((4-(3-methyl-1,2,4-oxadiazol-5-yl)bicyclo[2.2.2]octan-1-yl)methyl)cyclohexane carboxamide (76); N-((4-(3-cyclopropyl-1,2,4-oxadiazol-5-yl)bicyclo[2.2.2]octan-1-yl)methyl)-N-(3-(4-ethoxypyridin-2-yl)phenyl)cyclohexane carboxamide (77); N-((4-(3-cyclopropyl-1,2,4-oxadiazol-5-yl)bicyclo[2.2.2]octan-1-yl)methyl)-N-(3-(2-ethoxypyridin-4-yl)phenyl)cyclohexane carboxamide (78); N-((4-(3-cyclopropyl-1,2,4-oxadiazol-5-yl)bicyclo[2.2.2]octan-1-yl)methyl)-N-(3-(2-ethoxypyridin-4-yl)phenyl)-4,4-difluorocyclohexane-1-carboxamide (79); N-(3-(2-methoxypyridin-4-yl)phenyl)-N-((4-(5-methyl-1,3,4-thiadiazol-2-yl)bicyclo[2.2.2]octan-1-yl)methyl)cyclohexanecarboxamide (80); N-(3-(2-methoxypyridin-4-yl)phenyl)-N-((4-(5-methyl-1,3,4-thiadiazol-2-yl)bicyclo[2.2.2]octan-1-yl)methyl)tetrahydro-2H-pyran-4-carboxamide (81); 4,4-difluoro-N-(3-(2- methoxypyridin-4-yl)phenyl)-N-((4-(5-methyl-1,3,4-thiadiazol-2-yl)bicyclo[2.2.2]octan-1-yl)methyl)cyclohexane-1-carboxamide (82); N-((4-(3-cyclopropyl-1,2,4-oxadiazol-5-yl)bicyclo[2.2.2]octan-1-yl)methyl)-N-(3-(2-methoxypyridin-4-yl)phenyl)tetrahydro-2H-pyran-4-carboxamide (83); N-((4-(3-cyclopropyl-1,2,4-oxadiazol-5-yl)bicyclo[2.2.2]octan-1-yl)methyl)-N-(3-(2-methoxypyrimidin-4-yl)phenyl)tetrahydro-2H-pyran-4-carboxamide (84); N-((4-(3-cyclopropyl-1,2,4-oxadiazol-5-yl)bicyclo[2.2.2]octan-1-yl)methyl)-4,4-difluoro-N-(3-(2-methoxypyrimidin-4-yl)phenyl)cyclohexane-1-carboxamide (85); N-(3-(2-cyclopropoxypyrimidin-4-yl)phenyl)-N-((4-(3-cyclopropyl-1,2,4-oxadiazol-5-yl) bicyclo[2.2.2]octan-1-yl)methyl)tetrahydro-2H-pyran-4-carboxamide (86); N-((4-(3-(tert-butyl)-1,2,4-oxadiazol-5-yl)bicyclo[2.2.2]octan-1-yl)methyl)-N-(3-(2-ethoxypyrimidin-5-yl)phenyl)tetrahydro-2H-pyran-4-carboxamide (87); N-((4-(5-(tert-butyl)-1,2,4-oxadiazol-3-yl)bicyclo[2.2.2]octan-1-yl)methyl)-N-(3-(2-ethoxypyrimidin-5-yl)phenyl)tetrahydro-2H-pyran-4-carboxamide (88); N-((4-(5-(tert-butyl)-1,2,4-oxadiazol-3-yl) bicyclo[2.2.2]octan-1-yl)methyl)-N-(4'-(difluoromethoxy)-[1,1'-biphenyl]-3-yl)tetrahydro-2H-pyran-4-carboxamide (89); N-((4-(3-cyclopropyl-1,2,4-oxadiazol-5-yl) bicyclo[2.2.2]octan-1-yl)methyl)-N-(3-(2-methylbenzo[d]thiazol-6-yl)phenyl)cyclohexanecarboxamide (90); N-((4-(3-cyclopropyl-1,2,4-oxadiazol-5-yl) bicyclo[2.2.2]octan-1-yl)methyl)-N-(3-(2-methylbenzo[d]thiazol-6-yl)phenyl)tetrahydro-2H-pyran-4-carboxamide (91); N-((4-(3-cyclopropyl-1,2,4-oxadiazol-5-yl) bicyclo[2.2.2]octan-1-yl)methyl)-N-(3-(5-fluorobenzo[d]oxazol-2-yl)phenyl)tetrahydro-2H-pyran-3-carboxamide, racemate (92); N-((4-(3-cyclopropyl-1,2,4-oxadiazol-5-yl) bicyclo[2.2.2]octan-1-yl)methyl)-4,4-difluoro-N-(3-(5-fluorobenzo[d]oxazol-2-yl)phenyl)cyclohexane-1-carboxamide (93); N-(3'-methoxy-[1,1'-biphenyl]-3-yl)-N-(1-(4-(3-methyl-1,2,4-oxadiazol-5-yl)bicyclo[2.2.2]octan-1-yl)ethyl)cyclohexanecarboxamide (94-95); N-((3-(3-cyclopropyl-1,2,4-oxadiazol-5-yl)bicyclo[1.1.1]pentan-1-yl)methyl)-N-(3-(2-methoxypyridin-4-yl)phenyl)cyclohexanecarboxamide (96); N-(3-(2-methoxypyridin-4-yl)phenyl)-N-((3-(3-(tetrahydro-2H-pyran-4-yl)-1,2,4-oxadiazol-5-yl) bicyclo[1.1.1]pentan-1-yl)methyl)cyclohexanecarboxamide (97); N-cyclopropyl-4-((N-(3-(2-methoxypyridin-4-yl)phenyl)cyclohexanecarboxamido)methyl) bicyclo[2.2.2]octane-1-carboxamide (98); N-((4-cyanobicyclo[2.2.2]octan-1-yl)methyl)-N-(3-(2-methoxypyridin-4-yl)phenyl)cyclohexanecarboxamide (99); N-(3-(2-methoxypyridin-4-yl)phenyl)-N-((4-(1-methyl-1H-tetrazol-5-yl)bicyclo[2.2.2]octan-1-yl)methyl)cyclohexanecarboxamide (100); Methyl 2-(3-(N-((4-(3-methyl-1,2,4-oxadiazol-5-yl)bicyclo[2.2.2]octan-1-yl)methyl)cyclohexanecarboxamido)phenyl)cyclopropane-1-carboxylate (101-102); N-((4-(3-(tert-butyl)-1,2,4-oxadiazol-5-yl) bicyclo[2.2.2]octan-1-yl)methyl)-N-(3-(3-cyclopropyl-1,2,4-oxadiazol-5-yl)phenyl)-4,4-difluorocyclohexane-1-carboxamide (103); N-((4-(3-(tert-butyl)-1,2,4-oxadiazol-5-yl) bicyclo[2.2.2]octan-1-yl)methyl)-N-(3-(3-cyclopropyl-1,2,4-oxadiazol-5-yl)phenyl)tetrahydro-2H-pyran-4-carboxamide (104); N-((4-(5-(1,1-difluoroethyl)-1,2,4-oxadiazol-3-yl)bicyclo[2.2.2]octan-1-yl)methyl)-N-(4'-ethoxy-6-fluoro-[1,1'-biphenyl]-3-yl)-4,4-difluorocyclohexane-1-carboxamide (105); N-((4-(5-(1,1-difluoroethyl)-1,2,4-oxadiazol-3-yl)bicyclo[2.2.2]octan-1-yl)methyl)-N-(3-(2-ethoxypyrimidin-5-yl)-4-fluorophenyl)-4,4-difluorocyclohexane-1-carboxamide (106); N-((4-(5-(1,1-difluoroethyl)-1,2,4-oxadiazol-3-yl)bicyclo[2.2.2]octan-1-yl)methyl)-4,4-difluoro-N-(6-fluoro-4'-(methylsulfonyl)-[1,1'-biphenyl]-3-yl)cyclohexane-1-carboxamide (107); N-((4-(5-(1,1-difluoroethyl)-1,2,4-oxadiazol-3-yl)bicyclo[2.2.2]octan-1-yl)methyl)-4,4-difluoro-N-(4-fluoro-3-(2-methylbenzo[d]thiazol-6-yl)phenyl)cyclohexane-1-carboxamide (108); N-((4-(5-(1,1-difluoroethyl)-1,2,4-oxadiazol-3-yl)bicyclo[2.2.2]octan-1-yl)methyl)-N-(4'-(difluoromethoxy)-[1,1'-biphenyl]-3-yl)tetrahydro-2H-pyran-4-carboxamide (109); N-((4-(5-(1,1-difluoroethyl)-1,2,4-oxadiazol-3-yl)bicyclo[2.2.2]octan-1-yl)methyl)-N-(4'-(difluoromethoxy)-[1,1'-biphenyl]-3-yl)tetrahydro-2H-thiopyran-4-carboxamide 1,1-dioxide (110); N-((4-(5-(1,1-difluoroethyl)-1,2,4-oxadiazol-3-yl)bicyclo[2.2.2]octan-1-yl)methyl)-N-(4'-(difluoromethoxy)-[1,1'-biphenyl]-3-yl)-4,4-difluorocyclohexane-1-carboxamide (111); N-(3-(3-cyclopropyl-1,2,4-oxadiazol-5-yl)phenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide (112); N-((4-(5-(1,1-difluoroethyl)-1,2,4-oxadiazol-3-yl)bicyclo[2.2.2]octan-1-yl)methyl)-N-(4'-ethoxy-[1,1'-biphenyl]-3-yl)-4,4-difluorocyclohexane-1-carboxamide (113); N-((4-(3-(tert-butyl)-1,2,4-oxadiazol-5-yl) bicyclo[2.2.2]octan-1-yl)methyl)-N-(3-(3-cyclopropyl-1,2,4-oxadiazol-5-yl)-5-fluorophenyl)-4,4-difluorocyclohexane-1-carboxamide (114); N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)-5-fluorophenyl)tetrahydro-2H-pyran-4-carboxamide (115); N-((4-(5-(tert-butyl)-1,2,4-oxadiazol-3-yl)bicyclo[2.2.2]octan-1-yl)methyl)-N-(3-(3-cyclopropyl-1,2,4-oxadiazol-5-yl)phenyl)tetrahydro-2H-pyran-4-carboxamide (116); N-((4-(5-(tert-butyl)-1,2,4-oxadiazol-3-yl)bicyclo[2.2.2]octan-1-yl)methyl)-N-(3-(3-cyclopropyl-1,2,4-oxadiazol-5-yl)phenyl)tetrahydro-2H-thiopyran-4-carboxamide 1,1-dioxide (117); N-((4-(5-(tert-butyl)-1,2,4-oxadiazol-3-yl)bicyclo[2.2.2]octan-1-yl)methyl)-N-(3-(3-cyclopropyl-1,2,4-oxadiazol-5-yl)phenyl)-1-methylpiperidine-4-carboxamide (118); N-(3-(2-cyclopropylpyrimidin-5-yl)phenyl)-4,4-difluoro-N-((4-(5-(trifluoromethyl)-1,2,4-oxadiazol-3-yl)bicyclo[2.2.2]octan-1-yl)methyl)cyclohexane-1-carboxamide (119); N-(3-(2-cyclopropylpyrimidin-5-yl)phenyl)-4,4-difluoro-N-((4-(5-(3-hydroxy-3-(trifluoromethyl)cyclobutyl)-1,2,4-oxadiazol-3-yl)bicyclo[2.2.2]octan-1-yl)methyl)cyclohexane-1-carboxamide (120); N-((4-(5-(tert-butyl)-1,2,4-oxadiazol-3-yl) bicyclo[2.2.2]octan-1-yl)methyl)-N-(4'-(dimethylphosphoryl)-[1,1'-biphenyl]-3-yl)tetrahydro-2H-pyran-4-carboxamide (121); N-((4-(5-(1,1-difluoroethyl)-1,2,4-oxadiazol-3-yl)bicyclo[2.2.2]octan-1-yl)methyl)-N-(4'-(dimethylphosphoryl)-6-fluoro-[1,1'-biphenyl]-3-yl)tetrahydro-2H-pyran-4-carboxamide (122); N-((4-(5-(tert-Butyl)-1,3,4-oxadiazol-2-yl)bicyclo[2.2.2]octan-1-yl)methyl)-N-(3-(3-cyclopropyl-1,2,4-oxadiazol-5-yl)phenyl)-4,4-difluorocyclohexane-1-carboxamide (123); N-((4-(5-(tert-Butyl)-1,3,4-oxadiazol-2-yl)bicyclo[2.2.2]octan-1-yl) methyl)-N-(3-(5-cyclopropylisoxazol-3-yl)phenyl)-4,4-difluorocyclohexane-1-carboxamide (124); N-((4-(3-(tert-butyl)-1,2,4-oxadiazol-5-yl)bicyclo[2.2.2]octan-1-yl)methyl)-3,5-dichloro-N-(3-(2-ethoxypyrimidin-5-yl)phenyl)benzamide (125); N-((4-(3-(tert-Butyl)-1,2,4-oxadiazol-5-yl) bicyclo[2.2.2]octan-1-yl)methyl)-3-chloro-N-(3-(2-ethoxypyrimidin-5-yl)phenyl)benzamide (126); N-((4-(3-(tert-Butyl)-1,2,4-oxadiazol-5-yl)bicyclo[2.2.2]octan-1-yl)methyl)-4,4-difluoro-N-(3-(6-oxo-1,6-dihydropyridin-4-yl)phenyl)cyclohexane-1-carboxamide (127); N-((4-(5-(2-fluoropropan-2-yl)-1,2,4-oxadiazol-3-yl) bicyclo[2.2.2]octan-1-yl)methyl)-N-(3-(6-oxo-1,6-dihydropyridazin-4-yl)phenyl)tetrahydro-2H-pyran-4-carboxamide (128); N-((4-(5-(1,1-difluoroethyl)-1,2,4-oxadiazol-3-yl)bicyclo[2.2.2]octan-1-yl)methyl)-N-(3-(6-oxo-1,6-dihydropyridazin-4-yl)phenyl)tetrahydro-2H-pyran-4-carboxamide (129); N-((4-(5-(1,1-difluoroethyl)-1,2,4-oxadiazol-3-yl)bicyclo[2.2.2]octan-1-yl)methyl)-4,4-difluoro-N-(4'-(methylsulfonyl)-[1,1'-biphenyl]-3-yl)cyclohexane-1-carboxamide (130); N-((4-(3-cyclopropyl-1-methyl-1H-pyrazol-5-yl)bicyclo[2.2.2]octan-1-yl)methyl)-N-(3-(5-cyclopropylisoxazol-3-yl)phenyl)tetrahydro-2H-thiopyran-4-carboxamide 1,1-dioxide (131); N-((4-(3-cyclopropyl-1-methyl-1H-pyrazol-5-yl)bicyclo[2.2.2]octan-1-yl)methyl)-N-(3-(5-cyclopropylisoxazol-3-yl)phenyl)tetrahydro-2H-pyran-4-carboxamide (132); N-((4-(3-cyclopropyl-1-methyl-1H-pyrazol-5-yl)bicyclo[2.2.2]octan-1-yl)methyl)-N-(3-(5-cyclopropylisoxazol-3-yl)phenyl)-1-methylpiperidine-4-carboxamide (133); N-((4-(3-cyclopropyl-1-methyl-1H-pyrazol-5-yl)bicyclo[2.2.2]octan-1-yl)methyl)-N-(4'-(methylsulfonyl)-[1,1'-biphenyl]-3-yl)tetrahydro-2H-pyran-4-carboxamide (134); N-((4-(3-cyclopropyl-1-methyl-1H-pyrazol-5-yl)bicyclo[2.2.2]octan-1-yl)methyl)-N-(4'-(methylsulfonyl)-[1,1'-biphenyl]-3-yl)tetrahydro-2H-thiopyran-4-carboxamide 1,1-dioxide (135); N-((4-(3-cyclopropyl-1-methyl-1H-pyrazol-5-yl)bicyclo[2.2.2]octan-1-yl)methyl)-1-methyl-N-(4'-(methylsulfonyl)-[1,1'-biphenyl]-3-yl)piperidine-4-carboxamide (136); N-((4-(3-cyclopropyl-1-methyl-1H-pyrazol-5-yl)bicyclo[2.2.2]octan-1-yl)methyl)-4,4-difluoro-N-(3-(2-methylbenzo[d]thiazol-6-yl)phenyl)cyclohexane-1-carboxamide (137); N-((4-(3-cyclopropyl-1-methyl-1H-pyrazol-5-yl)bicyclo[2.2.2]octan-1-yl)methyl)-N-(3-(3-cyclopropylisoxazol-5-yl)phenyl)tetrahydro-2H-thiopyran-4-carboxamide 1,1-dioxide (138); N-((4-(3-cyclopropyl-1-methyl-1H-pyrazol-5-yl)bicyclo[2.2.2]octan-1-yl)methyl)-N-(3-(3-cyclopropylisoxazol-5-yl)phenyl)tetrahydro-2H-pyran-4-carboxamide (139); N-((4-(3-cyclopropyl-1-methyl-1H-pyrazol-5-yl)bicyclo[2.2.2]octan-1-yl)methyl)-N-(3-(3-cyclopropylisoxazol-5-yl)phenyl)-1-methylpiperidine-4-carboxamide (140); N-((4-(3-(tert-butyl)-1,2,4-oxadiazol-5-yl)bicyclo[2.2.2]octan-1-yl)methyl)-N-(3-(6-chloropyrazolo[1,5-a]pyrimidin-3-yl)phenyl)-4,4-difluorocyclohexane-1-carboxamide (141); N-((4-(3-(tert-butyl)-1,2,4-oxadiazol-5-yl)bicyclo[2.2.2]octan-1-yl)methyl)-4,4-difluoro-N-(3-(4-methyl-1H-imidazol-1-yl)phenyl)cyclohexane-1-carboxamide (142); N-(3-(2-ethoxypyrimidin-5-yl)phenyl)-N-((4-(5-(2-fluoropropan-2-yl)-1,2,4-oxadiazol-3-yl)bicyclo[2.2.2]octan-1-yl)methyl)-4-methoxybenzamide (143); 4-(difluoromethoxy)-N-(3-(2-ethoxypyrimidin-5-yl)phenyl)-N-((4-(5-(2-fluoropropan-2-yl)-1,2,4-oxadiazol-3-yl)bicyclo[2.2.2]octan-1-yl)methyl)benzamide (144); N-((4-(3-(tert-butyl)-1,2,4-oxadiazol-5-yl)bicyclo[2.2.2]octan-1-yl)methyl)-N-(4'-ethoxy-[1,1'-biphenyl]-3-yl)-4-methoxycyclohexane-1-carboxamide (145-146); N-((4-(3-(tert-butyl)-1,2,4-oxadiazol-5-yl)bicyclo[2.2.2]octan-1-yl)methyl)-N-(3-(3-cyclopropylisoxazol-5-yl)phenyl)-4,4-difluorocyclohexane-1-carboxamide (147); N-((4-(5-(tert-butyl)-1,2,4-oxadiazol-3-yl)bicyclo[2.2.2]octan-1-yl)methyl)-N-(3-(3-cyclopropylisoxazol-5-yl)phenyl)-4,4-difluorocyclohexane-1-carboxamide (148); N-(3-(3-cyclopropylisoxazol-5-yl)phenyl)-4,4-difluoro-N-((4-(5-(1-(trifluoromethyl)cyclopropyl)-1,2,4-oxadiazol-3-yl) bicyclo[2.2.2]octan-1-yl)methyl)cyclohexane-1-carboxamide (149); N-(3-(3-cyclopropylisoxazol-5-yl)phenyl)-N-((4-(5-(1,1-difluoroethyl)-1,2,4-oxadiazol-3-yl) bicyclo[2.2.2]octan-1-yl)methyl)-4,4-difluorocyclohexane-1-carboxamide (150); N-((4-(3-cyclopropyl-1,2,4-oxadiazol-5-yl)bicyclo[2.2.2] octan-1-yl)methyl)-N-(3-(3-cyclopropylisoxazol-5-yl)phenyl)-4,4-difluorocyclohexane-1-carboxamide (151); N-((4-(3-cyclopropyl-1,2,4-oxadiazol-5-yl)bicyclo[2.2.2]octan-1-yl)methyl)-N-(3-(3-cyclopropylisoxazol-5-yl)phenyl)tetrahydro-2H-thiopyran-4-carboxamide 1,1-dioxide (152); N-((4-(3-cyclopropyl-1,2,4-oxadiazol-5-yl)bicyclo[2.2.2]octan-1-yl)methyl)-N-(3-(3-cyclopropylisoxazol-5-yl)phenyl)tetrahydro-2H-pyran-4-carboxamide (153); N-(3-(5-cyclopropylisoxazol-3-yl)phenyl)-N-((4-(5-(1,1-difluoroethyl)-1,2,4-oxadiazol-3-yl) bicyclo[2.2.2]octan-1-yl)methyl)-4,4-difluorocyclohexane-1-carboxamide (154); N-(3-(5-cyclopropylisoxazol-3-yl)phenyl)-N-((4-(5-(1,1-difluoroethyl)-1,2,4-oxadiazol-3-yl) bicyclo[2.2.2]octan-1-yl)methyl)tetrahydro-2H-thiopyran-4-carboxamide 1,1-dioxide (155); N-(3-(5-cyclopropylisoxazol-3-yl)phenyl)-N-((4-(5-(1,1-difluoroethyl)-1,2,4-oxadiazol-3-yl)bicyclo[2.2.2]octan-1-yl)methyl)tetrahydro-2H-pyran-4-carboxamide (156); N-(3-(5-cyclopropylisoxazol-3-yl)phenyl)-N-((4-(5-(1,1-difluoroethyl)-1,2,4-oxadiazol-3-yl)bicyclo[2.2.2]octan-1-yl)methyl)-4-hydroxy-4-(trifluoromethyl)cyclohexane-1-carboxamide (157-158); N-((4-(3-(tert-butyl)-1,2,4-oxadiazol-5-yl) bicyclo[2.2.2]octan-1-yl)methyl)-N-(3-(5-cyclopropylisoxazol-3-yl)phenyl)-4,4-difluorocyclohexane-1-carboxamide (159); N-((4-(3-(tert-butyl)-1,2,4-oxadiazol-5-yl) bicyclo[2.2.2]octan-1-yl)methyl)-N-(3-(5-cyclopropylisoxazol-3-yl)phenyl)tetrahydro-2H-thiopyran-4-carboxamide 1,1-dioxide (160); N-((4-(3-(tert-butyl)-1,2,4-oxadiazol-5-yl)bicyclo[2.2.2]octan-1-yl)methyl)-N-(3-(5-cyclopropylisoxazol-3-yl)phenyl)tetrahydro-2H-pyran-4-carboxamide (161); N-((4-(5-(tert-butyl)-1,2,4-oxadiazol-3-yl) bicyclo[2.2.2]octan-1-yl)methyl)-N-(3-(5-cyclopropylisoxazol-3-yl)phenyl)-4,4-difluorocyclohexane-1-carboxamide (162); N-((4-(3-cyclopropyl-1-methyl-1H-pyrazol-5-yl)bicyclo[2.2.2]octan-1-yl)methyl)-N-(3-(5-cyclopropylisoxazol-3-yl)phenyl)-4,4-difluorocyclohexane-1-carboxamide (163); N-((4-(5-(1,1-difluoroethyl)-1,2,4-oxadiazol-3-yl)bicyclo[2.2.2]octan-1-yl)methyl)-N-(4'-ethoxy-6-fluoro-[1,1'-biphenyl]-3-yl)-4-hydroxy-4-(trifluoromethyl)cyclohexane-1-carboxamide (164-165); or N-((4-(3-(tert-butyl)-1,2,4-oxadiazol-5-yl)bicyclo[2.2.2]octan-1-yl)methyl)-N-(4'-ethoxy-6-fluoro-[1,1'-biphenyl]-3-yl)-4-hydroxy-4-methylcyclohexane-1-carboxamide (166).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "hydroxy" refers to the group —OH.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "haloalkyl" as used herein is intended to include both branched and straight-chain saturated aliphatic hydrocarbon groups substituted with one or more halo atoms. For example, "$C_{1-4}$ haloalkyl" is intended to include $C_1$, $C_2$, $C_3$, and $C_4$ alkyl groups substituted with one or more halo atoms. Representative examples of haloalkyl groups include, but are not limited to, —CF$_3$, —CCl$_3$, —CHF$_2$, and —CF$_2$CCl$_3$.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "alkoxy" as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "haloalkoxy" and "—O(haloalkyl)" represent a haloalkyl group as defined above attached through an oxygen linkage (—O—). For example, "$C_{1-4}$ haloalkoxy" is intended to include $C_1$, $C_2$, $C_3$, and $C_4$ haloalkoxy groups.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The terms "carbocyclo", "carbocyclic" or "carbocyclyl" may be used interchangeably and refer to cyclic groups having at least one saturated or partially saturated non-aromatic ring wherein all atoms of all rings are carbon, and includes groups having one or more bridged rings in which the bridged ring occurs when one or more carbon atoms link two non-adjacent carbon atoms. The term includes nonaromatic rings such as for example, cycloalkyl and cycloalkenyl, bicyclo[1.1.1]pentyl, bicyclo[2.2.2]octanyl, adamantyl, and tetrahydronaphthyl.

The term "aryl" as used herein, refers to a group of atoms derived from a molecule containing aromatic ring(s) by removing one hydrogen that is bonded to the aromatic ring(s). Representative examples of aryl groups include, but are not limited to, phenyl and naphthyl. The aryl ring may be unsubstituted or may contain one or more substituents as valence allows.

The term "heteroatom" refers to oxygen (O), sulfur (S), and nitrogen (N).

The terms "heterocyclo", "heterocyclic", or "heterocyclyl" may be used interchangeably and refer to cyclic groups having at least saturated or partially saturated non-aromatic ring and wherein one or more of the rings have at least one heteroatom (0, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, dihydroisoindolyl, and tetrahydroquinolinyl.

The term "heteroaryl" refers to substituted and unsubstituted aromatic 5- or 6-membered monocyclic groups and 9- or 10-membered bicyclic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain only carbon atoms. The nitrogen and sulfur atoms may optionally be oxidized and the nitrogen atoms may optionally be quaternized. Bicyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

As used herein, the term "tautomer" refers to each of two or more isomers of a compound that exist together in equilibrium, and are readily interchanged by migration of an atom or group within the molecule. For example, one skilled in the art would readily understand that a 1,2,3-triazole exists in two tautomeric forms as defined above:

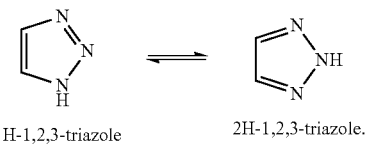

1H-1,2,3-triazole    2H-1,2,3-triazole.

Thus, this disclosure is intended to cover all possible tautomers even when a structure depicts only one of them. For example, the compounds of Formula (Ia) wherein when $R^{5c}$ is hydroxy and each of $R^{5a}$, $R^{5b}$, and $R^{5d}$ are hydrogen, can exist in tautomeric forms:

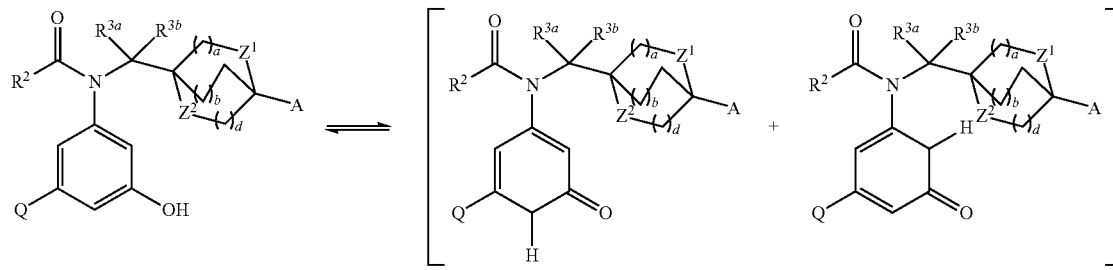

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization. Lists of suitable salts are found in *Remington's Pharmaceutical Sciences*, 18th Edition, Mack Publishing Company, Easton, PA (1990), the disclosure of which is hereby incorporated by reference.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

e) Rautio, J. et al., *Nature Review Drug Discovery*, 17, 559-587, (2018).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist of FXR, or effective to treat or prevent disorders associated with dysregulation of bile acids, such as pathological fibrosis, cancer, inflammatory disorders, metabolic, or cholestatic disorders.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

Utility

In one embodiment, the present invention provides a method for the treatment of a disease, disorder, or condition associated with dysregulation of bile acids in a patient in need of such treatment, and the method comprises administering a therapeutically effective amount of a compound of the present invention, or a stereoisomer, a tautomer, or a pharmaceutically acceptable salt or solvate thereof, to the patient.

In another embodiment, the present invention provides a method for the treatment of a disease, disorder, or condition associated with activity of farnesoid X receptor (FXR) in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an farnesoid X receptor (FXR) agonizing effect in a patient comprising administering a therapeutically effective amount of a compound of the present invention, or a stereoisomer, a tautomer, or a pharmaceutically acceptable salt or solvate thereof, to the patient.

In some embodiments, the disease, disorder, or condition is associated with FXR dysfunction include pathological fibrosis, cancer, inflammatory disorders, metabolic, or cholestatic disorders.

In some embodiments, the disease, disorder, or condition is associated with fibrosis, including liver, biliary, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the liver, gall bladder, small intestine, large intestine, kidney, prostate, bladder, blood, bone, brain, breast, central nervous system, cervix, colon, endometrium, esophagus, genitalia, genitourinary tract, head, larynx, lung, muscle tissue, neck, oral or nasal mucosa, ovary, pancreas, skin, spleen, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of FXR that can be prevented, modulated, or treated according to the present invention include, but are not limited to, transplant injection, fibrotic disorders (e.g., liver fibrosis, kidney fibrosis), inflammatory disorders (e.g., acute hepatitis, chronic hepatitis, non-alcoholic steatohepatitis (NASH), irritable bowel syndrome (IBS), inflammatory bowel disease (IBD)), as well as cell-proliferative disorders (e.g., cancer, myeloma, fibroma, hepatocellular carcinoma, colorectal cancer, prostate cancer, leukemia, Kaposi's sarcoma, solid tumors).

The fibrotic disorders, inflammatory disorders, as well as cell-proliferative disorders that are suitable to be prevented or treated by the compounds of the present invention include, but are not limited to, non-alcoholic fatty liver disease (NAFLD), alcoholic or non-alcoholic steatohepatitis (NASH), acute hepatitis, chronic hepatitis, liver cirrhosis, primary biliary cirrhosis, primary sclerosing cholangitis, drug-induced hepatitis, biliary cirrhosis, portal hypertension, regenerative failure, liver hypofunction, hepatic blood flow disorder, nephropathy, irritable bowel syndrome (IBS), inflammatory bowel disease (IBD), abnormal pancreatic secretion, benign prostatic hyperplasia, neuropathic bladder disease, diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocellular carcinoma, colorectal cancer, prostate cancer, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: TGFβ receptor inhibitors (for example, galunisertib), inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-αvβ6 integrin monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol,
3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, Sar$^9$, Met($O_2$)$^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic β2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as liver, biliary, and kidney fibrosis, Non-Alcoholic Fatty Liver Disease (NALFD), Non-Alcoholic Steato-Hepatitis (NASH), cardiac fibrosis, Idiopathic Pulmonary Fibrosis (IPF), and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example, BMS-986020 and SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997 or selonsertib), ACC inhibitors (for example, CP-640186 and NDI-010976 or GS-0976), FGF21 mimetics (for example, LY2405319 and BMS-986036), caspase inhibitors (for example, emricasan), NOX4 inhibitors (for example, GKT137831), MGAT2 inhibitor (for example, BMS-963272), αV integrin inhibitors (for example, abituzumab) and bile acid/fatty acid conjugates (for example aramchol). The FXR agonists of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 receptor agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunoncology agents, such as alemtuzumab, atezolizumab, ipilimumab, nivolumab, ofatumumab, pembrolizumab, and rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 Volumes), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.01 to about 1000 mg per day, and most preferably between about 0.01 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., ASK-1 inhibitors, CCR2/5 antagonists, autotaxin inhibitors, LPA1 receptor antagonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC)

or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The compounds of the present invention are also useful as standard or reference compounds, for example as a quality standard or control, in tests or assays involving FXR agonists. Such compounds may be provided in a commercial kit, for example, for use in pharmaceutical research involving FXR agonist activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined below. Common intermediates are generally useful for the preparation of more than one Example and are identified sequentially (e.g., Intermediate 1, Intermediate 2) and are abbreviated as Int. 1 or I1, Int. 2 or I2. Compounds of the Examples are identified by the example and STEP in which they were prepared (e.g., "1-A" denotes the Example 1, STEP A), or by the example only where the compound is the title compound of the example (for example, "1" denotes the title compound of Example 1). In some instances, alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear STEPs. The intent of describing alternative preparations is to further enable the preparation of the examples of this invention. In some instances, some functional groups in the outlined examples and claims may be replaced by well-known bioisosteric replacements known in the art, for example, replacement of a carboxylic acid group with a tetrazole or a phosphate moiety. $^1$H NMR data collected in deuterated dimethyl sulfoxide used water suppression in the data processing. The reported spectra are uncorrected for the effects of water suppression. Protons adjacent to the water suppression frequency of 3.35 ppm exhibit diminished signal intensity.

Abbreviations

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RBF" for round bottom flask, "atm" for atmosphere, "psi" for pounds per square inch, "conc." for concentrated, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$_1$H" for proton, "S" for delta, "s" for singlet, "d" for doublet, "t" for triplet, "q" for quartet, "m" for multiplet, "br" for broad, "Hz" for hertz, and "a", "p", "R", "S", "E", and "Z" are stereochemical designations familiar to one skilled in the art.

The following abbreviations are employed in the Schemes, Examples and elsewhere herein:
EtOAc=ethyl acetate
DMF=dimethylformamide
THF=tetrahydrofuran
K$_2$CO$_3$=potassium carbonate
Na$_2$CO$_3$=sodium carbonate
MgSO$_4$=magnesium sulfate
DCM=CH$_2$Cl$_2$=methylene chloride
MeOH=methanol
HCl=hydrochloric acid
AcOH=acetic acid
Cs$_2$CO$_3$=cesium carbonate
DMSO=dimethylsulfoxide
TEA=triethylamine
BOP=(benzotriazol-1-yloxy)tris(dimethylamino)phosphonium hexafluorophosphate
DMAP=4-dimethylaminopyridine
2-DMAP=2-dimethylaminopyridine
PCC=pyridinium chlorochromate
PDC=pyridinium dichromate
DIBAL-H=diisobutylaluminium hydride
rotovap=rotary evaporation
min=minute(s)
h or hr=hour(s)
d=day(s)
rt=room temperature
mL=milliliter
g=gram(s)
mg=milligram(s)
mmol=millimole(s)
LRMS=low resolution mass spectrometry
NMR=nuclear magnetic resonance
HPLC=high performance liquid chromatography Synthesis The compounds of the present invention can be prepared in a number of ways well known to one skilled in the art of organic synthesis. The compounds of the present invention can be synthesized using the methods described below, together with synthetic methods known in the art of organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

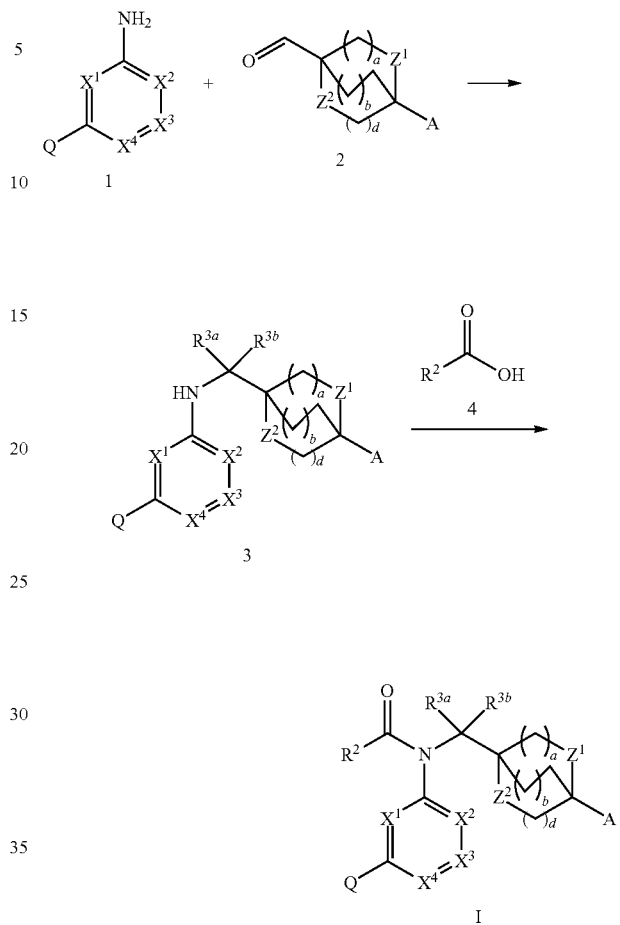

Scheme 1 describes the synthesis of compounds of Formula I. Intermediate 3 can be synthesized by coupling intermediate 1 and intermediate 2 under reductive amination conditions which are known methods recognizable by one skilled in the art. The imine synthesis can occur in presence of acid such as acetic acid in a suitable polar protic solvent (e.g. MeOH and EtOH) at room temperature or reflux temperature followed by reduction of imine with reducing agents (e.g. sodium cyanoborohydride and sodium triacetoxyborohydride) to afford intermediate 3. Intermediate 4 can be obtained from commercial sources or can be synthesized by known methods readily recognizable by one skilled in the art. Intermediate 4 can be activated for acylation using any number of reagents recognizable by one skilled in the art (e.g. phosphorus oxychloride, thionyl chloride, oxalyl chloride, methylchloroformate, and ethylchloroformate), in a polar aprotic solvent (e.g. DCM and THF), at temperatures ranging between −30° C. to 0° C. The activated acid intermediate can then be reacted with intermediate 3 in presence of a base (e.g. pyridine, DMAP, 2-(dimethylamino) pyridine, and N-methylmorpholine or a combination of at least two of these) to generate compounds of Formula I.

Intermediates 1(a-m) (Scheme 1) can be accessed in various ways as depicted in scheme 2-10 using numerous known methods recognized by the one skilled in the art including but not limited to the following methods.

SCHEME 2

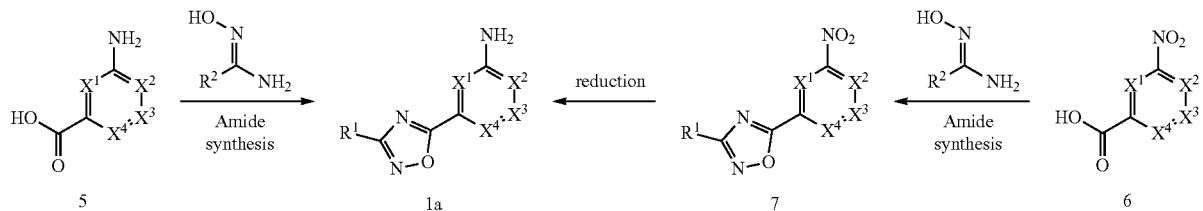

Scheme 2 describes the synthesis of intermediate 1a. Intermediates 5 and 6 can be obtained from commercial sources or can be synthesized by known methods readily recognizable by one skilled in the art. Intermediate 5 or 6 can be coupled with various substituted amide oximes (derived from the corresponding nitriles by reaction with hydroxylamine; see Hirawat, S., et al. WO 2006/110483) using an amide bond coupling reagent (e.g. CDI, BOP, and EDC) in a polar aprotic solvent (e.g. THF, 1,4-dioxane, and DMF) at room temperature. The acyclic intermediate can be subsequently cyclized at elevated temperatures (60° C. to 100° C.) to obtain intermediates 1a or intermediate 7. Alternatively, in situ cyclization can be accomplished by conducting the coupling of compound 5 or 6 with amide oximes at elevated temperatures (60° C. to 100° C.). The nitro intermediate 7 so obtained can be reduced using the conditions recognized by one skilled in the art including but not limited to reduction in presence of catalyst such as Pd and hydrogen gas at ambient pressure and temperature to yield intermediate 1a.

SCHEME 3

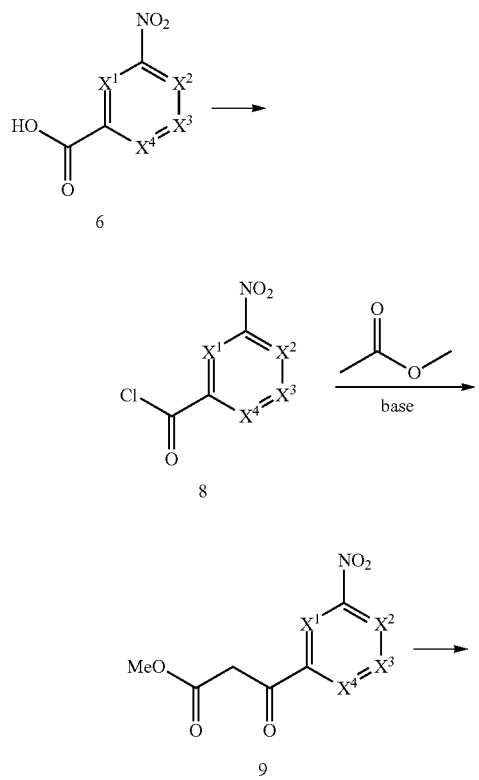

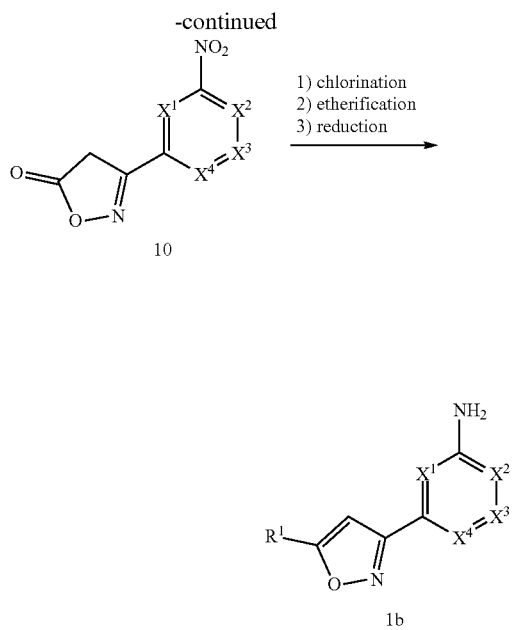

Scheme 3 describes the synthesis of intermediates 1b. Intermediate 8 can be prepared from intermediate 6 by using any number of reagents recognizable by one skilled in the art but not limited to the ones described here (e.g. phosphorus oxychloride, thionyl chloride, oxalyl chloride, methylchloroformate, and ethylchloroformate), in a polar aprotic solvent (e.g. DCM and THF), at temperatures ranging between −30° C. to reflux. Intermediate 8 can be treated with methyl acetate pre-treated with base such as n-BuLi in a solvent such as but not limited to THF or ether to afford intermediate 9 (as described by Douglass, T. et al. *J. Am. Chem. Soc.*, 1987, 109, 7488-7494). Alternatively, intermediate 9 can be synthesized as described in France, S. et al. *Org. Lett.* 2016, 18, 4218-4221. Intermediate 9 can be treated with hydroxylamine hydrochloride in polar protic solvent such as MeOH, EtOH and water in presence of base such as $K_2CO_3$ to afford intermediates represented by formula 10 (as described in Wittman, M. D., et al. WO 2015/195880 A1). Intermediate 10 can be treated with reagents such as $POCl_3$ and $SOCl_2$ in presence of base such as $Et_3N$ and DIPEA for chlorination (as described in Wittman, M. D., et al. WO 2015/195880 A1) followed by treatment with metal alkoxides to afford corresponding substituted intermediates which can be reduced in presence of catalyst such as Pd and hydrogen gas at ambient pressure and temperature to yield intermediate 1b.

SCHEME 4

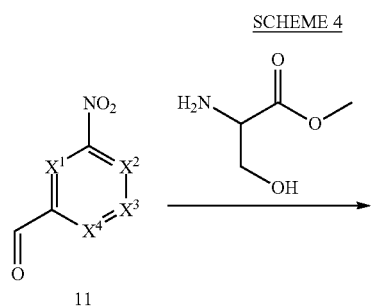

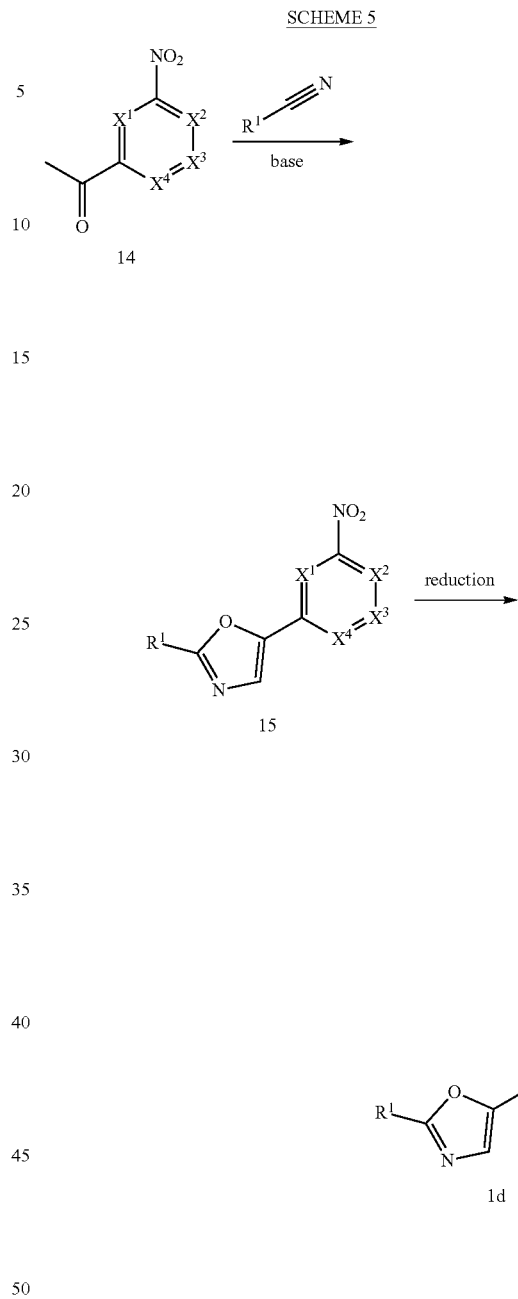

Scheme 4 describes the synthesis of intermediates 1c. Intermediate 11 can be obtained from commercial sources or can be synthesized by known methods readily recognizable by one skilled in the art. Intermediate 11 can be condensed with serine ester in presence of base (e.g. Et$_3$N and DIPEA) and dehydrating agent such as MgSO$_4$ to afford intermediate 12. Intermediate 12 can be converted to intermediate 13 by treatment with BrCCl$_3$ and base such as DBU in chlorinated solvent (e.g. CH$_2$Cl$_2$ and DCE) at ambient temperature as described in Graham, T. H., *Org. Lett.*, 2010, 12, 3614-3617. The nitro intermediate 13 can be reduced, using the conditions recognized by one skilled in the art including but not limited to reduction in presence of catalyst such as Pd and hydrogen gas at ambient pressure and temperature to yield intermediates 1c.

Scheme 5 describes the synthesis of intermediates 1d. Intermediates 14 can be obtained from commercial sources or can be synthesized by known methods readily recognizable by one skilled in the art. Intermediates 14 can be treated with iodobenzene diacetate in presence of trifluoromethane sulfonic acid and substituted nitrile to afford oxazoles as described in Varma, R. S. et al *J. Heterocyclic Chem.* 1998, 35, 1533. The nitro intermediate 15 so obtained can be reduced, using the conditions recognized by one skilled in the art, including but not limited to reduction in presence of catalyst such as Pd and hydrogen gas at ambient pressure and temperature to yield intermediates 1d.

SCHEME 6

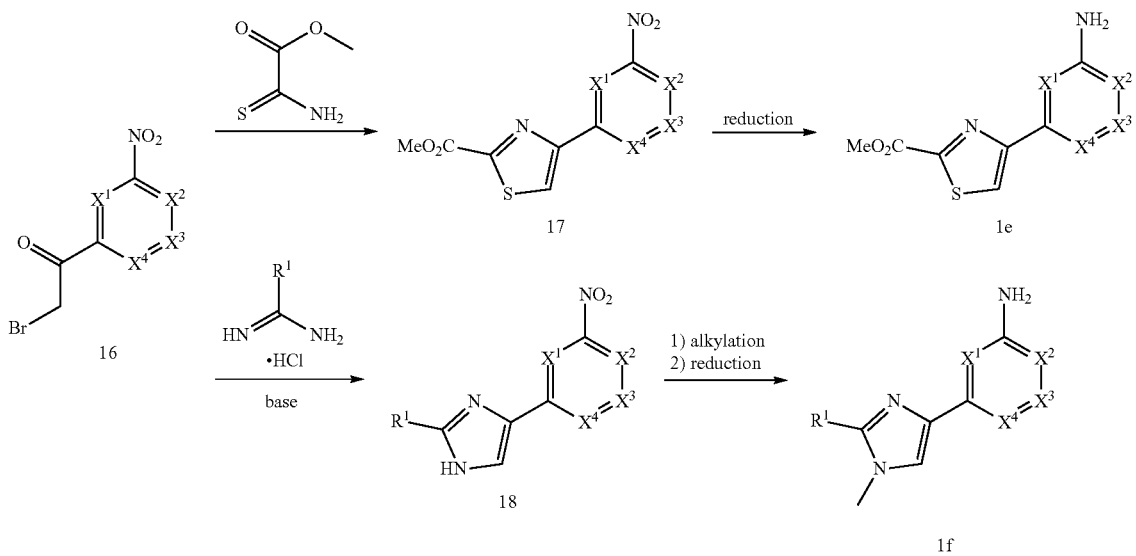

Scheme 6 describes the synthesis of intermediates 1e and 1f. Intermediate 16 can be obtained from commercial sources or can be synthesized by known methods or their modifications readily recognizable by one skilled in the art (described as in *Bioorg. & Med. Chem. Lett,* 2017, 27, 2192-2196). Intermediate 16 can be treated with methyl thiooxamate under heating conditions in protic polar solvent (e.g. MeOH and EtOH) to afford compounds represented by intermediate 17 as described in Wright, S. W., *J. Med. Chem.* 2002, 45, 3865-3877. The nitro intermediate 17 so obtained can be reduced, using the conditions recognized by one skilled in the art, including but not limited to reduction in presence of catalyst such as Pd and hydrogen gas at ambient pressure and temperature to yield intermediates 1e. Alternatively, intermediate 16 can be treated with an amidine in polar aprotic solvent (e.g. MeCN and DMF) in presence of base such as $K_2CO_3$ under heating conditions to afford intermediate 18. Intermediate 18 can be alkylated, using numerous known methods recognized by one skilled in the art, including but not limited to, treatment under basic conditions in presence of alkylating agent to generate N-alkyl imidazole intermediate which can be reduced in presence of catalyst such as Pd and hydrogen gas at ambient pressure and temperature to yield intermediate 1f.

SCHEME 7

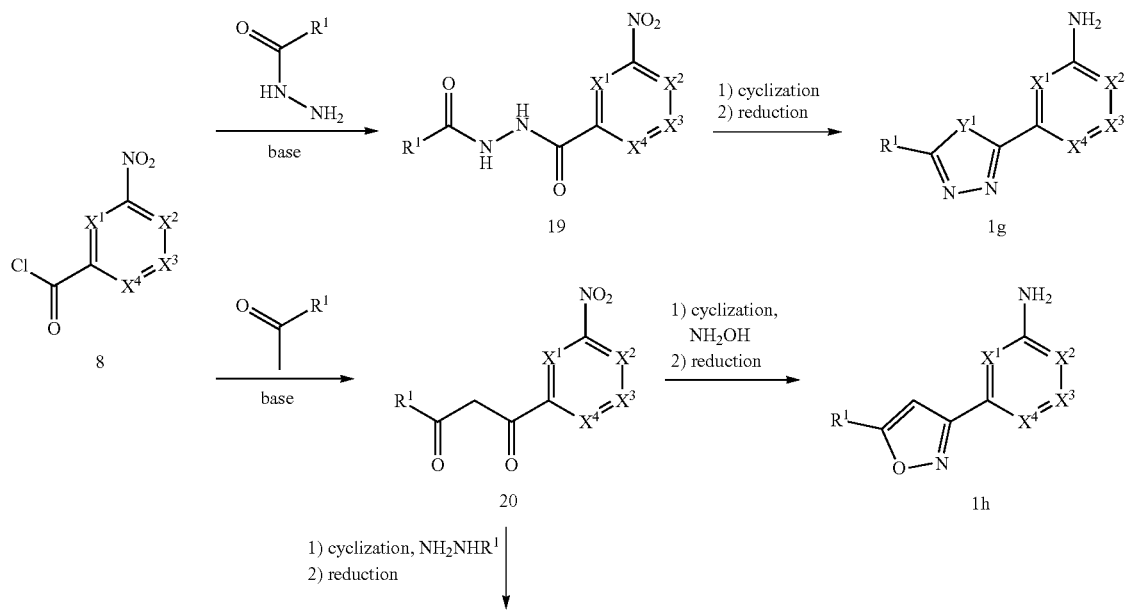

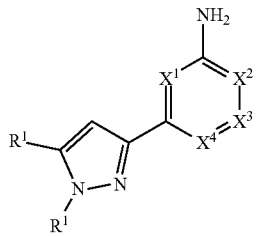

1i

Intermediates 1g, 1h, or 1i can be synthesized from intermediate 8 following the synthetic procedures outlined in Scheme 7. Intermediate 8 can be coupled with acid hydrazide in a polar aprotic solvent (e.g. THF, 1,4-dioxane DMF, and MeCN) and in presence of base (e.g. Et$_3$N and DIPEA) to obtain intermediate 19. Intermediate 19 can then be cyclized to either 1,3,4-oxadiazole or 1,3,4-thiadiazole using respectively, 4-toluenesulfonic acid (Stabile, P. et al. *Tetrahedron Lett.* 2010, 51, 4801-4805) or Lawesson's reagent (Kitamura, S., et al. PCT Int. Appl., 2008011130, 2008). The cyclized intermediate so obtained can be reduced in presence of catalyst such as Pd and hydrogen gas at ambient pressure and temperature to yield intermediate 1g.

Methyl ketones can be pre-treated with base and then reacted with intermediate 8 to afford intermediate 20 as described in France, S. et al. *Org. Lett.* 2016, 18, 4218-4221. Intermediate 20 can be treated with a hydrazine salt in polar protic solvent (such as MeOH and EtOH) under heating conditions to afford a pyrazole. (As described in Cadilla, R., et al. WO 03/074495 A1). The nitro intermediate so obtained can be reduced in presence of catalyst such as Pd and hydrogen gas at ambient pressure and temperature to yield intermediate 1i.

The intermediate 20 can also be subjected to reaction with hydroxyl amine hydrochloride salt in polar protic solvent such as ethanol at reflux temperature to afford substituted isoxazole (as described in Cadilla, R., et al. WO 03/074495 A1). The nitro intermediate so obtained can be reduced in presence of catalyst such as Pd and hydrogen gas at ambient pressure and temperature to yield intermediate 1h.

SCHEME 8

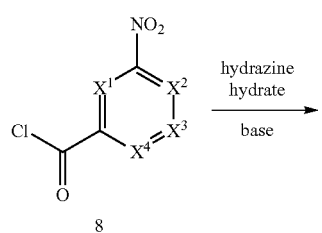

Intermediate 8 can be coupled with hydrazine hydrate in a polar aprotic solvent (e.g. THF, 1,4-dioxane DMF, and MeCN) and in presence of base (e.g. Et$_3$N and DIPEA) to obtain intermediate 21. Intermediate 21 can be subjected to reaction with substituted amide in presence of trifluoromethanesulfonic anhydride and 2-fluoropyridine under heating conditions to afford intermediate 22 as described by Charette, A. B. et al. *Org. Lett.*, 2015, 17, 1184-1187. Intermediate 22 so obtained can be reduced, using the conditions recognized by one skilled in the art including but not limited to reduction in the presence of a catalyst such as Pd and hydrogen gas at ambient pressure and temperature to yield intermediate 1j.

SCHEME 9

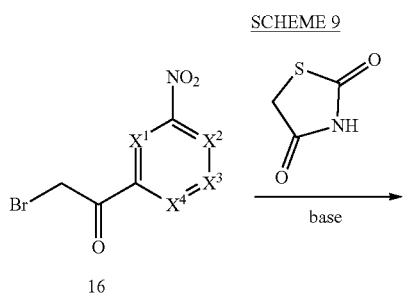

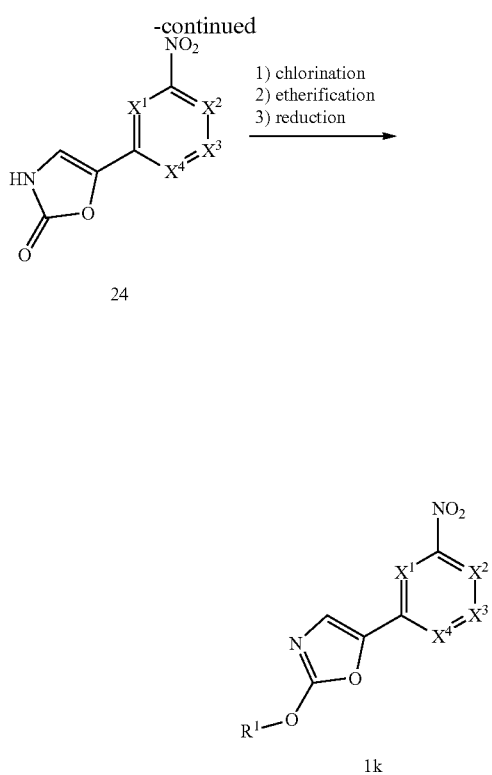

Scheme 9 describes the synthesis of intermediates 1k. Intermediate 16 can be obtained from commercial sources or can be synthesized by known methods or their modifications readily recognizable by one skilled in the art (described as in *Bioorg & Med. Chem. Lett.*, 2017, 2% 2192-2196). Intermediate 16 can be treated with thiazolidinedione in polar solvents such as DMF and DMAc in presence of base such as $K_2CO_3$ and $Na_2CO_3$ at room temperature or heating conditions to afford intermediate 24 (as described in Brown, M. L. et al. WO 2004/032882 A2). Intermediate 24 can be treated with reagents such as $POCl_3$ and $SOCl_2$ in presence of base such as $Et_3N$ and DIPEA for chlorination (as described in Brown, M. L. et al. WO 2004/032882 A2) followed by treatment with metal alkoxides to afford corresponding substituted intermediates which upon reduction as described in Scheme 3 afford intermediate 1k.

Scheme 10 describes synthesis of intermediates 11 (where $Y^2$ is 'N'-atom). Intermediates 85 and 86 can be obtained from commercial sources or can be synthesized by known methods readily recognizable by one skilled in the art. Intermediates 85 and 86 can be subjected to various metal catalyzed reactions (including but not limited to reactions such as Ullmann and Buchwald) in presence of metal catalyst (e.g. CuI, CuBr, $Cu(OAc)_2$, $Cu_2O$, $Pd(OAc)_2$, $Pd_2(dba)_3$, and $Pd(dppf)Cl_2$) and appropriate ligand (including but not limited to ligands such as 1,10-phenanthroline, L-proline, tricyclohexylphosphine, dppf, and β-ketoesters) when necessary. The Ullmann and Buchwald coupling reactions of intermediate 85 and 86 can be carried out with various coupling partners including but not limited to substituted or unsubstituted pyrrole, pyrazole, imidazole, triazole, indole, indazole, benzimidazole, benzotriazole, and cyclic amides. The coupling reactions can be carried out in presence of base whenever necessary (bases including but not limited to $Na_2CO_3$, $K_2CO_3$, $Cs_2CO_3$, $K_3PO_4$, NaOtBu, and DBU) and solvent (e.g. dioxane, THF, DME, MeCN, DMSO, DMF, and MeOH) under heating conditions to afford intermediate 11 from intermediate 86. The coupled N-linked heteroaryl nitro intermediate obtained from 85 can be subjected to reduction using the conditions recognized by one skilled in the art including but not limited to reduction in presence of catalyst such as Pd and hydrogen gas or Zn and ammonium chloride or Fe and acetic acid to yield intermediate 11.

SCHEME 10B

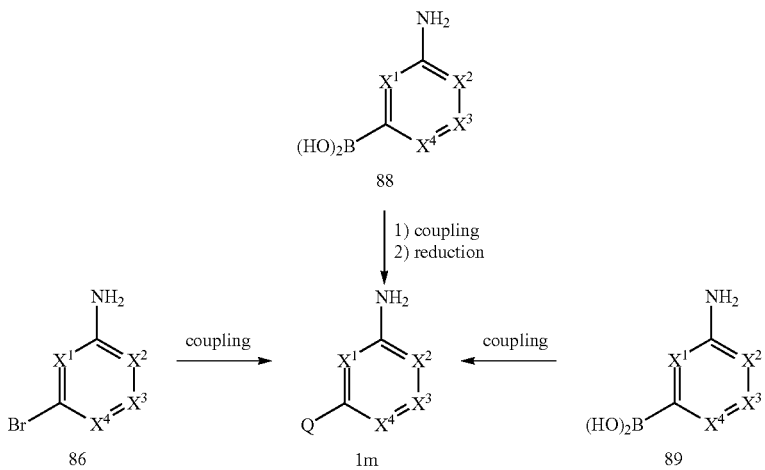

Intermediate 1m can be accessed in various ways as depicted in Scheme 11. Intermediates 86, 88 and 89 can be obtained from commercial sources or can be synthesized by known methods readily recognizable by one skilled in the art. Intermediates 86, 88 and 89 can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediate 86, 88 and 89 can be subjected to various metal catalyzed reactions (including but not limited to reactions such as Ullmann, Buchwald, Suzuki, and Stille coupling). These coupling reactions can be carried out in presence of metal catalyst (e.g. CuBr, Pd(OAc)$_2$, Pd$_2$(dba)$_3$, Pd(PPh$_3$)$_4$, Pd(PPh$_3$)$_2$Cl$_2$, and Pd(dppf)Cl$_2$) and appropriate ligand (including but not limited to ligands such as proline, 1,10-phenanthroline, tricyclohexylphosphine, and dppf) when required. The Ullmann and Buchwald coupling reactions of intermediate 86 can be carried out with various coupling partners such as heterocyclyl or heteroaryl amines. The Suzuki, Chan-Lam coupling reaction of intermediate 88 and 89 can be carried out with various coupling partners such as cycloalkenyl, aryl or heteroaryl halides, and triflates. Intermediate 86 can be subjected to Suzuki and Stille, cross couplings with coupling partners such as cycloalkyl or alkenyl or aryl or heteroaryl boronic acids, boronic acid esters, and organotin reagents. The coupling reactions can be carried out in presence of base as necessary (including but not limited to Na$_2$CO$_3$, K$_2$CO$_3$, NaHCO$_3$, K$_3$PO$_4$, and NaOtBu) and solvent (e.g. dioxane, THF, DME, toluene, methanol, DMF, and water, or the mixture of two or more of these solvents) under heating conditions to afford intermediate 1m. Alternatively, intermediate 86 can be converted to organotin reagent using hexamethylditin in presence of a palladium catalyst and in solvent (e.g. Toluene and THF) at reflux temperature, which upon coupling with suitable coupling partners such as cycloalkenyl, aryl or heteroaryl halides, and triflates in a Stille coupling (Sherer, B., et al. PCT Int. Appl., 2016/039734, 2016) to afford intermediate 1m. Intermediate 86 can be converted to organoboron reagent using, for example, bis(pinacolato)diboron or bis(neopentyl glycolato)diboron in presence of a palladium catalyst such as Pd(dppf)Cl$_2$ and base such as potassium acetate in solvent (e.g. dioxane and DMSO) at reflux temperature, which then can be coupled with suitable coupling partners such as cycloalkenyl, aryl or heteroaryl halides, and triflates in a Suzuki coupling to afford intermediate 1m. Intermediate 88 followed by the coupling reactions as described above afforded the nitro intermediate, which can be reduced using the conditions recognized by one skilled in the art including but not limited to reduction in presence of catalyst such as Pd and hydrogen gas at ambient pressure and temperature to yield intermediate 1m.

SCHEME 10C

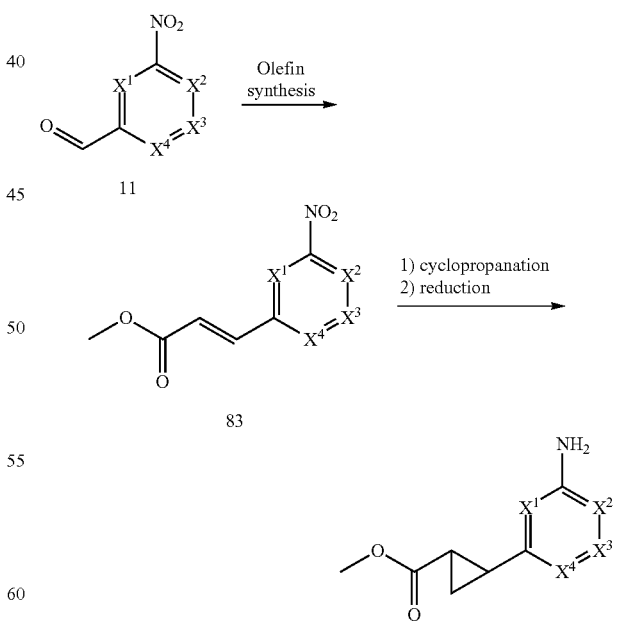

Scheme 10C describes the synthesis of intermediates 1n. Intermediate 11 can be obtained from commercial sources or can be synthesized by known methods readily recognizable by one skilled in the art. Intermediate 11 can be subjected to reaction with alkyl 2-(dimethoxyphosphoryl)acetate in presence of a base (e.g. $K_2CO_3$ and $Na_2CO_3$) in polar protic solvent (e.g. water, methanol, and ethanol) to afford intermediate 83. Intermediate 83 can be subjected to cyclopropanation reaction by treating it with diazomethane solution at −78° C. in solvent mixture containing diethyl ether and DCM in presence of $Pd(OAc)_2$ to afford nitro intermediate, which can be reduced to intermediate in using the conditions recognized by one skilled in the art including but not limited to one described such as heating in presence of reagent such as tin(II) chloride in polar protic solvent. Intermediate in can be converted to compounds of formula I by using steps described in Scheme 1.

Intermediates 2 (Scheme 1) can be accessed in various ways as depicted in Scheme 11 using numerous known methods recognized by the one skilled in the art including but not limited to the following methods.

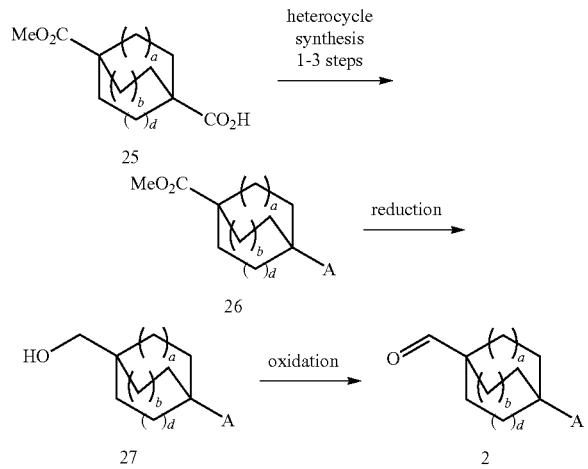

SCHEME 11

Scheme 11 describes the synthesis of intermediate 2. Commercially available 4-(methoxycarbonyl)bicyclo[2.2.2] octane-1-carboxylic acid 25 can be subjected to heterocycle ring synthesis to afford compounds of intermediate 26.

Heterocycle formation (A). The carboxylic acid moiety of compound 25 can be converted to various heterocycles (A) using numerous known methods recognized by one skilled in the art, including but not limited to the following methods:

A=1,2,4-oxadiazole. Intermediate 25 can be coupled with various amide oximes (derived from the corresponding nitriles by reaction with hydroxylamine; see Hirawat, S., et al. WO 2006/110483) using an amide bond coupling reagent (e.g. CDI, BOP, and EDC) in a polar aprotic solvent (e.g. THF, 1,4-dioxane, and DMF) at room temperature. The acyclic intermediate can be subsequently cyclized at elevated temperatures (60° C. to 100° C.). Alternatively, in situ cyclization can be accomplished by conducting the coupling of acid 25 with amide oximes at elevated temperatures (60° C. to 100° C.).

A=1,2,5-oxadiazole. Intermediate 25 can be converted to 1,2,5-oxadiazole as described in Broström, J. et al. *J. Med. Chem.* 2012, 55, 1817-1830 and references described therein.

A=1,3,4-oxadiazole or A=1,3,4-thiadiazole. Intermediate 25 can be coupled with acetic acid hydrazide (described in WO 2014/071247, Bradner, J. E., et al.), using an amide bond coupling reagent (e.g. CDI, BOP, and EDC) in a polar aprotic solvent (e.g. THF, 1,4-dioxane DMF, and MeCN). The acyclic hydrazide intermediate can then be cyclized to either 1,3,4-oxadiazole or 1,3,4-thiadiazole using respectively, 4-toluenesulfonic acid (Stabile, P. et al. *Tetrahedron Lett.* 2010, 51, 4801-4805) or Laweson's reagent (Kitamura, S., et al. PCT Int. Appl., 2008011130, 2008).

A=3-substituted 5-alkyl-1-methyl-1H-pyrazole. Methyl ketones can be treated with base and acid chloride of intermediate 25 to afford a diketone, which upon reaction with substituted or unsubstituted hydrazine salt in polar protic solvent such as ethanol at reflux temperature afforded ester 26 where A is alkyl substituted or unsubstituted pyrazole. (As described in Cadilla, R., et al. WO 03/074495 A1).

A=Isoxazole. The diketone prepared from intermediate 25 as described above can be upon reaction with hydroxyl amine hydrochloride salt in polar protic solvent such as ethanol at reflux temperature afforded ester 26 where A is alkyl substituted isoxazole (as described in Cadilla, R., et al. WO 03/074495 A1).

A=5-(3-alkyl-1-methyl-1H-pyrazole). The diketone prepared from intermediate 25 as described above can be upon reaction with alkyl hydrazine in polar protic solvent such as ethanol at reflux temperature afforded ester 26 where A is alkyl substituted pyrazole.

A=substituted heteroaryl. Intermediate 25 can be subjected to Minisci reaction with substituted heteroaryl compounds such as quinoline and pyrazole in presence of silver nitrate and potassium persulfate or ammonium persulfate in DCM (or any other conditions that can be used to generate carbon-centered radical) and water mixture as a solvent at ambient temperature to afford ester 26 (as described in Ling-Bo, Qu et al. *Org. Biomol. Chem.*, 2015, 13, 2750-2755 and Review: Duncton, M. A. *J. Med. Chem. Commun.*, 2011, 2, 1135-1161 and references described therein).

A=2-Benzothiazole. Method A: Intermediate 25 can be coupled with substituted 2-aminobenzenethiol (See generally Chedekel, M. R., et al. *Synth. Commun.* 1980, 10, 167-173; synthesis of various 2-aminobenzenethiols), using an amide bond coupling reagent (e.g. BOP, T3P, and EDC) in a polar aprotic solvent (e.g. DCE and THF). The coupling reaction can be conducted at elevated temperatures (60° C. to 80° C.) thereby accomplishing the in situ formation of the cyclized 2-benzothiazole.

Method B: Alternatively, intermediate 25 can be coupled with substituted 2-chloroaniline (commercial available) using an amide bond coupling reagent (e.g. T3P and BOP), or by activating intermediate 25 for acylation using any number of reagents (e.g. oxalyl chloride, and $POCl_3$). The resultant carboxamide can be treated with Lawesson's reagent at elevated temperature (120° C.), thereby accomplishing an in situ cyclization to 2-benzothiazole.

A=2-Benzoxazole. Intermediate 25 can be coupled with substituted 2-aminophenol (commercial available) using an amide bond coupling reagent (e.g. BOP and EDC) in a polar aprotic solvent (e.g. DMF and THF). Cyclization can be accomplished in refluxing toluene in the presence of tosic acid.

A=2-Benzimidazole. Intermediate 25 can be coupled with ethyl 3,4-diaminobenzoate using an amide bond coupling reagent (e.g. TBTU, T3P, and PyBOP) in a polar aprotic solvent (e.g. DMF and NMP), then cyclized to the 2-benzimidazole under acidic conditions (AcOH neat) at elevated temperatures (115° C.).

A=2-Quinazoline. Intermediate 25 can be coupled with 4-amino-3-(aminomethyl)benzoate dihydrochloride (Pascal, R. et al. *Eur. J. Org. Chem.* 2000, 22, 3755-3761), using an amide bond coupling reagent (e.g. HBTU, EDC, and PyBOP) in a polar aprotic solvent (e.g. MeCN and THF). Cyclization can be accomplished under acidic conditions (AcOH neat) at elevated temperatures (115° C.). The resultant dihydroquinazoline intermediate can be oxidized to the 2-quinazoline using an oxidizing agent such as DDQ.

A=1-triazole. Intermediate 25 can be converted to corresponding amine via Curtius rearrangement (as described in Shioiri, T. et al. *J. Am. Chem. Soc.* 1972, 94, 6203-6205). The amine upon treatment with reagent such asp-toluene sulfonyl azide can be converted to corresponding azide which upon reaction with suitable alkyne (as described in Boren, B. C. et al *J. Am. Chem. Soc.,* 2008, 130, 8923-8930) afforded triazole.

A=Substituted 1,2,4-triazole. Intermediate 25 can be converted to corresponding hydrazide and can be subjected to reaction with substituted carboxamide in presence of trifluoromethanesulfonic anhydride and 2-fluoropyridine under heating conditions as described by Charette, A. B. et al. *Org. Lett.,* 2015, 17, 1184-1187.

'A' can be other heterocycles such as substituted as well as unsubstituted oxazoles, thiazoles imidazoles, isoxazoles, triazoles, pyrazoles and can be synthesized as described in reference: Wlochal, J. et al *Org. Lett.* 2014, 16, 4094-4097 and references cited therein. Alternatively, acid functional group of intermediate 25 can be converted to heterocycles as described in schemes 2-9 using methods and literature references described therein.

Intermediate 26 can be subjected to reduction by a reducing agent (e.g. LAH, DIBAL-H, and NaBH$_4$) in chlorinated or ethereal solvent (e.g. DCM, ether, 1,4-dioxane, and THF) to afford intermediate 27. Intermediate 27 can be oxidized by methodologies recognized by one skilled in the art using oxidation conditions (e.g. Dess-Martin periodane, Swern oxidation conditions, and PDC) to afford intermediate 2.

Scheme 12 (FIG. 1) describes an alternative synthesis of compounds of Formula I with the modified sequence of steps. Commercially available 4-(methoxycarbonyl)bicyclo[2.2.2]octane-1-carboxylic acid 25 can be subjected to reduction in presence of hydride based reducing agent (e.g. LAH, DIBAL-H, and NaBH$_4$) to afford intermediate 28. Intermediate 28 can be oxidized to intermediate 29, by methodologies recognized by one skilled in the art using oxidation conditions (e.g. Dess-Martin periodane, Swern oxidation conditions, PDC, and PCC). The intermediate 1 and intermediate 29 can be reacted in presence of acid such as acetic acid in a suitable polar protic solvent (e.g. MeOH and EtOH) at room temperature or reflux temperature followed by reduction with reducing agents (e.g. sodium cyanoborohydride and sodium triacetoxyborohydride) to afford intermediate 30. Intermediate 4 can be activated for acylation using any number of reagents recognizable by one skilled in the art (e.g. Thionyl chloride, phosphorus oxychloride, oxalyl chloride, methylchloroformate, and ethylchloroformate) in a polar aprotic solvent (e.g. DCM and THF), at temperatures ranging between −30° C. to 0° C. The activated acid intermediate can be reacted with intermediate 30 in presence of a base to generate corresponding amide. Subsequent hydrolysis of the methyl ester with an alkali hydroxide base can provide intermediate 31. Intermediate 31 can be converted to various heterocycles (A) using numerous known methods recognized by one skilled in the art, including but not limited to the methods described in Scheme 11 to afford compounds of formula I.

Alternatively, intermediate 29 and intermediate 86 can be subjected to reductive amination using numerous known methods recognizable by one skilled in the art. The imine synthesis in presence of acid such as acetic acid in a suitable polar protic solvent (e.g. MeOH and EtOH) at room temperature or reflux temperature followed by reduction of imine with reducing agents (e.g. sodium cyanoborohydride and sodium triacetoxyborohydride) afforded intermediate 30a. Intermediate 4 can be activated for acylation using any number of reagents recognizable by one skilled in the art (e.g. Thionyl chloride, phosphorus oxychloride, oxalyl chloride, methylchloroformate, and ethylchloroformate), in a polar aprotic solvent (e.g. DCM and THF) at temperatures ranging between −30° C. to 0° C. The activated acid intermediate can be reacted with intermediate 30a in presence of a base to generate corresponding amide. Subsequent hydrolysis of the methyl ester with an alkali hydroxide base can provide intermediate 31a. Intermediate 31a can be converted to various heterocycles (A) using numerous known methods recognized by one skilled in the art, including but not limited to the methods described in Scheme 11 to afford intermediate 31b. Intermediate 31b can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediate 31b can be subjected to various metal catalyzed reactions (including but not limited to reactions such as Ullmann, Buchwald, Suzuki, and Stille coupling). These coupling reactions can be carried out in presence of metal catalyst (for example, CuBr, Pd(OAc)$_2$, Pd$_2$(dba)$_3$, Pd(PPh$_3$)$_4$, Pd(PPh$_3$)$_2$Cl$_2$, and Pd(dppf)Cl$_2$) and appropriate ligand (including but not limited to ligands such as proline, 1,10-phenanthroline, tricyclohexylphosphine, and dppf) when required. The Ullmann and Buchwald coupling reactions of intermediate 31b can be carried out with various coupling partners such as heterocyclyl or heteroaryl amines. Intermediate 31b can be subjected to Suzuki and Stille cross couplings with coupling partners such as cycloalkyl or alkenyl or aryl or heteroaryl boronic acids, boronic acid esters, and organotin reagents. The coupling reactions can be carried out in presence of base as necessary (including but not limited to Na$_2$CO$_3$, K$_2$CO$_3$, NaHCO$_3$, K$_3$PO$_4$, and NaOtBu) and solvent (e.g. dioxane, THF, DME, toluene, methanol, DMF, and water or the mixture of two or more of these solvents) under heating conditions to afford compounds of formula I. Alternatively, intermediate 31b can be converted to organotin reagent using hexamethylditin in presence of a palladium catalyst and in solvent (e.g. Toluene and THF) at reflux temperature, which upon coupling with suitable coupling partners such as cycloalkenyl, aryl or heteroaryl halides, and triflates in a Stille coupling (Sherer, B., et al. PCT Int. Appl., 2016/039734, 2016) afforded compounds represented by formula I. Intermediate 31b can be converted to organoboron reagent using bis(pinacolato)diboron and bis(neopentyl glycolato)diboron in presence of a palladium catalyst such as Pd(dppf)Cl$_2$ and base such as potassium acetate in solvent (e.g. dioxane and DMSO) at reflux temperature, which upon coupling with suitable coupling partners such as cycloalkenyl, aryl or heteroaryl halides, and triflates in a Suzuki coupling afforded compounds represented by formula I.

Figure 2:
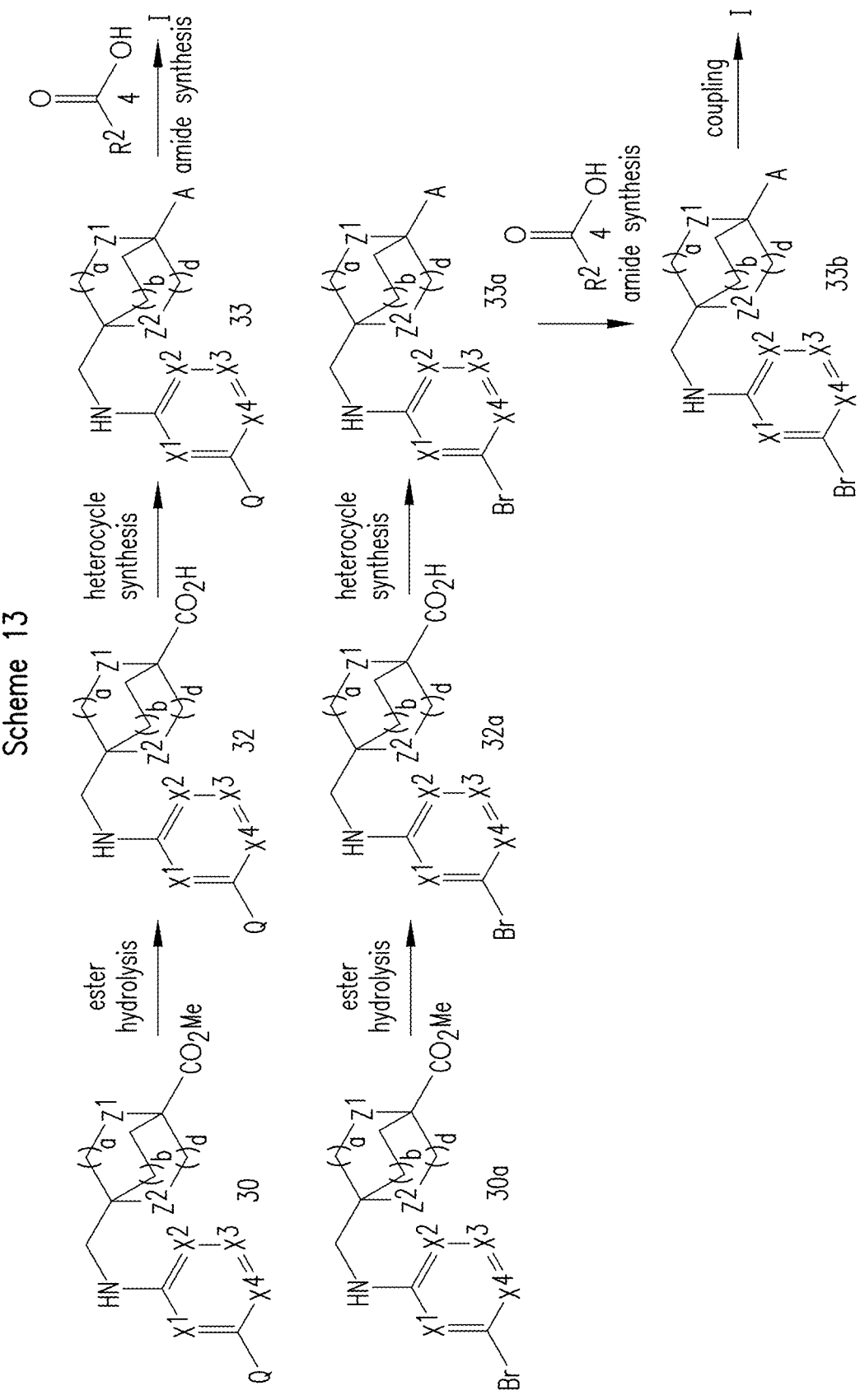
FIG. 2 shows the general reaction Scheme 13.

Scheme 13 (FIG. 2) describes an alternative synthesis of compounds of Formula I with the modified sequence of steps.

Intermediate 30 (described in Scheme 12) can be subjected to hydrolysis of the methyl ester with an alkali hydroxide base to provide intermediate 32. Intermediate 32 (or intermediate 100) can be converted to various heterocycles (A) using numerous known methods recognized by one skilled in the art, including but not limited to the methods described in Scheme 11 to afford compounds of formula 33. Intermediate 4 can be activated for acylation using any number of reagents recognizable by one skilled in the art (e.g. Thionyl chloride, phosphorus oxychloride, oxalyl chloride, methylchloroformate, and ethylchloroformate), in a polar aprotic solvent (e.g. DCM and THF) at temperatures ranging between −30° C. to 0° C. The activated acid intermediate can be reacted with intermediate 33 in presence of a base to generate compounds of formula I.

Alternatively, intermediate 30a (described in Scheme 12) can be subjected to hydrolysis of the methyl ester with an alkali hydroxide base to provide intermediate 32a. Intermediate 32a (or intermediate 100a) can be converted to various heterocycles (A) using numerous known methods recognized by one skilled in the art, including but not limited to the methods described in Scheme 11 to afford compounds of formula 33a. Intermediate 4 can be activated for acylation using any number of reagents recognizable by one skilled in the art (e.g. Thionyl chloride, phosphorus oxychloride, oxalyl chloride, methylchloroformate, and ethylchloroformate), in a polar aprotic solvent (e.g. DCM and THF) at temperatures ranging between −30° C. to 0° C. The activated acid intermediate can be reacted with intermediate 33a in presence of a base to generate intermediate 33b. Intermediate 33b can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. The amide intermediate can be subjected to various metal catalyzed reactions (including, for example, reactions such as Ullmann, Buchwald, Suzuki, and Stille coupling). These coupling reactions can be carried out in presence of metal catalyst (e.g. CuBr, Pd(OAc)$_2$, Pd$_2$(dba)$_3$, Pd(PPh$_3$)$_4$, Pd(PPh$_3$)$_2$Cl$_2$, and Pd(dppf)Cl$_2$) and appropriate ligand (including but not limited to ligands such as proline, 1,10-phenanthroline, tricyclohexylphosphine, and dppf) when required. The Ullmann and Buchwald coupling reactions of intermediate 33b can be carried out with various coupling partners such as heterocyclyl or heteroaryl amines. Intermediate 33b can be subjected to Suzuki and Stille cross couplings with coupling partners such as cycloalkyl or alkenyl or aryl or heteroaryl boronic acids, boronic acid esters, and organotin reagents. The coupling reactions can be carried out in presence of base as necessary (including but not limited to Na$_2$CO$_3$, K$_2$CO$_3$, NaHCO$_3$, K$_3$PO$_4$, and NaOtBu) and solvent (e.g. dioxane, THF, DME, toluene, methanol, DMF, and water or the mixture of two or more of these solvents) under heating conditions to afford compounds of formula I. Alternatively, intermediate 33b can be converted to organotin reagent using hexamethylditin in presence of a palladium catalyst and in solvent (e.g. Toluene and THF) at reflux temperature, which upon coupling with suitable coupling partners such as cycloalkenyl, aryl or heteroaryl halides, and triflates in a Stille coupling (Sherer, B., et al. PCT Int. Appl., 2016/039734, 2016) afforded compounds represented by formula I. Intermediate 33b can be converted to organoboron reagent using bis(pinacolato)diboron and bis(neopentyl glycolato) diboron in the presence of a palladium catalyst such as Pd(dppf)Cl$_2$ and base such as potassium acetate in solvent (e.g. dioxane and DMSO) at reflux temperature, which upon coupling with suitable coupling partners such as cycloalkenyl, aryl or heteroaryl halides, and triflates in a Suzuki coupling afforded compounds represented by formula I.

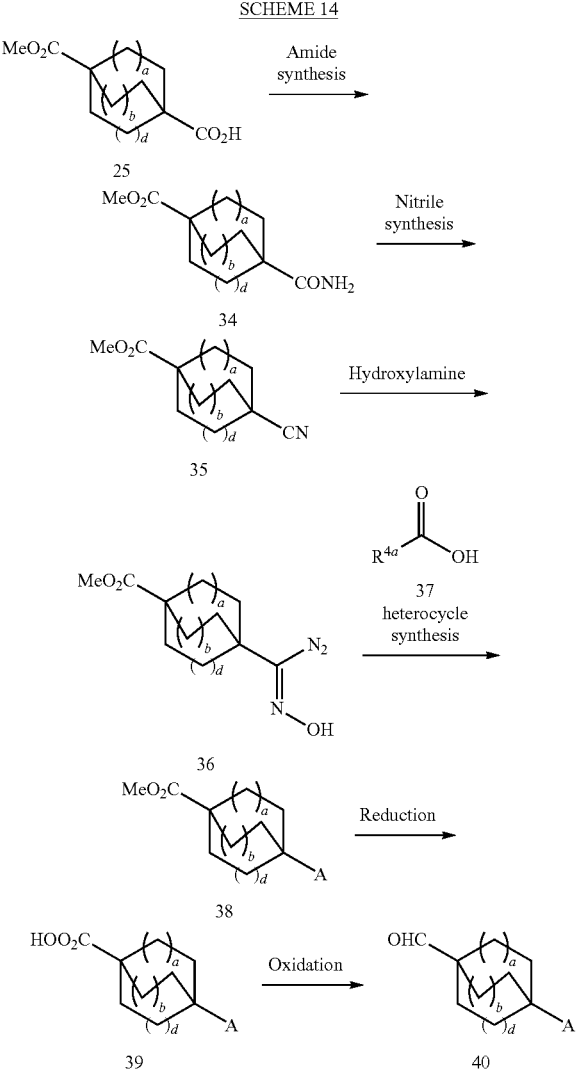

SCHEME 14

Scheme 14 describes the synthesis of intermediate 40 where A is 3-(5-substituted-1,2,4-oxadiazolyl) ring. Commercially available 4-(methoxycarbonyl)bicyclo[2.2.2]octane-1-carboxylic acid 25 can be subjected to amide synthesis by treating with activation agent such as BOP and HATU in presence of solvent such as DCM and DMF and an organic base such as Et$_3$N and DIPEA at ambient temperature in presence of ammonium chloride to afford intermediate 34. Intermediate 34 can be converted to intermediate 35 by treatment with trifluoroacetic anhydride in pyridine at 0° C. or by treatment with POCl$_3$ and a base such as imidazole. Intermediate 36 can be synthesized by reaction of intermediate 35 with hydroxylamine; see Hirawat, S., et al. WO 2006/110483. Variously substituted intermediates 37 can be coupled with intermediates 36 using an amide bond coupling reagent (e.g. CDI, BOP, and EDC) in a polar aprotic solvent (e.g. THF, 1,4-dioxane, and DMF) at room temperature. The acyclic intermediate can be subsequently cyclized at elevated temperatures (60° C. to 100° C.).

Alternatively, in situ cyclization can be accomplished by conducting the coupling of acids 37 with amide oximes 36 at elevated temperatures (60° C. to 100° C.) to afford intermediates of formula 38. Intermediate 38 can be subjected to reduction in presence of hydride based reducing agents (e.g. LAH, DIBAL-H, and NaBH₄) in chlorinated or ethereal solvent such as DCM, ether, 1,4-dioxane, and THF to afford intermediate 39. Intermediate 39 can be oxidized to intermediate 40, by methodologies recognized by one skilled in the art using oxidation conditions (e.g. Dess-Martin periodane, Swern oxidation conditions, PDC, and PCC). Intermediates 40 can be converted to compounds of formula I by steps described in Scheme 1.

Figure 3:
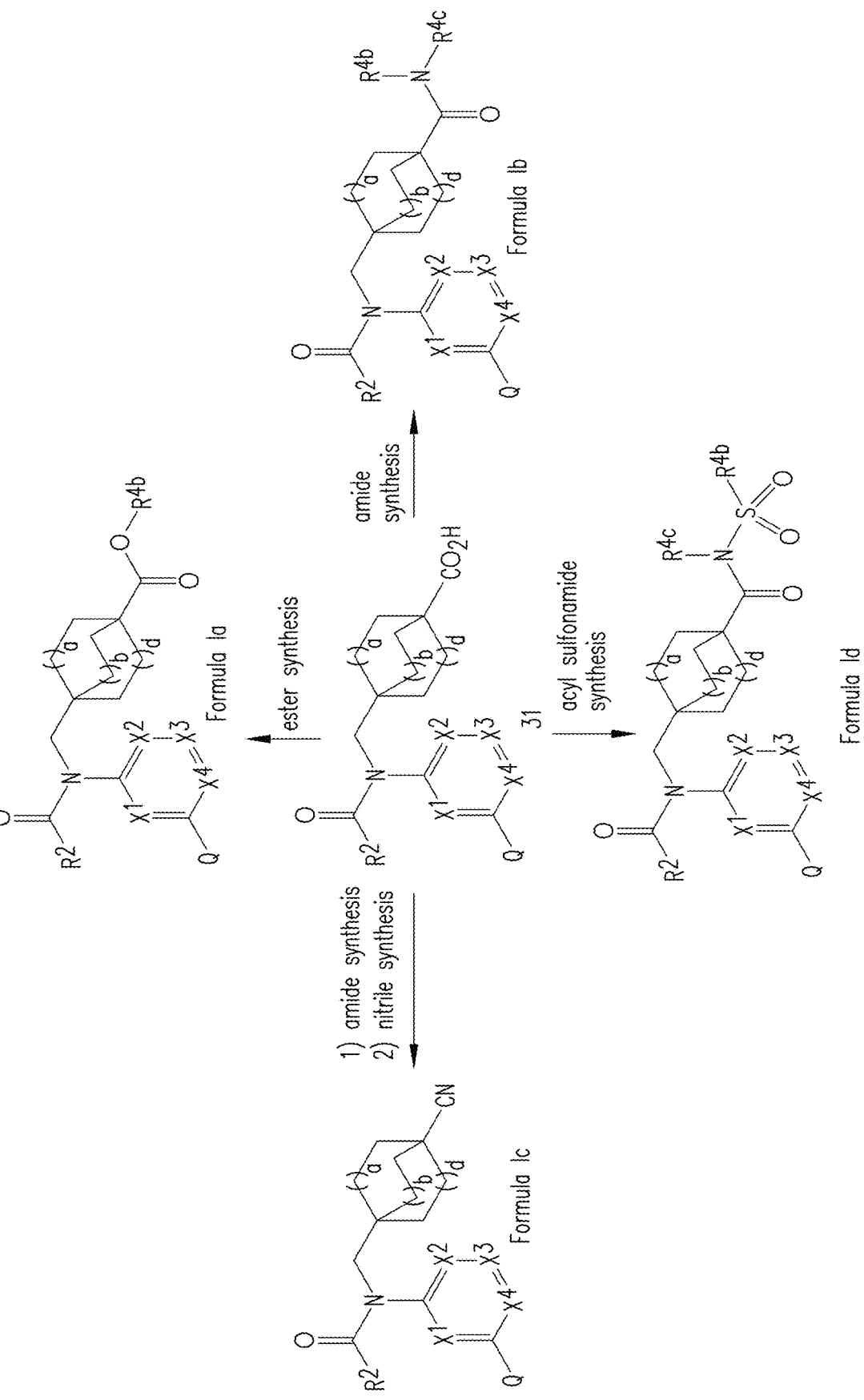
FIG. 3 shows the general reaction Scheme 15.

Scheme 15 (FIG. 3) describes the synthesis of compounds of formula I(a-d). The intermediates represented by formula 31 (synthesis described in Scheme 12) can be subjected to esterification. Intermediate 31 can be activated for acylation using any number of reagents recognizable by one skilled in the art (e.g. Thionyl chloride, phosphorus oxychloride, oxalyl chloride, methylchloroformate, and ethylchloroformate), in a polar aprotic solvent (e.g. DCM and THF), at temperatures ranging between −30° C. to 0° C. The activated acid intermediate can be reacted with alcohols in presence of a base to generate compounds of formula Ia. Intermediate 31 can be subjected to amide synthesis by activating acid with activation agent (e.g. BOP, CDI, and HATU) in solvent (e.g. DCM and DMF) in presence of base (e.g. Et₃N and DIPEA) at ambient temperature or heating conditions in presence of ammonium chloride or substituted amine (e.g. alkyl, cycloalkyl, aryl, and heteroaryl amines) to afford amides of formula Ib. Intermediate 31 can be subjected to primary amide synthesis by treating with activation agent (e.g. BOP, CDI, and HATU) in solvent (e.g. DCM and DMF) in presence of base (e.g. Et₃N and DIPEA) and ammonium chloride at ambient temperature. The primary amide so obtained can be treated with i) trifluoroacetic anhydride in pyridine at 0° C. or ii) POCl₃ and imidazole to afford nitriles of formula Ic. Intermediate 31 can be activated using any number of reagents recognizable by one skilled in the art (e.g. Thionyl chloride, phosphorus oxychloride, oxalyl chloride, methylchloroformate, and ethylchloroformate), in a polar aprotic solvent (e.g. DCM and THF), at temperatures ranging between −30° C. to 0° C. The activated acid intermediate can be reacted with a sulfonamides in presence of a base (e.g. pyridine, DMAP, 2-(dimethylamino)pyridine, and N-methylmorpholine) in a polar aprotic solvent (e.g. DCM and THF), at temperatures ranging between 0° C. to 90° C. to generate acyl sulfonamides of formula Id.

SCHEME 16

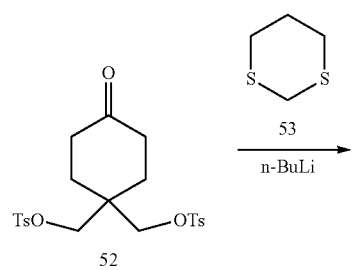

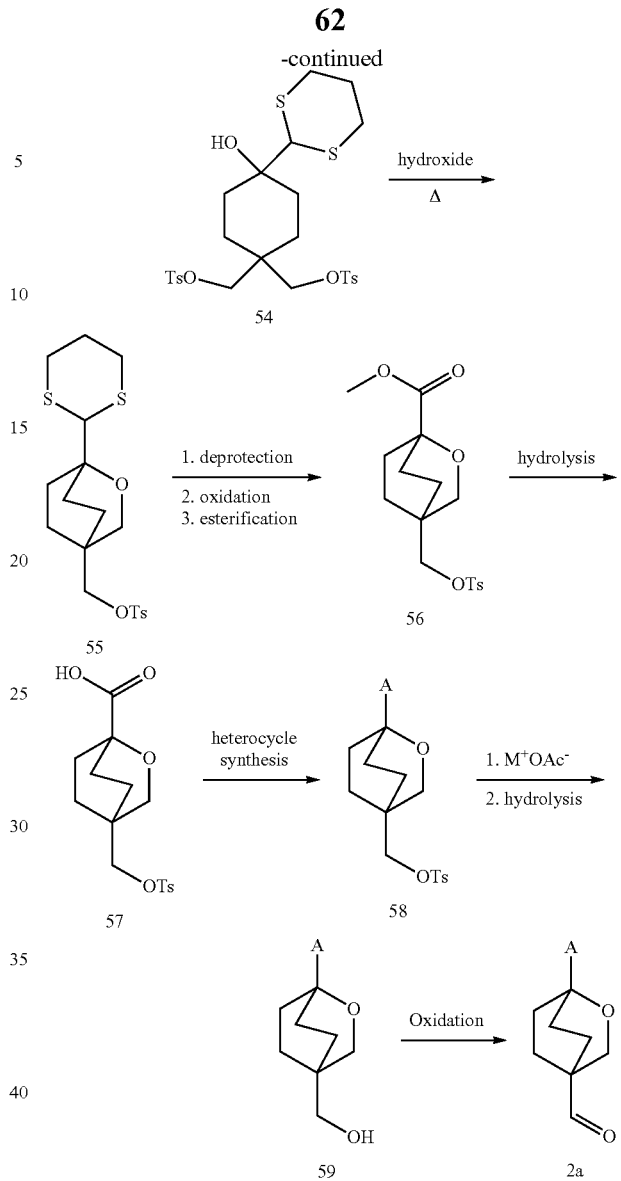

Scheme 16 describes the synthesis of intermediate 2a. Intermediate 52 can be synthesized according to methods described by Singh, S. B. et al. (*ACS Med. Chem. Lett.* 2014, 5, 609-614). Intermediate 53 can be deprotonated with n-BuLi in an ethereal solvent (e.g. THF and 1,4-dioxane) with temperature varying between −78° C. and 0° C., then reacted with intermediate 52 to yield intermediate 54. Intermediate 54 can be cyclized in the presence of an alkali hydroxide base at elevated temperature (70° C.) to form intermediate 55. Thioacetal deprotection can be accomplished using any number of reagents (e.g. NCS, Hg(ClO₄)₂, and DDQ) to provide the aldehyde, which can be oxidized to the acid by use of an oxidizing agent (NaClO₂, PCC or PDC, and KMnO₄) then subsequently esterified by reaction with iodomethane to provide intermediate 56. Subsequent hydrolysis of the intermediate 56 with an alkali hydroxide base can provide intermediate 57. Intermediate 57 can be converted to various heterocycles (A) using numerous known methods recognized by one skilled in the art, including but not limited to the methods described in Scheme 11 to afford compounds of intermediate 58. Intermediate 58 can be treated with an acetate salt (e.g. CsOAc, and KOAc) in a polar aprotic solvent (e.g. DMF and NMP) at elevated temperatures (120° C.) to provide corresponding acetate, which upon subsequent hydrolysis under acidic conditions (HCl) afforded intermediate 59. Intermediate 59 can be oxidized by methodologies recognized by one skilled in the art using oxidation conditions (e.g. Dess-Martin periodane, Swern oxidation conditions, PDC, and PCC) to afford compounds of formula 2a. The intermediates 2a can be converted to compounds of formula I by using steps described in Scheme 1.

oxidized by methodologies recognized by one skilled in the art using oxidation conditions (e.g. Dess-Martin periodane, Swern oxidation conditions, PDC, and PCC) to afford intermediate 2b. Intermediate 2b can be converted to compounds of formula I by using steps described in Scheme 1.

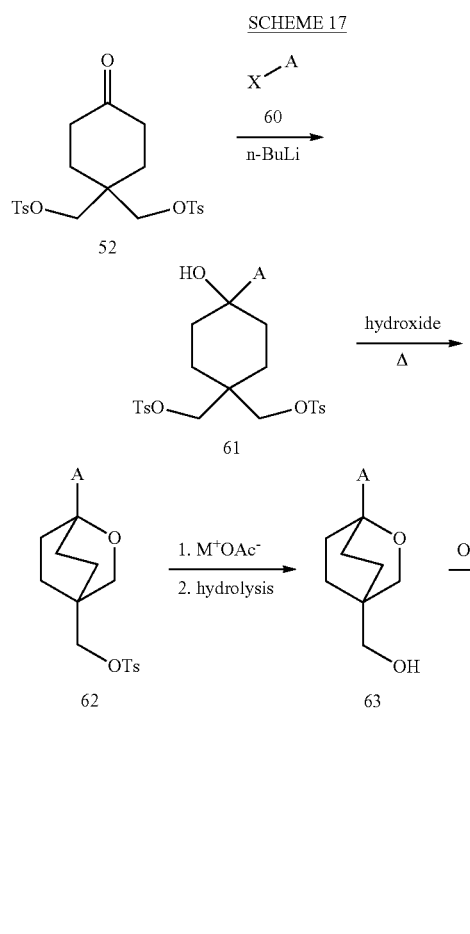

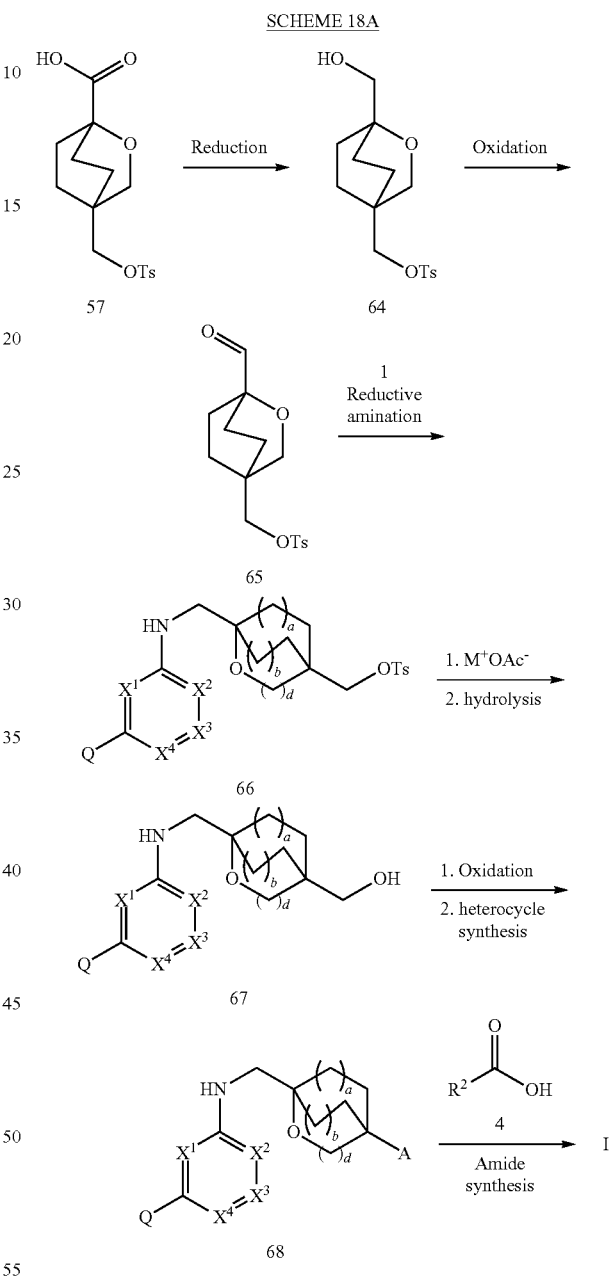

Scheme 17 describes an alternative synthesis of intermediate 2b. Intermediate 52 can be synthesized according to methods described by Singh, S. B. et al. (*ACS Med. Chem. Lett.* 2014, 5, 609-614). Halogenated heterocycles, 60, (commercially available or obtained by methods known by one skilled in the art) can be treated with base such as (n-BuLi, s-BuLi, and MeLi) in an ethereal solvent (e.g. THF and 1,4-dioxane) with temperature varying between −78° C. and 0° C., and then reacted with ketone 52 to afford intermediate 61. Intermediate 61 can be cyclized in the presence of an alkali hydroxide base at elevated temperature (70° C.) to afford intermediate 62. Intermediate 62 can be treated with an acetate salt (e.g. CsOAc and KOAc) in a polar aprotic solvent (e.g. DMF and NMP) at elevated temperatures (120° C.) to provide corresponding acetate, which upon subsequent hydrolysis under acidic conditions (HCl) afforded intermediate 63. Intermediate 63 can be Scheme 18A describes an alternative synthesis of compounds of Formula I. Intermediate 57 (synthesis described in Scheme 16) can be subjected to reduction in presence of hydride based reducing agent (e.g. LAH, DIBAL-H, and NaBH₄) to afford intermediate 64. The intermediate 64 can be oxidized to aldehyde 65, by methodologies recognized by one skilled in the art using oxidation conditions (e.g. Dess-Martin periodane, Swern oxidation conditions, PDC, and PCC). The intermediate 1 and intermediate 65 can be subjected to reductive amination, using numerous known methods recognizable by one skilled in the arts, in presence of acid such as acetic acid in a suitable polar protic solvent (e.g. MeOH and EtOH) at room temperature or reflux temperature followed by reduction of imine with reducing agents (e.g. sodium cyanoborohydride and sodium triacetoxyborohydride) afforded intermediate 66. Intermediate 66 can be treated with an acetate salt (e.g. CsOAc and KOAc) in a polar aprotic solvent (e.g. DMF and NMP) at elevated temperatures (120° C.) to provide corresponding acetate, which upon subsequent hydrolysis under acidic conditions (HCl) afforded intermediate 67. The intermediate 67 can be oxidized to the acid by use of an oxidizing agent (NaClO$_2$, PCC, PDC, and KMnO$_4$) followed by synthesis of various heterocycles (A) using numerous known methods recognized by one skilled in the art, including but not limited to the methods described in Scheme 11 to afford intermediate 68. Intermediate 4 can be activated for acylation using any number of reagents recognizable by one skilled in the art (e.g. Thionyl chloride, phosphorus oxychloride, oxalyl chloride, methylchloroformate, and ethylchloroformate) in a polar aprotic solvent (e.g. DCM and THF) at temperatures ranging between −30° C. to 0° C. The activated acid intermediate can be reacted with intermediate 68 in presence of a base to generate compounds of formula I.

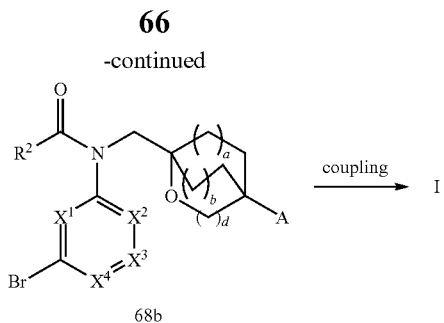

Scheme 18B describes an alternative synthesis of compounds of Formula I. The intermediate 86 and intermediate 65 (as described in Scheme 18A) can be subjected to reductive amination, using numerous known methods recognizable by one skilled in the art, in presence of acid such as acetic acid in a suitable polar protic solvent (e.g. MeOH and EtOH) at room temperature or reflux temperature followed by reduction of imine with reducing agents (e.g. sodium cyanoborohydride and sodium triacetoxyborohydride) afforded intermediate 66a. Intermediate 66a can be treated with an acetate salt (e.g. CsOAc and KOAc) in a polar aprotic solvent (e.g. DMF and NMP) at elevated temperatures (120° C.) to provide corresponding acetate, which upon subsequent hydrolysis under acidic conditions (HCl) afforded intermediate 67a. The intermediate 67a can be oxidized to the acid by use of an oxidizing agent (NaClO$_2$, PCC, PDC, and KMnO$_4$) followed by synthesis of various heterocycles (A) using numerous known methods recognized by one skilled in the art, including but not limited to the methods described in Scheme 11 to afford intermediate 68a. Intermediate 68a can be converted to compounds of formula I by following steps described in Scheme 13.

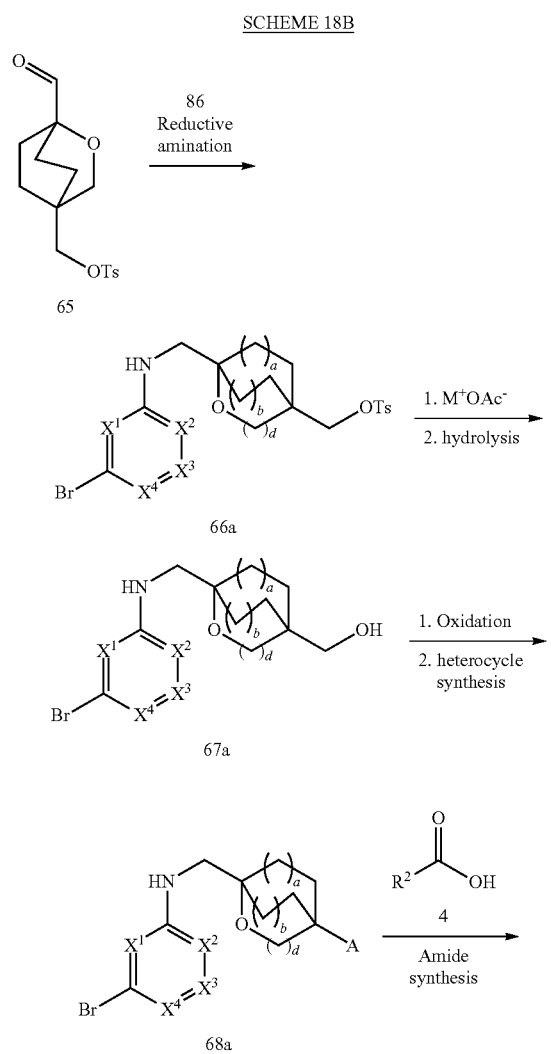

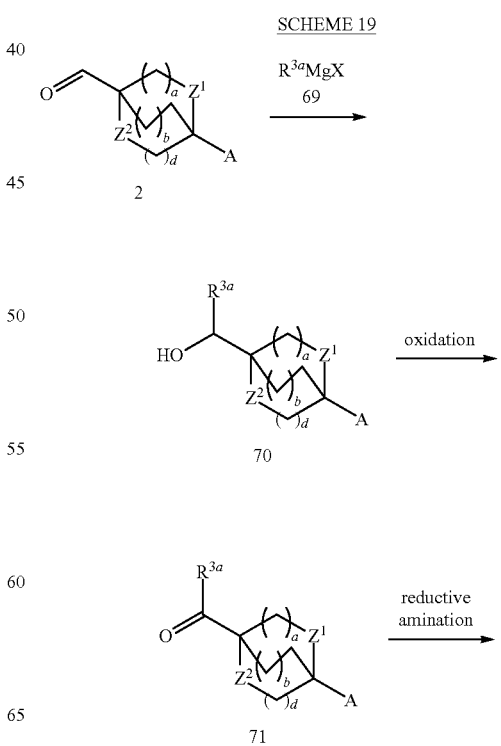

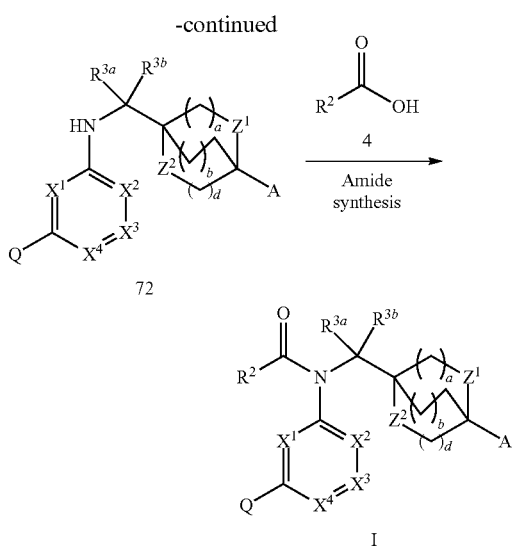

Scheme 19 describes an alternative synthesis of compounds of Formula I. Intermediate 2 can be subjected to treatment with organo magnesium reagents in ethereal solvent (such as $Et_2O$ and THF) with temperature varying between −78° C. and 0° C. to afford intermediate 70. The intermediate 70 can be oxidized to intermediate 71, by methodologies recognized by one skilled in the art under oxidation conditions using oxidizing agents such as Dess-Martin periodane, PDC, and PCC. Intermediate 71 and intermediate 1 in polar protic solvent such as MeOH and EtOH, can be treated with triethyl silane and indium chloride at ambient temperature to afford intermediates of formula 72. Intermediate 4 can be activated for acylation using any number of reagents recognizable by one skilled in the art (e.g. Thionyl chloride, phosphorus oxychloride, oxalyl chloride, methylchloroformate, and ethylchloroformate) in a polar aprotic solvent (e.g. DCM and THF) at temperatures ranging between −30° C. to 0° C. The activated acid intermediate can be reacted with intermediate 72 in presence of a base to generate compounds of formula I.

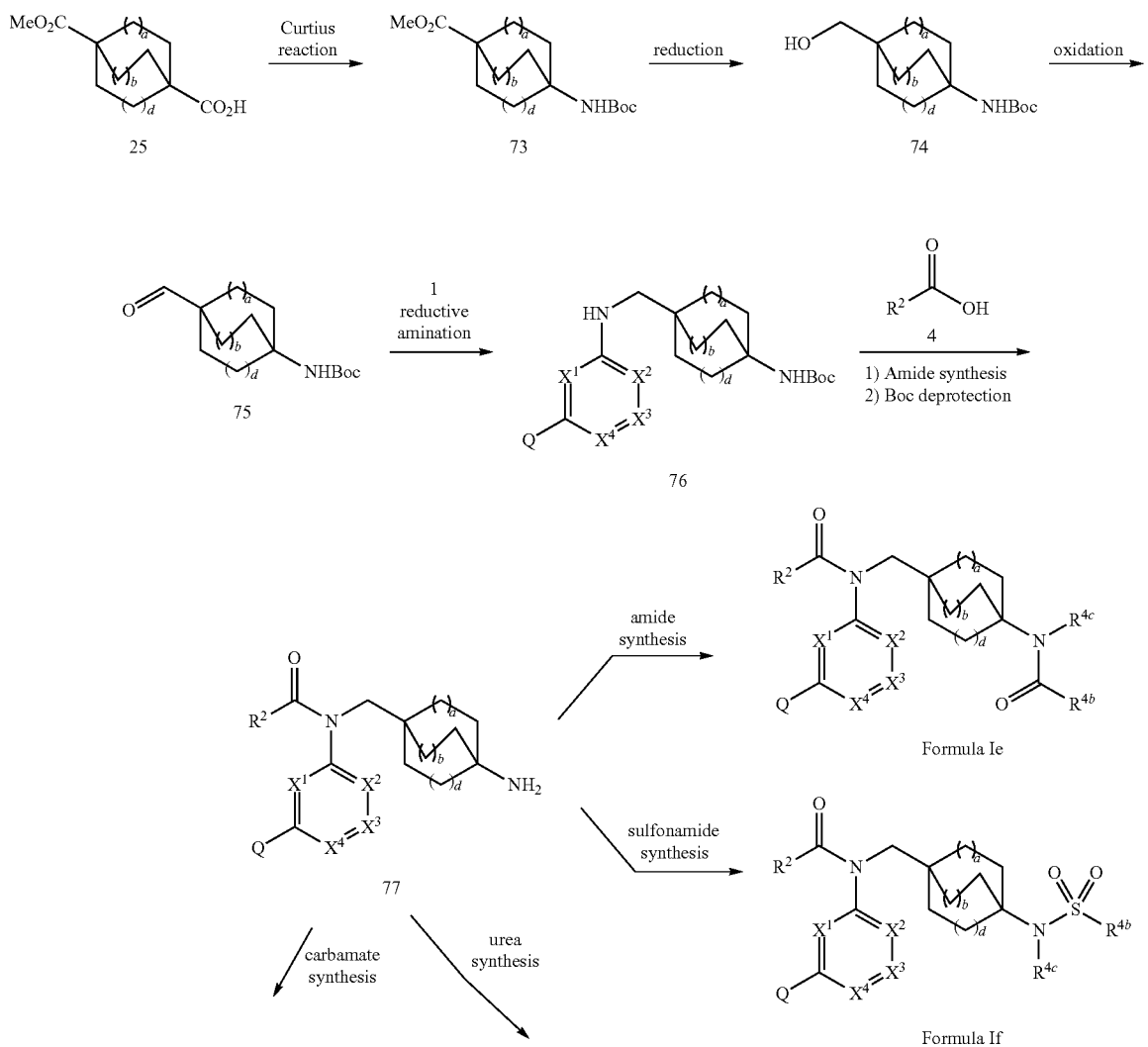

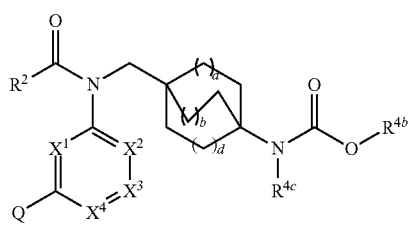

Formula Ih

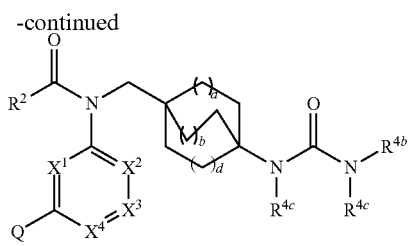

Formula Ig

Scheme 20 describes synthesis of compounds of formula I(e-g) (where 'A' is amide, sulfonamide, urea or carbamate). Intermediate 25 can be converted to intermediate 73 via Curtius rearrangement (as described in Shioiri, T. et al. *J. Am. Chem. Soc.* 1972, 94, 6203-6205). Intermediate 73 can be subjected to reduction in presence of hydride based reducing agent (e.g. LAH, DIBAL-H, and NaBH$_4$) to afford intermediate 74. The intermediate 74 can be oxidized to aldehyde 75, by methodologies recognized by one skilled in the art using oxidation conditions (e.g. Dess-Martin periodane, Swern oxidation conditions, PDC, and PCC). The intermediate 1 and intermediate 75 can be subjected to reductive amination, using numerous known methods recognizable by one skilled in the art, in presence of acid such as acetic acid in a suitable polar protic solvent (e.g. MeOH and EtOH) at room temperature or reflux temperature followed by reduction of imine with reducing agents (e.g. sodium cyanoborohydride and sodium triacetoxyborohydride) to afford intermediate 76. Intermediate 4 can be activated for acylation using any number of reagents recognizable by one skilled in the art (e.g. Thionyl chloride, phosphorus oxychloride, oxalyl chloride, methylchloroformate, and ethylchloroformate), in a polar aprotic solvent (e.g. DCM and THF) at temperatures ranging between −30° C. to 0° C. The activated acid intermediate can be reacted with intermediate 76 in presence of a base to generate corresponding amide. The amide intermediate can be subjected to Boc-deprotection in polar aprotic solvent (e.g. DCM and THF) using trifluoroacetic acid at room temperature to afford intermediate 77. Intermediate 77 can be subjected to a variety of different transformations using numerous known methods recognized by one skilled in the art, including but not limited to the following methods to afford variations of Formula I:

Amides: Intermediate 77 can be reacted with activated acid intermediates in presence of base (e.g. pyridine, DMAP, 2-(dimethylamino)pyridine, and N-methylmorpholine) in polar aprotic solvent (e.g. DCM and THF) to generate amides of Formula Ie.

Sulfonamides: Intermediate 77 can be treated with sulfonyl chlorides in presence of a base (e.g. pyridine, DMAP, 2-(dimethylamino)pyridine, and N-methylmorpholine) in a polar aprotic solvent at temperatures ranging between 0° C. to 90° C. to generate sulfonamides of Formula If.

Ureas: Intermediate 77 can be subjected to treatment with isocyanates in presence of base (e.g. Et$_3$N, DIPEA, and pyridine) in polar aprotic solvent (e.g. DCM and DCE) at room temperature to afford ureas represented by formula Ig. Alternatively, intermediate 77 can be activated by treatment with triphosgene in presence of base (e.g. Et$_3$N and DIPEA) in solvent (e.g. DCM and DCE) at 0° C. to room temperature. The activated intermediate 77 can then be treated with substituted alkyl or aryl or heteroaryl amine in presence of base (e.g. Et$_3$N and DIPEA) in solvent (e.g. DCM and DCE) at room temperature to afford ureas represented by formula Ig.

Carbamates: Intermediate 77 can be treated with chloroformates (or alcohols, activated as carbonates) in presence of base (e.g. Et$_3$N, DIPEA, and pyridine) in polar aprotic solvent (e.g. DCM, DCE, and THF) at 0° C. to room temperature to afford carbamates represented by formula Ih.

SCHEME 21

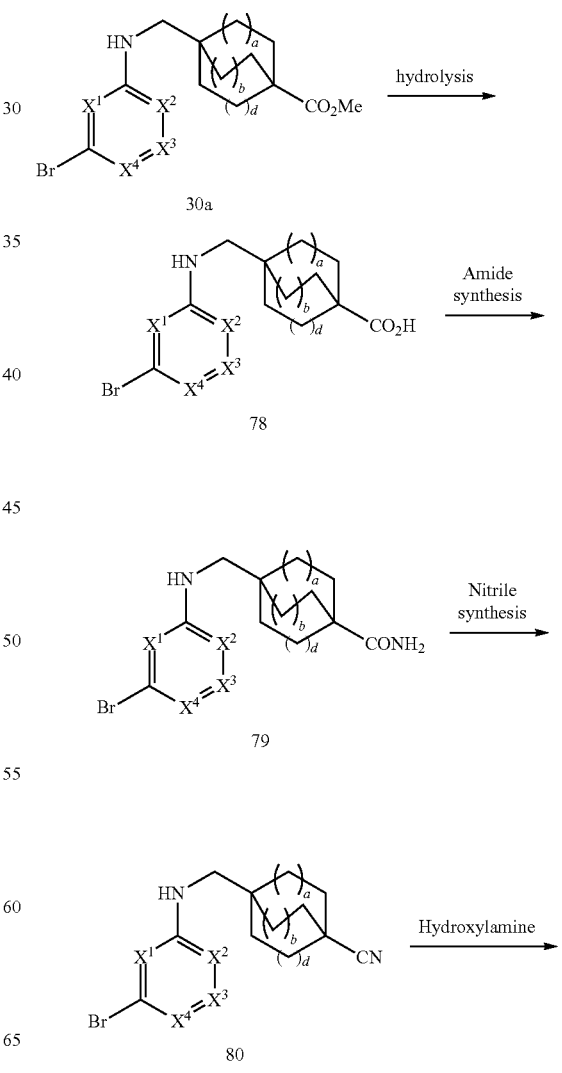

-continued

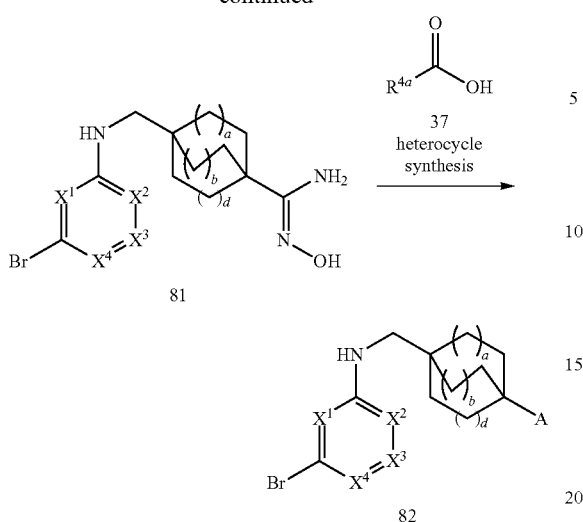

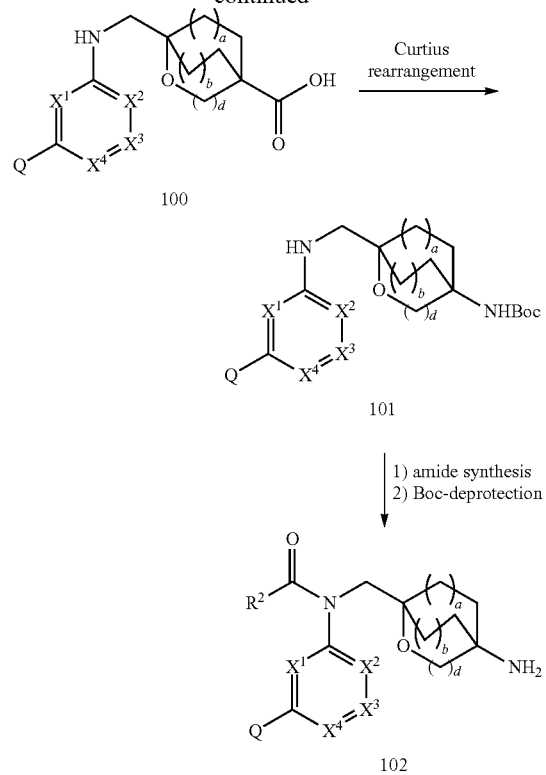

Scheme 21 describes the synthesis of intermediates 82 where A is 3-(5-substituted-1,2,4-oxadiazolyl) ring. Intermediate 30a (synthesized as described in Scheme 12) can be hydrolyzed with an alkali hydroxide base to afford intermediate 78. Intermediate 78 can be subjected to primary amide synthesis by activating acid with activation agent (BOP, CDI, and HATU) in polar aprotic solvent (DCM and DMF) in presence of base (e.g. $Et_3N$ and DIPEA) at ambient temperature in presence of ammonium chloride to afford intermediate 79. Intermediate 79 can be converted to intermediate 80 using various methods recognized by those skilled in the art including but not limited to the treatment with reagent (for example, $POCl_3$, $SOCl_2$, and TFAA) and base (imidazole, $Et_3N$, and DIPEA). Intermediate 81 can be synthesized by reaction of intermediate 80 with hydroxylamine; see Hirawat, S., et al. WO 2006/110483. Intermediate 37 can be obtained from commercial sources or can be synthesized by known methods readily recognizable by one skilled in the art. Intermediates 37 can be coupled with intermediates 81 using an amide bond coupling reagent (e.g. CDI, BOP, and EDC) in a polar aprotic solvent (e.g. THF, 1,4-dioxane, and DMF) at room temperature. The acyclic intermediate can be subsequently cyclized at elevated temperatures (60° C. to 100° C.). Alternatively, in situ cyclization can be accomplished by conducting the coupling of intermediates 37 with intermediates 81 at elevated temperatures (60° C. to 100° C.) to afford oxadiazoles 82. Intermediates 82 can be converted to compounds of formula I via a sequential amide synthesis and coupling as described in Scheme 13.

SCHEME 22

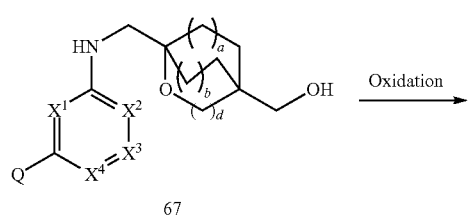

Scheme 22 describes alternative synthesis of compounds of formula I (where 'A' is amide, sulfonamide, urea or carbamate). Intermediate 67 (synthesized as described in Scheme 18A) can be oxidized by use of an oxidizing agent ($NaClO_2$, PCC, PDC, and $KMnO_4$) to afford intermediate 100. Intermediate 100 can be converted to intermediate 101 via Curtius rearrangement (as described in Shioiri, T. et al. J. Am. Chem. Soc. 1972, 94, 6203-6205). Intermediates 101 can be subjected to sequential amide synthesis and boc-deprotection as described in Scheme 20 to afford the amine intermediate 102. Intermediate 102 can be subjected to a variety of different transformations using numerous known methods recognized by one skilled in the art, including but not limited to the methods described in Scheme 20 to afford variations of Formula I (where 'A' is amide, sulfonamide, urea or carbamate).

Figure 4:
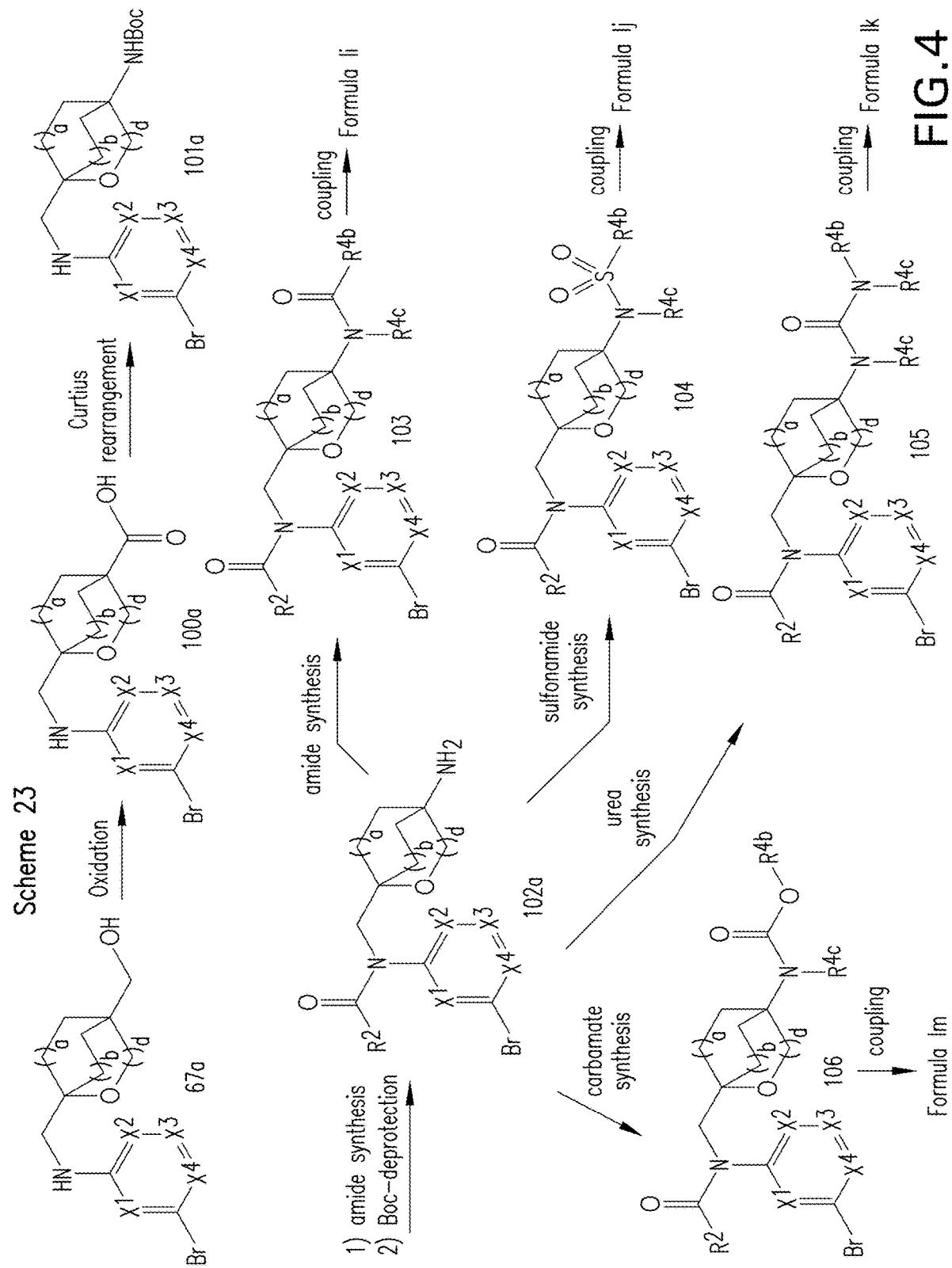
FIG. 4 shows the general reaction Scheme 23.

Scheme 23 (FIG. 4) describes synthesis of compounds of formula I(i,j,k,m) (where 'A' is amide, sulfonamide, urea or carbamate). Intermediate 67a (synthesized as described in Scheme 181B) can be oxidized by use of an oxidizing agent ($NaClO_2$, PCC, PDC, and $KMnO_4$) to afford intermediate 100a. Intermediate 100a can be converted to intermediate 101a via Curtius rearrangement (as described in Shioiri, T. et al. J. Am. Chem. Soc. 1972, 94, 6203-6205). Intermediates 101a can be subjected to sequential amide synthesis and boc-deprotection as described in Scheme 20 to afford the amine intermediate 102a.

Intermediate 102a can be subjected to a variety of different transformations using numerous known methods recognized by one skilled in the art, including but not limited to the following methods to afford variations of Formula I:

Amides: Intermediate 102a can be reacted with activated acid intermediates in presence of base (e.g. pyridine, DMAP, 2-(dimethylamino)pyridine, and N-methylmorpholine) in polar aprotic solvent (e.g. DCM and THF) to generate intermediate 103.

Sulfonamides: Intermediate 102a can be treated with sulfonyl chlorides in presence of a base (e.g. pyridine, DMAP, 2-(dimethylamino)pyridine, and N-methylmorpholine) in a polar aprotic solvent (e.g. DCM and THF) at temperatures ranging between 0° C. to 90° C. to generate intermediate 104.

Ureas: Intermediate 102a can be subjected to treatment with isocyanates in presence of base (e.g. Et$_3$N, DIPEA, and pyridine) in polar aprotic solvent (e.g. DCM and DCE) at room temperature to afford intermediate 105. Alternatively, intermediate 102a can be activated by treatment with triphosgene in presence of base (e.g. Et$_3$N and DIPEA) in solvent (e.g. DCM and DCE) at 0° C. to room temperature. The activated intermediate 102a can then be treated with substituted alkyl or aryl or heteroaryl amine in presence of base (e.g. Et$_3$N and DIPEA) in solvent (e.g. DCM and DCE) at room temperature to afford intermediate 105.

Carbamates: Intermediate 102a can be treated with chloroformates (or alcohols, activated as carbonates) in presence of base (e.g. Et$_3$N, DIPEA, and pyridine) in polar aprotic solvent (e.g. DCM, DCE, and THF) at 0° C. to room temperature to afford intermediate 106.

Intermediates 103-106 can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediates 103-106 can be subjected to various metal catalyzed reactions (including but not limited to reactions such as Ullmann, Buchwald, Suzuki, and Stille coupling) These coupling reactions can be carried out in presence of metal catalyst (e.g. CuBr, Pd(OAc)$_2$, Pd$_2$(dba)$_3$, Pd(PPh$_3$)$_4$, Pd(PPh$_3$)$_2$Cl$_2$, and Pd(dppf)Cl$_2$) and appropriate ligand (including but not limited to ligands such as proline, 1,10-phenanthroline, tricyclohexylphosphine, and dppf) as and when required. The Ullmann and Buchwald coupling reactions of intermediates 103-106 can be carried out with various coupling partners such as heterocyclyl and heteroaryl amines. Intermediates 103-106 can be subjected to Suzuki and Stille cross couplings with coupling partners such as cycloalkyl or alkenyl or aryl or heteroaryl boronic acids, boronic acid esters, and organotin reagents. The coupling reactions can be carried out in presence of base as necessary (including but not limited to Na$_2$CO$_3$, K$_2$CO$_3$, NaHCO$_3$, K$_3$PO$_4$, and NaOtBu) and solvent (e.g. dioxane, THF, DME, toluene, methanol, DMF, and water, or the mixture of two or more of these solvents) under heating conditions to afford compounds of formula I. Alternatively, intermediates 103-106 can be converted to organotin reagent using hexamethylditin in presence of a palladium catalyst and in solvent (e.g. Toluene and THF) at reflux temperature, which upon coupling with suitable coupling partners such as cycloalkenyl, aryl or heteroaryl halides, and triflates in a Stille coupling (Sherer, B., et al. PCT Int. Appl., 2016/039734, 2016) afforded compounds represented by formula I. Intermediates 103-106 can be converted to organoboron reagent using bis(pinacolato)diboron and bis(neopentyl glycolato)diboron in presence of a palladium catalyst such as Pd(dppf)Cl$_2$ and base such as potassium acetate in solvent (e.g. dioxane and DMSO) at reflux temperature, which upon coupling with suitable coupling partners such as cycloalkenyl, aryl halides, heteroaryl halides, and triflates in a Suzuki coupling afforded compounds represented by formula I(i,j, k,m).

The sequence of the steps involving installation of groups 'Q' and 'A' can be interchangeably performed in the scheme as appropriate. The oxadiazole regio-isomers can be generated by using sequence described in schemes 11 and 14 attached to the oxabicyclo ring system.

Example 1

N-((4-(3-methyl-1,2,4-oxadiazol-5-yl)bicyclo[2.2.2]octan-1-yl)methyl)-N-(3-(3-methyl-1,2,4-oxadiazol-5-yl)phenyl)cyclohexanecarboxamide

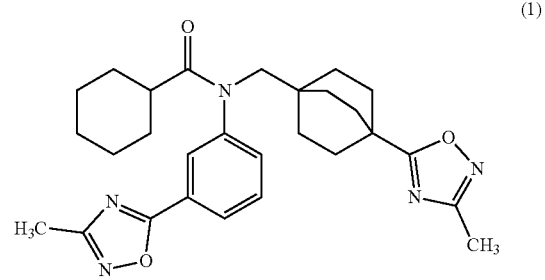 [SMILES: Cc1noc(-c2cccc(N(CC34CCC(c5nc(C)no5)(CC3)CC4)C(=O)C3CCCCC3)c2)n1]

(1)

Step A. Intermediate 1A. Preparation of methyl 4-(3-methyl-1,2,4-oxadiazol-5-yl) bicyclo[2.2.2]octane-1-carboxylate

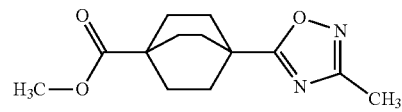

To a stirred solution of 4-(methoxycarbonyl)bicyclo[2.2.2]octane-1-carboxylic acid (2 g, 9.42 mmol) in DMF (20 mL) were added (E)-N'-hydroxyacetimidamide (1.4 g, 19 mmol), BOP (4.17 g, 9.4 mmol) followed by TEA (3.94 mL, 28.3 mmol) at room temperature. The reaction mixture was stirred at room temperature for 2 h and then heated at 110° C. overnight. The reaction mixture was cooled to room temperature and poured into water (100 mL). The aqueous layer was extracted with EtOAc (2×30 mL). The combined organic layers were washed with water, brine solution, dried over anhydrous sodium sulphate and concentrated under reduced pressure. The crude material was purified by flash chromatography (12 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (0.6 g, 2.28 mmol, 24% yield) as white solid. $^1$H NMR (400 MHz, DMSO-d$_6$) δ 3.60 (s, 3H), 2.29 (s, 3H), 1.95-1.86 (m, 6H), 1.86-1.78 (m, 6H).

Step B. Intermediate 1B. Preparation of (4-(3-methyl-1,2,4-oxadiazol-5-yl) bicyclo[2.2.2]octan-1-yl)methanol

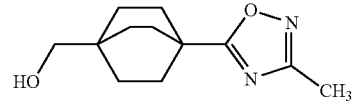

A solution of Intermediate 1A (0.6 g, 2.397 mmol) in tetrahydrofuran (20 mL) was cooled to −78° C. DIBAL-H (6 mL, 6 mmol) was added drop wise to the reaction under nitrogen atmosphere. The reaction mixture was allowed to warm to room temperature and stirred for 1 h. The reaction mixture was cooled to 0° C. and quenched with aq. 1.5 N HCl solution (20 mL) and diluted with water (30 mL). The reaction mixture was extracted with EtOAc (2×25 mL). The combined organic extracts were washed with brine (10 mL), dried over anhydrous sodium sulphate, filtered and concentrated under reduced pressure. The crude material was purified by flash chromatography (24 g silica gel cartridge; A=Hex, B=EtOAc; 30 min grad.; 0% B to 50% B; flow rate=40 mL/min). The pure fractions were combined, concentrated under reduced pressure and dried in vacuo to afford the title compound (0.58 g, 2.35 mmol, 98% yield) as off-white solid. $^1$H NMR (400 MHz, DMSO-$d_6$) δ 4.41 (br. s., 1H), 3.08 (s, 2H), 2.29 (s, 3H), 1.90-1.80 (m, 6H), 1.50-1.40 (m, 6H).

Step C. Intermediate 1C. Preparation of 4-(3-methyl-1,2,4-oxadiazol-5-yl)bicyclo[2.2.2]octane-1-carbaldehyde

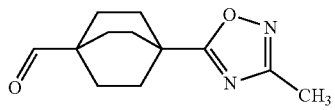 [SMILES: Cc1noc(C23CCC(C=O)(CC2)CC3)n1]

To a stirred solution of Intermediate 1B (0.58 g, 2.61 mmol) in dichloromethane (10 mL) was added Dess-Martin periodinane (2.21 g, 5.22 mmol) at 0° C. under nitrogen atmosphere. The reaction mixture was stirred at the same temperature for 1 h. The reaction mixture was allowed to warm to room temperature and filtered through Celite bed. The filtrate was washed with aq. 10% sodium bicarbonate solution (2×50 mL). The organic layer was dried over anhydrous sodium sulphate and concentrated under reduced pressure. The crude material was purified by flash chromatography (12 g silica gel cartridge; A=Hex, B=EtOAc; 30 min grad.; 0% B to 20% B; flow rate=24 mL/min). The pure fractions were combined, concentrated under reduced pressure and dried in vacuo to afford the title compound (0.46 g, 1.98 mmol, 76% yield) as white solid. $^1$H NMR (400 MHz, DMSO-$d_6$) δ 9.46 (s, 1H), 2.30 (s, H), 1.96-1.84 (m, 6H), 1.73-1.66 (m, 6H).

Step D. Intermediate 1D. Preparation of 3-methyl-5-(3-nitrophenyl)-1,2,4-oxadiazole

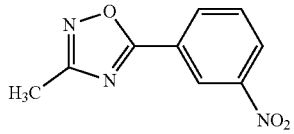

To a stirred solution of 3-nitrobenzoic acid (1 g, 5.98 mmol, commercially available) in DMF (10 mL) were added (E)-N'-hydroxyacetimidamide (0.887 g, 11.97 mmol, commercially available), BOP (2.65 g, 5.98 mmol) followed by TEA (2.50 mL, 17.95 mmol) at room temperature. The reaction mixture was stirred at room temperature for 1 h and then heated at 100° C. for 2 h. The reaction mixture was cooled to room temperature, poured into water (50 mL) and extracted with EtOAc (2×30 mL). The combined organic layers were washed with water, brine solution, dried over anhydrous sodium sulphate and concentrated under reduced pressure. The crude material was purified by flash chromatography (24 g silica gel cartridge; A=Hex, B=EtOAc; 30 min grad.; 0% B to 20% B; flow rate=30 mL/min). The pure fractions were combined, concentrated under reduced pressure and dried in vacuo to afford the title compound (0.3 g, 1.39 mmol, 23% yield) as white solid. $^1$H NMR (400 MHz, DMSO-$d_6$) δ 8.75 (s, 1H), 8.50-8.54 (m, 2H), 7.94 (t, J=8.00 Hz, 1H), 2.47 (s, 3H).

Step E. Intermediate 1E. Preparation of 3-(3-methyl-1,2,4-oxadiazol-5-yl)aniline

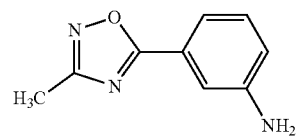

To a stirred solution of Intermediate 1A (0.15 g, 0.73 mmol) in ethanol (5 mL) and water (0.2 mL) was added tin(II) chloride (0.69 g, 3.66 mmol) at room temperature. The reaction mixture was stirred at 90° C. for 2 h. The reaction mixture was cooled to room temperature and concentrated under reduced pressure. The crude material was dissolved in EtOAc (30 mL), washed with aqueous 10% NaHCO$_3$ (10 mL), brine solution (25 mL), dried over anhydrous sodium sulphate and concentrated under reduced pressure. The crude material was purified by flash chromatography (24 g silica gel cartridge; A=Hex, B=EtOAc; 30 min grad.; 0% B to 20% B; flow rate=24 mL/min). The pure fractions were combined, concentrated under reduced pressure and dried in vacuo to afford the title compound (0.13 g, 0.70 mmol, 96% yield) as an off-white solid. $^1$H NMR (400 MHz, DMSO-$d_6$) δ 7.35-7.15 (m, 3H), 6.83 (ddd, J=7.8, 2.3, 1.3 Hz, 1H), 5.54 (s, 2H), 2.39 (s, 3H). MS (ESI) 176 (M+H).

Step F. Intermediate 1F. Preparation of Afford 3-(3-methyl-1,2,4-oxadiazol-5-yl)-N-((4-(3-methyl-1,2,4-oxadiazol-5-yl)bicyclo[2.2.2]octan-1-yl)methyl)aniline

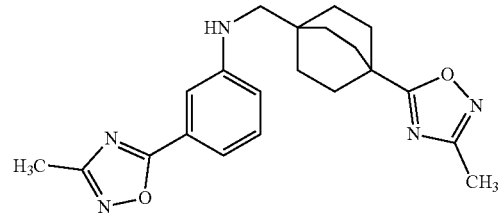 [SMILES: Cc1noc(-c2cccc(NCC34CCC(c5nc(C)no5)(CC3)CC4)c2)n1]

To a stirred solution of Intermediate 1C (50 mg, 0.22 mmol) and Intermediate 1E (39.8 mg, 0.22 mmol) in methanol (2 mL) was added acetic acid (0.03 mL, 0.45 mmol) followed by molecular sieves 4A (5 mg) at room temperature. The reaction mixture was heated at 60° C. for 16 h. The reaction mixture was cooled to 0° C. Sodium cyanoborohydride (28 mg, 0.45 mmol) was added to the reaction mass and stirred for 1 h at room temperature. The reaction mixture was poured into water (10 mL) and extracted with EtOAc (2×20 mL). The combined organic extracts were dried over anhydrous sodium sulphate and concentrated under reduced pressure. The crude material was purified by flash chromatography (12 g silica gel cartridge; A=Hex, B=EtOAc; 30 min grad.; 0% B to 30% B; flow rate=24 mL/min). The pure fractions were combined, concentrated under reduced pressure and dried in vacuo to afford the title compound (70 mg, 0.09 mmol, 41% yield) as a pale yellow solid. MS (ESI) 380 (M+H).

Step G. Example 1. Preparation of N-((4-(3-methyl-1,2,4-oxadiazol-5-yl)bicyclo[2.2.2]octan-1-yl)methyl)-N-(3-(3-methyl-1,2,4-oxadiazol-5-yl)phenyl)cyclohexanecarboxamide To a stirred solution of Intermediate 1F (50 mg, 0.08 mmol) in dichloromethane (2 mL) were added TEA (0.04 mL, 0.24 mmol) followed by cyclohexanecarbonyl chloride (12 mg, 0.08 mmol) 0° C. The reaction mixture was warmed to room temperature and stirred for 1 h. The reaction mixture was concentrated under reduced pressure. The crude material which was purified via preparative HPLC with the following conditions: (Column: Waters XBridge C18, 19×150 mm, 5-μm particles; Mobile Phase A: 10-mM ammonium acetate; Mobile Phase B: acetonitrile; Gradient: 10-45% B over 25 minutes, then a 5-minute hold at 100% B; Flow: 15 mL/min). Fractions containing the product were combined and dried via centrifugal evaporation to afford the title compound (28 mg, 0.057 mmol, 72% yield). $^1$H NMR (400 MHz, DMSO-$d_6$) δ 8.04 (s, 2H), 7.83-7.62 (m, 2H), 3.63 (br. s., 2H), 2.44 (s, 3H), 2.26 (s, 3H), 2.21 (br. s., 1H), 1.86-1.70 (m, 6H), 1.60 (br. s., 4H), 1.48 (br. s., 1H), 1.45-1.27 (m, 8H), 1.09 (d, J=13.0 Hz, 1H), 0.89 (br. s., 2H). FXR $EC_{50}$ (nM) 736; MS (ESI) 490 (M+H).

Example 2

Methyl 5-(3-(N-((4-(3-cyclopropyl-1,2,4-oxadiazol-5-yl)bicyclo[2.2.2]octan-1-yl)methyl)cyclohexanecarboxamido)phenyl)-1,2,4-oxadiazole-3-carboxylate (2)

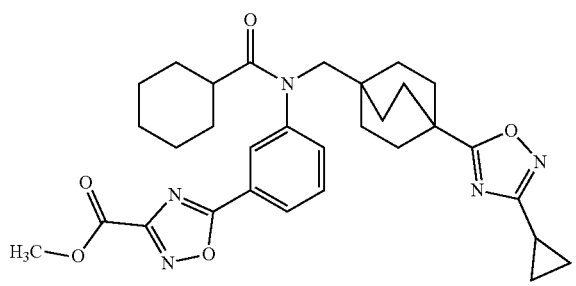

Step A. Intermediate 2A. Preparation of methyl (Z)-2-amino-2-(((3-nitrobenzoyl)oxy)imino)acetate

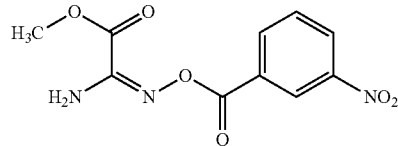 [SMILES: COC(=O)/C(N)=N\OC(=O)c1cccc([N+](=O)[O-])c1]

To a stirred solution of methyl (E)-2-amino-2-(hydroxyimino)acetate (5.60 g, 47.4 mmol, commercially available) and DIPEA (15.06 mL, 86 mmol) in DCM (10 mL) was added 3-nitrobenzoyl chloride (8 g, 43.1 mmol, commercially available) at 0° C. The reaction mixture was warmed to room temperature and stirred for 12 h. The solid material was filtered, washed with petroleum ether and dried in vacuo to afford the title compound (7.4 g, 27.4 mmol, 64% yield) as off white solid. MS (ESI) 266 (M−H).

Step B. Intermediate 2B. Preparation of methyl 5-(3-nitrophenyl)-1,2,4-oxadiazole-3-carboxylate

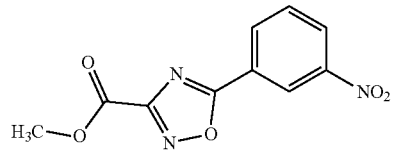 [SMILES: COC(=O)c1noc(-c2cccc(N)c2)n1]

To a stirred solution of Intermediate 2A (7.4 g, 27.7 mmol) in THF (100 mL) was added TBAF 1M solution in THF (28 mL, 27.7 mmol) at 0° C. The reaction mixture was warmed to room temperature and stirred for 3 h. The reaction mixture was poured into cold water (100 mL) and the aqueous solution was extracted with EtOAc (2×50 mL). The combined organic layers were dried over anhydrous sodium sulphate and concentrated under reduced pressure. The crude material was purified by flash chromatography (40 g silica gel cartridge; A=Hex, B=EtOAc; 30 min grad.; 0% B to 50% B; flow rate=40 mL/min). The pure fractions were combined, concentrated under reduced pressure and dried in vacuo to afford the title compound (3.5 g, 14.05 mmol, 51% yield). $^1$H NMR (400 MHz, DMSO-$d_6$) δ 8.81 (d, J=4.00 Hz, 1H), 8.56-8.60 (m, 2H), 7.97 (d, J=16.00 Hz, 1H), 3.90 (s, 3H).

Step C. Intermediate 2C. Preparation of methyl 5-(3-aminophenyl)-1,2,4-oxadiazole-3-carboxylate

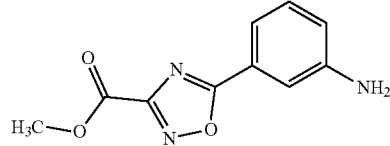

To a stirred solution of Intermediate 2B (1 g, 4.0 mmol) in MeOH (5 mL) was added tin(II) chloride dihydrate (2.72 g, 12.04 mmol) at 0° C. The reaction mixture was warmed to room temperature and heated at 70° C. for 3 h. The reaction mixture was cooled to room temperature, concentrated under reduced pressure and the residue was suspended in ethyl acetate (100 mL). The suspension was filtered through Celite pad and washed with aqueous 10% sodium bicarbonate solution. The filtrate was extracted with EtOAc (2×50 mL). The combined organic layers were dried over anhydrous sodium sulphate and concentrated under reduced pressure to afford the title compound (0.45 g, 1.5 mmol, 37% yield). MS (ESI) 220 (M+H).

Step D. Intermediate 2D. Preparation of methyl 4-(3-cyclopropyl-1,2,4-oxadiazol-5-yl) bicyclo [2.2.2]octane-1-carboxylate

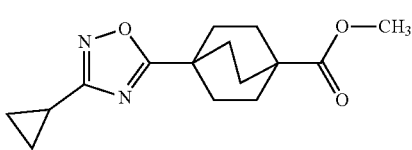 [SMILES: COC(=O)C12CCC(c3nc(C4CC4)no3)(CC1)CC2]

The title compound was prepared according to the method described for the synthesis of Intermediate 1A by substituting 4-(methoxycarbonyl)bicyclo[2.2.2]octane-1-carboxylic acid and (Z)—N'-hydroxycyclopropanecarboximidamide (commercially available). The crude material was purified by flash chromatography (12 g silica gel cartridge; A=Hex, B=EtOAc; 30 min grad.; 0% B to 30% B; flow rate=40 mL/min). The pure fractions were combined, concentrated under reduced pressure and dried in vacuo to afford the title compound (490 mg, 1.67 mmol, 71% yield). MS (ESI) 277 (M+H).

Step E. Intermediate 2E. Preparation of (4-(3-cyclopropyl-1,2,4-oxadiazol-5-yl) bicyclo[2.2.2]octan-1-yl)methanol

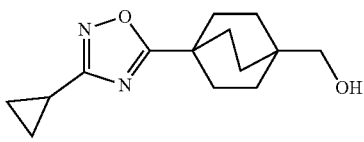 [SMILES: OCC12CCC(c3nc(C4CC4)no3)(CC1)CC2]

The title compound was prepared according to the method described for the synthesis of Intermediate 1B by substituting Intermediate 2D where appropriate: (500 mg, 1.087 mmol, 61% yield). MS (ESI) 249 (M+H).

Step F. Intermediate 2F. Preparation of 4-(3-cyclopropyl-1,2,4-oxadiazol-5-yl) bicyclo[2.2.2]octane-1-carbaldehyde

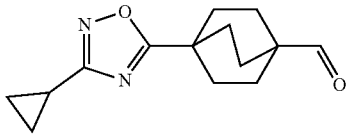 [SMILES: O=CC12CCC(c3nc(C4CC4)no3)(CC1)CC2]

The title compound was prepared according to the method described for the synthesis of Intermediate 1C by substituting Intermediate 2E where appropriate: (350 mg, 1.42 mmol, 71% yield). MS (ESI) 247 (M+H).

Step G. Intermediate 2G. Preparation of methyl 5-(3-(((4-(3-cyclopropyl-1,2,4-oxadiazol-5-yl)bicyclo[2.2.2]octan-1-yl)methyl)amino)phenyl)-1,2,4-oxadiazole-3-carboxylate

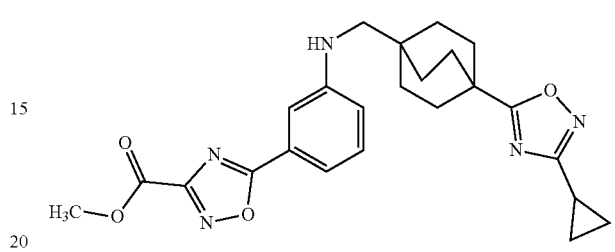

The title compound was prepared according to the method described for the synthesis of Intermediate 1F by substituting Intermediate 2C and Intermediate 2F where appropriate: (50 mg, 0.086 mmol, 42% yield). MS (ESI) 450 (M+H).

Step H. Example 2. Preparation of methyl 5-(3-(N-((4-(3-cyclopropyl-1,2,4-oxadiazol-5-yl)bicyclo[2.2.2]octan-1-yl)methyl)cyclohexanecarboxamido)phenyl)-1,2,4-oxadiazole-3-carboxylate The title compound was prepared according to the method described for the synthesis of Example 1 by substituting Intermediate 2G and cyclohexanecarbonyl chloride where appropriate: (15 mg, 0.027 mmol, 40% yield). $^1$H NMR (400 MHz, DMSO-$d_6$) δ 8.12 (br. s., 2H), 7.80 (br. s., 1H), 7.77-7.63 (m, 1H), 3.98 (s, 3H), 3.64 (br. s., 2H), 2.21 (br. s., 1H), 2.07-1.97 (m, 1H), 1.82-1.71 (m, 6H), 1.61 (br. s., 4H), 1.48 (br. s., 1H), 1.43-1.29 (m, 8H), 1.17-1.05 (m, 1H), 1.05-0.96 (m, 2H), 0.94-0.74 (m, 4H); FXR $EC_{50}$ (nM) 211; MS (ESI) 379 (M+H).

Example 3

N-(4'-methoxy-[1,1'-biphenyl]-3-yl)-N-((4-(3-methyl-1,2,4-oxadiazol-5-yl) bicyclo[2.2.2]octan-1-yl)methyl)cyclohexane carboxamide (3)

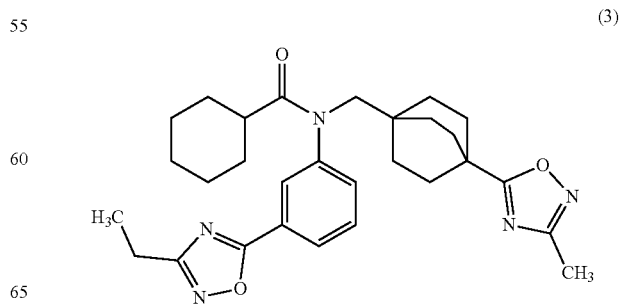

Step A. Intermediate 3A. Preparation of 3-ethyl-5-(3-nitrophenyl)-1,2,4-oxadiazole

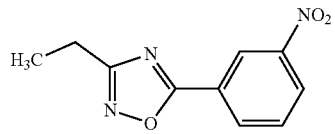 [SMILES: CCc1noc(-c2cccc([N+](=O)[O-])c2)n1]

To a stirred solution of (E)-N'-hydroxypropionimidamide (0.522 g, 5.93 mmol) and DIPEA (1.882 mL, 10.78 mmol) in dichloromethane (10 mL) was added 3-nitrobenzoyl chloride (1 g, 5.39 mmol) at 0° C. The reaction mixture was warmed to room temperature and stirred for 16 h. The reaction mixture was concentrated under reduced pressure and the residue was dissolved in EtOAc (20 mL). The organic solution was washed with water, brine solution, dried over anhydrous sodium sulphate and concentrated under reduced pressure. The crude material was dissolved in tetrahydrofuran (10 mL) and cooled to 0° C. A solution of 1 M TBAF in THF (5 mL, 5.06 mmol) was added to the reaction mixture under nitrogen atmosphere. The reaction mixture was warmed to room temperature and stirred overnight. The reaction mixture was concentrated under reduced pressure. The crude material was purified by flash chromatography (40 g silica gel cartridge; A=Hex, B=EtOAc; 30 min grad.; 0% B to 15% B; flow rate=40 mL/min). The pure fractions were combined, concentrated under reduced pressure and dried in vacuo to afford the title compound (0.8 g, 3.47 mmol, 69% yield) as white solid. $^1$H NMR (400 MHz, DMSO-$d_6$) δ 8.78-8.74 (m, 1H), 8.57-8.50 (m, 2H), 7.98-7.91 (m, 1H), 2.90-2.80 (m, 2H), 1.37-1.28 (m, 3H).

Step B. Intermediate 3B. Preparation of 3-(3-ethyl-1,2,4-oxadiazol-5-yl)aniline

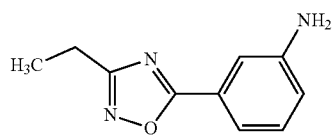

To a stirred solution of Intermediate 3A (1 g, 4.56 mmol) in ethanol (10 mL) was added tin(II) chloride (2.60 g, 13.7 mmol) at room temperature. The reaction mixture was heated at 90° C. for 3 h. The reaction mixture was concentrated under reduced pressure. The residue was dissolved in EtOAc (20 mL), washed with aqueous 10% NaHCO$_3$ solution, brine solution, dried over anhydrous sodium sulphate and concentrated under reduced pressure to afford the title compound (0.6 g, 2.85 mmol, 63% yield) as an off-white solid. $^1$H NMR (400 MHz, DMSO-$d_6$) δ 7.33-7.29 (m, 1H), 7.27-7.17 (m, 2H), 6.88-6.80 (m, 1H), 5.53 (s, 2H), 2.78 (q, J=7.5 Hz, 2H), 1.28 (t, J=7.5 Hz, 3H). MS (ESI) 190 (M+H).

Step C. Intermediate 3C. Preparation of 3-(3-ethyl-1,2,4-oxadiazol-5-yl)-N-((4-(3-methyl-1,2,4-oxadiazol-5-yl)bicyclo[2.2.2]octan-1-yl)methyl)aniline

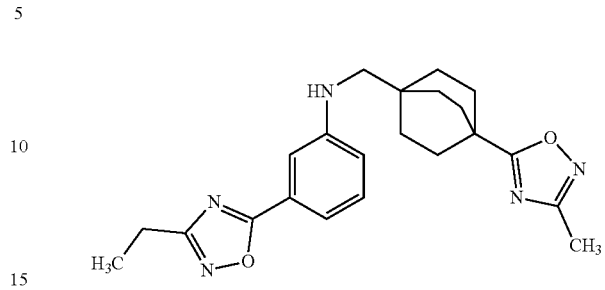

The title compound was prepared according to the method described for the synthesis of Intermediate 1F by substituting Intermediate 3B and Intermediate 1C where appropriate: (0.13 g, 0.297 mmol, 52% yield) as an off-white solid. $^1$H NMR (400 MHz, DMSO-$d_6$) δ 7.34-7.24 (m, 2H), 7.22-7.17 (m, 1H), 6.92 (dd, J=7.9, 1.8 Hz, 1H), 5.99 (t, J=5.5 Hz, 1H), 2.89 (d, J=5.9 Hz, 2H), 2.78 (q, J=7.6 Hz, 2H), 2.30 (s, 3H), 1.95-1.85 (m, 6H), 1.65-1.55 (m, 6H), 1.28 (t, J=7.6 Hz, 3H). MS (ESI) 394 (M+H).

Step D. Example 3. Preparation of N-(4'-methoxy-[1,1'-biphenyl]-3-yl)-N-((4-(3-methyl-1,2,4-oxadiazol-5-yl)bicyclo[2.2.2]octan-1-yl)methyl)cyclohexane carboxamide The title compound was prepared according to the method described for the synthesis of Example 1 by substituting Intermediate 3C and cyclohexanecarbonyl chloride. (40 mg, 0.079 mmol, 89% yield). $^1$H NMR (400 MHz, DMSO-$d_6$) δ 8.17-7.91 (m, 2H), 7.86-7.59 (m, 2H), 3.65 (br. s., 2H), 2.82 (q, J=7.6 Hz, 2H), 2.27 (s, 3H), 2.21 (br. s., 1H), 1.88-1.72 (m, 6H), 1.61 (br. s., 4H), 1.45-1.24 (m, 12H), 1.17-1.03 (m, 1H), 0.90 (br. s., 2H). FXR EC$_{50}$ (nM) 158; MS (ESI) 504 (M+H).

Example 4

N-((4-(3-cyclopropyl-1,2,4-oxadiazol-5-yl)bicyclo[2.2.2]octan-1-yl)methyl)-N-(3-(3-ethyl-1,2,4-oxadiazol-5-yl)phenyl)cyclohexanecarboxamide (4)

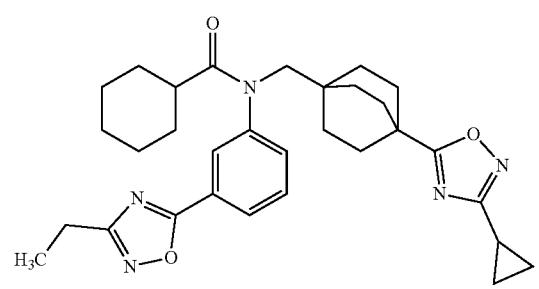

Step A. Intermediate 4A. Preparation of N-((4-(3-cyclopropyl-1,2,4-oxadiazol-5-yl) bicyclo[2.2.2]octan-1-yl)methyl)-3-(3-ethyl-1,2,4-oxadiazol-5-yl)aniline

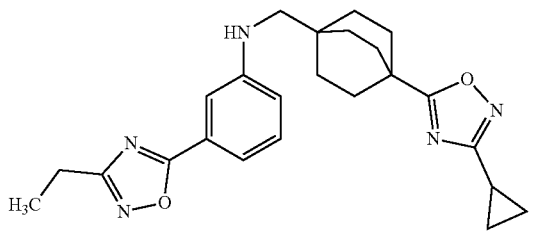 [SMILES: CCc1noc(-c2cccc(NCC34CCC(c5nc(C6CC6)no5)(CC3)CC4)c2)n1]

The title compound was prepared according to the method described for the synthesis of Intermediate 1F by substituting Intermediate 3B and Intermediate 2F where appropriate: (40 mg, 0.086 mmol, 42% yield) as an off-white solid. $^1$H NMR (400 MHz, DMSO-$d_6$) δ 7.35-7.22 (m, 2H), 7.22-7.15 (m, 1H), 6.91 (dd, J=7.5, 2.0 Hz, 1H), 5.95 (t, J=6.0 Hz, 1H), 2.87 (d, J=6.0 Hz, 2H), 2.77 (q, J=7.5 Hz, 2H), 2.11-2.01 (m, 1H), 1.92-1.80 (m, 6H), 1.63-1.52 (m, 6H), 1.28 (t, J=8.00 Hz, 3H), 1.07-0.98 (m, 2H), 0.88-0.82 (m, 2H). MS (ESI) 420 (M+H).

Step B. Example 4. Preparation of N-((4-(3-cyclopropyl-1,2,4-oxadiazol-5-yl)bicyclo[2.2.2]octan-1-yl)methyl)-N-(3-(3-ethyl-1,2,4-oxadiazol-5-yl)phenyl)cyclohexane carboxamide The title compound was prepared according to the method described for the synthesis of Example 1 by substituting Intermediate 4A and cyclohexanecarbonyl chloride where appropriate: (37 mg, 0.070 mmol, 73% yield). $^1$H NMR (400 MHz, DMSO-$d_6$) δ 8.18-7.95 (m, 2H), 7.85-7.60 (m, 2H), 3.64 (br. s., 2H), 2.82 (q, J=7.6 Hz, 2H), 2.20 (br. s., 1H), 2.09-1.97 (m, 1H), 1.85-1.69 (m, 6H), 1.61 (br. s., 4H), 1.48 (br. s., 1H), 1.44-1.34 (m, 7H), 1.34-1.22 (m, 4H), 1.04-0.97 (m, 3H), 0.95-0.74 (m, 4H). FXR EC$_{50}$ (nM) 49; MS (ESI) 530 (M+H).

Example 5

N-((4-(3-cyclopropyl-1,2,4-oxadiazol-5-yl)bicyclo[2.2.2]octan-1-yl)methyl)-N-(3-(3-ethyl-1,2,4-oxadiazol-5-yl)phenyl)-4,4-difluorocyclohexane-1-carboxamide (5)

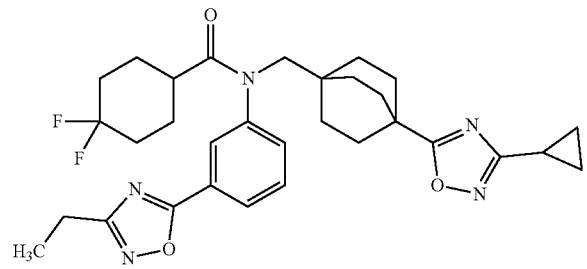

To a solution of Intermediate 4A (20 mg, 0.05 mmol) and 4,4-difluorocyclohexane-1-carboxylic acid (9.39 mg, 0.06 mmol) in dichloromethane (2 mL) was added pyridine (0.019 mL, 0.238 mmol) at 0° C. POCl$_3$ (0.013 mL, 0.143 mmol) was added to the reaction mixture. The reaction mixture was warmed to room temperature and stirred for 1 h. The reaction mixture was concentrated under reduced pressure. The crude material was purified via preparative HPLC using the following conditions: (Sunfire C18, 19×250 mm, 5-µm particles; Mobile Phase A: 10 m M Ammonium acetate PH-4.5 with CH3COOH; Mobile Phase B: acetonitrile; Gradient: 65-100% B over 25 minutes, then a 5-minute hold at 0% B; Flow: 17 mL/min). Fractions containing the product were combined and dried via centrifugal evaporation to afford the title compound. (8 mg, 0.014 mmol, 30% yield). $^1$H NMR (400 MHz, DMSO-$d_6$) δ 8.19-8.01 (m, 2H), 7.78 (br. s., 1H), 7.72 (d, J=8.1 Hz, 1H), 3.64 (br. s., 2H), 2.83 (q, J=7.6 Hz, 2H), 2.39 (br. s., 1H), 2.09-1.85 (m, 3H), 1.82-1.68 (m, 7H), 1.62 (d, J=10.3 Hz, 4H), 1.45-1.34 (m, 5H), 1.31 (t, J=7.6 Hz, 3H), 1.25 (s, 2H), 1.09-0.98 (m, 2H), 0.91-0.76 (m, 2H). FXR EC$_{50}$ (nM) 799; MS (ESI) 566 (M+H).

Example 6

N-(3-(2-methoxyoxazol-5-yl)phenyl)-N-((4-(3-methyl-1,2,4-oxadiazol-5-yl) bicyclo[2.2.2]octan-1-yl)methyl)cyclohexanecarboxamide (6)

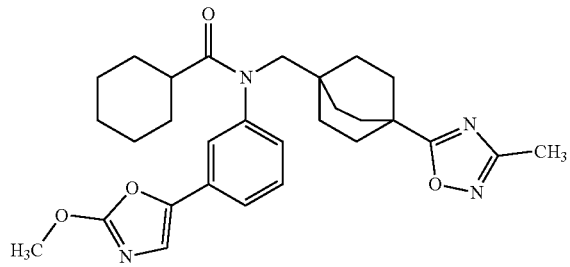

Step A. Intermediate 6A. Preparation of 5-(3-nitrophenyl)oxazol-2(3H)-one

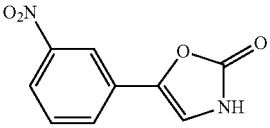

To a stirred solution of 2-bromo-1-(3-nitrophenyl)ethan-1-one (5.0 g, 20.49 mmol, commercially available) and thiazolidine-2,4-dione (2.78 g, 23.77 mmol, commercially available) in DMF (22 mL) was added potassium carbonate (3.96 g, 28.7 mmol) at room temperature. The reaction mixture was stirred at room temperature for 2 h. The reaction mixture was poured into ice cold water (200 mL) and stirred for 5 min. The precipitated solid was filtered, washed with water (100 mL) and dried in vacuo. The crude compound was dissolved in water (45 mL) and THF (45 mL). Lithium hydroxide monohydrate (3.44 g, 82 mmol) was added to the reaction mixture at room temperature and stirred for 30 min. The reaction mixture was poured into acetic acid (4.7 mL, 82 mmol) in ice water (200 mL) and stirred for 5 min. The precipitated solid was filtered washed with water (50 mL) and dried in vacuo to afford the title compound (2.2 g, 10.67 mmol, 52% yield) as yellow solid. $^1$H NMR (400 MHz, DMSO-$d_6$) δ 11.07 (br. s, 1H), 8.29 (t, J=2.0 Hz, 1H), 8.13-8.09 (m, 1H), 7.93 (d, J=8.0 Hz, 1H), 7.85 (s, 1H), 7.74-7.69 (m, 1H). MS (ESI) 205 (M−H).

Step B. Intermediate 6B. Preparation of 2-chloro-5-(3-nitrophenyl)oxazole

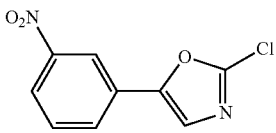 [SMILES: O=[N+]([O-])c1cccc(-c2cnc(Cl)o2)c1]

To a stirred solution of Intermediate 6A (1.0 g, 4.85 mmol) in acetonitrile (10 mL) were added tetraethyl ammonium chloride (1.929 g, 11.64 mmol) and N,N'-diethylaniline (0.724 g, 4.85 mmol) at room temperature. Phosphorus oxychloride (4.61 g, 30.1 mmol) was added drop wise to the reaction mixture and then heated at reflux overnight. The reaction mixture was concentrated under reduced pressure. The crude material was poured into crushed ice and extracted with ethyl acetate (2×50 mL). The combined organic layer were washed with water (50 mL), brine solution (50 mL), dried over anhydrous sodium sulphate and concentrated under reduced pressure to afford the title compound (220 mg, 0.98 mmol, 20% yield) as a pale yellow solid. $^1$H NMR (400 MHz, DMSO-$d_6$) δ 8.49 (t, J=2.0 Hz, 1H), 8.25 (dt, J=7.4, 1.6 Hz, 1H), 8.16-8.13 (m, 1H), 8.08 (s, 1H), 7.80 (t, J=8.0 Hz, 1H). MS (ESI) 226 (M+H).

Step C. Intermediate 6C. Preparation of 2-methoxy-5-(3-nitrophenyl)oxazole

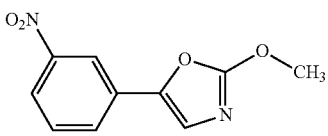 [SMILES: COc1ncc(-c2cccc([N+](=O)[O-])c2)o1]

To a stirred solution of sodium methoxide (144 mg, 0.67 mmol) in THF (1 mL) was added Intermediate 6B (100 mg, 0.445 mmol) in THF (1 mL) drop wise over a period of 2 min at room temperature and stirred for 15 min. The reaction was quenched with water (2 mL). The reaction mixture was extracted with ethyl acetate (2×10 mL). The combined organic layer were washed with water (5 mL), brine solution (5 mL), dried over anhydrous sodium sulphate and concentrated under reduced pressure to afford the title compound (60 mg, 0.27 mmol, 61% yield) as white solid. $^1$H NMR (400 MHz, DMSO-$d_6$) δ 8.36 (t, J=2.0 Hz, 1H), 8.17-8.10 (m, 1H), 8.02 (dt, J=8.3, 1.1 Hz, 1H), 7.77-7.71 (m, 2H), 4.10 (s, 3H). MS (ESI) 221 (M+H).

Step D. Intermediate 6D. Preparation of 3-(2-methoxyoxazol-5-yl)aniline

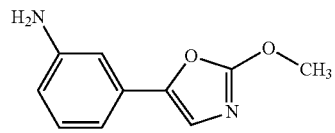

Intermediate 6C (290 mg, 1.317 mmol) was dissolved in a mixture of ethanol (4.0 mL), THF (2.0 mL) and water (1 mL). To this solution were added zinc (1292 mg, 19.76 mmol) followed by ammonium chloride (1057 mg, 19.76 mmol) at room temperature. The reaction mixture was stirred at the same temperature overnight. The reaction mixture was concentrated under reduced pressure and the residue was diluted with water (20 mL). The aqueous solution was extracted with ethyl acetate (2×20 mL). The combined organic layer were washed with water, brine solution, dried over anhydrous sodium sulphate and concentrated under reduced pressure to afford the title compound (210 mg, 1.10 mmol, 84% yield). MS (ESI) 191 (M+H).

Step E. Intermediate 6E. Preparation of 3-(2-methoxyoxazol-5-yl)-N-((4-(3-methyl-1,2,4-oxadiazol-5-yl)bicyclo[2.2.2]octan-1-yl)methyl)aniline

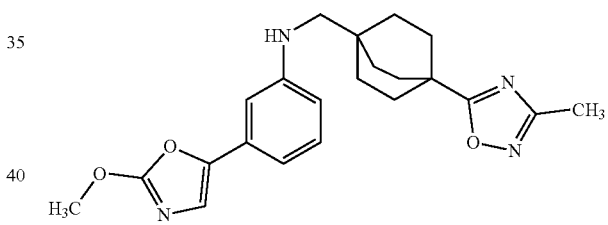

The title compound was prepared according to the method described for the synthesis of Intermediate 1F by substituting Intermediate 6D and Intermediate 1C where appropriate: (20 mg, 0.051 mmol, 54% yield). $^1$H NMR (400 MHz, DMSO-$d_6$) δ 7.21 (s, 1H), 7.05 (t, J=7.8 Hz, 1H), 6.77-6.70 (m, 2H), 6.50 (ddd, J=8.0, 2.0, 1.0 Hz, 1H), 5.20 (s, 2H), 4.04 (s, 3H). MS (ESI) 395 (M+H).

Step F. Example 6. Preparation of N-(3-(2-methoxyoxazol-5-yl)phenyl)-N-((4-(3-methyl-1,2,4-oxadiazol-5-yl)bicyclo[2.2.2]octan-1-yl)methyl)cyclohexanecarboxamide The title compound was prepared according to the method described for the synthesis of Example 1 by substituting Intermediate 6E and cyclohexanecarbonyl chloride where appropriate: (3.1 mg, 6.14 μmol, 12% yield). $^1$H NMR (400 MHz, DMSO-$d_6$) δ 7.66-7.42 (m, 4H), 7.33 (m, 1H), 4.07 (s, 3H), 2.27 (s, 3H), 1.96-1.85 (m, 1H), 1.82-1.72 (m, 6H), 1.65-1.55 (m, 4H), 1.55-1.34 (m, 9H), 1.09-1.01 (m, 1H), 0.89-0.7 (m, 2H) Note: 2H merged in DMSO moisture peak. FXR $EC_{50}$ (nM)=118; MS (ESI) 505 (M+H).

Example 7

N-((4-(3-cyclopropyl-1,2,4-oxadiazol-5-yl)bicyclo[2.2.2]octan-1-yl)methyl)-N-(3-(2-methoxyoxazol-5-yl)phenyl)cyclohexanecarboxamide

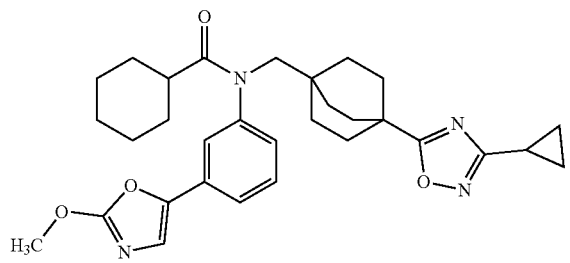

(7)

Step A. Intermediate 7A. Preparation of N-((4-(3-cyclopropyl-1,2,4-oxadiazol-5-yl) bicyclo[2.2.2]octan-1-yl)methyl)-3-(2-methoxyoxazol-5-yl)aniline

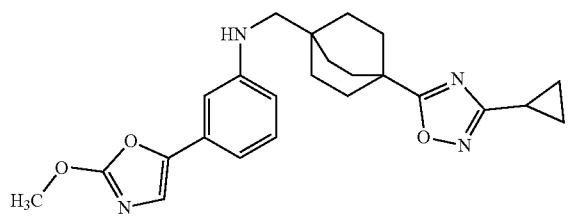 [SMILES: COc1ncc(-c2cccc(NCC34CCC(c5nc(C6CC6)no5)(CC3)CC4)c2)o1]

The title compound was prepared according to the method described for the synthesis of Intermediate 1F by substituting Intermediate 6D and Intermediate 2F where appropriate: (100 mg, 0.02 mmol, 45% yield). $^1$H NMR (400 MHz, DMSO-$d_6$) δ 7.26 (s, 1H), 7.12-7.04 (m, 1H), 6.70 (d, J=9.0 Hz, 1H), 6.55 (s, 1H), 6.43 (s, 1H), 5.60 (s, 1H), 4.04 (s, 3H), 2.06 (s, 2H), 1.91-1.75 (m, 6H), 1.58 (d, J=7.5 Hz, 3H), 1.48-1.40 (m, 3H), 1.06-0.97 (m, 2H), 0.85 (dd, J=4.5, 2.5 Hz, 2H) (2H buried under DMSO solvent peak). MS (ESI) 421 (M+H).

Step B. Example 7. Preparation of N-((4-(3-cyclopropyl-1,2,4-oxadiazol-5-yl)bicyclo[2.2.2]octan-1-yl)methyl)-N-(3-(2-methoxyoxazol-5-yl)phenyl)cyclohexanecarboxamide The title compound was prepared according to the method described for the synthesis of Example 1 by substituting Intermediate 7A and cyclohexanecarbonyl chloride where appropriate: (100 mg, 0.024 mmol, 45% yield). $^1$H NMR (400 MHz, DMSO-$d_6$) δ 7.61-7.39 (m, 4H), 7.31 (d, J=7.1 Hz, 1H), 4.07 (s, 3H), 3.59 (br. s., 2H), 2.22 (t, J=9.9 Hz, 1H), 2.11-1.98 (m, 1H), 1.88-1.69 (m, 6H), 1.60 (d, J=10.8 Hz, 4H), 1.50 (d, J=12.2 Hz, 1H), 1.44-1.21 (m, 8H), 1.18-0.95 (m, 3H), 0.95-0.71 (m, 4H). FXR $EC_{50}$ (nM)=51; MS (ESI) 531 (M+H).

Example 8

N-((4-(3-cyclopropyl-1,2,4-oxadiazol-5-yl)bicyclo[2.2.2]octan-1-yl)methyl)-N-(3-(2-ethoxyoxazol-5-yl)phenyl)cyclohexanecarboxamide

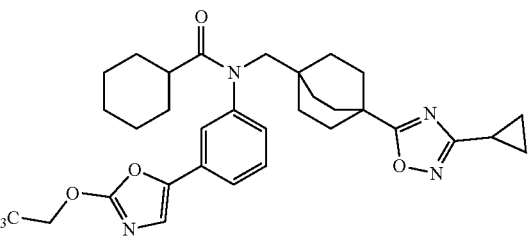

(8)

Step A. Intermediate 8A. Preparation of 2-ethoxy-5-(3-nitrophenyl)oxazole

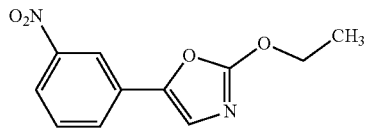 [SMILES: CCOc1ncc(-c2cccc([N+](=O)[O-])c2)o1]

To a cooled (0-5° C.) solution of sodium ethoxide (144 mg, 0.445 mmol) in THF (1.0 mL) was added drop wise a solution of Intermediate 6B (100 mg, 0.445 mmol) in THF (1.0 mL) at room temperature. The reaction mixture was stirred at room temperature for 30 min. The reaction was quenched with water (1 mL). The reaction mixture was concentrated under reduced pressure. The residue was diluted with ethyl acetate (10 mL), washed with water (5 mL), brine solution (5 mL), dried over anhydrous sodium sulphate and concentrated under reduced pressure to afford the title compound (80 mg, 0.34 mmol, 77% yield) as white solid. $^1$H NMR (400 MHz, DMSO-$d_6$) δ 8.34 (t, J=2.0 Hz, 1H), 8.16-8.09 (m, 1H), 8.04-7.97 (m, 1H), 7.77-7.68 (m, 2H), 4.49 (q, J=7.0 Hz, 2H), 1.39 (t, J=7.0 Hz, 3H). MS (ESI) 235 (M+H).

Step B. Intermediate 8B. Preparation of 3-(2-ethoxyoxazol-5-yl)aniline

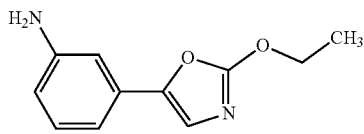

Intermediate 8A (80 mg, 0.342 mmol) was dissolved in a mixture of ethanol (0.8 mL), THF (0.4 mL) and water (0.2 mL). To this solution were added zinc (335 mg, 5.12 mmol) followed by ammonium chloride (274 mg, 5.12 mmol) at room temperature and stirred overnight. The reaction mixture was concentrated under reduced pressure and the residue was diluted with water (2 mL). The aqueous layer was extracted with ethyl acetate (2×10 mL). The combined organic layer were washed with water (5 mL), brine solution (5 mL), dried over anhydrous sodium sulphate and concentrated under reduced pressure to afford the title compound (60 mg, 0.29 mmol, 86% yield) as brown solid. $^1$H NMR (400 MHz, DMSO-$d_6$) δ 7.19 (s, 1H), 7.05 (t, J=7.8 Hz, 1H), 6.77-6.69 (m, 2H), 6.50 (ddd, J=8.0, 2.0, 1.0 Hz, 1H), 5.20 (s, 2H), 4.43 (q, J=7.0 Hz, 2H), 1.38 (t, J=7.3 Hz, 3H). MS (ESI) 205 (M+H).

Step C. Intermediate 8C. Preparation of N-((4-(3-cyclopropyl-1,2,4-oxadiazol-5-yl) bicyclo[2.2.2]octan-1-yl)methyl)-3-(2-ethoxyoxazol-5-yl)aniline

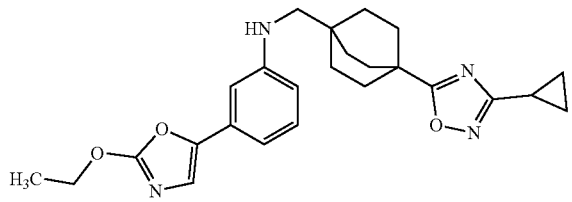 [SMILES: CCOc1ncc(-c2cccc(NCC34CCC(c5nc(C6CC6)no5)(CC3)CC4)c2)o1]

The title compound was prepared according to the method described for the synthesis of Intermediate 1F by substituting Intermediate 8B and Intermediate 2F where appropriate: (50 mg, 0.115 mmol, 59% yield) as brown wax. $^1$H NMR (400 MHz, DMSO-$d_6$) δ 7.25 (s, 1H), 7.07 (t, J=7.9 Hz, 1H), 6.80-6.74 (m, 1H), 6.70 (d, J=7.6 Hz, 1H), 6.56 (d, J=9.8 Hz, 1H), 5.61 (t, J=6.0 Hz, 1H), 4.43 (q, J=7.0 Hz, 2H), 2.84 (d, J=6.1 Hz, 2H), 2.12-2.00 (m, 1H), 1.91-1.77 (m, 6H), 1.62-1.51 (m, 6H), 1.37 (t, J=7.1 Hz, 3H), 1.07-0.98 (m, 2H), 0.89-0.81 (m, 2H). MS (ESI) 435 (M+H).

Step D. Example 8. Preparation of N-((4-(3-cyclopropyl-1,2,4-oxadiazol-5-yl) bicyclo[2.2.2]octan-1-yl)methyl)-N-(3-(2-ethoxyoxazol-5-yl)phenyl)cyclohexanecarboxamide The title compound was prepared according to the method described for the synthesis of Example 1 by substituting Intermediate 8C and cyclohexanecarbonyl chloride where appropriate: (27.1 mg, 0.049 mmol, 36% yield). $^1$H NMR (400 MHz, DMSO-$d_6$) δ 7.59-7.46 (m, 4H), 7.31 (d, J=7.3 Hz, 1H), 4.47 (q, J=6.9 Hz, 2H), 3.59 (s, 2H), 2.23 (s, 1H), 2.09-2.01 (m, 1H), 1.83-1.70 (m, 6H), 1.60 (d, J=10.5 Hz, 4H), 1.50 (d, J=11.0 Hz, 1H), 1.43-1.27 (m, 11H), 1.16-0.98 (m, 3H), 0.96-0.73 (m, 4H). FXR $EC_{50}$ (nM)=19; MS (ESI) 545 (M+H).

The following compound was prepared according to the method described for the synthesis of Example 5 by substituting Intermediate 8C and corresponding acid where appropriate:

| Ex. No. | Structure | MS (ESI) (M + H) | FXR $EC_{50}$ (nM) |
|---|---|---|---|
| 9 | | 581 | 142 |

9 $^1$H NMR (400 MHz, DMSO-$d_6$) δ 7.60 (s, 1H), 7.56-7.43 (m, 3H), 7.34 (d, J = 7.3 Hz, 1H), 4.46 (q, J = 7.0 Hz, 2H), 3.5-3.60 (br. s, 2H), 2.30-2.40 (m, 1H), 2.09-1.86 (m, 4H), 1.82-1.52 (m, 10H), 1.52-1.32 (m, 9H), 1.23-1.21 (m, 1H), 1.08-0.92 (m, 2H), 0.90-0.75 (m, 2H).

Example 10

N-(3-(2-ethoxyoxazol-5-yl)phenyl)-N-((4-(3-methyl-1,2,4-oxadiazol-5-yl) bicyclo[2.2.2]octan-1-yl)methyl)cyclohexanecarboxamide

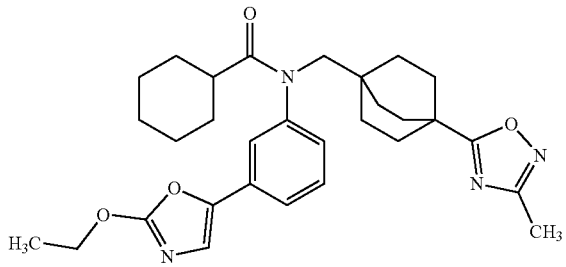

(10)

Step A. Intermediate 10A. Preparation of 3-(2-ethoxyoxazol-5-yl)-N-((4-(3-methyl-1,2,4-oxadiazol-5-yl)bicyclo[2.2.2]octan-1-yl)methyl)aniline

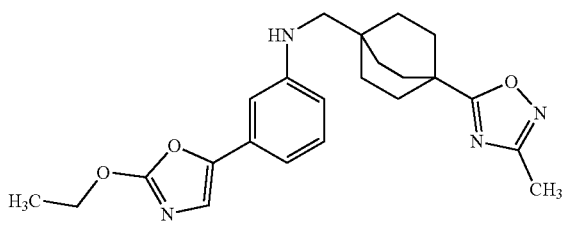 [SMILES: CCOc1ncc(-c2cccc(NCC34CCC(c5nc(C)no5)(CC3)CC4)c2)o1]

The title compound was prepared according to the method described for the synthesis of Intermediate 1F by substituting Intermediate 8B and Intermediate 1C where appropriate: (50 mg, 0.122 mmol, 63% yield) as brown wax. MS (ESI) 409 (M+H).

Step B. Example 10. Preparation of N-(3-(2-ethoxyoxazol-5-yl)phenyl)-N-((4-(3-methyl-1,2,4-oxadiazol-5-yl)bicyclo[2.2.2]octan-1-yl)methyl)cyclohexanecarboxamide The title compound was prepared according to the method described for the synthesis of Example 1 by substituting Intermediate 10A and cyclohexanecarbonyl chloride where appropriate: (9 mg, 0.017 mmol, 14% yield). $^1$H NMR (400 MHz, DMSO-$d_6$) δ 7.58 (s, 1H), 7.55-7.41 (m, 3H), 7.32 (d, J=7.1 Hz, 1H), 4.47 (q, J=7.1 Hz, 2H), 3.60 (br s, 2H), 2.37-2.12 (m, 4H), 1.84-1.73 (m, 7H), 1.61 (d, J=11.0 Hz, 4H), 1.54-1.46 (m, 2H), 1.46-1.27 (m, 9H), 1.16-1.00 (m, 1H), 0.88 (d, J=14.4 Hz, 2H); FXR EC$_{50}$ (nM)=71; MS (ESI) 519 (M+H).

Example 11

N-(3-(5-methoxyisoxazol-3-yl)phenyl)-N-((4-(3-methyl-1,2,4-oxadiazol-5-yl) bicyclo[2.2.2]octan-1-yl)methyl)cyclohexanecarboxamide

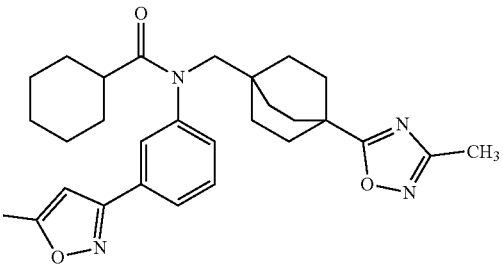

(11)

Step A. Intermediate 11A. Preparation of 3-(3-nitrophenyl)isoxazol-5(4H)-one

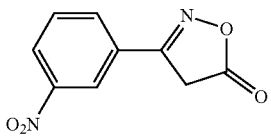 [SMILES: O=C1CC(c2cccc([N+](=O)[O-])c2)=NO1]

To a stirred solution of methyl 3-(3-nitrophenyl)-3-oxo-propanoate (1.0 g, 4.48 mmol, commercially available) in ethanol (8 mL) was added a solution of hydroxylamine hydrochloride (0.342 g, 4.93 mmol) in water (8 mL) at room temperature and stirred overnight. The reaction mixture was concentrated under reduced pressure and the residue was diluted with water (50 mL). The precipitated solid was filtered, washed with water (20 mL) and dried in vacuo to afford the title compound (800 mg, 3.88 mmol, 87% yield) as yellow solid. $^1$H NMR (400 MHz, DMSO-$d_6$) δ 8.58-8.50 (m, 1H), 8.35 (br. s., 1H), 8.22 (d, J=7.5 Hz, 1H), 7.88-7.78 (m, 1H), 5.93 (br. s., 1H), 4.44 (br. s., 1H). MS (ESI) 207 (M+H).

Step B. Intermediate 11B. Preparation of 5-chloro-3-(3-nitrophenyl)isoxazole

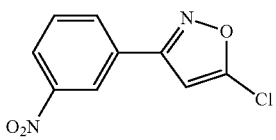

To a stirred solution of Intermediate 11A (0.8 g, 3.88 mmol) in POCl$_3$ (2.170 ml, 23.28 mmol) was added TEA (0.6 ml, 4.27 mmol) at room temperature. The reaction mixture was heated at 120° C. for 2 h. The reaction mixture was cooled to room temperature and concentrated under reduced pressure. The residue was poured into crushed ice and extracted with ethyl acetate (2×20 mL). The combined organic layer were washed with water (20 mL), brine solution (20 mL), dried over anhydrous sodium sulphate and concentrated under reduced pressure. The crude material was purified by flash chromatography (12 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (130 mg, 0.58 mmol, 15% yield) as white solid. $^1$H NMR (400 MHz, DMSO-$d_6$) δ 8.66 (t, J=2.0 Hz, 1H), 8.41 (ddd, J=8.3, 2.3, 1.0 Hz, 1H), 8.34 (dt, J=7.9, 1.3 Hz, 1H), 7.87 (t, J=8.0 Hz, 1H), 7.60 (s, 1H). MS (ESI) 242 (M+H).

Step C. Intermediate 11C. Preparation of 5-methoxy-3-(3-nitrophenyl)isoxazole

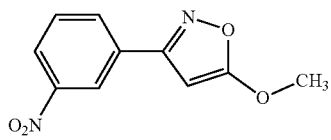

To a cooled (0-5° C.) solution of sodium methoxide (144 mg, 0.67 mmol) in THF (2 mL) was added a solution of Intermediate 11B (100 mg, 0.445 mmol) in THF (1 mL) drop wise. The reaction mixture was warmed to room temperature and stirred for 30 min. The reaction was quenched with water (1 mL). The reaction mixture was concentrated under reduced pressure. The residue was diluted with ethyl acetate (5 mL), washed with water (5 mL), brine solution (5 mL), dried over anhydrous sodium sulphate and concentrated under reduced pressure to afford the title compound (80 mg, 0.36 mmol, 82% yield) as yellow solid. $^1$H NMR (400 MHz, DMSO-$d_6$) δ 8.59 (t, J=2.0 Hz, 1H), 8.40-8.33 (m, 1H), 8.31-8.25 (m, 1H), 7.84 (t, J=8.0 Hz, 1H), 6.47 (s, 1H), 4.09 (s, 3H) MS(ESI) 221 (M+H).

Step D. Intermediate 11D. Preparation of 3-(5-methoxyisoxazol-3-yl)aniline

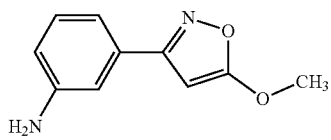 [SMILES: COc1cc(-c2cccc([N+](=O)[O-])c2)no1]

Intermediate 11C (1.2 g, 5.45 mmol) was dissolved in a mixture of ethanol (12 mL), THF (6.0 mL) and water (3.0 mL). To this solution was added zinc (5.34 g, 82 mmol) followed by ammonium chloride (4.37 g, 82 mmol) at room temperature and stirred overnight. The reaction mixture was filtered through Celite bed and washed with ethyl acetate (50 mL). The filtrate was concentrated under reduced pressure. The residue obtained was reconstituted in water (50 mL) and extracted with ethyl acetate (2×50 mL). The combined organic layer were washed with water (50 mL), brine solution (50 mL), dried over anhydrous sodium sulphate and concentrated under reduced pressure to afford the title compound (1.0 g, 5.26 mmol, 96% yield) as brown wax. $^1$H NMR (400 MHz, DMSO-$d_6$) δ 7.12 (t, J=7.8 Hz, 1H), 7.00 (t, J=2.0 Hz, 1H), 6.93-6.86 (m, 1H), 6.66 (dt, J=7.9, 1.3 Hz, 1H), 5.97 (s, 1H), 5.26 (s, 2H), 4.02 (s, 3H). MS (ESI) 191 (M+H)

Step E. Intermediate 11E. Preparation of 3-(5-methoxyisoxazol-3-yl)-N-((4-(3-methyl-1,2,4-oxadiazol-5-yl)bicyclo[2.2.2]octan-1-yl)methyl)aniline

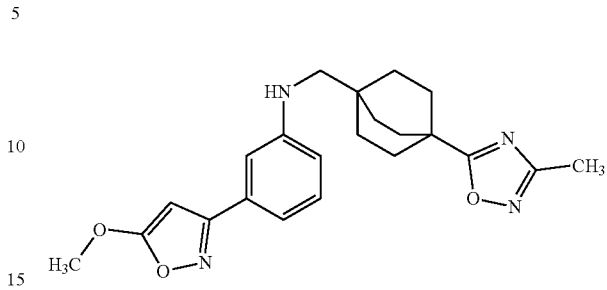

The title compound was prepared according to the method described for the synthesis of Intermediate 1F by substituting Intermediate 11D and Intermediate 1C where appropriate: (60 mg, 0.152 mmol, 41% yield) as brown wax. $^1$H NMR (400 MHz, DMSO-$d_6$) δ 7.18-7.10 (m, 1H), 7.02 (s, 1H), 6.89 (d, J=7.5 Hz, 1H), 6.77-6.71 (m, 1H), 6.03 (s, 1H), 5.71-5.63 (m, 1H), 4.03 (s, 3H), 2.86 (d, J=6.0 Hz, 2H), 2.29 (s, 3H), 1.95-1.80 (m, 6H), 1.66-1.53 (m, 6H). MS (ESI) 395 (M+H).

Step F. Example 11. Preparation of N-(3-(5-methoxyisoxazol-3-yl)phenyl)-N-((4-(3-methyl-1,2,4-oxadiazol-5-yl)bicyclo[2.2.2]octan-1-yl)methyl)cyclohexanecarboxamide The title compound was prepared according to the method described for the synthesis of Example 1 by substituting Intermediate 11E and cyclohexanecarbonyl chloride where appropriate: (11 mg, 0.022 mmol, 11% yield). $^1$H NMR (400 MHz, DMSO-$d_6$) δ 7.80 (s., 2H), 7.64-7.45 (m, 2H), 6.32 (s, 1H), 4.07 (s, 3H), 3.63 (s., 2H), 2.32-2.17 (m, 4H), 1.90-1.72 (m, 6H), 1.67-1.61 (m, 4H), 1.56-1.28 (m, 9H), 1.16-1.01 (m, 1H), 0.88 (d, J=11.7 Hz, 2H). FXR $EC_{50}$ (nM)=660; MS (ESI) 505 (M+H).

Example 12

N-((4-(3-cyclopropyl-1,2,4-oxadiazol-5-yl)bicyclo[2.2.2]octan-1-yl)methyl)-N-(3-(5-methoxyisoxazol-3-yl)phenyl)cyclohexanecarboxamide (12)

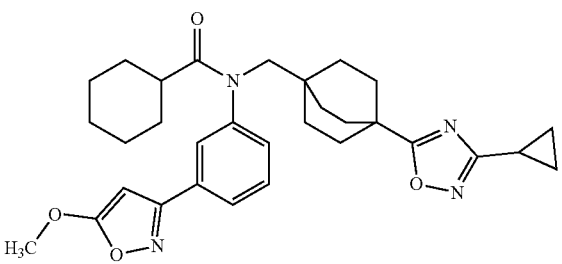

Step A. Intermediate 12A. Preparation of N-((4-(3-cyclopropyl-1,2,4-oxadiazol-5-yl) bicyclo[2.2.2]octan-1-yl)methyl)-3-(5-methoxyisoxazol-3-yl)aniline

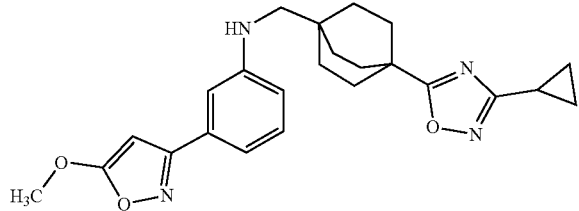 [SMILES: COc1cc(-c2cccc(NCC34CCC(c5nc(C6CC6)no5)(CC3)CC4)c2)no1]

The title compound was prepared according to the method described for the synthesis of Intermediate 1F by substituting Intermediate 11D and Intermediate 2F where appropriate: (160 mg, 0.380 mmol, 72% yield) as brown wax. $^1$H NMR (400 MHz, DMSO-$d_6$) δ 7.14 (t, J=7.8 Hz, 1H), 7.01 (s, 1H), 6.88 (d, J=7.5 Hz, 1H), 6.74 (d, J=8.0 Hz, 1H), 6.03 (s, 1H), 5.67 (t, J=6.3 Hz, 1H), 4.03 (s, 3H), 2.86 (d, J=6.0 Hz, 2H), 2.11-2.01 (m, 1H), 1.91-1.77 (m, 6H), 1.63-1.51 (m, 6H), 1.07-0.97 (m, 2H), 0.89-0.79 (m, 2H) M S (ESI) 421 (M+H).

Step B. Example 12. Preparation of N-((4-(3-cyclopropyl-1,2,4-oxadiazol-5-yl)bicyclo[2.2.2]octan-1-yl)methyl)-N-(3-(5-methoxyisoxazol-3-yl)phenyl)cyclohexanecarboxamide The title compound was prepared according to the method described for the synthesis of Example 1 by substituting Intermediate 12A and cyclohexanecarbonyl chloride where appropriate: (100 mg, 0.187 mmol, 60% yield). $^1$H NMR (400 MHz, DMSO-$d_6$) δ 7.79 (s, 2H), 7.62-7.40 (m, 2H), 6.32 (s, 1H), 4.07 (s, 3H), 3.63 (s, 2H), 2.22 (s, 1H), 2.10-1.97 (m, 1H), 1.87-1.71 (m, 6H), 1.60 (d, J=10.0 Hz, 4H), 1.49 (s, 1H), 1.45-1.28 (m, 8H), 1.17-0.97 (m, 3H), 0.96-0.76 (m, 4H). FXR EC$_{50}$ (nM)=129; MS (ESI) 531 (M+H).

Example 13

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)cyclohexanecarboxamide (13)

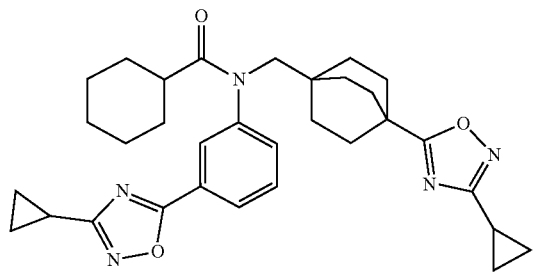

Step A. Intermediate 13A. Preparation of 3-(3-cyclopropyl-1,2,4-oxadiazol-5-yl)aniline

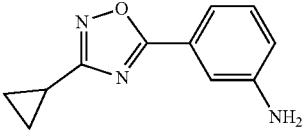 [SMILES: Nc1cccc(-c2nc(C3CC3)no2)c1]

To a stirred solution of 3-aminobenzoic acid (2000 mg, 14.58 mmol, commercially available) in DMF (20 mL) were added (Z)—N'-hydroxycyclopropanecarboximidamide (2190 mg, 21.88 mmol), TEA (8.2 mL, 58.3 mmol) followed by BOP (7095 mg, 16.04 mmol) at room temperature. The reaction mixture was stirred at room temperature for 1 h and then heated at 110° C. overnight. The reaction mixture was concentrated under reduced pressure, diluted with water and extracted with ethyl acetate (2×50 mL). The combined organic layer were dried over anhydrous sodium sulphate and concentrated under reduced pressure. The crude material was purified by flash chromatography (40 g silica gel cartridge; A=Hex, B=EtOAc; 30 min grad.; 0% B to 30% B; flow rate=40 mL/min). The pure fractions were combined, concentrated under reduced pressure and dried in vacuo to afford the title compound (2.3 g, 10.40 mmol, 71% yield) as solid. $^1$H NMR (400 MHz, DMSO-$d_6$) δ 7.30-7.21 (m, 2H), 7.14 (d, J=7.5 Hz, 1H), 6.89 (dd, J=8.3, 1.8 Hz, 1H), 5.95 (t, J=6.0 Hz, 1H), 2.86 (d, J=6.0 Hz, 2H), 2.20-2.12 (m, 1H), 2.10-2.02 (m, 1H), 1.91-1.81 (m, 6H), 1.62-1.52 (m, 6H), 1.13-1.06 (m, 2H), 1.06-0.99 (m, 2H), 0.99-0.94 (m, 2H), 0.89-0.82 (m, 2H), MS (ESI) 432 (M+H).

Step B. Intermediate 13B. Preparation of 3-(3-cyclopropyl-1,2,4-oxadiazol-5-yl)-N-((4-(3-cyclopropyl-1,2,4-oxadiazol-5-yl)bicyclo[2.2.2]octan-1-yl)methyl)aniline

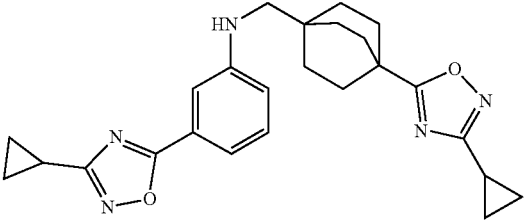 [SMILES: c1cc(NCC23CCC(c4nc(C5CC5)no4)(CC2)CC3)cc(-c2nc(C3CC3)no2)c1]

The title compound was prepared according to the method described for the synthesis of Intermediate 1F by substituting Intermediate 13A and Intermediate 2F where appropriate: (100 mg, 0.23 mmol, 57% yield) as white solid. $^1$H NMR (400 MHz, DMSO-$d_6$) δ 7.30-7.21 (m, 2H), 7.14 (d, J=7.5 Hz, 1H), 6.89 (dd, J=8.3, 1.8 Hz, 1H), 5.95 (t, J=6.0 Hz, 1H), 2.86 (d, J=6.0 Hz, 2H), 2.20-2.12 (m, 1H), 2.10-2.02 (m, 1H), 1.91-1.81 (m, 6H), 1.62-1.52 (m, 6H), 1.13-1.06 (m, 2H), 1.06-0.99 (m, 2H), 0.99-0.94 (m, 2H), 0.89-0.82 (m, 2H). MS (ESI) 432 (M+H).

Step C. Example 13. Preparation of N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)cyclohexane carboxamide The title compound was prepared according to the method described for the synthesis of Example 1 by substituting Intermediate 13B and cyclohexanecarbonyl chloride where appropriate: (20 mg, 0.037 mmol, 80% yield). $^1$H NMR (400 MHz, DMSO-d$_6$) δ 8.12-7.92 (m, 2H), 7.75 (d, J=7.3 Hz, 1H), 7.68 (t, J=7.7 Hz, 1H), 3.63 (br. s., 2H), 2.28-2.12 (m, 2H), 2.10-1.93 (m, 1H), 1.87-1.70 (m, 6H), 1.61 (br. s., 4H), 1.49 (br. s., 1H), 1.43-1.28 (m, 6H), 1.25 (s, 1H), 1.19-0.97 (m, 6H), 0.96-0.75 (m, 4H). FXR EC$_{50}$ (nM) 82; MS (ESI) 542 (M+H).

The following compounds were synthesized according to the method described for the synthesis of Example 5 by substituting intermediate 13B and corresponding acids.

| Ex. No. | Structure | MS (ESI) (M + H) | FXR EC$_{50}$ (nM) |
|---|---|---|---|
| 14 | 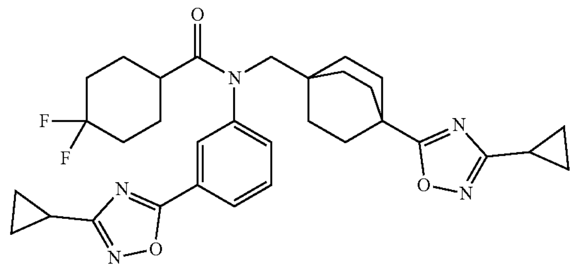 [SMILES: O=C(C1CCC(F)(F)CC1)N(CC12CCC(c3nc(C4CC4)no3)(CC1)CC2)c1cccc(-c2nc(C3CC3)no2)c1] | 578 | 272 |
| 15 | 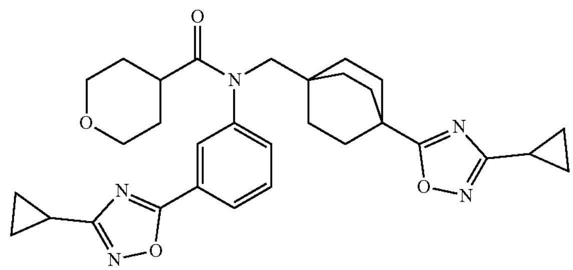 [SMILES: O=C(C1CCOCC1)N(CC12CCC(c3nc(C4CC4)no3)(CC1)CC2)c1cccc(-c2nc(C3CC3)no2)c1] | 544 | 134 |
| 16 | (racemate) | 544 | 226 |
| 17 | 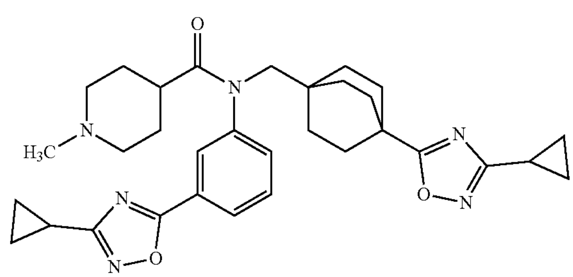 [SMILES: CN1CCC(C(=O)N(CC23CCC(c4nc(C5CC5)no4)(CC2)CC3)c2cccc(-c3nc(C4CC4)no3)c2)CC1] | 557 | 3019 |

| Ex. No. | Structure | MS (ESI) (M + H) | FXR EC$_{50}$ (nM) |
|---|---|---|---|
| 18 | 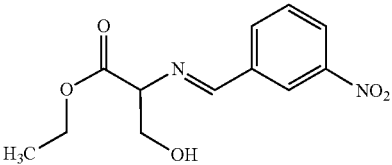 [SMILES: CCOC(=O)C(CO)/N=C/c1cccc([N+](=O)[O-])c1] | 592 | 1166 |

14  $^1$H NMR (400 MHz, DMSO-d$_6$) δ 8.17-7.90 (m, 2H), 7.79 (d, J = 7.6 Hz, 1H), 7.69 (t, J = 8.1 Hz, 1H), 3.64 (br. s., 2H), 2.38 (br. s., 1H), 2.27-2.15 (m, 1H), 2.11-2.01 (m, 1H), 1.96 (br. s., 1H), 1.82-1.55 (m, 11H), 1.50 (br. s., 1H), 1.45-1.33 (m, 6H), 1.25 (s, 1H), 1.18-1.08 (m, 2H), 1.07-0.95 (m, 4H), 0.91-0.78 (m, 2H).

15  $^1$H NMR (400 MHz, DMSO-d$_6$) δ 8.18-7.91 (m, 2H), 7.78 (d, J = 7.1 Hz, 1H), 7.74-7.62 (m, 1H), 3.74 (d, J = 9.3 Hz, 2H), 3.64 (br. s., 2H), 3.00 (t, J = 10.6 Hz, 2H), 2.48-2.45 (m, 1H), 2.28-2.14 (m, 1H), 2.05-2.03 (m, 1H), 1.86-1.68 (m, 6H), 1.68-1.53 (m, 2H), 1.47 (br. s., 1H), 1.44-1.28 (m, 7H), 1.22-1.08 (m, 2H), 1.08-0.90 (m, 4H), 0.89-0.68 (m, 2H).

16  $^1$H NMR (400 MHz, DMSO-d$_6$) δ 8.12-7.93 (m, 2H), 7.81 (d, J = 8.3 Hz, 1H), 7.71 (t, J = 7.8 Hz, 1H), 3.78 (br. s., 1H), 3.71-3.57 (m, 3H), 3.52 (d, J = 11.2 Hz, 1H), 3.29-3.22 (m, 2H), 2.46 (br. s., 1H), 2.27-2.17 (m, 1H), 2.09-2.00 (m, 1H), 1.91-1.84 (m, 1H), 1.81-1.71 (m, 6H), 1.71-1.53 (m, 2H), 1.50-1.30 (m, 6H), 1.21-1.08 (m, 2H), 1.06-0.91 (m, 4H), 0.87-0.76 (m, 2H).

17  $^1$H NMR (400 MHz, DMSO-d$_6$) δ 8.02 (br. s., 2H), 7.77 (d, J = 6.6 Hz, 1H), 7.72-7.58 (m, 1H), 3.63 (br. s., 2H), 2.70 (d, J = 16.1 Hz, 2H), 2.27-2.14 (m, 2H), 2.14-1.99 (m, 4H), 1.86-1.70 (m, 6H), 1.61 (d, J = 8.6 Hz, 6H), 1.45-1.30 (m, 6H), 1.17-1.08 (m, 2H), 1.07-0.94 (m, 4H), 0.87-0.77 (m, 2H).

18  $^1$H NMR (400 MHz, DMSO-d$_6$) δ 8.15-7.93 (m, 2H), 7.78 (d, J = 7.6 Hz, 1H), 7.69 (t, J = 7.8 Hz, 1H), 3.63 (br. s., 2H), 2.96 (br. s., 3H), 2.68-2.60 (m, 1H), 2.21 (td, J = 8.5, 4.3 Hz, 1H), 2.12-1.91 (m, 6H), 1.85-1.63 (m, 6H), 1.55-1.31 (m, 6H), 1.18-1.08 (m, 2H), 1.07-0.91 (m, 4H), 0.87-0.76 (m, 2H).

Example 19

Ethyl 2-(3-(N-((4-(3-methyl-1,2,4-oxadiazol-5-yl)bicyclo[2.2.2]octan-1-yl)methyl)cyclohexanecarboxamido)phenyl)oxazole-4-carboxylate

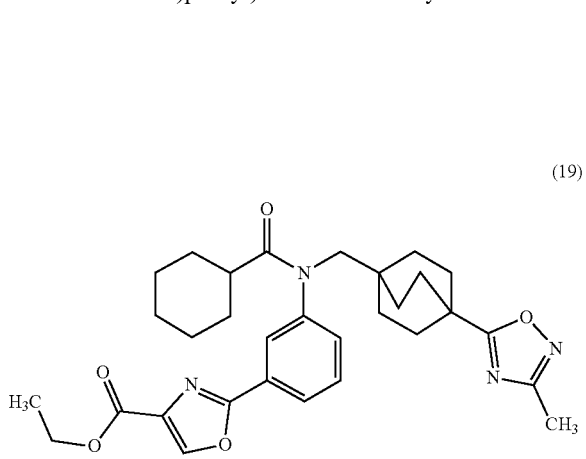

(19)

Step A. Intermediate 19A. Preparation of ethyl (Z)-3-hydroxy-2-((3-nitrobenzylidene)amino) propionate To a stirred solution of L-serine ethyl ester hydrochloride (2.81 g, 16.54 mmol, commercially available) in THF (160 mL) were added Et$_3$N (4.6 mL, 33.1 mmol), magnesium sulphate (1.99 g, 16.54 mmol) and 3-nitrobenzaldehyde (2.5 g, 16.54 mmol, commercially available) at room temperature. The reaction mixture was stirred at room temperature for 12 h. The reaction mixture was filtered through Celite pad and the residue was washed with MTBE (10 mL). The filtrate was concentrated under reduced pressure to afford the title compound (4.5 g, 8.28 mmol, 50% yield). MS (ESI) 265 (M−H).

Step B. Intermediate 19B. Preparation of ethyl 2-(3-nitrophenyl)oxazole-4-carboxylate

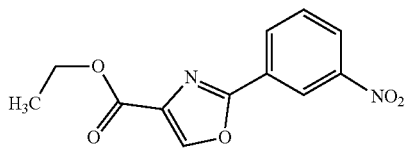 [SMILES: CCOC(=O)c1coc(-c2cccc([N+](=O)[O-])c2)n1]

To a stirred solution of Intermediate 19A (5 g, 18.78 mmol) in DCM (160 mL) were added bromotrichloromethane (5.58 mL, 56.3 mmol) and DBU (8.5 mL, 56.3 mmol) at 0° C. The reaction mixture was warmed to room temperature and stirred for 12 h. The reaction mixture was poured into cold water and the aqueous solution was extracted with EtOAc (2×100 mL). The combined organic layers were dried over anhydrous sodium sulphate and concentrated under reduced pressure. The crude material was purified by flash chromatography (40 g silica gel cartridge; A=Hex, B=EtOAc; 30 min grad.; 0% B to 40% B; flow rate=40 mL/min). The pure fractions were combined, concentrated under reduced pressure and dried in vacuo to afford the title compound (3 g, 11.33 mmol, 60% yield). MS (ESI) 263 (M+H).

Step C. Intermediate 19C. Preparation of ethyl 2-(3-aminophenyl)oxazole-4-carboxylate

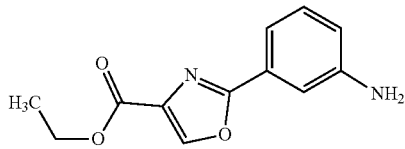 [SMILES: CCOC(=O)c1coc(-c2cccc(N)c2)n1]

A stirred solution of Intermediate 19B (1 g, 3.81 mmol) in 1,4-dioxane (20 mL) was purged and flushed with nitrogen. Pd—C (0.20 g, 1.91 mmol) was added to the reaction mixture and stirred under hydrogen (1 atm, balloon) overnight. The reaction mixture was filtered through Celite and the filtrate was concentrated under reduced pressure to afford title compound (800 mg, 3.31 mmol, 87% yield). MS (ESI) 233 (M+H).

Step D. Intermediate 19D. Preparation of ethyl 2-(3-(((4-(3-methyl-1,2,4-oxadiazol-5-yl)bicyclo [2.2.2]octan-1-yl)methyl)amino)phenyl)oxazole-4-carboxylate

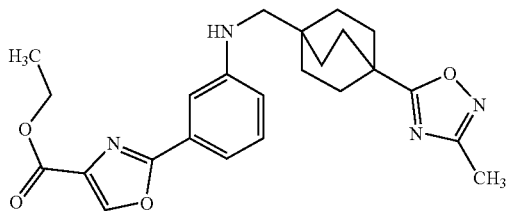 [SMILES: CCOC(=O)c1coc(-c2cccc(NCC34CCC(c5nc(C)no5)(CC3)CC4)c2)n1]

The title compound was prepared according to the method described for the synthesis of Intermediate 1F by substituting Intermediate 19C and Intermediate 1C where appropriate: (40 mg, 0.092 mmol, 27% yield). MS (ESI) 437 (M+H).

Step E. Example 19. Preparation of Ethyl 2-(3-(N-((4-(3-methyl-1,2,4-oxadiazol-5-yl) bicyclo[2.2.2] octan-1-yl)methyl)cyclohexanecarboxamido)phenyl) oxazole-4-carboxylate The title compound was prepared according to the method described for the synthesis of Example 1 by substituting Intermediate 19D and cyclohexanecarbonyl chloride where appropriate: (4.0 mg, 7.32 μmol, 16% yield). $^1$H NMR (400 MHz, DMSO-$d_6$) δ 8.99 (s, 1H), 7.98 (br. s., 1H), 7.95 (s, 1H), 7.65 (br. s., 2H), 4.34 (q, J=7.1 Hz, 2H), 3.64 (br. s., 3H), 2.31-2.16 (m, 4H), 1.85-1.72 (m, 6H), 1.61 (br. s., 4H), 1.49 (br. s., 1H), 1.46-1.35 (m, 6H), 1.33 (t, J=7.1 Hz, 6H), 0.86 (br. s., 2H); FXR $EC_{50}$ (nM) 1562; MS (ESI) 547 (M+H).

Example 20

Ethyl 2-(3-(N-((4-(3-cyclopropyl-1,2,4-oxadiazol-5-yl)bicyclo[2.2.2]octan-1-yl)methyl)cyclohexanecarboxamido)phenyl)oxazole-4-carboxylate (20)

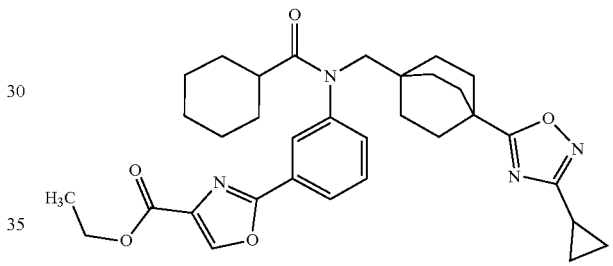

Step A. Intermediate 20A. Preparation of ethyl 2-(3-(((4-(3-cyclopropyl-1,2,4-oxadiazol-5-yl)bicyclo[2.2.2]octan-1-yl)methyl)amino)phenyl)oxazole-4-carboxylate

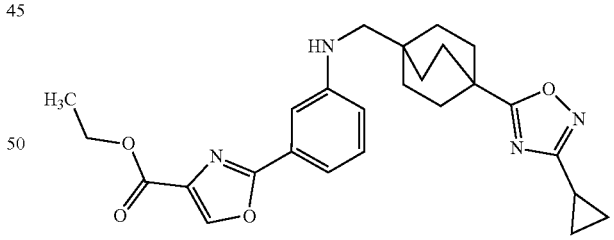

The title compound was prepared according to the method described for the synthesis of Intermediate 1F by substituting Intermediate 19C and Intermediate 2F where appropriate: (550 mg, 1.153 mmol, 54% yield). MS (ESI) 463 (M+H).

Step B. Example 20. Preparation of Ethyl 2-(3-(N-((4-(3-cyclopropyl-1,2,4-oxadiazol-5-yl)bicyclo [2.2.2]octan-1-yl)methyl)cyclohexanecarboxamido) phenyl)oxazole-4-carboxylate The title compound was prepared according to the method described for the synthesis of Example 1 by substituting Intermediate 20A and cyclohexanecarbonyl chloride where appropriate: (14.3 mg, 0.24 mmol, 57% yield). $^1$H NMR (400 MHz, DMSO-$d_6$) δ 9.00 (s, 1H), 8.04-7.88 (m, 2H), 7.65 (br. s., 2H), 4.34 (q, J=7.1 Hz, 2H), 3.63 (br. s., 2H), 2.22 (br. s., 1H), 2.12-2.07 (m, 1H), 2.07-1.96 (m, 1H), 1.86-1.70 (m, 6H), 1.60 (br. s., 4H), 1.48 (br. s., 1H), 1.44-1.28 (m, 10H), 1.16-0.98 (m, 3H), 0.94-0.74 (m, 4H); FXR EC$_{50}$ (nM) 672; MS (ESI) 573 (M+H).

Example 21

N-((4-(3-cyclopropyl-1,2,4-oxadiazol-5-yl)bicyclo[2.2.2]octan-1-yl)methyl)-N-(3-(4-(2-hydroxypropan-2-yl)oxazol-2-yl)phenyl)cyclohexanecarboxamide

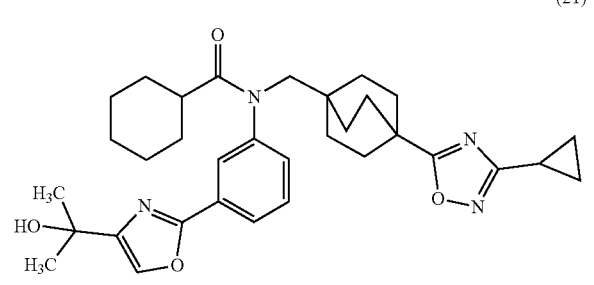

(21)

Step A. Intermediate 21A. Preparation of 2-(2-(3-(((4-(3-cyclopropyl-1,2,4-oxadiazol-5-yl)bicyclo[2.2.2]octan-1-yl)methyl)amino)phenyl)oxazol-4-yl)propan-2-ol

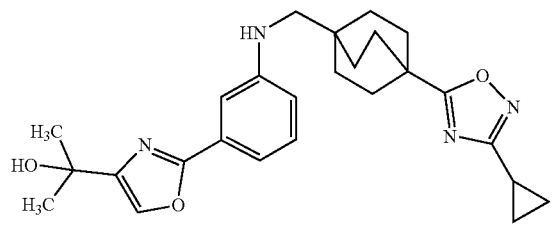 [SMILES: CC(C)(O)c1coc(-c2cccc(NCC34CCC(c5nc(C6CC6)no5)(CC3)CC4)c2)n1]

To a stirred solution of Intermediate 20A (50 mg, 0.108 mmol) in THF (2 mL) was added methylmagnesium bromide (0.11 mL, 0.32 mmol) at 0° C. The reaction mixture was stirred at 0° C. for 1 h. The reaction mixture was poured into aqueous ammonium chloride solution and the aqueous solution was extracted with EtOAc (2×10 mL). The combined organic layers were dried over anhydrous sodium sulphate and concentrated under reduced pressure to afford the title compound (30 mg, 0.067 mmol, 62% yield). MS (ESI) 449 (M+H).

Step B. Example 21. Preparation of N-((4-(3-cyclopropyl-1,2,4-oxadiazol-5-yl) bicyclo[2.2.2]octan-1-yl)methyl)-N-(3-(4-(2-hydroxypropan-2-yl)oxazol-2-yl)phenyl)cyclohexanecarboxamide The title compound was prepared according to the method described for the synthesis of Example 1 by substituting Intermediate 21A and cyclohexanecarbonyl chloride where appropriate: (7.2 mg, 0.013 mmol, 28% yield). $^1$H NMR (400 MHz, DMSO-$d_6$) δ 7.97 (s, 1H), 7.93 (d, J=7.3 Hz, 1H), 7.85 (s, 1H), 7.65-7.50 (m, 2H), 5.15 (s, 1H), 3.62 (br. s., 2H), 2.24 (d, J=10.0 Hz, 1H), 2.06-2.02 (m, 1H), 1.84-1.70 (m, 6H), 1.60 (br. s., 4H), 1.46 (s, 7H), 1.43-1.26 (m, 8H), 1.13-0.96 (m, 3H), 0.93-0.73 (m, 4H); FXR EC$_{50}$ (nM) 194; MS (ESI) 559 (M+H).

Example 22

N-((4-(3-cyclopropyl-1,2,4-oxadiazol-5-yl)bicyclo[2.2.2]octan-1-yl)methyl)-N-(3-(2-cyclopropyloxazol-5-yl)phenyl)cyclohexanecarboxamide

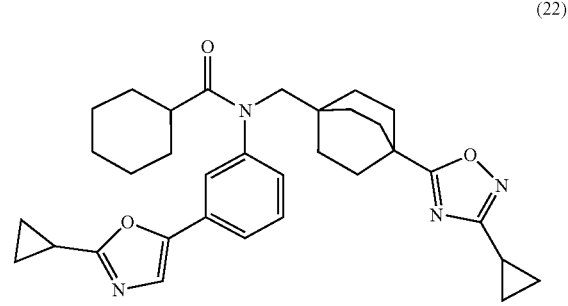 [SMILES: O=C(C1CCCCC1)N(CC12CCC(c3nc(C4CC4)no3)(CC1)CC2)c1cccc(-c2cnc(C3CC3)o2)c1]

(22)

Step A. Intermediate 22A. Preparation of 2-cyclopropyl-5-(3-nitrophenyl)oxazole

To a stirred solution of (diacetoxyiodo)benzene (1170 mg, 3.63 mmol) in cyclopropanecarbonitrile (50 mL) was added trifluoromethanesulfonic acid (2045 mg, 13.62 mmol) at room temperature. The reaction mixture was stirred at the same temperature for 20 min. 1-(3-nitrophenyl)ethan-1-one (500 mg, 3.03 mmol, commercially available) was added to the reaction mixture and heated at reflux for 2 h. The reaction mixture was concentrated under reduced pressure. The residue was diluted with DCM (100 mL), washed with brine solution (5×30 mL), dried over anhydrous sodium sulphate and concentrated under reduced pressure. The crude material was purified by flash chromatography (40 g silica gel cartridge; A=Hex, B=EtOAc; 30 min grad.; 0% B to 40% B; flow rate=40 mL/min). The pure fractions were combined, concentrated under reduced pressure and dried in vacuo to afford the title compound (800 mg, 0.556 mmol, 18% yield) as an orange red liquid. $^1$H NMR (400 MHz, DMSO-$d_6$) δ 8.42 (t, J=2.0 Hz, 1H), 8.18-8.13 (m, 1H), 8.13-8.06 (m, 1H), 7.81-7.70 (m, 2H), 1.93 (dd, J=7.8, 6.8 Hz, 1H), 1.16-1.01 (m, 2H), 0.97-0.88 (m, 2H). MS (ESI) 231 (M+H).

Step B. Intermediate 22B. Preparation of 3-(2-cyclopropyloxazol-5-yl)aniline

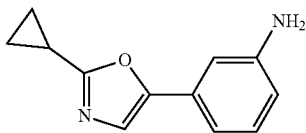 [SMILES: O=[N+]([O-])c1cccc(-c2cnc(C3CC3)o2)c1]

Intermediate 22A (300 mg, 1.303 mmol) was dissolved in a mixture of ethanol (8 mL), THF (2 mL) and water (4 mL). To this solution was added zinc (1278 mg, 19.55 mmol) followed by ammonium chloride (1046 mg, 19.55 mmol) at room temperature. The reaction mixture was stirred at room temperature overnight. The reaction mixture was concentrated under reduced pressure and the residue was suspended in water (10 mL) and EtOAc (10 mL). The organic layer was separated and the aqueous layer was extracted with ethyl acetate (2×10 mL). The combined organic layers were washed with water, brine solution, dried over anhydrous sodium sulphate and concentrated under reduced pressure to afford the title compound (220 mg, 1.099 mmol, 84% yield). $^1$H NMR (400 MHz, DMSO-$d_6$) δ 7.29 (s, 1H), 7.07 (t, J=7.8 Hz, 1H), 6.85-6.77 (m, 2H), 6.52 (dt, J=8.0, 1.3 Hz, 1H), 5.21 (s, 2H), 2.18-2.08 (m, 1H), 1.11-1.02 (m, 2H), 1.02-0.93 (m, 2H). MS (ESI) 201 (M+H).

Step C. Intermediate 22C. Preparation of N-((4-(3-cyclopropyl-1,2,4-oxadiazol-5-yl)bicyclo[2.2.2]octan-1-yl)methyl)-3-(2-cyclopropyloxazol-5-yl)aniline

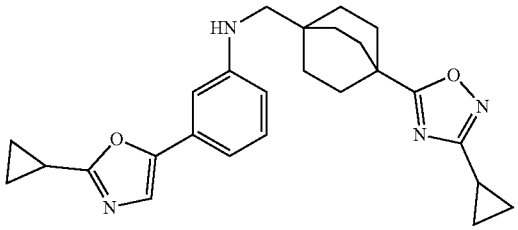 [SMILES: c1cc(NCC23CCC(c4nc(C5CC5)no4)(CC2)CC3)cc(-c2cnc(C3CC3)o2)c1]

The title compound was prepared according to the method described for the synthesis of Intermediate 1F by substituting Intermediate 22B and Intermediate 2F where appropriate: (220 mg, 0.511 mmol, 68% yield) as brown wax. $^1$H NMR (400 MHz, DMSO-$d_6$) δ 7.34 (s, 1H), 7.10 (t, J=8.0 Hz, 1H), 6.87 (d, J=1.5 Hz, 1H), 6.77 (d, J=7.5 Hz, 1H), 6.58 (dd, J=8.0, 1.5 Hz, 1H), 5.62 (t, J=5.8 Hz, 1H), 2.85 (d, J=6.0 Hz, 2H), 2.19-2.10 (m, 1H), 2.10-2.03 (m, 1H), 1.92-1.79 (m, 6H), 1.64-1.53 (m, 6H), 1.11-0.94 (m, 6H), 0.88-0.83 (m, 2H). MS (ESI) 431 (M+H).

Step D. Example 22. Preparation of N-((4-(3-cyclopropyl-1,2,4-oxadiazol-5-yl)bicyclo[2.2.2]octan-1-yl)methyl)-N-(3-(2-cyclopropyloxazol-5-yl)phenyl)cyclohexanecarboxamide The title compound was prepared according to the method described for the synthesis of Example 1 by substituting Intermediate 22C and cyclohexanecarbonyl chloride where appropriate: (10 mg, 0.018 mmol, 25% yield). $^1$H NMR (400 MHz, DMSO-$d_6$) δ 7.66 (s, 1H), 7.64-7.56 (m, 2H), 7.51 (t, J=8.1 Hz, 1H), 7.35 (d, J=7.3 Hz, 1H), 3.61 (br. s, 2H), 2.29-2.13 (m, 2H), 2.10-1.97 (m, 1H), 1.85-1.70 (m, 6H), 1.59 (m, 4H), 1.49 (m, 1H), 1.41 (d, J=8.6 Hz, 6H), 1.33 (m, 1H), 1.16-0.96 (m, 8H), 0.93-0.76 (m, 4H). FXR EC$_{50}$ (nM)=37; MS (ESI) 541 (M+H).

The following compounds were prepared according to the method described for the synthesis of Example 5 by substituting Intermediate 22C and corresponding acids where appropriate:

| Ex. No. | Structure | MS (ESI) (M + H) | FXR EC$_{50}$ (nM) |
|---|---|---|---|
| 23 | (structure shown) | 543 | 74 |

| Ex. No. | Structure | MS (ESI) (M + H) | FXR EC₅₀ (nM) |
|---|---|---|---|
| 24 | 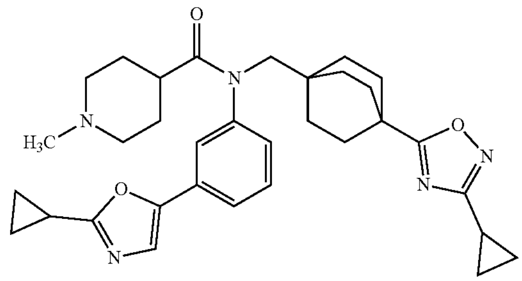 [SMILES: CN1CCC(C(=O)N(CC23CCC(c4nc(C5CC5)no4)(CC2)CC3)c2cccc(-c3cnc(C4CC4)o3)c2)CC1] | 556 | 4799 |
| 25 | (racemate) | 543 | 74 |
| 26 | 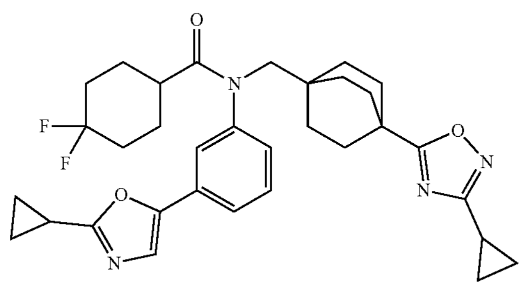 [SMILES: O=C(C1CCC(F)(F)CC1)N(CC12CCC(c3nc(C4CC4)no3)(CC1)CC2)c1cccc(-c2cnc(C3CC3)o2)c1] | 577 | 355 |

23 ¹H NMR (400 MHz, DMSO-d₆) δ 7.70 (s, 1H), 7.65-7.56 (m, 2H), 7.52 (t J = 7.8 Hz, 1H), 7.39 (d, J = 7.8 Hz, 1H), 3.75 (d, J = 8.6 Hz, 2H), 3.7-3.5 (m, 2H), 3.00 (t, J = 11.5 Hz, 2H), 2.18 (t, J = 4.8 Hz, 1H), 2.04 (td, J = 8.6, 4.4 Hz, 2H), 1.83-1.70 (m, 6H), 1.61 (m, 2H), 1.50-1.35 (m, 8H), 1.12-0.93 (m, 6H), 0.89-0.77 (m, 2H).

24 ¹H NMR (400 MHz, DMSO-d₆) δ 7.69 (s, 1H), 7.65-7.55 (m, 2H), 7.51 (t, J = 7.8 Hz, 1H), 7.37 (d, J = 7.6 Hz, 1H), 3.63 (br. s., 2H), 3.52 (br. s., 1H), 2.73 (br. s., 3H), 2.27-2.12 (m, 2H), 2.12-1.93 (m, 4H), 1.90-1.69 (m, 6H), 1.69-1.50 (m, 4H), 1.49-1.33 (m, 6H), 1.14-0.93 (m, 6H), 0.89-0.76 (m, 2H).

25 ¹H NMR (400 MHz, DMSO-d₆) δ 7.72 (m, 1H), 7.67-7.58 (m, 2H), 7.53 (t, J = 7.8 Hz, 1H), 7.42 (m, 1H), 3.77 (br. s., 1H), 3.67 (d, J = 6.4 Hz, 2H), 3.29-3.19 (m, 2H), 2.22-2.14 (m, 1H), 2.08-1.96 (m, 4H), 1.82-1.69 (m, 6H), 1.39 (m, 8H), 1.11-0.96 (m, 6H), 0.88-0.80 (m, 2H) (Note: 1H buried under DMSO peak).

26 ¹H NMR (400 MHz, DMSO-d₆) δ 7.69 (s, 1H), 7.64-7.54 (m, 2H), 7.51 (t, J = 7.8 Hz, 1H), 7.38 (d, J = 8.1 Hz, 1H), 3.61 (br. s, 2H), 2.39 (m, 1H), 2.23-2.13 (m, 1H), 2.08-1.87 (m, 3H), 1.81-1.64 (m, 8H), 1.64-1.52 (m, 2H), 1.50-1.47 (m, 2H), 1.44-1.33 (m, 6H), 1.13-0.92 (m, 6H), 0.88-0.74 (m, 2H).

Example 27

N-((4-(3-cyclopropyl-1,2,4-oxadiazol-5-yl)bicyclo[2.2.2]octan-1-yl)methyl)-N-(3-(5-ethoxyisoxazol-3-yl)phenyl)cyclohexanecarboxamide

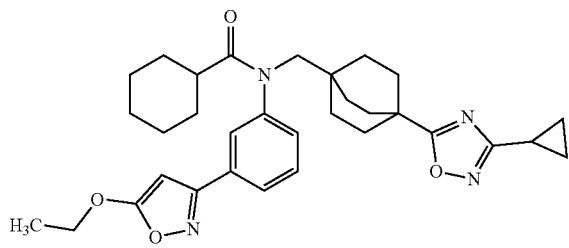

(27)

Step A. Intermediate 27A. Preparation of 5-ethoxy-3-(3-nitrophenyl)isoxazole

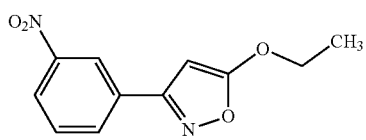 [SMILES: CCOc1cc(-c2cccc([N+](=O)[O-])c2)no1]

To a cooled (0-5° C.) solution of sodium ethoxide (151 mg, 2.226 mmol) in THF (5 mL) was added a solution of Intermediate 11B (500 mg, 2.226 mmol) in THF (5 mL) drop wise. The reaction mixture was warmed to room temperature and stirred for 30 min. The reaction mixture was quenched with water (1 mL) and concentrated under reduced pressure. The residue was diluted with ethyl acetate (5 mL), washed with water (5 mL), brine solution (5 mL), dried over anhydrous sodium sulphate and concentrated under reduced pressure to afford the title compound (450 mg, 1.92 mmol, 86% yield) as yellow solid. $^1$H NMR (400 MHz, DMSO-$d_6$) δ 8.58 (t, J=2.0 Hz, 1H), 8.34 (d, J=1.0 Hz, 1H), 8.30-8.23 (m, 1H), 7.82 (t, J=8.0 Hz, 1H), 6.45 (s, 1H), 4.38 (q, J=7.0 Hz, 2H), 1.42 (t, J=7.0 Hz, 3H). MS (ESI) 235 (M+H).

Step B. Intermediate 27B. Preparation of 3-(5-ethoxyisoxazol-3-yl)aniline

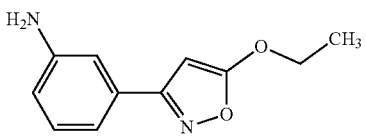

Intermediate 27A (450 mg, 1.921 mmol) was dissolved in a mixture of ethanol (4 mL), THF (1 mL) and water (2 mL). To this solution was added zinc (1884 mg, 28.8 mmol) followed by ammonium chloride (1542 mg, 28.8 mmol) at room temperature. The reaction mixture was stirred at the same temperature overnight. The reaction mixture was filtered through Celite pad and washed with methanol (5 mL). The filtrate was concentrated under reduced pressure. The residue was diluted with ethyl acetate (10 mL), washed with water (2×5 mL), brine solution (10 mL), dried over anhydrous sodium sulphate and concentrated under reduced pressure to afford the title compound (220 mg, 1.077 mmol, 56% yield) as brown wax. $^1$H NMR (400 MHz, DMSO-$d_6$) δ 7.15-7.07 (m, 1H), 7.00 (t, J=2.0 Hz, 1H), 6.91-6.86 (m, 1H), 6.69-6.62 (m, 1H), 5.96 (s, 1H), 5.25 (s, 2H), 4.32 (q, J=7.0 Hz, 2H), 1.42 (t, J=7.0 Hz, 3H). MS (ESI) 205 (M+H).

Step C. Intermediate 27C. Preparation of N-((4-(3-cyclopropyl-1,2,4-oxadiazol-5-yl) bicyclo[2.2.2]octan-1-yl)methyl)-3-(5-ethoxyisoxazol-3-yl)aniline

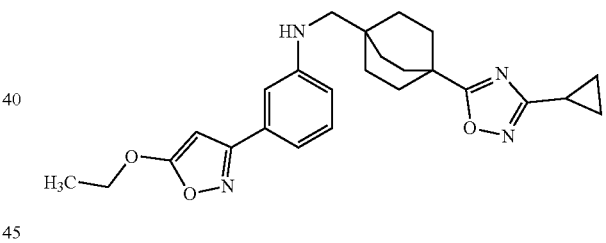

The title compound was prepared according to the method described for the synthesis of Intermediate 1F by substituting Intermediate 27B and Intermediate 2F where appropriate: (200 mg, 0.460 mmol, 63% yield) as brown wax. MS (ESI) 435 (M+H).

Step D. Example 27. Preparation of N-((4-(3-cyclopropyl-1,2,4-oxadiazol-5-yl)bicyclo[2.2.2]octan-1-yl)methyl)-N-(3-(5-ethoxyisoxazol-3-yl)phenyl)cyclohexanecarboxamide The title compound was prepared according to the method described for the synthesis of Example 1 by substituting Intermediate 27C and cyclohexanecarbonyl chloride where appropriate: (10 mg, 0.018 mmol, 39% yield). $^1$H NMR (400 MHz, DMSO-$d_6$) δ 7.79 (br. s., 2H), 7.61-7.50 (m, 2H), 6.32 (s, 1H), 4.36 (q, J=6.9 Hz, 2H), 3.62 (br. s., 2H), 2.28-2.17 (m, 1H), 2.10-2.00 (m, 1H), 1.83-1.70 (m, 6H), 1.60 (d, J=8.6 Hz, 4H), 1.48 (m, 1H), 1.44-1.27 (m, 11H), 1.14-0.96 (m, 3H), 0.94-0.73 (m, 4H). FXR $EC_{50}$ (nM)=75; MS (ESI) 545 (M+H).

Example 28

N-((4-(3-cyclopropyl-1,2,4-oxadiazol-5-yl)bicyclo[2.2.2]octan-1-yl)methyl)-N-(3-(2-propyloxazol-5-yl)phenyl)cyclohexanecarboxamide

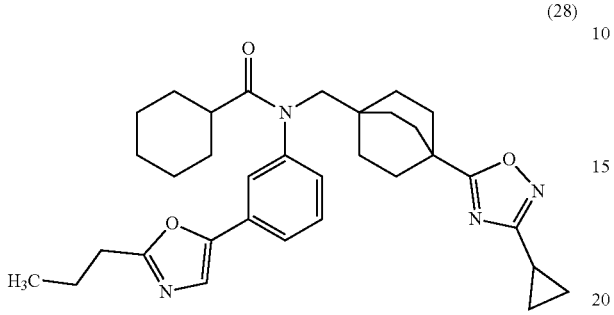

(28)

Step A. Intermediate 28A. Preparation of 5-(3-nitrophenyl)-2-propyloxazole

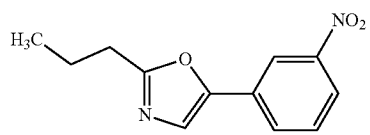 [SMILES: CCCc1ncc(-c2cccc([N+](=O)[O-])c2)o1]

To a stirred solution of (diacetoxyiodo)benzene (2.340 g, 7.27 mmol) in butyronitrile (10 mL) was added trifluoromethanesulfonic acid (4.09 g, 27.2 mmol) at room temperature. The reaction mixture was stirred at room temperature for 20 min. 1-(3-nitrophenyl)ethan-1-one (1.0 g, 6.06 mmol) was added to the reaction mixture and then heated at reflux for 2 h. The reaction mixture was concentrated under reduced pressure. The residue was diluted with DCM (100 mL), washed with brine solution, dried over anhydrous sodium sulphate and concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (300 mg, 1.292 mmol, 21% yield) as brown liquid. $^1$H NMR (400 MHz, DMSO-$d_6$) δ 8.76 (s, 1H), 8.59-8.53 (m, 1H), 8.24-8.11 (m, 2H), 7.73 (t, J=8.0 Hz, 1H), 2.80 (t, J=7.5 Hz, 2H), 1.82-1.70 (m, 2H), 0.97 (t, J=7.3 Hz, 3H). MS (ESI) 233 (M+H).

Step B. Intermediate 28B. Preparation of 3-(2-propyloxazol-5-yl)aniline

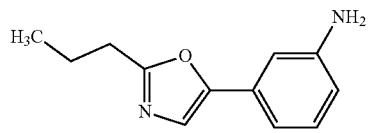

Intermediate 28A (300 mg, 1.292 mmol) was dissolved in a mixture of ethanol (8 mL), THF (2 mL), and water (4 mL). To this solution was added zinc (1267 mg, 19.38 mmol) followed by ammonium chloride (1036 mg, 19.38 mmol) at room temperature. The reaction mixture was stirred at same temperature overnight. The reaction mixture was concentrated under reduced pressure and the residue was diluted with water (10 mL) and extracted with ethyl acetate (2×10 mL). The combined organic layers were washed with water (10 mL), brine solution (10 mL), dried over anhydrous sodium sulphate and concentrated under reduced pressure to afford the title compound (220 mg, 1.088 mmol, 84% yield). $^1$H NMR (400 MHz, DMSO-$d_6$) δ 8.29 (s, 1H), 7.09-6.97 (m, 2H), 6.91-6.84 (m, 1H), 6.52-6.46 (m, 1H), 5.12 (s, 2H), 2.75 (t, J=7.3 Hz, 2H), 1.74 (q, J=7.4 Hz, 2H), 0.96 (t, J=7.3 Hz, 3H). MS (ESI) 203 (M+H).

Step C. Intermediate 28C. Preparation of N-((4-(3-cyclopropyl-1,2,4-oxadiazol-5-yl) bicyclo[2.2.2]octan-1-yl)methyl)-3-(2-propyloxazol-5-yl)aniline

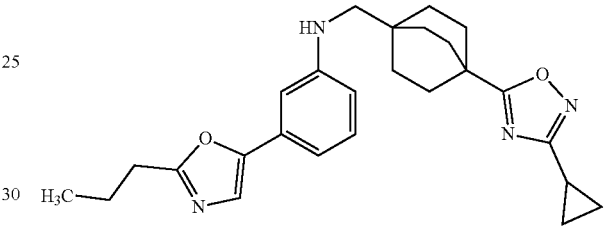

The title compound was prepared according to the method described for the synthesis of Intermediate 1F by substituting Intermediate 28B and Intermediate 2F where appropriate: (140 mg, 0.32 mmol, 66% yield) as brown wax. $^1$H NMR (400 MHz, DMSO-$d_6$) δ 8.33 (s, 1H), 7.10-7.06 (m, 1H), 7.04 (d, J=5.5 Hz, 1H), 6.87 (d, J=7.5 Hz, 1H), 6.56 (dd, J=8.3, 1.8 Hz, 1H), 5.53 (t, J=6.0 Hz, 1H), 2.85 (d, J=5.5 Hz, 2H), 2.76 (t, J=7.3 Hz, 2H), 2.11-2.03 (m, 1H), 1.92-1.82 (m, 6H), 1.80-1.69 (m, 2H), 1.63-1.54 (m, 6H), 1.07-1.00 (m, 2H), 0.96 (t, J=7.3 Hz, 3H), 0.89-0.83 (m, 2H). MS (ESI) 433 (M+H).

Step D. Example 28. Preparation of N-((4-(3-cyclopropyl-1,2,4-oxadiazol-5-yl) bicyclo[2.2.2]octan-1-yl)methyl)-N-(3-(2-propyloxazol-5-yl)phenyl)cyclohexanecarboxamide The title compound was prepared according to the method described for the synthesis of Example 1 by substituting Intermediate 28C and cyclohexanecarbonyl chloride where appropriate: (14.3 mg, 0.026 mmol, 56% yield). $^1$H NMR (400 MHz, DMSO-$d_6$) δ 8.60 (s, 1H), 7.77-7.67 (m, 2H), 7.49 (t, J=7.9 Hz, 1H), 7.33 (d, J=8.1 Hz, 1H), 3.63 (br. s., 2H), 2.84-2.73 (m, 2H), 2.30-2.19 (m, 1H), 2.04 (td, J=8.6, 4.4 Hz, 1H), 1.83-1.69 (m, 8H), 1.58 (m, 4H), 1.48-1.27 (m, 9H), 1.09-0.93 (m, 6H), 0.93-0.78 (m, 4H). FXR $EC_{50}$ (nM)=34; MS (ESI) 543 (M+H).

The following compounds were prepared according to the method described for the synthesis of Example 5 by substituting Intermediate 28C and corresponding acids where appropriate:

| Ex. No. | Structure | MS (ESI) (M + H) | FXR EC$_{50}$ (nM) |
|---|---|---|---|
| 29 | 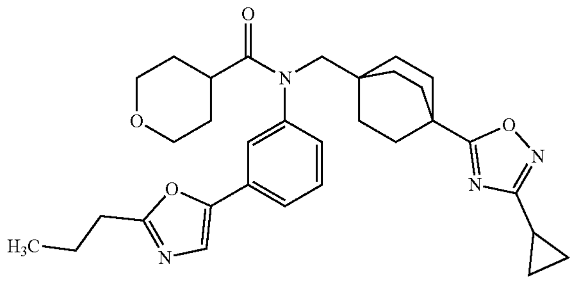 [SMILES: CCCc1ncc(-c2cccc(N(CC34CCC(c5nc(C6CC6)no5)(CC3)CC4)C(=O)C3CCOCC3)c2)o1] | 545 | 53 |
| 30 | (racemate) | 545 | 145 |

29 $^1$H NMR (400 MHz, DMSO-d$_6$) δ 8.60 (s, 1H), 7.81-7.69 (m, 2H), 7.50 (t, J = 8.1 Hz, 1H), 7.37 (d, J = 7.8 Hz, 1H), 3.75 (d, J = 11.2 Hz, 2H), 3.4-3.7 (br. s, 2H), 2.99 (t, J = 11.1 Hz, 2H), 2.78 (t, J = 7.3 Hz, 2H), 2.10-1.94 (m, 2H), 1.83-1.70 (m, 8H), 1.62 (d, J = 7.8 Hz, 2H), 1.52-1.33 (m, 8H), 1.08-0.92 (m, 5H), 0.88-0.75 (m, 2H).

30 $^1$H NMR (400 MHz, DMSO-d$_6$) δ 8.61 (s, 1H), 7.85-7.68 (m, 2H), 7.51 (t, J = 8.1 Hz, 1H), 7.39 (d, J = 7.6 Hz, 1H), 3.77 (br. s., 1H), 3.67 (d, J = 8.1 Hz, 1H), 3.52 (m, 2H), 3.31-3.15 (m, 3H), 2.79 (t, J = 7.3 Hz, 2H), 2.09-1.93 (m, 2H), 1.84-1.54 (m, 10H), 1.51-1.33 (m, 6H), 1.07-0.90 (m, 5H), 0.90-0.74 (m, 3H).

Example 31

Ethyl 4-(3-(N-((4-(3-cyclopropyl-1,2,4-oxadiazol-5-yl)bicyclo[2.2.2]octan-1-yl)methyl)cyclohexanecarboxamido)phenyl)thiazole-2-carboxylate

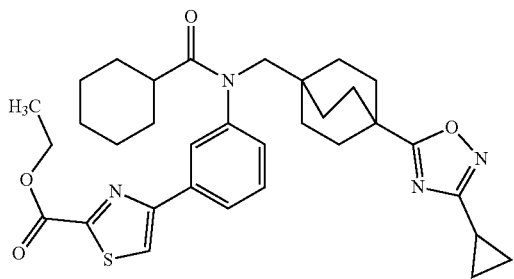

(31)

Step A. Intermediate 31A. Preparation of ethyl 4-(3-nitrophenyl)thiazole-2-carboxylate

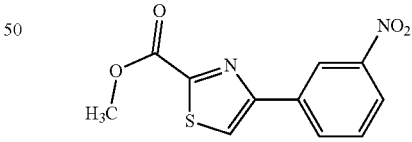

To a stirred solution of 2-bromo-1-(3-nitrophenyl)ethan-1-one (1.5 g, 6.15 mmol) in EtOH (15 mL) was added ethyl thiooxamate (0.818 g, 6.15 mmol) at room temperature and the reaction mixture was heated 90° C. for 2 h. The reaction mixture was concentrated under reduced pressure and the residue was suspended in cold water and extracted with EtOAc (2×50 mL). The combined organic layers were dried over anhydrous sodium sulphate and concentrated under reduced pressure to afford the title compound (1.2 g, 4.23 mmol, 69% yield). This compound was taken to next step without further purification. MS (ESI) 279 (M+H).

Step B. Intermediate 31B. Preparation of ethyl 4-(3-aminophenyl)thiazole-2-carboxylate

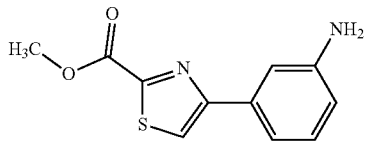 [SMILES: COC(=O)c1nc(-c2cccc(N)c2)cs1]

To a stirred solution of Intermediate 31A (500 mg, 1.80 mmol) in EtOH (10 mL) were added tin(II) chloride dihydrate (1338 mg, 5.93 mmol) and conc. HCl (1.8 mL, 59.2 mmol) at 0° C. The reaction mixture was warmed to room temperature and heated at 90° C. for 2 h. The reaction mixture was cooled to room temperature, concentrated under reduced pressure and the residue was diluted with cold water. The aqueous solution was basified with aqueous 10% sodium bicarbonate solution and extracted with EtOAc (2×70 mL). The combined organic layers were dried over anhydrous sodium sulphate and concentrated under reduced pressure to afford the title compound (250 mg, 0.886 mmol, 49% yield). MS (ESI) 249 (M+H).

Step C. Intermediate 31C. Preparation of ethyl 4-(3-(((4-(3-cyclopropyl-1,2,4-oxadiazol-5-yl)bicyclo[2.2.2]octan-1-yl)methyl)amino)phenyl)thiazole-2-carboxylate

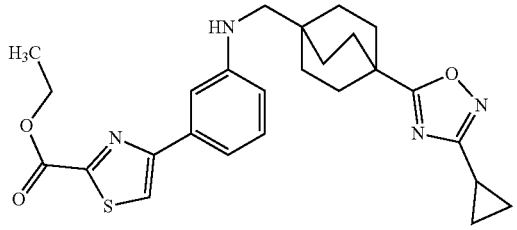 [SMILES: CCOC(=O)c1nc(-c2cccc(NCC34CCC(c5nc(C6CC6)no5)(CC3)CC4)c2)cs1]

The title compound was prepared according to the method described for the synthesis of Intermediate 1F by substituting Intermediate 31B and Intermediate 2F where appropriate: (240 mg, 0.466 mmol, 58% yield). MS (ESI) 479 (M+H).

Step D. Example 31. Preparation of Ethyl 4-(3-(N-((4-(3-cyclopropyl-1,2,4-oxadiazol-5-yl)bicyclo[2.2.2]octan-1-yl)methyl)cyclohexanecarboxamido)phenyl)thiazole-2-carboxylate The title compound was prepared according to the method described for the synthesis of Example 1 by substituting Intermediate 31C and cyclohexanecarbonyl chloride where appropriate: (11.3 mg, 0.019 mmol, 46% yield). $^1$H NMR (400 MHz, DMSO-$d_6$) δ 8.68 (s, 1H), 8.03-7.92 (m, 2H), 7.57 (t, J=7.9 Hz, 1H), 7.45d, J=8.6 Hz, 1H), 4.43 (q, J=7.3 Hz, 2H), 3.66 (br. s., 2H), 2.27 (br. s., 1H), 2.07-2.00 (m, 1H), 1.80-1.72 (m, 6H), 1.68-1.55 (m, 4H), 1.45-1.28 (m, 12H), 1.09 (d, J=8.6 Hz, 1H), 1.03-0.98 (m, 2H), 0.94-0.78 (m, 4H); FXR $EC_{50}$ (nM) 1199; MS (ESI) 589 (M+H).

Example 32

N-((4-(3-cyclopropyl-1,2,4-oxadiazol-5-yl)bicyclo[2.2.2]octan-1-yl)methyl)-N-(3-(2-(2-hydroxypropan-2-yl)thiazol-4-yl)phenyl)cyclohexanecarboxamide (32)

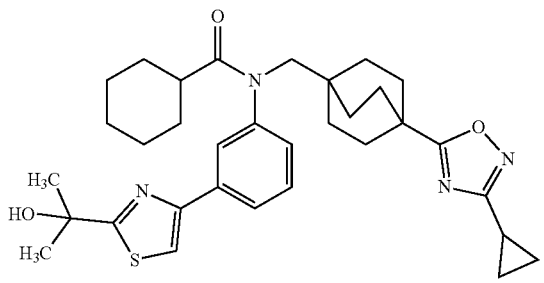

Step A. Intermediate 32A. Preparation of 2-(4-(3-(((4-(3-cyclopropyl-1,2,4-oxadiazol-5-yl)bicyclo[2.2.2]octan-1-yl)methyl)amino)phenyl)thiazol-2-yl)propan-2-ol

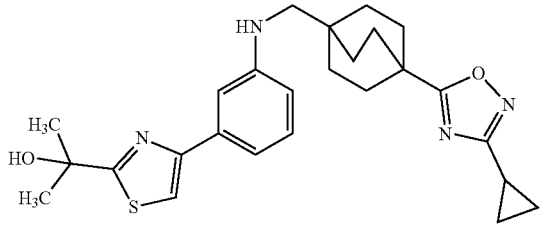 [SMILES: CC(C)(O)c1nc(-c2cccc(NCC34CCC(c5nc(C6CC6)no5)(CC3)CC4)c2)cs1]

To a stirred solution of Intermediate 31C (60 mg, 0.125 mmol) in THF (2 mL) was added methylmagnesium bromide (0.251 mL, 0.752 mmol) at 0° C. The reaction mixture was warmed to room temperature and stirred at for 12 h. The reaction mixture was poured into saturated aqueous ammonium chloride solution and the aqueous layer was extracted with EtOAc (2×50 mL). The combined organic layers were dried over anhydrous sodium sulphate and concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (40 mg, 0.067 mmol, 54% yield). MS (ESI) 465 (M+H).

Step B. Example 32. Preparation of N-((4-(3-cyclopropyl-1,2,4-oxadiazol-5-yl) bicyclo[2.2.2]octan-1-yl)methyl)-N-(3-(2-(2-hydroxypropan-2-yl)thiazol-4-yl)phenyl)cyclohexanecarboxamide The title compound was prepared according to the method described for the synthesis of Example 1 by substituting Intermediate 32A and cyclohexanecarbonyl chloride where appropriate: (6.3 mg, 10.85 μmol, 25% yield). $^1$H NMR (400 MHz, DMSO-$d_6$) δ 8.10 (s, 1H), 7.94-7.87 (m, 2H), 7.50 (t, J=7.7 Hz, 1H), 7.35 (d, J=6.1 Hz, 1H), 6.05 (s, 1H), 3.63 (br.

s., 2H), 2.28 (br. s., 1H), 2.09-2.00 (m, 1H), 1.84-1.71 (m, 6H), 1.68-1.54 (m, 10H), 1.48 (br. s., 1H), 1.44-1.28 (m, 8H), 1.15-0.98 (m, 3H), 0.95-0.78 (m, 4H); FXR EC$_{50}$ (nM) 320; MS (ESI) 575 (M+H).

Example 33

N-((4-(3-methyl-1,2,4-oxadiazol-5-yl)bicyclo[2.2.2]octan-1-yl)methyl)-N-(3-(2-(tetrahydro-2H-pyran-4-yl)oxazol-5-yl)phenyl)cyclohexanecarboxamide (33)

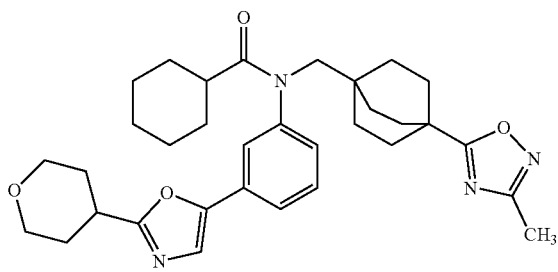

Step A. Intermediate 33A. Preparation of 5-(3-nitrophenyl)-2-(tetrahydro-2H-pyran-4-yl)oxazole

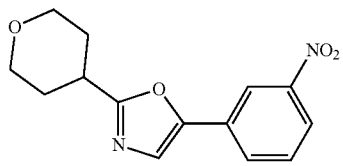

To a stirred solution of (diacetoxyiodo)benzene (1170 mg, 3.63 mmol) in oxane-4-carbonitrile (10 mL) was added trifluoromethanesulfonic acid (2045 mg, 13.62 mmol) at room temperature. The reaction mixture was stirred at room temperature for 20 min. 1-(3-nitrophenyl)ethan-1-one (500 mg, 3.03 mmol) was added to the reaction mixture and then heated at reflux for 2 h. The reaction mixture was concentrated under reduced pressure and the residue was diluted with DCM (100 mL). The organic layer was washed with aqueous 10% brine solution, dried over anhydrous sodium sulphate and concentrated under reduced pressure. The crude material was purified by flash chromatography (24 g silica gel cartridge; A=Hex, B=EtOAc; 30 min grad.; 0% B to 60% B; flow rate=30 mL/min). The pure fractions were combined, concentrated under reduced pressure and dried in vacuo to afford the title compound (200 mg, 0.729 mmol, 24% yield) as brown wax. MS (ESI) 275 (M+H).

Step B. Intermediate 33B. Preparation of 3-(2-(tetrahydro-2H-pyran-4-yl)oxazol-5-yl) aniline

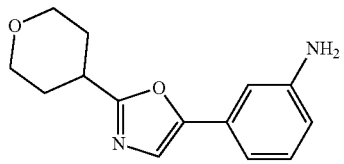 [SMILES: O=[N+]([O-])c1cccc(-c2cnc(C3CCOCC3)o2)c1]

Intermediate 33A (200 mg, 0.729 mmol) was dissolved in a mixture of ethanol (4 mL), THF (2 mL) and water (1 mL). To this solution was added zinc (715 mg, 10.94 mmol) followed by ammonium chloride (585 mg, 10.94 mmol) at room temperature. The reaction mixture was stirred at the same temperature overnight. The reaction mixture was filtered through Celite pad and the filtrate was concentrated under reduced pressure. The residue was diluted with ethyl acetate (50 mL). The organic layer was washed with water (20 mL), aqueous 10% sodium bicarbonate solution, brine solution, dried over anhydrous sodium sulphate and concentrated under reduced pressure. The crude material was purified by flash chromatography (24 g silica gel cartridge; A=Hex, B=EtOAc; 30 min grad.; 0% B to 70% B; flow rate=30 mL/min). The pure fractions were combined, concentrated under reduced pressure and dried in vacuo to afford the title compound (100 mg, 0.409 mmol, 56% yield) as brown wax. MS (ESI) 245 (M+H).

Step C. Intermediate 33C. Preparation of N-((4-(3-methyl-1,2,4-oxadiazol-5-yl) bicyclo[2.2.2]octan-1-yl)methyl)-3-(2-(tetrahydro-2H-pyran-4-yl)oxazol-5-yl)aniline

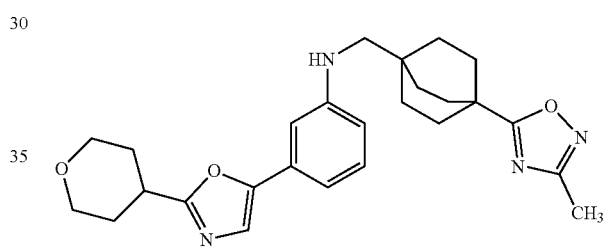

The title compound was prepared according to the method described for the synthesis of Intermediate 1F by substituting Intermediate 33B and Intermediate 1C where appropriate: (40 mg, 0.089 mmol, 44% yield) as brown wax. MS (ESI) 449 (M+H).

Step D. Example 33. Preparation of N-((4-(3-methyl-1,2,4-oxadiazol-5-yl) bicyclo[2.2.2]octan-1-yl)methyl)-N-(3-(2-(tetrahydro-2H-pyran-4-yl)oxazol-5-yl)phenyl)cyclohexanecarboxamide The title compound was prepared according to the method described for the synthesis of Example 1 by substituting Intermediate 33C and cyclohexanecarbonyl chloride where appropriate: (7.9 mg, 0.014 mmol, 32% yield). $^1$H NMR (400 MHz, DMSO-d$_6$) δ 7.77-7.67 (m, 2H), 7.64 (d, J=8.1 Hz, 1H), 7.53 (t, J=7.8 Hz, 1H), 7.39 (d, J=7.6 Hz, 1H), 3.97-3.85 (m, 2H), 3.63 (br. s., 2H), 3.49 (td, J=11.4, 2.2 Hz, 2H), 3.23-3.13 (m, 1H), 2.30-2.18 (m, 4H), 1.98 (d, J=10.8 Hz, 2H), 1.86-1.69 (m, 10H), 1.69-1.46 (m, 4H), 1.46-1.28 (m, 8H), 0.88 (d, J=13.7 Hz, 2H); FXR EC$_{50}$ (nM)=949; MS (ESI) 559 (M+H).

Example 34

N-((4-(3-cyclopropyl-1,2,4-oxadiazol-5-yl)bicyclo[2.2.2]octan-1-yl)methyl)-N-(3-(2-(tetrahydro-2H-pyran-4-yl)oxazol-5-yl)phenyl)cyclohexanecarboxamide (34)

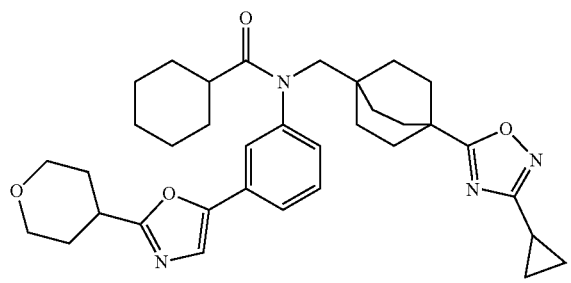

Step A. Intermediate 34A. Preparation of N-((4-(3-cyclopropyl-1,2,4-oxadiazol-5-yl) bicyclo[2.2.2]octan-1-yl)methyl)-3-(2-(tetrahydro-2H-pyran-4-yl)oxazol-5-yl)aniline

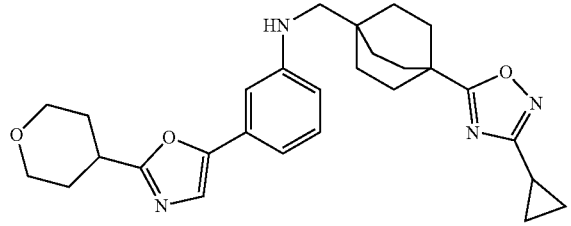 [SMILES: c1cc(NCC23CCC(c4nc(C5CC5)no4)(CC2)CC3)cc(-c2cnc(C3CCOCC3)o2)c1]

The title compound was prepared according to the method described for the synthesis of Intermediate 1F by substituting Intermediate 33B and Intermediate 2F where appropriate: (60 mg, 0.126 mmol, 62% yield) as brown wax. MS (ESI) 475 (M+H).

Step B. Example 34. Preparation of N-((4-(3-cyclopropyl-1,2,4-oxadiazol-5-yl) bicyclo[2.2.2]octan-1-yl)methyl)-N-(3-(2-(tetrahydro-2H-pyran-4-yl)oxazol-5-yl)phenyl)cyclohexanecarboxamide The title compound was prepared according to the method described for the synthesis of Example 1 by substituting Intermediate 34A and cyclohexanecarbonyl chloride where appropriate: (8.6 mg, 0.015 mmol, 35% yield). $^1$H NMR (400 MHz, DMSO-$d_6$) δ 7.75-7.67 (m, 2H), 7.64 (d, J=7.6 Hz, 1H), 7.53 (t, J=7.8 Hz, 1H), 7.38 (d, J=8.1 Hz, 1H), 3.97-3.85 (m, 2H), 3.62 (br. s., 2H), 3.53-3.43 (m, 2H), 3.23-3.11 (m, 1H), 2.24 (m, 1H), 2.11-1.93 (m, 4H), 1.85-1.71 (m, 9H), 1.61 (m, 4H), 1.44-1.26 (m, 9H), 1.16-0.96 (m, 2H), 0.94-0.76 (m, 3H); FXR EC$_{50}$ (nM)=212; MS (ESI) 585 (M+H).

Example 35

N-(3-(3-cyclopropyl-1,2,4-oxadiazol-5-yl)phenyl)-N-((4-(5-methyloxazol-2-yl)bicyclo[2.2.2]octan-1-yl)methyl)cyclohexanecarboxamide (35)

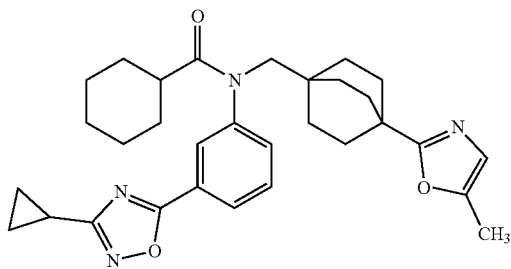

Step A. Intermediate 35A. Preparation of Methyl 4-((2-hydroxypropyl)carbamoyl)bicyclo[2.2.2]octane-1-carboxylate

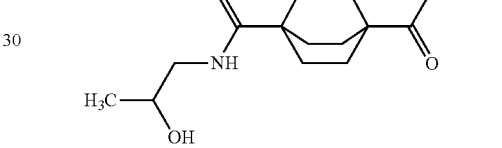

To a stirred solution of 4-(methoxycarbonyl)bicyclo[2.2.2]octane-1-carboxylic acid (1 g, 4.71 mmol) in DCM (20 mL) were added 1-hydroxybenzotriazole hydrate (0.722 g, 4.71 mmol) and 1-(3-dimethylaminopropyl)-3-ethylcarbodiimide hydrochloride (1.806 g, 9.42 mmol) at 0° C. The reaction mixture was stirred at the same temperature for 30 min. 1-aminopropan-2-ol (0.369 mL, 4.71 mmol) was added to the reaction mixture. The reaction mixture was stirred at 0° C. for 2 h and at room temperature overnight. The reaction mixture was concentrated under reduced pressure. The residue was diluted with water (10 mL) and EtOAc (30 mL). The organic layer was separated, washed with brine, dried over anhydrous sodium sulphate and concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (1.2 g, 4.37 mmol, 93% yield). MS (ESI) 268 (M−H).

Step B. Intermediate 35B. Preparation of Methyl 4-((2-oxopropyl)carbamoyl)bicyclo[2.2.2]octane-1-carboxylate

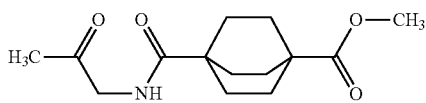 [SMILES: COC(=O)C12CCC(C(=O)NCC(C)=O)(CC1)CC2]

To a stirred solution of Intermediate 35A (1.2 g, 4.46 mmol) in DCM (15 mL) was added Dess-Martin periodinane (1.701 g, 4.01 mmol) and the reaction mixture was stirred at room temperature for 1 h. The reaction mixture was diluted with DCM (15 mL), washed with saturated aqueous NaHCO₃ solution (3×10 mL), dried over anhydrous sodium sulphate and concentrated under reduced pressure. The crude material was purified by flash chromatography (40 g silica gel cartridge; A=Hex, B=EtOAc; 30 min grad.; 0% B to 70% B; flow rate=40 mL/min). The pure fractions were combined, concentrated under reduced pressure and dried in vacuo to afford the title compound (950 mg, 80% yield). MS (ESI) 268 (M+H).

Step C. Intermediate 35C. Preparation of N-(3-(2-methoxypyridin-4-yl)phenyl)pyrimidin-2-amine

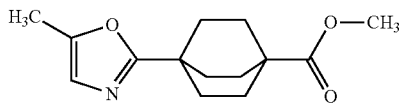

To a stirred solution of Intermediate 35B (0.4 g, 1.496 mmol) in DCM (10 mL) was added POCl₃ (5.58 mL, 59.9 mmol) at room temperature. The reaction mixture was heated at reflux for 2 h. The reaction mixture was cooled to room temperature and concentrated under reduced pressure. The residue was diluted with EtOAc (30 mL), washed with aqueous 10% NaHCO₃ solution (2×20 mL), brine solution, dried over anhydrous sodium sulphate and concentrated in vacuo to afford the title compound (0.25 g, 0.842 mmol, 56% yield). $^1$H NMR (400 MHz, DMSO-$d_6$) δ 6.77 (s, 1H), 3.59 (s, 3H), 2.24 (s, 3H), 1.9-1.7 (m, 12H). MS (ESI) 250 (M+H).

Step D. Intermediate 35D. Preparation of (4-(5-methyloxazol-2-yl)bicyclo[2.2.2]octan-1-yl)methanol

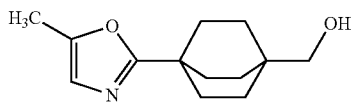

The title compound was prepared according to the method described for the synthesis of Intermediate 1B by substituting Intermediate 35C where appropriate: (65 mg, 0.294 mmol, 73% yield). $^1$H NMR (400 MHz, DMSO-$d_6$) δ 6.57 (s, 1H), 3.77 (s, 2H), 3.32 (s, 1H), 2.24 (s, 3H), 1.9-1.7 (m, 12H). MS (ESI) 222 (M+H).

Step E. Intermediate 35E: Preparation of 4-(5-methyloxazol-2-yl)bicyclo[2.2.2]octane-1-carbaldehyde

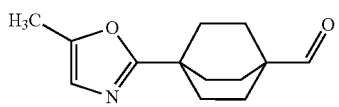 [SMILES: Cc1cnc(C23CCC(C=O)(CC2)CC3)o1]

The title compound was prepared according to the method described for the synthesis of Intermediate 1C by substituting Intermediate 35D where appropriate: (110 mg, 0.477 mmol, 56% yield). $^1$H NMR (400 MHz, DMSO-$d_6$) δ 9.45 (s, 1H), 6.68 (s, 1H), 2.24 (s, 3H), 1.87-1.83 (m, 6H), 1.68-1.65 (m, 6H). MS (ESI) 220 (M+H).

Step F. Intermediate 35F: Preparation of 3-(3-cyclopropyl-1,2,4-oxadiazol-5-yl)-N-((4-(5-methyloxazol-2-yl)bicyclo[2.2.2]octan-1-yl)methyl)aniline

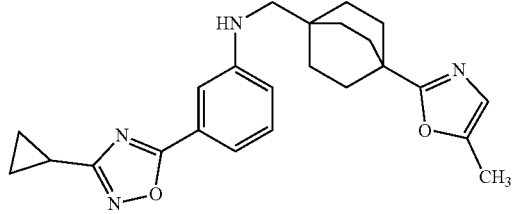 [SMILES: Cc1cnc(C23CCC(CNc4cccc(-c5nc(C6CC6)no5)c4)(CC2)CC3)o1]

The title compound was prepared according to the method described for the synthesis of Intermediate 1F by substituting Intermediate 13A and Intermediate 35E where appropriate: (105 mg, 0.259 mmol, 81% yield). $^1$H NMR (400 MHz, DMSO-$d_6$) δ 7.29-7.08 (m, 3H), 6.89-6.83 (m, 1H), 6.65 (s, 1H), 5.95 (s, 1H), 3.32 (s, 2H), 2.33 (s, 3H), 2.23-2.16 (m, 1H), 1.84-1.80 (m, 6H), 1.57-1.53 (m, 6H), 1.11-1.08 (m, 4H). MS (ESI) 405 (M+H).

Step G. Example 35: Preparation of N-(3-(3-cyclopropyl-1,2,4-oxadiazol-5-yl)phenyl)-N-((4-(5-methyloxazol-2-yl)bicyclo[2.2.2]octan-1-yl)methyl)cyclohexanecarboxamide The title compound was prepared according to the method described for the synthesis of Example 5 by substituting Intermediate 35F and corresponding acids where appropriate. (8.1 mg, 0.0159 mmol, 42% yield). $^1$H NMR (400 MHz, DMSO-$d_6$) δ 8.07-7.91 (m, 2H), 7.81-7.60 (m, 2H), 6.62 (d, J=1.2 Hz, 1H), 3.62 (br. s., 2H), 2.29-2.13 (m, 4H), 1.80-1.67 (m, 6H), 1.60 (m, 4H), 1.51 (m, 2H), 1.44-1.26 (m, 8H), 1.18-1.04 (m, 3H), 1.04-0.96 (m, 2H), 0.86 (br. s., 2H). FXR EC₅₀ (nM)=515; MS (ESI) 109 (M+H).

Example 36

N-((4-(3-cyclopropyl-1,2,4-oxadiazol-5-yl)bicyclo[2.2.2]octan-1-yl)methyl)-N-(3-(4-(difluoromethyl)oxazol-2-yl)phenyl)tetrahydro-2H-pyran-4-carboxamide (36)

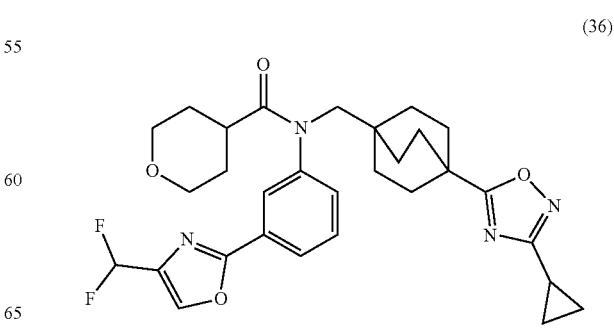

Step A. Intermediate 36A. Preparation of (2-(3-nitrophenyl)oxazol-4-yl)methanol

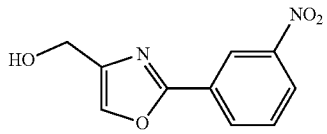 [SMILES: O=[N+]([O-])c1cccc(-c2nc(CO)co2)c1]

To a stirred solution of Intermediate 19B (1 g, 3.81 mmol) in THF (30 mL) was added DIBAL-H (7.63 mL, 7.63 mmol) at −78° C. The reaction mixture was stirred at the same temperature for 1 h. The reaction mixture was poured into aqueous ammonium chloride solution (10 mL) and EtOAc (50 mL). The organic layer was separated, washed with water, dried over anhydrous sodium sulphate and concentrated under reduced pressure. The crude material was purified by flash chromatography (24 g silica gel cartridge; A=Hex, B=EtOAc; 30 min grad.; 0% B to 50% B; flow rate=40 mL/min). The pure fractions were combined, concentrated under reduced pressure and dried in vacuo to afford the title compound (400 mg, 1.79 mmol, 47% yield). MS (ESI) 221 (M+H).

Step B. Intermediate 36B. Preparation of 2-(3-nitrophenyl)oxazole-4-carbaldehyde

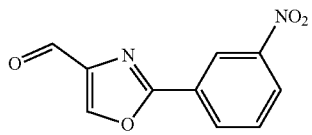 [SMILES: O=Cc1coc(-c2cccc([N+](=O)[O-])c2)n1]

To a stirred solution of Intermediate 36A (400 mg, 1.817 mmol) in DCM (15 mL) was added Dess-Martin periodinane (925 mg, 2.180 mmol) at 0° C. The reaction mixture was allowed to warm to room temperature and stirred for 1 h. The reaction mixture was poured into aqueous 10% sodium bicarbonate solution and the aqueous layer was extracted with EtOAc (2×50 mL). The combined organic layers were dried over anhydrous sodium sulphate and concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (370 mg, 1.594 mmol, 88% yield). MS (ESI) 219 (M+H).

Step C. Intermediate 36C. Preparation of 4-(difluoromethyl)-2-(3-nitrophenyl)oxazole

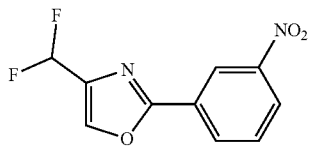 [SMILES: O=[N+]([O-])c1cccc(-c2nc(C(F)F)co2)c1]

To a stirred solution of Intermediate 36B (370 mg, 1.696 mmol) in DCM (10 mL) was added DAST (0.560 mL, 4.24 mmol) at −78° C. The reaction mixture was warmed to room temperature and stirred for 12 h. The reaction mixture was quenched with cold water and the aqueous solution was extracted with EtOAc (2×50 mL), dried over anhydrous sodium sulphate and concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (330 mg, 1.374 mmol, 81% yield). $^1$H NMR (400 MHz, DMSO-$d_6$) δ 8.91 (s, 1H), 8.33-8.41 (m, 2H), 8.01 (d, J=4.00 Hz, 1H), 7.69 (t, J=16.00 Hz, 1H), 6.74 (t, J=54.00 Hz, 1H).

Step D. Intermediate 36D. Preparation of 3-(4-(difluoromethyl)oxazol-2-yl)aniline

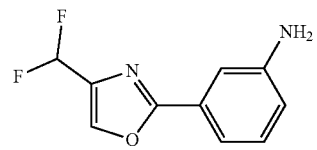 [SMILES: Nc1cccc(-c2nc(C(F)F)co2)c1]

To a stirred solution of Intermediate 38C (50 mg, 0.208 mmol) in EtOH (2.5 mL) were added tin(II) chloride dihydrate (164 mg, 0.729 mmol) and conc. HCl (0.190 mL, 6.25 mmol) at 0° C. The reaction mixture was warmed to room temperature and then heated at 90° C. for 2 h. The reaction mixture was cooled to room temperature and neutralized with aqueous sodium bicarbonate solution. The aqueous layer was extracted with EtOAc (2×50 mL). The combined organic layers were dried over anhydrous sodium sulphate and concentrated under reduced pressure to afford the title compound (30 mg, 0.131 mmol, 63% yield). MS (ESI) 211 (M+H).

Step E. Intermediate 36E. Preparation of N-((4-(3-cyclopropyl-1,2,4-oxadiazol-5-yl) bicyclo[2.2.2]octan-1-yl)methyl)-3-(4-(difluoromethyl)oxazol-2-yl)aniline

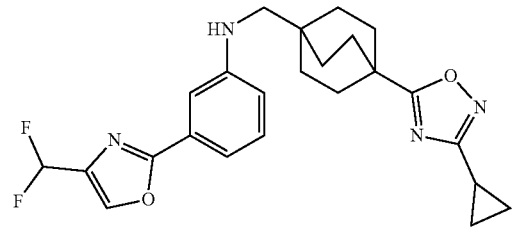 [SMILES: FC(F)c1coc(-c2cccc(NCC34CCC(c5nc(C6CC6)no5)(CC3)CC4)c2)n1]

The title compound was prepared according to the method described for the synthesis of Intermediate 1F by substituting Intermediate 36D and Intermediate 2F where appropriate: (290 mg, 0.658 mmol, 69% yield). MS (ESI) 441 (M+H).

Step F. Example 36. Preparation of N-((4-(3-cyclopropyl-1,2,4-oxadiazol-5-yl) bicyclo[2.2.2]octan-1-yl)methyl)-N-(3-(4-(difluoromethyl)oxazol-2-yl)phenyl)tetrahydro-2H-pyran-4-carboxamide The title compound was prepared according to the method described for the synthesis of Example 5 by substituting Intermediate 36E and corresponding acid where appropriate: (7.8 mg, 0.014 mmol, 30% yield). $^1$H NMR (400 MHz, DMSO-d$_6$) δ 8.68 (t, J=2.6 Hz, 1H), 8.05-7.89 (m, 2H), 7.74-7.57 (m, 2H), 7.15 (t, J=54.5 Hz, 1H), 3.74 (d, J=9.0 Hz, 2H), 3.62 (d, J=11.2 Hz, 2H), 3.00 (t, J=11.5 Hz, 2H), 2.10-1.99 (m, 1H), 1.84-1.69 (m, 7H), 1.68-1.54 (m, 2H), 1.52-1.30 (m, 8H), 1.06-0.95 (m, 2H), 0.87-0.78 (m, 2H); FXR EC$_{50}$ (nM) 525; MS (ESI) 553 (M+H).

The below compounds were synthesized according to the method described for the synthesis of Example 5 by substituting Intermediate 36E and corresponding acids where appropriate:

| Ex. No. | Structure | MS (ESI) (M + H) | FXR EC$_{50}$ (nM) |
|---|---|---|---|
| 37 | | 551 | 166 |
| 38 | | 652 | 4390 |

37 $^1$H NMR (400 MHz, DMSO-d$_6$) δ 8.69 (t, J = 2.4 Hz, 1H), 7.98 (br. s., 1H), 7.94 (s, 1H), 7.64 (br. s., 2H), 7.16 (t, J = 54.0 Hz, 1H), 3.63 (br. s., 2H), 2.22 (br. s., 1H), 2.10-1.97 (m, 1H), 1.85-1.66 (m, 6H), 1.60 (br. s., 4H), 1.48 (br. s., 1H), 1.45-1.26 (m, 8H), 1.14-0.96 (m, 3H), 0.95-0.74 (m, 4H)

38 $^1$H NMR (400 MHz, DMSO-d$_6$) δ 8.68 (br. s., 1H), 7.97 (br. s., 2H), 7.67 (br. s., 2H), 7.15 (t, J = 54.0 Hz, 1H), 3.83 (d, J = 13.4 Hz, 2H), 3.64 (br. s., 2H), 2.44 (br. s., 3H), 2.09-1.99 (m, 1H), 1.87-1.64 (m, 6H), 1.54 (br. s., 2H), 1.49-1.28 (m, 17H), 1.11-0.94 (m, 2H), 0.89-0.78 (m, 2H)

Example 39

N-((4-(3-cyclopropyl-1,2,4-oxadiazol-5-yl)bicyclo[2.2.2]octan-1-yl)methyl)-N-(3-(5-ethoxy-1,3,4-oxadiazol-2-yl)phenyl)-4,4-difluorocyclohexane-1-carboxamide (39)

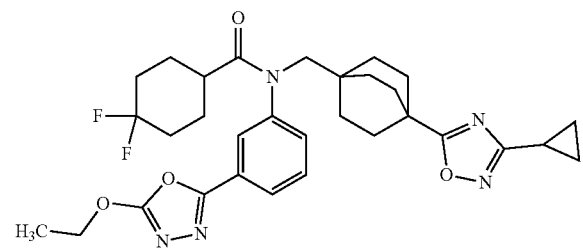

Step A. Intermediate 39A. Preparation of ethyl 2-(3-nitrobenzyl)hydrazine-1-carboxylate

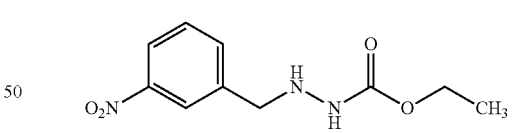

To a stirred solution of 1-(chloromethyl)-3-nitrobenzene (2 g, 11.66 mmol, commercially available) and ethyl hydrazine carboxylate (1.214 g, 11.66 mmol) in DMF (40 mL) was added K$_2$CO$_3$ (1.77 g, 12.82 mmol) followed by sodium iodide (0.349 g, 2.33 mmol) at room temperature. The reaction mixture was stirred at room temperature overnight. The reaction mixture was diluted with ethyl acetate (25 mL), washed with ice cold water (2×50 mL), brine solution (30 mL) and dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (1.05 g, 4.39 mmol, 38% yield) as a colorless gummy solid. ¹H NMR (400 MHz, DMSO-d₆) δ 8.53 (br. s., 1H), 8.22 (br. s., 1H), 8.14-8.09 (m, 1H), 7.78 (d, J=7.6 Hz, 1H), 7.64-7.58 (m, 1H), 5.22 (q, J=4.2 Hz, 1H), 4.05-3.95 (m, 4H), 1.13 (t, J=7.1 Hz, 3H). MS (ESI) 240 (M+H).

Step B. Intermediate 39B. Preparation of 2-ethoxy-5-(3-nitrophenyl)-1,3,4-oxadiazole

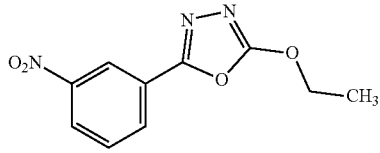 [SMILES: CCOc1nnc(-c2cccc([N+](=O)[O-])c2)o1]

To a stirred solution of Intermediate 39A (0.9 g, 3.76 mmol) in MeCN (90 mL) was added iodobenzene diacetate (2.67 g, 8.28 mmol) at room temperature. The reaction mixture was heated at 45° C. for 2 h. The reaction mixture was diluted with ethyl acetate (10 mL), washed with brine solution (2×10 mL), dried over anhydrous sodium sulphate and concentrated under reduced pressure. The crude material was purified by flash chromatography (24 g silica gel cartridge; A=Hex, B=EtOAc; 30 min grad.; 0% B to 50% B; flow rate=40 mL/min). The pure fractions were combined, concentrated under reduced pressure and dried in vacuo to afford the title compound (700 mg, 2.68 mmol, 71% yield) as brown gummy solid. ¹H NMR (400 MHz, DMSO-d₆) δ 8.58-8.54 (m, 1H), 8.42 (dd, J=8.4, 1.1 Hz, 1H), 8.34-8.29 (m, 1H), 7.88 (t, J=8.1 Hz, 1H), 4.60 (q, J=7.3 Hz, 3H), 1.45 (t, J=7.20 Hz, 3H). MS (ESI) 236 (M+H).

Step C. Intermediate 39C. Preparation of 3-(5-ethoxy-1,3,4-oxadiazol-2-yl)aniline

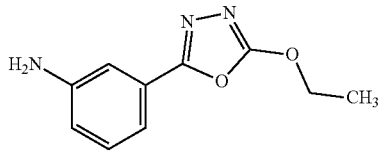

To a stirred solution of Intermediate 39B (600 mg, 2.55 mmol) in ethanol (6 mL) was added a solution of ammonium chloride (2047 mg, 38.3 mmol) in water (6 mL) followed by zinc (2502 mg, 38.3 mmol) at room temperature. The reaction mixture was stirred at room temperature overnight. The reaction mixture was diluted with DCM (20 mL) and filtered through Celite bed. The filtrate was washed with water, brine solution, dried over anhydrous sodium sulphate and concentrated under reduced pressure to afford the title compound (480 mg, 2.199 mmol, 86% yield) as brown solid. ¹H NMR (400 MHz, DMSO-d₆) δ 7.17 (t, J=7.8 Hz, 1H), 7.11-7.06 (m, 1H), 7.01-6.95 (m, 1H), 6.73 (dt, J=8.0, 1.3 Hz, 1H), 5.44 (br. s., 2H), 4.53 (q, J=7.0 Hz, 2H), 1.42 (t, J=7.0 Hz, 3H). MS (ESI) 206 (M+H).

Step D. Intermediate 39D. Preparation of N-((4-(3-cyclopropyl-1,2,4-oxadiazol-5-yl) bicyclo[2.2.2] octan-1-yl)methyl)-3-(5-ethoxy-1,3,4-oxadiazol-2-yl)aniline

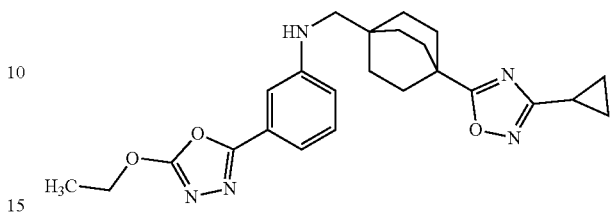

The title compound was prepared according to the method described for the synthesis of Intermediate 1F by substituting Intermediate 39C and Intermediate 2F where appropriate: (320 mg, 0.735 mmol, 60% yield) as brown gummy solid. ¹H NMR (400 MHz, DMSO-d₆) δ 7.25-7.16 (m, 1H), 7.11 (d, J=1.7 Hz, 1H), 6.98 (d, J=6.8 Hz, 1H), 6.83-6.78 (m, 1H), 4.54 (q, J=7.0 Hz, 2H), 2.86 (d, J=6.1 Hz, 2H), 2.10-2.01 (m, 1H), 1.90-1.80 (m, 6H), 1.61-1.51 (m, 6H), 1.42 (t, J=7.0 Hz, 3H), 1.06-1.00 (m, 2H), 0.89-0.82 (m, 2H). MS (ESI) 206 (M+H).

Step E. Example 39. N-((4-(3-cyclopropyl-1,2,4-oxadiazol-5-yl)bicyclo[2.2.2]octan-1-yl)methyl)-N-(3-(5-ethoxy-1,3,4-oxadiazol-2-yl)phenyl)-4,4-difluorocyclohexane-1-carboxamide The title compound was prepared according to the method described for the synthesis of Example 5 by substituting Intermediate 39D and 4,4-difluorocyclohexane-1-carboxylic acid (commercially available) where appropriate: (8.3 mg, 0.013 mmol, 32% yield). ¹HNMR (400 MHz, DMSO-d₆) δ 7.87 (br. s., 2H), 7.66 (br. s., 2H), 4.59 (q, J=7.1 Hz, 2H), 3.62 (br. s., 2H), 2.39 (br. s., 1H), 2.08-2.01 (m, 1H), 1.94 (d, J=17.9 Hz, 2H), 1.82-1.65 (m, 8H), 1.62 (d, J=11.0 Hz, 2H), 1.52 (d, J=10.0 Hz, 2H), 1.48-1.30 (m, 9H), 1.09-0.96 (m, 2H), 0.91-0.76 (m, 2H). FXR EC₅₀ (nM)=130; MS (ESI) 582 (M+H).

Example 40

N-((4-(3-cyclopropyl-1,2,4-oxadiazol-5-yl)bicyclo[2.2.2]octan-1-yl)methyl)-N-(3-(5-cyclopropylisoxazol-3-yl)phenyl)tetrahydro-2h-pyran-4-carboxamide (40)

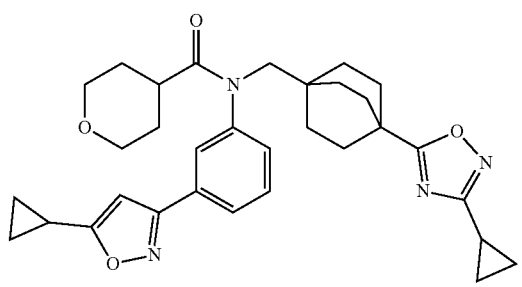

Step A. Intermediate 40A. Preparation of 1-cyclopropyl-3-(3-nitrophenyl)propane-1,3-dione

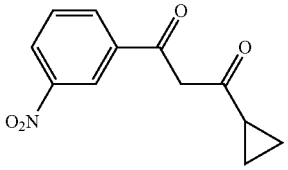 [SMILES: O=C(CC(=O)C1CC1)c1cccc([N+](=O)[O-])c1]

To a stirred solution of LiHMDS in THF (1M solution) (23.78 mL, 23.78 mmol) was added 1-cyclopropylethan-1-one (1.0 g, 11.89 mmol, commercially available) at −78° C. and the reaction mixture was stirred at the same temperature for 45 min. A solution of 3-nitrobenzoyl chloride (2.101 g, 11.32 mmol, commercially available) in THF (11 mL) was added to the reaction mixture drop wise over 20 min and the reaction mixture was stirred for 1 h at −78° C. The reaction mixture was quenched with aqueous saturated ammonium chloride solution (50 mL) and extracted with ethyl acetate (2×50 mL). The combined organic layers were washed with water (50 mL) followed by saturated brine solution (50 mL), dried over anhydrous sodium sulphate and concentrated under reduced pressure. The crude material was purified by flash chromatography (40 g silica gel cartridge; A=Hex, B=EtOAc; 30 min grad.; 0% B to 40% B; flow rate=40 mL/min). The pure fractions were combined, concentrated under reduced pressure and dried in vacuo to afford the title compound (1.6 g, 6.86 mmol, 61% yield) as yellow solid. $^1$H NMR (400 MHz, Chloroform-d) δ 16.16 (br. s., 1H), 8.75-8.60 (m, 1H), 8.43-8.27 (m, 1H), 8.20 (dt, J=7.9, 1.3 Hz, 1H), 7.65 (t, J=7.8 Hz, 1H), 6.36 (s, 1H), 1.90-1.77 (m, 1H), 1.28-1.15 (m, 2H), 1.06 (dq, J=7.8, 3.7 Hz, 2H). MS (ESI) 232 (M−H).

Step B. Intermediate 40B. Preparation of 5-cyclopropyl-3-(3-nitrophenyl)isoxazole

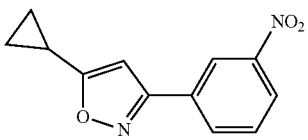 [SMILES: O=[N+]([O-])c1cccc(-c2cc(C3CC3)on2)c1]

To a stirred solution of Intermediate 40A (0.8 g, 3.43 mmol) in MeOH (30 mL) was added hydroxylamine hydrochloride (0.953 g, 13.72 mmol) at room temperature. The reaction mixture was stirred at the same temperature for 48 h. The reaction mixture was concentrated under reduced pressure and the residue was diluted with water (30 mL) and extracted with ethyl acetate (2×20 mL). The combined organic layers were washed with saturated brine solution (40 mL), dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=40 mL/min). The pure fractions were combined, concentrated under reduced pressure and dried in vacuo to afford the title compound (600 mg, 2.61 mmol, 76% yield) as brown oil. $^1$H NMR (400 MHz, DMSO-$d_6$) δ 8.60-8.56 (m, 1H), 8.36-8.31 (m, 1H), 8.30-8.23 (m, 1H), 7.86-7.79 (m, 1H), 6.98 (s, 1H), 2.26-2.18 (m, 1H), 1.17-1.11 (m, 2H), 1.00-0.94 (m, 2H). MS (ESI) 231 (M+H).

Step C. Intermediate 40C. Preparation of 3-(5-cyclopropylisoxazol-3-yl)aniline

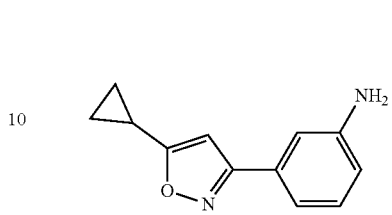

To a stirred solution of Intermediate 40B (700 mg, 3.04 mmol) in a mixture of ethanol (8 mL), THF (4 mL) and water (2 mL) was added zinc (2982 mg, 45.6 mmol) followed by ammonium chloride (2440 mg, 45.6 mmol) at room temperature. The reaction mixture was stirred at room temperature overnight. The reaction mixture was concentrated under reduced pressure and the residue was diluted with ethyl acetate (10 mL). The solution was filtered through Celite bed and the residue was washed with ethyl acetate (10 mL). The filtrate obtained was concentrated under reduced pressure. The crude material was purified by flash chromatography (24 g silica gel cartridge; A=Hex, B=EtOAc; 30 min grad.; 0% B to 30% B; flow rate=40 mL/min). The pure fractions were combined, concentrated under reduced pressure and dried in vacuo to afford the title compound (200 mg, 0.999 mmol, 33% yield) as brown wax. $^1$H NMR (400 MHz, DMSO-$d_6$) δ 7.10 (t, J=8.0 Hz, 1H), 7.03-6.99 (m, 1H), 6.88 (d, J=7.5 Hz, 1H), 6.64 (dd, J=8.0, 1.5 Hz, 1H), 6.57-6.51 (m, 1H), 5.24 (s, 2H), 2.20-2.09 (m, 1H), 1.12-1.04 (m, 2H), 0.96-0.88 (m, 2H). MS (ESI) 201 (M+H).

Step D. Intermediate 40D. Preparation of N-((4-(3-cyclopropyl-1,2,4-oxadiazol-5-yl) bicyclo[2.2.2]octan-1-yl)methyl)-3-(5-cyclopropylisoxazol-3-yl)aniline

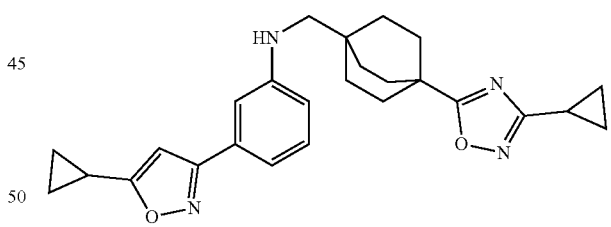

The title compound was prepared according to the method described for the synthesis of Intermediate 1F by substituting Intermediate 40C and 2F where appropriate: (350 mg, 0.813 mmol, 81% yield) as brown wax. MS (ESI) 431 (M+H).

Step E. Example 40. Preparation of N-((4-(3-cyclopropyl-1,2,4-oxadiazol-5-yl) bicyclo[2.2.2]octan-1-yl)methyl)-N-(3-(5-cyclopropylisoxazol-3-yl)phenyl)tetrahydro-2H-pyran-4-carboxamide The title compound was prepared according to the method described for the synthesis of Example 5 by substituting Intermediate 45D and the corresponding acid where appropriate: (5.9 mg, 10.87 μmol, 9% yield). $^1$H NMR (400 MHz, DMSO-d$_6$) δ 7.82 (s, 2H), 7.65-7.48 (m, 2H), 6.86 (s, 1H), 3.74 (d, J=8.3 Hz, 2H), 3.62 (br. s., 2H), 2.99 (t, J=12.2 Hz, 2H), 2.23-2.14 (m, 1H), 2.10-1.98 (m, 1H), 1.84-1.71 (m, 6H), 1.67-1.55 (m, 2H), 1.52-1.32 (m, 8H), 1.17-1.07 (m, 2H), 1.07-0.98 (m, 2H), 0.98-0.90 (m, 2H), 0.89-0.75 (m, 2H), Note: 1H-buried under DMSO peak. FXR EC$_{50}$ (nM) =78; MS (ESI) 543 (M+H).

Example 41

N-((4-(3-(cyclopropylmethyl)-1,2,4-oxadiazol-5-yl)bicyclo[2.2.2]octan-1-yl)methyl)-N-(3-(3-(cyclopropylmethyl)-1,2,4-oxadiazol-5-yl)phenyl)tetrahydro-2H-pyran-4-carboxamide (41)

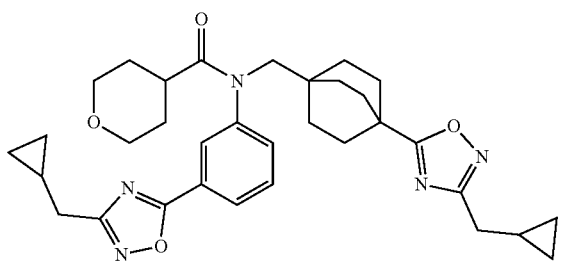

Step A. Intermediate 41A. Preparation of (E)-2-cyclopropyl-N'-hydroxyacetimidamide

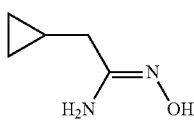

To a stirred solution of 2-cyclopropylacetonitrile (1.1 mL, 12.33 mmol, commercially available) in ethanol (10 mL) was added hydroxylamine (3.78 mL, 61.6 mmol) at room temperature. The reaction mixture was heated at reflux for 1 h. The reaction mixture was cooled to room temperature and concentrated under reduced pressure. The residue was diluted with water and the precipitated solid was filtered and dried in vacuo to afford the title compound (1200 mg, 10.51 mmol, 85% yield) as a pale gray solid. $^1$H NMR (400 MHz, DMSO-d$_6$) δ 8.70 (s, 1H), 5.32 (br. s., 2H), 1.84 (d, J=7.0 Hz, 2H), 1.00-0.87 (m, 1H), 0.48-0.33 (m, 2H), 0.14-0.07 (m, 2H). MS (ESI) 115 (M+H).

Step B. Intermediate 41B. Preparation of 3-(3-(cyclopropylmethyl)-1,2,4-oxadiazol-5-yl)aniline

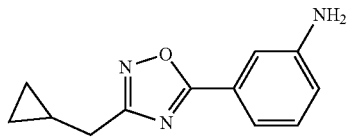 [SMILES: Nc1cccc(-c2nc(CC3CC3)no2)c1]

The title compound was prepared according to the method described for the synthesis of Intermediate 1A by substituting Intermediate 41A and 3-aminobenzoic acid where appropriate: (350 mg, 1.593 mmol, 87% yield) as yellow gummy liquid. $^1$H NMR (400 MHz, DMSO-d$_6$) δ 7.31 (t, J=1.8 Hz, 1H), 7.27-7.17 (m, 2H), 6.87-6.80 (m, 1H), 5.55 (s, 2H), 2.68 (d, J=6.80 Hz, 2H), 1.15-1.07 (m, 1H), 0.57-0.48 (m, 2H), 0.30-0.22 (m, 2H). MS (ESI) 216 (M+H).

Step C. Intermediate 41C. Preparation of methyl 4-(3-(cyclopropylmethyl)-1,2,4-oxadiazol-5-yl)bicyclo[2.2.2]octane-1-carboxylate

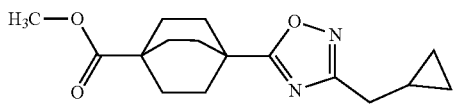

The title compound was prepared according to the method described for the synthesis of Intermediate 1A by substituting Intermediate 41A and 4-(methoxycarbonyl)bicyclo[2.2.2]octane-1-carboxylic acid where appropriate: (1000 mg, 2.411 mmol, 68% yield). $^1$H NMR (400 MHz, DMSO-d$_6$) δ 3.60 (s, 3H), 2.58 (d, J=7.0 Hz, 2H), 1.97-1.87 (m, 6H), 1.87-1.77 (m, 6H), 1.09-0.98 (m, 1H), 0.52-0.45 (m, 2H), 0.23-0.16 (m, 2H). MS (ESI) 291 (M+H).

Step D. Intermediate 41D. Preparation of (4-(3-(cyclopropylmethyl)-1,2,4-oxadiazol-5-yl)bicyclo[2.2.2]octan-1-yl)methanol

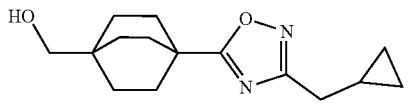

The title compound was prepared according to the method described for the synthesis of Intermediate 1B by substituting Intermediate 41C where appropriate: (650 mg, 2.478 mmol, 80% yield). MS (ESI) 263 (M+H).

Step E. Intermediate 41E. Preparation of 4-(3-(cyclopropylmethyl)-1,2,4-oxadiazol-5-yl) bicyclo[2.2.2]octane-1-carbaldehyde

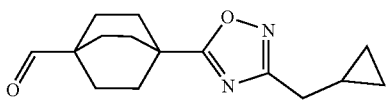

The title compound was prepared according to the method described for the synthesis of Intermediate 1C by substituting Intermediate 41D where appropriate: (500 mg, 1.921 mmol, 78% yield). $^1$H NMR (400 MHz, DMSO-d$_6$) δ 9.47 (s, 1H), 1.97-1.88 (m, 6H), 1.84-1.76 (m, 2H), 1.74-1.66 (m, 6H), 1.09-1.01 (m, 1H), 0.53-0.46 (m, 2H), 0.23-0.18 (m, 2H). MS (ESI) 261 (M+H).

Step F. Intermediate 41F. Preparation of 3-(3-(cyclopropylmethyl)-1,2,4-oxadiazol-5-yl)-N-((4-(3-(cyclopropylmethyl)-1,2,4-oxadiazol-5-yl)bicyclo[2.2.2]octan-1-yl)methyl) aniline

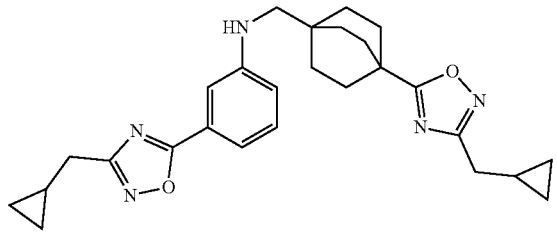 [SMILES: c1cc(NCC23CCC(c4nc(CC5CC5)no4)(CC2)CC3)cc(-c2nc(CC3CC3)no2)c1]

The title compound was prepared according to the method described for the synthesis of Intermediate 1F by substituting Intermediate 41B and 41E where appropriate: (180 mg, 0.392 mmol, 73% yield). $^1$H NMR (400 MHz, DMSO-d$_6$) δ 7.35-7.15 (m, 2H), 6.92 (dd, J=7.7, 2.1 Hz, 1H), 6.83 (ddd, J=7.6, 2.4, 1.5 Hz, 1H), 6.00 (s, 1H), 2.89 (d, J=5.9 Hz, 2H), 2.68 (dd, J=7.0, 3.3 Hz, 2H), 2.59 (d, J=6.8 Hz, 2H), 1.95-1.85 (m, 6H), 1.84-1.75 (m, 1H), 1.64-1.54 (m, 6H), 1.17-0.98 (m, 1H), 0.58-0.42 (m, 4H), 0.30-0.17 (m, 4H). MS (ESI) 460 (M+H).

Step G. Example 41. Preparation of N-((4-(3-(cyclopropylmethyl)-1,2,4-oxadiazol-5-yl) bicyclo[2.2.2]octan-1-yl)methyl)-N-(3-(3-(cyclopropylmethyl)-1,2,4-oxadiazol-5-yl)phenyl)tetrahydro-2H-pyran-4-carboxamide The title compound was prepared according to the method described for the synthesis of Example 5 by substituting Intermediate 41F and corresponding acid where appropriate: $^1$H NMR (400 MHz, DMSO-d$_6$) δ 8.14-7.99 (m, 2H), 7.79 (br. s., 1H), 7.75-7.63 (m, 1H), 3.75 (d, J=10.0 Hz, 2H), 3.67 (br. s., 2H), 3.01 (br. s., 2H), 2.73 (d, J=7.1 Hz, 2H), 2.56 (d, J=7.1 Hz, 2H), 1.91-1.71 (m, 6H), 1.68-1.56 (m, 2H), 1.55-1.31 (m, 8H), 1.20-1.09 (m, 2H), 1.07-0.96 (m, 1H), 0.58-0.51 (m, 2H), 0.51-0.42 (m, 2H), 0.34-0.25 (m, 2H), 0.23-0.12 (m, 2H) FXR EC$_{50}$ (nM)=229; MS (ESI) 572 (M+H).

The title compound was prepared according to the method described for the synthesis of Example 5 by substituting Intermediate 41F and corresponding acids where appropriate:

| Ex. No. | Structure | MS (ESI) (M + H) | FXR EC$_{50}$ (nM) |
|---|---|---|---|
| 42 | 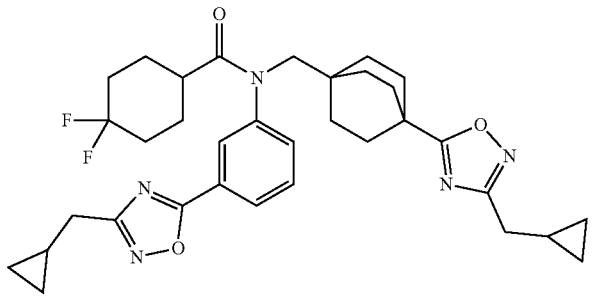 [SMILES: O=C(C1CCC(F)(F)CC1)N(CC12CCC(c3nc(CC4CC4)no3)(CC1)CC2)c1cccc(-c2nc(CC3CC3)no2)c1] | 606 | 536 |

42 $^1$H NMR (400 MHz, DMSO-d$_6$) δ 8.15-8.01 (m, 2H), 7.80 (br. s., 1H), 7.72 (d, J = 6.8 Hz, 1H), 3.65 (br. s., 2H), 2.73 (d, J = 7.1 Hz, 2H), 2.56 (d, J = 6.8 Hz, 1H), 2.41 (br. s., 1H), 1.95 (d, J = 10.3 Hz, 2H), 1.86-1.75 (m, 6H), 1.75-1.56 (m, 5H), 1.47-1.34 (m, 6H), 1.14 (td, J = 8.3, 4.2 Hz, 1H), 1.08-0.96 (m, 2H), 0.59-0.51 (m, 2H), 0.51-0.40 (m, 2H), 0.33-0.25 (m, 2H), 0.23-0.13 (m, 2H)

Example 43

N-((4-(3-cyclopropyl-1,2,4-oxadiazol-5-yl)bicyclo[2.2.2]octan-1-yl)methyl)-N-(3-(3-(cyclopropylmethyl)-1,2,4-oxadiazol-5-yl)phenyl)-4,4-difluorocyclohexane-1-carboxamide (43)

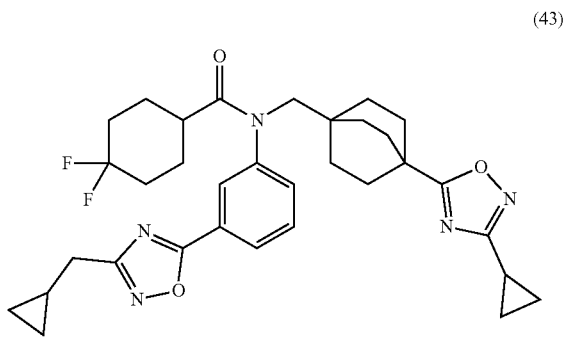 [SMILES: O=C(C1CCC(F)(F)CC1)N(CC12CCC(c3nc(C4CC4)no3)(CC1)CC2)c1cccc(-c2nc(CC3CC3)no2)c1]

Step A. Intermediate 43A. Preparation of N-((4-(3-cyclopropyl-1,2,4-oxadiazol-5-yl) bicyclo[2.2.2]octan-1-yl)methyl)-3-(3-(cyclopropylmethyl)-1,2,4-oxadiazol-5-yl)aniline

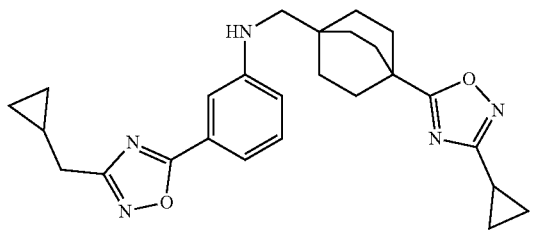 [SMILES: c1cc(NCC23CCC(c4nc(C5CC5)no4)(CC2)CC3)cc(-c2nc(CC3CC3)no2)c1]

The title compound was prepared according to the method described for the synthesis of Intermediate 1F by substituting Intermediates 41B and 2F where appropriate: (180 mg, 0.404 mmol, 71% yield). MS (ESI) 446 (M+H).

Step B. Example 43. Preparation of N-((4-(3-cyclopropyl-1,2,4-oxadiazol-5-yl) bicyclo[2.2.2]octan-1-yl)methyl)-N-(3-(3-(cyclopropylmethyl)-1,2,4-oxadiazol-5-yl)phenyl)-4,4-difluorocyclohexane-1-carboxamide The title compound was prepared according to the method described for the synthesis of Example 5 by substituting Intermediate 43A and corresponding acid where appropriate: (20.4 mg, 0.036 mmol, 40% yield). $^1$H NMR (400 MHz, DMSO-$d_6$) δ 8.18-7.94 (m, 2H), 7.79 (d, J=7.6 Hz, 1H), 7.70 (t, J=7.8 Hz, 1H), 3.64 (br. s., 2H), 2.72 (d, J=7.1 Hz, 2H), 2.39 (br. s., 1H), 2.08-1.99 (m, 1H), 1.95 (br. s., 2H), 1.83-1.57 (m, 10H), 1.52 (d, J=12.7 Hz, 2H), 1.45-1.29 (m, 6H), 1.14 (ddd, J=12.4, 7.6, 5.4 Hz, 1H), 1.07-0.93 (m, 2H), 0.90-0.75 (m, 2H), 0.62-0.44 (m, 2H), 0.28 (q, J=4.8 Hz, 2H). FXR EC$_{50}$ (nM)=379; MS (ESI) 592 (M+H).

The title compound was prepared according to the method described for the synthesis of Example 5 by substituting Intermediate 43A and corresponding acids where appropriate:

| Ex. No. | Structure | MS (ESI) (M + H) | FXR EC$_{50}$ (nM) |
|---|---|---|---|
| 44 |  | 558 | 118 |

44  $^1$H NMR (400 MHz, DMSO-$d_6$) δ 8.20-8.02 (m, 2H), 7.80 (d, J = 9.0 Hz, 1H), 7.76-7.60 (m, 1H), 3.74 (d, J = 9.8 Hz, 4H), 3.66 (br. s., 2H), 3.11-2.94 (m, 2H), 2.73 (d, J = 7.1 Hz, 2H), 2.10-1.99 (m, 1H), 1.88-1.68 (m, 6H), 1.67-1.53 (m, 2H), 1.48 (br. s., 1H), 1.45-1.30 (m, 6H), 1.19-1.09 (m, 1H), 1.07-0.94 (m, 2H), 0.89-0.72 (m, 2H), 0.64-0.47 (m, 2H), 0.35-0.19 (m, 2H)

Example 45

N-(3-(3-cyclopropyl-1,2,4-oxadiazol-5-yl)phenyl)-N-((4-(3-(cyclopropylmethyl)-1,2,4-oxadiazol-5-yl)bicyclo[2.2.2]octan-1-yl)methyl)tetrahydro-2H-pyran-4-carboxamide (45)

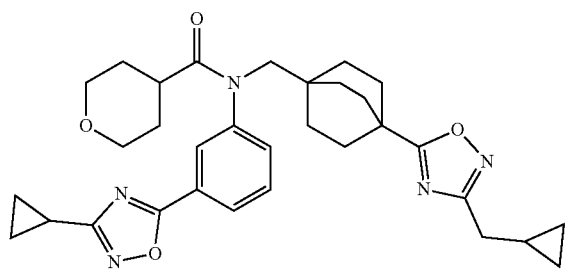

Step A. Intermediate 45A. Preparation of 3-(3-cyclopropyl-1,2,4-oxadiazol-5-yl)-N-((4-(3-(cyclopropylmethyl)-1,2,4-oxadiazol-5-yl)bicyclo[2.2.2]octan-1-yl)methyl)aniline

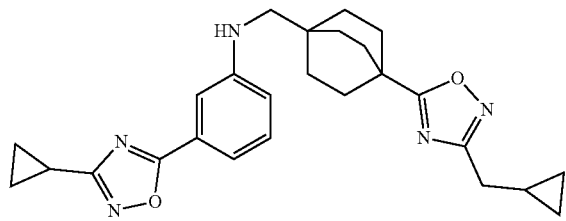 [SMILES: c1cc(NCC23CCC(c4nc(CC5CC5)no4)(CC2)CC3)cc(-c2nc(C3CC3)no2)c1]

The title compound was prepared according to the method described for the synthesis of Intermediate 1F by substituting Intermediate 13A and Intermediate 41E where appropriate: (180 mg, 0.404 mmol, 70% yield) as a pale brown solid. $^1$H NMR (400 MHz, DMSO-$d_6$) δ 7.32-7.21 (m, 2H), 7.15 (d, J=7.8 Hz, 1H), 6.90 (dd, J=8.2, 1.6 Hz, 1H), 5.98 (t, J=5.5 Hz, 1H), 2.88 (d, J=5.9 Hz, 2H), 2.60-2.56 (m, 2H), 2.23-2.11 (m, 1H), 1.97-1.83 (m, 6H), 1.65-1.53 (m, 6H), 1.13-1.06 (m, 2H), 1.00-0.93 (in, 2H), 0.89-0.83 (m, 1H), 0.53-0.45 (m, 2H), 0.23-0.18 (in, 2H). MS (ESI) 446 (M+H).

Step B. Example 45. Preparation of N-(3-(3-cyclopropyl-1,2,4-oxadiazol-5-yl)phenyl)-N-((4-(3-(cyclopropylmethyl)-1,2,4-oxadiazol-5-yl)bicyclo[2.2.2]octan-1-yl)methyl)tetrahydro-2H-pyran-4-carboxamide The title compound was prepared according to the method described for the synthesis of Example 5 by substituting Intermediate 45A and corresponding acid where appropriate: (8.4 mg, 0.015 mmol, 22% yield). $^1$H NMR (400 MHz, DMSO-$d_6$) δ 8.13-7.93 (m, 2H), 7.79 (d, J=7.3 Hz, 1H), 7.69 (t, J=7.8 Hz, 1H), 3.74 (d, J=8.6 Hz, 2H), 3.66 (br. s., 2H), 3.18 (d, J=5.4 Hz, 1H), 3.01 (br. s., 2H), 2.56 (d, J=6.8 Hz, 2H), 2.26-2.18 (m, 1H), 1.91-1.70 (m, 6H), 1.68-1.56 (m, 2H), 1.54-1.32 (m, 8H), 1.19-1.09 (m, 2H), 1.07-0.94 (m, 3H), 0.53-0.42 (m, 2H), 0.24-0.13 (m, 2H). FXR $EC_{50}$ (nM)=278. MS (ESI) 558 (M+H).

The following compounds were synthesized according to the method described for the synthesis of Example 5 by substituting Intermediate 45A and corresponding acids where appropriate:

| Ex. No. | Structure | MS (ESI) (M + H) | FXR $EC_{50}$ (nM) |
|---|---|---|---|
| 46 | 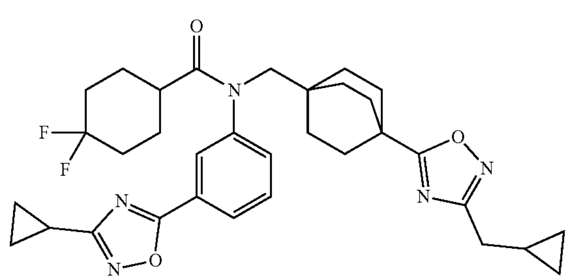 [SMILES: O=C(C1CCC(F)(F)CC1)N(CC12CCC(c3nc(CC4CC4)no3)(CC1)CC2)c1cccc(-c2nc(C3CC3)no2)c1] | 592 | 633 |

46 $^1$H NMR (400 MHz, DMSO-$d_6$) δ 8.16-7.90 (m, 2H), 7.78 (d, J = 7.6 Hz, 1H), 7.68 (t, J = 7.7 Hz, 1H), 3.64 (br. s., 2H), 2.55 (d, J = 6.8 Hz, 2H), 2.38 (br. s., 1H), 2.25-2.14 (m, 1H), 1.95 (br. s., 2H), 1.86-1.73 (m, 6H), 1.73-1.56 (m, 4H), 1.51 (d, J = 14.9 Hz, 1H), 1.47-1.27 (m, 6H), 1.20-1.07 (m, 2H), 1.07-0.89 (m, 4H), 0.55-0.37 (m, 2H), 0.17 (q, J = 4.8 Hz, 2H)

Example 47

N-((4-(3-cyclopropyl-1,2,4-oxadiazol-5-yl)bicyclo[2.2.2]octan-1-yl)methyl)-N-(3-(2-(methoxymethyl)thiazol-4-yl)phenyl)tetrahydro-2H-pyran-4-carboxamide (47)

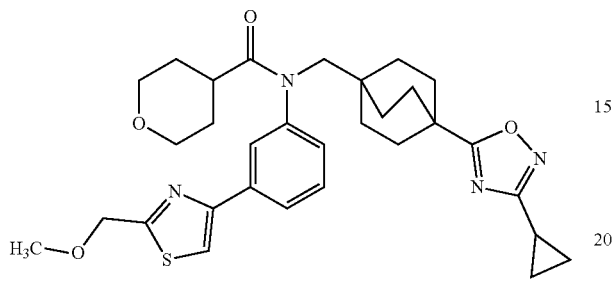

Step A. Intermediate 47A. Preparation of (4-(3-nitrophenyl)thiazol-2-yl)methanol

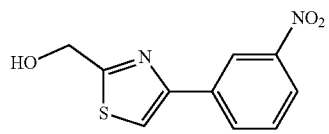 [SMILES: O=[N+]([O-])c1cccc(-c2csc(CO)n2)c1]

To a stirred solution of Intermediate 31A (750 mg, 2.70 mmol) in THF (20 mL) was added DIBAL-H (10.78 mL, 10.78 mmol) at −78° C. The reaction mixture was stirred at the same temperature for 2 h. The reaction mixture was warmed to room temperature and poured into a biphasic mixture of saturated aqueous ammonium chloride solution (10 mL) and EtOAc (50 mL). The organic layer was separated and the aqueous layer was extracted with EtOAc (2×50 mL). The combined organic layers were dried over anhydrous sodium sulphate and concentrated under reduced pressure. The crude material was purified by flash chromatography (40 g silica gel cartridge; A=Hex, B=EtOAc; 30 min grad.; 0% B to 40% B; flow rate=40 mL/min). The pure fractions were combined, concentrated under reduced pressure and dried in vacuo to afford the title compound (400 mg, 1.693 mmol, 63% yield). MS (ESI) 237 (M+H).

Step B. Intermediate 47B. Preparation of 2-(methoxymethyl)-4-(3-nitrophenyl)thiazole

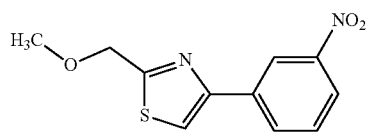 [SMILES: COCc1nc(-c2cccc([N+](=O)[O-])c2)cs1]

To a stirred solution of Intermediate 47A (400 mg, 1.693 mmol) in DMF (10 mL) was added NaH (135 mg, 3.39 mmol) at 0° C. MeI (0.212 mL, 3.39 mmol) were added and the reaction mixture was stirred at the same temperature for 2 h. The reaction was quenched with cold water and the aqueous solution was extracted with EtOAc (2×50 mL) The combined organic layers were dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=40 mL/min). The pure fractions were combined, concentrated under reduced pressure and dried in vacuo to afford the title compound (380 mg, 1.488 mmol, 88% yield). MS (ESI) 251 (M+H).

Step C. Intermediate 47C. Preparation of 3-(2-(methoxymethyl)thiazol-4-yl)aniline

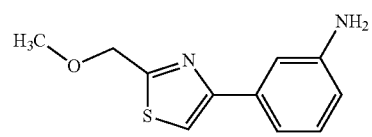

To a stirred solution of Intermediate 47B (380 mg, 1.518 mmol) in EtOH (10 mL) were added tin(II) chloride dihydrate (1199 mg, 5.31 mmol) and conc. HCl (1.4 mL, 45.6 mmol) at room temperature. The reaction mixture was heated at 90° C. for 2 h. The reaction mixture was concentrated under reduced pressure and the residue was extracted with EtOAc (2×100 mL). The combined organic layers were dried over anhydrous sodium sulphate and concentrated to afford the title compound (325 mg, 1.416 mmol, 93% yield). MS (ESI) 221 (M+H).

Step D. Intermediate 47D. Preparation of N-((4-(3-cyclopropyl-1,2,4-oxadiazol-5-yl) bicyclo[2.2.2]octan-1-yl)methyl)-3-(2-(methoxymethyl)thiazol-4-yl)aniline

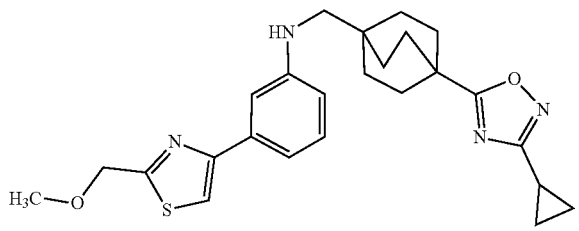 [SMILES: COCc1nc(-c2cccc(NCC34CCC(c5nc(C6CC6)no5)(CC3)CC4)c2)cs1]

The title compound was prepared according to the method described for the synthesis of Intermediate 1F by substituting Intermediate 47C and Intermediate 2F where appropriate: (250 mg, 0.388 mmol, 43% yield). MS (ESI) 451 (M+H).

Step E. Example 47. Preparation of N-((4-(3-cyclopropyl-1,2,4-oxadiazol-5-yl) bicyclo[2.2.2]octan-1-yl)methyl)-N-(3-(2-(methoxymethyl)thiazol-4-yl)phenyl)tetrahydro-2H-pyran-4-carboxamide The title compound was prepared according to the method described for the synthesis of Example 5 by substituting Intermediate 47D and corresponding acid where appropriate: $^1$H NMR (400 MHz, DMSO-d$_6$) δ 8.26 (s, 1H), 7.94 (br. s., 2H), 7.52 (t, J 8.1 Hz, 1H), 7.41 (d, J=8.3 Hz, 1H), 4.78 (s, 2H), 3.75 (d, J=8.1 Hz, 2H), 3.63 (br. s., 2H), 3.45 (s, 3H), 3.00 (t, J=11.2 Hz, 2H), 2.56-2.5 (m, 1H), 2.10-1.99 (m, 1H), 1.87-1.70 (m, 6H), 1.70-1.55 (m, 2H), 1.55-1.27 (m, 8H), 1.06-0.95 (m, 2H), 0.91-0.72 (m, 2H); FXR EC$_{50}$ (nM) 121; MS (ESI) 563 (M+H).

The below compounds were synthesized according to the method described for the synthesis of Example 5 by substituting Intermediate 47D and corresponding acids where appropriate:

| Ex. No. | Structure | MS (ESI) (M + H) | FXR EC$_{50}$ (nM) |
|---|---|---|---|
| 48 | 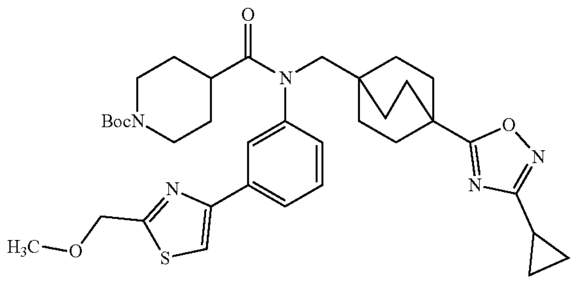 [SMILES: COCc1nc(-c2cccc(N(CC34CCC(c5nc(C6CC6)no5)(CC3)CC4)C(=O)C3CCN(C(=O)OC(C)(C)C)CC3)c2)cs1] | 662 | 856 |
| 49 | 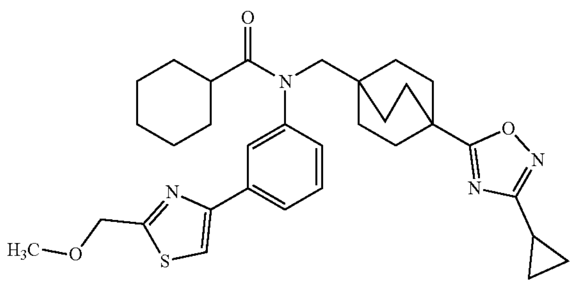 [SMILES: COCc1nc(-c2cccc(N(CC34CCC(c5nc(C6CC6)no5)(CC3)CC4)C(=O)C3CCCCC3)c2)cs1] | 561 | 105 |

48 $^1$H NMR (400 MHz, DMSO-d$_6$) δ 8.26 (s, 1H), 7.94 (br. s., 2H), 7.53 (t, J = 8.1 Hz, 1H), 7.41 (d, J = 7.8 Hz, 1H), 4.79 (s, 2H), 3.90-3.79 (m, 2H), 3.63 (br. s., 3H), 3.45 (s, 3H), 2.47 (br. s., 2H), 2.07-2.00 (m, 1H), 1.84-1.69 (m, 6H), 1.55 (br. s., 2H), 1.50-1.31 (m, 17H), 1.08-0.96 (m, 2H), 0.87-0.79 (m, 2H)

49 $^1$H NMR (400 MHz, DMSO-d$_6$) δ 8.27 (s, 1H), 8.01-7.87 (m, 2H), 7.52 (t, J = 7.7 Hz, 1H), 7.37 (d, J = 7.1 Hz, 1H), 4.79 (s, 2H), 3.63 (br. s., 2H), 3.45 (s, 3H), 2.27 (t, J = 10.8 Hz, 1H), 2.09-2.00 (m, 1H), 1.83-1.68 (m, 6H), 1.61 (br. s., 4H), 1.53-1.27 (m, 10H), 1.13-0.95 (m, 3H), 0.94-0.71 (m, 4H)

Example 50

N-((4-(3-cyclopropyl-1,2,4-oxadiazol-5-yl)bicyclo[2.2.2]octan-1-yl)methyl)-N-(3-(5-cyclopropyl-1-methyl-1H-pyrazol-3-yl)phenyl)tetrahydro-2H-pyran-4-carboxamide

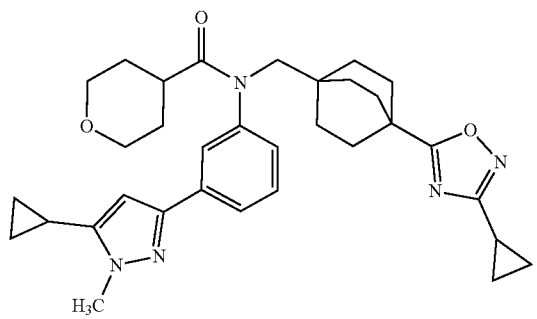

(50)

Step A. Intermediate 50A. Preparation of 5-cyclopropyl-3-(3-nitrophenyl)-1H-pyrazole

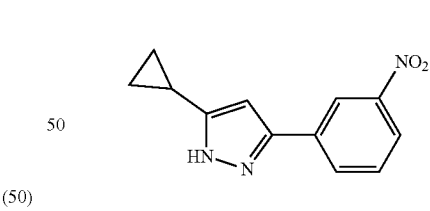

To a stirred solution of Intermediate 40A (0.8 g, 3.43 mmol) in ethanol (5 mL) were added hydrazine hydrate (0.343 g, 6.86 mmol) followed by acetic acid (10 mL) at room temperature. The reaction mixture was heated at 80° C. for 2 h. The reaction mixture was concentrated under reduced pressure and the residue was diluted water (10 mL) and extracted with ethyl acetate (2×10 mL). The combined organic layers were washed with brine solution (10 mL), dried over sodium sulphate and concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (700 mg, 3.05 mmol, 89% yield) as a yellow solid. MS (ESI) 230 (M+H).

Step B. Intermediate 50B. Preparation of 5-cyclopropyl-1-methyl-3-(3-nitrophenyl)-1H-pyrazole

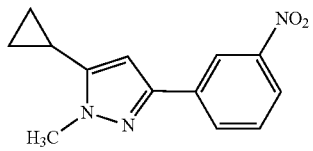

To a stirred solution of Intermediate 50A (700 mg, 3.05 mmol) in DMF (7 mL) were added $Cs_2CO_3$ (2985 mg, 9.16 mmol) and methyl iodide (0.382 mL, 6.11 mmol) at room temperature. The reaction mixture was stirred at room temperature overnight. The reaction mixture was diluted with ethyl acetate (20 mL). The organic solution was washed with saturated brine solution (5×20 mL), dried over anhydrous sodium sulphate and concentrated under reduced pressure. The crude material was purified by flash chromatography (24 g silica gel cartridge; A=Hex, B=EtOAc; 30 min grad.; 0% B to 50% B; flow rate=40 mL/min). The pure fractions were combined, concentrated under reduced pressure and dried in vacuo to afford the title compound (450 mg, 1.850 mmol, 61% yield) as a brown solid. MS (ESI) 244 (M+H).

Step C. Intermediate 50C. Preparation of 3-(5-cyclopropyl-1-methyl-1H-pyrazol-3-yl) aniline

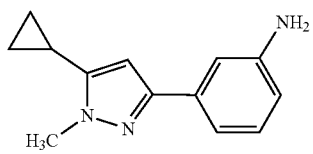 [SMILES: Cn1nc(-c2cccc(N)c2)cc1C1CC1]

To a stirred solution of Intermediate 50B (450 mg, 1.850 mmol) in a mixture of ethanol (4 mL), THF (2 mL), water (1 mL) was added zinc (1814 mg, 27.7 mmol) followed by ammonium chloride (1484 mg, 27.7 mmol) at room temperature. The reaction mixture was stirred at room temperature overnight. The reaction mixture was concentrated under reduced pressure and the residue was diluted with ethyl acetate (10 mL). The organic solution was filtered through a Celite bed and the Celite bed was washed with ethyl acetate (10 mL). The filtrate was washed with saturated brine solution (10 mL), dried over sodium sulphate and concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (350 mg, 1.64 mmol, 89% yield) as a brown wax. MS (ESI) 214 (M+H).

Step D. Intermediate 50D. Preparation of N-((4-(3-cyclopropyl-1,2,4-oxadiazol-5-yl) bicyclo[2.2.2]octan-1-yl)methyl)-3-(5-cyclopropyl-1-methyl-1H-pyrazol-3-yl)aniline

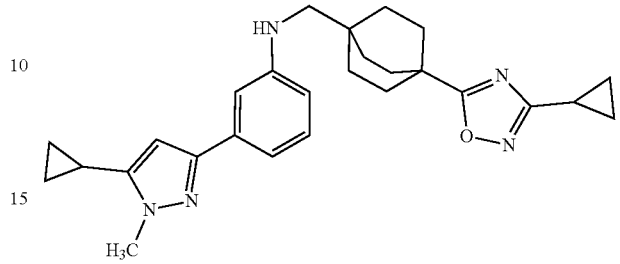

The title compound was prepared according to the method described for the synthesis of Intermediate 1F by substituting Intermediate 50C and Intermediate 2F where appropriate: (230 mg, 0.518 mmol, 55% yield) as brown wax. MS (ESI) 444 (M+H).

Step E. Example 50. Preparation of N-((4-(3-cyclopropyl-1,2,4-oxadiazol-5-yl) bicyclo[2.2.2]octan-1-yl)methyl)-N-(3-(5-cyclopropyl-1-methyl-1H-pyrazol-3-yl)phenyl)tetrahydro-2H-pyran-4-carboxamide The title compound was prepared according to the method described for the synthesis of Example 5 by substituting Intermediate 50D and corresponding acid where appropriate: (9.6 mg, 0.017 mmol, 19% yield). $^1$H NMR (400 MHz, DMSO-$d_6$) δ 7.74-7.61 (m, 2H), 7.44 (t, J=7.6 Hz, 1H), 7.30 (d, J=8.1 Hz, 1H), 6.46 (s, 1H), 3.88 (s, 3H), 3.74 (d, J=9.0 Hz, 2H), 3.62 (d, J=6.8 Hz, 2H), 2.98 (t, J=11.2 Hz, 2H), 2.07-2.00 (m, 1H), 1.96-1.88 (m, 1H), 1.84-1.69 (m, 6H), 1.67-1.54 (m, 2H), 1.54-1.28 (m, 8H), 1.07-0.91 (m, 4H), 0.89-0.78 (m, 2H), 0.74-0.64 (m, 2H) (Note: 1H is buried under DMSO-moisture peak); FXR $EC_{50}$ (nM)=334; MS (ESI) 556 (M+H).

Example 51

N-((4-(3-cyclopropyl-1,2,4-oxadiazol-5-yl)bicyclo[2.2.2]octan-1-yl)methyl)-N-(3-(3-ethyl-2-oxo-2,3-dihydrooxazol-5-yl)phenyl)tetrahydro-2H-pyran-4-carboxamide (51)

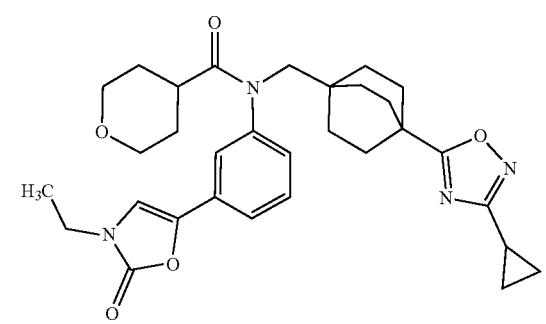

Step A. Intermediate 51A. Preparation of 3-ethyl-5-(3-nitrophenyl)oxazol-2(3H)-one

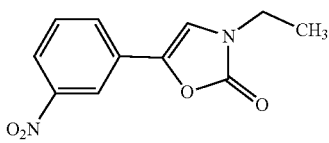 [SMILES: CCn1cc(-c2cccc([N+](=O)[O-])c2)oc1=O]

To a stirred solution of Intermediate 6A (500 mg, 2.425 mmol) in DMF (5 mL) was added iodoethane (0.388 mL, 4.85 mmol) followed by potassium carbonate (670 mg, 4.85 mmol) at room temperature. The reaction mixture was heated to 80° C. and stirred overnight. The reaction mixture was concentrated, diluted with water and extracted with ethyl acetate (2×20 mL). The combined organic layers were dried over sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (440 mg, 1.879 mmol, 77% yield) as yellow solid. $^1$H NMR (400 MHz, DMSO-$d_6$) δ 8.26 (t, J=1.8 Hz, 1H), 8.11 (dt, J=8.2, 1.2 Hz, 1H), 8.01 (s, 1H), 7.96-7.86 (m, 1H), 7.77-7.66 (m, 1H), 3.63 (q, J=7.5 Hz, 2H), 1.28 (t, J=4.00 Hz, 3H). MS (ESI) 235 (M+H).

Step B. Intermediate 51B. Preparation of 5-(3-aminophenyl)-3-ethyloxazol-2(3H)-one

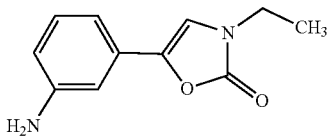

To a stirred solution of Intermediate 51A (440 mg, 1.879 mmol) in ethanol (5 mL) were added zinc (1842 mg, 28.2 mmol) and a solution of ammonium chloride (1507 mg, 28.2 mmol) in water (5 mL) at room temperature. The reaction mixture was stirred at the same temperature overnight. The reaction mixture was diluted with DCM (30 mL), filtered through Celite and concentrated under reduced pressure to afford the title compound (300 mg, 1.469 mmol, 78% yield)) as yellow solid. $^1$H NMR (400 MHz, DMSO-$d_6$) δ 7.49 (s, 1H), 7.04 (t, J=7.8 Hz, 1H), 6.71-6.62 (m, 2H), 6.48 (ddd, J=8.0, 2.0, 1.0 Hz, 1H), 5.23 (br. s., 2H), 3.58 (q, J=7.0 Hz, 2H), 1.24 (t, J=7.3 Hz, 3H). MS (ESI) 205 (M+H).

Step C. Intermediate 51C. Preparation of 5-(3-(((4-(3-cyclopropyl-1,2,4-oxadiazol-5-yl) bicyclo[2.2.2]octan-1-yl)methyl)amino)phenyl)-3-ethyloxazol-2(3H)-one

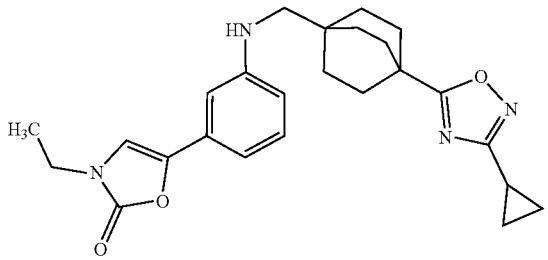 [SMILES: CCn1cc(-c2cccc(NCC34CCC(c5nc(C6CC6)no5)(CC3)CC4)c2)oc1=O]

The title compound was prepared according to the method described for the synthesis of Intermediate 1F by substituting Intermediate 51B and Intermediate 2F where appropriate: (160 mg, 0.368 mmol, 61% yield) as yellow solid. $^1$H NMR (400 MHz, DMSO-$d_6$) δ 7.54 (s, 1H), 7.07 (t, J=7.8 Hz, 1H), 6.71 (s, 1H), 6.64 (d, J=7.5 Hz, 1H), 6.58-6.54 (m, 1H), 5.63 (t, J=6.0 Hz, 1H), 3.58 (q, J=7.0 Hz, 2H), 2.84 (d, J=6.0 Hz, 2H), 2.11-2.03 (m, 1H), 1.94-1.79 (m, 6H), 1.60-1.53 (m, 6H), 1.25 (t, J=7.3 Hz, 3H), 1.06-1.00 (m, 2H), 0.89-0.84 (m, 2H). MS (ESI) 435 (M+H).

Step D. Example 51. Preparation of N-((4-(3-cyclopropyl-1,2,4-oxadiazol-5-yl) bicyclo[2.2.2]octan-1-yl)methyl)-N-(3-(3-ethyl-2-oxo-2,3-dihydrooxazol-5-yl)phenyl)tetrahydro-2H-pyran-4-carboxamide The title compound was prepared according to the method described for the synthesis of Example 5 by substituting Intermediate 51C and corresponding acid where appropriate: $^1$H NMR (400 MHz, DMSO-$d_6$) δ 7.80 (s, 1H), 7.53 (s, 1H), 7.51-7.40 (m, 2H), 7.34 (d, J=6.1 Hz, 1H), 3.75 (d, J=8.6 Hz, 2H), 3.61 (q, J=7.2 Hz, 4H), 3.07-2.94 (m, 2H), 2.09-2.01 (m, 1H), 1.86-1.69 (m, 6H), 1.67-1.52 (m, 2H), 1.51-1.33 (m, 7H), 1.31-1.23 (m, 4H), 1.06-0.94 (m, 3H), 0.88-0.79 (m, 2H). FXR EC$_{50}$ (nM)=1185; MS (ESI) 547 (M+H).

The following compound was prepared according to the method described for the synthesis of Example 5 by substituting Intermediate 51C and corresponding acid where appropriate:

| Ex. No. | Structure | MS (ESI) (M + H) | FXR EC$_{50}$ (nM) |
|---|---|---|---|
| 52 | 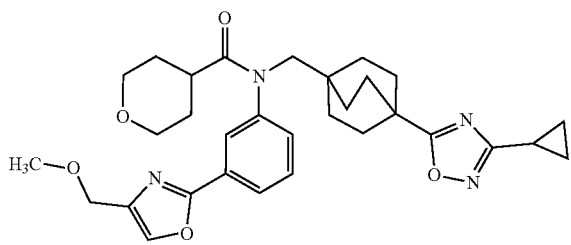 [SMILES: COCc1coc(-c2cccc(N(CC34CCC(c5nc(C6CC6)no5)(CC3)CC4)C(=O)C3CCOCC3)c2)n1]<br>(racemate) | 547 | 1333 |

52 $^1$H NMR (400 MHz, DMSO-d$_6$) δ 7.81 (s, 1H), 7.55 (br. s., 1H) 7.52-7.41 (m, 2H), 7.37 (br. s., 1H), 3.76 (br. s., 2H), 3.68 (d, J = 9.3 Hz, 2H), 3.62 (q, J = 7.2 Hz, 4H), 3.30-3.17 (m, 2H), 2.10-1.99 (m, 1H), 1.84-1.67 (m, 6H), 1.62 (d, J = 14.7 Hz, 1H), 1.47 (br. s., 1H), 1.44-1.32 (m, 6H), 1.31-1.09 (m, 4H), 1.06-0.97 (m, 2H), 0.89-0.79 (m, 2H)

Example 53

N-((4-(3-cyclopropyl-1,2,4-oxadiazol-5-yl)bicyclo[2.2.2]octan-1-yl)methyl)-N-(3-(4-(methoxymethyl)oxazol-2-yl)phenyl)tetrahydro-2H-pyran-4-carboxamide

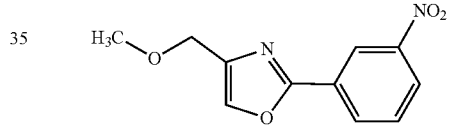

Step A. Intermediate 53A. Preparation of (2-(3-nitrophenyl)oxazol-4-yl)methanol

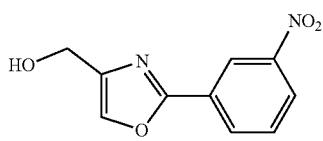

To a stirred solution of Intermediate 19B (1 g, 3.81 mmol) in THF (30 mL) was added DIBAL-H (7.63 mL, 7.63 mmol) at −78° C. and stirred for 1 h at −78° C. The reaction mixture was poured into a biphasic mixture of aqueous ammonium chloride solution (10 mL) and EtOAc (50 mL). The organic layer was separated and the aqueous layer was extracted with EtOAc (2×50 mL). The combined organic layers were dried over anhydrous sodium sulphate and concentrated under reduced pressure. The crude material was purified by flash chromatography (24 g silica gel cartridge; A=Hex, B=EtOAc; 30 min grad.; 0% B to 40% B; flow rate=30 mL/min). The pure fractions were combined, concentrated under reduced pressure and dried in vacuo to afford the title compound (400 mg, 1.798 mmol, 47% yield). MS (ESI) 221 (M+H).

Step B. Intermediate 53B. Preparation of 4-(methoxymethyl)-2-(3-nitrophenyl)oxazole To a stirred solution of Intermediate 53A (370 mg, 1.680 mmol) in DMF (6 mL) were added NaH (134 mg, 3.36 mmol) and MeI (0.210 mL, 3.36 mmol) at 0° C. The reaction mixture was stirred at the same temperature for 1 h. The reaction mixture was poured into cold water and the aqueous layer was extracted with EtOAc (2×50 mL). The combined organic layers were dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (350 mg, 1.464 mmol, 87% yield). MS (ESI) 235 (M+H).

Step C. Intermediate 53C. Preparation of 3-(4-(methoxymethyl)oxazol-2-yl)aniline

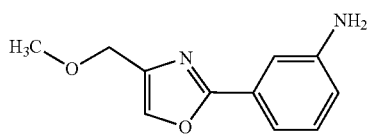

149

To a stirred solution of Intermediate 53B (360 mg, 1.537 mmol) in EtOH (10 mL were added tin(II) chloride dihydrate (1214 mg, 5.38 mmol) and conc. HCl (1.401 mL, 46.1 mmol) at 0° C. The reaction mixture was warmed to room temperature and heated at 90° C. for 2 h. The reaction mixture was cooled to room temperature and concentrated under reduced pressure. The residue was basified with aqueous saturated $NaHCO_3$ solution and extracted with EtOAc (2×100 mL). The combined organic layers were dried over $Na_2SO_4$ and concentrated under reduced pressure to afford the title compound (310 mg, 1.427 mmol, 93% yield). MS (ESI) 205 (M+H).

Step D. Intermediate 53D. Preparation of N-((4-(3-cyclopropyl-1,2,4-oxadiazol-5-yl) bicyclo[2.2.2]octan-1-yl)methyl)-3-(4-(methoxymethyl)oxazol-2-yl)aniline

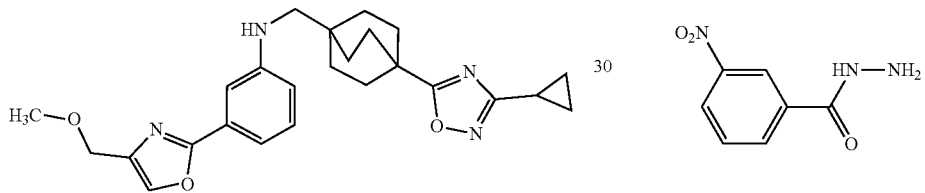

The title compound was prepared according to the method described for the synthesis of Intermediate 1F by substituting Intermediate 53C and Intermediate 2F where appropriate: (260 mg, 0.592 mmol, 61% yield). MS (ESI) 435 (M+H).

Step D. Example 53. Preparation of N-((4-(3-cyclopropyl-1,2,4-oxadiazol-5-yl) bicyclo[2.2.2]octan-1-yl)methyl)-N-(3-(4-(methoxymethyl)oxazol-2-yl)phenyl)tetrahydro-2H-pyran-4-carboxamide The title compound was prepared according to the method described for the synthesis of Example 5 by substituting Intermediate 53D and corresponding acid where appropriate (3 mg, 0.005 mmol, 9% yield). $^1$H NMR (400 MHz, DMSO-$d_6$) δ 8.23 (s, 1H), 8.02-7.86 (m, 2H), 7.62 (br. s., 2H), 4.38 (s, 2H), 3.74 (d, J=10.0 Hz, 2H), 3.62 (d, J=11.2 Hz, 2H), 3.33 (s, 3H), 3.00 (t, J=10.8 Hz, 2H), 2.10-1.98 (m, 1H), 1.91-1.68 (m, 6H), 1.68-1.53 (m, 3H), 1.53-1.28 (m, 8H), 1.08-0.95 (m, 2H), 0.91-0.74 (m, 2H); FXR $EC_{50}$ (nM) 189; MS (ESI) 547 (M+H).

150

Example 54

N-((4-(3-cyclopropyl-1,2,4-oxadiazol-5-yl)bicyclo[2.2.2]octan-1-yl)methyl)-N-(3-(5-cyclopropyl-1,3,4-oxadiazol-2-yl)phenyl)tetrahydro-2H-pyran-4-carboxamide (54)

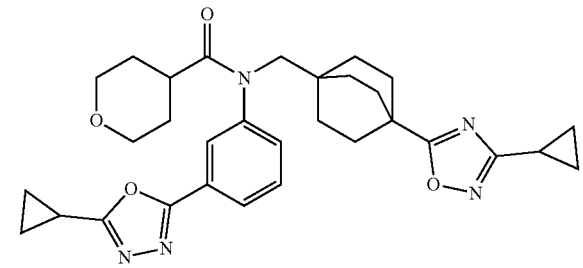

Step A. Intermediate 54A. Preparation of 3-nitrobenzohydrazide

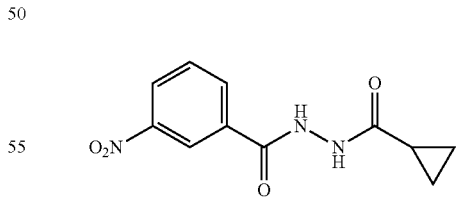

To a stirred solution of methyl 3-nitrobenzoate (5 g, 27.6 mmol, commercially available) in ethanol (75 mL) was added hydrazine hydrate (6.77 mL, 138 mmol) at room temperature. The reaction mixture was heated at reflux for 6 h. The reaction mixture was cooled to room temperature, precipitated solid was filtered, washed with ethanol (5 mL) and dried in vacuo to afford the title compound (4.2 g, 23.19 mmol, 84% yield) as an off-white solid. $^1$H NMR (400 MHz, DMSO-$d_6$) δ 10.17 (br. s., 1H), 8.65 (t, J=2.0 Hz, 1H), 8.37 (ddd, J=8.3, 2.3, 1.0 Hz, 1H), 8.31-8.23 (m, 1H), 7.78 (t, J=8.0 Hz, 1H), 4.63 (s, 2H).

Step B. Intermediate 54B. Preparation of N'-(cyclopropanecarbonyl)-3-nitrobenzohydrazide To a stirred solution of Intermediate 54A (3 g, 16.56 mmol) in DCM (45 mL) was added pyridine (2.68 mL, 33.1 mmol) followed by cyclopropanecarbonyl chloride (2.077 g, 19.87 mmol) at 0° C. The reaction mixture was stirred at the same temperature for 1 h. The reaction mixture was diluted with DCM (25 mL), washed with water (2×25 mL), aqueous 1.5 N HCl solution (2×25 mL), brine solution (2×25 mL), dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=40 mL/min). The pure fractions were combined, concentrated under reduced pressure and dried in vacuo to afford the title compound (3.8 g, 14.33 mmol, 87% yield) as white solid. $^1$H NMR (400 MHz, DMSO-d$_6$) δ 10.76 (d, J=1.5 Hz, 1H), 10.29 (d, J=1.5 Hz, 1H), 8.72-8.67 (m, 1H), 8.49-8.40 (m, 1H), 8.34-8.27 (m, 1H), 7.83 (t, J=8.0 Hz, 1H), 1.77-1.66 (m, 1H), 0.86-0.70 (m, 4H). MS (ESI) 250 (M+H).

Step C. Intermediate 54C. Preparation of 2-cyclopropyl-5-(3-nitrophenyl)-1,3,4-oxadiazole

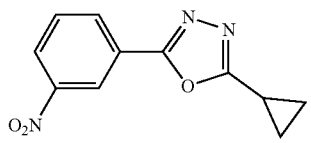

To a stirred solution of Intermediate 54B (3.3 g, 13.24 mmol) in acetonitrile (70 mL) was added CCl$_4$ (1.533 mL, 15.89 mmol) followed by triphenylphosphine (7.29 g, 27.8 mmol) at room temperature. The reaction mixture was heated reflux for 2 days. The reaction mixture was cooled to room temperature, diluted with ethyl acetate (50 mL), washed with water (2×50 mL), brine solution (30 mL), dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (1.5 g, 6.49 mmol, 49% yield) as white solid. MS (ESI) 232 (M+H).

Step D. Intermediate 54D. Preparation of 3-(5-cyclopropyl-1,3,4-oxadiazol-2-yl)aniline

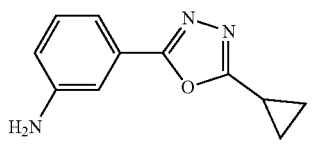 [SMILES: O=[N+]([O-])c1cccc(-c2nnc(C3CC3)o2)c1]

To a stirred solution of Intermediate 54C (1.5 g, 6.49 mmol) in ethanol (15 mL) were added zinc (6.36 g, 97 mmol) followed by a solution of ammonium chloride (5.21 g, 97 mmol) in water (15 mL) and stirred overnight. The reaction mixture was diluted with DCM (50 mL) and filtered through Celite. The filtrate was washed with brine solution (50 mL), dried over sodium sulphate, filtered and concentrated under reduced pressure. The crude material was purified by flash chromatography (24 g silica gel cartridge; A=Hex, B=EtOAc; 30 min grad.; 0% B to 35% B; flow rate=30 mL/min). The pure fractions were combined, concentrated under reduced pressure and dried in vacuo to afford the title compound (650 mg, 3.00 mmol, 46% yield) as yellow solid. $^1$H NMR (400 MHz, DMSO-d$_6$) δ 7.15-7.21 (m, 2H), 7.04-7.08 (m, 1H), 6.72-6.76 (m, 1H), 5.47 (s, 2H), 2.24-2.25 (m, 1H), 1.10-1.20 (m, 4H). MS (ESI) 202 (M+H).

Step E Intermediate 54E. Preparation of N-((4-(3-cyclopropyl-1,2,4-oxadiazol-5-yl) bicyclo[2.2.2] octan-1-yl)methyl)-3-(5-cyclopropyl-1,3,4-oxadiazol-2-yl)aniline

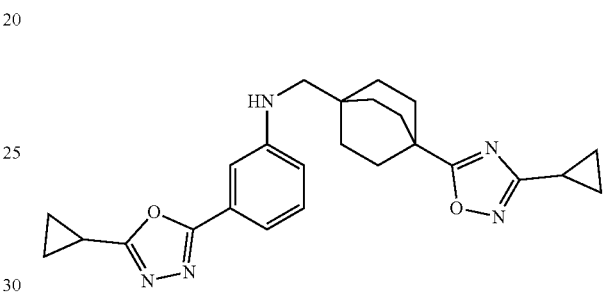

The title compound was prepared according to the method described for the synthesis of Intermediate 1F by substituting Intermediate 54D and Intermediate 2F where appropriate: (350 mg, 0.706 mmol, 58% yield) as white solid. $^1$H NMR (400 MHz, DMSO-d$_6$) δ 7.26-7.19 (m, 2H), 7.07-7.04 (m, 1H), 6.82 (dd, J=8.0, 2.0 Hz, 1H), 5.88 (t, J=6.0 Hz, 1H), 2.87 (d, J=5.5 Hz, 2H), 2.32-2.25 (m, 1H), 2.11-2.03 (m, 1H), 1.92-1.80 (m, 6H), 1.63-1.54 (m, 6H), 1.47-1.40 (m, 1H), 1.21-1.14 (m, 2H), 1.12-1.07 (m, 2H), 1.06-1.01 (m, 2H), 0.89-0.84 (m, 2H). MS (ESI) 432 (M+H).

Step F. Example 54. Preparation of N-((4-(3-cyclopropyl-1,2,4-oxadiazol-5-yl) bicyclo[2.2.2]octan-1-yl)methyl)-N-(3-(5-cyclopropyl-1,3,4-oxadiazol-2-yl)phenyl)tetrahydro-2H-pyran-4-carboxamide The title compound was prepared according to the method described for the synthesis of Example 5 by substituting Intermediate 54E and corresponding acid where appropriate: (20 mg, 0.037 mmol, 53% yield). $^1$HNMR (400 MHz, DMSO-d$_6$) δ 8.05-7.82 (m, 2H), 7.77-7.54 (m, 2H), 3.75 (d, J=9.8 Hz, 2H), 3.64 (br. s., 2H), 3.01 (t, J=10.8 Hz, 2H), 2.45-2.41 (m, 1H), 2.37-2.26 (m, 1H), 2.10-1.98 (m, 1H), 1.87-1.70 (m, 6H), 1.62 (qd, J=12.2, 3.9 Hz, 2H), 1.45-1.28 (m, 8H), 1.25-1.07 (m, 4H), 1.07-0.93 (m, 2H), 0.90-0.75 (m, 2H); FXR EC$_{50}$ (nM)=373; MS (ESI) 544 (M+H).

The following compound was prepared according to the method described for the synthesis of Example 5 by substituting Intermediate 54E and corresponding acid where appropriate:

| Ex. No. | Structure | MS (ESI) (M + H) | FXR EC$_{50}$ (nM) |
|---|---|---|---|
| 55 | 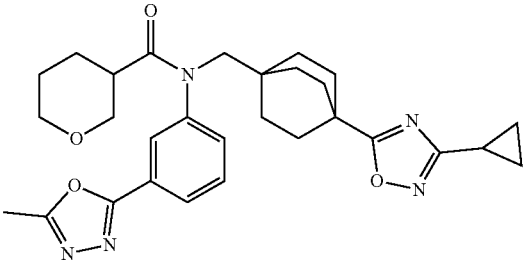<br>(racemate) | 544 | 929 |

55 $^{1}$H NMR (400 MHz, DMSO-d$_{6}$) δ 8.05-7.86 (m, 2H), 7.79-7.56 (m, 2H), 3.78-3.47 (m, 4H), 3.29-3.10 (m, 3H), 2.37-2.28 (m, 1H), 2.10-1.97 (m, 1H), 1.86-1.68 (m, 7H), 1.68-1.53 (m, 1H), 1.47 (br. s., 1H), 1.44-1.31 (m, 7H), 1.29-1.09 (m, 4H), 1.07-0.95 (m, 2H), 0.88-0.75 (m, 2H)

Example 56

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)morpholine-4-carboxamide (56)

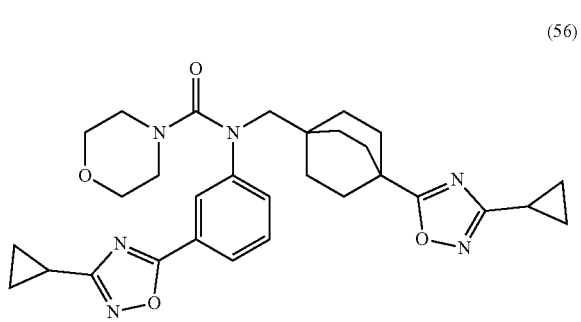 [SMILES: O=C(N1CCOCC1)N(CC12CCC(c3nc(C4CC4)no3)(CC1)CC2)c1cccc(-c2nc(C3CC3)no2)c1]

To a stirred solution of Intermediate 13B (30 mg, 0.070 mmol) in DCM (1 mL) was added triphosgene (22.69 mg, 0.076 mmol) at 0° C. The reaction mixture was warmed to room temperature and stirred overnight. To this reaction mixture were added a solution of morpholine (6.06 µl, 0.070 mmol) in DCM (1 mL) followed by TEA (0.058 mL, 0.417 mmol). The reaction mixture was stirred at room temperature for 1 h. The reaction mixture was concentrated and the crude material was purified via preparative LC/MS using following conditions: Column: Waters XBridge C18, 150 mm×19 mm, 5-m particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 30% B, 30-67% B over 20 minutes, then a 5-minute hold at 100% B; Flow Rate: 15 mL/min; Column Temperature: 25 C. Fraction collection was triggered by MS signals. Fractions containing the product were combined and dried via centrifugal evaporation to afford the title compound (15.6 mg, 0.028 mmol, 40% yield). $^{1}$H NMR (400 MHz, DMSO-d$_{6}$) δ 7.73 (d, J=7.6 Hz, 1H), 7.63 (s, 1H), 7.57 (t, J=7.9 Hz, 1H), 7.34 (d, J=9.8 Hz, 1H), 3.51 (s, 2H), 3.41 (d, J=4.6 Hz, 4H), 3.28-3.15 (m, 4H), 2.26-2.17 (m, 1H), 2.12-2.03 (m, 1H), 1.96-1.78 (m, 6H), 1.66-1.46 (m, 6H), 1.19-1.08 (m, 2H), 1.08-0.95 (m, 4H), 0.90-0.80 (n, 2H); FXR EC$_{50}$ (nM)=739; MS (ESI) 545 (M+H).

The following compounds were synthesized according to the method described for the synthesis of Example 56 by substituting Intermediate 13B and the corresponding amines (commercially available) where appropriate:

| Ex. No. | Structure | MS (ESI) (M + H) | FXR EC$_{50}$ (nM) |
|---|---|---|---|
| 57 | 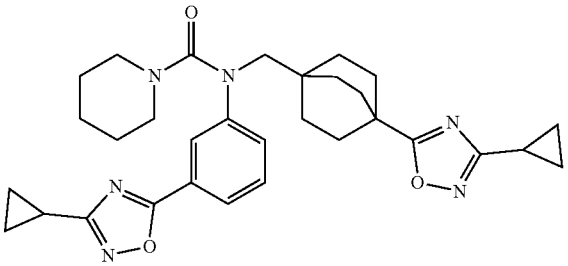 [SMILES: O=C(N1CCCCC1)N(CC12CCC(c3nc(C4CC4)no3)(CC1)CC2)c1cccc(-c2nc(C3CC3)no2)c1] | 543 | 819 |

| Ex. No. | Structure | MS (ESI) (M + H) | FXR EC$_{50}$ (nM) |
|---|---|---|---|
| 58 | 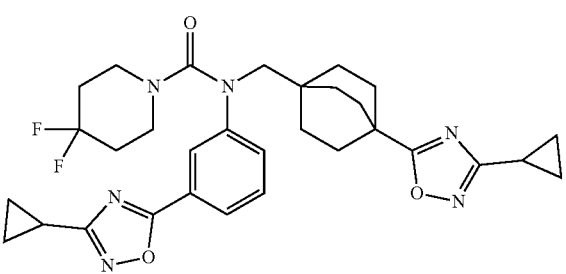 [SMILES: O=C(N1CCC(F)(F)CC1)N(CC12CCC(c3nc(C4CC4)no3)(CC1)CC2)c1cccc(-c2nc(C3CC3)no2)c1] | 579 | 413 |
| 59 | 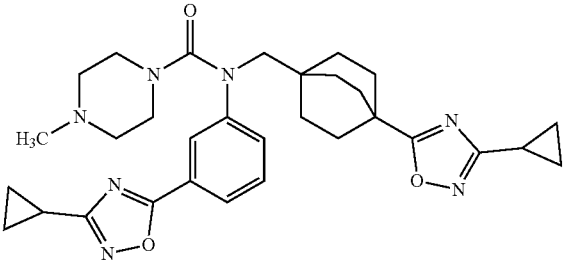 [SMILES: CC1CCN(C(=O)N(CC23CCC(c4nc(C5CC5)no4)(CC2)CC3)c2cccc(-c3nc(C4CC4)no3)c2)CC1] | 558 | 1376 |
| 60 | 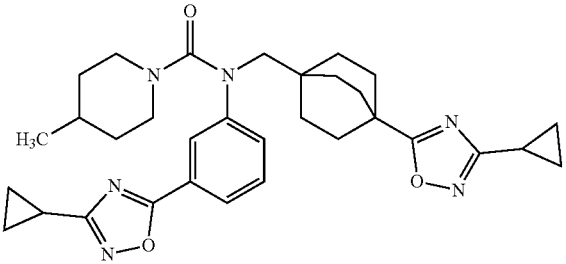 | 557 | 1021 |
| 61 | 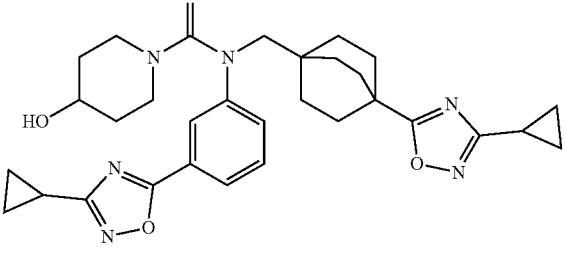 | 559 | 3670 |
| 62 | 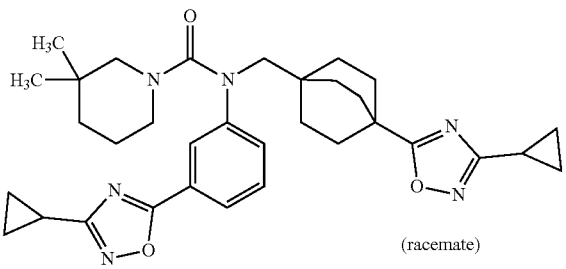 [SMILES: CC1(C)CCCN(C(=O)N(CC23CCC(c4nc(C5CC5)no4)(CC2)CC3)c2cccc(-c3nc(C4CC4)no3)c2)C1] (racemate) | 571 | 3814 |

| Ex. No. | Structure | MS (ESI) (M + H) | FXR EC$_{50}$ (nM) |
|---|---|---|---|
| 63 | 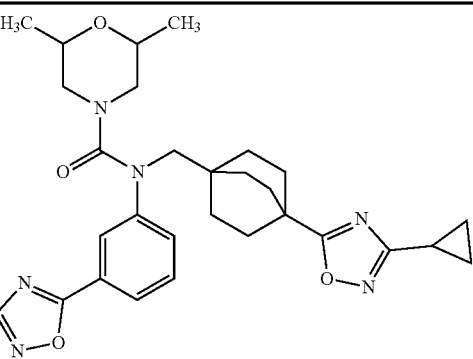 | 573 | 1126 |
| 64 | 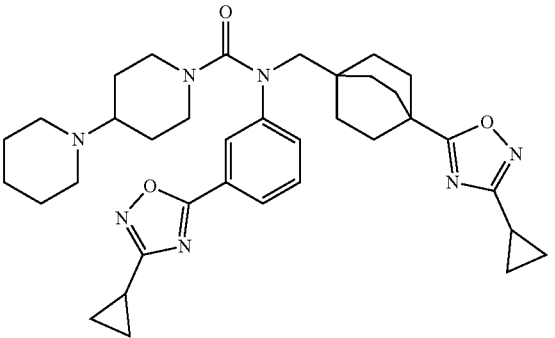 [SMILES: O=C(N1CCC(N2CCCCC2)CC1)N(CC12CCC(c3nc(C4CC4)no3)(CC1)CC2)c1cccc(-c2nc(C3CC3)no2)c1] | 626 | 4824 |
| 65 | 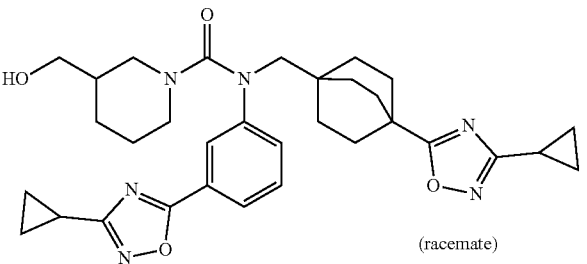 [SMILES: O=C(N1CCCC(CO)C1)N(CC12CCC(c3nc(C4CC4)no3)(CC1)CC2)c1cccc(-c2nc(C3CC3)no2)c1] (racemate) | 573 | 740 |

| | |
|---|---|
| 57 | $^1$H NMR (400 MHz, DMSO-d$_6$) δ 7.69 (d, J = 8.1 Hz, 1H), 7.62-7.43 (m, 2H), 7.29(dd, J = 8.2, 1.8 Hz, 1H), 3.48 (s, 2H), 3.31-3.16 (m, 4H), 2.90 (s, 2H), 2.74 (s, 2H), 2.25-2.13(m, 1H), 2.12-2.00 (m, 1H), 1.99-1.70 (m, 6H), 1.65-1.49 (m, 6H), 1.45 (d, J = 3.9 Hz, 2H), 1.32 (br. s., 4H), 1.07-0.92 (m, 4H) |
| 58 | $^1$H NMR (400 MHz, DMSO-d$_6$) δ 7.76 (d, J = 7.8 Hz, 1H), 7.68 (s, 1H), 7.58 (t, J = 7.9 Hz, 1H), 7.41 (dd, J = 8.3, 2.2 Hz, 1H), 3.51 (s, 2H), 3.31 (br. s., 2H), 2.26-2.17 (m, 1H), 2.14-2.00 (m, 1H), 1.94-1.66 (m, 10H), 1.62-1.37 (m, 6H), 1.19-1.08 (m, 2H), 1.08-0.91 (m, 4H), 0.90-0.77 (m, 2H), (2 buried under the solvent peak). |
| 59 | $^1$H NMR (400 MHz, DMSO-d$_6$) δ 7.71 (d, J = 7.3 Hz, 1H), 7.62-7.49 (m, 2H), 7.30 (dd, J = 8.7, 2.1 Hz, 1H), 3.50 (s, 2H), 3.23 (br. s., 4H), 3.18 (d, J = 5.4 Hz, 1H), 2.25-2.18 (m, 1H), 2.17-2.02 (m, 7H), 1.95-1.76 (m, 6H), 1.64-1.42 (m, 6H), 1.18-1.08 (m, 2H), 1.07-0.93 (m, 4H), 0.90-0.82 (m, 2H) |
| 60 | $^1$H NMR (400 MHz, DMSO-d$_6$) δ 7.67 (d, J = 7.5 Hz, 1H), 7.54 (dd, J = 5.0, 3.0 Hz, 2H), 7.27 (dd, J = 8.3, 1.8 Hz, 1H), 3.82 (d, J = 13.1 Hz, 2H), 2.68-2.58 (m, 3H), 2.23-2.14 (m, 1H), 2.09-2.01 (m, 1H), 1.89-1.81 (m, 6H), 1.57-1.48 (m, 6H), 1.45 (d, J = 12.0 Hz, 3H), 1.14-1.07 (m, 2H), 1.05-0.94 (m, 4H), 0.89-0.75 (m, 8H). |
| 61 | $^1$H NMR (400 MHz, DMSO-d$_6$) δ 7.69 (d, J = 8.0 Hz, 1H), 7.58-7.49 (m, 2H), 7.28 (dd, J = 7.8, 2.3 Hz, 1H), 4.65 (br. s., 1H), 4.07 (br. s., 2H), 3.57 (d, J = 14.1 Hz, 3H), 2.91 (t, J = 9.8 Hz, 2H), 2.23-2.13 (m, 1H), 2.10-2.01 (m, 1H), 1.92-1.81 (m, 6H), 1.63-1.48 (m, 6H), 1.21-1.07 (m, 4H), 1.06-0.95 (m, 4H), 0.88-0.81 (m, 2H) (2 Protons are buried under the solvent peak). |
| 62 | $^1$H NMR (400 MHz, DMSO-d$_6$) δ 7.70 (d, J = 8.0 Hz, 1H), 7.58-7.49 (m, 2H), 7.25 (d, J = 6.5 Hz, 1H), 3.46 (s, 2H), 3.08 (br. s., 2H), 2.22-2.13 (m, 1H), 2.09-2.01 (m, 1H), 1.90-1.81 (m, 6H), 1.60-1.49 (m, 6H), 1.33-1.19 (m, 4H), 1.14-1.06 (m, 2H), 1.05-0.92 (m, 4H), 0.87-0.79 (m, 8H) (2 Protons are buried under solvent peaks). |

| Ex. No. | Structure | MS (ESI) (M + H) | FXR EC$_{50}$ (nM) |
|---|---|---|---|
| 63 | $^1$H NMR (400 MHz, DMSO-d$_6$) δ 7.72 (d, J = 8.0 Hz, 1H), 7.61-7.51 (m, 2H), 7.31 (dd, J = 8.3, 1.8 Hz, 1H), 3.66 (d, J = 12.0 Hz, 2H), 3.17 (d, J = 5.0 Hz, 3H), 2.37-2.28 (m, 3H), 2.24-2.14 (m, 1H), 2.10-2.01 (m, 1H), 1.91-1.79 (m, 6H), 1.59-1.48 (m, 6H), 1.16-1.08 (m, 2H), 1.06-0.91 (m, 10H), 0.87-0.81 (m, 2H). | | |
| 64 | $^1$H NMR (400 MHz, DMSO-d$_6$) δ 7.71 (d, J = 8.0 Hz, 1H), 7.61-7.51 (m, 2H), 7.33 (d, J = 9.5 Hz, 1H), 3.87 (d, J = 11.5 Hz, 2H), 2.62 (d, J = 13.6 Hz, 2H), 2.29-2.13 (m, 6H), 2.09-2.01 (m, 2H), 1.89-1.81 (m, 6H), 1.58-1.44 (m, 8H), 1.38 (br. s., 4H), 1.30 (br. s., 2H), 1.17-1.07 (m, 4H), 1.07-0.93 (m, 5H), 0.88-0.81 (m, 2H). | | |
| 65 | $^1$H NMR (400 MHz, DMSO-d$_6$) δ 7.68 (d, J = 8.0 Hz, 1H), 7.57-7.50 (m, 2H), 7.25 (dd, J = 8.3, 1.8 Hz, 1H), 4.44 (t, J = 5.3 Hz, 1H), 3.89 (d, J = 10.5 Hz, 1H), 3.72 (d, J = 12.5 Hz, 1H), 3.26-3.19 (m, 1H), 3.17 (d, J = 5.0 Hz, 2H), 3.12-3.05 (m, 1H), 2.71-2.58 (m, 2H), 2.23-2.14 (m, 1H), 2.10-2.02 (m, 1H), 1.91-1.81 (m, 6H), 1.63-1.51 (m, 6H), 1.48 (d, J = 13.6 Hz, 1H), 1.41 (br. s., 1H), 1.25-1.08 (m, 4H), 1.07-0.95 (m, 5H), 0.88-0.81 (m, 2H). | | |

Example 66

N-(3-(3-cyclopropyl-1,2,4-oxadiazol-5-yl)phenyl)-N-((4-(4-cyclopropylthiazol-2-yl) bicyclo[2.2.2]octan-1-yl)methyl)tetrahydro-2H-pyran-3-carboxamide (racemate)

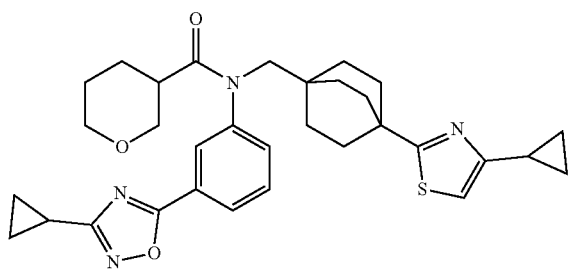

(66)

Step A. Intermediate 66A. Preparation of methyl 4-carbamoylbicyclo[2.2.2]octane-1-carboxylate

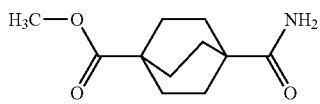

The title compound was prepared according to the method described for the synthesis of Intermediate 99C by substituting 4-(methoxycarbonyl)bicyclo[2.2.2]octane-1-carboxylic acid where appropriate: (9.0 g, 42.6 mmol, 90% yield). MS (ESI) 212 (M+1).

Step B. Intermediate 66B. Preparation of methyl 4-carbamothioylbicyclo[2.2.2]octane-1-carboxylate

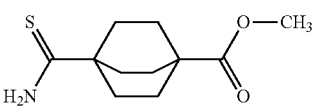

To a solution of Intermediate 66A (850 mg, 4.02 mmol) in THF (10 mL) was added Lawesson's reagent (976 mg, 2.414 mmol) and the reaction mixture was stirred at room temperature for 1 h. The reaction mixture was concentrated under reduced pressure and the residue was diluted with EtOAc (50 mL). The organic layer was washed with aqueous 10% NaHCO$_3$ solution, brine solution, dried over anhydrous Na$_2$SO$_4$ and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (0.65 g, 2.86 mmol, 71% yield). MS (ESI) 228 (M+H).

Step C. Intermediate 66C. Preparation of methyl 4-(4-cyclopropylthiazol-2-yl)bicyclo[2.2.2]octane-1-carboxylate

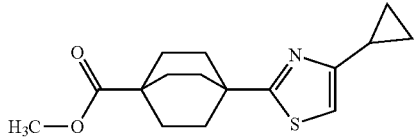

To a stirred solution of Intermediate 66B (150 mg, 0.660 mmol) in toluene (3 mL) was added 2-bromo-1-cyclopropylethan-1-one (161 mg, 0.990 mmol) at room temperature. The reaction mixture was heated at 100° C. overnight. The reaction mixture was cooled to room temperature and concentrated under reduced pressure. The crude material was purified by flash chromatography (12 g silica gel cartridge; A=Hex, B=EtOAc; 30 min grad.; 0% B to 20% B; flow rate=20 mL/min). The pure fractions were combined, concentrated under reduced pressure and dried in vacuo to afford the title compound (120 mg, 0.412 mmol, 62% yield). $^1$H NMR (400 MHz, DMSO-$d_6$) δ 7.05 (s, 1H), 3.58 (s, 3H), 2.76-2.71 (m, 1H), 1.87-1.79 (m, 12H), 0.87-0.67 (m, 4H). MS (ESI) 292 (M+H).

Step D. Intermediate 66D. Preparation of (4-(4-cyclopropylthiazol-2-yl) bicyclo[2.2.2]octan-1-yl) methanol

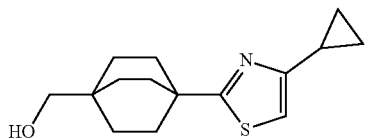 [SMILES: OCC12CCC(c3nc(C4CC4)cs3)(CC1)CC2]

The title compound was prepared according to the method described for the synthesis of Intermediate 1B by substituting Intermediate 66C where appropriate: (95 mg, 0.321 mmol, 62% yield). $^1$H NMR (400 MHz, DMSO-$d_6$) δ 7.02 (s, 1H), 4.38 (s, 1H), 3.07 (s, 2H), 1.99-1.97 (m, 1H), 1.82-1.77 (m, 6H), 1.46-1.41 (m, 6H), 0.87-0.67 (m, 4H). MS (ESI) 264 (M+H).

Step E. Intermediate 66E. Preparation of 4-(4-cyclopropylthiazol-2-yl)bicyclo[2.2.2]octane-1-carbaldehyde

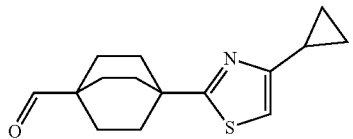 [SMILES: O=CC12CCC(c3nc(C4CC4)cs3)(CC1)CC2]

The title compound was prepared according to the method described for the synthesis of Intermediate 1C by substituting Intermediate 66D where appropriate: (50 mg, 0.191 mmol, 72% yield). MS (ESI) 262 (M+H).

Step F. Intermediate 66F. Preparation of 3-(3-cyclopropyl-1,2,4-oxadiazol-5-yl)-N-((4-(4-cyclopropylthiazol-2-yl)bicyclo[2.2.2]octan-1-yl)methyl)aniline

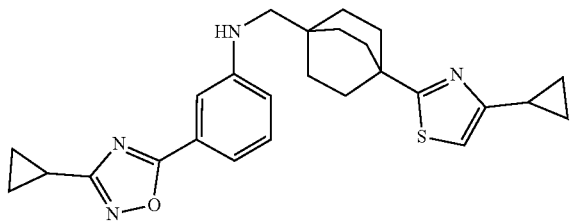 [SMILES: c1cc(NCC23CCC(c4nc(C5CC5)cs4)(CC2)CC3)cc(-c2nc(C3CC3)no2)c1]

The title compound was prepared according to the method described for the synthesis of Intermediate 1F by substituting Intermediate 13A and Intermediate 66E where appropriate: (55 mg, 0.101 mmol, 66% yield). $^1$H NMR (400 MHz, DMSO-$d_6$) δ 7.4-7.1 (m, 3H), 7.05 (s, 1H), 6.98-6.92 (m, 1H), 2.85 (s, 2H), 2.21-1.95 (m, 2H), 1.85-1.56 (m, 12H), 1.11-0.71 (m, 8H). MS (ESI) 447 (M+H).

Step G. Example 66. Preparation of N-(3-(3-cyclopropyl-1,2,4-oxadiazol-5-yl)phenyl)-N-((4-(4-cyclopropylthiazol-2-yl)bicyclo[2.2.2]octan-1-yl)methyl) tetrahydro-2H-pyran-3-carboxamide (racemate)

The title compound was prepared according to the method described for the synthesis of Example 5 by substituting Intermediate 66F and corresponding acid where appropriate (2 mg, 0.003 mmol, 10% yield). $^1$H NMR (400 MHz, DMSO-$d_6$) δ 8.02 (s, 1H), 8.05 (s, 1H), 7.79 (br. s., 1H), 7.69 (t, J=7.8 Hz, 1H), 7.00 (s, 1H), 3.79 (br. s., 1H), 3.72-3.55 (m, 3H), 3.49 (br. s., 1H), 3.26-3.15 (m, 2H), 2.28-2.14 (m, 1H), 2.02-1.92 (m, 1H), 1.85 (br. s., 1H), 1.78-1.52 (m, 8H), 1.50-1.30 (m, 6H), 1.23 (s, 1H), 1.21-1.05 (m, 3H), 1.05-0.94 (m, 2H), 0.88-0.78 (m, 2H), 0.77-0.66 (m, 2H). FXR $EC_{50}$ (nM) 1252; MS (ESI) 559 (M+H).

Example 67

N-(3-(3-cyclopropyl-1,2,4-oxadiazol-5-yl)phenyl)-N-((4-(5-cyclopropyl-1-methyl-1H-pyrazol-3-yl)bicyclo[2.2.2]octan-1-yl)methyl)tetrahydro-2H-pyran-3-carboxamide (Racemate)

(67)

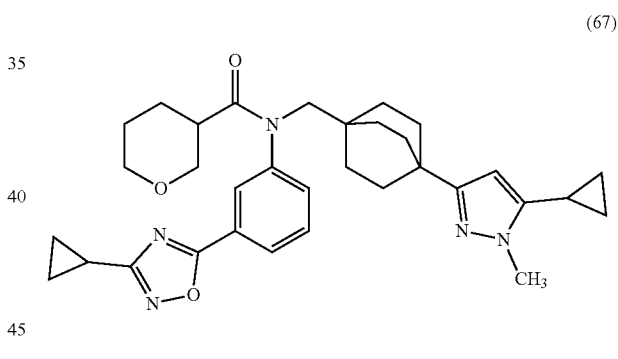

Step A. Intermediate 67A. Preparation of methyl 4-(chlorocarbonyl)bicyclo[2.2.2]octane-1-carboxylate

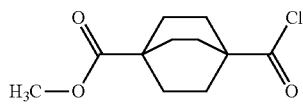

A solution of 4-(methoxycarbonyl)bicyclo[2.2.2]octane-1-carboxylic acid in SOCl$_2$ was heated at 60° C. for 2 h. Progress of the reaction was monitored by TLC (small amount was quenched with MeOH and checked TLC) showed completion of acid. The reaction mixture was concentrated under reduced pressure. The crude was so-distilled twice with DCM to afford the title compound (1.8 g, 7.80 mmol) as an off-white solid.

Step B. Intermediate 67B. Preparation of methyl 4-(3-cyclopropyl-3-oxopropanoyl)bicyclo[2.2.2]octane-1-carboxylate

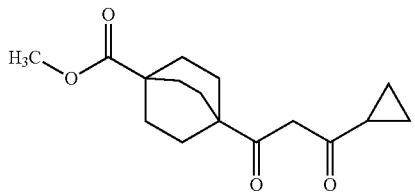 [SMILES: COC(=O)C12CCC(C(=O)CC(=O)C3CC3)(CC1)CC2]

To a stirred solution of LiHMDS (9.10 mL, 9.10 mmol) in THF was added 1-cyclopropylethan-1-one (0.383 g, 4.55 mmol) at −78° C. and stirred for 45 min. A solution of Intermediate 67A (1 g, 4.33 mmol) in tetrahydrofuran (10 mL) was added to the reaction mixture and stirred for additional 1 h at same temperature. The reaction mixture was quenched with aqueous ammonium chloride solution (20 mL) and extracted with EtOAc (2×50 mL). The combined organic layers were dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=40 mL/min). The pure fractions were combined, concentrated under reduced pressure and dried in vacuo to afford the title compound (800 mg, 2.73 mmol, 63% yield) as oil. MS (ESI) 279 (M+H).

Step C. Intermediate 67C1 and 67C2. Preparation of methyl 4-(5-cyclopropyl-1-methyl-1H-pyrazol-3-yl)bicyclo[2.2.2]octane-1-carboxylate and methyl 4-(3-cyclopropyl-1-methyl-1H-pyrazol-5-yl)bicyclo[2.2.2]octane-1-carboxylate

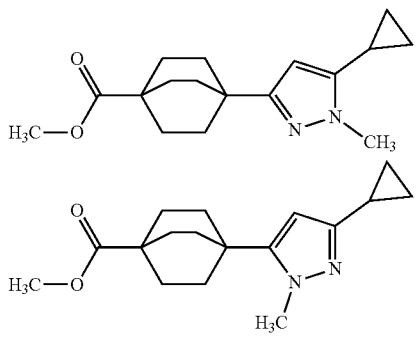

To a stirred solution of Intermediate 67B (800 mg, 2.87 mmol) in methanol (10 mL) was added methylhydrazine sulphate (1036 mg, 7.19 mmol) at room temperature. The reaction mixture was stirred overnight at 80° C. The reaction mixture was concentrated under reduced pressure. The crude material was poured into water and extracted with EtOAc (2×20 mL). The combined organic layers were washed with brine, dried over anhydrous sodium sulphate and concentrated under reduced pressure. The crude was purified by flash chromatography (Combiflash, 24 g Silica gel column) using 0-20% EtOAc in pet-ether as eluents. The compound containing fractions were concentrated to yield a mixture of compounds. The mixture was purified by prep-HPLC to yield the individual regio isomers. The first eluting isomer (RT=4.31 min or peak-1) Intermediate 67C1 (270 mg, 0.889 mmol, 31% yield); $^1$H NMR (400 MHz, DMSO-d$_6$) δ 5.65 (s, 1H), 3.71 (s, 3H), 3.57 (s, 3H), 1.69-1.81 (m, 13H), 0.88-0.91 (m, 2H), 0.52-0.57 (m, 2H) and second eluting isomer (RT=4.90 min or peak-2) Intermediate 67C2 (320 mg, 1.054 mmol, 37% yield); MS (ESI) 289 (M+H); $^1$H NMR (400 MHz, DMSO-d$_6$) δ 5.67 (s, 1H), 3.76 (s, 3H), 3.59 (s, 3H), 1.75-1.83 (m, 12H), 1.69-1.74 (m, 1H), 0.73-0.78 (m, 2H), 0.56-0.57 (m, 2H).

Step D. Intermediate 67D. Preparation of (4-(5-cyclopropyl-1-methyl-1H-pyrazol-3-yl)bicyclo[2.2.2]octan-1-yl)methanol

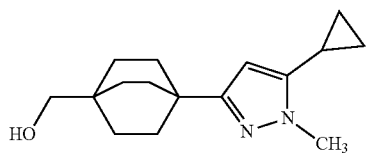

The title compound was prepared according to the method described for the synthesis of Intermediate 1B by substituting Intermediate 67C1 where appropriate: (160 mg, 0.584 mmol, 67% yield) as an off-white solid. $^1$H NMR (400 MHz, DMSO-d$_6$) δ 5.63 (s, 1H), 4.30 (t, J=7.20 Hz, 1H), 3.33 (s, 3H), 3.04 (d, J=7.20 Hz, 2H), 1.74-1.79 (m, 1H), 1.62-1.65 (m, 6H), 1.34-1.39 (m, 6H), 0.86-0.91 (m, 2H), 0.57-0.60 (m, 2H).

Step E. Intermediate 67E. Preparation of 4-(5-cyclopropyl-1-methyl-1H-pyrazol-3-yl)bicyclo[2.2.2]octane-1-carbaldehyde

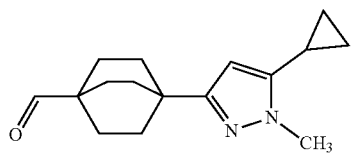

The title compound was prepared according to the method described for the synthesis of Intermediate 1C by substituting Intermediate 67D where appropriate: (160 mg, 0.557 mmol, 91% yield) as an off-white solid. $^1$H NMR (400 MHz, DMSO-d$_6$) δ 9.44 (s, 1H), 5.67 (s, 1H), 3.72 (s, 3H), 1.59-1.76 (m, 13H), 0.88-0.92 (m, 2H), 0.57-0.60 (m, 2H).

Step F. Intermediate 67F. Preparation of 3-(3-cyclopropyl-1,2,4-oxadiazol-5-yl)-N-((4-(5-cyclopropyl-1-methyl-1H-pyrazol-3-yl)bicyclo[2.2.2]octan-1-yl)methyl)aniline

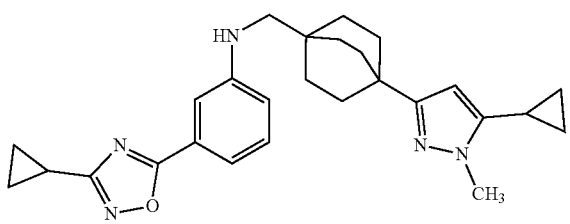 [SMILES: Cn1nc(C23CCC(CNc4cccc(-c5nc(C6CC6)no5)c4)(CC2)CC3)cc1C1CC1]

The title compound was prepared according to the method described for the synthesis of Intermediate 1F by substituting Intermediate 13A and Intermediate 67E where appropriate: (95 mg, 0.203 mmol, 33% yield) as an off-white solid. MS (ESI) 444 (M+H).

Step G. Example 67. Preparation of N-(3-(3-cyclopropyl-1,2,4-oxadiazol-5-yl)phenyl)-N-((4-(5-cyclopropyl-1-methyl-1H-pyrazol-3-yl)bicyclo[2.2.2]octan-1-yl)methyl)tetrahydro-2H-pyran-3-carboxamide (racemate)

The title compound was prepared according to the method described for the synthesis of Example 5 by substituting Intermediate 67F and corresponding acid where appropriate: $^1$H NMR (400 MHz, DMSO-$d_6$) δ 8.10-7.94 (m, 2H), 7.79 (br. s., 1H), 7.73-7.65 (m, 1H), 5.59 (s, 1H), 3.78 (br. s., 1H), 3.69 (s, 4H), 3.58 (br. s., 3H), 3.31-3.19 (m, 2H), 2.27-2.20 (m, 1H), 1.80-1.68 (m, 2H), 1.67-1.51 (m, 7H), 1.44 (d, J=10.5 Hz, 1H), 1.38-1.25 (m, 6H), 1.19-1.08 (m, 3H), 1.05-0.95 (m, 2H), 0.92-0.81 (m, 2H), 0.58-0.49 (m, 2H). FXR EC$_{50}$ (nM) 256; MS (ESI) 556 (M+H).

Example 68

N-((4-(3-cyclopropyl-1,2,4-oxadiazol-5-yl)bicyclo[2.2.2]octan-1-yl)methyl)-N-(3-(2-cyclopropyl-1-methyl-1H-imidazol-4-yl)phenyl)tetrahydro-2H-pyran-3-carboxamide (Racemate)

(68)

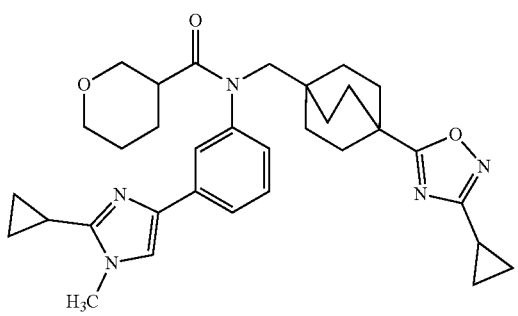

Step A. Intermediate 68A. Preparation of 2-cyclopropyl-4-(3-nitrophenyl)-1H-imidazole

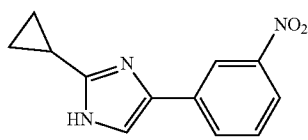 [SMILES: O=[N+]([O-])c1cccc(-c2c[nH]c(C3CC3)n2)c1]

To a stirred solution of 2-bromo-1-(3-nitrophenyl)ethan-1-one (4 g, 16.39 mmol, commercially available) and cyclopropanecarboximidamide hydrochloride (2.37 g, 19.67 mmol) in acetonitrile (60 mL) was added K$_2$CO$_3$ (6.80 g, 49.2 mmol) at room temperature. The reaction mixture was heated at 90° C. in a microwave reactor. The reaction mixture was poured into aqueous 10% NaHCO$_3$ solution and the aqueous layer was extracted with EtOAc (2×50 mL). The combined organic layers were dried over anhydrous sodium sulphate and concentrated under reduced pressure to afford the title compound (3.0 g, 13.09 mmol, 80% yield). MS (ESI) 230 (M+H).

Step B. Intermediate 68B. Preparation of 2-cyclopropyl-1-methyl-4-(3-nitrophenyl)-1H-imidazole

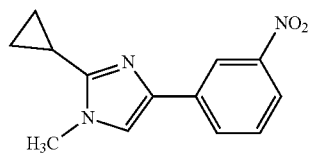 [SMILES: Cn1cc(-c2cccc([N+](=O)[O-])c2)nc1C1CC1]

To a stirred solution of Intermediate 68A (0.35 g, 1.527 mmol) in DMF (5 mL) was added NaH (0.073 g, 1.83 mmol) at 0° C. Iodomethane (0.01 mL, 1.53 mmol) was added to the reaction mixture at the same temperature. The reaction mixture was warmed to room temperature and stirred for 1 h. The reaction mixture was poured into ice-cold water and the aqueous layer was extracted with EtOAc (2×50 mL). The combined organic layers were dried over anhydrous sodium sulphate and concentrated under reduced pressure. The crude material was purified by flash chromatography (12 g silica gel cartridge; A=Hex, B=EtOAc; 30 min grad.; 0% B to 30% B; flow rate=24 mL/min). The pure fractions were combined, concentrated under reduced pressure and dried in vacuo to afford the title compound (200 mg, 0.822 mmol, 54% yield). MS (ESI) 244 (M+H).

Step C. Intermediate 68C. Preparation of 3-(2-cyclopropyl-1-methyl-1H-imidazol-4-yl)aniline

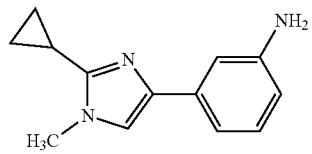

To a stirred solution of Intermediate 68B (250 mg, 1.028 mmol) in EtOH (2 mL) were added tin(II) chloride dihydrate (812 mg, 3.60 mmol) and conc. HCl (0.468 mL, 15.42 mmol) at 0° C. The reaction mixture was warmed to room temperature and then heated at 90° C. for 2 h. The reaction mixture was concentrated under reduced pressure, the residue was basified with aqueous 10% NaHCO$_3$ and extracted with EtOAc (2×100 mL). The combined organic layers were dried over anhydrous sodium sulphate, filtered and concentrated under reduced pressure to afford the title compound (210 mg, 0.985 mmol, 96% yield). MS (ESI) 214 (M+H).

Step D. Intermediate 68D. Preparation of N-((4-(3-cyclopropyl-1,2,4-oxadiazol-5-yl) bicyclo[2.2.2]octan-1-yl)meth 1-3-(2-cyclopropyl-1-methy-1H-imidazol-4-yl)aniline

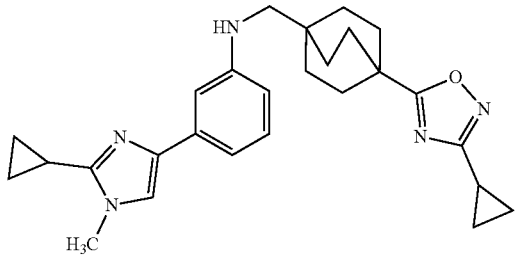 [SMILES: Cn1cc(-c2cccc(NCC34CCC(c5nc(C6CC6)no5)(CC3)CC4)c2)nc1C1CC1]

The title compound was prepared according to the method described for the synthesis of Intermediate 1F by substituting Intermediate 68C and Intermediate 2F where appropriate: (220 mg, 0.496 mmol, 71% yield). MS (ESI) 444 (M+H).

Step E. Example 68. Preparation of N-((4-(3-cyclopropyl-1,2,4-oxadiazol-5-yl) bicyclo[2.2.2]octan-1-yl)methyl)-N-(3-(2-cyclopropyl-1-methyl-1H-imidazol-4-yl)phenyl)tetrahydro-2H-pyran-3-carboxamide (racemate)

The title compound was prepared according to the method described for the synthesis of Example 5 by substituting Intermediate 68D and corresponding acid where appropriate (3.6 mg, 0.006 mmol, 9% yield). $^1$H NMR (400 MHz, DMSO-$d_6$) δ 7.76-7.55 (m, 3H), 7.40 (t, J=7.9 Hz, 1H), 7.20 (d, J=6.4 Hz, 1H), 3.83-3.68 (m, 6H), 3.65 (br. s., 1H), 3.62-3.48 (m, 2H), 3.29-3.24 (m, 1H), 3.23-3.11 (m, 1H), 2.10-1.94 (m, 2H), 1.81-1.70 (m, 6H), 1.70-1.51 (m, 2H), 1.51-1.27 (m, 6H), 1.18 (d, J=7.1 Hz, 1H), 1.05-0.97 (m, 2H), 0.97-0.85 (m, 4H), 0.85-0.77 (m, 2H); FXR EC$_{50}$ (nM) 4099; MS (ESI) 556 (M+H).

Example 69

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)phenyl)tetrahydro-2H-pyran-4-carboxamide (69)

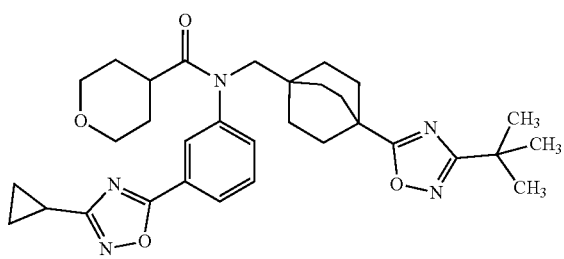

Step A. Intermediate 69A. Preparation of methyl 4-(3-(tert-butyl)-1,2,4-oxadiazol-5-yl) bicyclo[2.2.2]octane-1-carboxylate

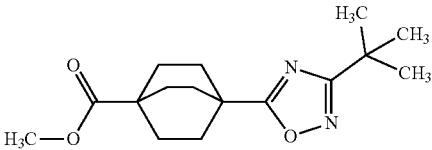

The title compound was prepared according to the method described for the synthesis of Intermediate 1A by substituting 4-(methoxycarbonyl)bicyclo[2.2.2]octane-1-carboxylic acid and Intermediate 68F where appropriate: (2.2 g, 7.52 mmol, 97% yield) as white solid. MS (ESI) 293 (M+H). $^1$H NMR (400 MHz, DMSO-$d_6$) δ 3.61 (s, 3H), 1.96-1.87 (m, 6H), 1.87-1.79 (m, 6H), 1.29 (s, 9H).

Step B. Intermediate 69B. Preparation of (4-(3-(tert-butyl)-1,2,4-oxadiazol-5-yl) bicyclo[2.2.2]octan-1-yl)methanol

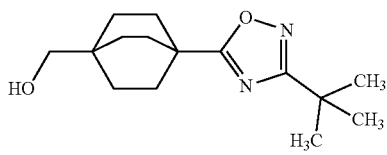 [SMILES: CC(C)(C)c1noc(C23CCC(CO)(CC2)CC3)n1]

The title compound was prepared according to the method described for the synthesis of Intermediate 1B by substituting Intermediate 69A where appropriate: (1.5 g, 5.62 mmol, 75% yield) as white solid. MS (ESI) 265 (M+H). $^1$H NMR (400 MHz, DMSO-$d_6$) δ 4.43 (t, J=5.5 Hz, 1H), 3.09 (d, J=5.5 Hz, 2H), 1.94-1.79 (m, 6H), 1.52-1.39 (m, 6H), 1.29 (s, 9H).

Step C. Intermediate 69C. Preparation of 4-(3-(tert-butyl)-1,2,4-oxadiazol-5-yl) bicyclo[2.2.2]octane-1-carbaldehyde

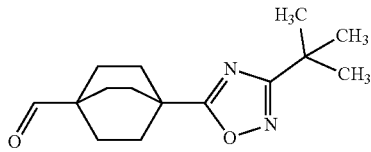 [SMILES: CC(C)(C)c1noc(C23CCC(C=O)(CC2)CC3)n1]

The title compound was prepared according to the method described for the synthesis of Intermediate 1C by substituting Intermediate 69B where appropriate: (1.1 g, 3.44 mmol, 61% yield) as white solid. MS (ESI) 263 (M+H). $^1$H NMR (400 MHz, DMSO-$d_6$) δ 9.47 (s, 1H), 1.97-1.88 (m, 6H), 1.76-1.65 (m, 6H), 1.29 (s, 9H).

Step D. Intermediate 69D. Preparation of N-((4-(3-(tert-butyl)-1,2,4-oxadiazol-5-yl) bicyclo[2.2.2]octan-1-yl)methyl)-3-(3-cyclopropyl-1,2,4-oxadiazol-5-yl)aniline

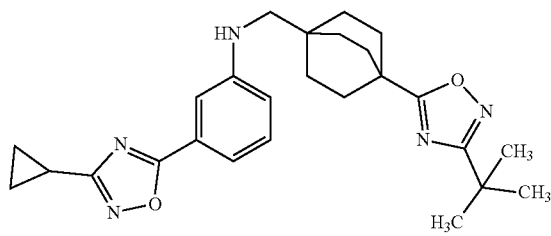 [SMILES: CC(C)(C)c1noc(C23CCC(CNc4cccc(-c5nc(C6CC6)no5)c4)(CC2)CC3)n1]

The title compound was prepared according to the method described for the synthesis of Intermediate 1F by substituting Intermediate 13A and Intermediate 69C where appropriate: (3 g, 6.70 mmol, 70% yield) as brown solid. MS (ESI) 448 (M+H).

Step E. Example 69. Preparation of N-((4-(3-(tert-butyl)-1,2,4-oxadiazol-5-yl) bicyclo[2.2.2]octan-1-yl)methyl)-N-(3-(3-cyclopropyl-1,2,4-oxadiazol-5-yl)phenyl) tetrahydro-2H-pyran-4-carboxamide The title compound was prepared according to the method described for the synthesis of Example 5 by substituting Intermediate 69D and corresponding acid where appropriate: (13.5 mg, 0.022 mmol, 33% yield). $^1$H NMR (400 MHz, DMSO-d$_6$) δ 8.16-7.90 (m, 2H), 7.78 (d, J=7.1 Hz, 1H), 7.69 (t, J=7.9 Hz, 1H), 3.74 (d, J=9.5 Hz, 2H), 3.66 (br. s., 2H), 3.11-2.89 (m, 2H), 2.27-2.14 (m, 1H), 1.88-1.73 (m, 6H), 1.68-1.54 (m, 2H), 1.54-1.30 (m, 8H), 1.30-1.17 (m, 9H), 1.16-1.09 (m, 2H), 1.05-0.92 (m, 2H), (1 Proton buried under moisture peak); FXR EC$_{50}$ (nM)=162; MS (ESI) 560 (M+H).

Examples 70 and 71

N-(3-(3-ethyl-1,2,4-oxadiazol-5-yl)phenyl)-N-(1-(4-(3-methyl-1,2,4-oxadiazol-5-yl) bicyclo[2.2.2]octan-1-yl)ethyl)cyclohexanecarboxamide (70-71)

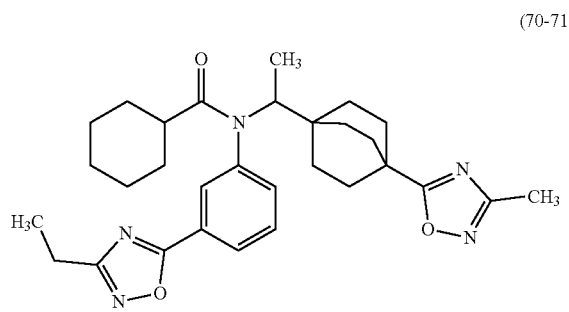

Step A. Intermediate 70A. Preparation of 1-(4-(3-methyl-1,2,4-oxadiazol-5-yl) bicyclo[2.2.2]octan-1-yl)ethan-1-ol

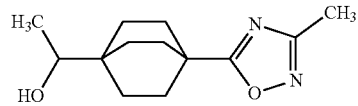 [SMILES: Cc1noc(C23CCC(C(C)O)(CC2)CC3)n1]

To a stirred solution of Intermediate 1C (0.5 g, 2.27 mmol) in dry tetrahydrofuran (15 mL) was added methyl magnesium bromide in diethyl ether (1.135 mL, 3.40 mmol) at −78° C. under nitrogen atmosphere and stirred for 1 h. The reaction was warm to 0° C. and quenched with aqueous NH$_4$Cl solution. The resulting solution was extracted with EtOAc (2×20 mL). The combined organic extracts were washed with brine, dried over anhydrous sodium sulphate and concentrated under reduced pressure. The crude material was purified by flash chromatography (24 g silica gel cartridge; A=Hex, B=EtOAc; 30 min grad.; 0% B to 40% B; flow rate=40 mL/min). The pure fractions were combined, concentrated under reduced pressure and dried in vacuo to afford the title compound (0.51 g, 2.050 mmol, 90% yield) as oil. $^1$H NMR (400 MHz, DMSO-d$_6$) δ 4.28 (d, J=5.20 Hz, 1H), 3.24-3.26 (m, 1H), 2.29 (s, 3H), 1.83-1.87 (m, 6H), 1.40-1.55 (m, 6H), 0.96 (d, J=6.40 Hz, 3H).

Step B. Intermediate 70B. Preparation of 1-(4-(3-methyl-1,2,4-oxadiazol-5-yl) bicyclo[2.2.2]octan-1-yl)ethan-1-one

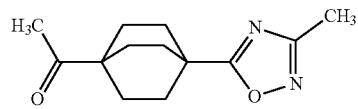 [SMILES: CC(=O)C12CCC(c3nc(C)no3)(CC1)CC2]

The title compound was prepared according to the method described for the synthesis of Intermediate 1C by substituting Intermediate 70A where appropriate: (0.3 g, 1.216 mmol, 72% yield) as white solid. $^1$H NMR (400 MHz, DMSO-d$_6$) δ 2.31 (s, 3H), 2.00 (s, 3H), 1.89-1.93 (m, 6H), 1.74-1.78 (m, 6H).

Step C. Intermediate 70C. Preparation of 3-(3-ethyl-1,2,4-oxadiazol-5-yl)-N-(1-(4-(3-methyl-1,2,4-oxadiazol-5-yl)bicyclo[2.2.2]octan-1-yl)ethyl)aniline

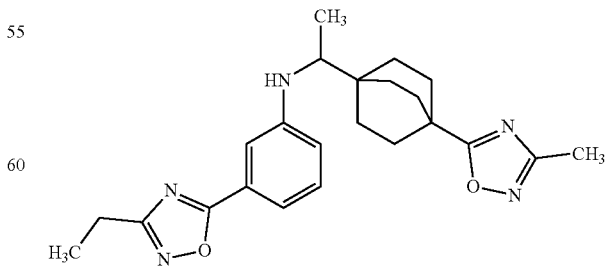

To a stirred solution of Intermediate 70B (75 mg, 0.320 mmol) in methanol (2 mL) was added Intermediate 3B (60.6 mg, 0.320 mmol) at room temperature and stirred for 1 h. To this reaction mixture were added triethylsilane (0.102 mL, 0.640 mmol) followed by indium(III) chloride (7 mg, 0.032 mmol). The reaction mixture was stirred overnight at room temperature. The reaction mixture was concentrated under reduced pressure and the residue was dissolved in EtOAc (20 mL). The organic solution was washed with water (10 mL), brine solution (10 mL), dried over anhydrous sodium sulphate and concentrated under reduced pressure. The crude material was purified by flash chromatography (4 g silica gel cartridge; A=Hex, B=EtOAc; 30 min grad.; 0% B to 40% B; flow rate=20 mL/min). The pure fractions were combined, concentrated under reduced pressure and dried in vacuo to afford the title compound (110 mg, 0.162 mmol, 51% yield) as a pale yellow oil. MS (ESI) 408.3 (M+H).

Step D. Example 70 & 71. Preparation of N-(3-(3-ethyl-1,2,4-oxadiazol-5-yl)phenyl)-N-(1-(4-(3-methyl-1,2,4-oxadiazol-5-yl)bicyclo[2.2.2]octan-1-yl)ethyl)cyclohexanecarboxamide To a solution of Intermediate 70C (70 mg, 0.172 mmol) in pyridine (2 mL) was added DMAP (20.99 mg, 0.172 mmol) followed by cyclohexanecarbonyl chloride (126 mg, 0.859 mmol) at room temperature. The reaction mixture was heated at 90° C. for 2 days. The reaction mixture was cooled, diluted with DCM (10 mL), washed with water (5 mL), brine solution (5 mL), dried over anhydrous sodium sulphate and concentrated under reduced pressure. The compound was purified by reverse phase preparative HPLC followed by chiral HPLC using following conditions Column: DAD-1 Cellulose-2 (250×4.6) 5.0 m; Isocratic Mode, Mobile phase: MeOH, Column Temperature: 30° C.; Total Flow: 2 mL/min.

Example 70—Enantiomer 1 (12 mg, 0.023 mmol, 13% yield): $^1$H NMR (400 MHz, DMSO-d$_6$) δ 8.15 (d, J=7.1 Hz, 1H), 7.89 (br. s., 1H), 7.79-7.68 (m, 1H), 7.63 (br. s., 1H), 4.86 (br. s., 1H), 2.83 (q, J=7.4 Hz, 2H), 2.32 (s, 3H), 1.83 (br. s., 7H), 1.53 (br. s., 11H), 1.41-1.27 (m, 5H), 1.12-1.00 (m, 3H), 0.97 (br. s., 1H), 0.89-0.66 (m, 2H), FXR EC$_{50}$ (nM) 1495.11; MS (ESI) 518.4 (M+H).

Example 71—Enantiomer 2 (12 mg, 0.023 mmol, 13% yield): $^1$H NMR (400 MHz, DMSO-d$_6$) δ 8.15 (d, J=7.1 Hz, 1H), 7.89 (br. s., 1H), 7.79-7.68 (m, 1H), 7.63 (br. s., 1H), 4.86 (br. s., 1H), 2.83 (q, J=7.4 Hz, 2H), 2.32 (s, 3H), 1.83 (br. s., 7H), 1.53 (br. s., 11H), 1.41-1.27 (m, 5H), 1.12-1.00 (m, 3H), 0.97 (br. s., 1H), 0.89-0.66 (m, 2H), FXR EC$_{50}$ (nM) 547.44; MS (ESI) 518.4 (M+H).

Example 72

N-(3'-methoxy-[1,1'-biphenyl]-3-yl)-N-((4-(3-methyl-1,2,4-oxadiazol-5-yl) bicyclo[2.2.2]octan-1-yl)methyl)cyclohexanecarboxamide

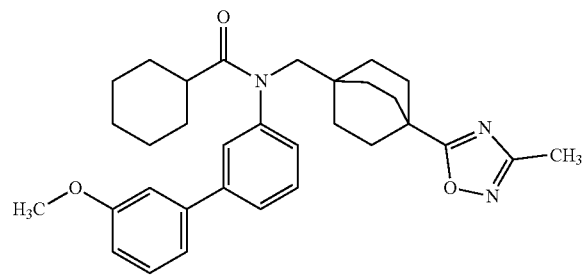

Step A. Intermediate 72A. Preparation of 3-methoxy-3'-nitro-1,1'-biphenyl

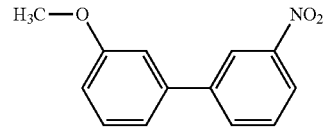 [SMILES: COc1cccc(-c2cccc([N+](=O)[O-])c2)c1]

To a stirred solution of 1-bromo-3-methoxybenzene (0.5 g, 2.67 mmol, commercially available) in toluene (5 mL) and ethanol (2 mL) was added (3-nitrophenyl)boronic acid (0.535 g, 3.21 mmol, commercially available) at room temperature. The reaction mixture was degassed and back-filled with argon. A solution of Na$_2$CO$_3$ (0.850 g, 8.02 mmol) in water (0.3 mL) was added to the reaction mass and degassed and back-filled with argon. Tetrakis(triphenylphosphine) palladium(0) (0.154 g, 0.134 mmol) was added and the reaction mixture was stirred at 110° C. overnight. The reaction mixture was cooled to room temperature, diluted with water (20 mL) and extracted with EtOAc (3×10 mL). The organic layers were combined, washed with brine solution (10 mL), dried over anhydrous sodium sulphate and concentrated under reduced pressure. The crude material was purified by flash column chromatography (12 g silica gel cartridge; A=Hex, B=EtOAc; 20 min grad.; 0% B to 15% B; flow rate=30 mL/min). The pure fractions were combined, concentrated and dried in vacuo to afford the title compound (0.48 g, 1.885 mmol, 70% yield) as white solid. $^1$H NMR (400 MHz, DMSO-d$_6$) δ 8.44 (t, J=2.1 Hz, 1H), 8.23 (dt, J=8.3, 1.1 Hz, 1H), 8.20-8.13 (m, 1H), 7.77 (t, J=7.9 Hz, 1H), 7.49-7.41 (m, 1H), 7.38-7.29 (m, 2H), 7.04 (dd, J=8.1, 2.4 Hz, 1H), 3.85 (s, 3H).

Step B. Intermediate 72B. Preparation of 3'-methoxy-[1,1'-biphenyl]-3-amine

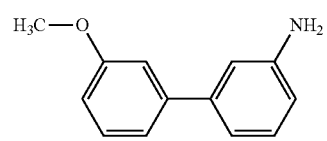

A solution of Intermediate 1D (0.48 g, 2.094 mmol) in methanol (10 mL) was purged and flushed with nitrogen. Pd—C (0.111 g, 0.105 mmol) was added to the reaction mixture and stirred under hydrogen (1 atm, balloon) overnight. The reaction mixture was filtered through Celite and the filtrate was concentrated under reduced pressure. The crude material was purified by flash column chromatography (24 g silica gel cartridge; A=Hex, B=EtOAc; 20 min grad.; 0% B to 20% B; flow rate=30 mL/min). The pure fractions were combined, concentrated and dried in vacuo to afford the title compound (0.38 g, 1.812 mmol, 87% yield) as oil. $^1$H NMR (400 MHz, DMSO-d$_6$) δ 7.37-7.31 (m, 1H), 7.14-7.05 (m, 3H), 6.90 (ddd, J=8.0, 2.5, 1.0 Hz, 1H), 6.84 (t, J=2.0 Hz, 1H), 6.80-6.75 (m, 1H), 6.61-6.53 (m, 1H), 5.13 (s, 2H), 3.81 (s, 3H). MS (ESI) 200 (M+H).

Step C. Intermediate 72C. Preparation of 3'-methoxy-N-((4-(3-methyl-1,2,4-oxadiazol-5-yl)bicyclo[2.2.2]octan-1-yl)methyl)-[1,1'-biphenyl]-3-amine

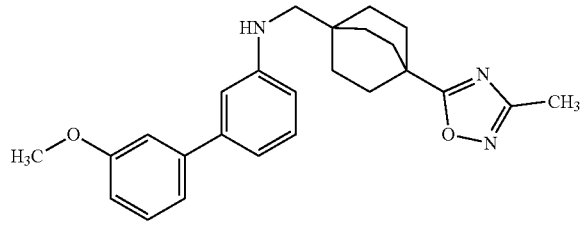

The title compound was prepared according to the method described for the synthesis of Intermediate 1F by substituting Intermediate 72B and Intermediate 1C where appropriate: compound (0.13 g, 0.29 mmol, 51% yield) as an off-white solid. MS (ESI) 404 (M+H).

Step D. Example 72. Preparation of N-(3'-methoxy-[1,1'-biphenyl]-3-yl)-N-((4-(3-methyl-1,2,4-oxadiazol-5-yl)bicyclo[2.2.2]octan-1-yl)methyl)cyclohexanecarboxamide The title compound was prepared according to the method described for the synthesis of Example 1 by substituting Intermediate 72C and corresponding acid where appropriate: (30 mg, 0.058 mmol, 67% yield). $^1$H NMR (400 MHz, DMSO-$d_6$) δ 7.66-7.63 (m, 2H), 7.53 (t, J=7.9 Hz, 1H), 7.42-7.37 (m, 2H), 7.28 (d, J=7.6 Hz, 1H), 7.23 (t, J=2.1 Hz, 1H), 6.98 (dd, J=8.1, 2.0 Hz, 1H), 3.85 (s, 3H), 3.65 (s, 2H), 2.27 (s, 4H), 1.86-1.73 (m, 6H), 1.63 (t, J=14.1 Hz, 4H), 1.51 (d, J=11.2 Hz, 1H), 1.48-1.30 (m, 8H), 1.17-1.03 (m, 1H), 0.89 (d, J=11.2 Hz, 2H). FXR EC$_{50}$ (nM) 307. MS (ESI) 514 (M+H).

Example 73

N-(3-(2-methoxypyridin-4-yl)phenyl)-N-((4-(3-methyl-1,2,4-oxadiazol-5-yl) bicyclo[2.2.2]octan-1-yl)methyl)cyclohexane carboxamide (73)

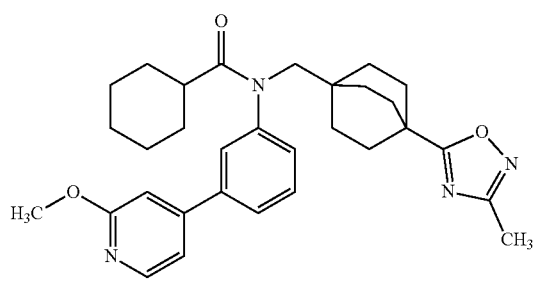

Step A. Intermediate 73A. Preparation of 3-(2-methoxypyridin-4-yl)aniline

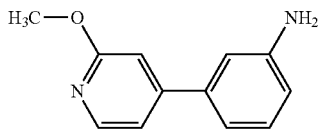

To a stirred solution of 4-bromo-2-methoxypyridine (5 g, 26.6 mmol, commercially available) in toluene (50 mL) was added (3-aminophenyl)boronic acid (commercially available) (4.4 g, 31.9 mmol). The reaction mixture was degassed and back-filled with argon. A solution of Na$_2$CO$_3$ (0.85 g, 8.02 mmol) in water (0.5 mL) was added and degassed and back-filled with argon. Tetrakis(triphenylphosphine) palladium(0) (1.536 g, 1.330 mmol) was added and the reaction mixture was stirred at 110° C. overnight. The reaction mixture was cooled to room temperature, diluted with water (50 mL) and extracted with EtOAc (3×25 mL). The organic layers were combined, washed with brine solution (30 mL), dried over anhydrous sodium sulphate and concentrated under reduced pressure. The crude material was purified by flash column chromatography (40 g silica gel cartridge; A=Hex, B=EtOAc; 20 min grad.; 0% B to 20% B; flow rate=30 mL/min). The pure fractions were combined, concentrated and dried in vacuo to afford the title compound (6 g, 27 mmol, 100% yield) as yellow solid. $^1$H NMR (400 MHz, DMSO-$d_6$) δ 8.19 (d, J=5.5 Hz, 1H), 7.22-7.10 (m, 2H), 6.98-6.83 (m, 3H), 6.66 (ddd, J=8.0, 2.0, 1.0 Hz, 1H), 5.23 (s, 2H), 3.88 (s, 3H). MS (ESI) 201 (M+H).

Step B. Intermediate 73B. Preparation of 3-(2-methoxypyridin-4-yl)-N-((4-(3-methyl-1,2,4-oxadiazol-5-yl)bicyclo[2.2.2]octan-1-yl)methyl)aniline

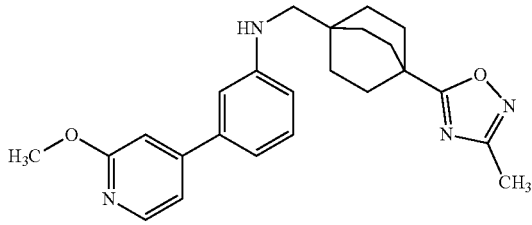 [SMILES: COc1cc(-c2cccc(NCC34CCC(c5nc(C)no5)(CC3)CC4)c2)ccn1]

The title compound was prepared according to the method described for the synthesis of Intermediate 1F by substituting Intermediate 73A and Intermediate 1C where appropriate (40 mg, 0.089 mmol, 39% yield) as an off-white solid. $^1$H NMR (400 MHz, DMSO-$d_6$) δ 8.19 (d, J=5.0 Hz, 1H), 7.24-7.11 (m, 2H), 7.00-6.92 (m, 2H), 6.84 (d, J=7.5 Hz, 1H), 6.71 (dd, J=8.3, 2.3 Hz, 1H), 5.62 (t, J=6.0 Hz, 1H), 3.88 (s, 3H), 2.90 (d, J=6.0 Hz, 2H), 2.29 (s, 3H), 1.96-1.84 (m, 6H), 1.66-1.53 (m, 6H). MS (ESI) 405 (M+H).

Step C. Example 73. Preparation of N-(3-(2-methoxypyridin-4-yl)phenyl)-N-((4-(3-methyl-1,2,4-oxadiazol-5-yl)bicyclo[2.2.2]octan-1-yl)methyl)cyclohexane carboxamide The title compound was prepared according to the method described for Example 1 by substituting Intermediate 73B and cyclohexanecarbonyl chloride where appropriate (30 mg, 0.058 mmol, 59% yield). $^1$H NMR (400 MHz, DMSO-d$_6$) δ 8.26 (d, J=5.4 Hz, 1H), 7.84 (s, 1H), 7.77 (d, J=8.1 Hz, 1H), 7.62-7.52 (m, 1H), 7.49 (d, J=8.6 Hz, 1H), 7.38 (dd, J=5.4, 1.5 Hz, 1H), 7.20 (s, 1H), 3.91 (s, 3H), 3.65 (br. s., 2H), 2.27 (s, 3H), 2.26-2.18 (m, 1H), 1.88-1.73 (m, 6H), 1.62 (t, J=13.7 Hz, 4H), 1.50 (d, J=11.2 Hz, 1H), 1.46-1.38 (m, 6H), 1.38-1.28 (m, 2H), 1.09 (d, J=12.0 Hz, 1H), 0.87 (d, J=10.5 Hz, 2H). FXR EC$_{50}$ (nM) 517; MS (ESI) 515 (M+H).

Example 74

N-((4-(3-cyclopropyl-1,2,4-oxadiazol-5-yl)bicyclo[2.2.2]octan-1-yl)methyl)-N-(3'-methoxy-[1,1'-biphenyl]-3-yl)cyclohexanecarboxamide

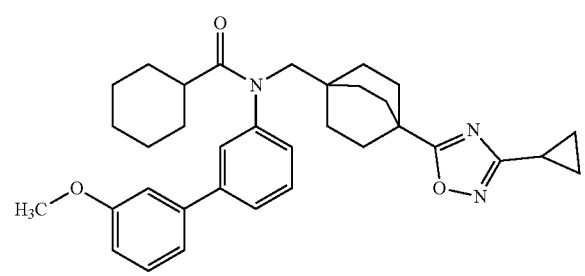

(74)

Step A. Intermediate 74A. Preparation of N-((4-(3-cyclopropyl-1,2,4-oxadiazol-5-yl) bicyclo[2.2.2]octan-1-yl)methyl)-3'-methoxy-[1,1'-biphenyl]-3-amine

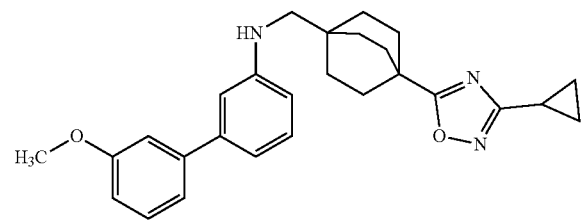 [SMILES: COc1cccc(-c2cccc(NCC34CCC(c5nc(C6CC6)no5)(CC3)CC4)c2)c1]

The title compound was prepared according to the method described for the synthesis of Intermediate 1F by substituting Intermediate 72B and Intermediate 2F where appropriate (40 mg, 0.084 mmol, 41% yield) as an off-white solid. $^1$H NMR (400 MHz, DMSO-d$_6$) δ 7.38-7.30 (m, 1H), 7.16-7.05 (m, 3H), 6.93-6.82 (m, 2H), 6.75 (d, J=8.0 Hz, 1H), 6.63-6.57 (m, 1H), 5.52 (t, J=6.0 Hz, 1H), 3.81 (s, 3H), 2.87 (d, J=6.0 Hz, 2H), 2.10-2.02 (m, 1H), 1.92-1.81 (m, 6H), 1.63-1.53 (m, 6H), 1.07-0.98 (m, 2H), 0.88-0.82 (m, 2H). MS (ESI) 430 (M+H).

Step B. Example 74. Preparation of N-((4-(3-cyclopropyl-1,2,4-oxadiazol-5-yl) bicyclo[2.2.2]octan-1-yl)methyl)-N-(3'-methoxy-[1,1'-biphenyl]-3-yl)cyclohexanecarboxamide The title compound was prepared according to the method described for the synthesis of Example 1 by substituting Intermediate 74A and cyclohexanecarbonyl chloride where appropriate (50 mg, 0.092 mmol, 99% yield). $^1$H NMR (400 MHz, DMSO-d$_6$) δ 7.77-7.61 (m, 2H), 7.53 (t, J=7.8 Hz, 1H), 7.40 (q, J=7.7 Hz, 2H), 7.28 (d, J=8.1 Hz, 1H), 7.23 (d, J=1.7 Hz, 1H), 6.98 (dd, J=7.8, 2.2 Hz, 1H), 3.84 (s, 3H), 3.63 (s, 2H), 2.32-2.19 (m, 1H), 2.12-1.98 (m, 1H), 1.86-1.70 (m, 6H), 1.69-1.56 (m, 4H), 1.51 (d, J=13.4 Hz, 1H), 1.47-1.26 (m, 8H), 1.10 (d, J=13.0 Hz, 1H), 1.05-0.96 (m, 2H), 0.96-0.75 (m, 4H). FXR EC$_{50}$ (nM) 151; MS (ESI) 540 (M+H).

Example 75

N-((4-(3-cyclopropyl-1,2,4-oxadiazol-5-yl)bicyclo[2.2.2]octan-1-yl)methyl)-N-(3-(2-methoxypyridin-4-yl)phenyl)cyclohexane carboxamide

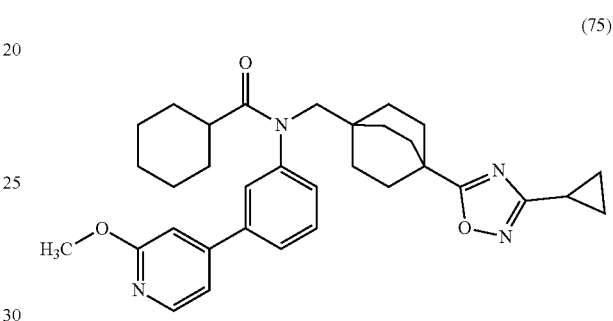

(75)

Step A. Intermediate 75A. Preparation of N-((4-(3-cyclopropyl-1,2,4-oxadiazol-5-yl) bicyclo[2.2.2]octan-1-yl)methyl)-3-(2-methoxypyridin-4-yl)aniline

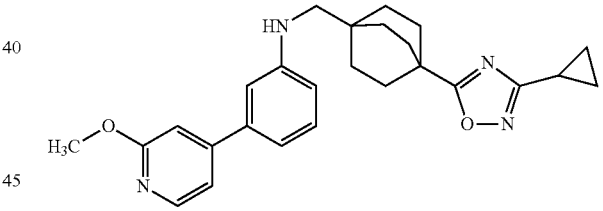

The title compound was prepared according to the method described for the synthesis of Intermediate 1F by substituting Intermediate 73A and Intermediate 2F where appropriate (40 mg, 0.084 mmol, 41% yield) as an off-white solid. $^1$H NMR (400 MHz, DMSO-d$_6$) δ 8.18 (d, J=5.0 Hz, 1H), 7.24-7.10 (m, 2H), 6.98 (s, 1H), 6.93 (s, 1H), 6.84 (d, J=7.0 Hz, 1H), 6.70 (d, J=8.0 Hz, 1H), 5.61 (s, 1H), 3.88 (s, 3H), 2.89 (d, J=6.0 Hz, 2H), 2.10-2.02 (m, 1H), 1.93-1.79 (m, 6H), 1.62-1.52 (m, 6H), 1.07-0.97 (m, 2H), 0.89-0.82 (m, 2H). MS (ESI) 431 (M+H).

Step B. Example 75. Preparation of N-((4-(3-cyclopropyl-1,2,4-oxadiazol-5-yl) bicyclo[2.2.2]octan-1-yl)methyl)-N-(3-(2-methoxypyridin-4-yl)phenyl) cyclohexane carboxamide The title compound was prepared according to the method described for the synthesis of Example 1 by substituting Intermediate 75A and cyclohexanecarbonyl chloride (50 mg, 0.092 mmol, 99% yield). $^1$H NMR (400 MHz, DMSO-d$_6$) δ

8.26 (d, J=5.4 Hz, 1H), 7.83 (s, 1H), 7.77 (d, J=7.8 Hz, 1H), 7.57 (t, J=7.8 Hz, 1H), 7.49 (d, J=7.8 Hz, 1H), 7.38 (dd, J=5.4, 1.5 Hz, 1H), 7.19 (s, 1H), 3.91 (s, 3H), 3.64 (br. s., 2H), 2.23 (t, J=11.5 Hz, 1H), 2.08-1.99 (m, 1H), 1.84-1.69 (m, 6H), 1.69-1.54 (m, 4H), 1.49 (d, J=11.7 Hz, 1H), 1.45-1.28 (m, 8H), 1.09 (d, J=12.7 Hz, 1H), 1.03-0.96 (m, 2H), 0.94-0.75 (m, 4H). FXR EC$_{50}$ (nM) 129; MS (ESI) 541 (M+H).

Example 76

N-(4'-methoxy-[1,1'-biphenyl]-3-yl)-N-((4-(3-methyl-1,2,4-oxadiazol-5-yl) bicyclo[2.2.2]octan-1-yl)methyl)cyclohexane carboxamide (76)

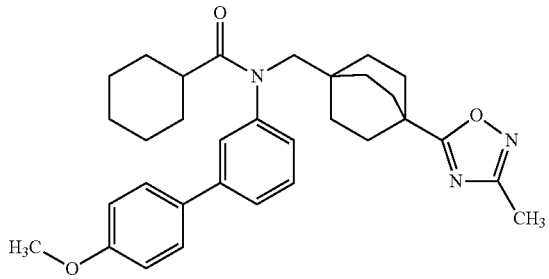

Step A. Intermediate 76A. Preparation of 4'-methoxy-3-nitro-1,1'-biphenyl

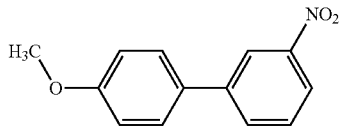 [SMILES: COc1ccc(-c2cccc([N+](=O)[O-])c2)cc1]

To a stirred solution of 1-bromo-4-methoxybenzene (0.5 g, 2.67 mmol, commercially available) in toluene (5 mL) and ethanol (2 mL) was added (3-nitrophenyl) boronic acid (0.535 g, 3.21 mmol). The reaction mixture was degassed and back-filled with argon. A solution of Na$_2$CO$_3$ (0.850 g, 8.02 mmol) in water (0.2 mL) was added and degassed and back-filled with argon. Tetrakis(triphenylphosphine) palladium(0) (0.150 g, 0.134 mmol) was added and the reaction mixture was stirred at 110° C. overnight. The reaction mixture was cooled to room temperature, diluted with water (20 mL) and extracted with EtOAc (3×20 mL). The organic layers were combined, washed with brine solution (10 mL), dried over anhydrous sodium sulphate and concentrated under reduced pressure. The crude material was purified by flash column chromatography (24 g silica gel cartridge; A=Hex, B=EtOAc; 20 min grad.; 0% B to 30% B; flow rate=30 mL/min). The pure fractions were combined, concentrated and dried in vacuo to afford the title compound (0.52 g, 2.042 mmol, 76% yield) as an off-white solid. $^1$H NMR (400 MHz, DMSO-d$_6$) δ 8.40 (t, J=2.0 Hz, 1H), 8.20-8.14 (m, 1H), 8.12 (dd, J=9.5, 1.0 Hz, 1H), 7.79-7.72 (m, 3H), 7.11-7.06 (m, 2H), 3.83 (s, 3H).

Step B. Intermediate 76B. Preparation of 4'-methoxy-[1,1'-biphenyl]-3-amine

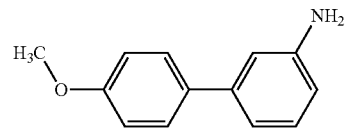

A solution of Intermediate 76A (520 mg, 2.26 mmol) in methanol (10 mL) was purged and flushed with nitrogen. Pd—C (120 mg, 0.113 mmol) was added to the reaction mixture and stirred under hydrogen (1 atm, balloon) overnight. The reaction mixture was filtered through Celite and the filtrate was concentrated under reduced pressure to afford title compound (0.4 g, 1.91 mmol, 84% yield) as an off-white solid. $^1$H NMR (400 MHz, DMSO-d$_6$) δ 7.51-7.45 (m, 2H), 7.07 (t, J=7.8 Hz, 1H), 7.02-6.96 (m, 2H), 6.80 (t, J=2.0 Hz, 1H), 6.75-6.70 (m, 1H), 6.54-6.49 (m, 1H), 5.09 (s, 2H), 3.79 (s, 3H). MS (ESI) 200 (M+H).

Step C. Intermediate 76C. Preparation of 4'-methoxy-N-((4-(3-methyl-1,2,4-oxadiazol-5-yl) bicyclo[2.2.2]octan-1-yl)methyl)-[1,1'-biphenyl]-3-amine

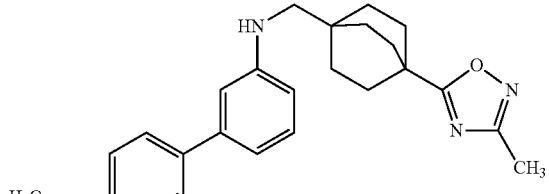

The title compound was prepared according to the method described for the synthesis of Intermediate 1F by substituting Intermediate 76B and Intermediate 1C where appropriate (50 mg, 0.112 mmol, 49% yield) as an off-white solid. $^1$H NMR (400 MHz, DMSO-d$_6$) δ 7.56-7.48 (m, 2H), 7.09 (t, J=8.0 Hz, 1H), 7.03-6.96 (m, 2H), 6.82 (t, J=1.8 Hz, 1H), 6.72 (d, J=7.5 Hz, 1H), 6.57 (dd, J=7.8, 2.3 Hz, 1H), 5.49 (t, J=5.8 Hz, 1H), 3.79 (s, 3H), 2.88 (d, J=6.0 Hz, 2H), 2.30 (s, 3H), 1.95-1.84 (m, 6H), 1.66-1.55 (m, 6H). MS (ESI) 404 (M+H).

Step D. Example 76. Preparation of N-(4'-methoxy-[1,1'-biphenyl]-3-yl)-N-((4-(3-methyl-1,2,4-oxadiazol-5-yl)bicyclo[2.2.2]octan-1-yl)methyl)cyclohexane carboxamide The title compound was prepared according to the method described for the synthesis of Example 1 by substituting Intermediate 76C and cyclohexanecarbonyl chloride where appropriate (43 mg, 0.084 mmol, 68% yield). $^1$H NMR (400 MHz, DMSO-d$_6$) δ 7.73-7.63 (m, J=8.8 Hz, 2H), 7.63-7.54 (m, 2H), 7.50 (t, J=7.8 Hz, 1H), 7.31 (d, J=9.0 Hz, 1H), 7.12-6.98 (m, J=8.6 Hz, 2H), 3.81 (s, 3H), 3.64 (br. s., 2H), 3.18 (d, J=5.1 Hz, 1H), 2.27 (s, 4H), 1.87-1.71 (m, 6H), 1.63 (br. s., 4H), 1.54-1.26 (m, 8H), 1.17-1.03 (m, 1H), 0.88 (d, J=14.4 Hz, 2H). FXR EC$_{50}$ (nM) 387; MS (ESI) 514 (M+H).

Example 77

N-((4-(3-cyclopropyl-1,2,4-oxadiazol-5-yl)bicyclo[2.2.2]octan-1-yl)methyl)-N-(3-(4-ethoxypyridin-2-yl)phenyl)cyclohexane carboxamide

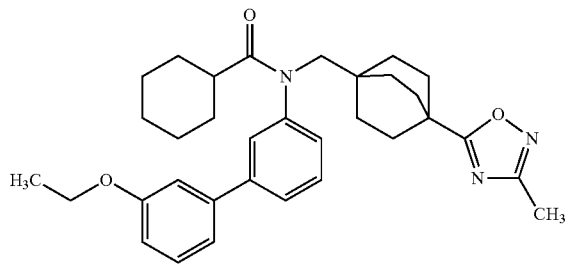

(77)

Step A. Intermediate 77A. Preparation of 2-chloro-4-ethoxypyridine

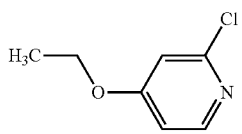

To a stirred solution of 4-bromo-2-chloropyridine (500 mg, 2.60 mmol) in ethanol (5 mL) was added sodium ethoxide in ethanol (1.4 g, 5.20 mmol) under nitrogen. The reaction mixture was stirred at room temperature overnight. The solvent was removed under reduced pressure and the residue was diluted with water (20 mL) and extracted with EtOAc (2×10 mL). The organic layers were combined, washed with brine (10 mL), dried over anhydrous sodium sulphate and concentrated under reduced pressure. The crude material was purified by flash chromatography (24 g silica gel cartridge; A=Hex, B=EtOAc; 20 min grad.; 0% B to 20% B; flow rate=30 mL/min). The pure fractions were combined, concentrated and dried in vacuo to afford the title compound (270 mg, 1.45 mmol, 56% yield) as a pale yellow oil. MS (ESI) 158 (M+H).

Step B. Intermediate 77B. Preparation of 4-ethoxy-2-(3-nitrophenyl)pyridine

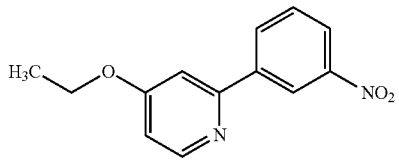 [SMILES: CCOc1ccnc(-c2cccc([N+](=O)[O-])c2)c1]

To a stirred solution of Intermediate 77A (270 mg, 1.71 mmol) in toluene (3 mL) and ethanol (3 mL) were added (3-nitrophenyl)boronic acid (286 mg, 1.71 mmol) and a solution of Na$_2$CO$_3$ (545 mg, 5.14 mmol) in water (2 mL). The reaction mixture was degassed and back-filled with argon. Tetrakis(triphenylphosphine) palladium(0) (98 mg, 0.085 mmol) was added and the resulting reaction mass was heated at 110° C. overnight. The reaction mixture was cooled to room temperature, diluted with water (10 mL) and extracted with EtOAc (2×10 mL). The organic layers were combined, washed with brine solution (10 mL), dried over anhydrous sodium sulphate and concentrated under reduced pressure. The crude material was purified by flash column chromatography (12 g silica gel cartridge; A=Hex, B=EtOAc; 20 min grad.; 0% B to 20% B; flow rate=30 mL/min). The pure fractions were combined, concentrated and dried in vacuo to afford the title compound (200 mg, 0.778 mmol, 45% yield) as an off-white solid. $^1$H NMR (400 MHz, DMSO-d$_6$) δ 8.96-8.92 (m, 1H), 8.59-8.52 (m, 2H), 8.32-8.26 (m, 1H), 7.79 (t, J=8.0 Hz, 1H), 7.68 (d, J=2.0 Hz, 1H), 7.06-7.01 (m, 1H), 4.26 (q, J=7.0 Hz, 2H), 1.40 (t, J=7.0 Hz, 3H). MS (ESI) 245 (M+H).

Step C. Intermediate 77C. Preparation of 3-(4-ethoxypyridin-2-yl)aniline

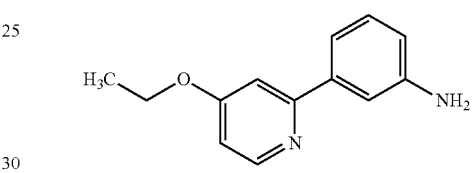

A solution of Intermediate 77B (200 mg, 0.819 mmol) in methanol (10 mL) was purged and flushed with nitrogen. Pd—C (43.6 mg, 0.041 mmol) was added and the reaction mixture was stirred under hydrogen (1 atm, balloon) overnight. The reaction mixture was filtered through Celite and the filtrate was concentrated to afford title compound (150 mg, 0.665 mmol, 81% yield) as a pale yellow oil. $^1$H NMR (400 MHz, DMSO-d$_6$) δ 8.41 (d, J=6.0 Hz, 1H), 7.32 (t, J=2.0 Hz, 1H), 7.27 (d, J=2.5 Hz, 1H), 7.19-7.15 (m, 1H), 7.12-7.07 (m, 1H), 6.88 (dd, J=5.5, 2.5 Hz, 1H), 6.64-6.59 (m, 1H), 5.13 (s, 2H), 4.19 (q, J=7.0 Hz, 2H), 1.37 (t, J=7.0 Hz, 3H). MS (ESI) 215 (M+H).

Step D. Intermediate 77D. Preparation of 3-(4-ethoxypyridin-2-yl)aniline

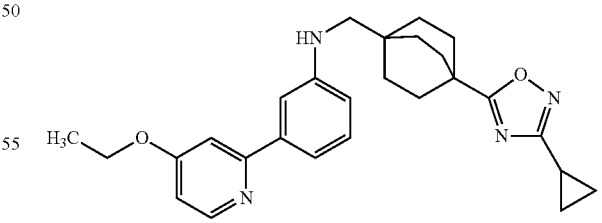

The title compound was prepared according to the method described for the synthesis of Intermediate 1F by substituting Intermediate 77C and Intermediate 2F where appropriate (110 mg, 0.235 mmol, 58% yield) as white solid. $^1$H NMR (400 MHz, DMSO-d$_6$) δ 8.42 (d, J=6.0 Hz, 1H), 7.36-7.28 (m, 2H), 7.18-7.09 (m, 2H), 6.91-6.86 (m, 1H), 6.67 (dt, J=7.8, 1.6 Hz, 1H), 5.52 (t, J=6.0 Hz, 1H), 4.19 (q, J=6.9 Hz, 2H), 2.88 (d, J=6.0 Hz, 2H), 2.10-2.02 (m, 1H), 1.90-1.82

(m, 6H), 1.63-1.53 (m, 6H), 1.37 (t, J=7.0 Hz, 3H), 1.06-0.98 (m, 2H), 0.89-0.82 (m, 2H). MS (ESI) 445 (M+H).

Step E. Example 77. Preparation of N-((4-(3-cyclopropyl-1,2,4-oxadiazol-5-yl) bicyclo[2.2.2]octan-1-yl)methyl)-N-(3-(4-ethoxypyridin-2-yl)phenyl)cyclohexane carboxamide The title compound was prepared according to the method described for the synthesis of Example 1 by substituting Intermediate 77D and cyclohexanecarbonyl chloride where appropriate (20 mg, 0.036 mmol, 80% yield). $^1$H NMR (400 MHz, DMSO-$d_6$) δ 8.60 (d, J=6.1 Hz, 1H), 8.13-7.95 (m, 2H), 7.70 (s, 1H), 7.62 (t, J=7.8 Hz, 1H), 7.56 (d, J=7.8 Hz, 1H), 7.24-7.15 (m, 1H), 4.37-4.32 (m, 2H), 4.03 (br. s., 2H), 2.26 (br. s., 1H), 2.07-2.01 (m, 1H), 1.81-1.73 (m, 6H), 1.62 (br. s., 4H), 1.50 (d, J=12.5 Hz, 1H), 1.46-1.29 (m, 12H), 1.10 (d, J=12.7 Hz, 1H), 1.04-0.96 (m, 2H), 0.94-0.80 (m, 3H). FXR $EC_{50}$ (nM) 268; MS (ESI) 555 (M+H).

Example 78

N-((4-(3-cyclopropyl-1,2,4-oxadiazol-5-yl)bicyclo[2.2.2]octan-1-yl)methyl)-N-(3-(2-ethoxypyridin-4-yl)phenyl)cyclohexane carboxamide

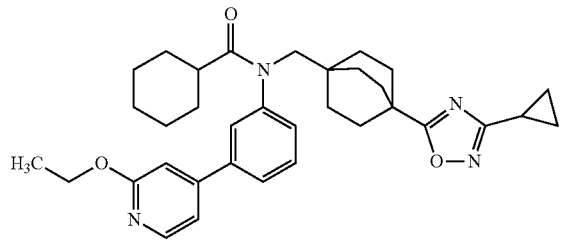

(78)

Step A. Intermediate 78A. Preparation of 2-chloro-4-(3-nitrophenyl) pyridine

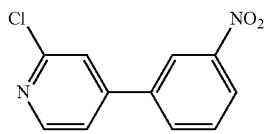

To a stirred solution of 4-bromo-2-chloropyridine (0.25 g, 1.30 mmol, commercially available) in toluene (5 mL) and ethanol (2 mL) were added (3-nitrophenyl)boronic acid (0.260 g, 1.56 mmol) and $Na_2CO_3$ (0.413 g, 3.90 mmol) in water (0.2 mL). The reaction mass was degassed and back-filled with argon. Tetrakis(triphenylphosphine) palladium(0) (0.075 g, 0.065 mmol) was added and the reaction mixture was heated at 90° C. overnight. The reaction mixture was cooled to room temperature, diluted with water (10 mL) and extracted with EtOAc (2×10 mL). The organic layers were combined, washed with brine solution (10 mL), dried over anhydrous sodium sulphate and concentrated under reduced pressure. The crude material was purified by flash column chromatography (12 g silica gel cartridge; A=Hex, B=EtOAc; 20 min grad.; 0% B to 20% B; flow rate=30 mL/min). The pure fractions were combined, concentrated and dried in vacuo to afford the title compound (0.15 g, 0.607 mmol, 47% yield) as white solid. $^1$H NMR (400 MHz, DMSO-$d_6$) δ 8.65 (t, J=2.0 Hz, 1H), 8.57-8.54 (m, 1H), 8.38-8.31 (m, 2H), 8.05-8.03 (m, 1H), 7.90 (dd, J=5.3, 1.8 Hz, 1H), 7.85 (t, J=8.0 Hz, 1H). MS (ESI) 235 (M+H).

Step B. Intermediate 78B. Preparation of 2-ethoxy-4-(3-nitrophenyl)pyridine

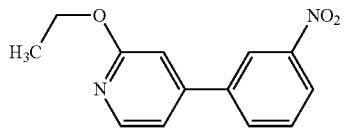 [SMILES: CCOc1cc(-c2cccc([N+](=O)[O-])c2)ccn1]

To a stirred solution of Intermediate 78A (0.15 g, 0.639 mmol) in ethanol (3 mL) was added sodium ethoxide in ethanol (0.29 g, 0.639 mmol) under inert atmosphere. The reaction mixture was stirred at room temperature overnight. The solvent was removed under reduced pressure and the residue was diluted with water (10 mL) and extracted with EtOAc (2×10 mL). The organic layers were combined, washed with brine (10 mL), dried over anhydrous sodium sulphate and concentrated under reduced pressure. The crude material was purified by flash chromatography (12 g silica gel cartridge; A=Hex, B=EtOAc; 20 min grad.; 0% B to 20% B; flow rate=30 mL/min). The pure fractions were combined, concentrated and dried in vacuo to afford the title compound (110 mg, 0.428 mmol, 67% yield) as a pale yellow oil. $^1$H NMR (400 MHz, DMSO-$d_6$) δ 8.53 (t, J=2.0 Hz, 1H), 8.35-8.21 (m, 3H), 7.80 (t, J=7.8 Hz, 1H), 7.41 (dd, J=5.3, 1.8 Hz, 1H), 7.22 (d, J=1.0 Hz, 1H), 4.37 (q, J=7.2 Hz, 2H), 1.35 (t, J=7.0 Hz, 3H). MS (ESI) 245 (M+H).

Step C. Intermediate 78C. Preparation of 3-(2-ethoxypyridin-4-yl)aniline

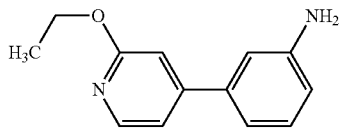

A solution of Intermediate 78B (100 mg, 0.409 mmol) in methanol (5 mL) was purged and flushed with nitrogen. Pd—C (21.79 mg, 0.020 mmol) was added and the reaction mixture was stirred under hydrogen (1 atm, balloon) at room temperature overnight. The reaction mixture was filtered through Celite and the filtrate was concentrated to afford title compound (80 mg, 0.355 mmol, 87% yield) as a pale yellow oil. $^1$H NMR (400 MHz, DMSO-d$_6$) δ 8.19-8.15 (m, 1H), 7.17-7.14 (m, 1H), 7.13 (d, J=7.5 Hz, 1H), 6.93-6.90 (m, 2H), 6.89-6.85 (m, 1H), 6.65 (ddd, J=8.0, 2.0, 1.0 Hz, 1H), 5.22 (s, 2H), 4.34 (q, J=7.0 Hz, 2H), 1.34 (t, J=7.0 Hz, 3H). MS (ESI) 215 (M+H).

Step D. Intermediate 78D. Preparation of N-((4-(3-cyclopropyl-1,2,4-oxadiazol-5-yl) bicyclo[2.2.2]octan-1-yl)methyl)-3-(2-ethoxypyridin-4-yl)aniline

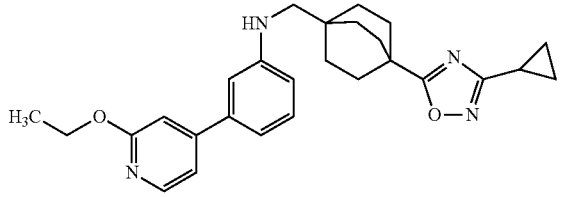 [SMILES: CCOc1cc(-c2cccc(NCC34CCC(c5nc(C6CC6)no5)(CC3)CC4)c2)ccn1]

The title compound was prepared according to the method described for the synthesis of Intermediate 1F by substituting Intermediate 78C and Intermediate 2F where appropriate (60 mg, 0.121 mmol, 60% yield) as a pale yellow oil. $^1$H NMR (400 MHz, DMSO-d$_6$) δ 8.17 (d, J=6.0 Hz, 1H), 7.23-7.11 (m, 2H), 6.98-6.91 (m, 2H), 6.85 (d, J=8.0 Hz, 1H), 6.71 (dd, J=8.3, 1.8 Hz, 1H), 5.61 (t, J=6.0 Hz, 1H), 4.35 (q, J=7.0 Hz, 2H), 2.90 (d, J=6.0 Hz, 2H), 2.12-2.03 (m, 1H), 1.93-1.81 (m, 6H), 1.64-1.51 (m, 6H), 1.34 (t, J=7.0 Hz, 3H), 1.07-0.99 (m, 2H), 0.90-0.81 (m, 2H). MS (ESI) 445 (M+H).

Step E. Example 78. Preparation of N-((4-(3-cyclopropyl-1,2,4-oxadiazol-5-yl) bicyclo[2.2.2]octan-1-yl)methyl)-N-(3-(2-ethoxypyridin-4-yl)phenyl)cyclohexane carboxamide The title compound was prepared according to the method described for the synthesis of Example 1 by substituting Intermediate 78D and cyclohexanecarbonyl chloride where appropriate (22.8 mg, 0.041 mmol, 91% yield). $^1$H NMR (400 MHz, DMSO-d$_6$) δ8.24 (d, J=5.4 Hz, 1H), 7.83 (s, 1H), 7.76 (d, J=6.8 Hz, 1H), 7.57 (t, J=7.9 Hz, 1H), 7.47 (d, J=7.3 Hz, 1H), 7.35 (d, J=5.4 Hz, 1H), 7.17 (s, 1H), 4.37 (q, J=7.0 Hz, 2H), 3.64 (br. s., 2H), 2.23 (br. s., 1H), 2.06-2.00 (m, 1H), 1.85-1.69 (m, 6H), 1.67-1.54 (m, 4H), 1.49 (br. s., 1H), 1.45-1.28 (m, 9H), 1.10 (d, J=13.0 Hz, 1H), 1.05-0.96 (m, 2H), 0.93-0.76 (m, 4H). FXR EC$_{50}$ (nM) 181; MS (ESI) 555 (M+H).

The following compound was prepared according to the method described for the synthesis of Example 5 by substituting Intermediate 78D and corresponding acid where appropriate.

| Ex. No. | Structure | MS (ESI) (M + H) | FXR EC$_{50}$ (nM) |
|---|---|---|---|
| 79 | | 591 | 408 |

| 79 | $^1$H NMR (400 MHz, DMSO-d$_6$) δ 8.24 (d, J = 5.4 Hz, 1H), 7.88 (s, 1H), 7.78 (d, J = 7.8 Hz, 1H), 7.60-7.51 (m, 2H), 7.37 (d, J = 5.1 Hz, 1H), 7.20 (s, 1H), 4.37 (q, J = 7.0 Hz, 2H), 3.65 (br. s., 2H), 2.42 (br. s., 1H), 2.10-2.06 (m, 1H), 2.06-1.88 (m, 3H), 1.82-1.68 (m, 8H), 1.68-1.53 (m, 3H), 1.53-1.38 (m, 6H), 1.35 (t, J = 7.1 Hz, 3H), 1.06-0.96 (m, 2H), 0.88-0.76 (m, 2H). |

Example 80

N-(3-(2-methoxypyridin-4-yl)phenyl)-N-((4-(5-methyl-1,3,4-thiadiazol-2-yl) bicyclo[2.2.2]octan-1-yl)methyl)cyclohexanecarboxamide (80)

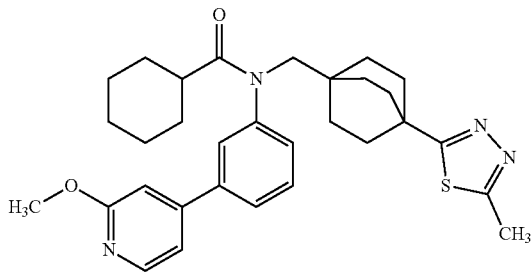

Step A. Intermediate 80A. Preparation of methyl 4-(2-acetylhydrazine-1-carbonyl)bicyclo[2.2.2]octane-1-carboxylate

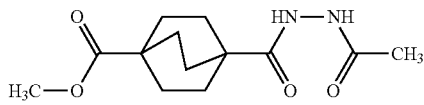

To a stirred solution of 4-(methoxycarbonyl)bicyclo[2.2.2]octane-1-carboxylic acid (500 mg, 2.356 mmol) in DMF (6 mL) were added acetohydrazide (commercially available) (192 mg, 2.59 mmol), DIPEA (1.234 mL, 7.07 mmol) followed by HATU (1164 mg, 3.06 mmol). The reaction mixture was stirred at room temperature overnight. The reaction mixture was concentrated under reduced pressure, residue was diluted with water and extracted with ethyl acetate (2×10 ml). The organic layers were combined, dried over anhydrous sodium sulphate and concentrated under reduced pressure. The crude material was purified by flash chromatography (24 g silica gel cartridge; A=Hex, B=EtOAc; 20 min grad.; 0% B to 30%; flow rate=30 mL/min). The pure fractions were combined, concentrated and dried in vacuo to afford the title compound (850 mg, 2.313 mmol, 98% yield) as white solid. $^1$H NMR (400 MHz, DMSO-$d_6$) δ 8.18 (br. s., 2H), 3.57 (s, 3H), 1.82 (s, 3H), 1.75-1.67 (m, 6H), 1.31-1.20 (m, 6H). MS (ESI) 269 (M+H).

Step B. Intermediate 80B. Preparation of methyl 4-(5-methyl-1,3,4-thiadiazol-2-yl) bicyclo[2.2.2]octane-1-carboxylate

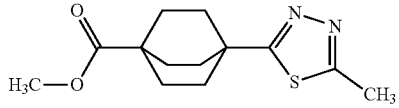

To a stirred solution of Intermediate 80A (1.2 g, 4.47 mmol) in toluene (12 mL) was added Lawesson's reagent (2 g, 4.92 mmol). The reaction mixture was heated at 100° C. overnight. The reaction mixture was cooled to room temperature washed with aqueous sodium bicarbonate solution (10 mL), water (10 mL), dried over anhydrous sodium sulphate and concentrated under reduced pressure. The crude material was purified by flash chromatography (40 g silica gel cartridge; A=Hex, B=EtOAc; 30 min grad.; 0% B to 40% B; flow rate=40 mL/min). The pure fractions were combined, concentrated and dried in vacuo to afford the title compound (700 mg, 2.63 mmol, 59% yield) as white solid. $^1$H NMR (400 MHz, DMSO-$d_6$) δ 3.60 (s, 3H), 2.69 (s, 3H), 1.95-1.80 (m, 12H). MS (ESI) 267 (M+H).

Step C. Intermediate 80C. Preparation of (4-(5-methyl-1,3,4-thiadiazol-2-yl) bicyclo[2.2.2]octan-1-yl)methanol

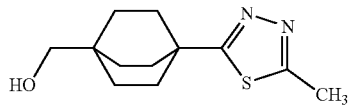 [SMILES: Cc1nnc(C23CCC(CO)(CC2)CC3)s1]

The title compound was prepared according to the method described for the synthesis of Intermediate 1B by substituting Intermediate 80B where appropriate (360 mg, 1.510 mmol, 50% yield). $^1$H NMR (400 MHz, DMSO-$d_6$) δ 4.40 (t, J=5.3 Hz, 1H), 3.08 (d, J=5.0 Hz, 2H), 2.63 (s, 3H), 1.90-1.82 (m, 6H), 1.53-1.41 (m, 6H). MS (ESI) 239 (M+H).

Step D. Intermediate 80D. Preparation of 4-(5-methyl-1,3,4-thiadiazol-2-yl) bicyclo[2.2.2]octane-1-carbaldehyde

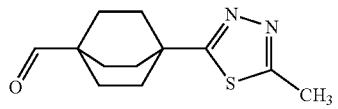 [SMILES: Cc1nnc(C23CCC(C=O)(CC2)CC3)s1]

To a stirred solution of oxalyl chloride (0.217 mL, 2.479 mmol) in DCM (4 mL) cooled to −78° C. A solution of DMSO (0.261 mL, 3.67 mmol) in DCM (0.1 mL) was added to the reaction mixture and stirred for 15 min. A solution of Intermediate 80C (350 mg, 1.46 mmol) in DCM (2 mL) was added and the reaction mixture was stirred at −78° C. for 3 h. TEA (1.433 mL, 10.28 mmol) was added to the reaction mixture at the same temperature. The reaction mixture was warmed to room temperature and stirred for 2 h. The reaction mixture was diluted with water, extracted with DCM (2×20 mL). The combined organic layers were dried over anhydrous sodium sulfate and concentrated under reduced pressure. The crude material was purified by flash chromatography (12 g silica gel cartridge; A=Hex, B=EtOAc; 30 min grad.; 0% B to 30% B; flow rate=24 mL/min). The pure fractions were combined, concentrated under reduced pressure and dried in vacuo to afford the title compound (240 mg, 1.016 mmol, 69% yield) (240 mg, 1.016 mmol, 69% yield). $^1$H NMR (400 MHz, DMSO-$d_6$) δ 9.46 (s, 1H), 2.67 (s, 3H), 1.97-1.89 (m, 6H), 1.76-1.67 (m, 6H). MS (ESI) 237 (M+H).

Step E. Intermediate 80E. Preparation of 3-(2-methoxypyridin-4-yl)-N-((4-(5-methyl-1,3,4-thiadiazol-2-yl)bicyclo[2.2.2]octan-1-yl)methyl)aniline

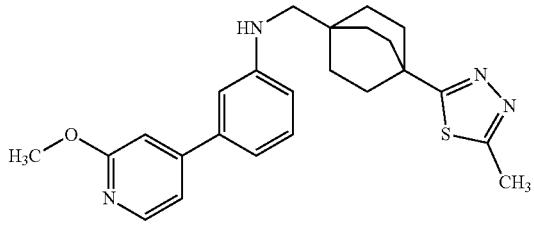 [SMILES: COc1cc(-c2cccc(NCC34CCC(c5nnc(C)s5)(CC3)CC4)c2)ccn1]

The title compound was prepared according to the method described for the synthesis of Intermediate 1F by substituting Intermediate 73A and Intermediate 80D where appropriate (240 mg, 0.571 mmol, 54% yield). $^1$H NMR (400 MHz, DMSO-d$_6$) δ 8.20 (d, J=5.5 Hz, 1H), 7.22 (d, J=5.0 Hz, 1H), 7.16 (t, J=8.0 Hz, 1H), 7.00 (s, 1H), 6.95 (s, 1H), 6.85 (d, J=8.0 Hz, 1H), 6.72 (d, J=8.5 Hz, 1H), 5.65 (s, 1H), 3.89 (s, 3H), 2.90 (d, J=5.5 Hz, 2H), 2.70 (s, 3H), 1.94-1.88 (m, 6H), 1.66-1.58 (m, 6H). MS (ESI) 421 (M+H).

Step F. Example 80. Preparation of N-(3-(2-methoxypyridin-4-yl)phenyl)-N-((4-(5-methyl-1,3,4-thiadiazol-2-yl)bicyclo[2.2.2]octan-1-yl)methyl)cyclohexanecarboxamide The title compound was prepared according to the method described for the synthesis of Example 1 by substituting Intermediate 80E and cyclohexanecarbonyl chloride where appropriate (1.1 mg, 2.073 μmol, 4% yield). $^1$H NMR (400 MHz, DMSO-d$_6$) δ 8.25 (d, J=5.6 Hz, 1H), 7.82 (br. s., 1H), 7.75 (d, J=7.1 Hz, 1H), 7.56 (t, J=7.8 Hz, 1H), 7.48 (d, J=6.6 Hz, 1H), 7.36 (d, J=5.4 Hz, 1H), 7.17 (s, 1H), 3.90 (s, 3H), 3.64 (br. s., 2H), 2.63 (s, 3H), 1.89-1.74 (m, 6H), 1.61 (br. s., 6H), 1.44 (br. s., 6H), 1.40-1.27 (m, 4H), 1.15-1.04 (m, 1H). FXR EC$_{50}$ (nM)=532; MS (ESI) 531 (M+H).

The following compounds were prepared according to the method described for the synthesis of Example 5 by substituting Intermediate 80E and corresponding acid (commercially available) where appropriate.

| Ex. No. | Structure | MS (ESI) (M + H) | FXR EC$_{50}$ (nM) |
|---|---|---|---|
| 81 | | 533 | 2498 |
| 82 | | 567 | 4757 |

| | |
|---|---|
| 81 | $^1$H NMR (400 MHz, DMSO-d$_6$) δ 8.26 (d, J = 5.4 Hz, 1H), 7.88 (s, 1H), 7.79 (d, J = 7.6 Hz, 1H), 7.62-7.49 (m, 2H), 7.40 (d, J = 6.6 Hz, 1H), 7.22 (s, 1H), 3.94-3.88 (m, 3H), 3.75 (d, J = 6.8 Hz, 2H), 3.62 (d, J = 11.0 Hz, 2H), 3.18 (d, J = 5.4 Hz, 2H), 3.00 (t, J = 11.1 Hz, 4H), 2.65 (s, 3H), 1.89-1.70 (m, 6H), 1.62 (d, J = 9.8 Hz, 1H), 1.55-1.35 (m, 6H) |
| 82 | $^1$H NMR (400 MHz, DMSO-d$_6$) δ 8.25 (d, J = 5.4 Hz, 1H), 7.85 (br. s., 1H), 7.77 (d, J = 7.8 Hz, 1H), 7.60-7.45 (m, 2H), 7.37 (d, J = 4.2 Hz, 1H), 7.19 (s, 1H), 3.90 (s, 3H), 3.64 (br. s., 2H), 2.73 (s, 1H), 2.63 (s, 3H), 1.94 (br. s., 2H), 1.84-1.69 (m, 7H), 1.68-1.55 (m, 3H), 1.45 (d, J = 7.3 Hz, 8H) |

Example 83

N-((4-(3-cyclopropyl-1,2,4-oxadiazol-5-yl)bicyclo[2.2.2]octan-1-yl)methyl)-N-(3-(2-methoxypyridin-4-yl)phenyl)tetrahydro-2H-pyran-4-carboxamide (83)

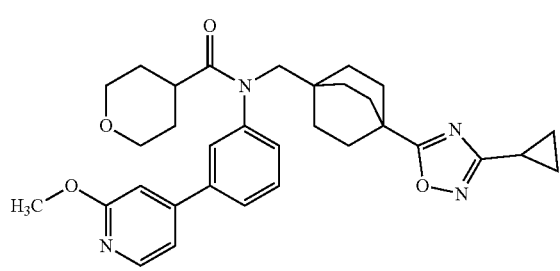

Step A. Intermediate 83A. Preparation of methyl 4-(hydroxymethyl)bicyclo[2.2.2]octane-1l-carboxylate

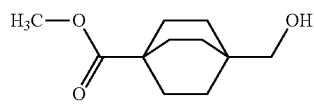

To a stirred solution of 4-(methoxycarbonyl)bicyclo[2.2.2]octane-1-carboxylic acid (10 g, 47.1 mmol) in THF (100 mL) was added slowly BH₃.DMS (14.3 mL, 141 mmol) at 0° C. The reaction mixture was warmed to room temperature and stirred for 2 h. The reaction mixture was cooled to 0° C. and carefully quenched with methanol. The reaction mixture was concentrated and the residue was diluted with water (50 mL). The aqueous solution was extracted with ethyl acetate (2×50 mL). The organic layers were combined, washed with brine (50 mL), dried over anhydrous sodium sulphate and concentrated under reduced pressure. The crude material was purified by flash chromatography (80 g silica gel cartridge; A=Hex, B=EtOAc; 30 min grad.; 0% B to 20% B; flow rate=40 mL/min). The pure fractions were combined, concentrated and dried in vacuo to afford the title compound (7 g, 35.3 mmol, 75% yield). ¹H NMR (400 MHz, DMSO-$d_6$) δ 4.12 (dd, J=28.40, Hz, 1H), 3.65 (s, 3H), 3.29 (s, 2H), 1.82-1.77 (m, 6H), 1.47-1.42 (m, 6H).

Step B. Intermediate 83B. Preparation of methyl 4-formylbicyclo[2.2.2]octane-1-carboxylate

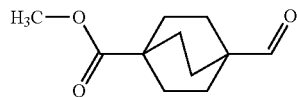

The title compound was prepared according to the method described for the synthesis of Intermediate 1B by substituting Intermediate 83A where appropriate (900 mg, 4.59 mmol, 91% yield) as gummy liquid. ¹H NMR (400 MHz, DMSO-$d_6$) δ 9.43 (s, 1H), 3.59 (s, 3H), 1.78-1.57 (m, 12H). MS (ESI) 197 (M+H).

Step C. Intermediate 83C. Preparation of methyl 4-(((3-(2-methoxypyridin-4-yl)phenyl)amino)methyl)bicyclo[2.2.2]octane-1-carboxylate

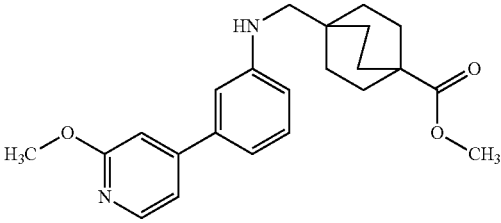

The title compound was prepared according to the method described for the synthesis of Intermediate 1F by substituting Intermediate 73A and Intermediate 83B where appropriate (1.4 g, 3.24 mmol, 71% yield) as brown solid. ¹H NMR (400 MHz, DMSO-$d_6$) δ 8.18 (d, J=5.0 Hz, 1H), 7.23-7.10 (m, 2H), 6.97 (d, J=1.0 Hz, 1H), 6.92 (t, J=2.0 Hz, 1H), 6.84 (d, J=7.5 Hz, 1H), 6.69 (dd, J=8.0, 1.5 Hz, 1H), 5.56 (t, J=5.8 Hz, 1H), 3.90 (s, 3H), 3.57 (s, 3H), 2.84 (d, J=6.0 Hz, 2H), 1.77-1.65 (m, 6H), 1.53-1.44 (m, 6H). MS (ESI) 381 (M+H).

Step D. Intermediate 83D. Preparation of get 4-(((3-(2-methoxypyridin-4-yl)phenyl) amino)methyl)bicyclo[2.2.2]octane-1-carboxylic acid

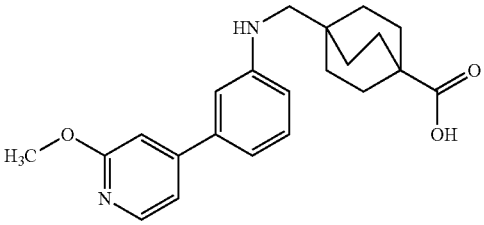 [SMILES: COc1cc(-c2cccc(NCC34CCC(C(=O)O)(CC3)CC4)c2)ccn1]

To a stirred solution of Intermediate 83C (250 mg, 0.657 mmol) in methanol (10 mL) was added a solution of NaOH (210 mg, 5.26 mmol) in water (5 mL). The reaction mixture was stirred at room temperature for 3 h. The reaction mixture was diluted with water (10 mL), acidified with aq. 1.5 N HCl and extracted with ethyl acetate (2×20 mL). The organic layers were combined, dried over anhydrous sodium sulphate, concentrated and dried in vacuo to afford the title compound (230 mg, 0.609 mmol, 93% yield). ¹H NMR (400 MHz, DMSO-$d_6$) δ 8.19 (d, J=5.5 Hz, 1H), 7.21 (dd, J=5.5, 1.5 Hz, 1H), 7.15 (t, J=7.8 Hz, 1H), 6.98 (s, 1H), 6.93 (t, J=2.0 Hz, 1H), 6.84 (d, J=7.5 Hz, 1H), 6.72-6.67 (m, 1H), 5.55 (t, J=5.5 Hz, 1H), 3.89 (s, 3H) 2.83 (d, J=6.0 Hz, 2H), 1.72-1.62 (m, 6H), 1.52-1.43 (m, 6H). MS (ESI) 367 (M+H).

Step E. Intermediate 83E. Preparation of N-((4-(3-cyclopropyl-1,2,4-oxadiazol-5-yl) bicyclo[2.2.2]octan-1-yl)methyl)-3-(2-methoxypyridin-4-yl)aniline

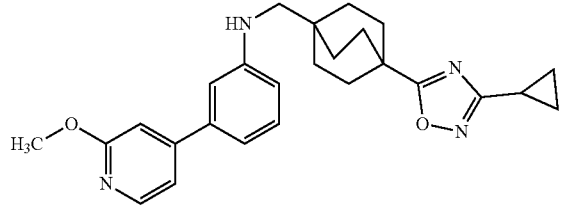 [SMILES: COc1cc(-c2cccc(NCC34CCC(c5nc(C6CC6)no5)(CC3)CC4)c2)ccn1]

The title compound was prepared according to the method described for the synthesis of Intermediate 1A by substituting Intermediate 83D and (Z)—N'-hydroxy cyclopropanecarboximidamide where appropriate (60 mg, 0.139 mmol, 64% yield). MS (ESI) 431 (M+H).

Step F. Example 83. Preparation of N-((4-(3-cyclopropyl-1,2,4-oxadiazol-5-yl) bicyclo[2.2.2]octan-1-yl)methyl)-N-(3-(2-methoxypyridin-4-yl)phenyl) tetrahydro-2H-pyran-4-carboxamide The title compound was prepared according to the method described for the synthesis of Example 5 by substituting Intermediate 83E and corresponding acid where appropriate (3.3 mg, 5.96 μmol, 9% yield). $^1$H NMR (400 MHz, DMSO-$d_6$) δ 8.25 (d, J=5.4 Hz, 1H), 7.85 (s, 1H), 7.77 (d, J=7.6 Hz, 1H), 7.58 (t, J=7.7 Hz, 1H), 7.51 (d, J=7.8 Hz, 1H), 7.38 (d, J=4.2 Hz, 1H), 7.19 (s, 1H), 3.90 (s, 3H), 3.74 (d, J=8.8 Hz, 2H), 3.17 (d, J=5.1 Hz, 1H), 2.98 (t, J=11.6 Hz, 2H), 2.08-1.96 (m, 2H), 1.84-1.67 (m, 6H), 1.66-1.53 (m, 2H), 1.52-1.32 (m, 8H), 1.23 (br. s., 1H), 1.07-0.94 (m, 2H), 0.87-0.74 (m, 2H). FXR $EC_{50}$ (nM)=303; MS (ESI) 543 (M+H).

Example 84

N-((4-(3-cyclopropyl-1,2,4-oxadiazol-5-yl)bicyclo[2.2.2]octan-1-yl)methyl)-N-(3-(2-methoxypyrimidin-4-yl)phenyl)tetrahydro-2H-pyran-4-carboxamide (84)

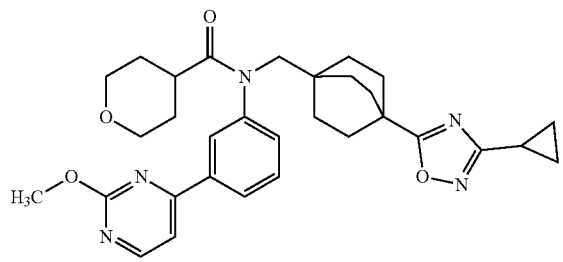

Step A. Intermediate 84A. Preparation of 2-chloro-4-(3-nitrophenyl)pyrimidine

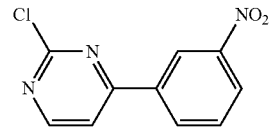 [SMILES: O=[N+]([O-])c1cccc(-c2ccnc(Cl)n2)c1]

To a stirred solution of 2,4-dichloropyrimidine (1 g, 6.71 mmol, commercially available) in 1,2-dimethoxyethane (15 mL) were added (3-nitrophenyl)boronic acid (1.12 g, 6.71 mmol) and a solution of sodium bicarbonate (1.13 g, 13.43 mmol) in water (1.5 mL). The reaction was degassed and back-filled with argon. Tetrakis(triphenylphosphine)palladium(0) (0.776 g, 0.67 mmol) was added and the reaction mixture was heated at 80° C. for 12 h. The reaction mixture was cooled to room temperature, diluted with water (15 mL) and extracted with EtOAc (2×15 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 40% B; flow rate=30 mL/min). The pure fractions were combined, concentrated and dried in vacuo to afford the title compound (1.1 g, 4.43 mmol, 66% yield) as a pale yellow solid. $^1$H NMR (400 MHz, DMSO-$d_6$) δ 8.94-8.95 (m, 2H), 8.64 (d, J=7.60 Hz, 1H), 8.44-8.47 (m, 1H), 8.36 (d, J=5.60 Hz, 1H), 7.89 (t, J=8.00 Hz, 1H). MS (ESI) 236 (M+H).

Step B. Intermediate 84B. Preparation of 2-methoxy-4-(3-nitrophenyl)pyrimidine

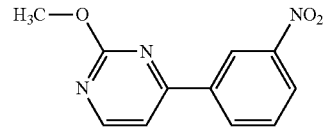

To a solution of Intermediate 84A (500 mg, 2.122 mmol) in methanol (5 mL) was added sodium methoxide in Methanol (1.38 g, 6.37 mmol). The reaction mixture was stirred at 80° C. overnight. The reaction mixture was concentrated under reduced pressure. The residue was dissolved in EtOAc (20 mL), washed with water (15 mL), brine solution (10 mL), dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated and dried in vacuo to afford the title compound (300 mg, 1.23 mmol, 58% yield) as solid. MS (ESI) 232 (M+H).

Step C. Intermediate 84C. Preparation of 3-(2-methoxypyrimidin-4-yl)aniline

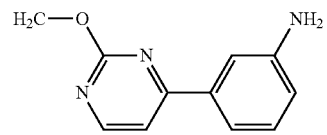

To a stirred solution of Intermediate 84B (0.3 g, 1.3 mmol) in tetrahydrofuran (2 mL) and ethanol (2 mL) were added zinc (1.27 g, 19.46 mmol) and an aqueous solution of ammonium chloride (1.0 g, 19.46 mmol) in water (2 mL). The reaction mixture was stirred at room temperature for 3 h. The reaction mixture was diluted with EtOAc (50 mL), filtered through Celite. The filtrate was washed with water (20 mL), brine solution (20 mL), dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated and dried in vacuo to afford the title compound (230 mg, 1.1 mmol, 84% yield) as solid. MS (ESI) 202 (M+H).

Step D. Intermediate 84D. Preparation of N-((4-(3-cyclopropyl-1,2,4-oxadiazol-5-yl) bicyclo[2.2.2]octan-1-yl)methyl)-3-(2-methoxypyrimidin-4-yl) aniline

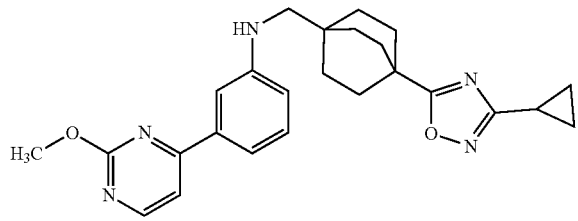 [SMILES: COc1nccc(-c2cccc(NCC34CCC(c5nc(C6CC6)no5)(CC3)CC4)c2)n1]

The title compound was prepared according to the method described for the synthesis of Intermediate 1F by substituting Intermediate 84C and Intermediate 2F where appropriate (160 mg, 0.352 mmol, 71% yield) as yellow solid. MS (ESI) 432 (M+H).

Step E. Example 84. Preparation of N-((4-(3-cyclopropyl-1,2,4-oxadiazol-5-yl) bicyclo[2.2.2]octan-1-yl)methyl)-N-(3-(2-methoxypyrimidin-4-yl)phenyl) tetrahydro-2H-pyran-4-carboxamide The title compound was prepared according to the method described for the synthesis of Example 5 by substituting Intermediate 84D and corresponding acid where appropriate (8 mg, 0.0142 mmol, 25% yield). $^1$H NMR (400 MHz, DMSO-$d_6$) δ 8.71 (d, J=5.1 Hz, 1H), 8.19 (s, 2H), 7.82 (d, J=5.1 Hz, 1H), 7.64 (br. s., 2H), 4.01 (s, 3H), 3.75 (d, J=9.8 Hz, 2H), 3.66 (br. s., 2H), 2.99 (t, J=11.1 Hz, 2H), 2.08-2.01 (m, 1H), 1.85-1.72 (m, 6H), 1.68-1.54 (m, 2H), 1.49 (br. s., 2H), 1.47-1.27 (m, 7H), 1.08-0.92 (m, 2H), 0.87-0.70 (m, 2H). FXR EC$_{50}$ (nM) 1767; MS (ESI) 544 (M+H).

The following compound was prepared according to the method described for the synthesis of Example 5 by substituting Intermediate 84D and corresponding acid where appropriate.

| Ex. No. | Structure | MS (ESI) (M + H) | FXR EC$_{50}$ (nM) |
|---|---|---|---|
| 85 | 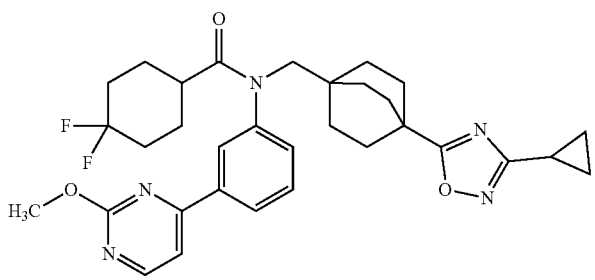 [SMILES: COc1nccc(-c2cccc(N(CC34CCC(c5nc(C6CC6)no5)(CC3)CC4)C(=O)C3CCC(F)(F)CC3)c2)n1] | 578 | 787 |

85    $^1$H NMR (400 MHz, DMSO-$d_6$) δ 8.71 (d, J = 5.4 Hz, 1H), 8 20 (br. s., 2H), 7.83 (d, J = 4.9 Hz, 1H), 7.65 (br. s., 2H), 4.08-3.98 (m, 3H), 3.66 (br. s., 2H), 2.42 (br. s., 1H), 2.10-2.01 (m, 1H), 1.94 (br. s., 2H), 1.87 (d, J = 7.8 Hz, 1H), 1.83-1.72 (m, 7H), 1.72-1.54 (m, 4H), 1.54-1.26 (m, 6H), 1.08-0.95 (m, 2H), 0.88-0.76 (m, 2H).

Example 86

N-(3-(2-cyclopropoxypyrimidin-4-yl)phenyl)-N-((4-(3-cyclopropyl-1,2,4-oxadiazol-5-yl)bicyclo[2.2.2]octan-1-yl)methyl)tetrahydro-2H-pyran-4-carboxamide (86)

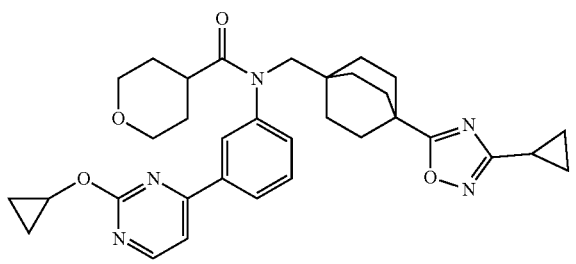

Step A. Intermediate 86A. Preparation of 2-cyclopropoxy-4-(3-nitrophenyl)pyrimidine

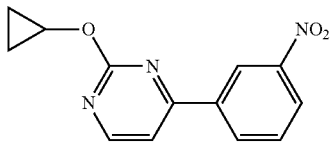 [SMILES: O=[N+]([O-])c1cccc(-c2ccnc(OC3CC3)n2)c1]

To a stirred solution of sodium hydride in mineral oil (138 mg, 3.44 mmol) in tetrahydrofuran (5 mL) was added cyclopropanol (100 mg, 1.722 mmol) at 0° C. The reaction mixture was stirred for 20 min and then Intermediate 40A (406 mg, 1.722 mmol) was added. The reaction mixture was warmed to room temperature and stirred for 1 h. The reaction was quenched with cold water (10 mL). The reaction mixture was extracted with EtOAc (2×10 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated and dried in vacuo to afford (0.3 g, 1.108 mmol, 64% yield) as a pale yellow solid. MS (ESI) 258 (M+H).

Step B. Intermediate 86B. Preparation of 3-(2-cyclopropoxypyrimidin-4-yl)aniline

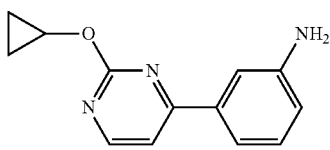

To a stirred solution of Intermediate 86A (300 mg, 1.166 mmol) in mixture of ethanol (2 mL) and tetrahydrofuran (2 mL) was added zinc (1.2 g, 18 mmol) at room temperature. A solution of ammonium chloride (936 mg, 18 mmol) in water (2 mL) was added to the reaction mixture and stirred at room temperature for 3 h. The reaction mixture was filtered through Celite. The crude material was purified by flash chromatography (12 g silica gel cartridge; A=Hex, B=EtOAc; 30 min grad.; 0% B to 50% B; flow rate=30 mL/min). The pure fractions were combined, concentrated and dried in vacuo to afford (200 mg, 0.836 mmol, 72% yield) as a pale yellow solid. MS (ESI) 228 (M+H).

Step C. Intermediate 86C. Preparation of 3-(2-cyclopropoxypyrimidin-4-yl)-N-((4-(3-cyclopropyl-1,2,4-oxadiazol-5-yl)bicyclo[2.2.2]octan-1-yl)methyl)aniline

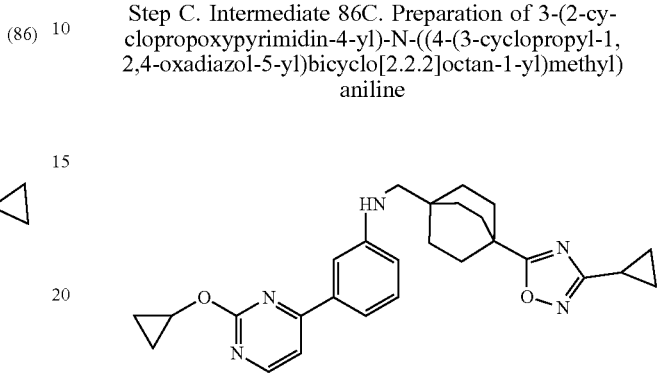

The title compound was prepared according to the method described for the synthesis of Intermediate 1F by substituting Intermediate 86B and Intermediate 2F where appropriate (130 mg, 0.270 mmol, 53% yield) as a pale yellow solid. MS (ESI) 458 (M+H).

Step D. Example 86. Preparation of N-(3-(2-cyclopropoxypyrimidin-4-yl)phenyl)-N-((4-(3-cyclopropyl-1,2,4-oxadiazol-5-yl)bicyclo[2.2.2]octan-1-yl)methyl)tetrahydro-2H-pyran-4-carboxamide The title compound was prepared according to the method described for the synthesis of Example 5 by substituting Intermediate 86C and corresponding acid where appropriate (10.8 mg, 0.018 mmol, 34% yield). $^1$H NMR (400 MHz, DMSO-$d_6$) δ 8.72 (d, J=5.1 Hz, 1H), 8.20 (s, 2H), 7.86 (d, J=5.1 Hz, 1H), 7.64 (br. s., 2H), 4.41-4.40 (m, 1H), 3.74 (d, J=10.0 Hz, 2H), 3.66 (br. s., 2H), 2.99 (t, J=11.7 Hz, 2H), 2.09-1.98 (m, 1H), 1.88-1.70 (m, 6H), 1.70-1.55 (m, 2H), 1.55-1.32 (m, 8H), 1.07-0.96 (m, 2H), 0.91-0.69 (m, 6H). One proton was buried under the solvent peak. FXR EC$_{50}$ (nM) 2469; MS (ESI) 570 (M+H).

Example 87

N-((4-(3-(tert-butyl)-1,2,4-oxadiazol-5-yl)bicyclo[2.2.2]octan-1-yl)methyl)-N-(3-(2-ethoxypyrimidin-5-yl)phenyl)tetrahydro-2H-pyran-4-carboxamide (87)

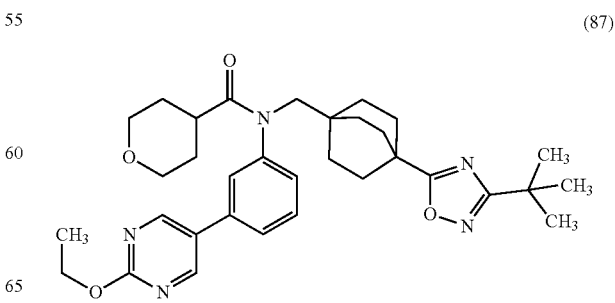

Step A. Intermediate 87A. Preparation of 3-bromo-N-((4-(3-(tert-butyl)-1,2,4-oxadiazol-5-yl)bicyclo[2.2.2]octan-1-yl)methyl)aniline

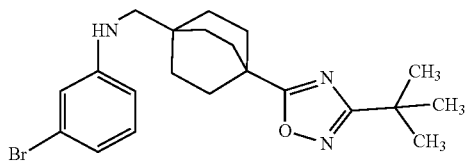 [SMILES: CC(C)(C)c1noc(C23CCC(CNc4cccc(Br)c4)(CC2)CC3)n1]

The title compound was prepared according to the method described for the synthesis of Intermediate 1F by substituting 3-bromoaniline and Intermediate 69C where appropriate (1.1 g, 2.445 mmol, 64% yield) as brown solid. MS (ESI) 418 (M+H).

Step B. Intermediate 87B. Preparation of N-((4-(3-(tert-butyl)-1,2,4-oxadiazol-5-yl) bicyclo[2.2.2]octan-1-yl)methyl)-3-(2-ethoxypyrimidin-5-yl)aniline

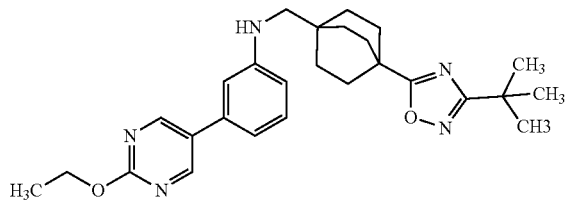 [SMILES: CCOc1ncc(-c2cccc(NCC34CCC(c5nc(C(C)(C)C)no5)(CC3)CC4)c2)cn1]

To a stirred solution of Intermediate 87A (100 mg, 0.239 mmol) and (2-ethoxypyrimidin-5-yl)boronic acid (60.2 mg, 0.36 mmol) in dioxane (3 mL) was added a solution of K$_2$CO$_3$ (66 mg, 0.48 mmol) in water (0.75 mL) at room temperature. The reaction mass was degassed and backfilled with argon. PdCl$_2$(dppf) (8.74 mg, 0.012 mmol) was added to the reaction mass and the vial was sealed. The reaction mixture was heated at 110° C. for 1 h. The reaction mixture was diluted with ethyl acetate (25 mL) and washed with brine solution (10 mL). The organic layer was dried over anhydrous sodium sulfate and concentrated under reduced pressure. The crude compound was purified by flash chromatography (12 g silica gel cartridge; A=Hex, B=EtOAc; 30 min grad.; 0% B to 50% B; flow rate=30 mL/min) to afford the title compound (70 mg, 0.144 mmol, 60% yield) as a brown solid. MS (ESI) 462 (M+H).

Step C. Example 87. Preparation of N-((4-(3-(tert-butyl)-1,2,4-oxadiazol-5-yl) bicyclo[2.2.2]octan-1-yl)methyl)-N-(3-(2-ethoxypyrimidin-5-yl)phenyl)tetrahydro-2H-pyran-4-carboxamide The title compound was prepared according to the method described for the synthesis of Example 5 by substituting Intermediate 87B and corresponding acid where appropriate (9.8 mg, 0.017 mmol, 31% yield). $^1$H NMR (400 MHz, DMSO-d$_6$) δ 9.00 (s, 2H), 7.83 (s, 1H), 7.73 (d, J=7.8 Hz, 1H), 7.57 (t, J=7.8 Hz, 1H), 7.45 (d, J=7.3 Hz, 1H), 4.42 (q, J=7.1 Hz, 2H), 3.75 (d, J=9.8 Hz, 2H), 3.66 (br. s., 2H), 3.01 (t, J=11.0 Hz, 2H), 1.94-1.71 (m, 6H), 1.69-1.54 (m, 2H), 1.54-1.31 (m, 11H), 1.31-1.15 (m, 9H). One proton buried under solvent peak. FXR EC$_{50}$ (nM)=274. MS (ESI) 574 (M+H).

Example 88

N-((4-(5-(tert-butyl)-1,2,4-oxadiazol-3-yl)bicyclo[2.2.2]octan-1-yl)methyl)-N-(3-(2-ethoxypyrimidin-5-yl)phenyl)tetrahydro-2H-pyran-4-carboxamide (88)

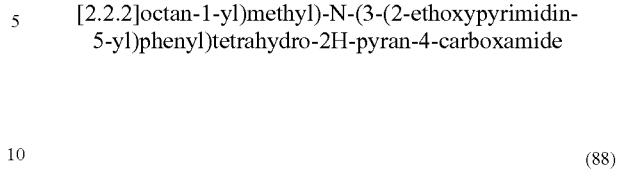

Step A. Intermediate 88A. Preparation of methyl 4-carbamoylbicyclo[2.2.2]octane-1-carboxylate

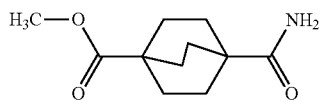

The title compound was prepared according to the method described for the synthesis of Intermediate 99C by substituting 4-(methoxycarbonyl)bicyclo[2.2.2]octane-1-carboxylic acid where appropriate (9.0 g, 42.6 mmol, 90% yield). MS (ESI) 212 (M+1).

Step B. Intermediate 88B. Preparation of methyl 4-cyanobicyclo[2.2.2]octane-1-carboxylate

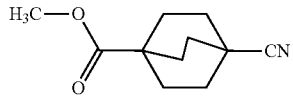

To a stirred solution of Intermediate 88A (2.5 g, 11.8 mmol) in pyridine (50 mL) was added TFAA (8.3 mL, 58.9 mmol) dropwise at 0° C. The reaction mixture was stirred at 0° C. for 1 h. The reaction mixture was diluted with ethyl acetate (100 mL), washed with aqueous 1.5 N HCl solution (2×20 mL), water (2×20 mL), brine solution (20 mL), dried over anhydrous sodium sulfate and concentrated under reduced pressure. The crude material was purified by flash chromatography (40 g silica gel cartridge; A=Hex, B=EtOAc; 30 min grad.; 0% B to 40% B; flow rate=40 mL/min). The pure fractions were combined, concentrated under reduced pressure and dried in vacuo to afford the title compound (1.5 g, 7.76 mmol, 66% yield) as white solid. MS (ESI) 211 (M+18) NH$_3$ adduct.

Step C. Intermediate 88C. Preparation of methyl 4-(N'-hydroxycarbamimidoyl)bicyclo[2.2.2]octane-1-carboxylate

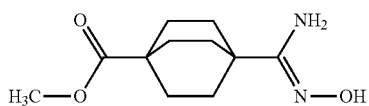

The title compound was prepared according to the method described for the synthesis of Intermediate 41A by substituting Intermediate 88B where appropriate (530 mg, 2.342 mmol, 91% yield) as white solid. MS (ESI) 227 (M+H).

Step D. Intermediate 88D. Preparation of methyl 4-(5-(tert-butyl)-1,2,4-oxadiazol-3-yl) bicyclo[2.2.2]octane-1-carboxylate

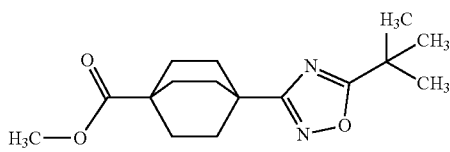 [SMILES: COC(=O)C12CCC(c3noc(C(C)(C)C)n3)(CC1)CC2]

The title compound was prepared according to the method described for the synthesis of Intermediate 1A by substituting Intermediate 88C and corresponding acid where appropriate (650 mg, 2.22 mmol, 95% yield) as gummy mass. MS (ESI) 293 (M+H).

Step E. Intermediate 88E. Preparation of (4-(5-(tert-butyl)-1,2,4-oxadiazol-3-yl) bicyclo[2.2.2]octan-1-yl)methanol

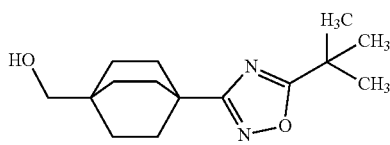 [SMILES: CC(C)(C)c1nc(C23CCC(CO)(CC2)CC3)no1]

The title compound was prepared according to the method described for the synthesis of Intermediate 1B by substituting Intermediate 88D where appropriate (500 mg, 1.89 mmol, 89% yield) as white solid. MS (ESI) 265 (M+H).

Step F. Intermediate 88F. Preparation of 4-(5-(tert-butyl)-1,2,4-oxadiazol-3-yl) bicyclo[2.2.2]octane-1-carbaldehyde

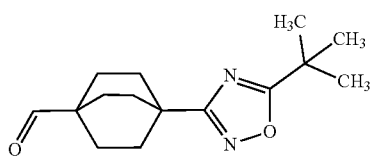 [SMILES: CC(C)(C)c1nc(C23CCC(C=O)(CC2)CC3)no1]

The title compound was prepared according to the method described for the synthesis of Intermediate 1C by substituting Intermediate 88E where appropriate (390 mg, 1.487 mmol, 82% yield) as a pale yellow solid. $^1$HNMR (400 MHz, DMSO-d6) δ 9.45 (s, 1H), 1.88-1.84 (m, 6H), 1.70-1.66 (m, 6H), 1.35 (s, 9H).

Step G. Intermediate 88G. Preparation of 3-bromo-N-((4-(5-(tert-butyl)-1,2,4-oxadiazol-3-yl)bicyclo[2.2.2]octan-1-yl)methyl)aniline

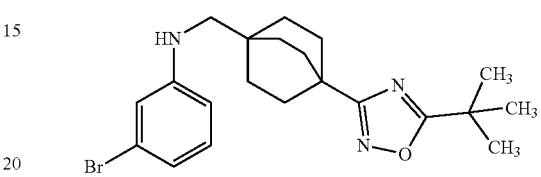

The title compound was prepared according to the method described for the synthesis of Intermediate 1F by substituting 3-bromoaniline and Intermediate 88F where appropriate (650 mg, 1.55 mmol, 84% yield) as white solid. MS (ESI) 418 (M+H).

Step H. Intermediate 88H. Preparation of N-((4-(5-(tert-butyl)-1,2,4-oxadiazol-3-yl) bicyclo[2.2.2]octan-1-yl)methyl)-3-(2-ethoxypyrimidin-5-yl)aniline

The title compound was prepared according to the method described for the synthesis of Intermediate 87B by substituting Intermediate 88G and (2-ethoxypyrimidin-5-yl)boronic acid where appropriate (110 mg, 0.236 mmol, 66% yield) as brown solid. MS (ESI) 462 (M+H).

Step I. Example 88. Preparation of N-((4-(5-(tert-butyl)-1,2,4-oxadiazol-3-yl) bicyclo[2.2.2]octan-1-yl)methyl)-N-(3-(2-ethoxypyrimidin-5-yl)phenyl)tetrahydro-2H-pyran-4-carboxamide The title compound was prepared according to the method described for the synthesis of Example 5 by substituting Intermediate 88H and corresponding acid where appropriate (4.5 mg, 7.51 µmol, 17% yield). $^1$H NMR (400 MHz, DMSO-d$_6$) δ 9.00 (s, 2H), 7.85 (s, 1H), 7.73 (d, J=7.3 Hz, 1H), 7.56 (t, J=7.6 Hz, 1H), 7.46 (d, J=7.3 Hz, 1H), 4.42 (q, J=7.0 Hz, 2H), 3.75 (d, J=10.3 Hz, 2H), 3.65 (br. s., 2H), 3.01 (t, J=11.5 Hz, 3H), 1.80-1.68 (m, 6H), 1.66-1.55 (m, 2H), 1.48 (d, J=13.0 Hz, 2H), 1.45-1.25 (m, 18H). 1H buried under solvent peak. FXR EC$_{50}$ (nM)=227. MS (ESI) 574 (M+H).

Example 89

N-((4-(5-(tert-butyl)-1,2,4-oxadiazol-3-yl)bicyclo[2.2.2]octan-1-yl)methyl)-N-(4'-(difluoromethoxy)-[1,1'-biphenyl]-3-yl)tetrahydro-2H-pyran-4-carboxamide (89)

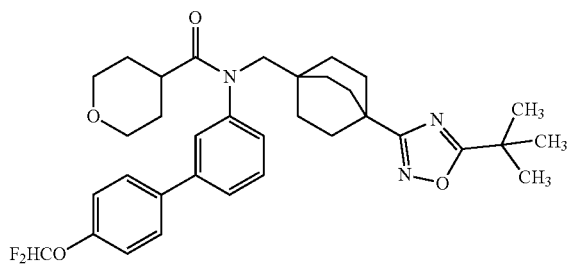

Step A. Intermediate 89A. Preparation of N-((4-(5-(tert-butyl)-1,2,4-oxadiazol-3-yl) bicyclo[2.2.2]octan-1-yl)methyl)-4'-(difluoromethoxy)-[1,1'-biphenyl]-3-amine

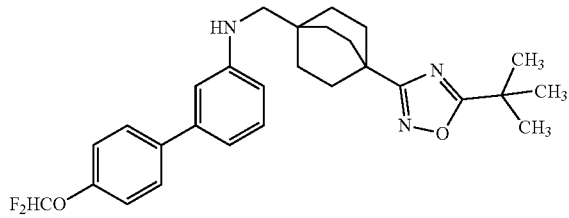 [SMILES: CC(C)(C)c1nc(C23CCC(CNc4cccc(-c5ccc(OC(F)F)cc5)c4)(CC2)CC3)no1]

The title compound was prepared according to the method described for the synthesis of Intermediate 87B by substituting Intermediate 88G and (4-(difluoromethoxy)phenyl) boronic acid where appropriate (130 mg, 0.267 mmol, 74% yield) as brown solid. $^1$H NMR (400 MHz, DMSO-$d_6$) δ 7.66-7.60 (m, 2H), 7.28-7.20 (m, 3H), 7.16-7.07 (m, 1H), 6.87-6.83 (m, 1H), 6.74 (d, J=8.5 Hz, 1H), 6.63 (dd, J=7.8, 1.8 Hz, 1H), 5.53 (t, J=6.3 Hz, 1H), 2.88 (d, J=6.0 Hz, 2H), 1.89-1.80 (m, 6H), 1.63-1.54 (m, 6H), 1.36 (s, 9H). MS (ESI) 482 (M+H).

Step B. Example 89. Preparation of N-((4-(5-(tert-butyl)-1,2,4-oxadiazol-3-yl) bicyclo[2.2.2]octan-1-yl)methyl)-N-(4'-(difluoromethoxy)-[1,1'-biphenyl]-3-yl)tetrahydro-2H-pyran-4-carboxamide The title compound was prepared according to the method described for the synthesis of Example 5 by substituting Intermediate 89A and corresponding acid where appropriate (7.3 mg, 0.012 mmol, 29% yield). $^1$H NMR (400 MHz, DMSO-$d_6$) δ 7.80 (d, J=8.8 Hz, 2H), 7.72 (s, 1H), 7.66 (d, J=7.8 Hz, 1H), 7.59-7.46 (m, 1H), 7.42 (d, J=7.6 Hz, 1H), 7.36-7.20 (m, 3H), 3.75 (d, J=9.5 Hz, 2H), 3.65 (br. s., 2H), 3.00 (t, J=11.7 Hz, 2H), 2.60-2.53 (m, 1H), 1.84-1.68 (m, 6H), 1.68-1.56 (m, 2H), 1.53-1.37 (m, 8H), 1.33 (s, 9H). FXR EC$_{50}$ (nM)=96. MS (ESI) 594 (M+H).

Example 90

N-((4-(3-cyclopropyl-1,2,4-oxadiazol-5-yl)bicyclo[2.2.2]octan-1-yl)methyl)-N-(3-(2-methylbenzo[d]thiazol-6-yl)phenyl)cyclohexanecarboxamide (90)

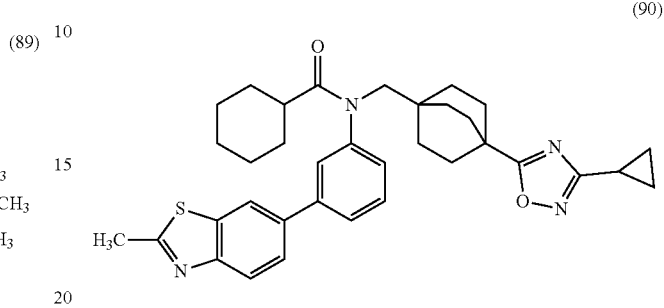

Step A. Intermediate 90A. Preparation of 3-(2-methylbenzo[d]thiazol-6-yl)aniline

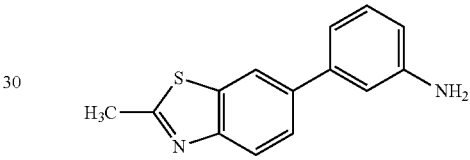

The title compound was prepared according to the method described for the synthesis of Intermediate 87B by substituting 6-bromo-2-methylbenzo[d]thiazole and (3-aminophenyl)boronic acid where appropriate (60 mg, 0.250 mmol, 57% yield) as white solid. $^1$H NMR (400 MHz, DMSO-$d_6$) δ 8.21 (d, J=1.5 Hz, 1H), 7.94 (d, J=8.5 Hz, 1H), 7.68-7.63 (m, 1H), 7.15-7.09 (m, 1H), 6.90 (t, J=2.0 Hz, 1H), 6.87-6.83 (m, 1H), 6.59 (ddd, J=8.0, 2.0, 1.0 Hz, 1H), 5.19 (s, 2H), 2.82 (s, 3H). MS (ESI) 241 (M+H).

Step B. Intermediate 90B. Preparation of N-((4-(3-cyclopropyl-1,2,4-oxadiazol-5-yl) bicyclo[2.2.2]octan-1-yl)methyl)-3-(2-methylbenzo[d]thiazol-6-yl)aniline

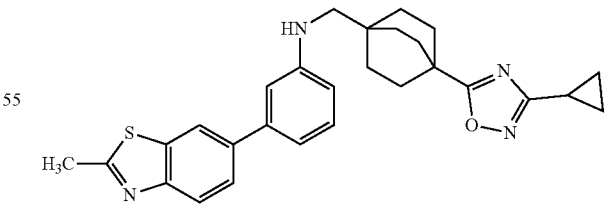

The title compound was prepared according to the method described for the synthesis of Intermediate 1F by substituting Intermediate 90A and Intermediate 2F where appropriate (90 mg, 0.182 mmol, 87% yield) as an off-white solid. $^1$H NMR (400 MHz, DMSO-$d_6$) δ 8.25 (d, J=1.5 Hz, 1H), 7.94 (d, J=8.5 Hz, 1H), 7.69 (dd, J=8.5, 2.0 Hz, 1H), 7.15 (t, J=7.8 Hz, 1H), 6.94 (s, 1H), 6.84 (d, J=7.5 Hz, 1H), 6.65 (d, J=8.5

Hz, 1H), 5.57 (t, J=6.0 Hz, 1H), 2.90 (d, J=6.0 Hz, 2H), 2.82 (s, 3H), 2.11-2.03 (m, 1H), 1.91-1.83 (m, 6H), 1.64-1.56 (m, 6H), 1.07-1.00 (m, 2H), 0.88-0.83 (m, 2H). MS (ESI) 471 (M+H).

Step C. Example 90. Preparation of N-((4-(3-cyclopropyl-1,2,4-oxadiazol-5-yl) bicyclo[2.2.2]octan-1-yl)methyl)-N-(3-(2-methylbenzo[d]thiazol-6-yl)phenyl)cyclohexane carboxamide The title compound was prepared according to the method described for the synthesis of Example 1 by substituting Intermediate 90B and cyclohexanecarbonyl chloride where appropriate (2.3 mg, 3.96 μmol, 9% yield). $^1$H NMR (400 MHz, DMSO-$d_6$) δ 8.45 (d, J=1.5 Hz, 1H), 8.00 (d, J=8.6 Hz, 1H), 7.84 (dd, J=8.4, 1.8 Hz, 1H), 7.78 (s, 1H), 7.74 (d, J=7.3 Hz, 1H), 7.56 (t, J=7.6 Hz, 1H), 7.40 (d, J=7.8 Hz, 1H), 3.63 (br. s., 2H), 2.84 (s, 3H), 2.29 (br. s., 1H), 2.10-1.98 (m, 1H), 1.84-1.70 (m, 6H), 1.63 (t, J=15.2 Hz, 4H), 1.54-1.28 (m, 8H), 1.24 (s, 1H), 1.10 (d, J=13.7 Hz, 1H), 1.04-0.96 (m, 2H), 0.95-0.75 (m, 4H). FXR EC$_{50}$ (nM) 36. MS (ESI) 581 (M+H).

The following compound was prepared according to the method described for the synthesis of Example 5 by substituting Intermediate 90B and corresponding acid.

| Ex. No. | Structure | MS (ESI) (M + H) | FXR EC$_{50}$ (nM) |
|---|---|---|---|
| 91 | | 583 | 97 |
| 91 | $^1$H NMR (400 MHz, DMSO-$d_6$) δ 8.46 (d, J = 1.7 Hz, 1H), 8.00 (d, J = 8.6 Hz, 1H), 7.89-7.78 (m, 2H), 7.75 (d, J = 8.3 Hz, 1H), 7.56 (t, J = 7.9 Hz, 1H), 7.44 (d, J = 8.3 Hz, 1H), 3.76 (d, J = 9.3 Hz, 2H), 3.62 (s, 1H), 3.08-2.94 (m, 2H), 2.84 (s, 3H), 2.58 (br. s., 2H), 2.07-1.99 (m, 1H), 1.84-1.71 (m, 6H), 1.69-1.56 (m, 2H), 1.51 (br. s., 2H), 1.44 (d, J = 7.3 Hz, 6H), 1.07-0.98 (m, 2H), 0.87-0.78 (m, 2H). | | |

Example 92

N-((4-(3-cyclopropyl-1,2,4-oxadiazol-5-yl)bicyclo[2.2.2]octan-1-yl)methyl)-N-(3-(5-fluorobenzo[d]oxazol-2-yl)phenyl)tetrahydro-2H-pyran-3-carboxamide (racemate)

(92)

Step A. Intermediate 92A. Preparation of N-(5-fluoro-2-hydroxyphenyl)-3-nitrobenzamide

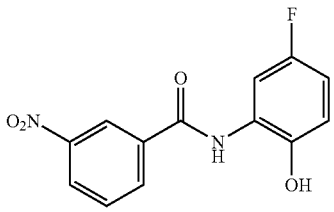 [SMILES: O=C(Nc1cc(F)ccc1O)c1cccc([N+](=O)[O-])c1]

To a stirred solution of 3-nitrobenzoyl chloride (2 g, 10.78 mmol, commercially available) in THF (40 mL) was added TEA (4.51 mL, 32.3 mmol) followed by 2-amino-4-fluorophenol (1.37 g, 10.78 mmol, commercially available) at room temperature. The reaction mixture was stirred at room temperature overnight. The reaction mixture was diluted with ethyl acetate (50 mL), washed with aq. 10% sodium bicarbonate (2×25 mL). The organic layers were combined, dried over anhydrous sodium sulphate, concentrated and dried in vacuo to afford the title compound (1.7 g, 5.48 mmol, 51% yield) as brown solid. MS (ESI) 277 (M+H).

Step B. Intermediate 92B. Preparation of 5-fluoro-2-(3-nitrophenyl)benzo[d]oxazole

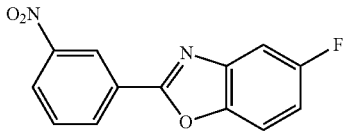 [SMILES: O=[N+]([O-])c1cccc(-c2nc3cc(F)ccc3o2)c1]

To a stirred solution of Intermediate 92A (1.6 g, 5.79 mmol) in xylene (35 mL) was added p-toluenesulfonic acid monohydrate (0.220 g, 1.158 mmol). The reaction mixture was heated at reflux with Dean-Stark condenser overnight. The reaction mixture was cooled to room temperature, concentrated, diluted with water (25 mL) and extracted with ethyl acetate (2×30 mL). The organic layers were combined, dried over anhydrous sodium sulphate and concentrated under reduced pressure. The crude material was purified by flash chromatography (40 g silica gel cartridge; A=Hex, B=EtOAc; 30 min grad.; 0% B to 40% B; flow rate=30 mL/min). The pure fractions were combined, concentrated and dried in vacuo to afford the title compound (1.25 g, 4.70 mmol, 81% yield) as brown solid. MS (ESI) 259 (M+H).

Step C. Intermediate 92C. Preparation of 3-(5-fluorobenzo[d]oxazol-2-yl)aniline

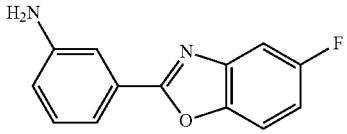

To a stirred solution of Intermediate 92B (1.2 g, 4.65 mmol) in ethanol (30 mL) and tetrahydrofuran (30 mL) was added zinc (4.56 g, 69.7 mmol) followed by a solution of ammonium chloride (3.73 g, 69.7 mmol) in water (10 mL). The reaction mixture was stirred at room temperature overnight. The reaction mixture was diluted with DCM (50 mL) and filtered through Celite. The filtrate was concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated and dried in vacuo to afford the title compound (0.5 g, 2.059 mmol, 44% yield) as brown solid. MS (ESI) 229 (M+H).

Step D. Intermediate 92D. Preparation of N-((4-(3-cyclopropyl-1,2,4-oxadiazol-5-yl)bicyclo[2.2.2]octan-1-yl)methyl)-3-(5-fluorobenzo[d]oxazol-2-yl)aniline

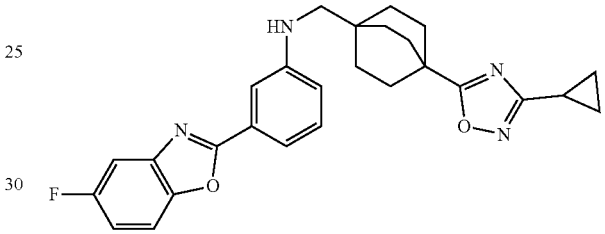

The title compound was prepared according to the method described for the synthesis of Intermediate 1F by substituting Intermediate 92C and Intermediate 2F where appropriate (180 mg, 0.377 mmol, 77% yield) as brown solid. $^1$H NMR (400 MHz, DMSO-$d_6$) δ 7.82 (dd, J=9.0, 4.5 Hz, 1H), 7.68 (dd, J=9.0, 2.5 Hz, 1H), 7.46-7.43 (m, 1H), 7.35-7.25 (m, 3H), 6.90 (dd, J=8.0, 1.0 Hz, 1H), 5.94 (t, J=6.0 Hz, 1H), 2.91 (d, J=6.0 Hz, 2H), 2.12-2.03 (m, 1H), 1.93-1.84 (m, 6H), 1.65-1.55 (m, 6H), 1.08-1.00 (m, 2H), 0.89-0.84 (m, 2H).

Step E. Example 92. Preparation of N-((4-(3-cyclopropyl-1,2,4-oxadiazol-5-yl) bicyclo[2.2.2]octan-1-yl)methyl)-N-(3-(5-fluorobenzo[d]oxazol-2-yl)phenyl)tetrahydro-2H-pyran-3-carboxamide (racemate)

The title compound was prepared according to the method described for the synthesis of Example 5 by substituting Intermediate 92D and corresponding acid where appropriate (10.5 mg, 0.018 mmol, 28% yield). $^1$H NMR (400 MHz, DMSO-$d_6$) δ 8.18 (br. s., 2H), 7.88 (dd, J=8.8, 4.4 Hz, 1H), 7.83-7.66 (m, 3H), 7.34 (td, J=9.4, 2.6 Hz, 1H), 3.80-3.67 (m, 4H), 3.31-3.17 (m, 2H), 2.10-1.99 (m, 1H), 1.85-1.71 (m, 6H), 1.71-1.54 (m, 2H), 1.51-1.32 (m, 7H), 1.29-1.11 (m, 1H), 1.08-0.95 (m, 2H), 0.88-0.74 (m, 2H). 1H buried under solvent peak. FXR EC$_{50}$ (nM)=589. MS (ESI) 571 (M+H).

The following compound was prepared according to the method described for the synthesis of Example 5 by substituting Intermediate 92D and corresponding acid where appropriate.

| Ex. No. | Structure | MS (ESI) (M + H) | FXR EC$_{50}$ (nM) |
|---|---|---|---|
| 93 | | 605 | 799 |

93  $^1$H NMR (400 MHz, DMSO-d$_6$) δ 8.26-8.10 (m, 2H), 7.88 (dd, J = 8.9, 4.3 Hz, 1H), 7.83-7.63 (m, 3H), 7.34 (td, J = 9.4, 2.6 Hz, 1H), 3.67 (br. s., 2H), 2.44 (br. s., 1H), 2.11-2.01 (m, 1H), 1.96 (br. s., 2H), 1.83-1.72 (m, 6H), 1.72-1.57 (m, 5H), 1.52 (d, J = 13.9 Hz, 1H), 1.47-1.32(m, 6H), 1.08-0.96 (m, 2H), 0.91-0.70 (m, 2H)

Examples 94 and 95

N-(3'-methoxy-[1,1'-biphenyl]-3-yl)-N-(1-(4-(3-methyl-1,2,4-oxadiazol-5-yl) bicyclo[2.2.2]octan-1-yl)ethyl)cyclohexanecarboxamide (94-95)

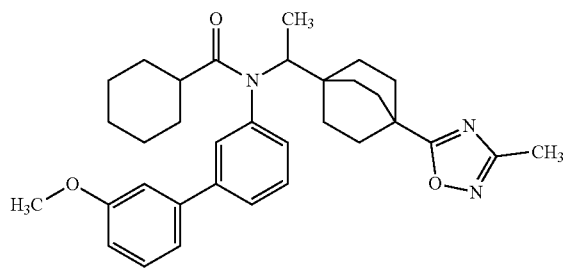

Step A. Intermediate 94A. Preparation of 3'-methoxy-N-(1-(4-(3-methyl-1,2,4-oxadiazol-5-yl) bicyclo[2.2.2]octan-1-yl)ethyl)-[1,1'-biphenyl]-3-amine

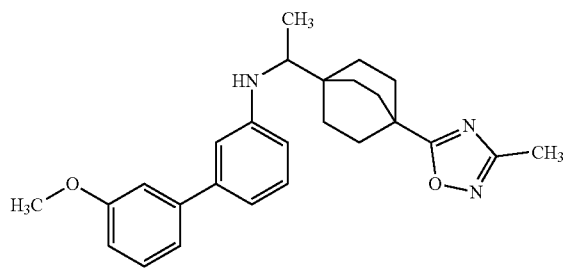

To a stirred solution of Intermediate 72B (0.25 g, 1.067 mmol) in methanol (3 mL) was added Intermediate 70B (0.213 g, 1.067 mmol) at room temperature and stirred for 1 h. To this reaction mass was added triethylsilane (0.341 mL, 2.134 mmol) followed by indium(III) chloride (0.024 g, 0.107 mmol) at room temperature and stirred overnight. The reaction mixture was concentrated under reduced pressure. The residue was diluted with EtOAc, washed with water, brine solution, dried over anhydrous sodium sulphate and concentrated under reduced pressure. The crude compound was purified by prep-HPLC and the fractions containing compound were concentrated under reduced pressure to afford the title compound (0.15 g, 0.359 mmol, 34% yield) as a pale yellow oil. MS (ESI) 418 (M+H).

Step B. Example 94 & 95. Preparation of N-(3'-methoxy-[1,1'-biphenyl]-3-yl)-N-(1-(4-(3-methyl-1, 2,4-oxadiazol-5-yl)bicyclo[2.2.2]octan-1-yl)ethyl) cyclohexanecarboxamide To a solution of Intermediate 94A (10 mg, 0.024 mmol) in pyridine (1 mL) was added DMAP (2.93 mg, 0.024 mmol) and the reaction mass was cooled to 0° C. Cyclohexanecarbonyl chloride (17.56 mg, 0.120 mmol) was added to the reaction mass at 0° C. The reaction mixture was warmed to room temperature and heated at 90° C. overnight. The reaction mixture was cooled to room temperature and diluted with ethyl acetate, washed with water, brine solution, dried over anhydrous sodium sulphate and concentrated under reduced pressure. The crude material was purified via preparative SFC with the following conditions Column: Lux Cellulose-4 (250×4.6) 5.0 μm; Isocratic Mode, Co-Solvent: 0.2% NH$_4$OH in MeOH+ACN (1:1); Co-Solvent percentage: 30%, Column Temperature: 30° C.; Back Pressure: 100 bars; Total Flow: 3 g/min. Example 94:

Example 94: Enantiomer 1 (3 mg, 5.46 μmol, 23% yield). $^1$H NMR (400 MHz, DMSO-d$_6$) δ 400 MHz, DMSO-d6: δ 7.71-7.72 (m, 1H), 7.50-7.55 (m, 2H), 7.38-7.43 (m, 1H), 7.15-7.25 (m, 3H), 6.96-6.99 (m, 1H), 4.84 (br. s., 1H), 3.83 (s, 3H), 2.28 (s, 3H), 1.83-1.86 (m, 7H), 1.46-1.57 (m, 12H), 1.34-1.38 (m, 2H), 1.02-1.07 (m, 3H), 0.83-0.85 (m, 2H). FXR EC$_{50}$ (nM) 3935; MS (ESI) 528 (M+H).

Example 95: Enantiomer 2 (3 mg, 5.46 μmol, 23% yield). $^1$H NMR (400 MHz, DMSO-d$_6$) δ 400 MHz, DMSO-d6: δ 7.71-7.72 (m, 1H), 7.50-7.55 (m, 2H), 7.38-7.43 (m, 1H), 7.15-7.25 (m, 3H), 6.96-6.99 (m, 1H), 4.84 (br. s., 1H), 3.83 (s, 3H), 2.28 (s, 3H), 1.83-1.86 (m, 7H), 1.46-1.57 (m, 12H), 1.34-1.38 (m, 2H), 1.02-1.07 (m, 3H), 0.83-0.85 (m, 2H). FXR EC$_{50}$ (nM) (6666); MS (ESI) 528 (M+H).

Example 96

N-((3-(3-cyclopropyl-1,2,4-oxadiazol-5-yl)bicyclo[1.1.1]pentan-1-yl)methyl)-N-(3-(2-methoxypyridin-4-yl)phenyl)cyclohexanecarboxamide (96)

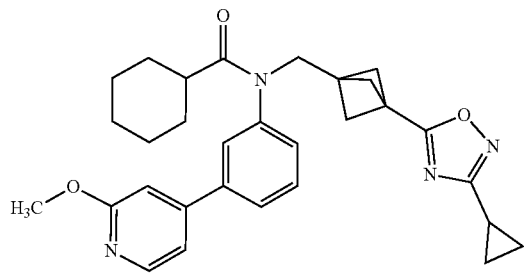

Step A. Intermediate 96A. Preparation of dimethyl bicyclo[1.1.1]pentane-1,3-dicarboxylate

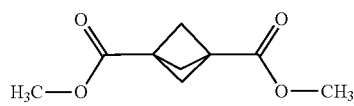

To a stirred solution of bicyclo[1.1.1]pentane-1,3-dicarboxylic acid (1.5 g, 9.61 mmol, commercially available) in DMF (30 mL) was added K$_2$CO$_3$ (3.98 g, 28.8 mmol) and stirred for 15 min. MeI (2.403 mL, 38.4 mmol) was added to the reaction mixture and stirred at room temperature overnight. The reaction mixture was concentrated under reduced pressure. The residue was diluted with water (30 mL) and extracted with ethyl acetate (2×40 mL). The combined organic layers were dried over sodium sulphate and concentrated under reduced pressure to afford the title compound (1.1 g, 5.97 mmol, 62% yield) as brown solid. $^1$H NMR (400 MHz, DMSO-d$_6$) δ 3.31 (s, 6H), 2.25 (s, 6H). MS (ESI) 185 (M+H).

Step B. Intermediate 96B. Preparation of 3-(methoxycarbonyl)bicyclo[1.1.1]pentane-1-carboxylic acid

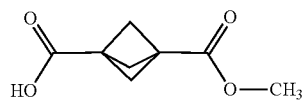

To a stirred solution of Intermediate 96A (1.1 g, 5.97 mmol) in MeOH (10 mL) was added a solution of NaOH (0.24 g, 5.97 mmol) in MeOH (2.5 mL) at room temperature. The reaction mixture was heated at 60° C. for 1 h. The reaction mixture was concentrated under reduced pressure. The residue was diluted with water (20 mL), acidified with aqueous 1.5 N aqueous HCl solution and extracted with ethyl acetate (2×30 mL). The combined organic layers were washed with brine solution, dried over anhydrous sodium sulphate and concentrated under reduced pressure to afford the title compound (750 mg, 4.36 mmol, 73% yield) as white solid. $^1$H NMR (400 MHz, DMSO-d$_6$) δ 3.62 (s, 3H), 2.20 (s, 6H). MS (ESI) 169 (M–H).

Step C. Intermediate 96C. Preparation of methyl 3-(hydroxymethyl)bicyclo[1.1.1]pentane-1-carboxylate

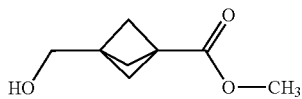

To a stirred solution of Intermediate 96B (350 mg, 2.057 mmol) in THF (5 mL) was added BH$_3$.DMS (0.586 mL, 6.17 mmol) at 0° C. The reaction mixture was warmed to room temperature and stirred for 2 h. The reaction was quenched with MeOH and the reaction mixture was concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated under reduced pressure and dried in vacuo to afford the title compound (250 mg, 1.601 mmol, 78% yield) as a colorless gummy. $^1$H NMR (400 MHz, DMSO-d$_6$) δ 4.55 (t, J=5.5 Hz, 1H), 3.58 (s, 3H), 3.38 (d, J=5.5 Hz, 2H), 1.85 (s, 6H).

Step D. Intermediate 96D. Preparation of methyl 3-formylbicyclo[1.1.1]pentane-1-carboxylate

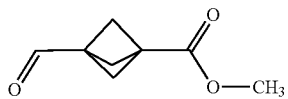

The title compound was prepared according to the method described for the synthesis of Intermediate 1C by substituting Intermediate 96C where appropriate (100 mg, 0.649 mmol, 40% yield) as a colorless gummy. $^1$H NMR (300 MHz, DMSO-d$_6$) δ 9.54 (s, 1H), 3.59 (s, 3H), 2.00-1.88 (m, 6H).

Step E. Intermediate 96E. Preparation of methyl 3-(((3-(2-methoxypyridin-4-yl)phenyl)amino)methyl)bicyclo[1.1.1]pentane-1-carboxylate

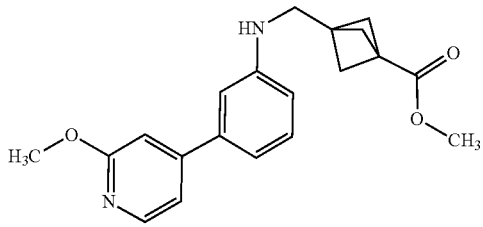

The title compound was prepared according to the method described for the synthesis of Intermediate 1F by substituting Intermediate 73A and Intermediate 96D where appropriate (110 mg, 0.322 mmol, 49% yield) as brown gummy. ¹H NMR (400 MHz, DMSO-d₆) δ 8.19 (d, J=5.5 Hz, 1H), 7.23-7.15 (m, 2H), 6.98 (d, J=1.0 Hz, 1H), 6.93-6.87 (m, 2H), 6.68 (dd, J=8.0, 1.5 Hz, 1H), 5.71 (t, J=5.8 Hz, 1H), 3.88 (s, 3H), 3.59 (s, 3H), 3.20 (d, J=5.5 Hz, 2H), 1.96 (s, 6H). MS (ESI) 339 (M+H).

Step F. Intermediate 96F. Preparation of methyl 3-((N-(3-(2-methoxypyridin-4-yl)phenyl)cyclohexanecarboxamido)methyl)bicyclo[1.1.1]pentane-1-carboxylate

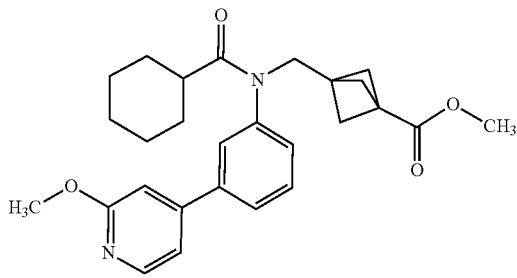

The title compound was prepared according to the method described for the synthesis of Example 1 by substituting Intermediate 96E and cyclohexanecarbonyl chloride where appropriate (75 mg, 0.167 mmol, 94% yield) as brown gummy. MS (ESI) 449 (M+H).

Step G. Intermediate 96G. Preparation of 3-((N-(3-(2-methoxypyridin-4-yl)phenyl)cyclohexanecarboxamido)methyl)bicyclo[1.1.1]pentane-1-carboxylic acid

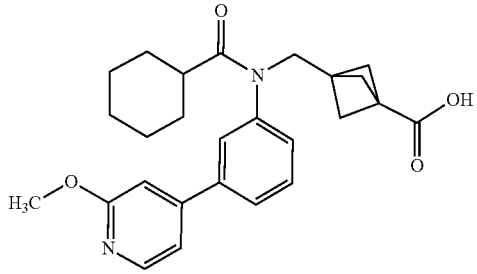 [SMILES: COc1cc(-c2cccc(N(CC34CC(C(=O)O)(C3)C4)C(=O)C3CCCCC3)c2)ccn1]

To a stirred solution of Intermediate 96F (70 mg, 0.156 mmol) in methanol (1 mL) and THF (1 mL) was added a solution of NaOH (31 mg, 0.780 mmol) in water (0.5 mL) at room temperature. The reaction mixture was stirred at room temperature for 4 h. The reaction mixture was concentrated under reduced pressure and the residue was diluted with (10 mL). The aqueous layer was acidified with aq. 1.5 N HCl solution and extracted with ethyl acetate (2×25 mL). The combined organic layers were dried over sodium sulphate and concentrated under reduced pressure to afford the title compound (65 mg, 0.150 mmol, 96% yield) as a brown gummy solid. ¹H NMR (400 MHz, DMSO-d₆) δ 12.1 (br. s., 1H), 8.25 (d, J=5.0 Hz, 1H), 7.81-7.69 (m, 2H), 7.57 (t, J=7.8 Hz, 1H), 7.41 (d, J=7.5 Hz, 1H), 7.35 (d, J=5.5 Hz, 1H), 7.16 (s, 1H), 3.91 (s, 3H), 3.79 (s, 2H), 2.20-2.19 (m, 1H), 1.79 (s, 6H), 1.72-1.55 (m, 4H), 1.43-1.30 (m, 4H), 0.9-0.87 (m, 2H). MS (ESI) 435 (M+H).

Step H. Example 96. Preparation of N-((3-(3-cyclopropyl-1,2,4-oxadiazol-5-yl) bicyclo[1.1.1]pentan-1-yl)methyl)-N-(3-(2-methoxypyridin-4-yl)phenyl) cyclohexanecarboxamide The title compound was prepared according to the method described for the synthesis of Intermediate 1A by substituting Intermediate 96G and corresponding amidoxime where appropriate (13.2 mg, 0.026 mmol, 57% yield). ¹HNMR (400 MHz, DMSO-d₆) δ 8.26 (d, J=5.4 Hz, 1H), 7.85-7.73 (m, 2H), 7.59 (t, J=7.6 Hz, 1H), 7.47 (d, J=7.6 Hz, 1H), 7.41-7.34 (m, 1H), 7.19 (s, 1H), 3.91 (s, 3H), 3.86 (s, 2H), 2.21 (br. s., 1H), 2.12-2.04 (m, 7H), 1.74-1.57 (m, 4H), 1.50 (br. s., 1H), 1.44-1.31 (m, 2H), 1.11 (d, J=13.4 Hz, 1H), 1.05-0.97 (m, 2H), 0.97-0.80 (m, 4H). FXR EC₅₀ (nM)=3428. MS (ESI) 499 (M+H).

Example 97

N-(3-(2-methoxypyridin-4-yl)phenyl)-N-((3-(3-(tetrahydro-2H-pyran-4-yl)-1,2,4-oxadiazol-5-yl)bicyclo[1.1.1]pentan-1-yl)methyl)cyclohexanecarboxamide (97)

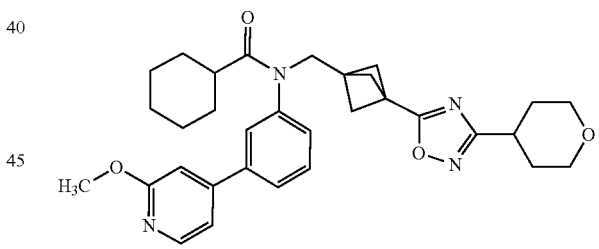

The title compound was prepared according to the method described for the synthesis of Intermediate 1A by substituting Intermediate 96G and corresponding amidoxime where appropriate (11.3 mg, 0.021 mmol, 45% yield). ¹HNMR (400 MHz, DMSO-d₆) δ 8.27 (d, J=5.6 Hz, 1H), 7.80 (s, 2H), 7.60 (t, J=7.7 Hz, 1H), 7.48 (d, J=8.3 Hz, 1H), 7.38 (d, J=4.2 Hz, 1H), 7.19 (s, 1H), 3.91 (s, 3H), 3.89-3.79 (m, 2H), 3.43 (td, J=11.6, 2.3 Hz, 2H), 3.08-2.96 (m, 1H), 2.23 (d, J=12.0 Hz, 1H), 2.15-2.04 (m, 6H), 1.88-1.78 (m, 2H), 1.73-1.55 (m, 6H), 1.51 (d, J=10.0 Hz, 1H), 1.45-1.29 (m, 2H), 1.10 (br. s., 1H), 0.98-0.79 (m, 2H); FXR EC₅₀ (nM)=1712. MS (ESI) 543 (M+H).

Example 98

N-cyclopropyl-4-((N-(3-(2-methoxypyridin-4-yl)phenyl)cyclohexanecarboxamido)methyl)bicyclo[2.2.2]octane-1-carboxamide

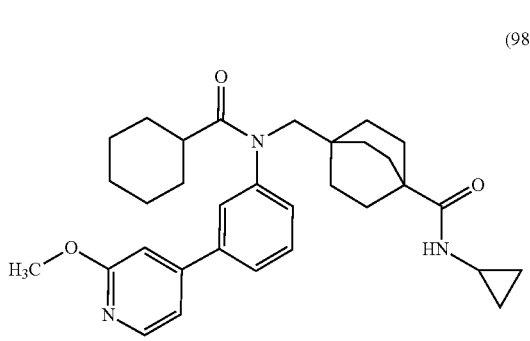 [SMILES: COc1cc(-c2cccc(N(CC34CCC(C(=O)NC5CC5)(CC3)CC4)C(=O)C3CCCCC3)c2)ccn1]

(98)

To a stirred solution of Intermediate 34B (20 mg, 0.042 mmol) in DMF (1 mL) were added cyclopropylamine (3 mg, 0.042 mmol), triethylamine (5 mg, 0.042 mmol) followed by ((1H-benzo[d][1,2,3]triazol-1-yl)oxy)tris(dimethylamino)phosphonium hexafluorophosphate(V) (18 mg, 0.042 mmol) at room temperature. The reaction mixture was stirred at room temperature for 1h. The reaction mass was purified via preparative HPLC with the following conditions: Column: Waters XBridge C18, 19×150 mm, 5-μmparticles; Mobile Phase A: 10-mM ammonium acetate; Mobile Phase B: acetonitrile; Gradient: 10-45% B over 25 minutes, then a 5-minute hold at 100% B; Flow: 15 mL/min. Fractions containing the product were combined and dried via centrifugal evaporation to afford the title compound (18 mg, 0.034 mmol, 85% yield). $^1$H NMR (400 MHz, DMSO-$d_6$) δ 8.26 (d, J=5.6 Hz, 1H), 7.83-7.68 (m, 2H), 7.56 (t, J=7.8 Hz, 1H), 7.44 (d, J=7.1 Hz, 1H), 7.38-7.32 (m, 1H), 7.24-7.11 (m, 2H), 3.92 (s, 3H), 3.59 (br. s., 2H), 3.18 (d, J=5.4 Hz, 2H), 2.60-2.55 (m, 1H), 1.61 (br. s., 4H), 1.55-1.42 (m, 6H), 1.40-1.20 (m, 8H), 1.09 (d, J=12.5 Hz, 1H), 0.88 (d, J=9.8 Hz, 2H), 0.59-0.48 (m, 2H), 0.41-0.26 (m, 2H). FXR $EC_{50}$ (nM)=399. MS (ESI) 516 (M+H).

Example 99

N-((4-cyanobicyclo[2.2.2]octan-1-yl)methyl)-N-(3-(2-methoxypyridin-4-yl)phenyl)cyclohexanecarboxamide

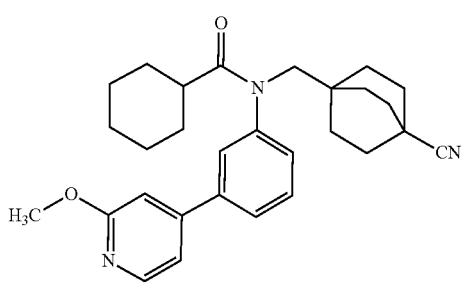

(99)

Step A. Intermediate 99A. Preparation of methyl 4-((N-(3-(2-methoxypyridin-4-yl)phenyl)cyclohexanecarboxamido)methyl)bicyclo[2.2.2]octane-1-carboxylate

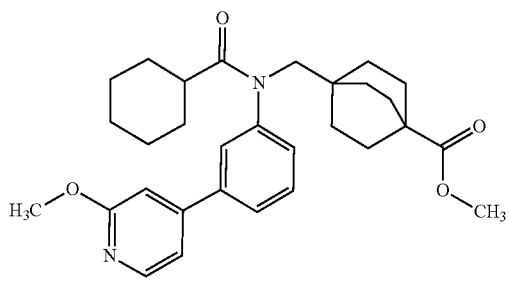

The title compound was prepared according to the method described for the synthesis of Example 1 by substituting Intermediate 83C and cyclohexanecarbonyl chloride where appropriate (6.7 mg, 0.014 mmol, 17% yield). $^1$H NMR (400 MHz, DMSO-$d_6$) δ 8.26 (d, J=5.6 Hz, 1H), 7.80 (s, 1H), 7.76 (d, J=7.3 Hz, 1H), 7.56 (t, J=7.8 Hz, 1H), 7.46 (d, J=8.3 Hz, 1H), 7.37 (dd, J=5.5, 1.6 Hz, 1H), 7.18 (s, 1H), 3.92 (s, 3H), 3.60 (br. s., 2H), 3.53 (s, 3H), 2.23 (br. s., 1H), 1.67-1.55 (m, 9H), 1.48 (br. s., 1H), 1.40-1.27 (m, 8H), 1.25 (s, 1H), 1.09 (d, J=13.2 Hz, 1H), 0.87 (d, J=6.4 Hz, 2H). MS (ESI) 491 (M+H).

Step B. Intermediate 99B. Preparation of 4-((N-(3-(2-methoxypyridin-4-yl)phenyl)cyclohexanecarboxamido)methyl)bicyclo[2.2.2]octane-1-carboxylic acid

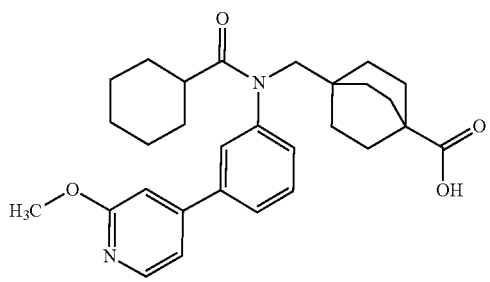 [SMILES: COc1cc(-c2cccc(N(CC34CCC(C(=O)O)(CC3)CC4)C(=O)C3CCCCC3)c2)ccn1]

The title compound was prepared according to the method described for the synthesis of Intermediate 83D by substituting Intermediate 99A where appropriate (10.8 mg, 0.023 mmol, 37% yield). $^1$H NMR (400 MHz, DMSO-$d_6$) δ 8.26 (d, J=5.4 Hz, 1H), 7.80 (s, 1H), 7.76 (d, J=7.8 Hz, 1H), 7.56 (t, J=7.6 Hz, 1H), 7.46 (d, J=8.1 Hz, 1H), 7.40-7.33 (m, 1H), 7.18 (s, 1H), 3.92 (s, 3H), 3.60 (br. s., 2H), 2.24 (d, J=9.5 Hz, 1H), 1.67-1.45 (m, 10H), 1.40-1.26 (m, 8H), 1.25 (s, 1H), 1.09 (d, J=12.0 Hz, 1H), 0.87 (d, J=7.6 Hz, 1H). MS (ESI) 477 (M+H).

Step C. Intermediate 99C. Preparation of 4-((N-(3-(2-methoxypyridin-4-yl)phenyl)cyclohexanecarboxamido)methyl)bicyclo[2.2.2]octane-1-carboxamide

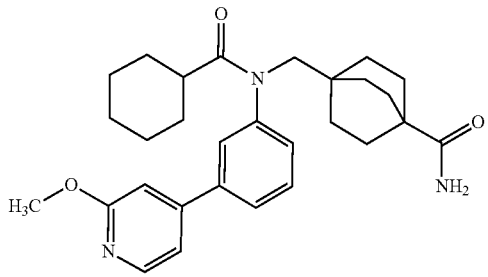 [SMILES: COc1cc(-c2cccc(N(CC34CCC(C(N)=O)(CC3)CC4)C(=O)C3CCCCC3)c2)ccn1]

To a stirred solution of Intermediate 99B (20 mg, 0.042 mmol) in DMF (1 mL) were added ammonium chloride (3 mg, 0.050 mmol), TEA (0.018 mL, 0.126 mmol) followed by BOP (20 mg, 0.046 mmol) at room temperature. The reaction mixture was stirred at room temperature for 1 h. The reaction mixture was concentrated under reduced pressure and the residue was purified via preparative HPLC with the following conditions: Column: Waters XBridge C18, 19×150 mm, 5-mparticles; Mobile Phase A: 10-mM ammonium acetate; Mobile Phase B: acetonitrile; Gradient: 10-45% B over 25 minutes, then a 5-minute hold at 100% B; Flow: 15 mL/min. Fractions containing the product were combined and dried via centrifugal evaporation to afford the title compound (12.4 mg, 62% yield). $^1$H NMR (400 MHz, DMSO-$d_6$) δ 8.26 (d, J=5.4 Hz, 1H), 7.84-7.72 (m, 2H), 7.57 (t, J=7.6 Hz, 1H), 7.45 (d, J=7.8 Hz, 1H), 7.36 (dd, J=5.4, 1.5 Hz, 1H), 7.18 (s, 1H), 6.81 (br. s., 1H), 6.60 (br. s., 1H), 3.92 (s, 3H), 3.60 (br. s., 2H), 2.24 (br. s., 1H), 1.61 (br. s., 4H), 1.59-1.46 (m, 8H), 1.40-1.23 (m, 10H). MS (ESI) 476 (M+H).

Step D. Example 99. Preparation of N-((4-cyanobicyclo[2.2.2]octan-1-yl)methyl)-N-(3-(2-methoxypyridin-4-yl)phenyl)cyclohexanecarboxamide To a stirred solution of Intermediate 99C (20 mg, 0.042 mmol) in pyridine (1 mL) was added trifluoroacetic anhydride (0.03 mL, 0.210 mmol) at 0° C. The reaction mixture was warmed to room temperature and stirred for 30 min. The reaction mixture was diluted with ice cold water and extracted with ethyl acetate (2×10 mL). The combined organic layers were dried over sodium sulphate and concentrated under reduced pressure. The crude material was purified via preparative LC/MS with the following conditions: Column: Waters XBridge C18, 19×150 mm, 5-m particles; Mobile Phase A: 10-mM ammonium acetate; Mobile Phase B: acetonitrile; Gradient: 25-67% B over 25 minutes, then a 5-minute hold at 100% B; Flow: 15 mL/min. Fractions containing the product were combined and dried via centrifugal evaporation to afford the title compound (8.3 mg, 0.018 mmol, 42% yield). $^1$H NMR (400 MHz, DMSO-$d_6$) δ 8.26 (d, J=5.1 Hz, 1H), 7.81 (s, 1H), 7.76 (d, J=8.3 Hz, 1H), 7.56 (t, J=7.9 Hz, 1H), 7.46 (d, J=8.6 Hz, 1H), 7.37 (dd, J=5.5, 1.6 Hz, 1H), 7.19 (s, 1H), 3.91 (s, 3H), 3.58 (br. s., 2H), 1.83-1.71 (m, 6H), 1.61 (br. s., 4H), 1.50 (d, J=14.4 Hz, 1H), 1.42-1.21 (m, 10H), 0.86 (d, J=12.7 Hz, 2H); FXR EC$_{50}$ (nM)=1531, MS (ESI) 458 (M+H).

Example 100

N-(3-(2-methoxypyridin-4-yl)phenyl)-N-((4-(1-methyl-1H-tetrazol-5-yl) bicyclo[2.2.2]octan-1-yl) methyl)cyclohexanecarboxamide (100)

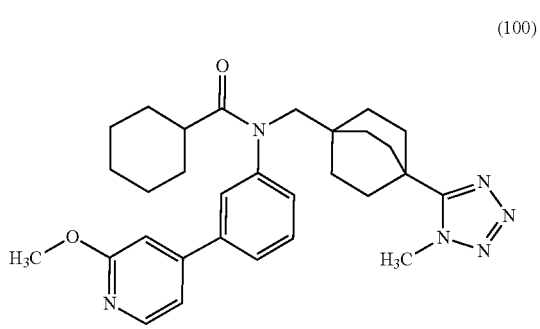 [SMILES: COc1cc(-c2cccc(N(CC34CCC(c5nnnn5C)(CC3)CC4)C(=O)C3CCCCC3)c2)ccn1]

Step A. Intermediate 100A. Preparation of N-((4-(1H-tetrazol-5-yl)bicyclo[2.2.2]octan-1-yl)methyl)-N-(3-(2-methoxypyridin-4-yl)phenyl)cyclohexanecarboxamide

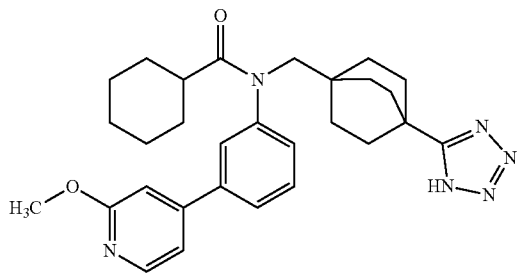 [SMILES: COc1cc(-c2cccc(N(CC34CCC(c5nnn[nH]5)(CC3)CC4)C(=O)C3CCCCC3)c2)ccn1]

To a stirred solution of Example 99 (100 mg, 0.219 mmol) in DME (2 mL) were added TMS-N$_3$ (0.12 mL, 0.874 mmol) and dibutyltin oxide (13 mg, 0.055 mmol) at room temperature. The reaction mixture was heated at 110° C. overnight. The reaction mixture was cooled to room temperature and concentrated under reduced pressure. The crude material was purified via preparative HPLC with the following conditions: Column: Waters XBridge C18, 19×150 mm, 5-mparticles; Mobile Phase A: 10-mM ammonium acetate; Mobile Phase B: acetonitrile; Gradient: 10-45% B over 25 minutes, then a 5-minute hold at 100% B; Flow: 15 mL/min. Fractions containing the product were combined and dried via centrifugal evaporation to afford the title compound (50 mg, 0.100 mmol, 46% yield). $^1$H NMR (400 MHz, DMSO-$d_6$) δ 8.26 (d, J=5.6 Hz, 1H), 7.84 (s, 1H), 7.78 (d, J=8.1 Hz, 1H), 7.58 (t, J=7.7 Hz, 1H), 7.50 (d, J=7.8 Hz, 1H), 7.39 (d, J=5.4 Hz, 1H), 7.20 (s, 1H), 3.91 (s, 3H), 3.66 (br. s., 2H), 2.30-2.20 (m, 1H), 1.83-1.73 (m, 6H), 1.62 (t, J=15.4 Hz, 4H), 1.54-1.39 (m, 7H), 1.35 (d, J=13.0 Hz, 2H), 1.10 (d, J=11.2 Hz, 2H), 0.88 (d, J=11.2 Hz, 2H). MS (ESI) 501 (M+H).

Step B. Example 100. Preparation of N-(3-(2-methoxypyridin-4-yl)phenyl)-N-((4-(1-methyl-1H-tetrazol-5-yl)bicyclo[2.2.2]octan-1-yl)methyl)cyclohexanecarboxamide To a stirred solution of Intermediate 100A (25 mg, 0.050 mmol) in DMF (1 mL) was added NaH (1.798 mg, 0.075 mmol) at 0° C. and stirred for 5 min. MeI (6.24 μL, 0.100 mmol) was added to the reaction mixture. The reaction mixture was warmed to room temperature and stirred for 1 h. The reaction mixture was concentrated under reduced pressure. The crude material was purified via preparative HPLC with the following conditions: Column: Waters XBridge C18, 19×150 mm, 5-mparticles; Mobile Phase A: 10-mM ammonium acetate; Mobile Phase B: acetonitrile; Gradient: 10-45% B over 25 minutes, then a 5-minute hold at 100% B; Flow: 15 mL/min. Fractions containing the product were combined and dried via centrifugal evaporation to afford title compound (2.2 mg, 4.22 μmol, 8% yield). $^1$H NMR (400 MHz, DMSO-$d_6$) δ 8.25 (d, J=5.4 Hz, 1H), 7.81 (s, 1H), 7.76 (d, J=7.8 Hz, 1H), 7.58 (t, J=7.8 Hz, 1H), 7.49 (d, J=7.8 Hz, 1H), 7.37 (dd, J=5.4, 1.5 Hz, 1H), 7.17 (s, 1H), 4.08 (s, 3H), 3.90 (s, 3H), 3.64 (br. s., 2H), 2.73 (d, J=0.5 Hz, 1H), 1.92-1.79 (m, 6H), 1.61 (t, J=12.3 Hz, 4H), 1.54-1.25 (m, 10H), 1.09 (d, J=13.2 Hz, 2H). FXR EC$_{50}$ (nM)=506. MS (ESI) 515 (M+H).

Examples 101 and 102

Methyl 2-(3-(N-((4-(3-methyl-1,2,4-oxadiazol-5-yl) bicyclo[2.2.2]octan-1-yl)methyl)cyclohexanecarboxamido)phenyl)cyclopropane-1-carboxylate

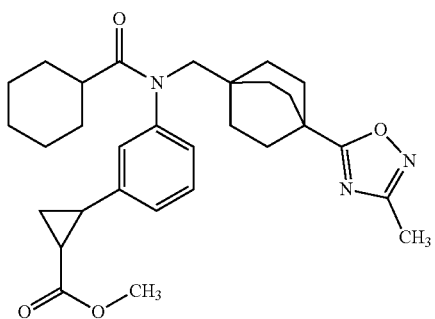

(101-102)

Step A. Intermediate 101A. Preparation of methyl 2-(3-nitrophenyl)cyclopropane-1-carboxylate

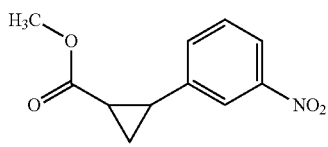 [SMILES: COC(=O)C1CC1c1cccc([N+](=O)[O-])c1]

A solution of KOH (0.070 g, 0.627 mmol) in water (2 mL) and diethyl ether (10 mL) was cooled to −10° C. N-nitroso-N-methylurea (1.29 g, 12.55 mmol) was added to the reaction mixture portion wise under slow stirring (with glass rod). The organic layer was decanted to a conical flask containing anhydrous sodium sulphate at −10° C. (diazomethane solution). To a stirred solution of methyl (E)-3-(3-nitrophenyl)acrylate (0.13 g, 0.627 mmol) in diethyl ether (5 mL) and dry DCM (2 mL) was added PdOAc$_2$ (0.014 g, 0.063 mmol) and the mixture was cooled to −78° C. Diazomethane solution (prepared above) was added to this reaction mixture and stirred at −78° C. for 1 h. The reaction mixture was warmed to room temperature and stirred overnight. The mixture was filtered through Celite. The filtrate was concentrated under reduced pressure to afford the title compound (0.12 g, 0.488 mmol, 78% yield) as a pale yellow oil (racemic mixture). $^1$H NMR (400 MHz, DMSO-$d_6$) δ 8.08-8.03 (m, 2H), 7.65 (dt, J=7.9, 1.3 Hz, 1H), 7.60-7.54 (m, 1H), 3.65 (s, 3H), 2.70-2.63 (m, 1H), 2.13-2.07 (m, 1H), 1.56-1.51 (m, 2H).

Step B. Intermediate 101B. Preparation of methyl 2-(3-nitrophenyl)cyclopropane-1-carboxylate

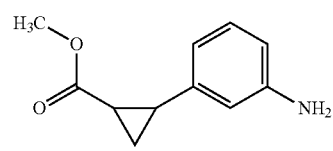

To a stirred solution of Intermediate 101A (0.12 g, 0.542 mmol) in ethanol (10 mL) was added tin(II) chloride (0.514 g, 2.71 mmol) at room temperature. The reaction mixture was heated at 90° C. for 3 h. The reaction mixture was concentrated under reduced pressure. The residue was diluted with EtOAc (10 mL), washed with aq. 10% NaHCO$_3$ solution (10 mL), brine solution (5 mL), dried over anhydrous sodium sulphate and concentrated under reduced pressure. The crude material was purified by flash chromatography (12 g silica gel cartridge; A=Hex, B=EtOAc; 30 min grad.; 0% B to 30% B; flow rate=30 mL/min). The pure fractions were combined, concentrated under reduced pressure and dried in vacuo to afford the title compound (0.08 g, 0.397 mmol, 73% yield) as a pale yellow oil (mixture of isomers). $^1$H NMR (400 MHz, DMSO-$d_6$) δ 6.90 (t, J=7.5 Hz, 1H), 6.41-6.37 (m, 1H), 6.33 (t, J=2.0 Hz, 1H), 6.29 (d, J=7.5 Hz, 1H), 4.97 (s, 2H), 3.63 (s, 3H), 2.25 (ddd, J=9.5, 6.5, 4.0 Hz, 1H), 1.84-1.75 (m, 1H), 1.45-1.35 (m, 1H), 1.28 (ddd, J=8.4, 6.7, 4.5 Hz, 1H). MS (ESI) 192 (M+H).

Step C. Intermediate 101C. Preparation of methyl 2-(3-(((4-(3-methyl-1,2,4-oxadiazol-5-yl)bicyclo [2.2.2]octan-1-yl)methyl)amino)phenyl)cyclopropane-1-carboxylate

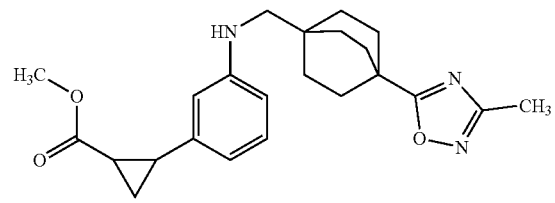 [SMILES: COC(=O)C1CC1c1cccc(NCC23CCC(c4nc(C)no4)(CC2)CC3)c1]

The title compound (mixture of isomers) was prepared according to the method described for the synthesis of Intermediate 1F by substituting Intermediate 101B and Intermediate 1C. (50 mg, 0.088 mmol, 39% yield) as a pale yellow solid. MS (ESI) 396 (M+H).

Step B. Examples 101 and 102. Preparation of methyl 2-(3-(N-((4-(3-methyl-1,2,4-oxadiazol-5-yl) bicyclo[2.2.2]octan-1-yl)methyl)cyclohexanecarboxamido)phenyl)cyclopropane-1-carboxylate The title compound (mixture of isomers) was prepared according to the method described for the synthesis of Example 1 by substituting Intermediate 101C and cyclohexanecarbonyl chloride. The isomers were separated by chiral separation Chiral HPLC (Column: LUX-Cellulose C2 (250 mm×21.2 mm ID, 5 μm), Mobile phase A=0.1% DEA in MeOH, Flow 20 mL/min) to afford Example 101 Isomer 1 (RT=8.5 min); (4 mg, 7.91 μmol, 9% yield) as an off-white solid. $^1$H NMR (400 MHz, DMSO-d$_6$) δ 7.41-7.29 (m, 1H), 7.26-7.05 (m, 3H), 3.65 (s, 3H), 3.55 (br. s., 2H), 2.72 (q, J=6.8 Hz, 1H), 2.27 (s, 3H), 2.14 (br. s., 1H), 1.99 (br. s., 1H), 1.76 (d, J=7.8 Hz, 6H), 1.58-1.56 (m, 3H), 1.53-1.47 (m, 2H), 1.45-1.18 (m, 8H), 1.07 (t, J=7.1 Hz, 3H), 0.86 (d, J=13.4 Hz, 2H). FXR EC$_{50}$ (nM) 245; MS (ESI) 506 (M+H) and Example 102 Isomer 2 (RT=9.5 min); (4 mg, 7.75 μmol, 8% yield) as an off-white solid. $^1$H NMR (400 MHz, DMSO-d$_6$) δ 7.41-7.29 (m, 1H), 7.26-7.05 (m, 3H), 3.65 (s, 3H), 3.55 (br. s., 2H), 2.72 (q, J=6.8 Hz, 1H), 2.27 (s, 3H), 2.14 (br. s., 1H), 1.99 (br. s., 1H), 1.76 (d, J=7.8 Hz, 6H), 1.58-1.56 (m, 3H), 1.53-1.47 (m, 2H), 1.45-1.18 (m, 8H), 1.07 (t, J=7.1 Hz, 3H), 0.86 (d, J=13.4 Hz, 2H). FXR EC$_{50}$ (nM) 518; MS (ESI) 506 (M+H).

Example 103

N-((4-(3-(tert-butyl)-1,2,4-oxadiazol-5-yl)bicyclo [2.2.2]octan-1-yl)methyl)-N-(3-(3-cyclopropyl-1,2, 4-oxadiazol-5-yl)phenyl)-4,4-difluorocyclohexane-1-carboxamide (103)

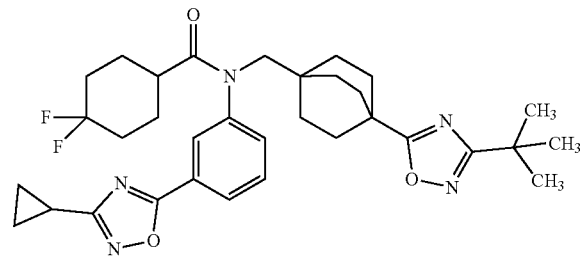

The title compound was prepared according to the method described for the synthesis of Example 5 by substituting Intermediate 69D and corresponding acid where appropriate: (11.9 mg, 0.020 mmol, 30% yield). $^1$H NMR (400 MHz, DMSO-d$_6$) δ 8.12-7.94 (m, 2H), 7.79 (d, J=8.1 Hz, 1H), 7.69 (t, J=7.5 Hz, 1H), 3.64 (br. s., 2H), 2.38 (br. s., 1H), 2.25-2.18 (m, 1H), 2.02-1.95 (m, 2H), 1.85-1.74 (m, H), 1.74-1.57 (m, 5H), 1.52 (d, J=12.0 Hz, 1H), 1.46-1.32 (m, 6H), 1.29-1.17 (m, 9H), 1.17-1.09 (m, 2H), 1.05-0.93 (m, 2H). FXR EC$_{50}$ (nM)=250; MS (ESI) 594 (M+H).

Example 104

N-((4-(3-(tert-butyl)-1,2,4-oxadiazol-5-yl)bicyclo [2.2.2]octan-1-yl)methyl)-N-(3-(3-cyclopropyl-1,2, 4-oxadiazol-5-yl)phenyl)tetrahydro-2H-pyran-4-carboxamide (104)

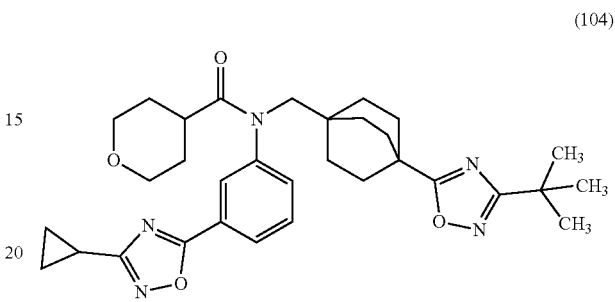

Step A. Intermediate 104A. Preparation N-((4-(5-(tert-butyl)-1,2,4-oxadiazol-3-yl) bicyclo[2.2.2]octan-1-yl)methyl)-3-(3-cyclopropyl-1,2,4-oxadiazol-5-yl)aniline

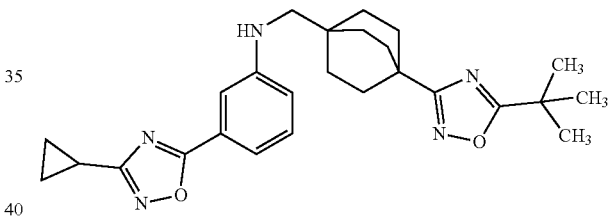

The title compound was prepared according to the method described for the synthesis of Intermediate 1F by substituting Intermediate 13A and Intermediate 88F where appropriate: (1.3 g, 2.90 mmol, 69% yield) as brown solid. MS (ESI) 448 (M+H).

Step B. Example 104. Preparation of N-((4-(3-(tert-butyl)-1,2,4-oxadiazol-5-yl) bicyclo[2.2.2]octan-1-yl)methyl)-N-(3-(3-cyclopropyl-1,2,4-oxadiazol-5-yl)phenyl)tetrahydro-2H-pyran-4-carboxamide The title compound was prepared according to the method described for the synthesis of Example 5 by substituting Intermediate 104A and corresponding acid where appropriate: (11 mg, 0.019 mmol, 27% yield). $^1$H NMR (400 MHz, DMSO-d$_6$) δ 8.09-7.90 (m, 2H), 7.79 (d, J=7.3 Hz, 1H), 7.73-7.63 (m, 1H), 3.63 (br. s., 2H), 2.38 (br. s., 1H), 2.25-2.17 (m, 1H), 1.95 (br. s., 2H), 1.83-1.57 (m, 10H), 1.51 (d, J=19.1 Hz, 2H), 1.44-1.35 (m, 6H), 1.33 (s, 9H), 1.19-1.07 (m, 2H), 1.04-0.97 (m, 2H). FXR EC$_{50}$ (nM)=119; MS (ESI) 594 (M+H).

Example 105

N-((4-(5-(1,1-difluoroethyl)-1,2,4-oxadiazol-3-yl)bicyclo[2.2.2]octan-1-yl)methyl)-N-(4'-ethoxy-6-fluoro-[1,1'-biphenyl]-3-yl)-4,4-difluorocyclohexane-1-carboxamide

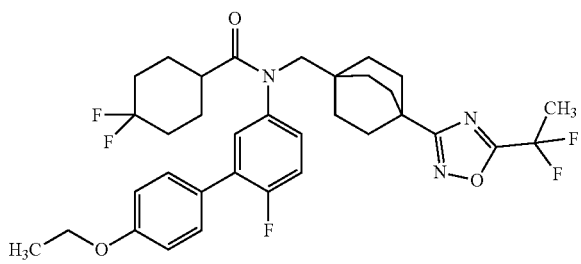 [SMILES: CCOc1ccc(-c2cc(N(CC34CCC(c5noc(C(C)(F)F)n5)(CC3)CC4)C(=O)C3CCC(F)(F)CC3)ccc2F)cc1]

Step A. Intermediate 105A. Preparation of methyl 4-(5-(1,1-difluoroethyl)-1,2,4-oxadiazol-3-yl)bicyclo[2.2.2]octane-1-carboxylate

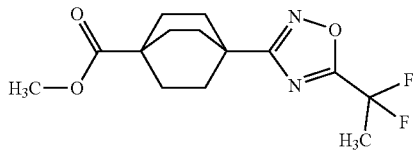 [SMILES: COC(=O)C12CCC(c3noc(C(C)(F)F)n3)(CC1)CC2]

The title compound was prepared according to the method described for the synthesis of Intermediate 1A by substituting Intermediate 88C and corresponding acid where appropriate (4.2 g, 11.75 mmol, 53% yield) colorless gummy solid. MS (ESI) 301 (M+H).

Step B. Intermediate 105B. Preparation of (4-(5-(1,1-difluoroethyl)-1,2,4-oxadiazol-3-yl)bicyclo[2.2.2]octan-1-yl)methanol

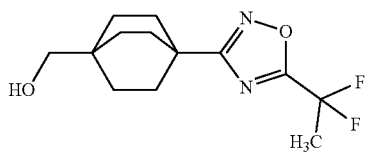

The title compound was prepared according to the method described for the synthesis of Intermediate 1B by substituting Intermediate 105A where appropriate (3000 mg, 10.58 mmol, 76% yield) as a colorless liquid. MS (ESI) 273 (M+H).

Step C. Intermediate 105C. Preparation of 4-(5-(1,1-difluoroethyl)-1,2,4-oxadiazol-3-yl) bicyclo[2.2.2]octane-1-carbaldehyde

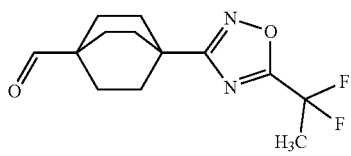 [SMILES: CC(F)(F)c1nc(C23CCC(C=O)(CC2)CC3)no1]

The title compound was prepared according to the method described for the synthesis of Intermediate 1C by substituting Intermediate 105B where appropriate (2000 mg, 7.40 mmol, 67% yield) as a colorless white gummy solid. $^1$H NMR (400 MHz, DMSO-d$_6$) δ 9.46 (br. s., 1H), 2.16 (t, J=19.6 Hz, 3H), 1.94-1.76 (m, 12H).

Step D. Intermediate 105D. Preparation of 3-bromo-N-((4-(5-(1,1-difluoroethyl)-1,2,4-oxadiazol-3-yl)bicyclo[2.2.2]octan-1-yl)methyl)-4-fluoroaniline

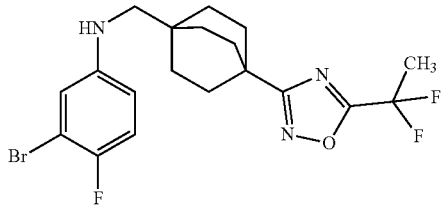 [SMILES: CC(F)(F)c1nc(C23CCC(CNc4ccc(F)c(Br)c4)(CC2)CC3)no1]

The title compound was prepared according to the method described for the synthesis of Intermediate 1F by substituting Intermediate 105C and 3-bromo-4-fluoroaniline where appropriate (500 mg, 0.416 mmol, 28% yield) as gummy solid. MS (ESI) 444 (M+H).

Step E. Intermediate 105E. Preparation of N-(3-bromo-4-fluorophenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide

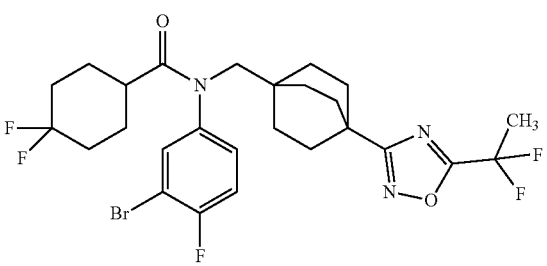 [SMILES: CC(F)(F)c1nc(C23CCC(CN(C(=O)C4CCC(F)(F)CC4)c4ccc(F)c(Br)c4)(CC2)CC3)no1]

The title compound was prepared according to the method described for the synthesis of Example 5 by substituting Intermediate 105D and corresponding acid where appropriate (170 mg, 0.288 mmol, 64% yield) as gummy solid. MS (ESI) 590 (M+H).

Step F: Example 105. Preparation of N-((4-(5-(1,1-difluoroethyl)-1,2,4-oxadiazol-3-yl)bicyclo[2.2.2]octan-1-yl)methyl)-N-(4'-ethoxy-6-fluoro-[1,1'-biphenyl]-3-yl)-4,4-difluorocyclohexane-1-carboxamide The title compound was prepared according to the method described for the synthesis of Intermediate 87B by substituting Intermediate 105E and corresponding boronic acid where appropriate (6.7 mg, 10.53 μmol, 21% yield). $^1$H NMR (400 MHz, DMSO-$d_6$) δ 7.67-7.47 (m, 3H), 7.43 (d, J=8.1 Hz, 1H), 7.39-7.30 (m, 1H), 7.05 (d, J=8.8 Hz, 2H), 4.09 (q, J=7.1 Hz, 2H), 3.61 (br. s., 2H), 2.42 (br. s., 1H), 2.23-2.06 (m, 3H), 1.98 (br. s., 2H), 1.85-1.72 (m, 8H), 1.72-1.50 (m, 4H), 1.50-1.39 (in, 6H), 1.36 (t, J=7.0 Hz, 3H) FXR $EC_{50}$ (nM)=637. MS (ESI) 632 (M+H).

The following compounds were prepared according to the method described for the synthesis of Intermediate 87B by substituting Intermediate 105E and corresponding boronic acids where appropriate:

| Ex. No. | Structure | MS (ESI) (M + H) | FXR $EC_{50}$ (nM) |
|---|---|---|---|
| 106 | | 634 | 406 |
| 107 | | 666 | 1021 |
| 108 | | 659 | 250 |

| | |
|---|---|
| 106 | $^1$H NMR (400 MHz, DMSO-$d_6$) δ 8.86 (d, J = 1.2 Hz, 2H), 7.80 (dd, J = 2.6, 7.2 Hz, 1H), 7.59-7.52 (m, 1H), 7.49-7.41 (m, 1H), 4.46-4.39 (m, 2H), 3.61 (s, 2H), 2.47-2.39 (m, 1H), 2.23-2.07 (m, 3H), 1.83-1.70 (m, 8H), 1.68-1.51 (m, 6H), 1.49-1.41 (m, 6H), 1.40-1.34 (m, 3H) |
| 107 | $^1$H NMR (400 MHz, DMSO-$d_6$) δ 8.05 (d, J = 8.6 Hz, 2H), 7.87 (d, J = 7.6 Hz, 2H), 7.76-7.68 (m, 1H), 7.62-7.54 (m, 1H), 7.50-7.41 (m, 1H), 3.69-3.53(m, 2H), 3.28 (s, 3H), 2.13 (t, J = 19.7 Hz, 3H), 2.02-1.88 (m, 2H), 1.84-1.70 (m, 8H), 1.68-1.52 (m, 4H), 1.49-1.36 (m, 6H) Note: One proton buried under solvent peak |
| 108 | $^1$H NMR (400 MHz, DMSO-$d_6$) δ 8.30 (s, 1H), 8.02 (d, J = 8.6 Hz, 1H), 7.77-7.60 (m, 2H), 7.53(dd, J = 8.1, 3.9 Hz, 1H), 7.46-7.37 (m, 1H), 3.71 (br. s., 1H), 3.58 (br. s., 1H), 2.91-2.77 (m, 3H), 2.24-2.07 (m, 3H), 1.98 (br. s., 2H), 1.83-1.71(m, 7H), 1.62 (dd, J = 18.1, 8.6 Hz, 5H), 1.46 (br. s., 6H) Note: One proton buried under solvent peak |

Example 109

N-((4-(5-(1,1-difluoroethyl)-1,2,4-oxadiazol-3-yl)bicyclo[2.2.2]octan-1-yl)methyl)-N-(4'-(difluoromethoxy)-[1,1'-biphenyl]-3-yl)tetrahydro-2H-pyran-4-carboxamide

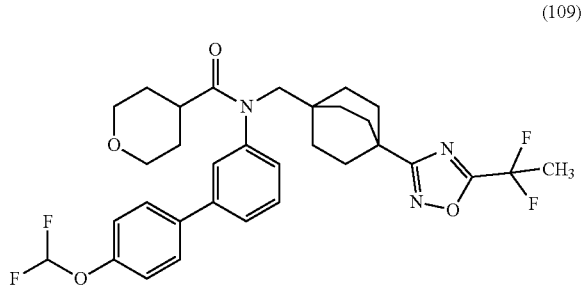 [SMILES: CC(F)(F)c1nc(C23CCC(CN(C(=O)C4CCOCC4)c4cccc(-c5ccc(OC(F)F)cc5)c4)(CC2)CC3)no1]

(109)

Step A: Intermediate 109A: Preparation of 3-bromo-N-((4-(5-(1,1-difluoroethyl)-1,2,4-oxadiazol-3-yl)bicyclo[2.2.2]octan-1-yl)methyl)aniline

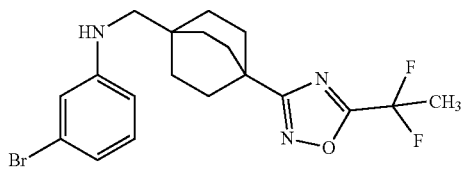 [SMILES: CC(F)(F)c1nc(C23CCC(CNc4cccc(Br)c4)(CC2)CC3)no1]

The title compound was prepared according to the method described for the synthesis of Intermediate 1B by substituting Intermediate 105C and 3-bromoaniline where appropriate (1400 mg, 3.28 mmol, 68% yield) as gummy solid. MS (ESI) 426 (M+H).

Step B: Intermediate 109B: Preparation of N-((4-(5-(1,1-difluoroethyl)-1,2,4-oxadiazol-3-yl)bicyclo[2.2.2]octan-1-yl)methyl)-4'-(difluoromethoxy)-[1,1'-biphenyl]-3-amine

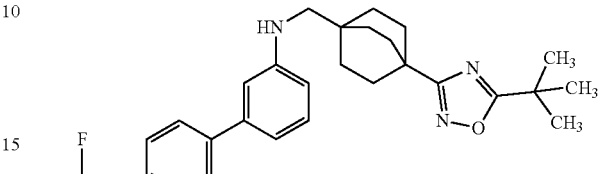

The title compound was prepared according to the method described for the synthesis of Intermediate 87B by substituting Intermediate 109A and corresponding boronic acid where appropriate (1.15 g, 2.349 mmol, 71% yield) as white solid. MS (ESI) 490 (M+H).

Step C: Example 109. Preparation of N-((4-(5-(1,1-difluoroethyl)-1,2,4-oxadiazol-3-yl)bicyclo[2.2.2]octan-1-yl)methyl)-N-(4'-(difluoromethoxy)-[1,1'-biphenyl]-3-yl)tetrahydro-2H-pyran-4-carboxamide The title compound was prepared according to the method described for the synthesis of Example 5 by substituting Intermediate 109B and corresponding acid where appropriate (5.3 mg, 8.81 μmol, 22% yield). $^1$H NMR (400 MHz, DMSO-$d_6$) δ 7.80 (d, J=8.8 Hz, 2H), 7.73 (s, 1H), 7.67 (br d, J=8.3 Hz, 1H), 7.54 (t, J=7.8 Hz, 1H), 7.50-7.10 (m, 4H), 3.75 (br dd, J=2.7, 10.8 Hz, 2H), 3.69-3.56 (m, 2H), 3.07-2.92 (m, 2H), 2.55 (br s, 1H), 2.21-2.04 (m, 3H), 1.86-1.71 (m, 6H), 1.63 (br dd, J=3.4, 12.0 Hz, 2H), 1.53-1.34 (m, 8H) FXR EC$_{50}$ (nM)=50. MS (ESI) 602 (M+H).

The following compounds were prepared according to the method described for the synthesis of Example 5 by substituting Intermediate 109B and corresponding acids where appropriate:

| Ex. No. | Structure | MS (ESI) (M + H) | FXR EC$_{50}$ (nM) |
|---|---|---|---|
| 110 | 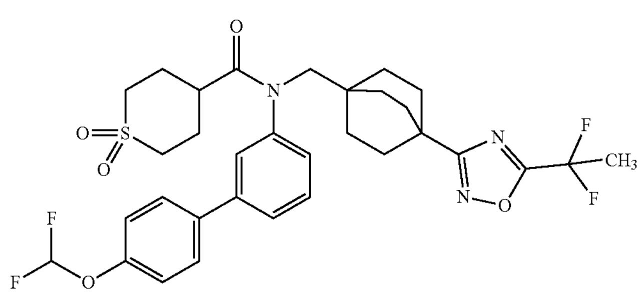 [SMILES: CC(F)(F)c1nc(C23CCC(CN(C(=O)C4CCS(=O)(=O)CC4)c4cccc(-c5ccc(OC(F)F)cc5)c4)(CC2)CC3)no1] | 650 | 467 |

| Ex. No. | Structure | MS (ESI) (M + H) | FXR EC$_{50}$ (nM) |
|---|---|---|---|
| 111 | | 636 | 69 |

| 110 | $^1$H NMR (400 MHz, DMSO-d$_6$) δ 7.81 (d, J = 8.6 Hz, 2H), 7.75 (s, 1H) 7.68 (d, J = 7.8 Hz, 1H), 7.55 (t, J = 7.7 Hz, 1H), 7.50-7.11 (m, 4H), 3.75-3.54 (m, 2H), 3.06-2.85 (m, 4H), 2.76-2.67 (m, 1H), 2.13 (t, J = 19.7 Hz, 3H), 2.03 (br d, J = 5.1 Hz, 4H), 1.84-1.65 (m, 6H), 1.44 (br dd, J = 6.8, 8.8 Hz, 6H) |
| 111 | $^1$H NMR (400 MHz, DMSO-d$_6$) δ 7.80 (d, J = 8.8 Hz, 2H), 7.73 (s, 1H), 7.67 (d, J = 8.1 Hz, 1H), 7.55 (t, J = 7.7 Hz, 1H), 7.50-7.20 (m, 4H), 3.66 (br. s., 2H), 2.45 (br. s., 1H), 2.13 (t, J = 19.7 Hz, 3H), 1.96 (br. s., 2H), 1.85-1.70 (m, 8H), 1.70-1.51 (m, 3H), 1.51-1.29 (m, 7H) |

Example 112

N-(3-(3-cyclopropyl-1,2,4-oxadiazol-5-yl)phenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide (112)

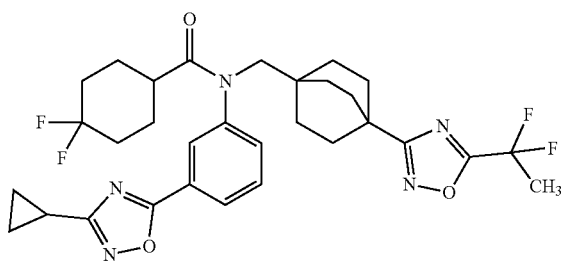

Step A. Intermediate 112A. Preparation of 3-(3-cyclopropyl-1,2,4-oxadiazol-5-yl)-N-((4-(5-(1,1-difluoroethyl)-1,2,4-oxadiazol-3-yl)bicyclo[2.2.2]octan-1-yl)methyl)aniline The title compound was prepared according to the method described for the synthesis of Intermediate 1F by substituting Intermediate 13A and Intermediate 105C where appropriate: (60 mg, 0.130 mmol, 70% yield) as a brown solid. MS (ESI) 456 (M+H).

Step B. Example 112. Preparation of N-(3-(3-cyclopropyl-1,2,4-oxadiazol-5-yl)phenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide The title compound was prepared according to the method described for the synthesis of Example 5 by substituting Intermediate 112A and corresponding acid where appropriate: (5.1 mg, 8.48 µmol, 19% yield). $^1$H NMR (400 MHz, DMSO-d$_6$) δ 8.16-7.92 (m, 2H), 7.79 (d, J=7.1 Hz, 1H), 7.69 (t, J=7.7 Hz, 1H), 3.65 (br. s., 2H), 2.39 (br. s., 1H), 2.27-2.05 (m, 4H), 1.95 (br. s., 2H), 1.86-1.57 (m, 12H), 1.47-1.28 (m, 6H), 1.18-1.07 (m, 2H), 1.04-0.97 (m, 2H). FXR EC$_{50}$ (nM)=142; MS (ESI) 602 (M+H).

Example 113

N-((4-(5-(1,1-difluoroethyl)-1,2,4-oxadiazol-3-yl)bicyclo[2.2.2]octan-1-yl)methyl)-N-(4'-ethoxy-[1,1'-biphenyl]-3-yl)-4,4-difluorocyclohexane-1-carboxamide (113)

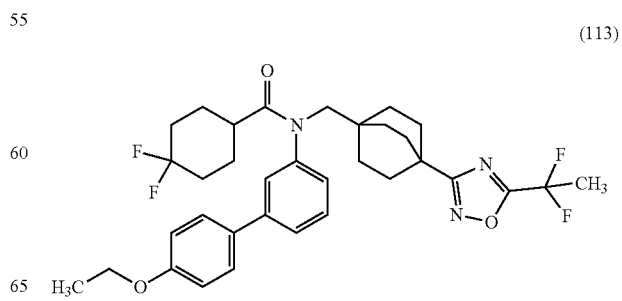

Step A: Intermediate 113A: Preparation of 4'-ethoxy-[1,1'-biphenyl]-3-amine

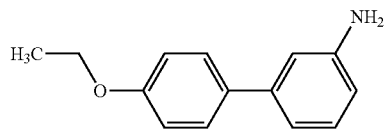 [SMILES: CCOc1ccc(-c2cccc(N)c2)cc1]

The title compound was prepared according to the method described for the synthesis of Intermediate 87B by substituting 3-bromoaninline and corresponding boronic acid where appropriate (1.3 g, 6.10 mmol, 42% yield) as green solid. MS (ESI) 214 (M+H).

Step B: Intermediate 113B: Preparation of N-((4-(5-(1,1-difluoroethyl)-1,2,4-oxadiazol-3-yl)bicyclo[2.2.2]octan-1-yl)methyl)-4'-ethoxy-[1,1'-biphenyl]-3-amine

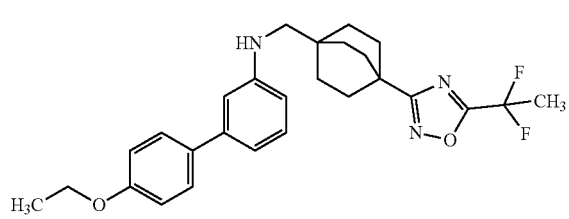 [SMILES: CCOc1ccc(-c2cccc(NCC34CCC(c5noc(C(C)(F)F)n5)(CC3)CC4)c2)cc1]

The title compound was prepared according to the method described for the synthesis of Intermediate 1F by substituting Intermediate 113A and Intermediate 105C where appropriate (600 mg, 1.283 mmol, 58% yield) as green solid. MS (ESI) 468 (M+H).

Step C: Example 113: Preparation of N-((4-(5-(1,1-difluoroethyl)-1,2,4-oxadiazol-3-yl)bicyclo[2.2.2]octan-1-yl)methyl)-N-(4'-ethoxy-[1,1'-biphenyl]-3-yl)-4,4-difluorocyclohexane-1-carboxamide The title compound was prepared according to the method described for the synthesis of Example 5 by substituting Intermediate 113B and corresponding acid where appropriate (5.5 mg, 8.67 μmol, 16% yield). $^1$H NMR (400 MHz, DMSO-$d_6$) δ 7.72-7.64 (m, 3H), 7.62 (d, J=7.8 Hz, 1H), 7.53-7.46 (m, 1H), 7.39-7.32 (m, 1H), 7.08-7.00 (m, 2H), 4.08 (q, J=7.1 Hz, 2H), 3.70-3.61 (m, 2H), 2.48-2.41 (m, 1H), 2.13 (t, J=19.7 Hz, 3H), 2.02-1.85 (m, 3H), 1.82-1.70 (m, 8H), 1.69-1.52 (m, 3H), 1.49-1.40 (m, 6H), 1.38-1.31 (m, 3H). FXR EC$_{50}$ (nM)=665. MS (ESI) 614 (M+H).

Example 114

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)-5-fluorophenyl)-4,4-difluorocyclohexane-1-carboxamide (114)

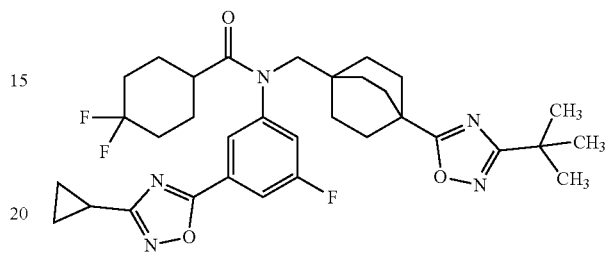

Step A. Intermediate 114A. Preparation of 3-(3-cyclopropyl-1,2,4-oxadiazol-5-yl)-5-fluoroaniline

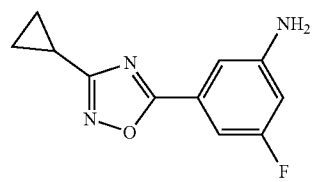 [SMILES: Nc1cc(F)cc(-c2nc(C3CC3)no2)c1]

The title compound was prepared according to the method described for the synthesis of Intermediate 1A by substituting 3-amino-5-fluorobenzoic acid and N'-hydroxycyclopropanecarboximidamide where appropriate: (800 mg, 3.28 mmol, 56% yield) as a brown solid. MS (ESI) 220 (M+H).

Step B. Intermediate 114B. Preparation of N-((4-(3-(tert-butyl)-1,2,4-oxadiazol-5-yl) bicyclo[2.2.2]octan-1-yl)methyl)-3-(3-cyclopropyl-1,2,4-oxadiazol-5-yl)-5-fluoroaniline

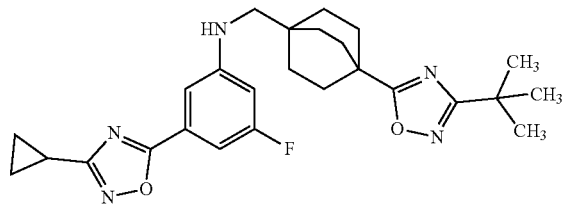 [SMILES: CC(C)(C)c1noc(C23CCC(CNc4cc(F)cc(-c5nc(C6CC6)no5)c4)(CC2)CC3)n1]

The title compound was prepared according to the method described for the synthesis of Intermediate 1F by substituting Intermediate 114A and Intermediate 69C where appropriate: (350 mg, 0.744 mmol, 65% yield) as brown solid. MS (ESI) 466 (M+H).

Step C. Example 114. Preparation of N-((4-(3-(tert-butyl)-1,2,4-oxadiazol-5-yl) bicyclo[2.2.2]octan-1-yl)methyl)-N-(3-(3-cyclopropyl-1,2,4-oxadiazol-5-yl)-5-fluorophenyl)-4,4-difluorocyclohexane-1-carboxamide The title compound was prepared according to the method described for the synthesis of Example 5 by substituting Intermediate 114B and corresponding acid where appropriate: (6.7 mg, 10.95 μmol, 20% yield). $^1$H NMR (400 MHz, DMSO-$d_6$) δ 7.92 (s, 1H), 7.88-7.72 (m, 2H), 3.73-3.55 (m, 2H), 2.48-2.37 (m, 1H), 2.27-2.17 (m, 1H), 2.04-1.88 (m, 2H), 1.87-1.69 (m, 8H), 1.68-1.50 (m, 4H), 1.48-1.35 (m, 6H), 1.30-1.21 (m, 9H), 1.18-1.10 (m, 2H), 1.04-0.96 (m, 2H). FXR EC$_{50}$ (nM)=325; MS (ESI) 612 (M+H).

Example 115

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)-5-fluorophenyl)tetrahydro-2H-pyran-4-carboxamide (115)

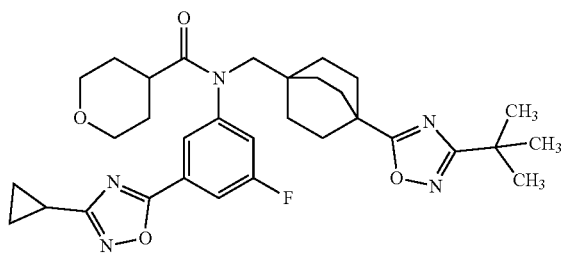

The title compound was prepared according to the method described for the synthesis of Example 5 by substituting Intermediate 114B and corresponding acid where appropriate: (8.3 mg, 0.014 mmol, 27% yield). $^1$H NMR (400 MHz, DMSO-$d_6$) δ 7.92 (s, 1H), 7.87-7.77 (m, 2H), 3.81-3.71 (m, 2H), 3.68-3.51 (m, 2H), 3.17-2.95 (m, 2H), 2.63-2.54 (m, 1H), 2.27-2.17 (m, 1H), 1.79 (br dd, J=6.6, 8.8 Hz, 6H), 1.67-1.54 (m, 2H), 1.54-1.45 (m, 2H), 1.44-1.34 (m, 6H), 1.26 (s, 9H), 1.17-1.08 (m, 2H), 1.03-0.96 (m, 2H). FXR EC$_{50}$ (nM)=83; MS (ESI) 578 (M+H).

Example 116

N-((4-(5-(tert-butyl)-1,2,4-oxadiazol-3-yl)bicyclo[2.2.2]octan-1-yl)methyl)-N-(3-(3-cyclopropyl-1,2,4-oxadiazol-5-yl)phenyl)tetrahydro-2H-pyran-4-carboxamide (116)

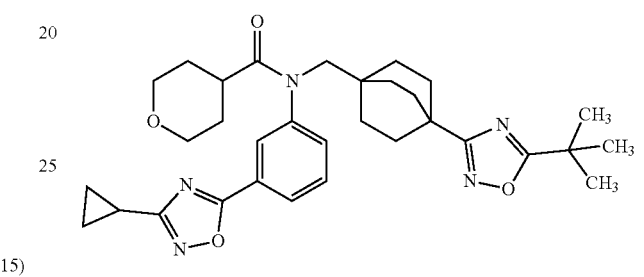

The title compound was prepared according to the method described for the synthesis of Example 5 by substituting Intermediate 104A and corresponding acid where appropriate (6.7 mg, 0.012 mmol, 260 yield). $^1$H N(R (400 MHz, DMSO-$d_6$) δ 8.11-7.94 (m, 2H), 7.79 (br d, J=6.8 Hz, 1H), 7.73-7.63 (m, 1H), 3.80-3.69 (m, 2H), 3.69-3.51 (m, 2H), 3.09-2.91 (m, 2H), 2.48 (br s, 1H), 2.26-2.14 (m, 1H), 1.80-1.67 (m, 6H), 1.66-1.54 (m, 2H), 1.47 (br d, J=1.5 Hz, 2H), 1.42-1.35 (m, 6H), 1.33 (s, 9H), 1.17-1.08 (m, 2H), 1.03-0.96 (in, 2H). FXR EC$_{50}$ ((nM)=61. MS (ESI) 560 (M+H).

The following compounds were prepared according to the method described for the synthesis of Example 5 by substituting Intermediate 104A and corresponding acids where appropriate:

| Ex. No. | Structure | MS (ESI) (M + H) | FXR EC$_{50}$ (nM) |
|---|---|---|---|
| 117 | 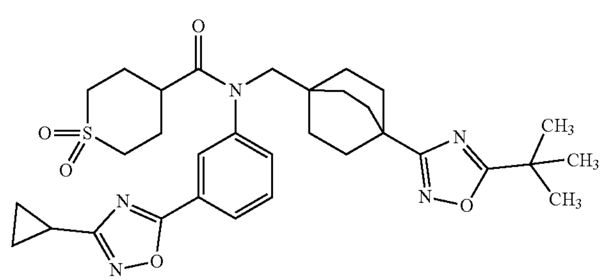 [SMILES: CC(C)(C)c1nc(C23CCC(CN(C(=O)C4CCS(=O)(=O)CC4)c4cccc(-c5nc(C6CC6)no5)c4)(CC2)CC3)no1] | 608 | 729 |

| Ex. No. | Structure | MS (ESI) (M + H) | FXR EC$_{50}$ (nM) |
|---|---|---|---|
| 118 | | 573 | 1946 |

| 117 | $^1$H NMR (400 MHz, DMSO-d$_6$) δ 8.11-7.98 (m, 2H), 7.79 (br d, J = 7.8 Hz, 1H), 7.70 (d, J = 7.8 Hz, 1H), 3.74-3.54 (m, 2H), 3.06-2.87 (m, 4H), 2.67-2.60 (m, 1H), 2.26-2.18 (m, 1H), 2.10-1.91 (m, 4H), 1.80-1.63 (m, 6H), 1.45-1.35 (m, 6H), 1.33 (s, 9H), 1.17-1.09 (m, 2H), 1.04-0.96 (m, 2H) |
|---|---|
| 118 | $^1$H NMR (400 MHz, DMSO-d$_6$) δ 8.10-7.93 (m, 2H), 7.83-7.74 (m, 1H), 7.72-7.64 (m, 1H), 3.72-3.54 (m, 2H), 2.92-2.71 (m, 2H), 2.27-2.06 (m, 5H), 1.86-1.49 (m, 12H), 1.45-1.34 (m, 6H), 1.34-1.22 (m, 9H), 1.17-1.07 (m, 2H), 1.03-0.97 (m, 2H) |

Example 119

N-(3-(2-cyclopropylpyrimidin-5-yl)phenyl)-4,4-difluoro-N-((4-(5-(trifluoromethyl)-1,2,4-oxadiazol-3-yl)bicyclo[2.2.2]octan-1-yl)methyl)cyclohexane-1-carboxamide (119)

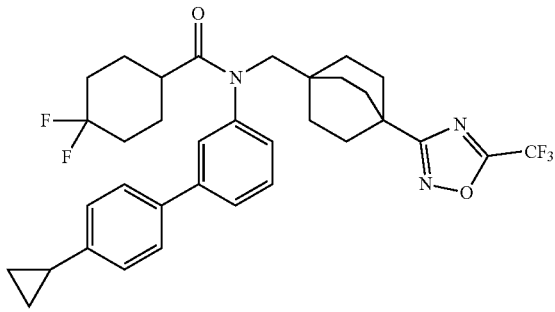

Step A: Intermediate 119A: Preparation of 3-(2-cyclopropylpyrimidin-5-yl)aniline

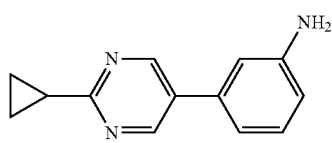

The title compound was prepared according to the method described for the synthesis of Intermediate 87B by substituting 3-bromoaninline and corresponding boronic acid where appropriate (160 mg, 0.757 mmol, 65% yield) as brown solid. MS (ESI) 212 (M+H).

Step B: Intermediate 119B: Preparation of methyl 4-(5-(trifluoromethyl)-1,2,4-oxadiazol-3-yl)bicyclo[2.2.2]octane-1-carboxylate

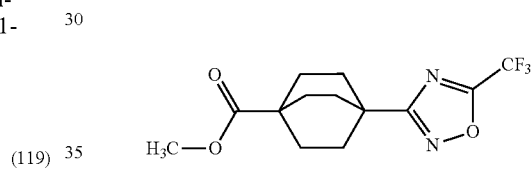

To a stirred solution of Intermediate 88C (5.0 g, 22.10 mmol) in DMF (50 mL) were added pyridine (8.90 mL, 110 mmol) and 2,2,2-trifluoroacetic anhydride (4.6 mL, 33.1 mmol) at 0° C. The reaction mixture was warmed to room temperature and stirred overnight. The reaction mixture was diluted with cold water and extracted with ethyl acetate (2×50 mL). The combined organic layers were dried over sodium sulphate, concentrated under reduced pressure. The crude material was purified by flash chromatography (40 g silica gel cartridge; A=Hex, B=EtOAc; 30 min grad.; 0% B to 30% B; flow rate=40 mL/min). The pure fractions were combined, concentrated under reduced pressure and dried in vacuo to afford the title compound (4.8 g, 15.78 mmol, 71% yield) as a gummy solid. MS (ESI) 305 (M+H).

Step C: Intermediate 119C: Preparation of (4-(5-(trifluoromethyl)-1,2,4-oxadiazol-3-yl) bicyclo[2.2.2]octan-1-yl)methanol

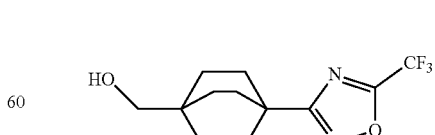

The title compound was prepared according to the method described for the synthesis of Intermediate 1B by substituting Intermediate 119B where appropriate (2.1 g, 7.60 mmol, 48% yield) as gummy liquid. MS (ESI) 277 (M+H).

Step D: Intermediate 119D: Preparation of 4-(5-(trifluoromethyl)-1,2,4-oxadiazol-3-yl) bicyclo[2.2.2]octane-1-carbaldehyde

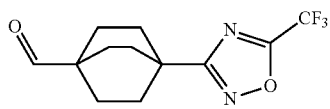 [SMILES: O=CC12CCC(c3noc(C(F)(F)F)n3)(CC1)CC2]

The title compound was prepared according to the method described for the synthesis of Intermediate 1C by substituting Intermediate 119C where appropriate (1.3 g, 4.74 mmol, 65% yield) as white solid. MS (ESI) 275 (M+H).

Step E: Intermediate 119E: Preparation of 3-(2-cyclopropylpyrimidin-5-yl)-N-((4-(5-(trifluoromethyl)-1,2,4-oxadiazol-3-yl)bicyclo[2.2.2]octan-1-yl)methyl)aniline

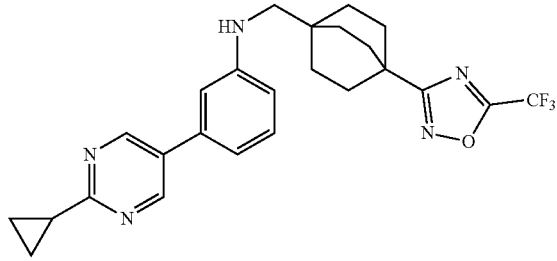 [SMILES: FC(F)(F)c1nc(C23CCC(CNc4cccc(-c5cnc(C6CC6)nc5)c4)(CC2)CC3)no1]

The title compound was prepared according to the method described for the synthesis of Intermediate 1F by substituting Intermediate 119A and Intermediate 119D where appropriate (380 mg, 0.809 mmol, 63% yield) as gummy solid. MS (ESI) 470 (M+H).

Step D: Example 119: Preparation of N-(3-(2-cyclopropylpyrimidin-5-yl)phenyl)-4,4-difluoro-N-((4-(5-(trifluoromethyl)-1,2,4-oxadiazol-3-yl)bicyclo[2.2.2]octan-1-yl) methyl)cyclohexane-1-carboxamide The title compound was prepared according to the method described for the synthesis of Example 5 by substituting Intermediate 119E and corresponding acid where appropriate (23.6 mg, 0.038 mmol, 72% yield). $^1$H NMR (400 MHz, DMSO-d$_6$) δ 9.02 (s, 2H), 8.85 (s, 1H), 7.88 (s, 1H), 7.75 (d, J=7.8 Hz, 1H), 7.59 (t, J=7.9 Hz, 1H), 7.53-7.46 (m, 1H), 3.72-3.60 (m, 2H), 2.47-2.39 (m, 1H), 2.31-2.22 (m, 1H), 2.03-1.85 (m, 3H), 1.83-1.69 (m, 7H), 1.67-1.56 (m, 3H), 1.55-1.38 (m, 6H), 1.13-1.02 (m, 4H) FXR EC$_{50}$ (nM)=290. MS (ESI) 616 (M+H).

Example 120

N-(3-(2-cyclopropylpyrimidin-5-yl)phenyl)-4,4-difluoro-N-((4-(5-(3-hydroxy-3-(trifluoromethyl)cyclobutyl)-1,2,4-oxadiazol-3-yl)bicyclo[2.2.2]octan-1-yl)methyl)cyclohexane-1-carboxamide (120)

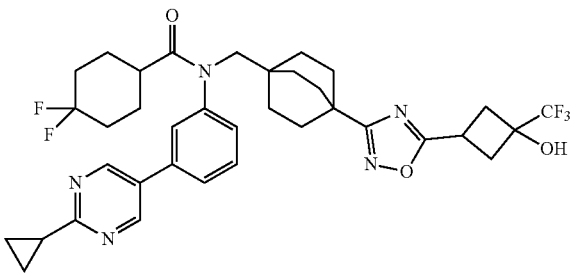

Step A. Intermediate 120A. Preparation of methyl 4-(hydroxymethyl)bicyclo[2.2.2]octane-1-carboxylate

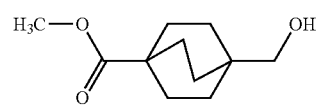

To a stirred solution of 4-(methoxycarbonyl)bicyclo[2.2.2]octane-1-carboxylic acid (10 g, 47.1 mmol) in THF (100 mL) was added BH$_3$.DMS (14.28 mL, 141 mmol) at 0° C. The reaction mixture was warmed to room temperature and stirred for 2 h. The reaction was quenched with slow addition of methanol at 0° C. The reaction mixture was stirred overnight at room temperature. The reaction mixture was concentrated and the residue was diluted with water. The aqueous solution was extracted with ethyl acetate (2×50 mL). The combined organic layers were dried over sodium sulphate and concentrated under reduced pressure. The crude material was purified by flash chromatography (40 g silica gel cartridge; A=Hex, B=EtOAc; 30 min grad.; 0% B to 40% B; flow rate=40 mL/min). The pure fractions were combined, concentrated under reduced pressure and dried in vacuo to afford the title compound (7 g, 35.3 mmol, 75% yield). $^1$H NMR (400 MHz, DMSO-d$_6$) δ 4.12 (dd, J=2.8, 4.0 Hz, 1H), 3.65 (s, 3H), 3.29 (s, 2H), 1.82-1.77 (m, 6H), 1.47-1.42 (m, 6H).

Step B Intermediate 120B. Preparation of methyl 4-formylbicyclo[2.2.2]octane-1-carboxylate

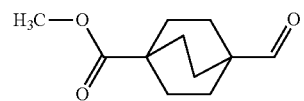

The title compound was prepared according to the method described for the synthesis of Intermediate 1C by substituting Intermediate 120A where appropriate: (900 mg, 4.59 mmol, 91% yield) as a gummy solid. $^1$H NMR (400 MHz, DMSO-d$_6$) δ 9.43 (s, 1H), 3.59 (s, 3H), 1.78-1.57 (m, 12H). MS (ESI) 197 (M+H).

Step C. Intermediate 120C. Preparation of methyl 4-(((3-bromophenyl)amino) methyl)bicyclo[2.2.2] octane-1-carboxylate

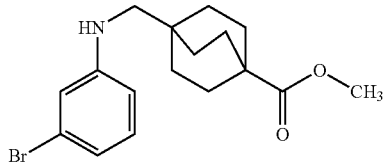 [SMILES: COC(=O)C12CCC(CNc3cccc(Br)c3)(CC1)CC2]

The title compound was prepared according to the method described for the synthesis of Intermediate 1F by substituting 3-bromoaniline and Intermediate 88B where appropriate: (2.0 g, 5.68 mmol, 81% yield) as brown wax. MS (ESI) 352 (M+H).

Step D. Intermediate 120D. Preparation of 4-(((3-bromophenyl)amino)methyl) bicyclo[2.2.2]octane-1-carboxylic acid

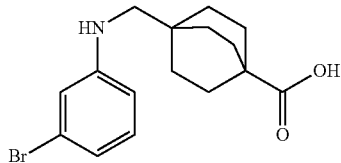 [SMILES: O=C(O)C12CCC(CNc3cccc(Br)c3)(CC1)CC2]

To a stirred solution of Intermediate 120C (3 g, 8.52 mmol) in MeOH (30 mL) was added a solution of NaOH (1.70 g, 42.6 mmol) in water (10 mL) at room temperature. The reaction mixture was heated at 60° C. for 1 h. The reaction mixture was concentrated under reduced pressure, diluted with water (20 mL), acidified with aqueous 1.5N HCl (20 mL) and extracted with ethyl acetate (2×20 mL). The combined organic layers were dried over anhydrous sodium sulphate and concentrated under reduced pressure to afford the title compound (2.8 g, 8.28 mmol, 97% yield) as a brownish solid. MS (ESI) 338 (M+H).

Step E. Intermediate 120E. Preparation of 4-(((3-bromophenyl)amino)methyl) bicyclo[2.2.2]octane-1-carboxamide

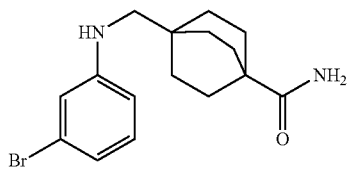 [SMILES: NC(=O)C12CCC(CNc3cccc(Br)c3)(CC1)CC2]

The title compound was prepared according to the method described for the synthesis of Intermediate 99C by substituting Intermediate 120D where appropriate: (2.0 g, 5.93 mmol, 100% yield). MS (ESI) 338 (M+H).

Step F. Intermediate 120F. Preparation of 4-(((3-bromophenyl)amino)methyl) bicyclo[2.2.2]octane-1-carbonitrile

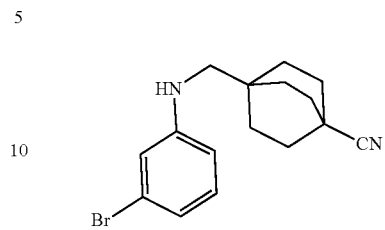

To a stirred solution of Intermediate 120E (2.0 g, 5.93 mmol) in pyridine (50 mL) was added imidazole (1.009 g, 14.83 mmol) at room temperature. The reaction mixture was cooled to 0-5° C. POCl$_3$ (0.60 mL, 6.52 mmol) was added drop wise to the reaction mixture. The reaction mixture was warmed to room temperature and stirred for 5 h. The reaction mixture was diluted with ice cold water (100 mL) and extracted with ethyl acetate (2×70 mL). The combined organic layers were washed with aqueous 1.5 N HCl solution (2×50 mL), water (100 mL), brine solution (100 mL), dried over anhydrous sodium sulphate and concentrated under reduced pressure. The crude material was purified by flash chromatography (40 g silica gel cartridge; A=Hex, B=EtOAc; 30 min grad.; 0% B to 60% B; flow rate=40 mL/min). The pure fractions were combined, concentrated under reduced pressure and dried in vacuo to afford the title compound (1.0 g, 3.13 mmol, 53% yield) as white solid. MS (ESI) 336 (M+18) (NH$_3$ adduct).

Step G. Intermediate 120G. Preparation of (Z)-4-(((3-bromophenyl)amino)methyl)-N'-hydroxybicyclo [2.2.2]octane-1-carboximidamide

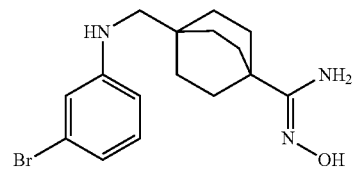 [SMILES: N/C(=N\O)C12CCC(CNc3cccc(Br)c3)(CC1)CC2]

The title compound was prepared according to the method described for the synthesis of Intermediate 41A by substituting Intermediate 120F where appropriate: (1.0 g, 2.84 mmol, 91% yield) as a white solid. MS (ESI) 352 (M+H).

Step H. Intermediate 120H. Preparation of 3-(3-(4-(((3-bromophenyl)amino)methyl) bicyclo[2.2.2] octan-1-yl)-1,2,4-oxadiazol-5-yl)-1-(trifluoromethyl) cyclobutan-1-ol

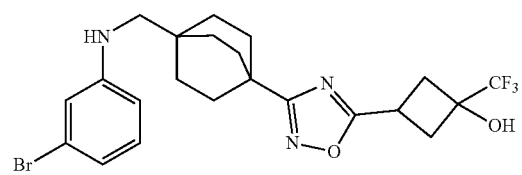 [SMILES: OC1(C(F)(F)F)CC(c2nc(C34CCC(CNc5cccc(Br)c5)(CC3)CC4)no2)C1]

The title compound was prepared according to the method described for the synthesis of Intermediate 1A by substituting Intermediate 120G and corresponding acid where appropriate (360 mg, 0.719 mmol, 84% yield) as gummy solid. MS (ESI) 500 (M+H).

Step I. Intermediate 120I. Preparation of 3-(3-(4-(((3-(2-cyclopropylpyrimidin-5-yl)phenyl)amino)methyl)bicyclo[2.2.2]octan-1-yl)-1,2,4-oxadiazol-5-yl)-1-(trifluoromethyl)cyclobutan-1-ol

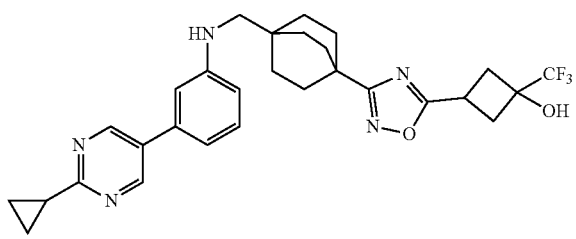 [SMILES: OC1(C(F)(F)F)CC(c2nc(C34CCC(CNc5cccc(-c6cnc(C7CC7)nc6)c5)(CC3)CC4)no2)C1]

The title compound was prepared according to the method described for the synthesis of Intermediate 87B by substituting Intermediate 120H where appropriate (100 mg, 0.185 mmol, 77% yield) as gummy solid. MS (ESI) 540 (M+H).

Step J. Example 120: Preparation of N-(3-(2-cyclopropylpyrimidin-5-yl)phenyl)-4,4-difluoro-N-((4-(5-(3-hydroxy-3-(trifluoromethyl)cyclobutyl)-1,2,4-oxadiazol-3-yl) bicyclo[2.2.2]octan-1-yl)methyl) cyclohexane-1-carboxamide The title compound was prepared according to the method described for the synthesis of Example 5 by substituting Intermediate 120I and corresponding acid where appropriate (5.4 mg, 7.87 μmol, 21% yield). $^1$H NMR (400 MHz, DMSO-$d_6$) δ 9.02 (s, 2H), 7.87 (s, 1H), 7.75 (br d, J=7.3 Hz, 1H), 7.58 (t, J=7.8 Hz, 1H), 7.53-7.43 (m, 1H), 6.86 (s, 1H), 3.65 (s, 2H), 3.49 (t, J=9.0 Hz, 1H), 2.91-2.83 (m, 2H), 2.47-2.38 (m, 2H), 2.30-2.23 (m, 1H), 2.02-1.88 (m, 2H), 1.82-1.68 (m, 9H), 1.67-1.48 (m, 4H), 1.46-1.38 (m, 6H), 1.13-1.03 (m, 4H). FXR $EC_{50}$ (nM)=2000. MS (ESI) 686 (M+H).

Example 121

N-((4-(5-(tert-butyl)-1,2,4-oxadiazol-3-yl)bicyclo[2.2.2]octan-1-yl)methyl)-N-(4'-(dimethylphosphoryl)-[1,1'-biphenyl]-3-yl)tetrahydro-2H-pyran-4-carboxamide (121)

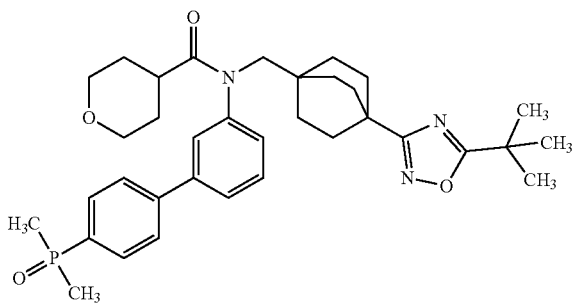

Step A. Intermediate 121A. Preparation of (4-bromophenyl)dimethylphosphine oxide

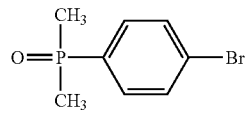

To a stirred solution of 1-bromo-4-iodobenzene (5 g, 17.67 mmol) in DMF (10 mL) were added dimethylphosphine oxide (1.517 g, 19.44 mmol), tripotassium phosphate (4.13 g, 19.44 mmol) and XantPhos (0.614 g, 1.060 mmol) at room temperature. The reaction mixture was degassed and back-filled with argon. PdOAc$_2$ (0.594 g, 0.884 mmol) was added to the reaction mixture and the reaction vial was sealed. The reaction mixture was heated at 120° C. overnight. The reaction mixture was cooled to room temperature and concentrated under reduced pressure. The crude material was purified by flash chromatography (40 g silica gel cartridge; A=chloroform, B=methanol; 30 min grad.; 0% B to 5% B; flow rate=40 mL/min). The pure fractions were combined, concentrated under reduced pressure and dried in vacuo to afford the title compound (3.7 g, 12.07 mmol, 68% yield) as brown solid. MS (ESI) 233 (M+H).

Step B. Intermediate 121B. Preparation of (4-(5,5-dimethyl-1,3,2-dioxaborinan-2-yl)phenyl)dimethylphosphine oxide

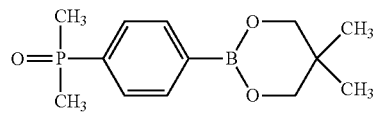

To a stirred solution of Intermediate 121A (750 mg, 3.22 mmol) in dioxane (20 mL) was added bis(neopentyl glycolato)diboron (1454 mg, 6.44 mmol) followed by potassium acetate (1420 mg, 14.48 mmol) at room temperature. The reaction mixture was degassed and back-filled with argon. PdCl$_2$(dppf) (118 mg, 0.161 mmol) was added to the reaction mixture and the reaction vial was sealed. The reaction mixture was heated at 110° C. for 3 h. The reaction mixture was cooled to room temperature, diluted with ethyl acetate (50 mL), washed with water (2×50 mL), brine solution (30 mL), dried over anhydrous sodium sulfate and concentrated under reduced pressure. The crude material was purified by flash chromatography (40 g silica gel cartridge; A=Hex, B=EtOAc; 30 min grad.; 0% B to 40% B; flow rate=40 mL/min). The pure fractions were combined, concentrated under reduced pressure and dried in vacuo to afford the title compound (650 mg, 2.052 mmol, 64% yield) as white solid. MS (ESI) 199 (M+H). (boronic acid fragment pattern).

Step C. Intermediate 121C. Preparation of (5'-amino-2'-fluoro-[1,1'-biphenyl]-4-yl) dimethylphosphine oxide (220 mg, 0.836 mmol, 53% yield)

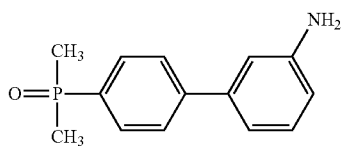

The title compound was prepared according to the method described for the synthesis of Intermediate 87B by substituting Intermediate 121B and 3-bromoaniline where appropriate (220 mg, 0.836 mmol, 53% yield) as a black gummy solid. MS (ESI) 264 (M+H).

Step D. Intermediate 121D. Preparation of (5'-(((4-(5-(tert-butyl)-1,2,4-oxadiazol-3-yl) bicyclo[2.2.2]octan-1-yl)methyl)amino)-2'-fluoro-[1,1'-biphenyl]-4-yl)dimethylphosphine oxide

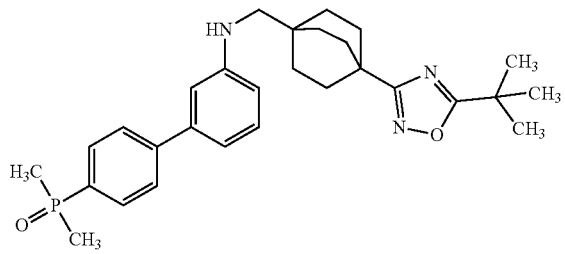 [SMILES: CC(C)(C)c1nc(C23CCC(CNc4cccc(-c5ccc(P(C)(C)=O)cc5)c4)(CC2)CC3)no1]

The title compound was prepared according to the method described for the synthesis of Intermediate 1F by substituting Intermediate 121C and Intermediate 88F where appropriate ((150 mg, 0.288 mmol, 76% yield) as black gummy solid. MS (ESI) 510 (M+H).

Step E. Example 121. Preparation of N-((4-(5-(tert-butyl)-1,2,4-oxadiazol-3-yl) bicyclo[2.2.2]octan-1-yl)methyl)-N-(4'-(dimethylphosphoryl)-[1,1'-biphenyl]-3-yl)tetrahydro-2H-pyran-4-carboxamide The title compound was prepared according to the method described for the synthesis of Example 5 by substituting Intermediate 121D and corresponding acid where appropriate (12.5 mg, 0.018 mmol, 47% yield). $^1$H NMR (400 MHz, DMSO-$d_6$) δ 7.90 (dd, J=8.3, 11.2 Hz, 2H), 7.77-7.62 (m, 3H), 7.57-7.49 (m, 1H), 7.47-7.39 (m, 1H), 3.82-3.72 (m, 2H), 3.68-3.54 (m, 3H), 3.13-3.00 (m, 2H), 1.79-1.69 (m, 9H), 1.68 (s, 3H), 1.64-1.55 (m, 2H), 1.52-1.37 (m, 8H), 1.33 (s, 9H) FXR EC$_{50}$ (nM)=1480. MS (ESI) 622 (M+H).

Example 122

N-((4-(5-(1,1-difluoroethyl)-1,2,4-oxadiazol-3-yl) bicyclo[2.2.2]octan-1-yl)methyl)-N-(4'-(dimethylphosphoryl)-6-fluoro-[1,1'-biphenyl]-3-yl)tetrahydro-2H-pyran-4-carboxamide (122)

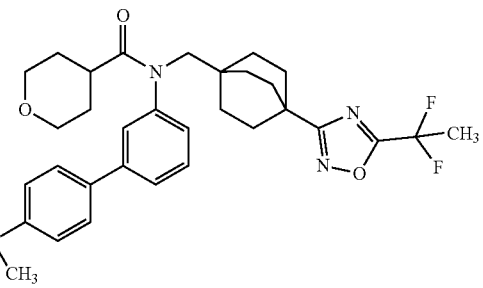

Step A. Intermediate 122A: Preparation of (5'-(((4-(5-(1,1-difluoroethyl)-1,2,4-oxadiazol-3-yl)bicyclo[2.2.2]octan-1-yl)methyl)amino)-2'-fluoro-[1,1'-biphenyl]-4-yl) dimethylphosphine oxide

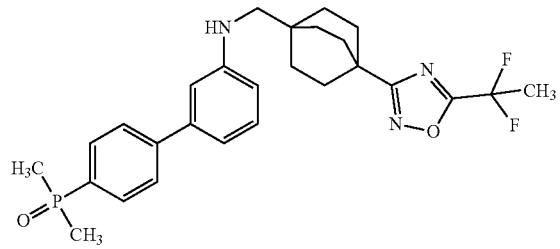 [SMILES: CC(F)(F)c1nc(C23CCC(CNc4cccc(-c5ccc(P(C)(C)=O)cc5)c4)(CC2)CC3)no1]

The title compound was prepared according to the method described for the synthesis of Intermediate 1F by substituting Intermediate 121C and Intermediate 105C where appropriate (120 mg, 0.232 mmol, 63% yield) as brown gummy solid. MS (ESI) 518 (M+H).

Step B. Example 122: Preparation of N-((4-(5-(1,1-difluoroethyl)-1,2,4-oxadiazol-3-yl) bicyclo[2.2.2]octan-1-yl)methyl)-N-(4'-(dimethylphosphoryl)-6-fluoro-[1,1'-biphenyl]-3-yl)tetrahydro-2H-pyran-4-carboxamide The title compound was prepared according to the method described for the synthesis of Example 5 by substituting Intermediate 122A and corresponding acid where appropriate (11.4 mg, 0.017 mmol, 43% yield). $^1$H NMR (400 MHz, DMSO-$d_6$) δ 7.90 (dd, J=8.4, 11.1 Hz, 2H), 7.78-7.64 (m, 3H), 7.59-7.51 (m, 1H), 7.47-7.37 (m, 1H), 3.82-3.72 (m, 2H), 3.70-3.55 (m, 3H), 3.12-2.99 (m, 2H), 2.14 (t, J=19.7 Hz, 3H), 1.83-1.74 (m, 6H), 1.71 (s, 3H), 1.68 (s, 3H), 1.65-1.55 (m, 2H), 1.53-1.37 (m, 8H) FXR EC$_{50}$ (nM) =1323. MS (ESI) 630 (M+H).

Example 123

N-((4-(5-(tert-Butyl)-1,3,4-oxadiazol-2-yl)bicyclo[2.2.2]octan-1-yl)methyl)-N-(3-(3-cyclopropyl-1,2,4-oxadiazol-5-yl)phenyl)-4,4-difluorocyclohexane-1-carboxamide

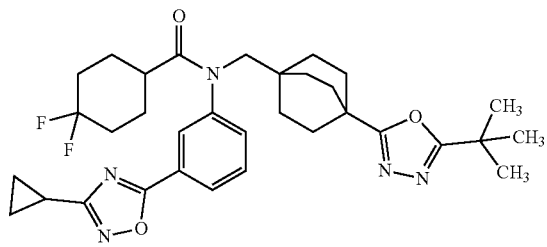

(123)

Step A. Intermediate 123A. Preparation of methyl 4-(2-pivaloylhydrazine-1-carbonyl)bicyclo[2.2.2]octane-1-carboxylate

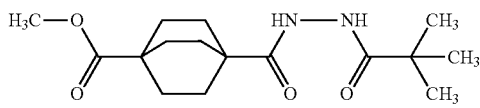

To a stirred solution of 4-(methoxycarbonyl)bicyclo[2.2.2]octane-1-carboxylic acid (1 g, 4.71 mmol) in DMF (10 mL) were added pivalohydrazide (0.60 g, 5.18 mmol), HATU (2.33 g, 6.12 mmol) and DIPEA (2.5 mL, 14.13 mmol) at room temperature. The reaction mixture was stirred at room temperature for 12 h. The reaction mixture was poured into cold water and extracted with ethyl acetate (2×150 mL). The combined organic layers were dried over anhydrous sodium sulphate and concentrated under reduced pressure. The crude material was purified by flash chromatography (40 g silica gel cartridge; A=Hex, B=EtOAc; 30 min grad.; 0% B to 30% B; flow rate=40 mL/min). The pure fractions were combined, concentrated under reduced pressure and dried in vacuo to afford the title compound (900 mg, 2.90 mmol, 61% yield). $^1$H NMR (300 MHz, DMSO-$d_6$) δ 9.21 (d, J=0.90 Hz, 1H), 9.15 (s, 1H), 3.57 (s, 3H), 1.85-1.60 (m, 12H), 1.12 (s, 9H). MS (ESI) 311 (M+H).

Step B. Intermediate 123B. Preparation of methyl 4-(5-(tert-butyl)-1,3,4-oxadiazol-2-yl)bicyclo[2.2.2]octane-1-carboxylate

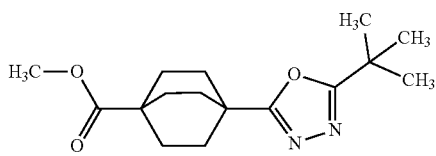 [SMILES: COC(=O)C12CCC(c3nnc(C(C)(C)C)o3)(CC1)CC2]

To a stirred solution of Intermediate 123A (700 mg, 2.25 mmol) in MeCN (1 mL) were added triphenylphosphine (1240 mg, 4.74 mmol) and CCl$_4$ (0.24 mL, 2.481 mmol) at room temperature. The reaction mixture was heated at 90° C. for 12 h. The reaction mixture was cooled to room temperature and concentrated under reduced pressure. The residue was dissolved in EtOAc (50 mL), washed with water (30 mL), dried over anhydrous sodium sulphate and evaporated under reduced pressure. The crude material was purified by flash chromatography (24 g silica gel cartridge; A=Hex, B=EtOAc; 30 min grad.; 0% B to 60% B; flow rate=30 mL/min). The pure fractions were combined, concentrated under reduced pressure and dried in vacuo to afford the title compound (650 mg, 2.22 mmol, 99% yield). $^1$H NMR (300 MHz, DMSO-$d_6$) δ 3.60 (s, 3H), 1.89-1.80 (m, 12H), 1.32 (s, 9H). MS (ESI) 293.1 (M+H).

Step C. Intermediate 123C. Preparation of (4-(5-(tert-butyl)-1,3,4-oxadiazol-2-yl) bicyclo[2.2.2]octan-1-yl)methanol

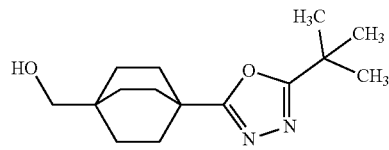 [SMILES: CC(C)(C)c1nnc(C23CCC(CO)(CC2)CC3)o1]

The title compound was prepared according to the method described for the synthesis of Intermediate 1B by substituting Intermediate 123B where appropriate (720 mg, 2.72 mmol, 100% yield). $^1$H NMR (400 MHz, DMSO-$d_6$) δ 4.40 (t, J=5.5 Hz, 1H), 3.08 (d, J=5.5 Hz, 2H), 1.89-1.75 (m, 6H), 1.51-1.37 (m, 6H), 1.38 (s, 9H).

Step D. Intermediate 123D. Preparation of 4-(5-(tert-butyl)-1,3,4-oxadiazol-2-yl) bicyclo[2.2.2]octane-1-carbaldehyde

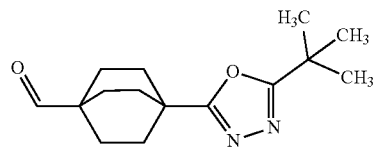 [SMILES: CC(C)(C)c1nnc(C23CCC(C=O)(CC2)CC3)o1]

The title compound was prepared according to the method described for the synthesis of Intermediate 1C by substituting Intermediate 123C where appropriate (600 mg, 2.287 mmol, 86% yield). $^1$H NMR (400 MHz, DMSO-$d_6$) δ 9.46 (s, 1H), 1.96-1.83 (m, 6H), 1.75-1.63 (m, 6H), 1.33 (s, 9H). MS (ESI) 263.2 (M+H).

Step E. Intermediate 123E. Preparation of N-((4-(5-(tert-Butyl)-1,3,4-oxadiazol-2-yl) bicyclo[2.2.2]octan-1-yl)methyl)-3-(3-cyclopropyl-1,2,4-oxadiazol-5-yl)aniline

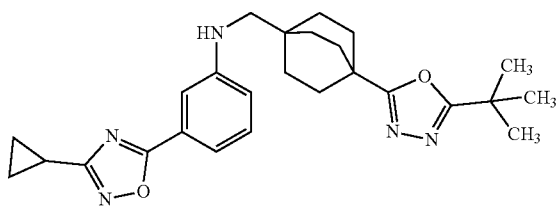 [SMILES: CC(C)(C)c1nnc(C23CCC(CNc4cccc(-c5nc(C6CC6)no5)c4)(CC2)CC3)o1]

The title compound was prepared according to the method described for the synthesis of Intermediate 1F by substituting Intermediate 13A and 133D where appropriate: (60 mg, 0.134 mmol, 50% yield) as white solid. MS (ESI) 448 (M+H).

Step F. Example 123. Preparation of N-((4-(5-(tert-Butyl)-1,3,4-oxadiazol-2-yl) bicyclo[2.2.2]octan-1-yl)methyl)-N-(3-(3-cyclopropyl-1,2,4-oxadiazol-5-yl)phenyl)-4,4-difluorocyclohexane-1-carboxamide The title compound was prepared according to the method described for the synthesis of Example 5 by substituting Intermediate 123E and commercially available 4,4-difluorocyclohexane-1-carboxylic acid where appropriate: (3 mg, 5.05 μmol, 11% yield). $^1$H NMR (400 MHz, DMSO-d$_6$) δ 8.11-7.97 (m, 2H), 7.79 (d, J=8.1 Hz, 1H), 7.69 (t, J=7.8 Hz, 1H), 3.64 (br. s., 2H), 2.38 (br. s., 1H), 2.22 (ddd, J=13.0, 8.4, 4.8 Hz, 1H), 1.96 (br. s., 1H), 1.82-1.55 (m, 11H), 1.48 (d, J=16.1 Hz, 2H), 1.45-1.35 (m, 6H), 1.30 (s, 9H), 1.16-1.11 (m, 2H), 1.04-0.97 (m, 2H). FXR EC$_{50}$ (nM)=280; MS (ESI) 594 (M+H).

The title compound was prepared according to the method described for the synthesis of Intermediate 1F by substituting Intermediate 40C and Intermediate 123D where appropriate: (60 mg, 0.085 mmol, 42% yield) as a brown solid. MS (ESI) 447 (M+H).

Step B. Example 124. Preparation of N-((4-(5-(tert-Butyl)-1,3,4-oxadiazol-2-yl) bicyclo[2.2.2]octan-1-yl)methyl)-N-(3-(5-cyclopropylisoxazol-3-yl)phenyl)-4,4-difluorocyclohexane-1-carboxamide The title compound was prepared according to the method described for the synthesis of Example 5 by substituting Intermediate 124A and commercially available 4,4-difluorocyclohexane-1-carboxylic acid where appropriate: (3.1 mg, 0.05 mmol, 11% yield). $^1$H NMR (400 MHz, DMSO-d$_6$) δ 7.91-7.73 (m, 2H), 7.66-7.48 (m, 2H), 6.85 (s, 1H), 3.62 (br. s., 2H), 2.39 (br. s., 1H), 2.23-2.12 (m, 1H), 1.94 (br. s., 2H), 1.85 (br. s., 1H), 1.80-1.67 (m, 7H), 1.67-1.53 (m, 4H), 1.53-1.35 (m, 6H), 1.34-1.27 (m, 9H), 1.16-1.08 (m, 2H), 0.99-0.88 (m, 2H). FXR EC$_{50}$ (nM)=467; MS (ESI) 593 (M+H).

Example 124

N-((4-(5-(tert-Butyl)-1,3,4-oxadiazol-2-yl)bicyclo[2.2.2]octan-1-yl)methyl)-N-(3-(5-cyclopropylisoxazol-3-yl)phenyl)-4,4-difluorocyclohexane-1-carboxamide Example 125

N-((4-(3-(tert-Butyl)-1,2,4-oxadiazol-5-yl)bicyclo[2.2.2]octan-1-yl)methyl)-3,5-dichloro-N-(3-(2-ethoxypyrimidin-5-yl)phenyl)benzamide

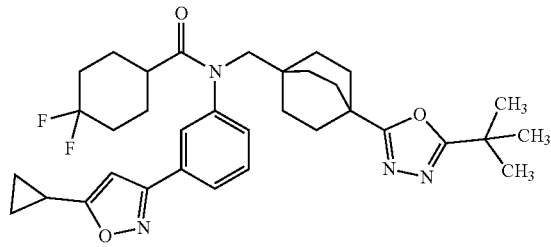

(124)

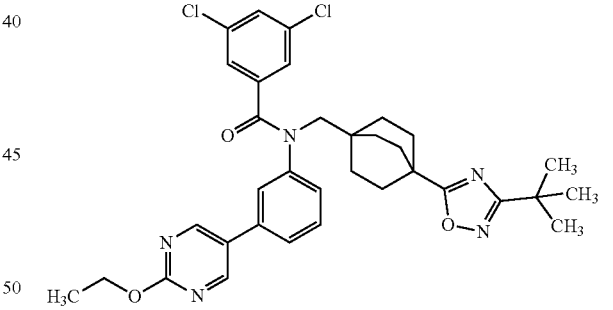

(125)

Step A. Intermediate 124A. Preparation of N-((4-(5-(tert-Butyl)-1,3,4-oxadiazol-2-yl) bicyclo[2.2.2]octan-1-yl)methyl)-3-(5-cyclopropylisoxazol-3-yl)aniline

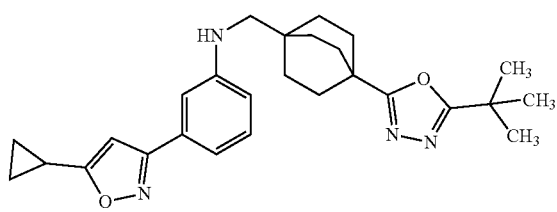 [SMILES: CC(C)(C)c1nnc(C23CCC(CNc4cccc(-c5cc(C6CC6)on5)c4)(CC2)CC3)o1]

The title compound was prepared according to the method described for the synthesis of Example 5 by substituting Intermediate 87B and commercially available 3,5-dichlorobenzoic acid where appropriate (7.1 mg, 0.011 mmol, 25% yield). $^1$H NMR (400 MHz, DMSO-d$_6$) δ 8.83 (s, 2H), 7.77 (s, 1H), 7.54 (d, J=7.8 Hz, 1H), 7.50-7.45 (m, 1H), 7.42-7.35 (m, 1H), 7.34-7.22 (m, 3H), 4.40 (q, J=6.9 Hz, 2H), 3.86 (s, 2H), 1.88-1.71 (m, 6H), 1.60-1.43 (m, 6H), 1.36 (t, J=7.1 Hz, 3H), 1.26 (s, 9H). FXR EC$_{50}$ (nM)=726. MS (ESI) 634 (M+H).

Example 126

N-((4-(3-(tert-Butyl)-1,2,4-oxadiazol-5-yl)bicyclo[2.2.2]octan-1-yl)methyl)-3-chloro-N-(3-(2-ethoxypyrimidin-5-yl)phenyl)benzamide

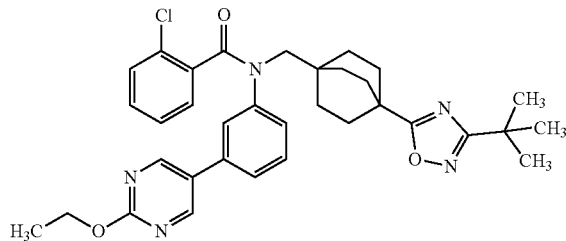

(126)

The title compound was prepared according to the method described for the synthesis of Example 5 by substituting Intermediate 87B and commercially available 2-chlorobenzoic acid where appropriate (5.8 mg, 0.009 mmol, 22% yield). $^1$H NMR (400 MHz, DMSO-$d_6$) δ 8.77 (s, 2H), 7.66 (s, 1H), 7.50-7.41 (m, 1H), 7.37-7.26 (m, 4H), 7.24-7.14 (m, 2H), 4.40 (q, J=7.1 Hz, 2H), 3.98-3.86 (m, 2H), 1.88-1.78 (m, 6H), 1.59-1.48 (m, 6H), 1.36 (t, J=7.1 Hz, 3H), 1.26 (s, 9H). FXR $EC_{50}$ (nM)=154. MS (ESI) 600 (M+H).

Example 127

N-((4-(3-(tert-Butyl)-1,2,4-oxadiazol-5-yl)bicyclo[2.2.2]octan-1-yl)methyl)-4,4-difluoro-N-(3-(6-oxo-1,6-dihydropyridazin-4-yl)phenyl)cyclohexane-1-carboxamide

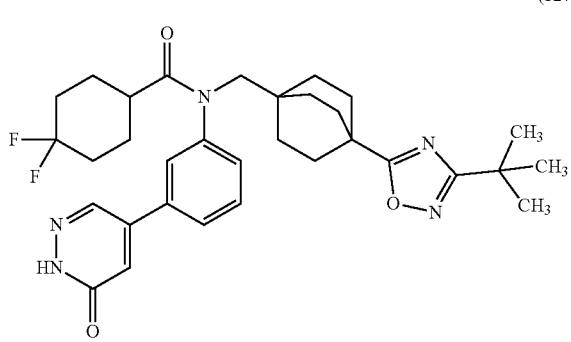

(127)

Step A. Intermediate 127A. Preparation of 5-(3-aminophenyl)pyridazin-3(2H)-one

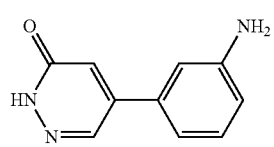 [SMILES: Nc1cccc(-c2cn[nH]c(=O)c2)c1]

The title compound was prepared according to the method described for the synthesis of Intermediate 87B by substituting 5-chloropyridazin-3(2H)-one and (3-aminophenyl)boronic acid where appropriate (450 mg, 2.404 mmol, 66% yield) as a white solid. MS (ESI) 188 (M+H).

Step B. Intermediate 127B. Preparation of 5-(3-(((4-(3-(tert-Butyl)-1,2,4-oxadiazol-5-yl)bicyclo[2.2.2]octan-1-yl)methyl)amino)phenyl)pyridazin-3(2H)-one

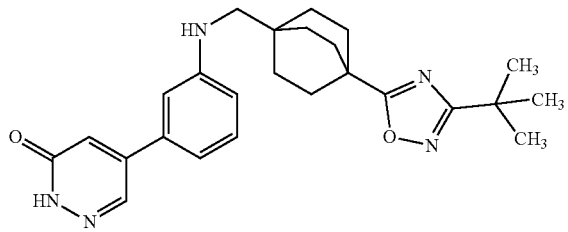 [SMILES: CC(C)(C)c1noc(C23CCC(CNc4cccc(-c5cn[nH]c(=O)c5)c4)(CC2)CC3)n1]

The title compound was prepared according to the method described for the synthesis of Intermediate 1F by substituting Intermediate 127A and Intermediate 69C where appropriate (75 mg, 0.173 mmol, 65% yield) as an off-white solid. MS (ESI) 434 (M+H).

Step C. Example 127. Preparation of N-((4-(3-(tert-Butyl)-1,2,4-oxadiazol-5-yl) bicyclo[2.2.2]octan-1-yl)methyl)-4,4-difluoro-N-(3-(6-oxo-1,6-dihydropyridazin-4-yl)phenyl)cyclohexane-1-carboxamide The title compound was prepared according to the method described for the synthesis of Example 5 by substituting Intermediate 127C and commercially available 4,4-difluorocyclohexane-1-carboxylic acid where appropriate (4 mg, 6.90 µmol, 15% yield). $^1$H NMR (400 MHz, DMSO-$d_6$) δ 13.16 (s, 1H), 8.43-8.32 (m, 1H), 7.94 (s, 1H), 7.86-7.77 (m, 1H), 7.64-7.53 (m, 2H), 7.28 (s, 1H), 3.65 (br s, 2H), 2.44-2.37 (m, 1H), 2.02-1.88 (m, 2H), 1.85-1.69 (m, 8H), 1.67-1.47 (m, 4H), 1.47-1.35 (m, 6H), 1.26 (s, 9H). FXR $EC_{50}$ (nM)=4000. MS (ESI) 580 (M+H).

Example 128

N-((4-(5-(2-fluoropropan-2-yl)-1,2,4-oxadiazol-3-yl)bicyclo[2.2.2]octan-1-yl)methyl)-N-(3-(6-oxo-1,6-dihydropyridazin-4-yl)phenyl)tetrahydro-2H-pyran-4-carboxamide

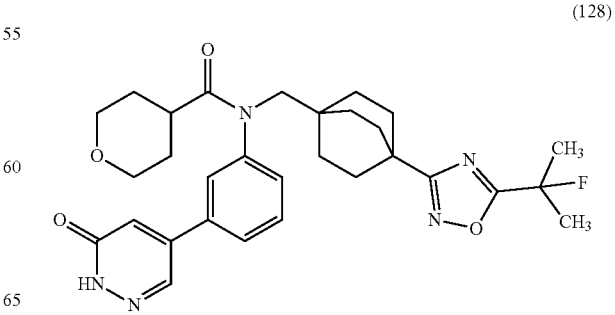

(128)

Step A. Intermediate 128A. Preparation of methyl 4-(5-(2-fluoropropan-2-yl)-1,2,4-oxadiazol-3-yl)bicyclo[2.2.2]octane-1-carboxylate

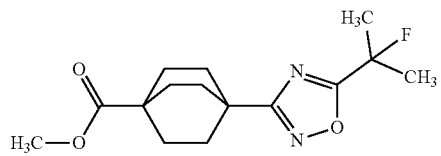 [SMILES: COC(=O)C12CCC(c3noc(C(C)(C)F)n3)(CC1)CC2]

The title compound was prepared according to the method described for the synthesis of Intermediate 1A by substituting Intermediate 88C and corresponding acid where appropriate (8.2 g, 27.7 mmol, 62% yield) colorless gummy solid. MS (ESI) 297 (M+H).

Step B. Intermediate 128B. Preparation of (4-(5-(2-fluoropropan-2-yl)-1,2,4-oxadiazol-3-yl)bicyclo[2.2.2]octan-1-yl)methanol

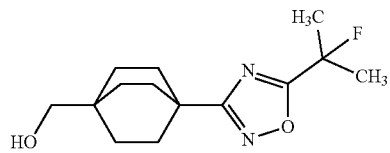 [SMILES: CC(C)(F)c1nc(C23CCC(CO)(CC2)CC3)no1]

The title compound was prepared according to the method described for the synthesis of Intermediate 1B by substituting Intermediate 128A where appropriate (6.5 g, 24.22 mmol, 96% yield) as a colorless liquid. MS (ESI) 269 (M+H).

Step C. Intermediate 128C. Preparation of 4-(5-(2-fluoropropan-2-yl)-1,2,4-oxadiazol-3-yl)bicyclo[2.2.2]octane-1-carbaldehyde

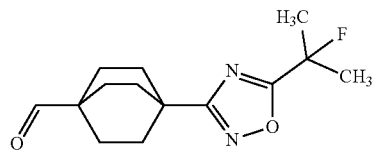 [SMILES: CC(C)(F)c1nc(C23CCC(C=O)(CC2)CC3)no1]

The title compound was prepared according to the method described for the synthesis of Intermediate 1C by substituting Intermediate 128B where appropriate (1.9 g, 7.13 mmol, 63% yield) as a colorless white gummy solid. $^1$H NMR (400 MHz, DMSO-$d_6$) δ 9.50-9.40 (m, 1H), 1.97-1.50 (m, 18H).

Step D. Intermediate 128D. Preparation of 5-(3-(((4-(5-(2-fluoropropan-2-yl)-1,2,4-oxadiazol-3-yl)bicyclo[2.2.2]octan-1-yl)methyl)amino)phenyl)pyridazin-3(2H)-one

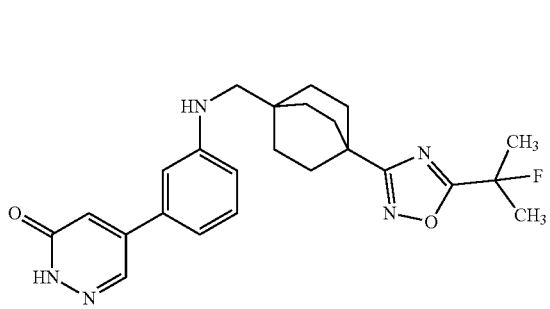 [SMILES: CC(C)(F)c1nc(C23CCC(CNc4cccc(-c5cn[nH]c(=O)c5)c4)(CC2)CC3)no1]

The title compound was prepared according to the method described for the synthesis of Intermediate 1F by substituting Intermediate 127A and Intermediate 128C where appropriate (110 mg, 0.251 mmol, 47% yield) as an off-white solid. MS (ESI) 438 (M+H).

Step E: Example 128. Preparation of N-((4-(5-(2-fluoropropan-2-yl)-1,2,4-oxadiazol-3-yl)bicyclo[2.2.2]octan-1-yl)methyl)-N-(3-(6-oxo-1,6-dihydropyridazin-4-yl)phenyl)tetrahydro-2H-pyran-4-carboxamide The title compound was prepared according to the method described for the synthesis of Example 5 by substituting Intermediate 128D and commercially available tetrahydro-2H-pyran-4-carboxylic acid where appropriate (6.4 mg, 0.012 mmol, 26% yield). $^1$H NMR (400 MHz, DMSO-$d_6$) δ 13.22-13.09 (m, 1H), 8.38 (d, J=2.0 Hz, 1H), 7.95 (s, 1H), 7.86-7.75 (m, 1H), 7.64-7.53 (m, 2H), 7.31-7.23 (m, 1H), 3.79-3.71 (m, 2H), 3.69-3.58 (m, 1H), 3.07-2.94 (m, 2H), 2.49-2.45 (m, 1H), 1.84-1.71 (m, 12H), 1.67-1.55 (m, 2H), 1.52-1.33 (m, 8H). One proton buried under solvent peak. FXR $EC_{50}$ (nM)=4000. MS (ESI) 550 (M+H).

Example 129

N-((4-(5-(1,1-difluoroethyl)-1,2,4-oxadiazol-3-yl)bicyclo[2.2.2]octan-1-yl)methyl)-N-(3-(6-oxo-1,6-dihydropyridazin-4-yl)phenyl)tetrahydro-2H-pyran-4-carboxamide (129)

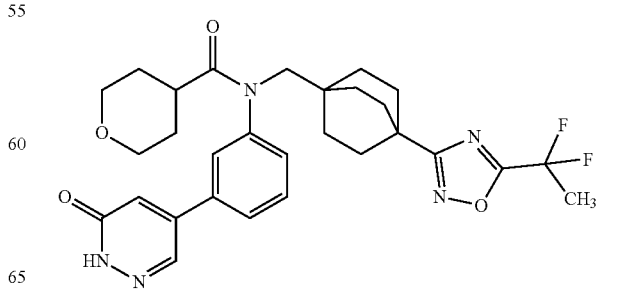

Step A. Intermediate 129A. Preparation of 5-(3-(((4-(5-(1,1-difluoroethyl)-1,2,4-oxadiazol-3-yl)bicyclo[2.2.2]octan-1-yl)methyl)amino)phenyl)pyridazin-3(2H)-one

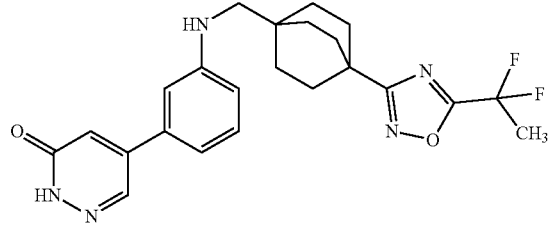 [SMILES: CC(F)(F)c1nc(C23CCC(CNc4cccc(-c5cn[nH]c(=O)c5)c4)(CC2)CC3)no1]

The title compound was prepared according to the method described for the synthesis of Intermediate 1F by substituting Intermediate 127A and Intermediate 105C where appropriate (110 mg, 0.249 mmol, 46% yield) as an off-white solid. MS (ESI) 442 (M+H).

Step B. Example 129. Preparation of N-((4-(5-(1,1-difluoroethyl)-1,2,4-oxadiazol-3-yl) bicyclo[2.2.2]octan-1-yl)methyl)-N-(3-(6-oxo-1,6-dihydropyridazin-4-yl)phenyl)tetrahydro-2H-pyran-4-carboxamide The title compound was prepared according to the method described for the synthesis of Example 5 by substituting Intermediate 129A and commercially available tetrahydro-2H-pyran-4-carboxylic acid where appropriate (4.2 mg, 7.28 μmol, 16% yield). 1H NMR (400 MHz, DMSO-$d_6$) δ=13.15 (br d, J=1.0 Hz, 1H), 8.38 (d, J=2.2 Hz, 1H), 7.95 (s, 1H), 7.87-7.75 (m, 1H), 7.59 (br d, J=5.1 Hz, 2H), 7.27 (s, 1H), 3.79-3.71 (m, 2H), 3.70-3.53 (m, 2H), 3.07-2.94 (m, 2H), 2.55-2.45 (m, 1H, merged with DMSO-d6), 2.20-2.08 (m, 3H), 1.77 (br dd, J=5.6, 9.8 Hz, 6H), 1.67-1.55 (m, 2H), 1.53-1.34 (m, 8H). FXR $EC_{50}$ (nM)=1482. MS (ESI) 554 (M+H).

Example 130

N-((4-(5-(1,1-difluoroethyl)-1,2,4-oxadiazol-3-yl)bicyclo[2.2.2]octan-1-yl)methyl)-4,4-difluoro-N-(4'-(methylsulfonyl)-[1,1'-biphenyl]-3-yl)cyclohexane-1-carboxamide (130)

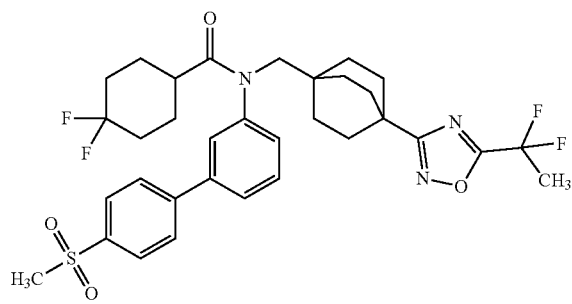

Step A. Intermediate 130A. Preparation of 4'-(methylsulfonyl)-[1,1'-biphenyl]-3-amine

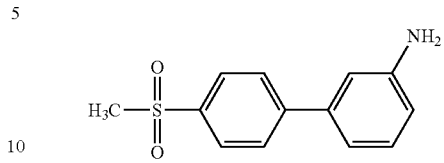

The title compound was prepared according to the method described for the synthesis of Intermediate 87B by substituting (3-aminophenyl)boronic acid and 1-bromo-4-(methylsulfonyl)benzene where appropriate (150 mg, 0.607 mmol, 55% yield) as Off-white solid. MS (ESI) 248 (M+H).

Step B. Intermediate 130B. Preparation of N-((4-(5-(1,1-difluoroethyl)-1,2,4-oxadiazol-3-yl)bicyclo[2.2.2]octan-1-yl)methyl)-4'-(methylsulfonyl)-[1,1'-biphenyl]-3-amine

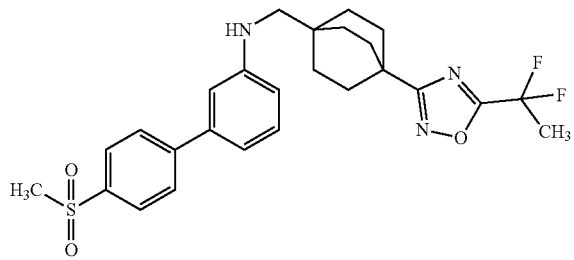 [SMILES: CC(F)(F)c1nc(C23CCC(CNc4cccc(-c5ccc(S(C)(=O)=O)cc5)c4)(CC2)CC3)no1]

The title compound was prepared according to the method described for the synthesis of Intermediate 1F by substituting Intermediate 130 A and Intermediate 105C where appropriate (30 mg, 0.057 mmol, 31% yield). MS (ESI) 502 (M+H).

Step C. Example 130. Preparation of N-((4-(5-(1,1-difluoroethyl)-1,2,4-oxadiazol-3-yl)bicyclo[2.2.2]octan-1-yl)methyl)-4,4-difluoro-N-(4'-(methylsulfonyl)-[1,1'-biphenyl]-3-yl)cyclohexane-1-carboxamide The title compound was prepared according to the method described for the synthesis of Example 5 by substituting Intermediate 130B and corresponding acid where appropriate (4 mg, 6.18 μmol, 15% yield). 1H NMR (400 MHz, DMSO-$d_6$) δ 8.03 (s, 4H), 7.86 (s, 1H), 7.77 (d, J=7.6 Hz, 1H), 7.64-7.56 (m, 1H), 7.56-7.47 (m, 1H), 3.78-3.57 (m, 2H), 3.27 (s, 3H), 2.48-2.39 (m, 1H), 2.13 (t, J=19.7 Hz, 3H), 2.02-1.88 (m, 2H), 1.84-1.71 (m, 8H), 1.69-1.56 (m, 3H), 1.55-1.34 (m, 7H). FXR $EC_{50}$ (nM)=205; MS (ESI) 648 (M+H).

Example 131

N-((4-(3-cyclopropyl-1-methyl-1H-pyrazol-5-yl)bicyclo[2.2.2]octan-1-yl)methyl)-N-(3-(5-cyclopropylisoxazol-3-yl)phenyl)tetrahydro-2H-thiopyran-4-carboxamide 1,1-dioxide (131)

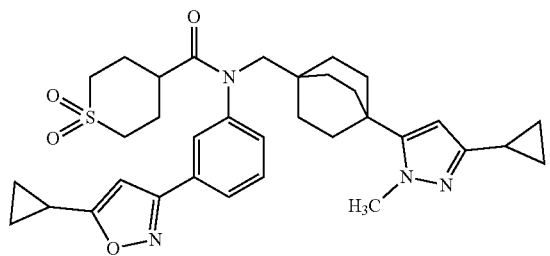

Step A. Intermediate 131A. Preparation of (4-(3-cyclopropyl-1-methyl-1H-pyrazol-5-yl) bicyclo[2.2.2]octan-1-yl)methanol

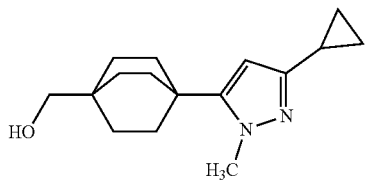 [SMILES: Cn1nc(C2CC2)cc1C12CCC(CO)(CC1)CC2]

The title compound was prepared according to the method described for the synthesis of Intermediate 1B by substituting Intermediate 67C2 where appropriate: (120 mg, 0.438 mmol, 42% yield) as a pale yellow oil. $^1$H NMR (400 MHz, DMSO-$d_6$) δ 5.65 (s, 1H), 3.75 (s, 3H), 3.05 (s, 2H), 1.68-1.79 (m, 7H), 1.35-1.44 (m, 6H), 0.72-0.78 (m, 2H), 0.50-0.56 (m, 2H).

Step B. Intermediate 131B. Preparation of 4-(3-cyclopropyl-1-methyl-1H-pyrazol-5-yl) bicyclo[2.2.2]octane-1-carbaldehyde

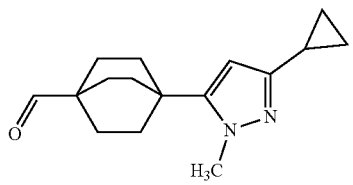 [SMILES: Cn1nc(C2CC2)cc1C12CCC(C=O)(CC1)CC2]

The title compound was prepared according to the method described for the synthesis of Intermediate 3C by substituting Intermediate 126A where appropriate: (90 mg, 0.348 mmol, 76% yield) as an off-white solid. $^1$H NMR (400 MHz, DMSO-$d_6$) δ 9.45 (s, 1H), 5.69 (s, 1H), 3.77 (s, 3H), 1.68-1.79 (m, 7H), 1.55-1.61 (m, 6H), 0.73-0.79 (m, 2H), 0.53-0.58 (m, 2H).

Step C. Intermediate 131C. Preparation of N-((4-(3-cyclopropyl-1-methyl-1H-pyrazol-5-yl)bicyclo[2.2.2]octan-1-yl)methyl)-3-(5-cyclopropylisoxazol-3-yl)aniline

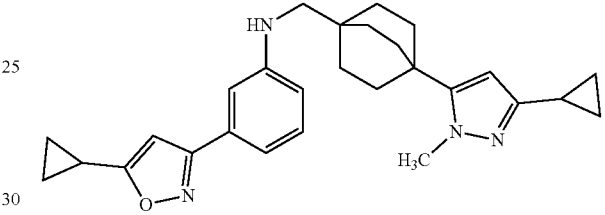

The title compound was prepared according to the method described for the synthesis of Intermediate 1F by substituting Intermediate 131B and Intermediate 40C where appropriate: (110 mg, 0.236 mmol, 76% yield). MS (ESI) 443 (M+H).

Example 131: Preparation of N-((4-(3-cyclopropyl-1-methyl-1H-pyrazol-5-yl) bicyclo[2.2.2]octan-1-yl)methyl)-N-(3-(5-cyclopropylisoxazol-3-yl)phenyl)tetrahydro-2H-thiopyran-4-carboxamide 1,1-dioxide The title compound was prepared according to the method described for the synthesis of Example 5 by substituting Intermediate 131C and corresponding acid where appropriate (6 mg, 9.95 µmol, 17% yield). $^1$H NMR (400 MHz, DMSO-$d_6$) δ 7.86-7.77 (m, 2H), 7.65-7.47 (m, 2H), 6.85 (s, 1H), 5.61 (s, 1H), 3.71 (s, 3H), 3.61 (br d, J=10.8 Hz, 2H), 2.98 (br s, 4H), 2.68 (br s, 1H), 2.23-2.13 (m, 1H), 2.07 (br d, J=11.2 Hz, 1H), 2.00 (br s, 3H), 1.75-1.64 (m, 7H), 1.45-1.32 (m, 6H), 1.16-1.06 (m, 2H), 0.96-0.91 (m, 2H), 0.77-0.71 (m, 2H), 0.55-0.50 (m, 2H). FXR $EC_{50}$ (nM)=1930; MS (ESI) 603 (M+H).

The following compounds were prepared according to the method described for the synthesis of Example 5 by substituting Intermediate 131C and corresponding acids where appropriate:

| Ex. No. | Structure | MS (ESI) (M + H) | FXR EC$_{50}$ (nM) |
|---|---|---|---|
| 132 | | 555 | 227 |
| 133 | | 568 | 2000 |

| 132 | $^1$H NMR (400 MHz, DMSO-d$_6$) δ 7.87-7.75 (m, 2H), 7.56 (s, 2H), 6.86 (s, 1H), 5.61 (s, 1H), 3.81-3.66 (m, 5H), 3.64-3.48 (m, 2H), 3.07-2.87 (m, 4H), 2.25-2.15 (m, 1H), 2.06-1.95 (m, 1H), 1.77-1.65 (m, 7H), 1.64-1.53 (m, 2H), 1.50-1.29 (m, 6H), 1.15-1.08 (m, 2H), 0.97-0.90 (m, 2H), 0.77-0.70 (m, 2H), 0.56-0.49 (m, 2H) |
|---|---|
| 133 | $^1$H NMR (400 MHz, DMSO-d$_6$) δ 7.89-7.69 (m, 2H), 7.63-7.43 (m, 2H), 6.85 (s, 1H), 5.61 (s, 1H), 3.71 (s, 3H), 3.66-3.55 (m, 2H), 2.83-2.71 (m, 2H), 2.27-2.01 (m, 5H), 1.80-1.48 (m, 13H), 1.45-1.30 (m, 6H), 1.16-1.07 (m, 2H), 0.98-0.87 (m, 2H), 0.79-0.68 (m, 2H), 0.58-0.48 (m, 2H) |

Example 134

N-((4-(3-cyclopropyl-1-methyl-1H-pyrazol-5-yl)bicyclo[2.2.2]octan-1-yl)methyl)-N-(4'-(methyl-sulfonyl)-[1,1'-biphenyl]-3-yl)tetrahydro-2H-pyran-4-carboxamide (134)

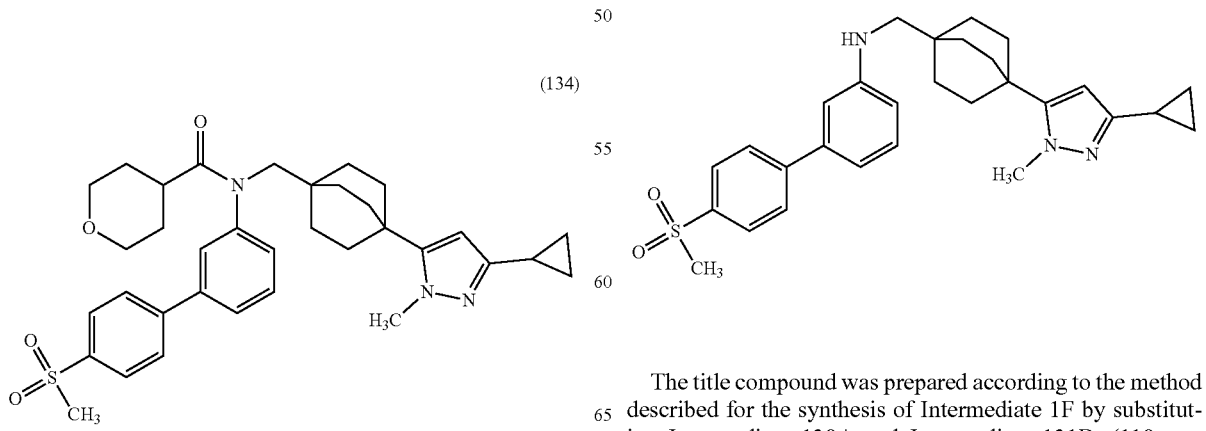

Step A. Intermediate 134A. Preparation of N-((4-(3-cyclopropyl-1-methyl-1H-pyrazol-5-yl)bicyclo[2.2.2]octan-1-yl)methyl)-4'-(methylsulfonyl)-[1,1'-biphenyl]-3-amine The title compound was prepared according to the method described for the synthesis of Intermediate 1F by substituting Intermediate 130A and Intermediate 131B. (110 mg, 0.236 mmol, 76% yield). MS (ESI) 443 (M+H).

Step B. Example 134. Preparation of N-((4-(3-cyclopropyl-1-methyl-1H-pyrazol-5-yl)bicyclo[2.2.2]octan-1-yl)methyl)-N-(4'-(methylsulfonyl)-[1,1'-biphenyl]-3-yl)tetrahydro-2H-pyran-4-carboxamide The title compound was prepared according to the method described for the synthesis of Example 5 by substituting Intermediate 134 A and corresponding acid where appropriate (5.5 mg, 8.77 μmol, 17% yield). $^1$H NMR (400 MHz, DMSO-d$_6$) δ 8.02 (s, 4H), 7.83 (s, 1H), 7.76 (s, 1H), 7.60 (s, 1H), 7.52 (s, 1H), 5.61 (s, 1H), 3.83-3.50 (m, 7H), 3.27 (s, 3H), 3.07-2.93 (m, 2H), 2.62-2.53 (m, 1H), 1.79-1.66 (m, 7H), 1.65-1.55 (m, 2H), 1.54-1.45 (m, 2H), 1.44-1.30 (m, 6H), 0.80-0.67 (m, 2H), 0.57-0.46 (m, 2H). FXR EC$_{50}$ (nM)=511; MS (ESI) 602 (M+H).

The following compounds were prepared according to the method described for the synthesis of Example 5 by substituting Intermediate 134A and corresponding acids where appropriate:

| Ex. No. | Structure | MS (ESI) (M + H) | FXR EC$_{50}$ (nM) |
|---|---|---|---|
| 135 | 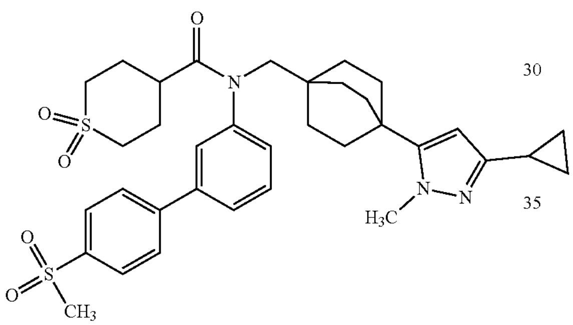 [SMILES: Cn1nc(C2CC2)cc1C12CCC(CN(C(=O)C3CCS(=O)(=O)CC3)c3cccc(-c4ccc(S(C)(=O)=O)cc4)c3)(CC1)CC2] | 602 | 4000 |
| 136 | 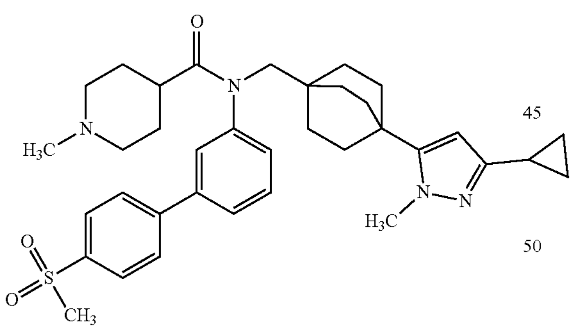 [SMILES: CN1CCC(C(=O)N(CC23CCC(c4cc(C5CC5)nn4C)(CC2)CC3)c2cccc(-c3ccc(S(C)(=O)=O)cc3)c2)CC1] | 615 | 4000 |

| | |
|---|---|
| 135 | $^1$H NMR (400 MHz, DMSO-d$_6$) δ 8.02 (s, 4H), 7.83 (s, 1H), 7.76 (s, 1H), 7.60 (s, 1H), 7.52 (s, 1H), 5.61 (s, 1H), 3.83-3.50 (m, 7H), 3.27 (s, 3H), 3.07-2.93 (m, 2H), 2.62-2.53 (m, 1H), 1.79-1.66 (m, 7H), 1.65-1.55 (m, 2H), 1.54-1.45 (m, 2H), 1.44-1.30 (m, 6H), 0.80-0.67 (m, 2H), 0.57-0.46 (m, 2H) |
| 136 | $^1$H NMR (400 MHz, DMSO-d$_6$) δ 8.03 (s, 4H), 7.86 (s, 1H), 7.79 (br d, J = 7.8 Hz, 1H), 7.65-7.58 (m, 1H), 7.57-7.50 (m, 1H), 5.62 (s, 1H), 3.72 (s, 3H), 3.36-3.30 (m, 2H), 3.28 (s, 3H), 2.80-2.69 (m, 2H), 2.64 (br s, 2H), 1.93-1.77 (m, 4H), 1.76-1.55 (m, 10H), 1.50-1.34 (m, 6H), 1.28-1.21 (m, 1H), 0.79-0.69 (m, 2H), 0.56-0.47 (m, 2H) |

Example 137

N-((4-(3-cyclopropyl-1-methyl-1H-pyrazol-5-yl)bicyclo[2.2.2]octan-1-yl)methyl)-4,4-difluoro-N-(3-(2-methylbenzo[d]thiazol-6-yl)phenyl)cyclohexane-1-carboxamide (137)

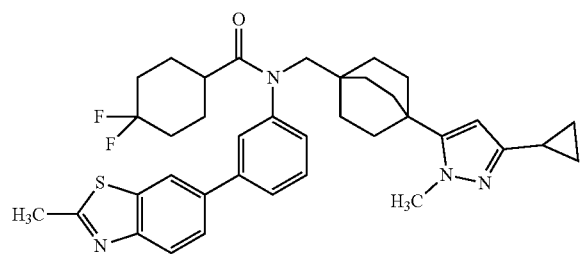

Step A. Intermediate 137A. Preparation of N-((4-(3-cyclopropyl-1-methyl-1H-pyrazol-5-yl)bicyclo[2.2.2]octan-1-yl)methyl)-3-(2-methylbenzo[d]thiazol-6-yl)aniline

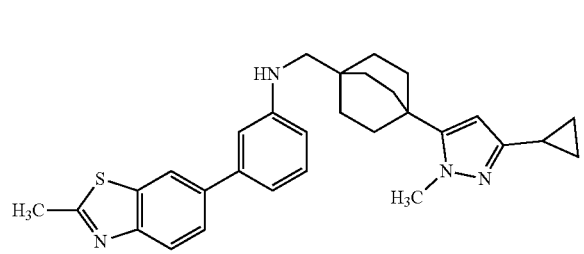 [SMILES: Cc1nc2ccc(-c3cccc(NCC45CCC(c6cc(C7CC7)nn6C)(CC4)CC5)c3)cc2s1]

The title compound was prepared according to the method described for the synthesis of Intermediate 1F by substituting Intermediate 131B and Intermediate 90A. (72 mg, 0.149 mmol, 64% yield) MS (ESI) 483 (M+H).

Step B. Example 137. Preparation of N-((4-(3-cyclopropyl-1-methyl-1H-pyrazol-5-yl)bicyclo[2.2.2]octan-1-yl)methyl)-4,4-difluoro-N-(3-(2-methylbenzo[d]thiazol-6-yl)phenyl)cyclohexane-1-carboxamide The title compound was prepared according to the method described for the synthesis of Example 5 by substituting Intermediate 137 A and corresponding acid where appropriate (6.9 mg, 10.61 μmol, 17% yield). $^1$H NMR (400 MHz, DMSO-$d_6$) δ 8.45 (d, J=1.5 Hz, 1H), 8.00 (d, J=8.6 Hz, 1H), 7.87-7.78 (m, 2H), 7.75 (br d, J=7.3 Hz, 1H), 7.56 (t, J=7.8 Hz, 1H), 7.47-7.39 (m, 1H), 5.63 (s, 1H), 3.72 (s, 5H), 2.86-2.80 (m, 3H), 2.03-1.91 (m, 2H), 1.86-1.50 (m, 14H), 1.47-1.34 (m, 6H), 0.78-0.70 (m, 2H), 0.57-0.51 (m, 2H). FXR $EC_{50}$ (nM)=449; MS (ESI) 629 (M+H).

Example 138

N-((4-(3-cyclopropyl-1-methyl-1H-pyrazol-5-yl)bicyclo[2.2.2]octan-1-yl)methyl)-N-(3-(3-cyclopropylisoxazol-5-yl)phenyl)tetrahydro-2H-thiopyran-4-carboxamide 1,1-dioxide (138)

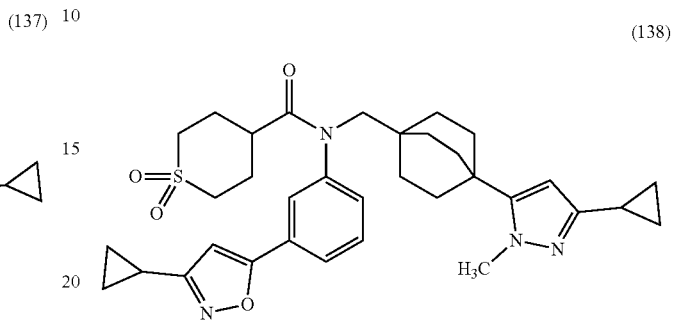

Step A. Intermediate 138A. Preparation of N-((4-(3-cyclopropyl-1-methyl-1H-pyrazol-5-yl)bicyclo[2.2.2]octan-1-yl)methyl)-3-(3-cyclopropylisoxazol-5-yl)aniline

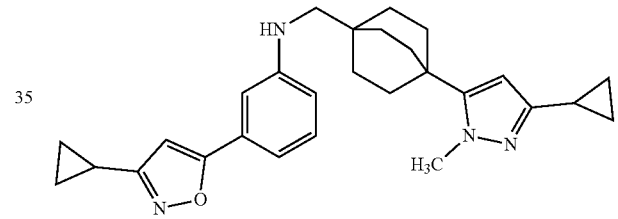

The title compound was prepared according to the method described for the synthesis of Intermediate 1F by substituting Intermediate 131B and Intermediate 147B. (110 mg, 0.236 mmol, 76% yield). MS (ESI) 443 (M+H).

Step B. Example 138. Preparation of N-((4-(3-cyclopropyl-1-methyl-1H-pyrazol-5-yl)bicyclo[2.2.2]octan-1-yl)methyl)-N-(3-(3-cyclopropylisoxazol-5-yl)phenyl)tetrahydro-2H-thiopyran-4-carboxamide 1,1-dioxide The title compound was prepared according to the method described for the synthesis of Example 5 by substituting Intermediate 138A and corresponding acid where appropriate (10.3 mg, 0.017 mmol, 29% yield). $^1$H NMR (400 MHz, DMSO-$d_6$) δ 7.85 (s, 1H), 7.78 (d, J=7.6 Hz, 1H), 7.64-7.48 (m, 2H), 6.92 (s, 1H), 5.61 (s, 1H), 3.71 (s, 3H), 3.66-3.44 (m, 2H), 3.10-2.86 (m, 4H), 2.73-2.63 (m, 1H), 2.13-1.88 (m, 5H), 1.79-1.60 (m, 6H), 1.48-1.30 (m, 7H), 1.12-1.01 (m, 2H), 0.87-0.78 (m, 2H), 0.77-0.69 (m, 2H), 0.55-0.49 (m, 2H). FXR $EC_{50}$ (nM)=1582; MS (ESI) 603 (M+H).

The following compounds were prepared according to the method described for the synthesis of Example 5 by substituting Intermediate 138A and corresponding acids where appropriate:

| Ex. No. | Structure | MS (ESI) (M + H) | FXR EC$_{50}$ (nM) |
|---|---|---|---|
| 139 | | 554 | 87 |
| 140 | | 568 | 2644 |
| 139 | $^1$H NMR (400 MHz, DMSO-d$_6$) δ 7.84 (s, 1H), 7.77 (br d, J = 7.3 Hz, 1H), 7.64-7.44 (m, 2H), 6.92 (s, 1H), 5.61 (s, 1H), 3.82-3.68 (m, 6H), 3.65-3.40 (m, 2H), 3.09-2.89 (m, 2H), 2.12-1.98 (m, 1H), 1.78-1.52 (m, 9H), 1.50-1.25 (m, 8H), 1.13-0.99 (m, 2H), 0.87-0.78 (m, 2H), 0.77-0.68 (m, 2H), 0.57-0.46 (m, 2H) | | |
| 140 | $^1$H NMR (400 MHz, DMSO-d$_6$) δ 7.83 (s, 1H), 7.77 (br d, J = 7.3 Hz, 1H), 7.63-7.56 (m, 1H), 7.55-7.46 (m, 1H), 6.92 (s, 1H), 5.61 (s, 1H), 3.71 (s, 3H), 3.67-3.46 (m, 2H), 2.70 (tdd, J = 1.9, 4.1, 11.2 Hz, 2H), 2.23-2.13 (m, 1H), 2.11-1.95 (m, 4H), 1.78-1.64 (m, 7H), 1.63-1.45 (m, 6H), 1.43-1.26 (m, 6H), 1.11-1.01 (m, 2H), 0.86-0.79 (m, 2H), 0.78-0.69 (m, 2H), 0.56-0.47 (m, 2H) | | |

Example 141

N-((4-(3-(tert-butyl)-1,2,4-oxadiazol-5-yl)bicyclo[2.2.2]octan-1-yl)methyl)-N-(3-(6-chloropyrazolo[1,5-a]pyrimidin-3-yl)phenyl)-4,4-difluorocyclohexane-1-carboxamide

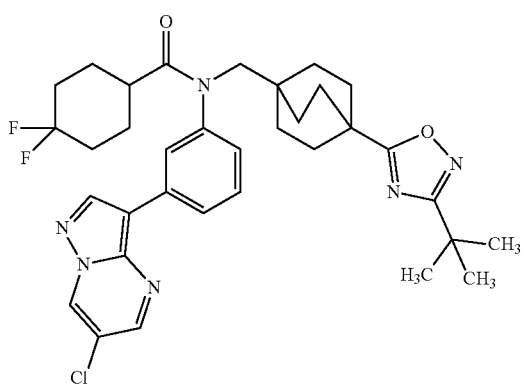

(141)

Step A: Intermediate 141A. Preparation of 3-(6-chloropyrazolo[1,5-a]pyrimidin-3-yl) aniline

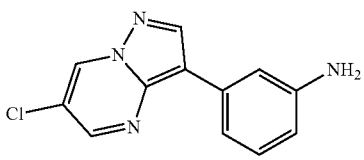 [SMILES: Nc1cccc(-c2cnn3cc(Cl)cnc23)c1]

To a stirred solution of 3-bromo-6-chloropyrazolo[1,5-a]pyrimidine (600 mg, 2.58 mmol) and (3-aminophenyl)boronic acid (424 mg, 3.10 mmol) in dioxane (10 mL) was added a solution of potassium phosphate tribasic (1644 mg, 7.74 mmol) in water (1.0 mL) at room temperature. The reaction mixture was degassed and back-filled with argon. PdCl$_2$(dppf)-CH$_2$Cl$_2$ adduct (105 mg, 0.129 mmol) was added to the reaction mixture and the vial was sealed. The reaction mixture was heated at 110° C. for 4 h. The reaction mixture was cooled to room temperature, diluted with ethyl acetate (25 mL), washed with brine solution (10 mL), dried over anhydrous sodium sulphate and concentrated under reduced pressure. The crude material was purified via flash chromatography (12 g silica gel cartridge; A=Hex, B=EtOAc; 30 min grad.; 0% B to 50% B; flow rate=30 mL/min) to afford the title compound (350 mg, 1.430 mmol, 55% yield) as a yellow solid. MS (ESI) 245 (M+H).

Step B: Intermediate 141B. Preparation of N-((4-(3-(tert-butyl)-1,2,4-oxadiazol-5-yl) bicyclo[2.2.2]octan-1-yl)methyl)-3-(6-chloropyrazolo[1,5-a]pyrimidin-3-yl)aniline

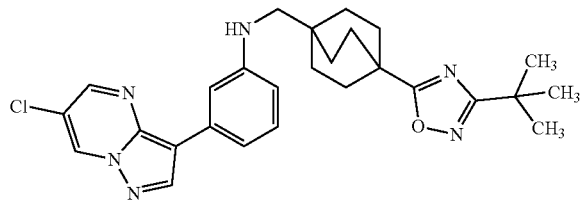 [SMILES: CC(C)(C)c1noc(C23CCC(CNc4cccc(-c5cnn6cc(Cl)cnc56)c4)(CC2)CC3)n1]

The title compound was prepared according to the method described for the synthesis of Intermediate 1F by substituting Intermediate 141A and Intermediate 69C where appropriate (190 mg, 0.387 mmol, 72% yield) MS (ESI) 491 (M+H).

Step C: Example 141. Preparation of N-((4-(3-(tert-butyl)-1,2,4-oxadiazol-5-yl)bicyclo[2.2.2]octan-1-yl)methyl)-N-(3-(6-chloropyrazolo[1,5-a]pyrimidin-3-yl)phenyl)-4,4-difluorocyclohexane-1-carboxamide The title compound was prepared according to the method described for the synthesis of Example 5 by substituting Intermediate 141B and corresponding acid where appropriate (0.7 mg, 1.099 μmol, 4% yield). $^1$H NMR (400 MHz, DMSO-$d_6$) δ 9.62 (d, J=2.2 Hz, 1H), 8.90 (s, 1H), 8.75 (d, J=2.2 Hz, 1H), 8.14 (s, 1H), 8.09 (d, J=7.8 Hz, 1H), 7.53 (t, J=7.8 Hz, 1H), 7.33 (br d, J=8.1 Hz, 1H), 3.65 (s, 2H), 2.03-1.91 (m, 2H), 1.85-1.73 (m, 8H), 1.70-1.50 (m, 4H), 1.48-1.37 (m, 7H), 1.25 (s, 9H). FXR EC$_{50}$ (nM)=549. MS (ESI) 637 (M+H).

Example 142

N-((4-(3-(tert-butyl)-1,2,4-oxadiazol-5-yl)bicyclo[2.2.2]octan-1-yl)methyl)-4,4-difluoro-N-(3-(4-methyl-1H-imidazol-1-yl)phenyl)cyclohexane-1-carboxamide (142)

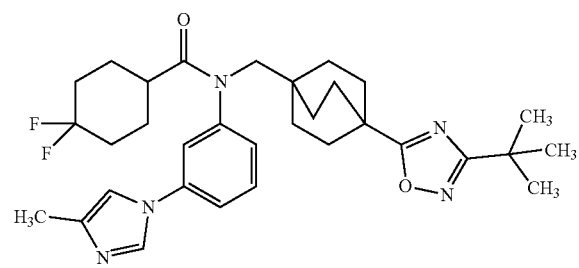

Step A. Intermediate 142A. Preparation of 3-(4-methyl-1H-imidazol-1-yl) aniline

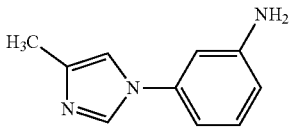

A mixture of 3-iodoaniline (1.5 g, 6.85 mmol), 4-methyl-1H-imidazole (0.84 g, 10.27 mmol), copper(I) oxide (0.196 g, 1.37 mmol), KOH (0.385 g, 6.87 mmol) and DMSO (15 mL) was stirred at 120° C. overnight. The reaction mixture was cooled to room temperature and diluted with ethyl acetate (20 mL) and water (30 mL). The organic layer was separated and the aqueous layer was extracted with ethyl acetate (2×20 mL). The combined organic layers were washed with brine (50 mL), dried over anhydrous Na$_2$SO$_4$ and concentrated under reduced pressure. The crude material was purified by flash chromatography (12 g silica gel cartridge; A=Hex, B=EtOAc; 30 min grad.; 0% B to 40% B; flow rate=30 mL/min). The pure fractions were combined, concentrated under reduced pressure and dried in vacuo to afford the title compound (0.68 g, 3.93 mmol, 57% yield) as an off white solid. MS (ESI) 174 (M+H).

Step B. Intermediate 142B. Preparation of N-((4-(3-(tert-butyl)-1,2,4-oxadiazol-5-yl) bicyclo[2.2.2]octan-1-yl)methyl)-3-(4-methyl-1H-imidazol-1-yl) aniline

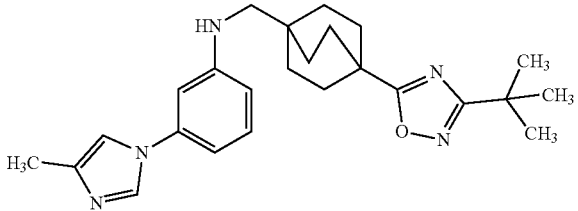 [SMILES: Cc1cn(-c2cccc(NCC34CCC(c5nc(C(C)(C)C)no5)(CC3)CC4)c2)cn1]

The title compound was prepared according to the method described for the synthesis of Intermediate 1F by substituting Intermediate 142A and Intermediate 69C where appropriate (220 mg, 0.524 mmol, 69% yield). MS (ESI) 420 (M+H).

Step C. Example 142. Preparation of N-((4-(3-(tert-butyl)-1,2,4-oxadiazol-5-yl) bicyclo[2.2.2]octan-1-yl)methyl)-4,4-difluoro-N-(3-(4-methyl-1H-imidazol-1-yl)phenyl)cyclohexane-1-carboxamide The title compound was prepared according to the method described for the synthesis of Example 5 by substituting Intermediate 142B and corresponding acid where appropriate (11.9 mg, 0.020 mmol, 42% yield). $^1$H NMR (400 MHz, DMSO-$d_6$) δ 8.28 (s, 1H), 7.76 (s, 1H), 7.66-7.60 (m, 1H), 7.59-7.50 (m, 2H), 7.43-7.34 (m, 1H), 3.72-3.55 (m, 2H), 2.48-2.39 (m, 1H), 2.23-2.13 (m, 3H), 2.03-1.89 (m, 2H), 1.85-1.68 (m, 8H), 1.67-1.49 (m, 4H), 1.46-1.38 (m, 6H), 1.29-1.23 (m, 9H). FXR EC$_{50}$ (nM)=721. MS (ESI) 566 (M+H).

Example 143

N-(3-(2-ethoxypyrimidin-5-yl)phenyl)-N-((4-(5-(2-fluoropropan-2-yl)-1,2,4-oxadiazol-3-yl)bicyclo[2.2.2]octan-1-yl)methyl)-4-methoxybenzamide

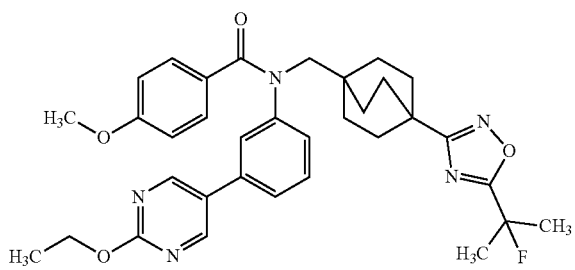

(143)

Step A: Intermediate 143A Preparation of 3-(2-ethoxypyrimidin-5-yl) aniline

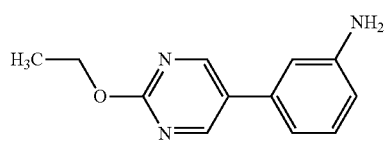 [SMILES: CCOc1ncc(-c2cccc(N)c2)cn1]

The title compound was prepared according to the method described for the synthesis of Intermediate 87B by substituting 5-bromo-2-ethoxypyrimidine and (3-aminophenyl)boronic acid where appropriate (0.9 g, 4.18 mmol, 71% yield). MS (ESI) 216 (M+H).

Step B: Intermediate 143B. Preparation of 3-(2-ethoxypyrimidin-5-yl)-N-((4-(5-(2-fluoropropan-2-yl)-1,2,4-oxadiazol-3-yl)bicyclo[2.2.2]octan-1-yl)methyl)aniline

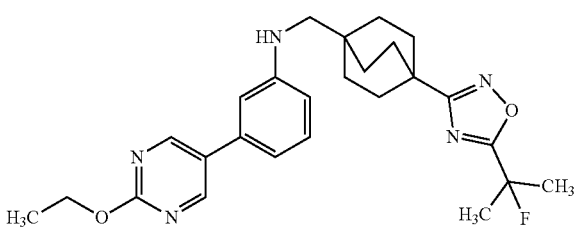 [SMILES: CCOc1ncc(-c2cccc(NCC34CCC(c5noc(C(C)(C)F)n5)(CC3)CC4)c2)cn1]

The title compound was prepared according to the method described for the synthesis of Intermediate 1F by substituting Intermediate 143A and Intermediate 128C where appropriate (260 mg, 0.558 mmol, 74% yield). MS (ESI) 466 (M+H).

Step C: Example 143. Preparation of N-(3-(2-ethoxypyrimidin-5-yl)phenyl)-N-((4-(5-(2-fluoropropan-2-yl)-1,2,4-oxadiazol-3-yl)bicyclo[2.2.2]octan-1-yl)methyl)-4-methoxybenzamide The title compound was prepared according to the method described for the synthesis of Example 5 by substituting Intermediate 143B and corresponding acid where appropriate (2.1 mg, 3.42 μmol, 10% yield). $^1$H NMR (400 MHz, DMSO-$d_6$) δ 8.80 (s, 2H), 7.64 (s, 1H), 7.45-7.52 (m, 1H), 7.32 (t, J=7.83 Hz, 1H), 7.10-7.22 (m, 3H), 6.70-6.78 (m, 2H), 4.40 (q, J=7.01 Hz, 2H), 3.91 (s, 2H), 3.68 (s, 3H), 1.70-1.81 (m, 12H), 1.43-1.54 (m, 6H), 1.36 (t, J=6.97 Hz, 3H). FXR EC$_{50}$ (nM)=202. MS (ESI) 600 (M+H).

Example 144

4-(difluoromethoxy)-N-(3-(2-ethoxypyrimidin-5-yl)phenyl)-N-((4-(5-(2-fluoropropan-2-yl)-1,2,4-oxadiazol-3-yl)bicyclo[2.2.2]octan-1-yl)methyl)benzamide

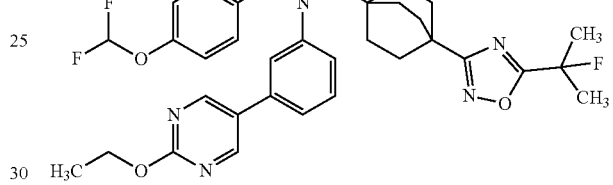

(144)

The title compound was prepared according to the method described for the synthesis of Example 5 by substituting Intermediate 143B and corresponding acid where appropriate (4.3 mg, 6.76 μmol, 21% yield). $^1$H NMR (400 MHz, DMSO-$d_6$) δ 8.80 (s, 2H), 7.63-7.71 (m, 1H), 7.46-7.54 (m, 1H), 7.07-7.41 (m, 5H), 6.89-7.04 (m, 2H), 4.40 (q, J=7.09 Hz, 2H), 3.92 (s, 2H), 1.71-1.85 (m, 12H), 1.42-1.57 (m, 6H), 1.36 (t, J=7.09 Hz, 3H). FXR EC$_{50}$ (nM)=334. MS (ESI) 636 (M+H).

Examples 145 and 146

N-((4-(3-(tert-butyl)-1,2,4-oxadiazol-5-yl)bicyclo[2.2.2]octan-1-yl)methyl)-N-(4'-ethoxy-[1,1'-biphenyl]-3-yl)-4-methoxycyclohexane-1-carboxamide (Isomer I & Isomer II)

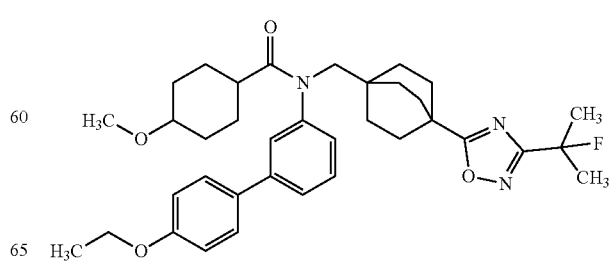

(145-146)

Step A: Intermediate 145A. Preparation of N-((4-(3-(tert-butyl)-1,2,4-oxadiazol-5-yl) bicyclo[2.2.2]octan-1-yl)methyl)-4'-ethoxy-[1,1'-biphenyl]-3-amine

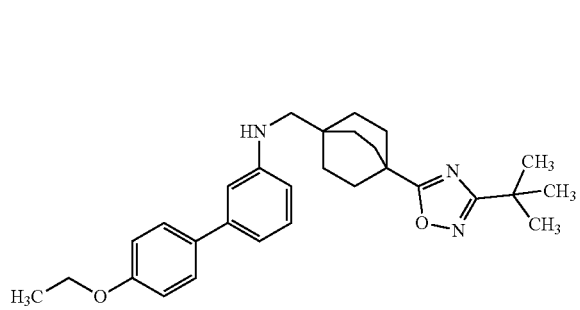 [SMILES: CCOc1ccc(-c2cccc(NCC34CCC(c5nc(C(C)(C)C)no5)(CC3)CC4)c2)cc1]

The title compound was prepared according to the method described for the synthesis of Intermediate 1F by substituting Intermediate 113A and Intermediate 69C where appropriate (320 mg, 0.696 mmol, 91% yield) as an off-white solid. MS (ESI) 460 (M+H).

Step B: Example 145 & 146. Preparation of 2-(5-(4-((N-(4'-ethoxy-[1,1'-biphenyl]-3-yl)-4-methoxycyclohexane-1-carboxamido) methyl)bicyclo[2.2.2]octan-1-yl)-1,2,4-oxadiazol-3-yl)-2-methylpropan-1-ylium The title compounds were prepared according to the method described for the synthesis of Example 5 by substituting Intermediate 145A and corresponding acid where appropriate.

Example 145: Isomer-I: (4.2 mg, 7.01 μmol, 21% yield). $^1$H NMR (400 MHz, DMSO-$d_6$) δ 7.56-7.71 (m, 4H), 7.43-7.54 (m, 1H), 7.32 (br d, J=7.34 Hz, 1H), 6.98-7.09 (m, 2H), 4.08 (q, J=7.09 Hz, 2H), 3.57-3.70 (m, 2H), 3.11-3.19 (m, 3H), 2.96-3.07 (m, 1H), 2.15-2.27 (m, 1H), 1.88-2.00 (m, 2H), 1.74-1.86 (m, 6H), 1.64-1.72 (m, 2H), 1.38-1.50 (m, 8H), 1.36 (t, J=6.97 Hz, 3H), 1.22-1.29 (m, 9H), 0.64-0.78 (m, 2H). FXR $EC_{50}$ (nM)=303. MS (ESI) 600 (M+H).

Example 146: Isomer-II: (8.3 mg, 0.014 mmol, 42% yield). $^1$H NMR (400 MHz, DMSO-$d_6$) δ 7.54-7.70 (m, 4H), 7.43-7.53 (m, 1H), 7.26-7.35 (m, 1H), 7.03 (d, J=8.80 Hz, 2H), 4.02-4.14 (m, 2H), 3.57-3.68 (m, 2H), 3.22-3.27 (m, 1H), 3.16 (s, 3H), 2.27-2.36 (m, 1H), 1.72-1.95 (m, 8H), 1.56-1.71 (m, 2H), 1.31-1.50 (m, 11H), 1.17-1.30 (m, 9H), 0.98-1.11 (m, 2H). FXR $EC_{50}$ (nM)=402. MS (ESI) 600 (M+H).

Example 147

N-((4-(3-(tert-butyl)-1,2,4-oxadiazol-5-yl)bicyclo[2.2.2]octan-1-yl)methyl)-N-(3-(3-cyclopropylisoxazol-5-yl)phenyl)-4,4-difluorocyclohexane-1-carboxamide

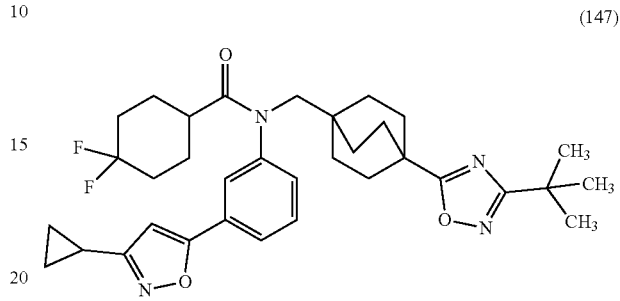

(147)

Step A. Intermediate 147A1 and 147A2. Preparation of 3-cyclopropyl-5-(3-nitrophenyl)isoxazole and 5-cyclopropyl-3-(3-nitrophenyl)isoxazole

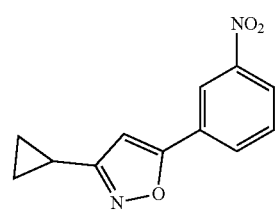

Intermediate 147A1

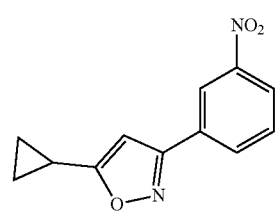

Intermediate 147A2

To a stirred solution of Intermediate 40A (1.7 g, 7.29 mmol) in MeOH (30 mL) was added hydroxylamine hydrochloride (2.026 g, 29.2 mmol) at room temperature. The reaction mixture was heated at 80° C. overnight. The reaction mixture was cooled to room temperature, concentrated under reduced pressure, diluted with water (30 mL) and extracted with ethyl acetate (2×30 mL). The combined organic layer was washed with saturated brine solution (40 mL), dried over anhydrous sodium sulphate and concentrated under reduced pressure. The crude material was purified by flash chromatography (40 g silica gel cartridge; A=Hex, B=EtOAc; 30 min grad.; 0% B to 40% B; flow rate=40 mL/min). The pure fractions were combined, concentrated under reduced pressure and dried in vacuo to afford the title compound (1.5 g) as an off-white solid (mixture of isomers). The isomers were separated by using SFC to afford Intermediate 147A1 (400 mg, 1.73 mmol, 24% yield) as an off-white solid, MS (ESI) 231.2 (M+H) and Intermediate 147A2 (900 mg, 3.91 mmol, 53% yield) as an off-white solid, MS (ESI) 231.2 (M+H).

Step B. Intermediate 147B. Preparation of 3-(3-cyclopropylisoxazol-5-yl)aniline

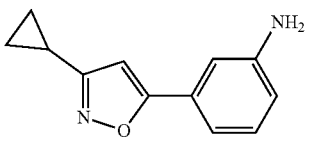 [SMILES: Nc1cccc(-c2cc(C3CC3)no2)c1]

To a stirred solution of Intermediate 147A1 (400 mg, 1.74 mmol) in ethanol (8 mL), THF (4 mL) and water (2 mL) were added zinc (1704 mg, 26.1 mmol) and ammonium chloride (1394 mg, 26.1 mmol) at room temperature. The reaction mixture was stirred at room temperature for overnight. The reaction mixture was concentrated under reduced pressure, the residue was diluted with ethyl acetate and filtered through Celite bed. The filtrate was washed with brine solution (10 m L), dried over anhydrous sodium sulphate and evaporated under reduced pressure. The crude material was purified by flash chromatography (24 g silica gel cartridge; A=Hex, B=EtOAc; 30 min grad.; 0% B to 60% B; flow rate=30 mL/min). The pure fractions were combined, concentrated under reduced pressure and dried in vacuo to afford the title compound (300 mg, 1.498 mmol, 86% yield) as brown solid, MS (ESI) 201 (M+1).

Step C. Intermediate 147C. Preparation of N-((4-(3-(tert-butyl)-1,2,4-oxadiazol-5-yl) bicyclo[2.2.2]octan-1-yl)methyl)-3-(3-cyclopropylisoxazol-5-yl)aniline

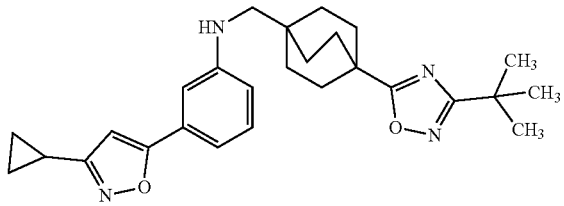 [SMILES: CC(C)(C)c1noc(C23CCC(CNc4cccc(-c5cc(C6CC6)no5)c4)(CC2)CC3)n1]

The title compound was prepared according to the method described for the synthesis of intermediate 1F by substituting Intermediate 147B and Intermediate 69C where appropriate: (40 mg, 0.090 mmol, 60% yield) as brown wax. MS (ESI) 447.2 (M+H).

Step D. Example 147. Preparation of N-((4-(3-(tert-butyl)-1,2,4-oxadiazol-5-yl) bicyclo[2.2.2]octan-1-yl)methyl)-N-(3-(3-cyclopropylisoxazol-5-yl)phenyl)-4,4-difluorocyclohexane-1-carboxamide The title compound was prepared according to the method described for the synthesis of Example 5 by substituting Intermediate 147C and the corresponding acid where appropriate: (3.0 mg, 5.06 μmol, 11% yield). $^1$H NMR (400 MHz, DMSO-$d_6$) δ 7.85 (s, 1H), 7.78 (d, J=7.8 Hz, 1H), 7.65-7.46 (m, 2H), 6.91 (s, 1H), 3.63 (br. s., 2H), 2.39 (br. s., 1H), 2.11-2.04 (m, 1H), 1.96 (br. s., 2H), 1.86-1.74 (m, 6H), 1.74-1.54 (m, 6H), 1.46-1.36 (m, 6H), 1.31-1.20 (m, 9H), 1.11-1.01 (m, 2H), 0.87-0.77 (m, 2H). FXR $EC_{50}$ (nM)=205; MS (ESI) 593 (M+H).

Example 148

N-((4-(5-(tert-butyl)-1,2,4-oxadiazol-3-yl)bicyclo[2.2.2]octan-1-yl)methyl)-N-(3-(3-cyclopropylisoxazol-5-yl)phenyl)-4,4-difluorocyclohexane-1-carboxamide

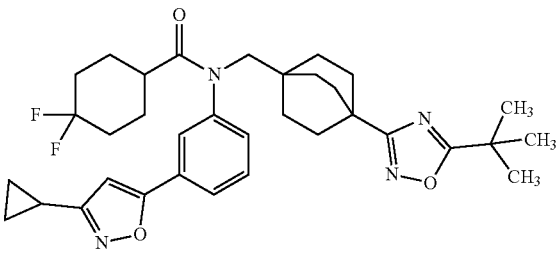

(148)

Step A. Intermediate 148A. Preparation of N-((4-(5-(tert-butyl)-1,2,4-oxadiazol-3-yl) bicyclo[2.2.2]octan-1-yl)methyl)-3-(3-cyclopropylisoxazol-5-yl)aniline

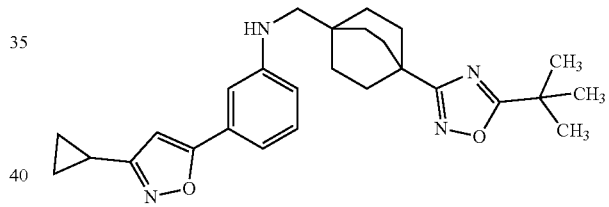

The title compound was prepared according to the method described for the synthesis of Intermediate 1F by substituting Intermediate 147B and Intermediate 88F where appropriate: (40 mg, 0.090 mmol, 59% yield) as brown wax. MS (ESI) 447 (M+H).

Step B. Example 148. Preparation of N-((4-(5-(tert-butyl)-1,2,4-oxadiazol-3-yl) bicyclo[2.2.2]octan-1-yl)methyl)-N-(3-(3-cyclopropylisoxazol-5-yl)phenyl)-4,4-difluorocyclohexane-1-carboxamide The title compound was prepared according to the method described for the synthesis of Example 5 by substituting Intermediate 148A and the corresponding acid where appropriate: (3.1 mg, 5.17 μmol, 11% yield). $^1$H NMR (400 MHz, DMSO-$d_6$) δ 7.85 (br. s., 1H), 7.78 (d, J=6.4 Hz, 1H), 7.66-7.45 (m, 2H), 6.92 (s, 1H), 3.62 (br. s., 2H), 2.39 (br. s., 1H), 2.12-2.02 (m, 1H), 1.96 (br. s., 2H), 1.82-1.49 (m, 12H), 1.46-1.29 (m, 15H), 1.11-1.00 (m, 2H), 0.90-0.77 (m, 2H). FXR $EC_{50}$ (nM)=107; MS (ESI) 593 (M+H).

Example 149

N-(3-(3-cyclopropylisoxazol-5-yl)phenyl)-4,4-difluoro-N-((4-(5-(1-(trifluoromethyl)cyclopropyl)-1,2,4-oxadiazol-3-yl)bicyclo[2.2.2]octan-1-yl)methyl)cyclohexane-1-carboxamide

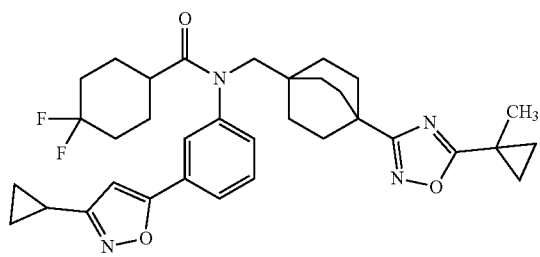

(149)

Step A. Intermediate 149A. Preparation of methyl 4-(5-(1-(trifluoromethyl)cyclopropyl)-1,2,4-oxadiazol-3-yl)bicyclo[2.2.2]octane-1-carboxylate

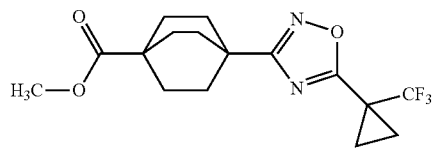 [SMILES: COC(=O)C12CCC(c3noc(C4(C(F)(F)F)CC4)n3)(CC1)CC2]

The title compound was prepared according to the method described for the synthesis of Intermediate 1A by substituting Intermediate 88C where appropriate: (900 mg, 2.61 mmol, 84% yield) white solid. MS (ESI) 345 (M+H).

Step B. Intermediate 149B. Preparation of (4-(5-(1-(trifluoromethyl)cyclopropyl)-1,2,4-oxadiazol-3-yl)bicyclo[2.2.2]octan-1-yl)methanol

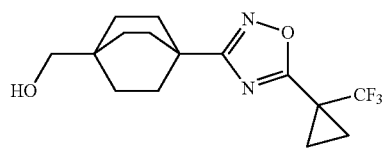 [SMILES: OCC12CCC(c3noc(C4(C(F)(F)F)CC4)n3)(CC1)CC2]

The title compound was prepared according to the method described for the synthesis of Intermediate 1B by substituting Intermediate 149A where appropriate: (750 mg, 2.371 mmol, 91% yield) as white solid. MS (ESI) 317 (M+H).

Step C. Intermediate 149C. Preparation of 4-(5-(1-(trifluoromethyl)cyclopropyl)-1,2,4-oxadiazol-3-yl)bicyclo[2.2.2]octane-1-carbaldehyde

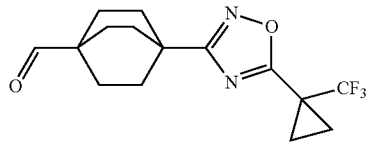 [SMILES: O=CC12CCC(c3noc(C4(C(F)(F)F)CC4)n3)(CC1)CC2]

The title compound was prepared according to the method described for the synthesis of Intermediate 1C by substituting Intermediate 149B where appropriate: (600 mg, 1.871 mmol, 79% yield) as a white solid. MS (ESI) 315 (M+H).

Step D. Intermediate 149D. Preparation of 3-(3-cyclopropylisoxazol-5-yl)-N-((4-(5-(1-(trifluoromethyl)cyclopropyl)-1,2,4-oxadiazol-3-yl)bicyclo[2.2.2]octan-1-yl)methyl) aniline

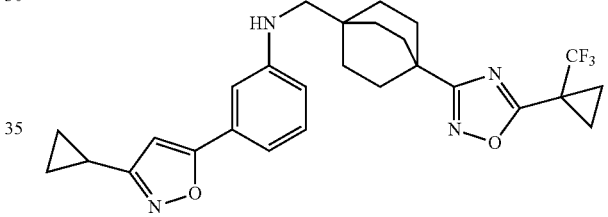

The title compound was prepared according to the method described for the synthesis of Intermediate 1F by substituting Intermediate 147B and Intermediate 149C where appropriate: (40 mg, 0.080 mmol, 57% yield) as a brown wax. MS (ESI) 499.2 (M+H).

Step E. Example 149. Preparation of N-(3-(3-cyclopropylisoxazol-5-yl)phenyl)-4,4-difluoro-N-((4-(5-(1-(trifluoromethyl)cyclopropyl)-1,2,4-oxadiazol-3-yl) bicyclo[2.2.2]octan-1-yl)methyl)cyclohexane-1-carboxamide The title compound was prepared according to the method described for the synthesis of Example 5 by substituting Intermediate 149D and the corresponding acid where appropriate: (1.5 mg, 2.327 μmol, 6% yield). $^1$H NMR (400 MHz, DMSO-$d_6$) δ 7.85 (s, 1H), 7.77 (d, J=6.8 Hz, 1H), 7.66-7.48 (m, 2H), 6.91 (s, 1H), 3.61 (br. s., 2H), 2.37 (br. s., 1H), 2.11-2.02 (m, 1H), 1.95 (m, 2H), 1.82-1.55 (m, 14H), 1.49 (d, J=12.5 Hz, 2H), 1.45-1.29 (m, 6H), 1.10-1.01 (m, 2H), 0.87-0.75 (m, 2H). FXR $EC_{50}$ (nM)=78; MS (ESI) 645 (M+H).

Example 150

N-(3-(3-cyclopropylisoxazol-5-yl)phenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide (150)

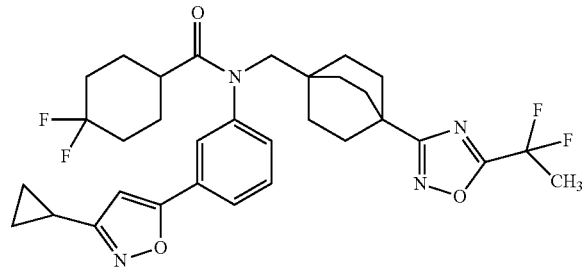

Step A. Intermediate 150A. Preparation of 3-(3-cyclopropylisoxazol-5-yl)-N-((4-(5-(1,1-difluoroethyl)-1,2,4-oxadiazol-3-yl)bicyclo[2.2.2]octan-1-yl)methyl)aniline

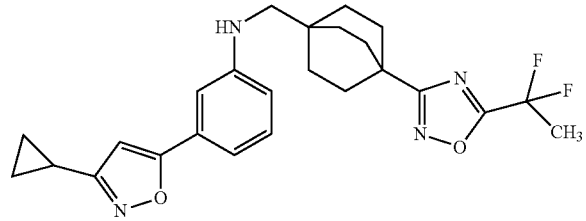 [SMILES: CC(F)(F)c1nc(C23CCC(CNc4cccc(-c5cc(C6CC6)no5)c4)(CC2)CC3)no1]

The title compound was prepared according to the method described for the synthesis of Intermediate 1F by substituting Intermediate 147B and Intermediate 105C where appropriate: (100 mg, 0.220 mmol, 55% yield) as a brown wax. MS (ESI) 455.2 (M+H).

Step B. Example 150. Preparation of N-(3-(3-cyclopropylisoxazol-5-yl)phenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide The title compound was prepared according to the method described for the synthesis of Example 5 by substituting Intermediate 150A and the corresponding acid where appropriate: (5.3 mg, 8.82 μmol, 20% yield). $^1$H NMR (400 MHz, DMSO-$d_6$) δ 7.86 (s, 1H), 7.78 (br d, J=7.3 Hz, 1H), 7.65-7.48 (m, 2H), 6.92 (s, 1H), 3.77-3.49 (m, 2H), 2.44-2.35 (m, 1H), 2.21-2.01 (m, 4H), 1.99-1.85 (m, 2H), 1.82-1.66 (m, 8H), 1.64-1.47 (m, 4H), 1.46-1.31 (m, 6H), 1.11-1.01 (m, 2H), 0.87-0.76 (m, 2H). FXR $EC_{50}$ (nM)=38; MS (ESI) 601 (M+H).

Example 151

N-((4-(3-cyclopropyl-1,2,4-oxadiazol-5-yl)bicyclo[2.2.2]octan-1-yl)methyl)-N-(3-(3-cyclopropylisoxazol-5-yl)phenyl)-4,4-difluorocyclohexane-1-carboxamide (151)

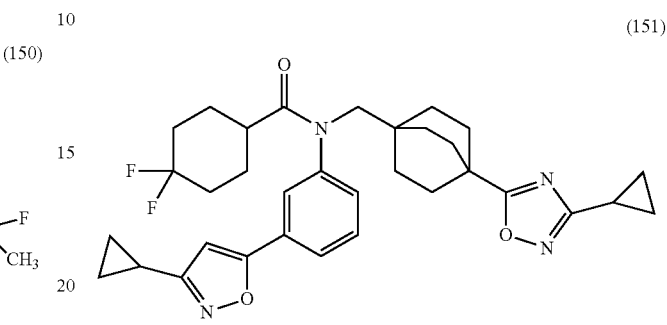

Step A. Intermediate 151A. Preparation of N-((4-(5-cyclopropyl-1,2,4-oxadiazol-3-yl) bicyclo[2.2.2]octan-1-yl)methyl)-3-(3-cyclopropylisoxazol-5-yl)aniline

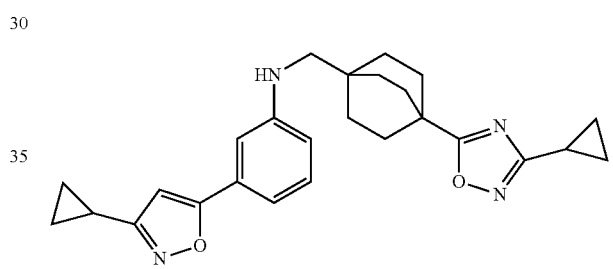

The title compound was prepared according to the method described for the synthesis of Intermediate 1F by substituting Intermediate 147B and Intermediate 2F where appropriate: (190 mg, 0.441 mmol, 88% yield) as a brown wax. MS (ESI) 431.2 (M+H).

Step B. Example 151. Preparation of N-((4-(3-cyclopropyl-1,2,4-oxadiazol-5-yl) bicyclo[2.2.2]octan-1-yl)methyl)-N-(3-(3-cyclopropylisoxazol-5-yl)phenyl)-4,4-difluorocyclohexane-1-carboxamide The title compound was prepared according to the method described for the synthesis of Example 5 by substituting Intermediate 151A and the corresponding acid where appropriate: (0.5 mg, 0.867 μmol, 2% yield). $^1$H NMR (400 MHz, DMSO-$d_6$) δ 7.84 (s, 1H), 7.77 (br d, J=7.3 Hz, 1H), 7.65-7.47 (m, 2H), 6.91 (s, 1H), 3.73-3.48 (m, 2H), 2.89 (s, 1H), 2.73 (s, 1H), 2.43-2.34 (m, 1H), 2.11-1.86 (m, 5H), 1.83-1.67 (m, 9H), 1.66-1.54 (m, 3H), 1.48 (br d, J=2.4 Hz, 1H), 1.44-1.29 (m, 6H), 1.23 (s, 1H), 1.10-0.97 (m, 4H), 0.84-0.79 (m, 4H) FXR $EC_{50}$ (nM)=38; MS (ESI) 577 (M+H).

The title compound was prepared according to the method described for the synthesis of Example 5 by substituting Intermediate 151A and corresponding acids where appropriate:

| Ex. No. | Structure | MS (ESI) (M + H) | FXR EC$_{50}$ (nM) |
|---|---|---|---|
| 152 | | 591 | 662 |
| 153 | | 543 | 57 |

| | |
|---|---|
| 152 | $^1$H NMR (400 MHz, DMSO-d$_6$) δ 7.86 (s, 1H), 7.78 (d, J = 7.6 Hz, 1H), 7.63-7.52 (m, 2H), 6.91 (s, 1H), 3.68-3.51 (m, 2H), 3.03-2.89 (m, 4H), 2.66-2.59 (m, 1H), 2.11-1.93 (m, 6H), 1.81-1.71 (m, 6H), 1.45-1.35 (m, 6H), 1.11-1.05 (m, 2H), 1.04-0.98 (m, 2H), 0.86-0.79 (m, 4H) |
| 153 | $^1$H NMR (400 MHz, DMSO-d$_6$) δ 7.85 (s, 1H), 7.80-7.73 (m, 1H), 7.66-7.49 (m, 2H), 6.92 (s, 1H), 3.80-3.69 (m, 2H), 3.68-3.45 (m, 2H), 3.06-2.91(m, 2H), 2.10-1.99 (m, 2H), 1.82-1.72 (m, 6H), 1.67-1.53 (m, 2H), 1.51-1.31 (m, 8H), 1.11-0.97 (m, 4H), 0.86-0.79 (m, 4H) (Note: 1H buried under DMSO peak) |

Example 154

N-(3-(5-cyclopropylisoxazol-3-yl)phenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide (154)

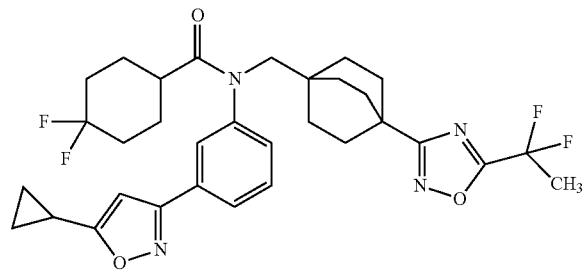

Step A. Intermediate 154A. Preparation of 3-(5-cyclopropylisoxazol-3-yl)aniline

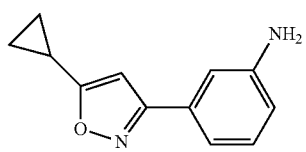 [SMILES: Nc1cccc(-c2cc(C3CC3)on2)c1]

To a stirred solution of Intermediate 147A (900 mg, 3.91 mmol) in ethanol (8 mL), THF (4 mL) and water (2 mL) were added zinc (3834 mg, 58.6 mmol) and ammonium chloride (3137 mg, 58.6 mmol) at room temperature. The reaction mixture was concentrated under reduced pressure. The reaction mixture was concentrated under reduced pressure, the residue was diluted with ethyl acetate and filtered through Celite bed. The filtrate was washed with brine solution (10 m L), dried over anhydrous sodium sulphate and evaporated under reduced pressure. The crude material was purified by flash chromatography (24 g silica gel cartridge; A=Hex, B=EtOAc; 30 min grad.; 0% B to 60% B;

flow rate=30 mL/min). The pure fractions were combined, concentrated under reduced pressure and dried in vacuo to afford the title compound (700 mg, 3.50 mmol, 89% yield) as brown wax. MS (ESI) 201 (M+1).

Step B. Intermediate 154B. Preparation of 3-(5-cyclopropylisoxazol-3-yl)-N-((4-(5-(1,1-difluoroethyl)-1,2,4-oxadiazol-3-yl)bicyclo[2.2.2]octan-1-yl)methyl)aniline

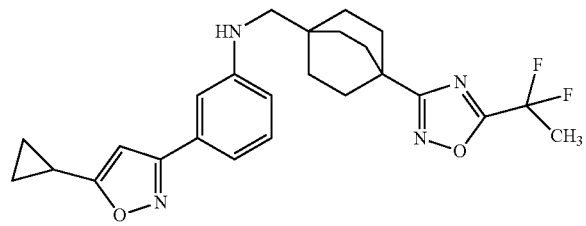 [SMILES: CC(F)(F)c1nc(C23CCC(CNc4cccc(-c5cc(C6CC6)on5)c4)(CC2)CC3)no1]

The title compound was prepared according to the method described for the synthesis of Intermediate 1F by substituting Intermediate 154A and Intermediate 105C where appropriate: (150 mg, 0.330 mmol, 83% yield) as brown wax. MS (ESI) 455 (M+H).

Step C. Example 154. Preparation of N-(3-(5-cyclopropylisoxazol-3-yl)phenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide The title compound was prepared according to the method described for the synthesis of Example 5 by substituting Intermediate 154B and the corresponding acid where appropriate: (3.0 mg, 4.99 μmol, 11% yield). $^1$H NMR (400 MHz, DMSO-$d_6$) δ 7.93-7.73 (m, 2H), 7.57 (br. s., 2H), 6.85 (s, 1H), 3.64 (br. s., 2H), 2.41 (d, J=8.6 Hz, 1H), 2.26-2.06 (m, 4H), 1.97 (br. s., 2H), 1.86-1.53 (m, 12H), 1.53-1.29 (m, 6H), 1.18-1.07 (m, 2H), 1.00-0.89 (in, 2H). FXR EC$_{50}$ (nM)=57; MS (ESI) 601 (M+H).

The following compounds were synthesized according to the method described for the synthesis of Example 5 by substituting Intermediate 154B and corresponding acids where appropriate:

| Ex. No. | Structure | MS (ESI) (M + H) | FXR EC$_{50}$ (nM) |
|---|---|---|---|
| 155 | | 615 | 289 |
| 156 | | 567 | 44 |

155 $^1$H NMR (400 MHz, DMSO-$d_6$) δ 7.89-7.76 (m, 2H), 7.63-7.48 (m, 2H), 6.86 (s, 1H), 3.80-3.53 (m, 2H), 3.06-2.87 (m, 4H), 2.72-2.64 (m, 1H), 2.25-1.89 (m, 8H), 1.84-1.68 (m, 6H), 1.50-1.35 (m, 6H), 1.15-1.06 (m, 2H), 0.98-0.89 (m, 2H)

156 $^1$H NMR (400 MHz, DMSO-$d_6$) δ 7.88-7.75 (m, 2H), 7.64-7.54 (m, 2H), 6.86 (s, 1H), 3.81-3.47 (m, 4H), 3.06-2.92 (m, 2H), 2.49-2.42 (m, 1H), 2.25-2.05 (m, 4H), 1.85-1.69 (m, 5H), 1.68-1.55 (m, 2H), 1.52-1.30 (m, 7H), 1.16-1.07 (m, 2H), 0.97-0.88 (m, 2H)

Examples 157 and 158

N-(3-(5-cyclopropylisoxazol-3-yl)phenyl)-N-((4-(5-(1,1-difluoroethyl)-1,2,4-oxadiazol-3-yl)bicyclo[2.2.2]octan-1-yl)methyl)-4-hydroxy-4-(trifluoromethyl)cyclohexane-1-carboxamide

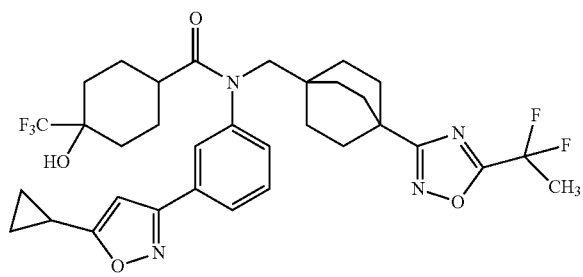

(157-158)

Step A. Intermediate 157A. Preparation of benzyl 4-oxocyclohexane-1-carboxylate

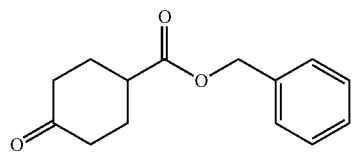 [SMILES: O=C1CCC(C(=O)OCc2ccccc2)CC1]

To a stirred solution of 4-oxocyclohexane-1-carboxylic acid (10 g, 70.3 mmol) in acetone (20 mL) were added $K_2CO_3$ (19.44 g, 141 mmol) and benzyl bromide at room temperature. The reaction mixture was heated at 60° C. overnight. The reaction mixture was cooled to room temperature and concentrated under reduced pressure. The residue was diluted with ethyl acetate (100 mL), washed with water (50 mL), brine solution (50 mL) dried over anhydrous sodium sulphate and concentrated under reduced pressure The crude material was purified by flash chromatography (80 g silica gel cartridge; A=Hex, B=EtOAc; 30 min grad.; 0% B to 60% B; flow rate=40 mL/min). The pure fractions were combined, concentrated under reduced pressure and dried in vacuo to afford the title compound (14 g, 60 mmol, 86% yield) as a brown oil. MS (ESI) 233.2 (M+H).

Step B. Intermediate 157B. Preparation of benzyl 4-hydroxy-4-(trifluoromethyl)cyclohexane-1-carboxylate

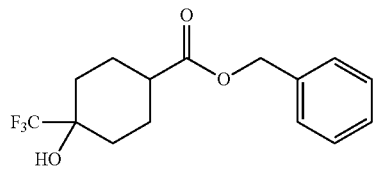

To a stirred solution of Intermediate 157A (5.5 g, 23.68 mmol) in THF (200 mL) was added trimethyl(trifluoromethyl)silane (5.05 g, 35.5 mmol) at 0° C. The reaction mixture was stirred at the same temperature for 10 min. TBAF (7.10 mL, 7.10 mmol) was added to the reaction at 0° C. The reaction mixture was warmed to room temperature and stirred overnight. The reaction mixture was concentrated under reduced pressure and the residue was diluted with ethyl acetate (100 mL). The organic layer was washed with water, brine solution, dried over anhydrous sodium sulphate and concentrated under reduced pressure. The crude material was purified by flash chromatography (120 g silica gel cartridge; A=Hex, B=EtOAc; 30 min grad.; 0% B to 30% B; flow rate=40 mL/min). The pure fractions were combined, concentrated under reduced pressure and dried in vacuo to afford the title compound as diastereomeric mixture (500 mg, 1.654 mmol, 7% yield) as a brown wax. MS (ESI) 320 (M+18).

Step C. Intermediate 157C. Preparation of 4-hydroxy-4-(trifluoromethyl)cyclohexane-1-carboxylic acid (Mixture of cis and trans isomers)

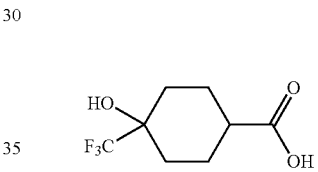

A stirred solution of Intermediate 157B (500 mg, 1.654 mmol) in ethyl acetate (10 mL) was degassed and back-filled with argon. Pd—C (176 mg, 0.165 mmol) was added to the reaction mass and stirred under hydrogen (1 atm, balloon) for overnight. The reaction was filtered through Celite and the filtrate was concentrated to afford title compound as diastereomeric mixture (300 mg, 1.414 mmol, 85% yield). $^1H$ NMR (400 MHz, DMSO-$d_6$) δ 1.55-1.65 (m, 3H), 1.70-1.90 (m, 5H), 5.72 (s, 1H), 12.20 (s, 1H). This crude compound was taken to the next step as such without further purification.

Step D. Example 157 & 158. Preparation of N-(3-(5-cyclopropylisoxazol-3-yl)phenyl)-N-((4-(5-(1,1-difluoroethyl)-1,2,4-oxadiazol-3-yl)bicyclo[2.2.2]octan-1-yl)methyl)-4-hydroxy-4-(trifluoromethyl)cyclohexane-1-carboxamide The title compound was prepared according to the method described for the synthesis of Example 5 by substituting Intermediate 154B and Intermediate 157C where appropriate. The isomers were purified by preparative HPLC to afford:

Example 157 (1 mg, 1.542 µmol, 3% yield). $^1$H NMR (400 MHz, DMSO-d$_6$) δ 7.86-7.75 (m, 2H), 7.63-7.47 (m, 2H), 6.85 (s, 1H), 3.73-3.60 (m, 2H), 2.95-2.84 (m, 1H), 2.82-2.69 (m, 2H), 2.38-2.27 (m, 2H), 2.24-2.05 (m, 4H), 1.86-1.68 (m, 6H), 1.52-1.35 (m, 6H), 1.16-1.07 (m, 2H), 0.97-0.86 (m, 2H). FXR EC$_{50}$ (nM)=242; MS (ESI) 649 (M+H).

Example 158 (1 mg, 1.542 µmol, 3% yield). $^1$H NMR (400 MHz, DMSO-d$_6$) δ 7.84-7.76 (m, 2H), 7.61-7.50 (m, 2H), 6.84 (s, 1H), 5.68 (s, 1H), 3.62 (br s, 2H), 2.23-2.05 (m, 5H), 1.83-1.69 (m, 8H), 1.67-1.59 (m, 4H), 1.57-1.46 (m, 6H), 1.16-1.04 (m, 4H), 0.97-0.91 (m, 2H). FXR EC$_{50}$ (nM)=195; MS (ESI) 649 (M+H)

Example 159

N-((4-(3-(tert-butyl)-1,2,4-oxadiazol-5-yl)bicyclo[2.2.2]octan-1-yl)methyl)-N-(3-(5-cyclopropylisoxazol-3-yl)phenyl)-4,4-difluorocyclohexane-1-carboxamide (159)

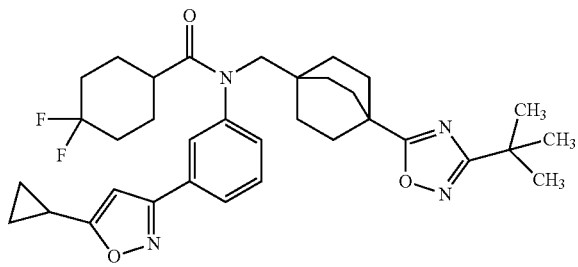

Step A. Intermediate 159A. Preparation of N-((4-(3-(tert-butyl)-1,2,4-oxadiazol-5-yl) bicyclo[2.2.2]octan-1-yl)methyl)-3-(5-cyclopropylisoxazol-3-yl) aniline

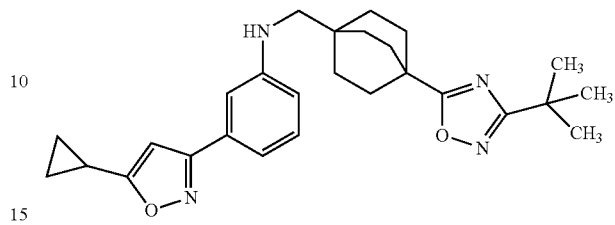

The title compound was prepared according to the method described for the synthesis of Intermediate 1F by substituting Intermediate 154A and intermediate 69C where appropriate: (40 mg, 0.090 mmol, 59% yield) as brown wax. MS (ESI) 447.2 (M+H).

Step B. Example 159. Preparation of N-((4-(3-(tert-butyl)-1,2,4-oxadiazol-5-yl) bicyclo[2.2.2]octan-1-yl)methyl)-N-(3-(5-cyclopropylisoxazol-3-yl)phenyl)-4,4-difluorocyclohexane-1-carboxamide The title compound was prepared according to the method described for the synthesis of Example 5 by substituting Intermediate 159A and the corresponding acid where appropriate: (4.1 mg, 6.92 µmol, 15% yield). $^1$H NMR (400 MHz, DMSO-d$_6$) δ 7.87-7.76 (m, 2H), 7.62-7.50 (m, 2H), 6.86 (s, 1H), 3.63 (br s, 2H), 2.46-2.36 (m, 1H), 2.24-2.16 (m, 1H), 1.95 (ddd, J=3.1, 3.8, 8.1 Hz, 2H), 1.85-1.75 (m, 6H), 1.74-1.47 (m, 6H), 1.45-1.34 (m, 6H), 1.26 (s, 9H), 1.15-1.07 (m, 2H), 0.97-0.90 (m, 2H). FXR EC$_{50}$ (nM)=78; MS (ESI) 593 (M+H).

The following compounds were synthesized according to the method described for the synthesis of Example 5 by substituting Intermediate 159A and corresponding acids where appropriate:

| Ex. No. | Structure | MS (ESI) (M + H) | FXR EC$_{50}$ (nM) |
|---|---|---|---|
| 160 | ![structure] | 607 | 701 |
| 161 | ![structure] | 559 | 77 |

| Ex. No. | Structure | MS (ESI) (M + H) | FXR EC$_{50}$ (nM) |
|---|---|---|---|
| 160 | $^1$H NMR (400 MHz, DMSO-d$_6$) δ = 7.87-7.78 (m, 2H), 7.62-7.53 (m, 2H), 6.85 (s, 1H), 3.74-3.51 (m, 2H), 3.03-2.91 (m, 4H), 2.70-2.63 (m, 1H), 2.24-2.16 (m, 1H), 2.10-1.90 (m, 4H), 1.87-1.70 (m, 6H), 1.46-1.36 (m, 6H), 1.25 (s, 9H), 1.16-1.07 (m, 2H), 0.97-0.90 (m, 2H) | | |
| 161 | $^1$H NMR (400 MHz, DMSO-d$_6$) δ 7.81-7.79 (m, 2H), 7.57-7.56 (m, 2H), 6.58 (s, 1H), 3.70-3.55 (m, 2H), 3.80-3.70 (m, 2H), 3.50-2.90 (m, 3H), 2.25-2.15 (m, 1H), 1.85-1.75 (m, 6H), 1.65-1.55 (m, 2H), 1.50-1.40 (m, 8H), 1.25 (s, 9H), 1.25-1.10 (m, 2H), 1.00-0.90 (m, 2H) | | |

N-((4-(5-(tert-butyl)-1,2,4-oxadiazol-3-yl)bicyclo[2.2.2]octan-1-yl)methyl)-N-(3-(5-cyclopropylisoxazol-3-yl)phenyl)-4,4-difluorocyclohexane-1-carboxamide (162)

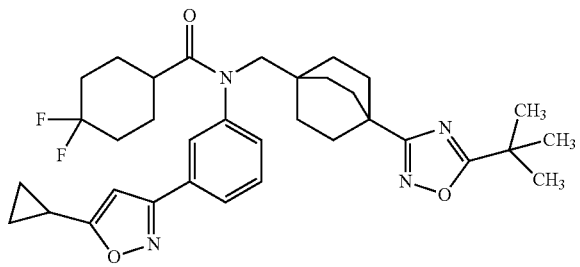

Step A. Intermediate 162A. Preparation of N-((4-(5-(tert-butyl)-1,2,4-oxadiazol-3-yl) bicyclo[2.2.2]octan-1-yl)methyl)-3-(5-cyclopropylisoxazol-3-yl) aniline The title compound was prepared according to the method described for the synthesis of Intermediate 1F by substituting Intermediate 154A and intermediate 88F where appropriate: (70 mg, 0.157 mmol, 100% yield) as brown wax. MS (ESI) 447 (M+H).

Step B. Example 162. Preparation of N-((4-(5-(tert-butyl)-1,2,4-oxadiazol-3-yl)bicyclo[2.2.2]octan-1-yl) methyl)-N-(3-(5-cyclopropylisoxazol-3-yl)phenyl)-4,4-difluorocyclohexane-1-carboxamide The title compound was prepared according to the method described for the synthesis of Example 5 by substituting Intermediate 162A and the corresponding acid where appropriate: (6.0 mg, 10.08 μmol, 22% yield). $^1$H NMR (400 MHz, DMSO-d$_6$) δ 7.89-7.73 (m, 2H), 7.64-7.47 (m, 2H), 6.86 (s, 1H), 3.77-3.44 (m, 2H), 2.44-2.35 (m, 1H), 2.19 (tt, J=4.9, 8.4 Hz, 1H), 2.05-1.87 (m, 2H), 1.82-1.66 (m, 9H), 1.65-1.53 (m, 3H), 1.53-1.46 (m, 1H), 1.43-1.35 (m, 6H), 1.33 (s, 9H), 1.16-1.06 (m, 2H), 0.97-0.88 (m, 2H). FXR EC$_{50}$ (nM)=41; MS (ESI) 593 (M+H).

Example 163

N-((4-(3-cyclopropyl-1-methyl-1H-pyrazol-5-yl)bicyclo[2.2.2]octan-1-yl)methyl)-N-(3-(5-cyclopropylisoxazol-3-yl)phenyl)-4,4-difluorocyclohexane-1-carboxamide (163)

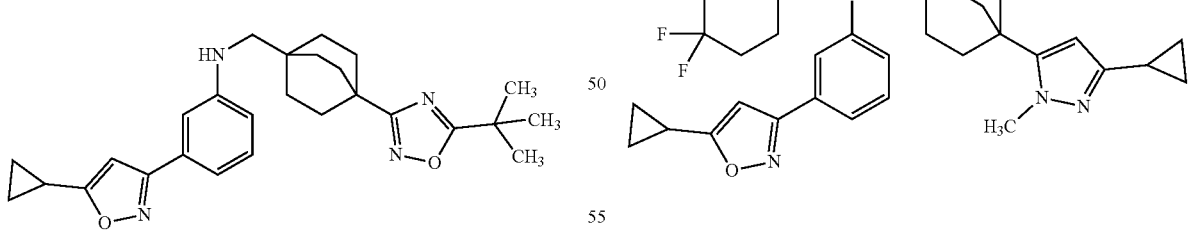

The title compound was prepared according to the method described for the synthesis of Example 5 by substituting Intermediate 139C and the corresponding acid where appropriate: (5.0 mg, 8.49 μmol, 19% yield). $^1$H NMR (400 MHz, DMSO-d$_6$) δ 7.89-7.73 (m, 2H), 7.64-7.44 (m, 2H), 6.86 (s, 1H), 5.61 (s, 1H), 3.71 (s, 3H), 3.61 (br. s., 2H), 2.40 (br. s., 1H), 2.25-2.14 (m, 1H), 1.97 (br. s., 2H), 1.85-1.55 (m, 11H), 1.50 (d, J=15.9 Hz, 2H), 1.42-1.30 (m, 6H), 1.17-1.08 (m, 2H), 0.98-0.88 (m, 2H), 0.78-0.67 (m, 2H), 0.59-0.47 (m, 2H). FXR EC$_{50}$ (nM)=130; MS (ESI) 589 (M+H).

Example 164

N-((4-(5-(1,1-difluoroethyl)-1,2,4-oxadiazol-3-yl)bicyclo[2.2.2]octan-1-yl)methyl)-N-(4'-ethoxy-6-fluoro-[1,1'-biphenyl]-3-yl)-4-hydroxy-4-(trifluoromethyl)cyclohexane-1-carboxamide (Isomer 1)

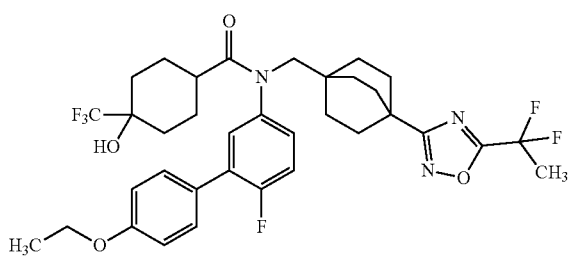

(164)

Step A. Intermediate 164A. Preparation of 3-bromo-N-((4-(5-(1,1-difluoroethyl)-1,2,4-oxadiazol-3-yl)bicyclo[2.2.2]octan-1-yl)methyl)-4-fluoroaniline

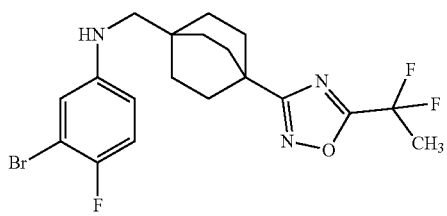 [SMILES: CC(F)(F)c1nc(C23CCC(CNc4ccc(F)c(Br)c4)(CC2)CC3)no1]

The title compound was prepared according to the method described for the synthesis of Intermediate 1F by substituting commercially available 3-bromo-4-fluoroaniline and Intermediate 105C where appropriate: (140 mg, 0.315 mmol, 24% yield) as brown wax. MS (ESI) 444 (M+H).

Step B. Intermediate 164B. Preparation of N-((4-(5-(1,1-difluoroethyl)-1,2,4-oxadiazol-3-yl)bicyclo[2.2.2]octan-1-yl)methyl)-4'-ethoxy-6-fluoro-[1,1'-biphenyl]-3-amine

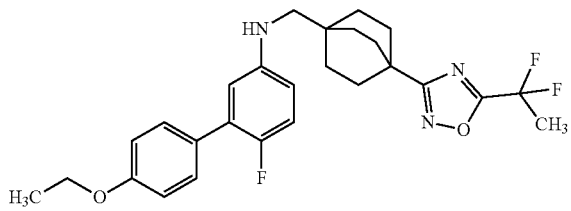 [SMILES: CCOc1ccc(-c2cc(NCC34CCC(c5noc(C(C)(F)F)n5)(CC3)CC4)ccc2F)cc1]

The title compound was prepared according to the method described for the synthesis of Intermediate 87B by substituting commercially available (4-ethoxyphenyl)boronic acid and Intermediate 164A where appropriate: (110 mg, 0.227 mmol, 63% yield) as brown wax. MS (ESI) 486 (M+H).

Step C. Intermediate 164C1 and 164C2. Preparation and isomer separation of benzyl 4-hydroxy-4-(trifluoromethyl)cyclohexane-1-carboxylate

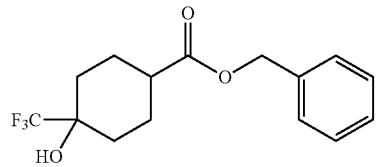

Isomer 1-164C1

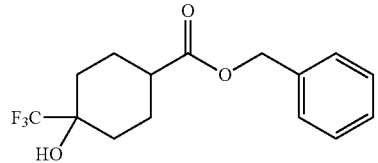

Isomer 2- 164C2

The title compound was prepared according to the method described for the synthesis of Intermediate 157B and the isomers (Cis and trans) were separated via flash silica gel column chromatography (silica 80 g column) using gradient elution from 0 to 5% ethyl acetate in pet-ether to afford Intermediate 164C1 (Isomer 1) (1.6 g, 5.29 mmol, 22% yield) as yellow oil, MS (ESI) 320 (M+18) and Intermediate 164C2 (Isomer 2) (1.5 g, 4.96 mmol, 21% yield) as a yellow oil. MS (ESI) 320 (M+18).

Step D. Intermediate 164D. Preparation of 4-hydroxy-4-(trifluoromethyl)cyclohexane-1-carboxylic acid

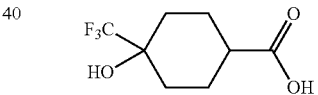

A stirred solution of Intermediate 164C1 (1.6 g, 5.29 mmol) in ethyl acetate (50 mL) was degassed and back-filled with argon. Pd—C (0.563 g, 0.529 mmol) was added to the reaction mixture and stirred under hydrogen (1 atm, balloon) for overnight. The reaction was filtered through Celite and the filtrate was concentrated to afford title compound (900 mg, 4.24 mmol, 80% yield). $^1$H NMR (400 MHz, DMSO-$d_6$) δ 12.13 (br. s, 1H), 5.70 (s, 1H), 2.15-2.26 (m, 1H), 1.40-1.80 (m, 8H).

Step E. Example 164. Preparation of N-((4-(5-(1,1-difluoroethyl)-1,2,4-oxadiazol-3-yl)bicyclo[2.2.2]octan-1-yl)methyl)-N-(4'-ethoxy-6-fluoro-[1,1'-biphenyl]-3-yl)-4-hydroxy-4-(trifluoromethyl)cyclohexane-1-carboxamide The title compound was prepared according to the method described for the synthesis of Example 5 by substituting Intermediate 164B and Intermediate 164D where appropriate: (8.0 mg, 0.012 mmol, 28% yield). $^1$H NMR (400 MHz, DMSO-$d_6$) δ 7.60-7.47 (m, 3H), 7.45-7.39 (m, 1H), 7.38-7.30 (m, 1H), 7.10-7.01 (m, 2H), 5.70 (s, 1H), 4.09 (q, J=7.1 Hz, 2H), 3.74-3.46 (m, 2H), 2.31-2.21 (m, 1H), 2.14 (t, J=19.7 Hz, 3H), 1.86-1.70 (m, 8H), 1.69-1.61 (m, 2H), 1.58-1.50 (m, 2H), 1.49-1.39 (m, 6H), 1.36 (t, J=7.1 Hz, 3H), 1.29-1.08 (m, 2H). FXR EC$_{50}$ (nM)=271; MS (ESI) 680.3 (M+1).

Example 165

N-((4-(5-(1,1-difluoroethyl)-1,2,4-oxadiazol-3-yl)bicyclo[2.2.2]octan-1-yl)methyl)-N-(4'-ethoxy-6-fluoro-[1,1'-biphenyl]-3-yl)-4-hydroxy-4-(trifluoromethyl)cyclohexane-1-carboxamide (Isomer 2)

(165)

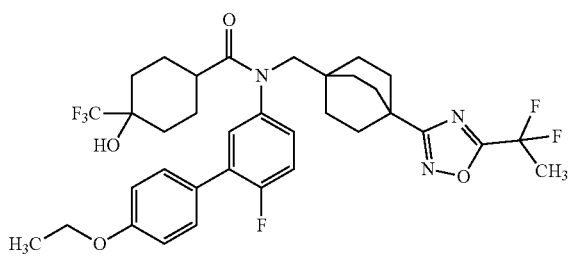

Step A. Intermediate 165A. Preparation of (1r,4r)-4-hydroxy-4-(trifluoromethyl)cyclohexane-1-carboxylic acid

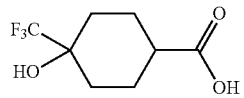

The title compound was prepared according to the method described for the synthesis of Intermediate 164D by substituting Intermediate 164C2 (Isomer 2) where appropriate: (400 mg, 1.885 mmol, 63% yield). $^1$H NMR (400 MHz, DMSO-d$_6$) δ 12.24 (br. s, 1H), 5.71 (s, 1H), 2.56-2.59 (m, 1H), 1.72-1.87 (m, 4H), 1.54-1.65 (m, 4H).

Step B. Example 165. Preparation of N-((4-(5-(1,1-difluoroethyl)-1,2,4-oxadiazol-3-yl)bicyclo[2.2.2]octan-1-yl)methyl)-N-(4'-ethoxy-6-fluoro-[1,1'-biphenyl]-3-yl)-4-hydroxy-4-(trifluoromethyl)cyclohexane-1-carboxamide The title compound was prepared according to the method described for the synthesis of Example 5 by substituting Intermediate 164B and Intermediate 165A where appropriate: (7.9 mg, 0.012 mmol, 28% yield). $^1$H NMR (400 MHz, DMSO-d$_6$) δ 7.61-7.48 (m, 3H), 7.43 (td, J=4.3, 7.5 Hz, 1H), 7.38-7.30 (m, 1H), 7.10-6.98 (m, 2H), 5.55 (s, 1H), 4.09 (q, J=7.1 Hz, 2H), 3.72-3.53 (m, 2H), 2.64-2.58 (m, 1H), 2.20-1.98 (m, 5H), 1.85-1.70 (m, 6H), 1.65-1.53 (m, 4H), 1.50-1.30 (m, 11H). FXR EC$_{50}$ (nM)=263; MS (ESI) 680.3 (M+1).

Example 166

N-((4-(3-(tert-butyl)-1,2,4-oxadiazol-5-yl)bicyclo[2.2.2]octan-1-yl)methyl)-N-(4'-ethoxy-6-fluoro-[1,1'-biphenyl]-3-yl)-4-hydroxy-4-methylcyclohexane-1-carboxamide (166)

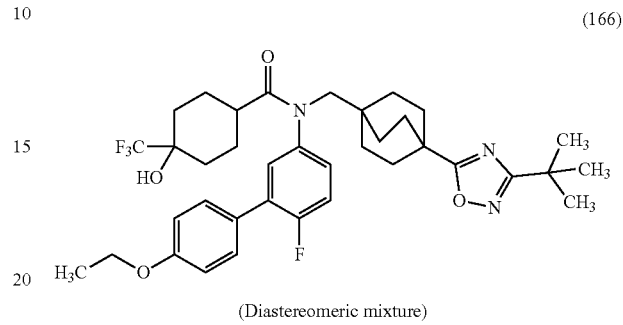

(Diastereomeric mixture)

Step A. Intermediate 166A. Preparation of 3-bromo-N-((4-(3-(tert-butyl)-1,2,4-oxadiazol-5-yl)bicyclo[2.2.2]octan-1-yl)methyl)-4-fluoroaniline

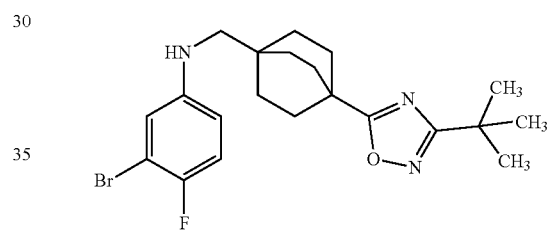

The title compound was prepared according to the method described for the synthesis of Intermediate 1F by substituting commercially available 3-bromo-4-fluoroaniline and Intermediate 69C where appropriate: (250 mg, 0.573 mmol, 57% yield) as brown wax. MS (ESI) 438 (M+2).

Step B. Intermediate 166B. Preparation of N-(3-bromo-4-fluorophenyl)-N-((4-(3-(tert-butyl)-1,2,4-oxadiazol-5-yl)bicyclo[2.2.2]octan-1-yl)methyl)-4-oxocyclohexane-1-carboxamide

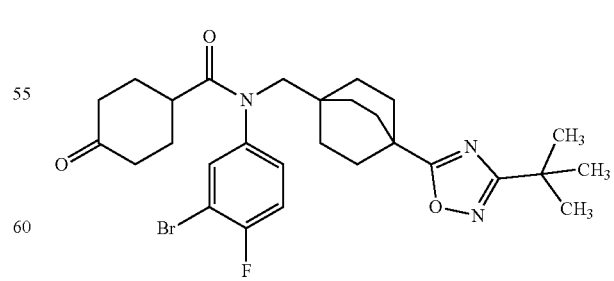

To a stirred solution of 4-oxocyclohexane-1-carboxylic acid (500 mg, 3.52 mmol) in DCM (10 mL) and DMF (0.5 mL) was added oxalyl chloride (0.65 mL, 7.03 mmol) at 0° C. The reaction mixture was warmed to room temperature and stirred overnight. The reaction mixture was concentrated under reduced pressure to afford 4-oxocyclohexane-1-carbonyl chloride. To a stirred solution of Intermediate 166A (150 mg, 0.344 mmol) in DCM (2 mL) was added TEA (0.15 mL, 1.031 mmol) and the reaction mixture was cooled to 0-5° C. 4-oxocyclohexane-1-carbonyl chloride (83 mg, 0.516 mmol) prepared above was added dropwise to this reaction mixture. The reaction mixture was warmed to room temperature and stirred at room temperature for 5 h. The reaction was quenched with cold water (5 mL). The organic layer was separated, washed with brine solution (10 mL), dried over anhydrous sodium sulfate and concentrated under reduced pressure. The crude material was purified by flash chromatography (24 g silica gel cartridge; A=Hex, B=EtOAc; 30 min grad.; 0% B to 30% B; flow rate=40 mL/min). The pure fractions were combined, concentrated under reduced pressure and dried in vacuo to afford the title compound (100 mg, 0.178 mmol, 52% yield) as a brown wax. MS (ESI) 560 (M+1).

Step C. Intermediate 166C. Preparation of N-((4-(3-(tert-butyl)-1,2,4-oxadiazol-5-yl) bicyclo[2.2.2]octan-1-yl)methyl)-N-(4'-ethoxy-6-fluoro-[1,1'-biphenyl]-3-yl)-4-oxocyclohexane-1-carboxamide

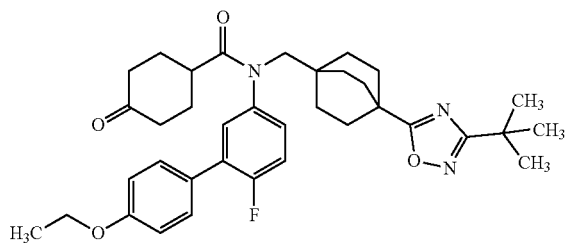 [SMILES: CCOc1ccc(-c2cc(N(CC34CCC(c5nc(C(C)(C)C)no5)(CC3)CC4)C(=O)C3CCC(=O)CC3)ccc2F)cc1]

The title compound was prepared according to the method described for the synthesis of Intermediate 87B by substituting Intermediate 166B and (4-ethoxyphenyl) boronic acid where appropriate (60 mg, 0.100 mmol, 70% yield) as a brown wax. MS (ESI) 602.2 (M+H).

Step D. Example 166. Preparation of N-((4-(3-(tert-butyl)-1,2,4-oxadiazol-5-yl) bicyclo[2.2.2]octan-1-yl)methyl)-N-(4'-ethoxy-6-fluoro-[1,1'-biphenyl]-3-yl)-4-hydroxy-4-methylcyclohexane-1-carboxamide To a stirred solution of Intermediate 166C (80 mg, 0.133 mmol) in THF (2 mL) was added methylmagnesium bromide (0.07 mL, 0.199 mmol) drop wise at −78° C. The reaction mixture was warmed to room temperature and stirred for 2 h. The reaction was quenched with saturated ammonium chloride solution (5 mL). The reaction mixture was extracted with ethyl acetate (2×5 mL). The combined organic layers were washed with water (5 mL), brine solution (5 mL), dried over anhydrous sodium sulphate and concentrated under reduced pressure. The crude material was purified by flash chromatography (12 g silica gel cartridge; A=Hex, B=EtOAc; 30 min grad.; 0% B to 30% B; flow rate=340 mL/min). The pure fractions were combined, concentrated under reduced pressure and dried in vacuo to afford the title compound as a diastereomeric mixture (3.1 mg, 5.02 μmol, 4% yield). $^1$H NMR (400 MHz, DMSO-d$_6$) δ 7.59-7.47 (m, 3H), 7.44-7.29 (m, 2H), 7.06 (d, J=8.8 Hz, 2H), 4.09 (q, J=6.9 Hz, 2H), 3.64-3.53 (m, 2H), 2.23-2.11 (m, 1H), 1.87-1.73 (m, 6H), 1.62-1.53 (m, 2H), 1.52-1.40 (m, 10H), 1.36 (t, J=6.9 Hz, 3H), 1.29-1.21 (m, 10H), 1.11-1.00 (m, 5H). FXR EC$_{50}$ (nM)=1076; MS (ESI) 618.2 (M+1).

Biological Evaluation

The exemplified compounds of the present invention were tested in the transient human FXR/Gal4-luciferase reporter assay, and assay results were described in the Examples section hereinbefore.

A Gal4-hFXR fusion construct reporter system was used as the primary assay to characterize compound activity. A construct including 5 copies of the Gal4 promoter response element upstream of a firefly luciferase reporter cDNA was stably expressed in HEK293 cells. This reporter cell line was maintained in Dulbecco's Modified Eagle's medium (DMEM; Gibco) supplemented with 1% penicillin-streptomycin (P/S) solution, 500 μg/mL Zeocin and 10% charcoal/dextran-treated fetal bovine serum (cs-FBS) at 37° C. in a humidified 5% CO$_2$ atmosphere. Another plasmid was constructed in which the human cytomegalovirus promoter in the pcDNA3.1 vector directs the expression of the cDNA encoding a fusion protein comprised of the DNA binding domain from the Gal4 transcription factor fused to the ligand binding domain from human FXR.

The day prior to transfection, the reporter cells in culture are detached from the plate with trypsin and plated into a T75 flask at a sufficient density to achieve approximately 90% confluence the next morning. The transfection reagents are prepared by separately diluting 25 μg of the pcDNA3.1-Gal4-FXR plasmid into 1.87 mL of Opti-MEM (Thermo-Fisher), and 40 μL of Lipofectamine 2000 (Thermo-Fisher) into 1.87 mL of Opti-MEM, and then adding the diluted DNA solution into the diluted Lipofectamine 2000 solution and incubating at room temperature for 15-20 minutes. The mixture is further diluted with 10 mL of a solution comprised of DMEM, 10% cs-FBS, and 1% P/S immediately prior to transferring to the cells. The maintenance culture media is aspirated from the cells and the final transfection mixture is added before the cells are incubated overnight at 37° C. in a humidified 5% CO$_2$ atmosphere. This protocol can be scaled up, and the transiently transfected cells can be cryopreserved in an assay-ready format.

For compound testing, 100 nL of the compounds (serial dilutions in DMSO) are dispensed with an Echo acoustic dispenser (Labcyte) into the wells of a Corning/Costar clear bottom 384-well white plate. The transfected cells are harvested, counted, and diluted such that 10-25,000 cells in 25 μL are plated into each well of the 384-well compound assay plate. The compound-treated cells are incubated overnight at 37° C. in a humidified 5% CO$_2$ atmosphere. The next morning 25 μL of Steady-Glo (Promega) are added to each well of the plate, the mixture is incubated for 15 min. with shaking, and luminescence is measured on an Envision (Perkin Elmer) plate reader. Background counts from cells treated with DMSO alone are subtracted from all raw counts, and the corrected values are converted to a percentage of the control response attained with 8 μM GW-4064. These data are fit to a 4-parameter log agonist-response equation to calculate an EC$_{50}$ value.

In Vivo Testing Example: Acute Mouse PK/PD

Male, C57BL6/NTac mice, weighing 25-28 g, are purchased from Taconic Labs (Hudson, NY) and maintained on Teklad Global 18% Protein Rodent Diet (Harlan Laboratories). After 1 week acclimation, mice are sorted into groups based upon body weight. Mice are administered a single oral dose of vehicle or experimental compound. Systemic compound exposure is evaluated in plasma derived from blood collected via the submandibular vein at 1 hour post-dose, and at study termination (6 h). At study termination, the animals are euthanized and rapidly dissected. The medial lobe of the liver is divided, with one half being homogenized and analyzed for compound exposure, and the other half saved in RNAlater (Thermo-Fisher Scientific). The ileum is also dissected and preserved in RNAlater. Tissue samples in RNAlater are homogenized with MP Biomedicals' beads. RNA is extracted using the MagMax-96 Total RNA Isolation kit (Thermo-Fisher Scientific) according to the manufacturer's protocol. RNA Concentration is determined with the Nano-Drop 8000 Spectrophotometer (Thermo Fisher). Reverse transcription is done with Invitrogen's SuperScript® VILO cDNA Synthesis Kit according to the manufacturer's protocol. Real time PCR is done with Applied Biosystems' Taqman PCR master mixture according to the manufacturer's protocol. All primers are purchased from Thermo-Fisher Scientific. Mouse genes analyzed include Nr0b2 (which encodes the small heterodimer partner, SHP), Abcb11 (which encodes the bile salt excretion pump, BSEP), Cyp7a1, & Cyp8b1 in liver, and Fgf15, Fabp6 (which encodes ileal bile acid binding protein, I-BABP), Slc51a (which encodes organic solute transporter alpha subunit, OSTA), and Slc51b (which encodes organic solute transporter beta subunit, OSTB) in the ileum. The statistical significant changes in FGF15 gene expression are expressed as fold increase and $CYP_{7A1}$ expression as a percent reduction relative to vehicle control.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:

1. A compound of Formula (I):

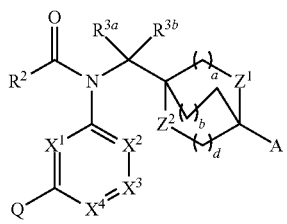

(I)

or a stereoisomer, a tautomer, or a salt thereof, wherein:
$X^1$ is $CR^{5a}$ or N;
$X^2$ is $CR^{5b}$ or N;
$X^3$ is $CR^{5c}$ or N;

$X^4$ is $CR^{5d}$ or N; provided that zero, 1, or 2 of $X^1$, $X^2$, $X^3$, and $X^4$ are N;

$Z^1$ and $Z^2$ are independently $CH_2$ or O; provided that at least one of $Z^1$ and $Z^2$ is $CH_2$;

a is zero or 1;

b is zero, 1, or 2;

d is zero, 1, or 2; provided that $Z^1$ and $Z^2$ are each $CH_2$ when a, b, and d are each zero;

Q is a cyclic group selected from 3- to 8-membered carbocyclyl, 6- to 10-membered aryl, 4- to 10-membered heterocyclyl, and 5- to 10-membered heteroaryl, wherein said cyclic group is substituted with zero to 4 $R^1$;

each $R^1$ is independently hydrogen, halo, cyano, hydroxyl, oxo, $C_{1-6}$ alkyl, $C_{2-6}$ alkenyl, $C_{2-6}$ alkynyl, $C_{1-6}$ alkoxy, —$NH_2$, —$NH(C_{1-6}$ alkyl), —$N(C_{1-6}$ alkyl$)_2$, —$C(O)(C_{1-6}$ alkyl), —$C(O)(C_{3-6}$ cycloalkyl), —$NR^xC(O)R^y$, —$C(O)OR^x$, —$C(O)NR^wR^w$, —$S(O)_2(C_{1-6}$ alkyl), —$S(O)_2(C_{3-6}$ cycloalkyl), —$NR^xS(O)_2(C_{1-6}$ alkyl), —$NR^xS(O)_2(C_{3-6}$ cycloalkyl), —$S(O)_2NR^zR^z$, —$P(O)R^yR^y$, —$(CH_2)_{0-3}(C_{3-6}$ carbocyclyl), —$O(C_{3-6}$ cycloalkyl), —$O(4-$ to 6-membered heterocyclyl), —$(CH_2)_{0-3}(4-$ to 6-membered heterocyclyl), or —$(CH_2)_{0-3}(5-$ or 6-membered heteroaryl), wherein each of said alkyl, alkoxy, alkenyl, and alkynyl is substituted with zero to 4 $R^{1a}$ and each of said cycloalkyl, heterocyclyl, and heteroaryl is substituted with zero to 4 $R^{1b}$;

each $R^{1a}$ is independently halo, hydroxyl, —$NR^wR^w$, oxo, cyano, $C_{1-3}$ alkoxy, $C_{1-3}$ haloalkoxy, —$C(O)OR^x$, —$C(O)NR^wR^w$, or —$NR^xC(O)R^y$;

each $R^{1b}$ is independently halo, oxo, cyano, hydroxyl, —$NH_2$, $C_{1-6}$ alkyl, $C_{1-6}$ alkoxy, —$NH(C_{1-6}$ alkyl), —$N(C_{1-6}$ alkyl$)_2$, or —$NR^xC(O)(C_{1-6}$ alkyl), wherein each of said alkyl and alkoxy is substituted with zero to 6 $R^{1a}$, $R^2$ is $C_{6-8}$ carbocyclyl, 6- to 7-membered heterocyclyl, phenyl, or 6-membered heteroaryl, wherein each of said carbocyclyl, heterocyclyl, phenyl, and heteroaryl is substituted with zero to 3 $R^{2b}$;

each $R^{2a}$ is independently halo, cyano, hydroxyl, oxo, $C_{1-3}$ haloalkyl, $C_{1-3}$ alkoxy, $C_{1-3}$ haloalkoxy, —$NR^xR^x$, —$C(O)(C_{1-6}$ alkyl), —$C(O)(C_{3-6}$ cycloalkyl), —$NR^xC(O)R^y$, —$C(O)(C_{1-6}$ alkyl), —$C(O)OR^x$, —$C(O)NR^wR^w$, —$S(O)_2R^y$, —$S(O)_2(C_{1-3}$ fluoroalkyl), —$NR^xS(O)_2(C_{1-3}$ alkyl), —$NR^xS(O)_2(C_{3-6}$ cycloalkyl), —$S(O)_2NR^zR^z$, or —$P(O)R^yR^y$;

each $R^{2b}$ is independently halo, cyano, hydroxyl, oxo, $C_{1-6}$ alkyl, $C_{1-6}$ alkoxy, —$NR^xR^x$, —$NR^xC(O)O(C_{1-3}$ alkyl), —$C(O)(C_{1-4}$ alkyl), —$C(O)O(C_{1-4}$ alkyl), or —$S(O)_2(C_{1-3}$ alkyl), wherein each of said alkyl and alkoxy is substituted with zero to 6 $R^{2a}$;

each $R^{2b}$ is independently halo, cyano, hydroxyl, oxo, $C_{1-6}$ alkyl, $C_{1-6}$ alkoxy, —$NR^xR^x$, —$NR^xC(O)O(C_{1-3}$ alkyl), —$C(O)(C_{1-4}$ alkyl), —$C(O)O(C_{1-4}$ alkyl), —$C(O)NR^wR^w$, —$NR^xC(O)R^y$, —$NR^xS(O)_2(C_{1-3}$ alkyl), —$NR^xS(O)_2(C_{3-6}$ cycloalkyl), —$S(O)_2NR^zR^z$, or —$S(O)_2(C_{1-3}$ alkyl), wherein each of said alkyl and alkoxy is substituted with zero to 6 $R^{2a}$, $R^{3a}$ and $R^{3b}$ are independently hydrogen, $C_{1-3}$ alkyl, $C_{1-3}$ haloalkyl, or $C_{3-6}$ cycloalkyl, or $R^{3a}$ and $R^{3b}$ taken together with the carbon atom to which they are attached, form a $C_{3-6}$ cycloalkyl;

A is:
(i) cyano;
(ii) a 5-membered heteroaryl containing 1 to 4 heteroatoms independently selected from N, O, and S, substituted with zero to 3 $R^{4a}$, or

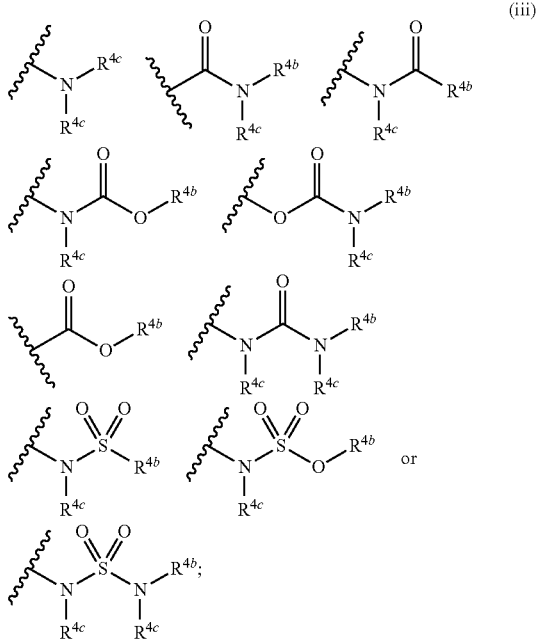

(iii)

each $R^{4a}$ is independently halo, cyano, hydroxyl, —$NH_2$, $C_{1-6}$ alkyl, $C_{2-6}$ alkenyl, $C_{2-6}$ alkynyl, $C_{1-6}$ alkoxy, —$(CH_2)_{0-3}NH(C_{1-6}$ alkyl), —$(CH_2)_{0-2}N(C_{1-6}$ alkyl)$_2$, —$(CH_2)_{0-3}(C_{3-6}$ cycloalkyl), or —$(CH_2)_{0-3}$(4- to 6-membered heterocyclyl), wherein each of said alkyl, alkoxy, alkenyl, and alkynyl is substituted with zero to 6 $R^{4d}$ and each of said cycloalkyl and heterocyclyl is substituted with zero to 3 $R^{4e}$;

$R^{4b}$ is $C_{1-6}$ alkyl, —$(CH_2)_{0-3}(C_{3-6}$ cycloalkyl), or —$(CH_2)_{0-3}$(4- to 6-membered heterocyclyl), wherein each of said alkyl is substituted with zero to 6 $R^{4d}$ and each of said cycloalkyl and heterocyclyl is substituted with zero to 3 $R^{4e}$;

each $R^{4c}$ is independently hydrogen, $C_{1-6}$ alkyl, $C_{3-6}$ cycloalkyl, —$S(O)_2(C_{1-3}$ alkyl), 4- to 6-membered heterocyclyl, phenyl, or 5- to 6-membered heteroaryl;

each $R^{4d}$ is independently halo, hydroxyl, —$NR^xR^x$, oxo, cyano, $C_{1-3}$ alkoxy, or $C_{1-3}$ haloalkoxy;

each $R^{4e}$ is independently halo, oxo, cyano, hydroxyl, —$NH_2$, $C_{1-6}$ alkyl, $C_{1-6}$ alkoxy, —$NH(C_{1-6}$ alkyl), or —$N(C_{1-6}$ alkyl)$_2$, wherein each of said alkyl and alkoxy is substituted with zero to 6 $R^{4d}$;

each of $R^{5a}$, $R^{5b}$, $R^{5c}$, and $R^{5d}$ is independently hydrogen, halo, hydroxy, cyano, $C_{1-6}$ alkyl substituted with zero to 6 $R^{5e}$, $C_{1-6}$ alkoxy substituted with zero to 6 $R^{5e}$, —C(O)$OR^x$, —C(O)$NR^wR^w$, —$S(O)_2R^y$, —$S(O)_2NR^zR^z$, or phenyl substituted with zero to 3 $R^{5f}$;

each of $R^{5e}$ is independently halo, hydroxyl, —$NR^xR^x$, oxo, cyano, $C_{1-3}$ alkoxy, or $C_{1-3}$ haloalkoxy;

each $R^{5f}$ is independently halo, oxo, cyano, hydroxyl, —$NH_2$, $C_{1-6}$ alkyl, $C_{1-6}$ alkoxy, —$NH(C_{1-6}$ alkyl), or —$N(C_{1-6}$ alkyl)$_2$, wherein each of said alkyl and alkoxy is substituted with zero to 6 $R^{5e}$;

each $R^w$ is independently hydrogen, $C_{1-6}$ alkyl, or $C_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S;

each $R^x$ is independently hydrogen, $C_{1-6}$ alkyl, or $C_{3-6}$ cycloalkyl;

$R^y$ is $C_{1-6}$ alkyl or $C_{3-6}$ cycloalkyl; and each $R^z$ is independently hydrogen, $C_{1-6}$ alkyl, or $C_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S.

2. The compound according to claim 1 or a stereoisomer, a tautomer, or a salt thereof, wherein:

Q is a cyclic group selected from 3- to 8-membered carbocyclyl, phenyl, 4- to 10-membered heterocyclyl, and 5- to 10-membered heteroaryl, wherein said cyclic group is substituted with zero to 3 $R^1$;

each $R^1$ is independently F, Cl, Br, cyano, hydroxyl, oxo, —$NR^xR^x$, $C_{1-5}$ alkyl, $C_{1-4}$ alkoxy, —$NR^x(C_{1-4}$ alkyl), —$NR^xC(O)$ $R^y$, —$C(O)(C_{1-4}$ alkyl), —$C(O)OR^x$, —$C(O)NR^wR^w$, —$S(O)_2(C_{1-4}$ alkyl), —$S(O)_2(C_{3-6}$ cycloalkyl), —$NR^xS(O)_2(C_{1-4}$ alkyl), —$NR^xS(O)_2(C_{3-6}$ cycloalkyl), —$S(O)_2NR^zR^z$, —$P(O)R^yR^y$, —$(CH_2)_{0-3}(C_{3-6}$ carbocyclyl), —$O(C_{3-6}$ cycloalkyl), —O(4- to 6-membered heterocyclyl), —$(CH_2)_{0-3}$(4- to 6-membered heterocyclyl), or —$(CH_2)_{0-3}$(5- or 6-membered heteroaryl), wherein each of said alkyl and alkoxy is substituted with zero to 4 $R^{1a}$ and each of said cycloalkyl, heterocyclyl, and heteroaryl is substituted with zero to 3 $R^{1b}$;

each $R^{1a}$ is independently F, Cl, hydroxyl, —$NR^wR^w$, oxo, cyano, $C_{1-3}$ alkoxy, $C_{1-3}$ haloalkoxy, or —C(O)OH;

each $R^{1b}$ is independently F, Cl, cyano, hydroxyl, oxo, —$NH_2$, $C_{1-4}$ alkyl, $C_{1-4}$ alkoxy, —$NH(C_{1-4}$ alkyl), —$N(C_{1-4}$ alkyl)$_2$, or —$NR^xC(O)(C_{1-6}$ alkyl), wherein each of said alkyl and alkoxy is substituted with zero to 6 $R^{1a}$;

$R^2$ is cyclohexyl, phenyl, or 6-membered heterocyclyl, wherein each of said cyclohexyl, phenyl, and heterocyclyl is substituted with zero to 3 $R^{2b}$;

each $R^{2a}$ is independently F, Cl, cyano, hydroxyl, oxo, $C_{1-3}$ haloalkyl, $C_{1-3}$ alkoxy, $C_{1-3}$ haloalkoxy, —$NR^xR^x$, —$C(O)(C_{1-4}$ alkyl), —$C(O)(C_{3-6}$ cycloalkyl), —$NR^xC(O)R^y$, —$C(O)(C_{1-4}$ alkyl), —C(O) $OR^x$, —$C(O)NR^wR^w$, —$S(O)_2R^y$, —$S(O)_2(C_{1-3}$ fluoroalkyl), —$NR^xS(O)_2(C_{1-3}$ alkyl), —$NR^xS(O)_2(C_{3-6}$ cycloalkyl), —$S(O)_2NR^zR^z$, or —$P(O)R^yR^y$;

each $R^{2b}$ is independently F, Cl, cyano, hydroxyl, oxo, $C_{1-4}$ alkyl, $C_{1-4}$ alkoxy, —$NR^xR^x$, —$NR^xC(O)O(C_{1-3}$ alkyl), —$C(O)(C_{1-4}$ alkyl), —$C(O)O(C_{1-4}$ alkyl), or —$S(O)_2(C_{1-3}$ alkyl), wherein each of said alkyl and alkoxy is substituted with zero to 6 $R^{2a}$;

A is:
(i) cyano;
(ii) a 5-membered heteroaryl containing 1 to 4 heteroatoms independently selected from N, O, and S, substituted with zero to 3 $R^{4a}$; or (iii)

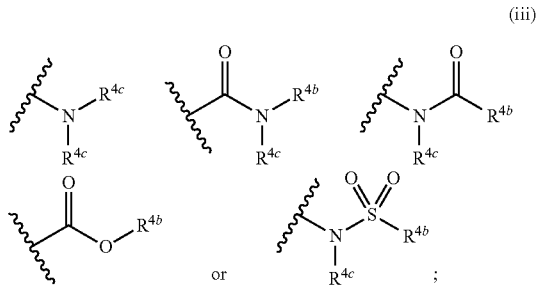

or each $R^{4a}$ is independently F, Cl, cyano, hydroxyl, —$NH_2$, $C_{1-4}$ alkyl, $C_{1-4}$ alkoxy, —$(CH_2)_{0-3}NH(C_{1-6}$ alkyl), —$(CH_2)_{0-3}N(C_{1-6}$ alkyl$)_2$, —$(CH_2)_{0-3}(C_{3-6}$ cycloalkyl), or —$(CH_2)_{0-3}$(4- to 6-membered heterocyclyl), wherein each of said alkyl and alkoxy is substituted with zero to 4 $R^{4d}$ and each of said cycloalkyl and heterocyclyl is substituted with zero to 3 $R^{4e}$;

$R^{4b}$ is $C_{1-4}$ alkyl, —$(CH_2)_{0-3}(C_{3-6}$ cycloalkyl), or —$(CH_2)_{0-3}$(4- to 6-membered heterocyclyl), wherein each of said alkyl is substituted with zero to 4 $R^{4d}$ and each of said cycloalkyl and heterocyclyl is substituted with zero to 3 $R^{4e}$;

each $R^{4c}$ is independently hydrogen, $C_{1-3}$ alkyl, or $C_{3-6}$ cycloalkyl;

each $R^{4d}$ is independently F, Cl, hydroxyl, —$NR^xR^x$, oxo, cyano, $C_{1-3}$ alkoxy, or $C_{1-3}$ fluoroalkoxy;

each $R^{4e}$ is independently F, Cl, oxo, cyano, hydroxyl, —$NH_2$, $C_{1-4}$ alkyl, $C_{1-4}$ alkoxy, or —$NH(C_{1-6}$ alkyl), or —$N(C_{1-6}$ alkyl$)_2$, wherein each of said alkyl and alkoxy is substituted with zero to 4 $R^{4d}$;

each of $R^{5a}$, $R^{5b}$, $R^{5c}$, and $R^{5d}$ is independently hydrogen, F, Cl, hydroxy, cyano, $C_{1-3}$ alkyl substituted with zero to 4 $R^{5e}$, $C_{1-3}$ alkoxy substituted with zero to 4 $R^{5e}$, —$C(O)OR^x$, —$C(O)NR^wR^w$, —$S(O)_2R^y$, —$S(O)_2NR^zR^z$, or phenyl substituted with zero to 3 $R^{5f}$;

each $R^w$ is independently hydrogen, $C_{1-4}$ alkyl, or $C_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S;

each $R^x$ is independently H, $C_{1-4}$ alkyl, or $C_{3-6}$ cycloalkyl;

$R^y$ is $C_{1-4}$ alkyl or $C_{3-6}$ cycloalkyl; and each $R^z$ is independently hydrogen, $C_{1-4}$ alkyl, or $C_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S.

3. The compound according to claim 1 or a stereoisomer, a tautomer, or a salt thereof, wherein:
$X^1$ is CH;
$X^2$ is CH;
$X^3$ is $CR^{5c}$;
$X^4$ is $CR^{5d}$;
a is zero or 1;
b is zero or 1;
d is zero or 1;
$Z^1$ and $Z^2$ are each $CH_2$;
Q is a cyclic group selected from cyclopropyl, imidazolyl, isoxazolyl, oxazolyl, oxadiazolyl, pyrazolyl, thiazolyl, phenyl, pyridinyl, pyridazinyl, pyrimidinyl, benzo[d]oxazolyl, benzo[d]thiazolyl, and pyrazolo[1,5-a]pyrimidinyl, wherein said cyclic group is substituted with zero to 2 $R^1$;

each $R^1$ is independently F, Cl, oxo, —$CH_3$, —$CH_2CH_3$, —$CH_2CH_2CH_3$, —$CHF_2$, —$C(CH_3)_2OH$, —$CH_2OCH_3$, —$OCH_3$, —$OCH_2CH_3$, —$OCHF_2$, —$C(O)OCH_3$, —$C(O)OCH_2CH_3$, —$S(O)_2CH_3$, —$P(O)(CH_3)_2$, cyclopropyl, —$CH_2$ (cyclopropyl), —O(cyclopropyl), or tetrahydropyranyl;

$R^2$ is cyclohexyl, morpholinyl, phenyl, piperazinyl, piperidinyl, tetrahydropyranyl, or tetrahydrothiopyranyl, each substituted with zero to 3 $R^{2b}$;

each $R^{2b}$ is independently F, Cl, hydroxyl, oxo, —$CH_3$, —$CF_3$, —$CH_2OH$, —$OCH_3$, —$OCHF_2$, —$C(O)OC(CH_3)_3$, or piperidinyl;

$R^{3a}$ is hydrogen or —$CH_3$;

$R^{3b}$ is hydrogen;

A is:
(i) cyano;
(ii) pyrazolyl, oxazolyl, thiazolyl, oxadiazolyl, thiadiazolyl, or tetrazolyl, each substituted with zero to 2 $R^{4a}$; or
(iii) —$C(O)NH$(cyclopropyl);

each $R^{4a}$ is independently —$CH_3$, —$C(CH_3)_3$, —$CF_3$, —$CF_2CH_3$, —$C(CH_3)_2F$, —$CH_2$ (cyclopropyl), cyclopropyl, trifluoromethylcyclobutyl, trifluoromethyl-hydroxycyclobutyl, or tetrahydropyranyl; and one $R^{5c}$ and $R^{5d}$ is hydrogen or F, and the other of $R^{5c}$ and $R^{5d}$ is hydrogen.

4. The compound according to claim 1 or a salt or solvate thereof, wherein:
$X^1$ is CH;
$X^2$ is CH;
$X^3$ is CH;
$X^4$ is CH or CF;
$Z^1$ and $Z^2$ are each $CH_2$;
a, b, and d are each zero; or a, b, and d are each 1;
Q is a cyclic group selected from cyclopropyl, imidazolyl, isoxazolyl, oxazolyl, oxadiazolyl, pyrazolyl, thiazolyl, phenyl, pyridinyl, pyridazinyl, pyrimidinyl, benzo[d]oxazolyl, benzo[d]thiazolyl, and pyrazolo[1,5-a]pyrimidinyl, wherein said cyclic group is substituted with zero to 2 $R^1$;

each $R^1$ is independently F, Cl, oxo, —$CH_3$, —$CH_2CH_3$, —$CH_2CH_2CH_3$, —$CHF_2$, —$C(CH_3)_2OH$, —$CH_2OCH_3$, —$OCH_3$, —$OCH_2CH_3$, —$OCHF_2$, —$C(O)OCH_3$, —$C(O)OCH_2CH_3$, —$S(O)_2CH_3$, —$P(O)(CH_3)_2$, cyclopropyl, —$CH_2$ (cyclopropyl), —O(cyclopropyl), or tetrahydropyranyl;

$R^2$ is cyclohexyl, morpholinyl, phenyl, piperazinyl, piperidinyl, tetrahydropyranyl, or tetrahydrothiopyranyl, each substituted with zero to 3 $R^{2b}$;

each $R^{2b}$ is independently F, Cl, hydroxyl, oxo, —$CH_3$, —$CF_3$, —$CH_2OH$, —$OCH_3$, —$OCHF_2$, —$C(O)OC(CH_3)_3$, or piperidinyl;

$R^{3a}$ is hydrogen or —$CH_3$;

$R^{3b}$ is hydrogen;

A is:
(i) cyano;
(ii) pyrazolyl, oxazolyl, thiazolyl, oxadiazolyl, thiadiazolyl, or tetrazolyl, each substituted with zero to 2 $R^{4a}$; or
(iii) —$C(O)NH$(cyclopropyl); and each $R^{4a}$ is independently —$CH_3$, —$C(CH_3)_3$, —$CF_3$, —$CF_2CH_3$, —$C(CH_3)_2F$, —$CH_2$ (cyclopropyl), cyclopropyl, trifluoromethylcyclobutyl, trifluoromethyl-hydroxycyclobutyl, or tetrahydropyranyl.

5. The compound according to claim 1 or a stereoisomer, a tautomer, or a salt thereof, wherein A is a 5-membered heteroaryl containing 1 to 4 heteroatoms independently selected from N, O, and S, substituted with zero to 3 $R^{4a}$.

6. The compound according to claim 1 or a stereoisomer, a tautomer, or a salt thereof, wherein A is pyrazolyl, oxazolyl, thiazolyl, oxadiazolyl, thiadiazolyl, or tetrazolyl, each substituted with zero to 2 $R^{4a}$.

7. The compound according to claim 1 or a stereoisomer, a tautomer, or a salt thereof, wherein A is a 5-membered heteroaryl containing 1 to 4 heteroatoms independently selected from N, O, and S, substituted with zero to 3 $R^{4a}$; and each of $Z^1$ and $Z^2$ is $CH_2$.

8. The compound according to claim 1 or a stereoisomer, a tautomer, or a salt thereof, wherein said compound is:
N-((4-(3-methyl-1,2,4-oxadiazol-5-yl)bicyclo[2.2.2]octan-1-yl)methyl)-N-(3-(3-methyl-1,2,4-oxadiazol-5-yl)phenyl)cyclohexanecarboxamide (1);
methyl 5-(3-(N-((4-(3-cyclopropyl-1,2,4-oxadiazol-5-yl)bicyclo[2.2.2]octan-1-yl)methyl)cyclohexanecarboxamido)phenyl)-1,2,4-oxadiazole-3-carboxylate (2);
N-(4'-methoxy-[1,1'-biphenyl]-3-yl)-N-((4-(3-methyl-1,2,4-oxadiazol-5-yl) bicyclo[2.2.2]octan-1-yl)methyl) cyclohexane carboxamide (3);
N-((4-(3-cyclopropyl-1,2,4-oxadiazol-5-yl)bicyclo[2.2.2]octan-1-yl)methyl)-N-(3-(3-ethyl-1,2,4-oxadiazol-5-yl)phenyl)cyclohexanecarboxamide (4);
N-((4-(3-cyclopropyl-1,2,4-oxadiazol-5-yl)bicyclo[2.2.2]octan-1-yl)methyl)-N-(3-(3-ethyl-1,2,4-oxadiazol-5-yl)phenyl)-4,4-difluorocyclohexane-1-carboxamide (5);
N-(3-(2-methoxyoxazol-5-yl)phenyl)-N-((4-(3-methyl-1,2,4-oxadiazol-5-yl) bicyclo[2.2.2]octan-1-yl)methyl) cyclohexanecarboxamide (6);
N-((4-(3-cyclopropyl-1,2,4-oxadiazol-5-yl)bicyclo[2.2.2]octan-1-yl)methyl)-N-(3-(2-methoxyoxazol-5-yl)phenyl)cyclohexanecarboxamide (7);
N-((4-(3-cyclopropyl-1,2,4-oxadiazol-5-yl)bicyclo[2.2.2]octan-1-yl)methyl)-N-(3-(2-ethoxyoxazol-5-yl)phenyl)cyclohexanecarboxamide (8);
N-((4-(3-cyclopropyl-1,2,4-oxadiazol-5-yl)bicyclo[2.2.2]octan-1-yl)methyl)-N-(3-(2-ethoxyoxazol-5-yl)phenyl)-4,4-difluorocyclohexane-1-carboxamide (9);
N-(3-(2-ethoxyoxazol-5-yl)phenyl)-N-((4-(3-methyl-1,2,4-oxadiazol-5-yl) bicyclo[2.2.2]octan-1-yl)methyl)cyclohexanecarboxamide (10);
N-(3-(5-methoxyisoxazol-3-yl)phenyl)-N-((4-(3-methyl-1,2,4-oxadiazol-5-yl) bicyclo[2.2.2]octan-1-yl)methyl) cyclohexanecarboxamide (11);
N-((4-(3-cyclopropyl-1,2,4-oxadiazol-5-yl)bicyclo[2.2.2]octan-1-yl)methyl)-N-(3-(5-methoxyisoxazol-3-yl)phenyl)cyclohexanecarboxamide (12);
N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)cyclohexanecarboxamide (13);
N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-4,4-difluorocyclohexane-1-carboxamide (14);
N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)tetrahydro-2H-pyran-4-carboxamide (15);
N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)tetrahydro-2H-pyran-3-carboxamide, racemate (16);
N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-1-methylpiperidine-4-carboxamide (17);
N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)tetrahydro-2H-thiopyran-4-carboxamide 1,1-dioxide (18);
ethyl 2-(3-(N-((4-(3-methyl-1,2,4-oxadiazol-5-yl)bicyclo[2.2.2]octan-1-yl)methyl)cyclohexanecarboxamido)phenyl) oxazole-4-carboxylate (19);
ethyl 2-(3-(N-((4-(3-cyclopropyl-1,2,4-oxadiazol-5-yl)bicyclo[2.2.2]octan-1-yl)methyl)cyclohexanecarboxamido)phenyl) oxazole-4-carboxylate (20);
N-((4-(3-cyclopropyl-1,2,4-oxadiazol-5-yl)bicyclo[2.2.2]octan-1-yl)methyl)-N-(3-(4-(2-hydroxypropan-2-yl)oxazol-2-yl)phenyl)cyclohexanecarboxamide (21);
N-((4-(3-cyclopropyl-1,2,4-oxadiazol-5-yl)bicyclo[2.2.2]octan-1-yl)methyl)-N-(3-(2-cyclopropyloxazol-5-yl)phenyl)cyclohexanecarboxamide (22);
N-((4-(3-cyclopropyl-1,2,4-oxadiazol-5-yl)bicyclo[2.2.2]octan-1-yl)methyl)-N-(3-(2-cyclopropyloxazol-5-yl)phenyl)tetrahydro-2H-pyran-4-carboxamide (23);
N-((4-(3-cyclopropyl-1,2,4-oxadiazol-5-yl)bicyclo[2.2.2]octan-1-yl)methyl)-N-(3-(2-cyclopropyloxazol-5-yl)phenyl)-1-methylpiperidine-4-carboxamide (24);
N-((4-(3-cyclopropyl-1,2,4-oxadiazol-5-yl)bicyclo[2.2.2]octan-1-yl)methyl)-N-(3-(2-cyclopropyloxazol-5-yl)phenyl)tetrahydro-2H-pyran-3-carboxamide, racemate (25);
N-((4-(3-cyclopropyl-1,2,4-oxadiazol-5-yl)bicyclo[2.2.2]octan-1-yl)methyl)-N-(3-(2-cyclopropyloxazol-5-yl)phenyl)-4,4-difluorocyclohexane-1-carboxamide (26);
N-((4-(3-cyclopropyl-1,2,4-oxadiazol-5-yl)bicyclo[2.2.2]octan-1-yl)methyl)-N-(3-(5-ethoxyisoxazol-3-yl)phenyl)cyclohexanecarboxamide (27);
N-((4-(3-cyclopropyl-1,2,4-oxadiazol-5-yl)bicyclo[2.2.2]octan-1-yl)methyl)-N-(3-(2-propyloxazol-5-yl)phenyl)cyclohexanecarboxamide (28);
N-((4-(3-cyclopropyl-1,2,4-oxadiazol-5-yl)bicyclo[2.2.2]octan-1-yl)methyl)-N-(3-(2-propyloxazol-5-yl)phenyl)tetrahydro-2H-pyran-4-carboxamide (29);
N-((4-(3-cyclopropyl-1,2,4-oxadiazol-5-yl)bicyclo[2.2.2]octan-1-yl)methyl)-N-(3-(2-propyloxazol-5-yl)phenyl)tetrahydro-2H-pyran-3-carboxamide, racemate (30);
ethyl 4-(3-(N-((4-(3-cyclopropyl-1,2,4-oxadiazol-5-yl)bicyclo[2.2.2]octan-1-yl)methyl)cyclohexanecarboxamido)phenyl) thiazole-2-carboxylate (31);
N-((4-(3-cyclopropyl-1,2,4-oxadiazol-5-yl)bicyclo[2.2.2]octan-1-yl)methyl)-N-(3-(2-(2-hydroxypropan-2-yl)thiazol-4-yl)phenyl)cyclohexanecarboxamide (32);
N-((4-(3-methyl-1,2,4-oxadiazol-5-yl)bicyclo[2.2.2]octan-1-yl)methyl)-N-(3-(2-(tetrahydro-2H-pyran-4-yl)oxazol-5-yl)phenyl)cyclohexanecarboxamide (33);
N-((4-(3-cyclopropyl-1,2,4-oxadiazol-5-yl)bicyclo[2.2.2]octan-1-yl)methyl)-N-(3-(2-(tetrahydro-2H-pyran-4-yl) oxazol-5-yl)phenyl)cyclohexanecarboxamide (34);
N-(3-(3-cyclopropyl-1,2,4-oxadiazol-5-yl)phenyl)-N-((4-(5-methyloxazol-2-yl) bicyclo[2.2.2]octan-1-yl)methyl)cyclohexanecarboxamide (35);
N-((4-(3-cyclopropyl-1,2,4-oxadiazol-5-yl)bicyclo[2.2.2]octan-1-yl)methyl)-N-(3-(4-(difluoromethyl) oxazol-2-yl)phenyl)tetrahydro-2H-pyran-4-carboxamide (36);
N-((4-(3-cyclopropyl-1,2,4-oxadiazol-5-yl)bicyclo[2.2.2]octan-1-yl)methyl)-N-(3-(4-(difluoromethyl) oxazol-2-yl)phenyl)cyclohexanecarboxamide (37);

tert-butyl 4-(((4-(3-cyclopropyl-1,2,4-oxadiazol-5-yl)bicyclo[2.2.2]octan-1-yl)methyl) (3-(4-(difluoromethyl)oxazol-2-yl)phenyl)carbamoyl)piperidine-1-carboxylate (38);

N-((4-(3-cyclopropyl-1,2,4-oxadiazol-5-yl)bicyclo[2.2.2]octan-1-yl)methyl)-N-(3-(5-ethoxy-1,3,4-oxadiazol-2-yl)phenyl)-4,4-difluorocyclohexane-1-carboxamide (39);

N-((4-(3-cyclopropyl-1,2,4-oxadiazol-5-yl)bicyclo[2.2.2]octan-1-yl)methyl)-N-(3-(5-cyclopropylisoxazol-3-yl)phenyl)tetrahydro-2h-pyran-4-carboxamide (40);

N-((4-(3-(cyclopropylmethyl)-1,2,4-oxadiazol-5-yl)bicyclo[2.2.2]octan-1-yl)methyl)-N-(3-(3-(cyclopropylmethyl)-1,2,4-oxadiazol-5-yl)phenyl)tetrahydro-2H-pyran-4-carboxamide (41);

N-((4-(3-(cyclopropylmethyl)-1,2,4-oxadiazol-5-yl)bicyclo[2.2.2]octan-1-yl)methyl)-N-(3-(3-(cyclopropylmethyl)-1,2,4-oxadiazol-5-yl)phenyl)-4,4-difluorocyclohexane-1-carboxamide (42);

N-((4-(3-cyclopropyl-1,2,4-oxadiazol-5-yl)bicyclo[2.2.2]octan-1-yl)methyl)-N-(3-(3-(cyclopropylmethyl)-1,2,4-oxadiazol-5-yl)phenyl)-4,4-difluorocyclohexane-1-carboxamide (43);

N-((4-(3-cyclopropyl-1,2,4-oxadiazol-5-yl)bicyclo[2.2.2]octan-1-yl)methyl)-N-(3-(3-(cyclopropylmethyl)-1,2,4-oxadiazol-5-yl)phenyl)tetrahydro-2H-pyran-4-carboxamide (44);

N-(3-(3-cyclopropyl-1,2,4-oxadiazol-5-yl)phenyl)-N-((4-(3-(cyclopropylmethyl)-1,2,4-oxadiazol-5-yl)bicyclo[2.2.2]octan-1-yl)methyl)tetrahydro-2H-pyran-4-carboxamide (45);

N-(3-(3-cyclopropyl-1,2,4-oxadiazol-5-yl)phenyl)-N-((4-(3-(cyclopropylmethyl)-1,2,4-oxadiazol-5-yl)bicyclo[2.2.2]octan-1-yl)methyl)-4,4-difluorocyclohexane-1-carboxamide (46);

N-((4-(3-cyclopropyl-1,2,4-oxadiazol-5-yl)bicyclo[2.2.2]octan-1-yl)methyl)-N-(3-(2-(methoxymethyl) thiazol-4-yl)phenyl)tetrahydro-2H-pyran-4-carboxamide (47);

tert-butyl 4-(((4-(3-cyclopropyl-1,2,4-oxadiazol-5-yl)bicyclo[2.2.2]octan-1-yl)methyl) (3-(2-(methoxymethyl)thiazol-4-yl)phenyl)carbamoyl)piperidine-1-carboxylate (48);

N-((4-(3-cyclopropyl-1,2,4-oxadiazol-5-yl)bicyclo[2.2.2]octan-1-yl)methyl)-N-(3-(2-(methoxymethyl) thiazol-4-yl)phenyl)cyclohexanecarboxamide (49);

N-((4-(3-cyclopropyl-1,2,4-oxadiazol-5-yl)bicyclo[2.2.2]octan-1-yl)methyl)-N-(3-(5-cyclopropyl-1-methyl-1H-pyrazol-3-yl)phenyl)tetrahydro-2H-pyran-4-carboxamide (50);

N-((4-(3-cyclopropyl-1,2,4-oxadiazol-5-yl)bicyclo[2.2.2]octan-1-yl)methyl)-N-(3-(3-ethyl-2-oxo-2,3-dihydrooxazol-5-yl)phenyl)tetrahydro-2H-pyran-4-carboxamide (51);

N-((4-(3-cyclopropyl-1,2,4-oxadiazol-5-yl)bicyclo[2.2.2]octan-1-yl)methyl)-N-(3-(3-ethyl-2-oxo-2,3-dihydrooxazol-5-yl)phenyl)tetrahydro-2H-pyran-3-carboxamide, racemate (52);

N-((4-(3-cyclopropyl-1,2,4-oxadiazol-5-yl)bicyclo[2.2.2]octan-1-yl)methyl)-N-(3-(4-(methoxymethyl) oxazol-2-yl)phenyl)tetrahydro-2H-pyran-4-carboxamide (53);

N-((4-(3-cyclopropyl-1,2,4-oxadiazol-5-yl)bicyclo[2.2.2]octan-1-yl)methyl)-N-(3-(5-cyclopropyl-1,3,4-oxadiazol-2-yl)phenyl)tetrahydro-2H-pyran-4-carboxamide (54);

N-((4-(3-cyclopropyl-1,2,4-oxadiazol-5-yl)bicyclo[2.2.2]octan-1-yl)methyl)-N-(3-(5-cyclopropyl-1,3,4-oxadiazol-2-yl)phenyl)tetrahydro-2H-pyran-3-carboxamide, racemate (55);

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl) morpholine-4-carboxamide (56);

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)piperidine-1-carboxamide (57);

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-4,4-difluoropiperidine-1-carboxamide (58);

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-4-methylpiperazine-1-carboxamide (59);

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-4-methylpiperidine-1-carboxamide (60);

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-4-hydroxypiperidine-1-carboxamide (61);

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-3,3-dimethylpiperidine-1-carboxamide, racemate (62);

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-2,6-dimethylmorpholine-4-carboxamide (63);

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-[1,4'-bipiperidine]-1'-carboxamide (64);

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-3-(hydroxymethyl)piperidine-1-carboxamide, racemate (65);

N-(3-(3-cyclopropyl-1,2,4-oxadiazol-5-yl)phenyl)-N-((4-(4-cyclopropylthiazol-2-yl) bicyclo[2.2.2]octan-1-yl)methyl)tetrahydro-2H-pyran-3-carboxamide, racemate (66);

N-(3-(3-cyclopropyl-1,2,4-oxadiazol-5-yl)phenyl)-N-((4-(5-cyclopropyl-1-methyl-1H-pyrazol-3-yl)bicyclo[2.2.2]octan-1-yl)methyl)tetrahydro-2H-pyran-3-carboxamide (67);

N-((4-(3-cyclopropyl-1,2,4-oxadiazol-5-yl)bicyclo[2.2.2]octan-1-yl)methyl)-N-(3-(2-cyclopropyl-1-methyl-1H-imidazol-4-yl)phenyl)tetrahydro-2H-pyran-3-carboxamide, racemate (68);

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)phenyl)tetrahydro-2H-pyran-4-carboxamide (69);

N-(3-(3-ethyl-1,2,4-oxadiazol-5-yl)phenyl)-N-(1-(4-(3-methyl-1,2,4-oxadiazol-5-yl) bicyclo[2.2.2]octan-1-yl)ethyl)cyclohexanecarboxamide (70-71);

N-(3'-methoxy-[1,1'-biphenyl]-3-yl)-N-((4-(3-methyl-1,2,4-oxadiazol-5-yl) bicyclo[2.2.2]octan-1-yl)methyl)cyclohexanecarboxamide (72);

N-(3-(2-methoxypyridin-4-yl)phenyl)-N-((4-(3-methyl-1,2,4-oxadiazol-5-yl) bicyclo[2.2.2]octan-1-yl)methyl)cyclohexane carboxamide (73);

N-((4-(3-cyclopropyl-1,2,4-oxadiazol-5-yl)bicyclo[2.2.2]octan-1-yl)methyl)-N-(3'-methoxy-[1,1'-biphenyl]-3-yl)cyclohexanecarboxamide (74);

N-((4-(3-cyclopropyl-1,2,4-oxadiazol-5-yl)bicyclo[2.2.2]octan-1-yl)methyl)-N-(3-(2-methoxypyridin-4-yl)phenyl)cyclohexane carboxamide (75);

N-(4'-methoxy-[1,1'-biphenyl]-3-yl)-N-((4-(3-methyl-1,2,4-oxadiazol-5-yl) bicyclo[2.2.2]octan-1-yl)methyl)cyclohexane carboxamide (76);

N-((4-(3-cyclopropyl-1,2,4-oxadiazol-5-yl)bicyclo[2.2.2]octan-1-yl)methyl)-N-(3-(4-ethoxypyridin-2-yl)phenyl)cyclohexane carboxamide (77);

N-((4-(3-cyclopropyl-1,2,4-oxadiazol-5-yl)bicyclo[2.2.2]octan-1-yl)methyl)-N-(3-(2-ethoxypyridin-4-yl)phenyl)cyclohexane carboxamide (78);

N-((4-(3-cyclopropyl-1,2,4-oxadiazol-5-yl)bicyclo[2.2.2]octan-1-yl)methyl)-N-(3-(2-ethoxypyridin-4-yl)phenyl)-4,4-difluorocyclohexane-1-carboxamide (79);

N-(3-(2-methoxypyridin-4-yl)phenyl)-N-((4-(5-methyl-1,3,4-thiadiazol-2-yl)bicyclo[2.2.2]octan-1-yl)methyl)cyclohexanecarboxamide (80);

N-(3-(2-methoxypyridin-4-yl)phenyl)-N-((4-(5-methyl-1,3,4-thiadiazol-2-yl)bicyclo[2.2.2]octan-1-yl)methyl)tetrahydro-2H-pyran-4-carboxamide (81);

4,4-difluoro-N-(3-(2-methoxypyridin-4-yl)phenyl)-N-((4-(5-methyl-1,3,4-thiadiazol-2-yl)bicyclo[2.2.2]octan-1-yl)methyl)cyclohexane-1-carboxamide (82);

N-((4-(3-cyclopropyl-1,2,4-oxadiazol-5-yl)bicyclo[2.2.2]octan-1-yl)methyl)-N-(3-(2-methoxypyridin-4-yl)phenyl)tetrahydro-2H-pyran-4-carboxamide (83);

N-((4-(3-cyclopropyl-1,2,4-oxadiazol-5-yl)bicyclo[2.2.2]octan-1-yl)methyl)-N-(3-(2-methoxypyrimidin-4-yl)phenyl)tetrahydro-2H-pyran-4-carboxamide (84);

N-((4-(3-cyclopropyl-1,2,4-oxadiazol-5-yl)bicyclo[2.2.2]octan-1-yl)methyl)-4,4-difluoro-N-(3-(2-methoxypyrimidin-4-yl)phenyl)cyclohexane-1-carboxamide (85);

N-(3-(2-cyclopropoxypyrimidin-4-yl)phenyl)-N-((4-(3-cyclopropyl-1,2,4-oxadiazol-5-yl)bicyclo[2.2.2]octan-1-yl)methyl)tetrahydro-2H-pyran-4-carboxamide (86);

N-((4-(3-(tert-butyl)-1,2,4-oxadiazol-5-yl)bicyclo[2.2.2]octan-1-yl)methyl)-N-(3-(2-ethoxypyrimidin-5-yl)phenyl)tetrahydro-2H-pyran-4-carboxamide (87);

N-((4-(5-(tert-butyl)-1,2,4-oxadiazol-3-yl)bicyclo[2.2.2]octan-1-yl)methyl)-N-(3-(2-ethoxypyrimidin-5-yl)phenyl)tetrahydro-2H-pyran-4-carboxamide (88);

N-((4-(5-(tert-butyl)-1,2,4-oxadiazol-3-yl)bicyclo[2.2.2]octan-1-yl)methyl)-N-(4'-(difluoromethoxy)-[1,1'-biphenyl]-3-yl)tetrahydro-2H-pyran-4-carboxamide (89);

N-((4-(3-cyclopropyl-1,2,4-oxadiazol-5-yl)bicyclo[2.2.2]octan-1-yl)methyl)-N-(3-(2-methylbenzo[d]thiazol-6-yl)phenyl)cyclohexanecarboxamide (90);

N-((4-(3-cyclopropyl-1,2,4-oxadiazol-5-yl)bicyclo[2.2.2]octan-1-yl)methyl)-N-(3-(2-methylbenzo[d]thiazol-6-yl)phenyl)tetrahydro-2H-pyran-4-carboxamide (91);

N-((4-(3-cyclopropyl-1,2,4-oxadiazol-5-yl)bicyclo[2.2.2]octan-1-yl)methyl)-N-(3-(5-fluorobenzo[d]oxazol-2-yl)phenyl)tetrahydro-2H-pyran-3-carboxamide, racemate (92);

N-((4-(3-cyclopropyl-1,2,4-oxadiazol-5-yl)bicyclo[2.2.2]octan-1-yl)methyl)-4,4-difluoro-N-(3-(5-fluorobenzo[d]oxazol-2-yl)phenyl)cyclohexane-1-carboxamide (93);

N-(3'-methoxy-[1,1'-biphenyl]-3-yl)-N-(1-(4-(3-methyl-1,2,4-oxadiazol-5-yl) bicyclo[2.2.2]octan-1-yl)ethyl)cyclohexanecarboxamide (94-95);

N-((3-(3-cyclopropyl-1,2,4-oxadiazol-5-yl)bicyclo[1.1.1]pentan-1-yl)methyl)-N-(3-(2-methoxypyridin-4-yl)phenyl)cyclohexanecarboxamide (96);

N-(3-(2-methoxypyridin-4-yl)phenyl)-N-((3-(3-(tetrahydro-2H-pyran-4-yl)-1,2,4-oxadiazol-5-yl)bicyclo[1.1.1]pentan-1-yl)methyl)cyclohexanecarboxamide (97);

N-cyclopropyl-4-((N-(3-(2-methoxypyridin-4-yl)phenyl)cyclohexanecarboxamido) methyl)bicyclo[2.2.2]octane-1-carboxamide (98);

N-((4-cyanobicyclo[2.2.2]octan-1-yl)methyl)-N-(3-(2-methoxypyridin-4-yl)phenyl)cyclohexanecarboxamide (99);

N-(3-(2-methoxypyridin-4-yl)phenyl)-N-((4-(1-methyl-1H-tetrazol-5-yl) bicyclo[2.2.2]octan-1-yl)methyl)cyclohexanecarboxamide (100);

methyl 2-(3-(N-((4-(3-methyl-1,2,4-oxadiazol-5-yl)bicyclo[2.2.2]octan-1-yl)methyl)cyclohexanecarboxamido)phenyl)cyclopropane-1-carboxylate (101-102);

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)phenyl)-4,4-difluorocyclohexane-1-carboxamide (103);

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)phenyl)tetrahydro-2H-pyran-4-carboxamide (104);

N-((4-(5-(1,1-difluoroethyl)-1,2,4-oxadiazol-3-yl)bicyclo[2.2.2]octan-1-yl)methyl)-N-(4'-ethoxy-6-fluoro-[1,1'-biphenyl]-3-yl)-4,4-difluorocyclohexane-1-carboxamide (105);

N-((4-(5-(1,1-difluoroethyl)-1,2,4-oxadiazol-3-yl)bicyclo[2.2.2]octan-1-yl)methyl)-N-(3-(2-ethoxypyrimidin-5-yl)-4-fluorophenyl)-4,4-difluorocyclohexane-1-carboxamide (106);

N-((4-(5-(1,1-difluoroethyl)-1,2,4-oxadiazol-3-yl)bicyclo[2.2.2]octan-1-yl)methyl)-4,4-difluoro-N-(6-fluoro-4'-(methylsulfonyl)-[1,1'-biphenyl]-3-yl)cyclohexane-1-carboxamide (107);

N-((4-(5-(1,1-difluoroethyl)-1,2,4-oxadiazol-3-yl)bicyclo[2.2.2]octan-1-yl)methyl)-4,4-difluoro-N-(4-fluoro-3-(2-methylbenzo[d]thiazol-6-yl)phenyl)cyclohexane-1-carboxamide (108);

N-((4-(5-(1,1-difluoroethyl)-1,2,4-oxadiazol-3-yl)bicyclo[2.2.2]octan-1-yl)methyl)-N-(4'-(difluoromethoxy)-[1,1'-biphenyl]-3-yl)tetrahydro-2H-pyran-4-carboxamide (109);

N-((4-(5-(1,1-difluoroethyl)-1,2,4-oxadiazol-3-yl)bicyclo[2.2.2]octan-1-yl)methyl)-N-(4'-(difluoromethoxy)-[1,1'-biphenyl]-3-yl)tetrahydro-2H-thiopyran-4-carboxamide 1,1-dioxide (110);

N-((4-(5-(1,1-difluoroethyl)-1,2,4-oxadiazol-3-yl)bicyclo[2.2.2]octan-1-yl)methyl)-N-(4'-(difluoromethoxy)-[1,1'-biphenyl]-3-yl)-4,4-difluorocyclohexane-1-carboxamide (111);

N-(3-(3-cyclopropyl-1,2,4-oxadiazol-5-yl)phenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide (112);

N-((4-(5-(1,1-difluoroethyl)-1,2,4-oxadiazol-3-yl)bicyclo[2.2.2]octan-1-yl)methyl)-N-(4'-ethoxy-[1,1'-biphenyl]-3-yl)-4,4-difluorocyclohexane-1-carboxamide (113);

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)-5-fluorophenyl)-4,4-difluorocyclohexane-1-carboxamide (114);

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)-5-fluorophenyl)tetrahydro-2H-pyran-4-carboxamide (115);

N-((4-(5-(tert-butyl)-1,2,4-oxadiazol-3-yl)bicyclo[2.2.2]octan-1-yl)methyl)-N-(3-(3-cyclopropyl-1,2,4-oxadiazol-5-yl)phenyl)tetrahydro-2H-pyran-4-carboxamide (116);

N-((4-(5-(tert-butyl)-1,2,4-oxadiazol-3-yl)bicyclo[2.2.2]octan-1-yl)methyl)-N-(3-(3-cyclopropyl-1,2,4-oxadiazol-5-yl)phenyl)tetrahydro-2H-thiopyran-4-carboxamide 1,1-dioxide (117);

N-((4-(5-(tert-butyl)-1,2,4-oxadiazol-3-yl)bicyclo[2.2.2]octan-1-yl)methyl)-N-(3-(3-cyclopropyl-1,2,4-oxadiazol-5-yl)phenyl)-1-methylpiperidine-4-carboxamide (118);

N-(3-(2-cyclopropylpyrimidin-5-yl)phenyl)-4,4-difluoro-N-((4-(5-(trifluoromethyl)-1,2,4-oxadiazol-3-yl)bicyclo[2.2.2]octan-1-yl)methyl)cyclohexane-1-carboxamide (119);

N-(3-(2-cyclopropylpyrimidin-5-yl)phenyl)-4,4-difluoro-N-((4-(5-(3-hydroxy-3-(trifluoromethyl)cyclobutyl)-1,2,4-oxadiazol-3-yl)bicyclo[2.2.2]octan-1-yl)methyl)cyclohexane-1-carboxamide (120);

N-((4-(5-(tert-butyl)-1,2,4-oxadiazol-3-yl)bicyclo[2.2.2]octan-1-yl)methyl)-N-(4'-(dimethylphosphoryl)-[1,1'-biphenyl]-3-yl)tetrahydro-2H-pyran-4-carboxamide (121);

N-((4-(5-(1,1-difluoroethyl)-1,2,4-oxadiazol-3-yl)bicyclo[2.2.2]octan-1-yl)methyl)-N-(4'-(dimethylphosphoryl)-6-fluoro-[1,1'-biphenyl]-3-yl)tetrahydro-2H-pyran-4-carboxamide (122);

N-((4-(5-(tert-butyl)-1,3,4-oxadiazol-2-yl)bicyclo[2.2.2]octan-1-yl)methyl)-N-(3-(3-cyclopropyl-1,2,4-oxadiazol-5-yl)phenyl)-4,4-difluorocyclohexane-1-carboxamide (123);

N-((4-(5-(tert-butyl)-1,3,4-oxadiazol-2-yl)bicyclo[2.2.2]octan-1-yl)methyl)-N-(3-(5-cyclopropylisoxazol-3-yl)phenyl)-4,4-difluorocyclohexane-1-carboxamide (124);

N-((4-(3-(tert-butyl)-1,2,4-oxadiazol-5-yl)bicyclo[2.2.2]octan-1-yl)methyl)-3,5-dichloro-N-(3-(2-ethoxypyrimidin-5-yl)phenyl)benzamide (125);

N-((4-(3-(tert-Butyl)-1,2,4-oxadiazol-5-yl)bicyclo[2.2.2]octan-1-yl)methyl)-3-chloro-N-(3-(2-ethoxypyrimidin-5-yl)phenyl)benzamide (126);

N-((4-(3-(tert-Butyl)-1,2,4-oxadiazol-5-yl)bicyclo[2.2.2]octan-1-yl)methyl)-4,4-difluoro-N-(3-(6-oxo-1,6-dihydropyridazin-4-yl)phenyl)cyclohexane-1-carboxamide (127);

N-((4-(5-(2-fluoropropan-2-yl)-1,2,4-oxadiazol-3-yl)bicyclo[2.2.2]octan-1-yl)methyl)-N-(3-(6-oxo-1,6-dihydropyridazin-4-yl)phenyl)tetrahydro-2H-pyran-4-carboxamide (128);

N-((4-(5-(1,1-difluoroethyl)-1,2,4-oxadiazol-3-yl)bicyclo[2.2.2]octan-1-yl)methyl)-N-(3-(6-oxo-1,6-dihydropyridazin-4-yl)phenyl)tetrahydro-2H-pyran-4-carboxamide (129);

N-((4-(5-(1,1-difluoroethyl)-1,2,4-oxadiazol-3-yl)bicyclo[2.2.2]octan-1-yl)methyl)-4,4-difluoro-N-(4'-(methylsulfonyl)-[1,1'-biphenyl]-3-yl)cyclohexane-1-carboxamide (130);

N-((4-(3-cyclopropyl-1-methyl-1H-pyrazol-5-yl)bicyclo[2.2.2]octan-1-yl)methyl)-N-(3-(5-cyclopropylisoxazol-3-yl)phenyl)tetrahydro-2H-thiopyran-4-carboxamide 1,1-dioxide (131);

N-((4-(3-cyclopropyl-1-methyl-1H-pyrazol-5-yl)bicyclo[2.2.2]octan-1-yl)methyl)-N-(3-(5-cyclopropylisoxazol-3-yl)phenyl)tetrahydro-2H-pyran-4-carboxamide (132);

N-((4-(3-cyclopropyl-1-methyl-1H-pyrazol-5-yl)bicyclo[2.2.2]octan-1-yl)methyl)-N-(3-(5-cyclopropylisoxazol-3-yl)phenyl)-1-methylpiperidine-4-carboxamide (133);

N-((4-(3-cyclopropyl-1-methyl-1H-pyrazol-5-yl)bicyclo[2.2.2]octan-1-yl)methyl)-N-(4'-(methylsulfonyl)-[1,1'-biphenyl]-3-yl)tetrahydro-2H-pyran-4-carboxamide (134);

N-((4-(3-cyclopropyl-1-methyl-1H-pyrazol-5-yl)bicyclo[2.2.2]octan-1-yl)methyl)-N-(4'-(methylsulfonyl)-[1,1'-biphenyl]-3-yl)tetrahydro-2H-thiopyran-4-carboxamide 1,1-dioxide (135);

N-((4-(3-cyclopropyl-1-methyl-1H-pyrazol-5-yl)bicyclo[2.2.2]octan-1-yl)methyl)-1-methyl-N-(4'-(methylsulfonyl)-[1,1'-biphenyl]-3-yl)piperidine-4-carboxamide (136);

N-((4-(3-cyclopropyl-1-methyl-1H-pyrazol-5-yl)bicyclo[2.2.2]octan-1-yl)methyl)-4,4-difluoro-N-(3-(2-methylbenzo[d]thiazol-6-yl)phenyl)cyclohexane-1-carboxamide (137);

N-((4-(3-cyclopropyl-1-methyl-1H-pyrazol-5-yl)bicyclo[2.2.2]octan-1-yl)methyl)-N-(3-(3-cyclopropylisoxazol-5-yl)phenyl)tetrahydro-2H-thiopyran-4-carboxamide 1,1-dioxide (138);

N-((4-(3-cyclopropyl-1-methyl-1H-pyrazol-5-yl)bicyclo[2.2.2]octan-1-yl)methyl)-N-(3-(3-cyclopropylisoxazol-5-yl)phenyl)tetrahydro-2H-pyran-4-carboxamide (139);

N-((4-(3-cyclopropyl-1-methyl-1H-pyrazol-5-yl)bicyclo[2.2.2]octan-1-yl)methyl)-N-(3-(3-cyclopropylisoxazol-5-yl)phenyl)-1-methylpiperidine-4-carboxamide (140);

N-((4-(3-(tert-butyl)-1,2,4-oxadiazol-5-yl)bicyclo[2.2.2]octan-1-yl)methyl)-N-(3-(6-chloropyrazolo[1,5-a]pyrimidin-3-yl)phenyl)-4,4-difluorocyclohexane-1-carboxamide (141);

N-((4-(3-(tert-butyl)-1,2,4-oxadiazol-5-yl)bicyclo[2.2.2]octan-1-yl)methyl)-4,4-difluoro-N-(3-(4-methyl-1H-imidazol-1-yl)phenyl)cyclohexane-1-carboxamide (142);

N-(3-(2-ethoxypyrimidin-5-yl)phenyl)-N-((4-(5-(2-fluoropropan-2-yl)-1,2,4-oxadiazol-3-yl)bicyclo[2.2.2]octan-1-yl)methyl)-4-methoxybenzamide (143);

4-(difluoromethoxy)-N-(3-(2-ethoxypyrimidin-5-yl)phenyl)-N-((4-(5-(2-fluoropropan-2-yl)-1,2,4-oxadiazol-3-yl)bicyclo[2.2.2]octan-1-yl)methyl)benzamide (144);

N-((4-(3-(tert-butyl)-1,2,4-oxadiazol-5-yl)bicyclo[2.2.2]octan-1-yl)methyl)-N-(4'-ethoxy-[1,1'-biphenyl]-3-yl)-4-methoxycyclohexane-1-carboxamide (145-146);

N-((4-(3-(tert-butyl)-1,2,4-oxadiazol-5-yl)bicyclo[2.2.2]octan-1-yl)methyl)-N-(3-(3-cyclopropylisoxazol-5-yl)phenyl)-4,4-difluorocyclohexane-1-carboxamide (147);

N-((4-(5-(tert-butyl)-1,2,4-oxadiazol-3-yl)bicyclo[2.2.2]octan-1-yl)methyl)-N-(3-(3-cyclopropylisoxazol-5-yl)phenyl)-4,4-difluorocyclohexane-1-carboxamide (148);

N-(3-(3-cyclopropylisoxazol-5-yl)phenyl)-4,4-difluoro-N-((4-(5-(1-(trifluoromethyl)cyclopropyl)-1,2,4-oxadiazol-3-yl)bicyclo[2.2.2]octan-1-yl)methyl)cyclohexane-1-carboxamide (149);

N-(3-(3-cyclopropylisoxazol-5-yl)phenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide (150);

N-((4-(3-cyclopropyl-1,2,4-oxadiazol-5-yl)bicyclo[2.2.2]octan-1-yl)methyl)-N-(3-(3-cyclopropylisoxazol-5-yl)phenyl)-4,4-difluorocyclohexane-1-carboxamide (151);

N-((4-(3-cyclopropyl-1,2,4-oxadiazol-5-yl)bicyclo[2.2.2]octan-1-yl)methyl)-N-(3-(3-cyclopropylisoxazol-5-yl)phenyl)tetrahydro-2H-thiopyran-4-carboxamide 1,1-dioxide (152);

N-((4-(3-cyclopropyl-1,2,4-oxadiazol-5-yl)bicyclo[2.2.2]octan-1-yl)methyl)-N-(3-(3-cyclopropylisoxazol-5-yl)phenyl)tetrahydro-2H-pyran-4-carboxamide (153);

N-(3-(5-cyclopropylisoxazol-3-yl)phenyl)-N-((4-(5-(1,1-difluoroethyl)-1,2,4-oxadiazol-3-yl)bicyclo[2.2.2]octan-1-yl)methyl)-4,4-difluorocyclohexane-1-carboxamide (154);

N-(3-(5-cyclopropylisoxazol-3-yl)phenyl)-N-((4-(5-(1,1-difluoroethyl)-1,2,4-oxadiazol-3-yl)bicyclo[2.2.2]octan-1-yl)methyl)tetrahydro-2H-thiopyran-4-carboxamide 1,1-dioxide (155);

N-(3-(5-cyclopropylisoxazol-3-yl)phenyl)-N-((4-(5-(1,1-difluoroethyl)-1,2,4-oxadiazol-3-yl)bicyclo[2.2.2]octan-1-yl)methyl)tetrahydro-2H-pyran-4-carboxamide (156);

N-(3-(5-cyclopropylisoxazol-3-yl)phenyl)-N-((4-(5-(1,1-difluoroethyl)-1,2,4-oxadiazol-3-yl)bicyclo[2.2.2]octan-1-yl)methyl)-4-hydroxy-4-(trifluoromethyl)cyclohexane-1-carboxamide (157-158);

N-((4-(3-(tert-butyl)-1,2,4-oxadiazol-5-yl)bicyclo[2.2.2]octan-1-yl)methyl)-N-(3-(5-cyclopropylisoxazol-3-yl)phenyl)-4,4-difluorocyclohexane-1-carboxamide (159);

N-((4-(3-(tert-butyl)-1,2,4-oxadiazol-5-yl)bicyclo[2.2.2]octan-1-yl)methyl)-N-(3-(5-cyclopropylisoxazol-3-yl)phenyl)tetrahydro-2H-thiopyran-4-carboxamide 1,1-dioxide (160);

N-((4-(3-(tert-butyl)-1,2,4-oxadiazol-5-yl)bicyclo[2.2.2]octan-1-yl)methyl)-N-(3-(5-cyclopropylisoxazol-3-yl)phenyl)tetrahydro-2H-pyran-4-carboxamide (161);

N-((4-(5-(tert-butyl)-1,2,4-oxadiazol-3-yl)bicyclo[2.2.2]octan-1-yl)methyl)-N-(3-(5-cyclopropylisoxazol-3-yl)phenyl)-4,4-difluorocyclohexane-1-carboxamide (162);

N-((4-(3-cyclopropyl-1-methyl-1H-pyrazol-5-yl)bicyclo[2.2.2]octan-1-yl)methyl)-N-(3-(5-cyclopropylisoxazol-3-yl)phenyl)-4,4-difluorocyclohexane-1-carboxamide (163);

N-((4-(5-(1,1-difluoroethyl)-1,2,4-oxadiazol-3-yl)bicyclo[2.2.2]octan-1-yl)methyl)-N-(4'-ethoxy-6-fluoro-[1,1'-biphenyl]-3-yl)-4-hydroxy-4-(trifluoromethyl)cyclohexane-1-carboxamide (164-165); or N-((4-(3-(tert-butyl)-1,2,4-oxadiazol-5-yl)bicyclo[2.2.2]octan-1-yl)methyl)-N-(4'-ethoxy-6-fluoro-[1,1'-biphenyl]-3-yl)-4-hydroxy-4-methylcyclohexane-1-carboxamide (166).

9. A pharmaceutical composition comprising a pharmaceutically acceptable carrier and a compound according to claim 1, or a stereoisomer, a tautomer, or a pharmaceutically acceptable salt thereof.

10. A method of treating a disease or disorder, comprising administering to a mammalian patient a compound according to claim 1 or a pharmaceutically acceptable salt thereof, wherein the disease or disorder is nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

11. A method of treating a disease or disorder, comprising administering to a mammalian patient a compound according to claim 1 or a pharmaceutically acceptable salt thereof, wherein the disease or disorder is idiopathic pulmonary fibrosis (IPF).

* * * * *